US012612448B2

(12) United States Patent
Hwang et al.

(10) Patent No.: US 12,612,448 B2
(45) Date of Patent: Apr. 28, 2026

(54) TUMOR-TARGETING A56 PROTEIN OR FRAGMENT THEREOF, ANTIBODY BINDING TO A56 PROTEIN, AND USE THEREOF

(71) Applicant: BIONOXX INC., Seongnam-si (KR)

(72) Inventors: Tae-Ho Hwang, Yangsan-si (KR); Mong Cho, Yangsan-si (KR); Euna Cho, Yangsan-si (KR)

(73) Assignee: BIONOXX INC., Seongnam-si (KR)

( * ) Notice: Subject to any disclaimer, the term of this patent is extended or adjusted under 35 U.S.C. 154(b) by 1081 days.

(21) Appl. No.: 17/642,868

(22) PCT Filed: Oct. 5, 2020

(86) PCT No.: PCT/KR2020/013485
§ 371 (c)(1),
(2) Date: Mar. 14, 2022

(87) PCT Pub. No.: WO2021/066612
PCT Pub. Date: Apr. 8, 2021

(65) Prior Publication Data
US 2022/0389085 A1 Dec. 8, 2022

(30) Foreign Application Priority Data
Oct. 2, 2019 (KR) ........................ 10-2019-0122076

(51) Int. Cl.
| | |
|---|---|
| *C07K 16/08* | (2006.01) |
| *A61K 35/768* | (2015.01) |
| *A61K 39/42* | (2006.01) |
| *A61K 47/68* | (2017.01) |
| *A61P 35/00* | (2006.01) |
| *C07K 14/005* | (2006.01) |
| *C07K 16/081* | (2026.01) |
| *C12N 7/00* | (2006.01) |
| *A61K 39/00* | (2006.01) |

(52) U.S. Cl.
CPC .......... *C07K 16/081* (2013.01); *A61K 35/768* (2013.01); *A61K 39/42* (2013.01); *A61K 47/6891* (2017.08); *A61P 35/00* (2018.01); *C07K 14/005* (2013.01); *C12N 7/00* (2013.01); *A61K 2039/585* (2013.01); *C07K 2317/565* (2013.01); *C12N 2710/24122* (2013.01); *C12N 2710/24132* (2013.01)

(58) Field of Classification Search
None
See application file for complete search history.

(56) References Cited

FOREIGN PATENT DOCUMENTS

| | | |
|---|---|---|
| CN | 109069613 B | 10/2022 |
| JP | 2022-548043 A | 11/2022 |
| WO | 2006/076003 A2 | 7/2006 |
| WO | 2008/100292 A2 | 8/2008 |
| WO | 2017/184951 A1 | 10/2017 |
| WO | 2019/106205 A1 | 6/2019 |
| WO | WO-2021046653 A1 * | 3/2021 .............. A61P 35/00 |

OTHER PUBLICATIONS

Meng et al.(Virology, 2011, 409:271-279) (IDS).*
Karsten Winkler, et al., "Changing the Antigen Binding Specificity by Single Point Mutations of an Anti-p24 (HIV-1) Antibody" The Journal of Immunology, Williams & Wilkins Co, XP002579393, US, vol. 165, No. 8, Oct. 15, 2000, pp. 4505-4514 (10 pages).
Stuart Rudikoff, et al., "Single amino acid substitution altering antigen-binding specificity", Proceedings of the National Academy of Sciences, National Academy of Sciences, vol. 79, No. 6, Mar. 1, 1982, XP002683593, pp. 1979-1983 (5 pages).
Makoto Seki, et al., "Hemadsorption and Fusion Inhibition Activities of Hemagglutinin Analyzed by Vaccinia Virus Mutants" Virology, Amsterdam, NL, 1990, vol. 175, No. 2, XP023056022, pp. 372-384 (13 pages).
Timothy R. Wagenaar, et al., "Expression of the A56 and K2 Proteins is Sufficient to Inhibit Vaccinia Virus Entry and Cell Fusion", Journal of Virology, vol. 83, No. 4, Feb. 2009, XP093087508, pp. 1546-1554 (9 pages).
Zong Sheng Guo, et al., "Vaccinia virus-mediated cancer immunotherapy: cancer vaccines and oncolytics", Journal for ImmunoTherapy of Cancer, 2019, vol. 7, No. 1, XP055677423, (21 pages).
Supplementary European Search Report dated Oct. 13, 2023 in EP Application No. 20871186.1.
Euna Cho et al., "Preclinical safety evaluation of hepatic arterial infusion of oncolytic poxvirus", Drug Design, Development and Therapy, 2018, vol. 12, pp. 2467-2474 (8 total pages).
Xiangzhi Meng et al., "Generation and characterization of a large panel of murine monoclonal antibodies against vaccinia virus", Virology, 2011, pp. 271-279, vol. 409.
NCBI, GenBank accession No. AMK98459.1, "hemagglutinin [Vaccinia virus]", Feb. 28, 2016, pp. 1-2.

(Continued)

*Primary Examiner* — Laura B Goddard
(74) *Attorney, Agent, or Firm* — Sughrue Mion, PLLC

(57) ABSTRACT

A tumor-targeting protein or a fragment thereof, an antibody binding thereto and a use thereof are disclosed. A vector containing a nucleic acid coding for protein A56 or a fragment thereof, and a use thereof are disclosed. An antibody binding to protein A56 or a fragment thereof, and a use thereof are disclosed. The vector containing A56-encoding nucleic acid, a fragment thereof or a mutant thereof uses an oncolytic virus as the vector, and thus, when administered in an individual, specifically kills only cancer cells, primarily. In addition, cancer cells which have survived even after being infected with the oncolytic virus express the protein A56 on the cell surfaces thereof, and thus may be targeted for secondary anticancer therapy employing protein A56-encoding nucleic acid or protein A56 or a fragment thereof, or an antibody binding to A56.

6 Claims, 72 Drawing Sheets

Specification includes a Sequence Listing.

(56)     References Cited

OTHER PUBLICATIONS

NCBI, GenBank accession No. KU950327.1, "Vaccinia virus isolate Colombia hemagglutinin (HA) gene, complete cds", Apr. 18, 2017, pp. 1-3.

Brian C. Dehaven et al., "The vaccinia virus A56 protein: a multifunctional transmembrane glycoprotein that anchors two secreted viral proteins", Journal of General Virology, 2011, pp. 1971-1980, vol. 92.

International Search Report of PCT/KR2020/013485 dated Feb. 26, 2021 [PCT/ISA/210].

* cited by examiner

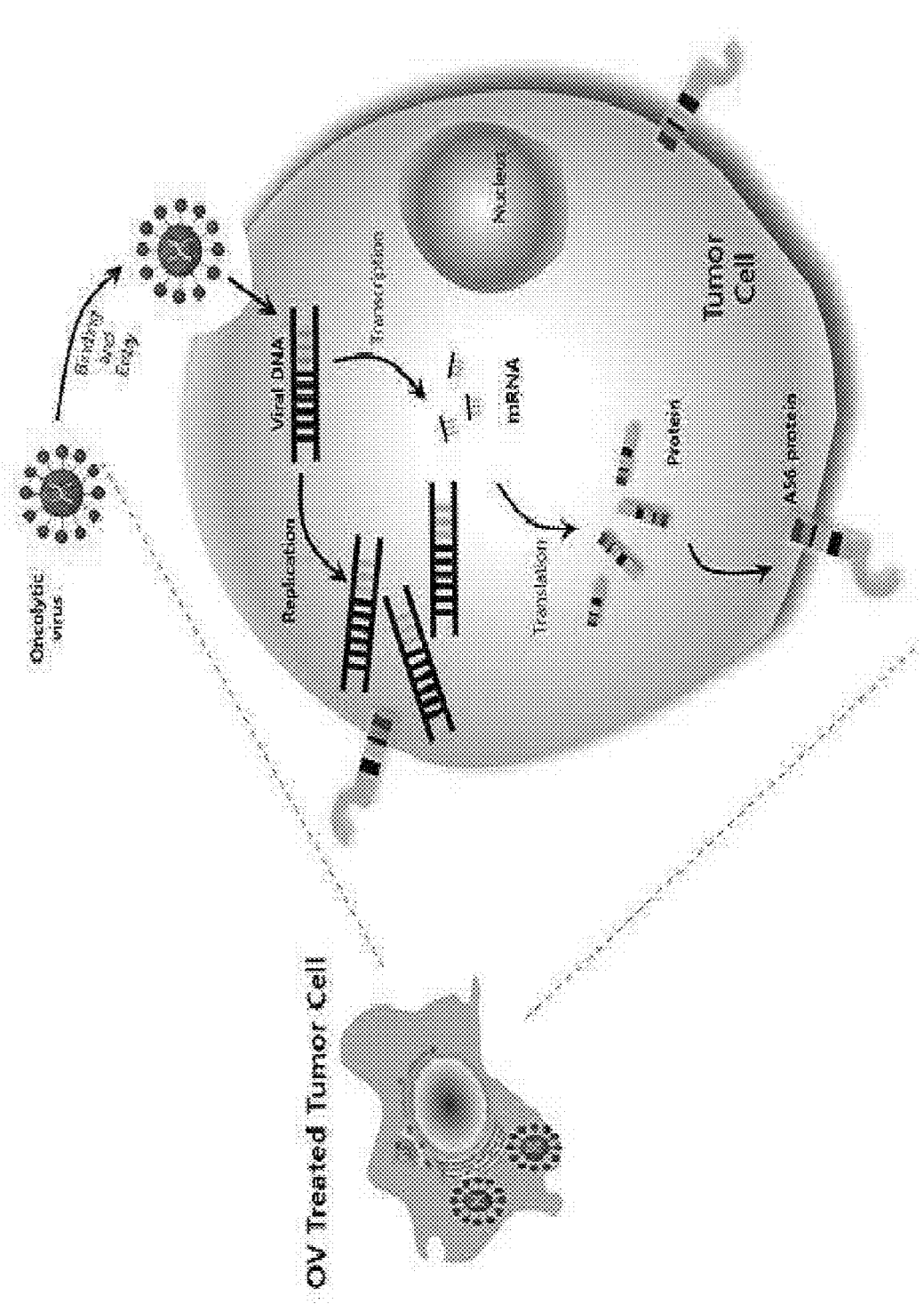
[FIG. 1]

[FIG. 2]
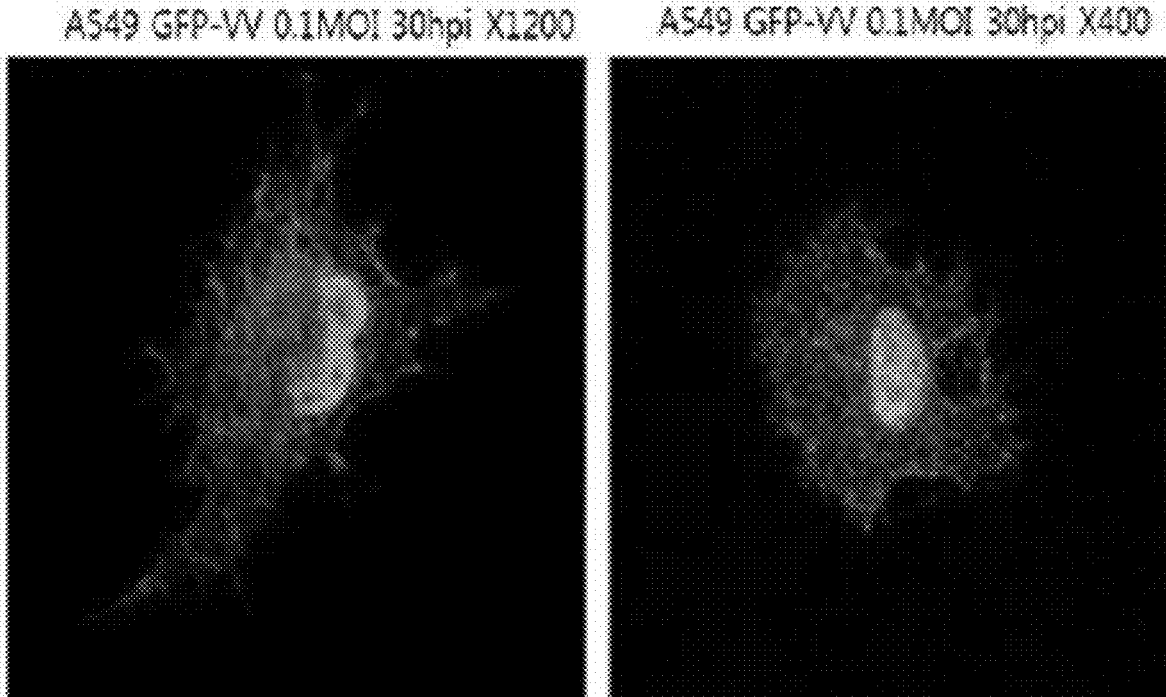
[FIG. 3]
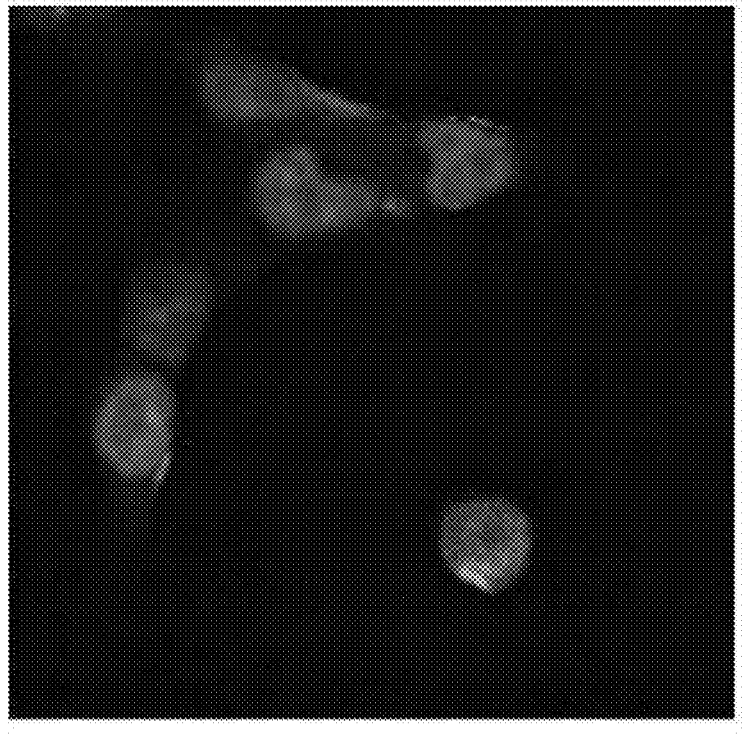

[FIG. 4]
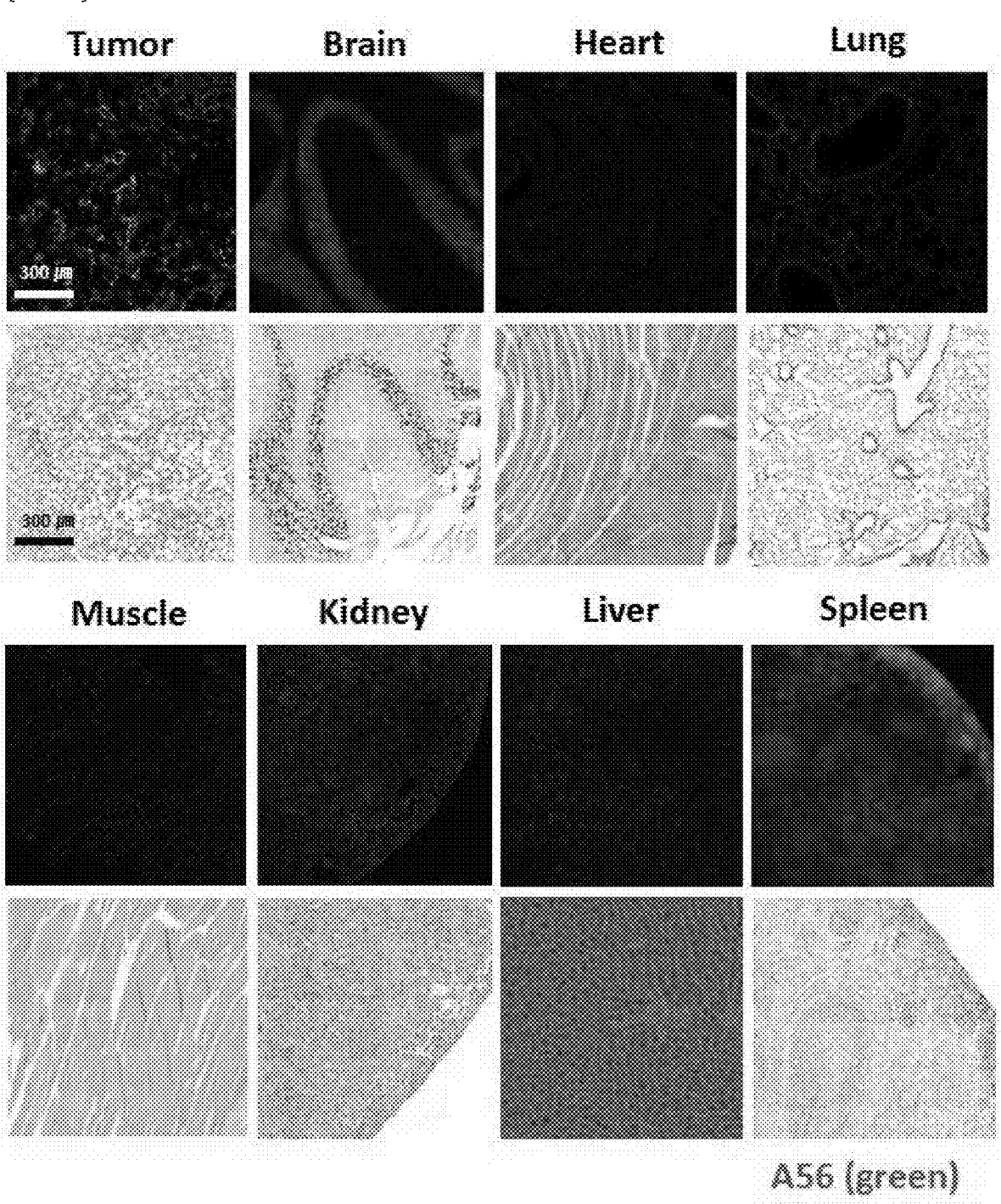
A56 (green)
Nuclei (blue)

[FIG. 5]
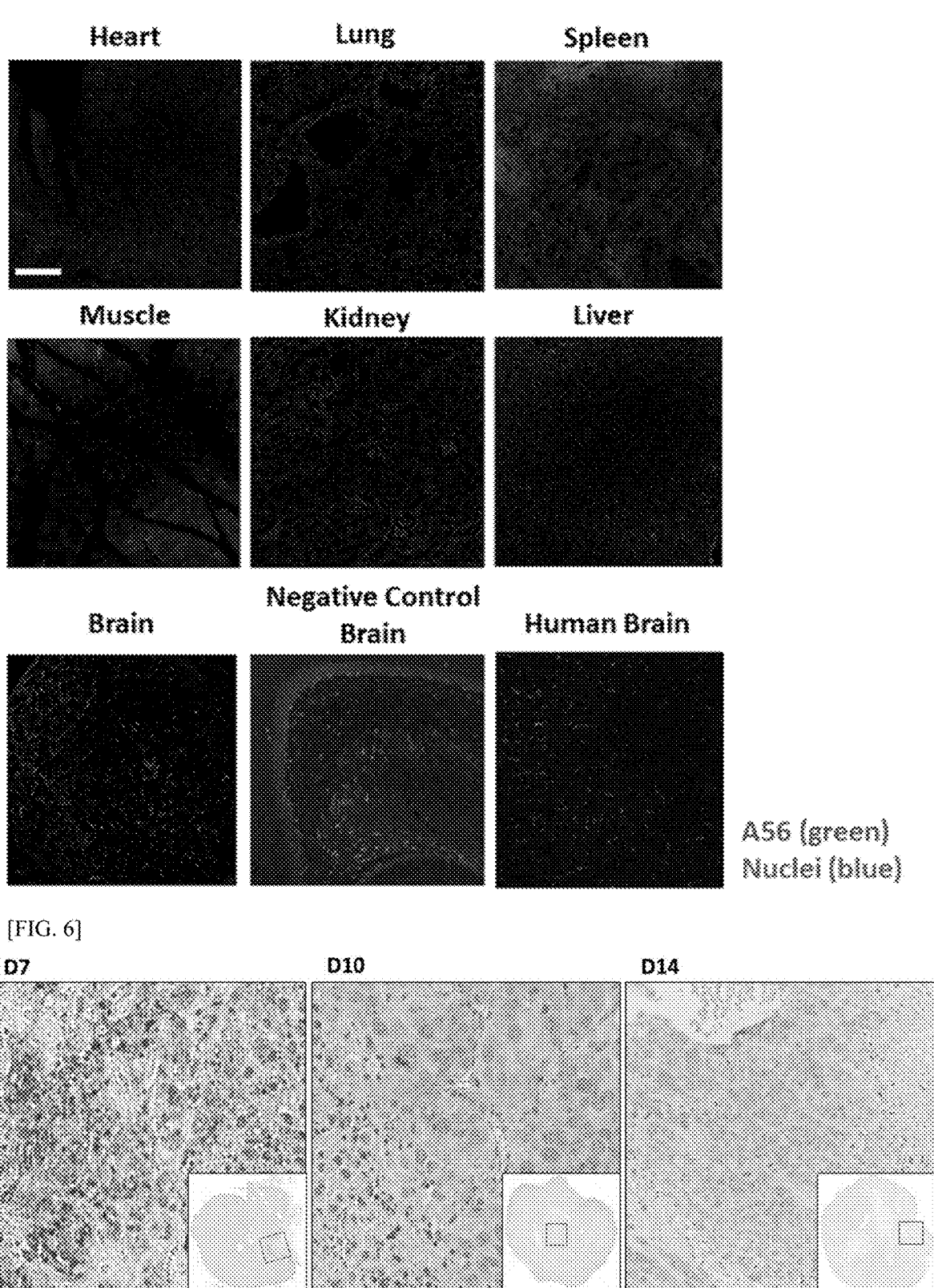
[FIG. 6]

[FIG. 10]
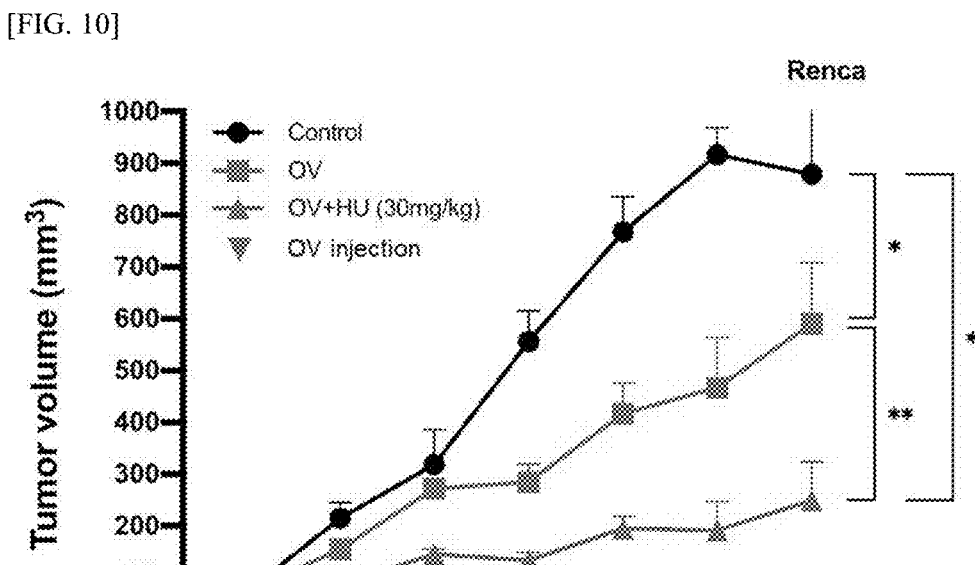
[FIG. 11]
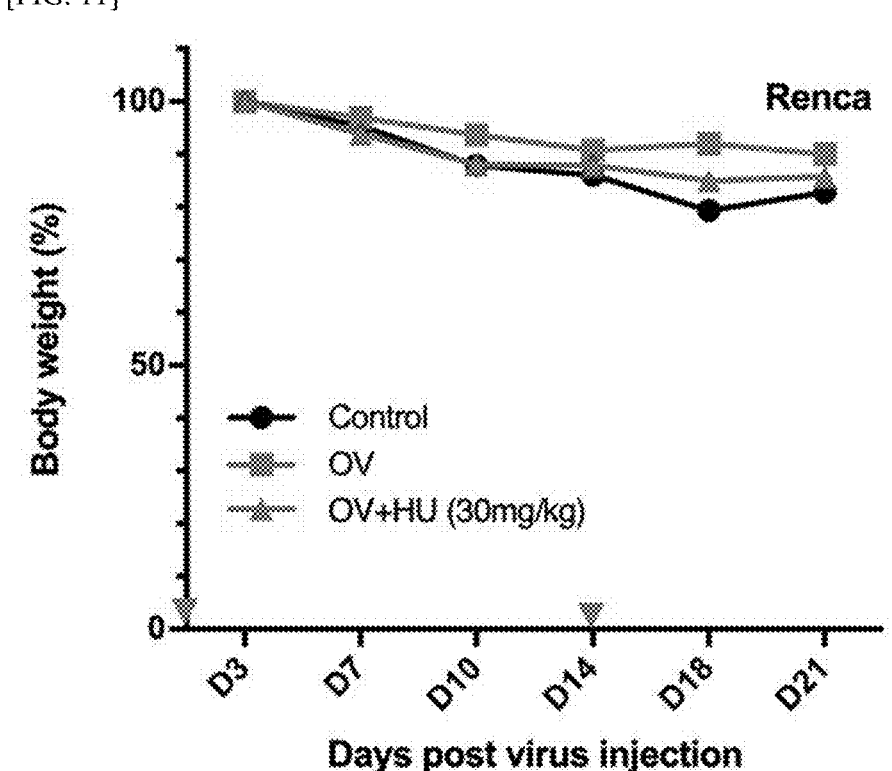

[FIG. 12]
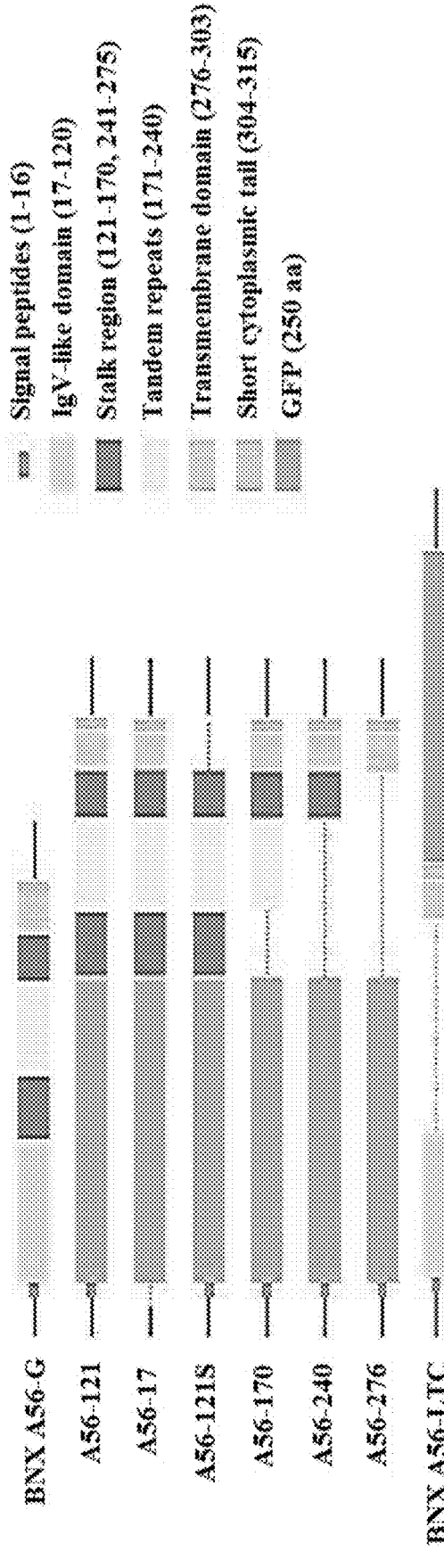

[FIG. 13]
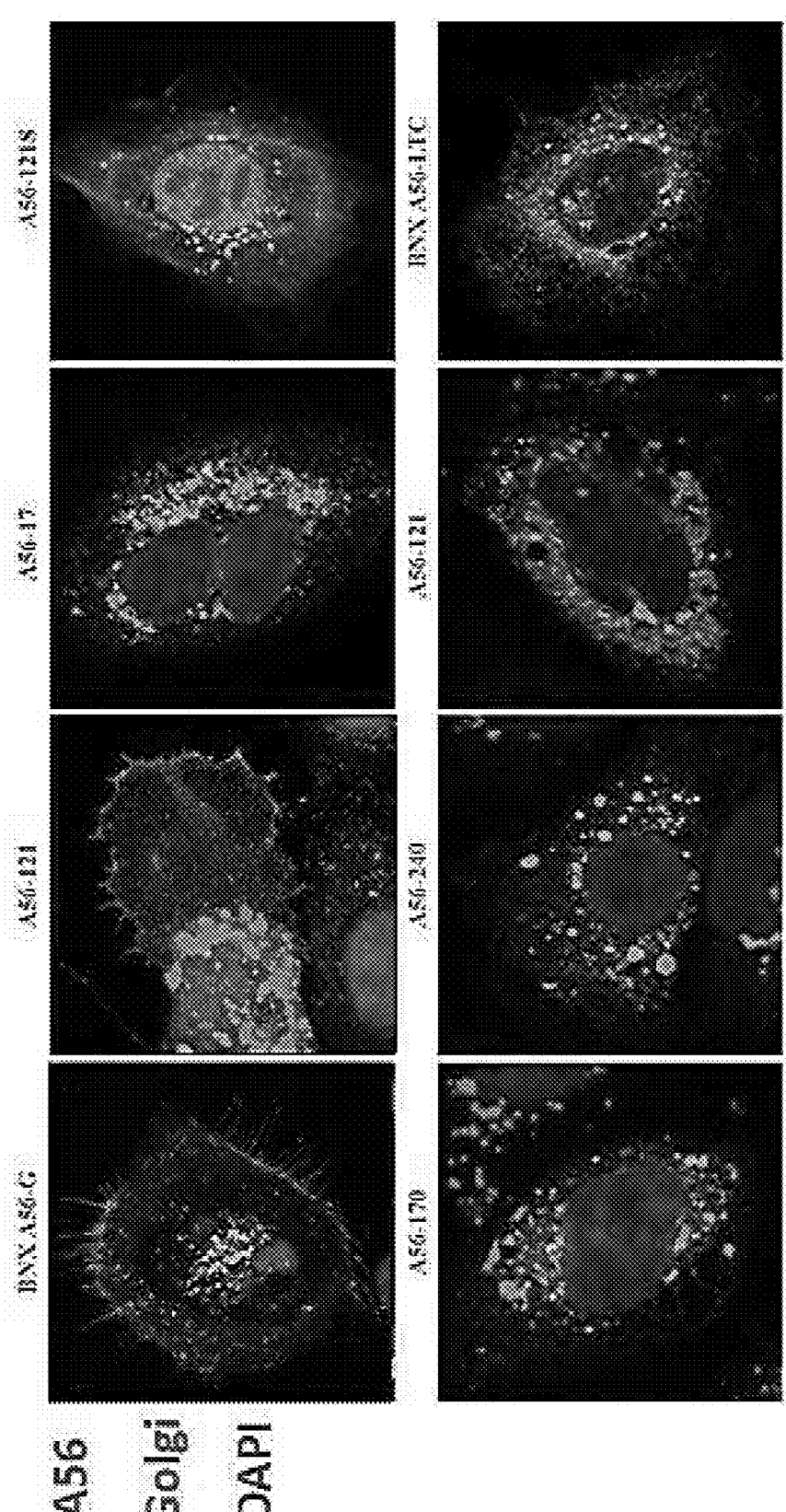

[FIG. 14]

A56 binding affinity test [1]

[FIG. 15]

A56 binding affinity test [2]

Coated with 100ng A56

Absorbance 450 nm

Cons (nM)

[FIG. 16]

A56 binding affinity test [3]

Coated with 100ng A56

[FIG. 17]

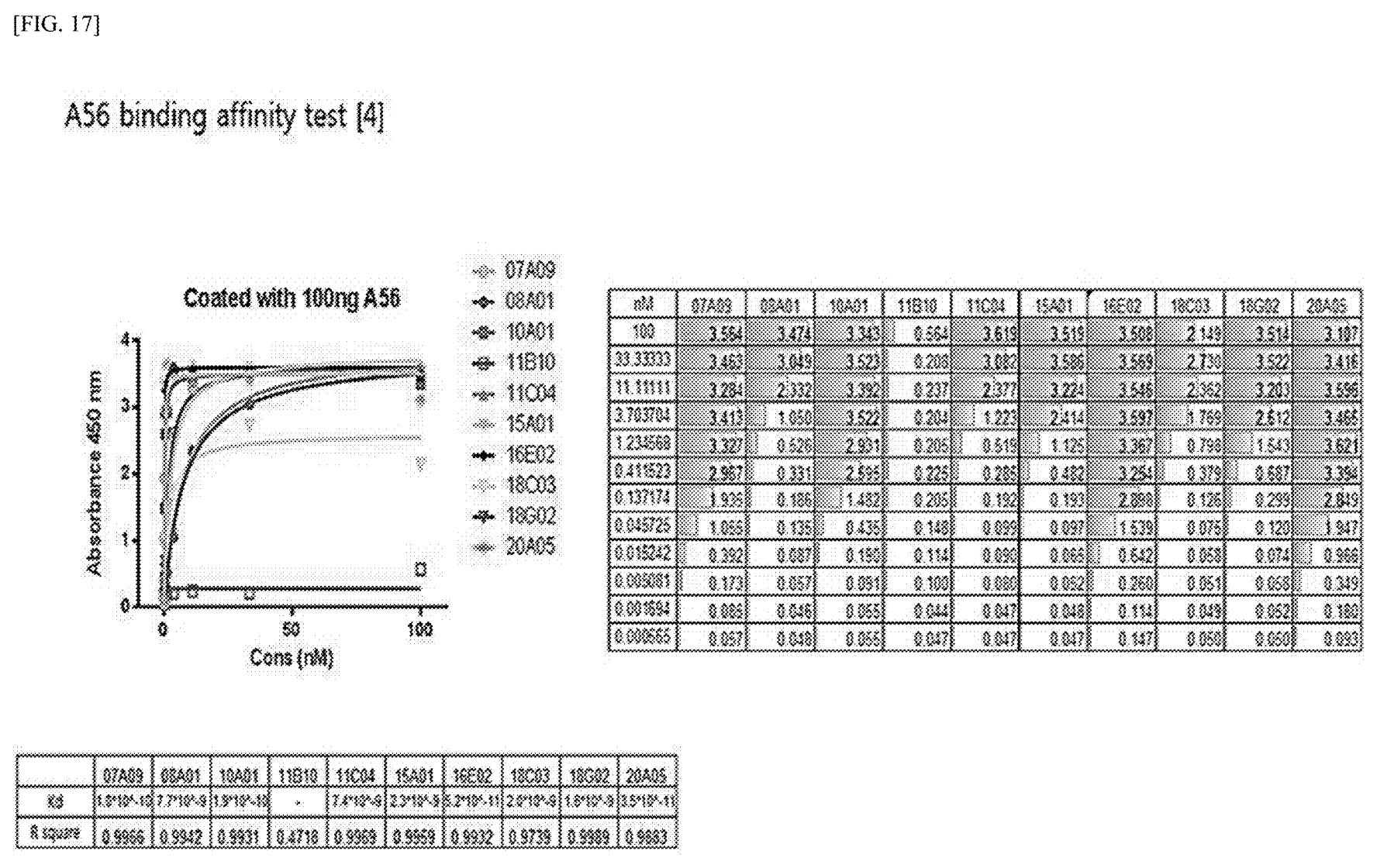

A56 binding affinity test [4]

Coated with 100ng A56

Absorbance 450 nm

Cons (nM)

A56 binding affinity test [5]

Coated with 100ng A56

Absorbance 450 nm

Cons (nM)

A56 binding affinity test [6]

Coated with 100ng A56

Absorbance 450 nm

Cons (nM)

[FIG. 20A]
| ID | NAME | Conc [mg/ml] | Protein [mg] | Productivity [mg/L] |
|---|---|---|---|---|
| SA2026 | A56-01A02 | 0.76 | 1.28 | 32 |
| SA2027 | A56-01A03 | 0.87 | 3.07 | 51.75 |
| SA2028 | A56-01A04 | 0.96 | 2.27 | 56.75 |
| SA2029 | A56-01A05 | 0.88 | 2.07 | 51.75 |
| SA2030 | A56-01B01 | 1.56 | 3.81 | 95.25 |
| SA2031 | A56-01C08 | 0.23 | 0.43 | 10.75 |
| SA2032 | A56-01C12 | 1.19 | 2.79 | 69.75 |
| SA2033 | A56-01F12 | 1.66 | 3.63 | 90.75 |
| SA2034 | A56-01G06 | 2.06 | 5.07 | 126.75 |
| SA2035 | A56-01G11 | 0.99 | 2.33 | 55.75 |
| SA2036 | A56-01H02 | 1.50 | 3.57 | 89.25 |
| SA2037 | A56-01H11 | 1.11 | 2.77 | 79.1 |
| SA2038 | A56-02A02 | 0.34 | 0.85 | 24.2 |
| SA2039 | A56-02B01 | 1.15 | 2.86 | 81.7 |
| SA2040 | A56-02B03 | 0.99 | 3.29 | 109.6 |
| SA2041 | A56-02B08 | 1.08 | 2.71 | 77.4 |
| SA2042 | A56-02B10 | 2.10 | 5.36 | 153.1 |
| SA2043 | A56-02C06 | 0.63 | 1.5 | 42.8 |
| SA2044 | A56-02C07 | 0.13 | 0.37 | 10.5 |
| SA2045 | A56-02C09 | 0.79 | 2 | 57.1 |
| SA2046 | A56-02E01 | 1.66 | 4.22 | 120.5 |
| SA2047 | A56-02E05 | 0.66 | 1.6 | 45.7 |
| SA2048 | A56-02F05 | 0.64 | 0.56 | 16 |
| SA2049 | A56-03A09 | 0.96 | 3.42 | 69.1 |
| SA2050 | A56-03B03 | 0.56 | 0.54 | 15.4 |
| SA2051 | A56-03D02 | 1.16 | 3 | 85.7 |
| SA2052 | A56-03H11 | 0.62 | 1.5 | 42.8 |
| SA2053 | A56-01H01 | 1.06 | 2.68 | 76.5 |
| SA2054 | A56-02B06 | 0.99 | 2.54 | 72.5 |
[FIG. 20B]
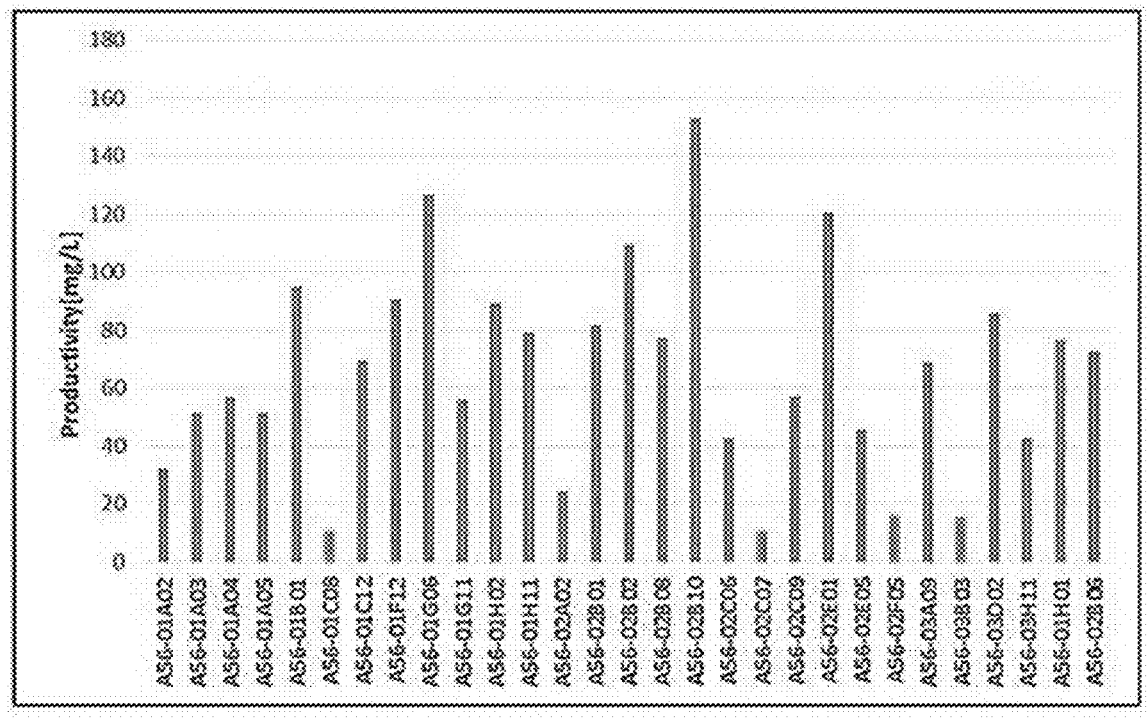

[FIG. 20C]

| ID | NAME | Conc [mg/ml] | Protein [mg] | Productivity [mg/L] |
|---|---|---|---|---|
| SA2055 | A56-02D04 | 0.95 | 2.28 | 57 |
| SA2056 | A56-07A09 | 0.33 | 0.7 | 17.5 |
| SA2057 | A56-08A01 | 0.46 | 1 | 25 |
| SA2058 | A56-10A01 | 0.21 | 0.4 | 10 |
| SA2059 | A56-11B10 | 0.88 | 2 | 50 |
| SA2060 | A56-11C04 | 0.09 | 0.16 | 4 |
| SA2061 | A56-15A01 | 0.72 | 1.5 | 37.5 |
| SA2062 | A56-16E02 | 0.78 | 1.83 | 45.75 |
| SA2063 | A56-18C03 | 0.35 | 0.67 | 16.75 |
| SA2064 | A56-18G02 | 0.11 | 0.2 | 5 |
| SA2065 | A56-20A05 | 1.04 | 2.57 | 73.4 |
| SA2066 | A56-20G03 | 0.72 | 1.7 | 48.6 |
| SA2067 | A56-20G12 | 0.66 | 1.6 | 45.7 |
| SA2068 | A56-21B10 | 0.62 | 1.5 | 42.8 |
| SA2069 | A56-21F02 | 0.01 | 0.02 | 0.71 |
| SA2070 | A56-21H04 | 0.55 | 1.34 | 38.3 |
| SA2071 | A56-22G10 | 0.81 | 2.05 | 58.6 |
| SA2072 | A56-24A05 | 0.55 | 1.35 | 38.6 |
| SA2073 | A56-30H01 | 0.38 | 0.95 | 27.1 |
| SA2074 | A56-32H08 | 0.43 | 1.09 | 31.1 |
| SA2075 | A56-35A06 | 1.01 | 2.57 | 73.4 |
| SA2076 | A56-35G07 | 2.02 | 5.09 | 145.4 |
| SA2077 | A56-36B11 | 0.32 | 0.81 | 23.1 |
| SA2078 | A56-41C01 | 0.63 | 1.88 | 53.7 |
| SA2079 | A56-42H07 | 1.26 | 3.21 | 91.7 |
| SA2080 | A56-44G01 | 0.70 | 1.76 | 50.3 |
| SA2081 | A56-46A07 | 0.90 | 2.26 | 64.6 |
| SA2082 | A56-50A09 | 0.29 | 0.74 | 21.1 |
| SA2083 | A56-50A11 | 0.30 | 0.75 | 21.4 |
| SA2084 | A56-54C01 | 0.05 | 0.13 | 3.7 |
| SA2085 | A56-59A11 | 0.62 | 1.56 | 44.6 |
| SA2086 | A56-59E12 | 0.74 | 1.74 | 49.7 |

[FIG. 21]
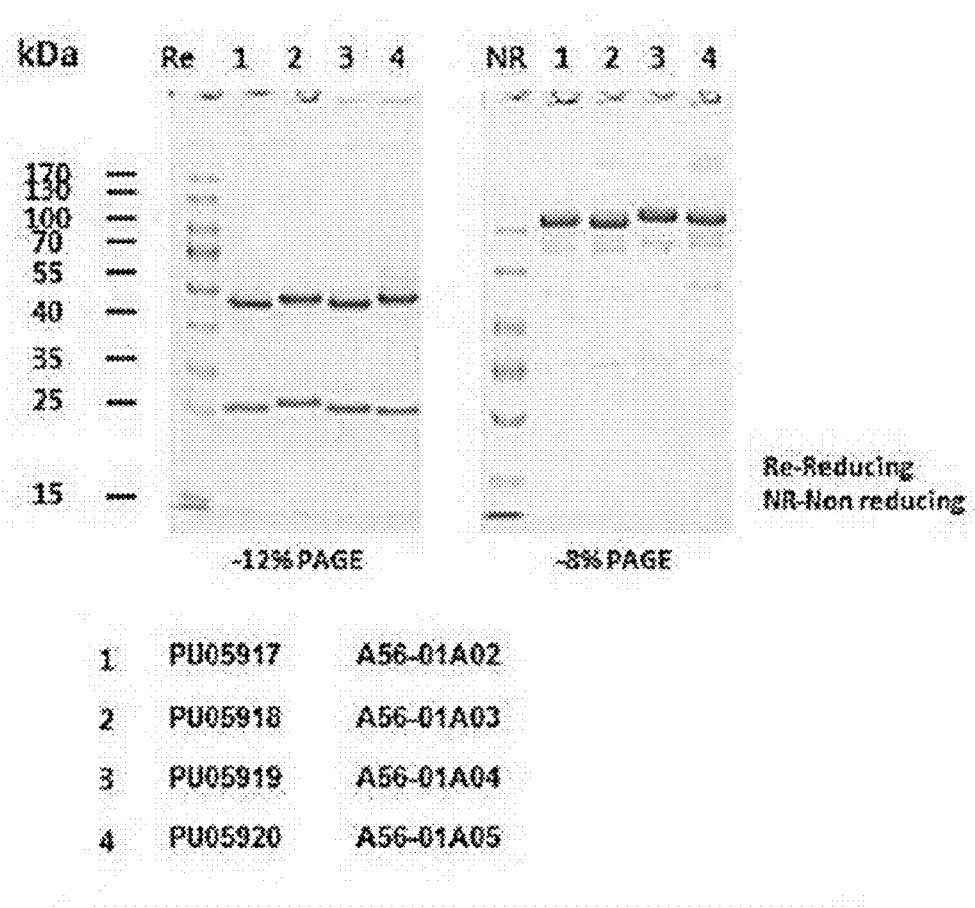
-Purified Protein

[FIG. 22]
-Purified Protein
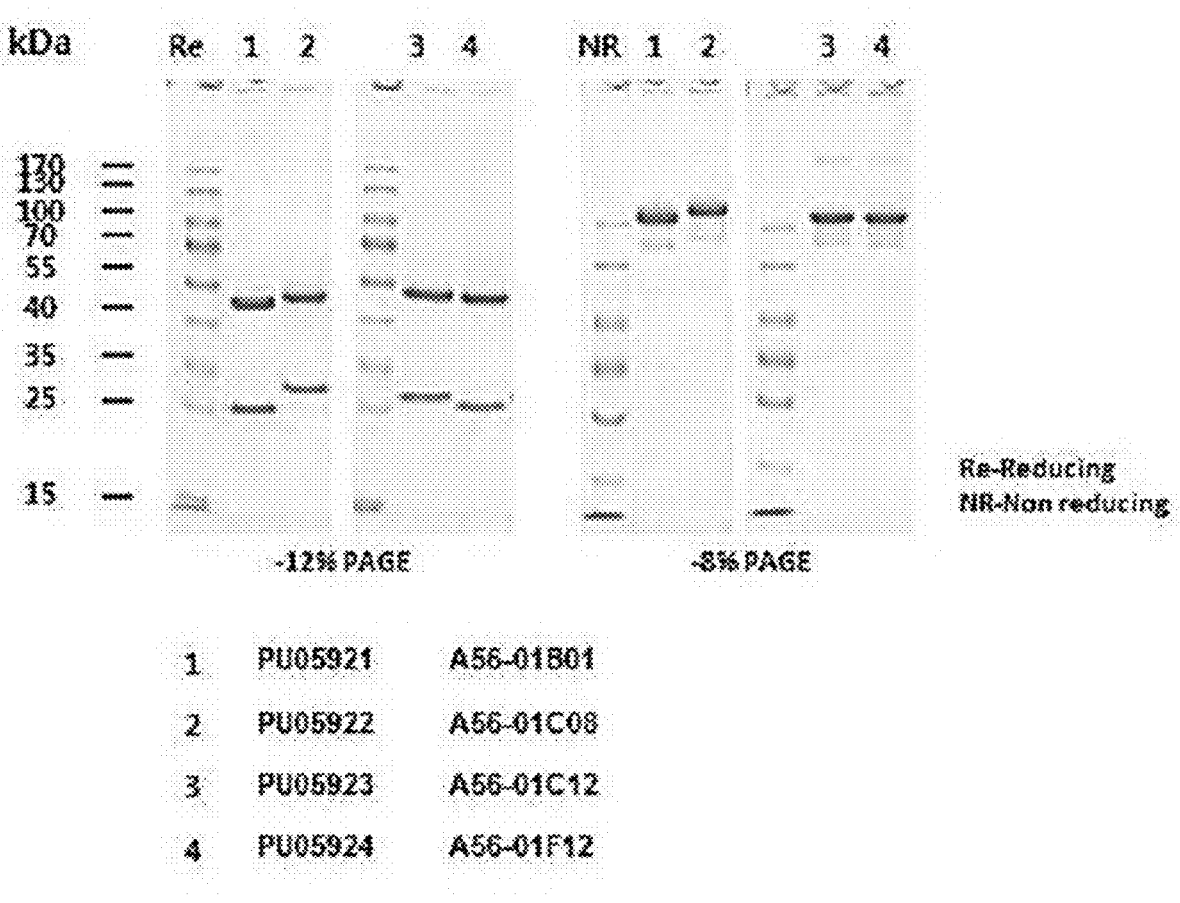
-12% PAGE     -8% PAGE
Re-Reducing
NR-Non reducing
| 1 | PU05921 | A56-01B01 |
| 2 | PU05922 | A56-01C08 |
| 3 | PU05923 | A56-01C12 |
| 4 | PU05924 | A56-01F12 |
-20ul loading(3ug)

[FIG. 23]
-Purified Protein
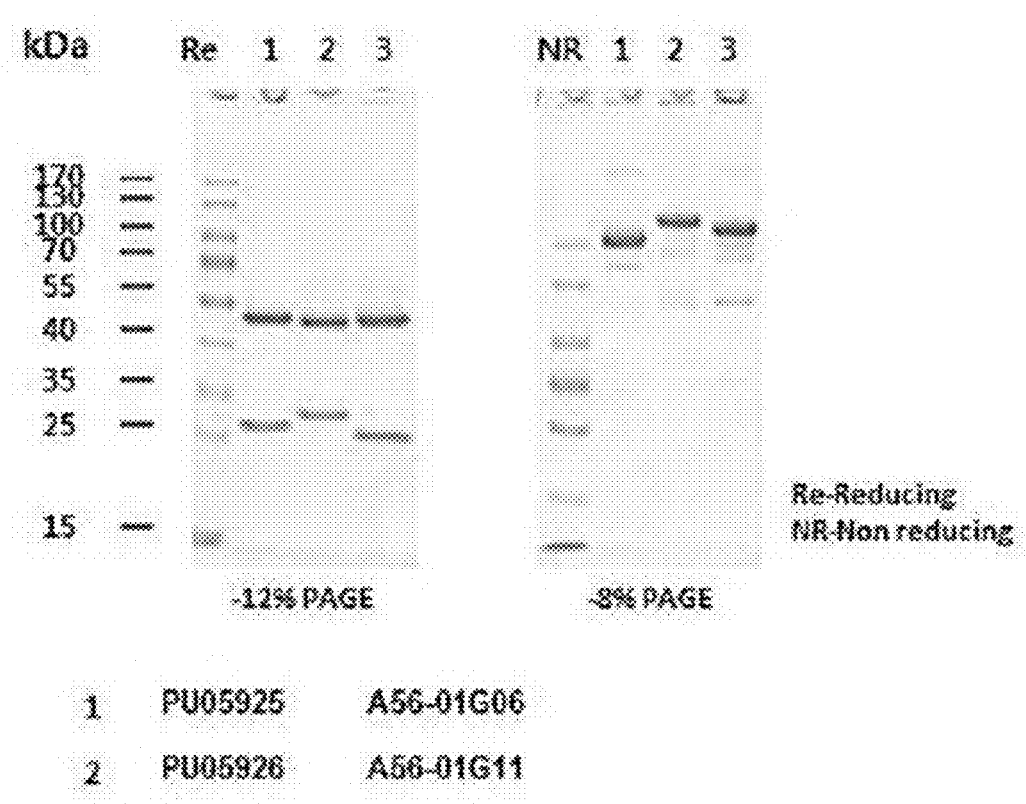
| | | |
|---|---|---|
| 1 | PU05925 | A56-01G06 |
| 2 | PU05926 | A56-01G11 |
| 3 | PU05927 | A56-01H02 |
-20ul loading(3ug)

[FIG. 24]
-Purified Protein
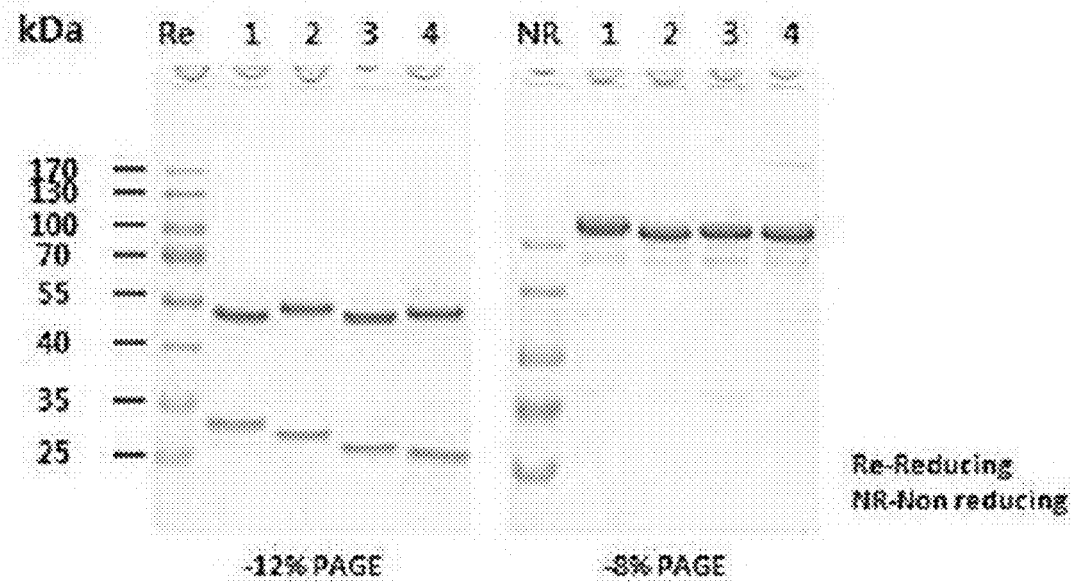
| | | |
|---|---|---|
| 1 | PU05928 | A56-01H11 |
| 2 | PU05929 | A56-02A02 |
| 3 | PU05930 | A56-02B01 |
| 4 | PU05931 | A56-02B02 |
-20ul loading(3ug)

[FIG. 25]
-Purified Protein
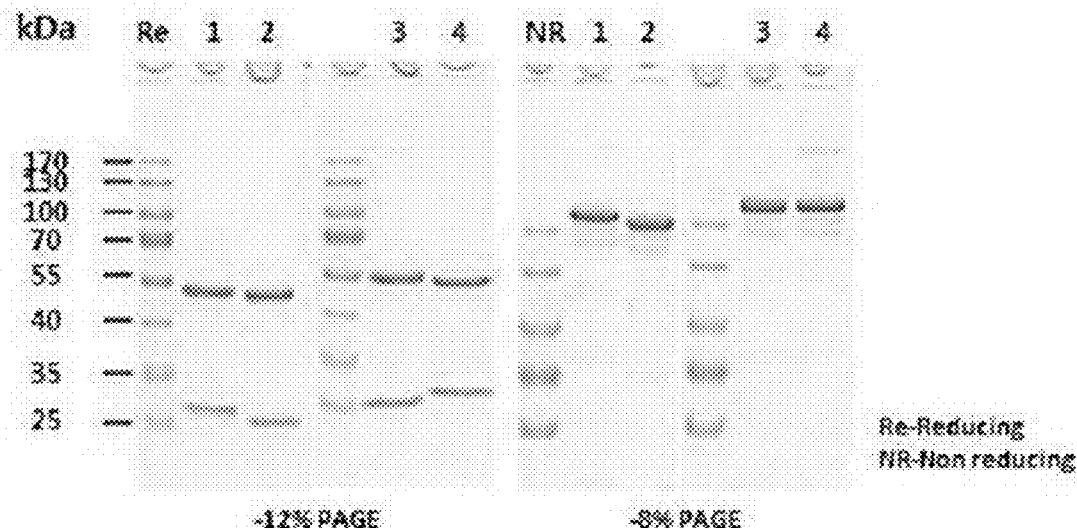
| 1 | PU05932 | A56-02B08 |
| 2 | PU05933 | A56-02B10 |
| 3 | PU05934 | A56-02C06 |
| 4 | PU05936 | A56-02C07 |
-20ul loading(3ug)

[FIG. 26]
-Purified Protein
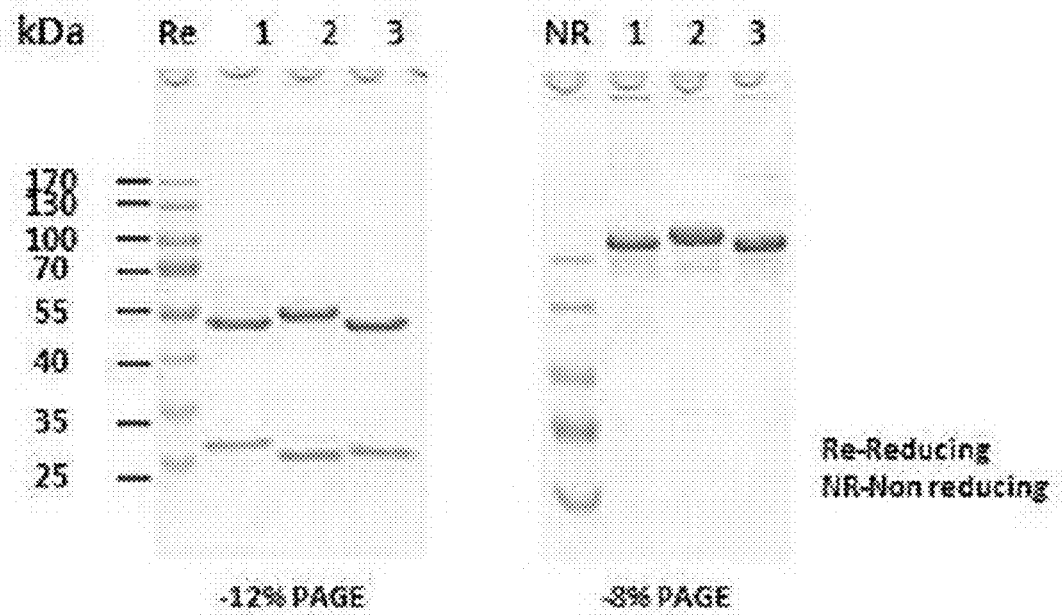
| 1 | PU05936 | A56-02C09 |
| 2 | PU05937 | A56-02E01 |
| 3 | PU05938 | A56-02E05 |
-20ul loading(3ug)

[FIG. 27]
-Purified Protein
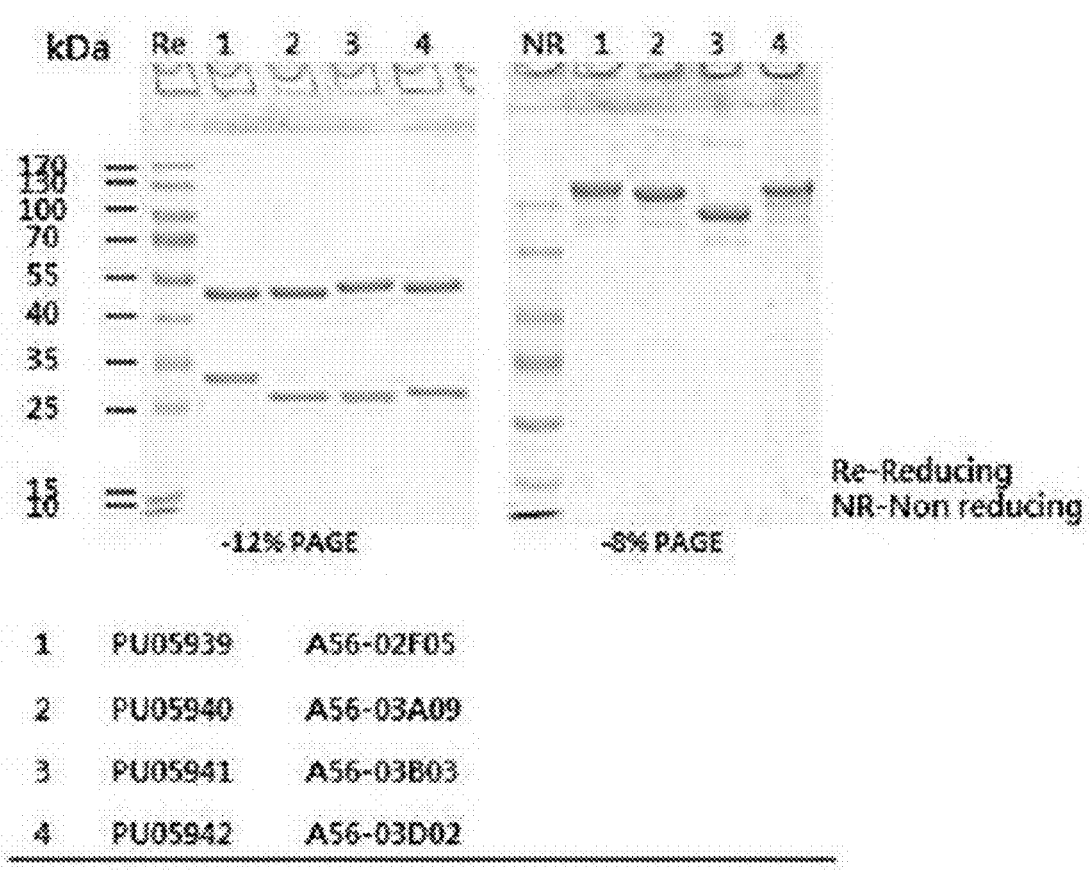
| | | |
|---|---|---|
| 1 | PU05939 | A56-02F05 |
| 2 | PU05940 | A56-03A09 |
| 3 | PU05941 | A56-03B03 |
| 4 | PU05942 | A56-03D02 |
-20ul loading(3ug)

[FIG. 28]
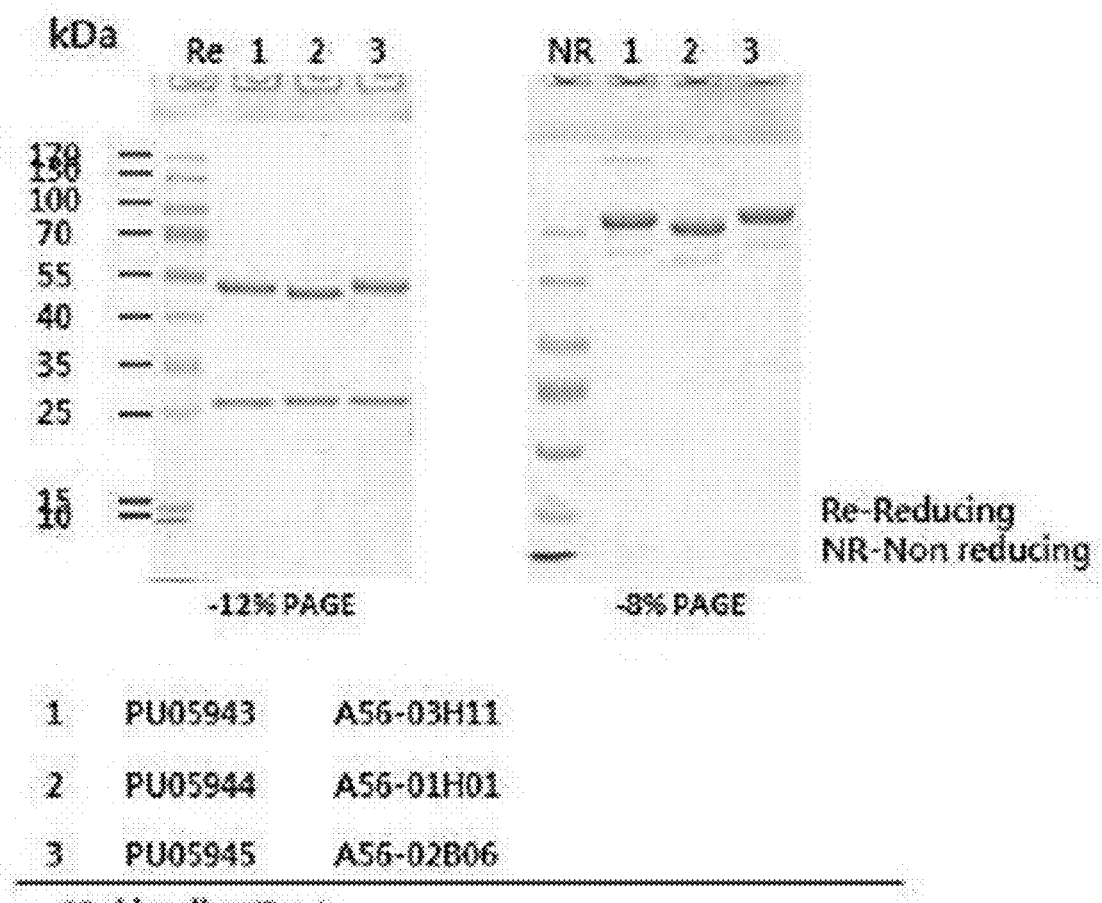
-Purified Protein
Re-Reducing
NR-Non reducing
| 1 | PU05943 | A56-03H11 |
| 2 | PU05944 | A56-01H01 |
| 3 | PU05945 | A56-02B06 |
-20ul loading(3ug)

[FIG. 29]
-Purified Protein
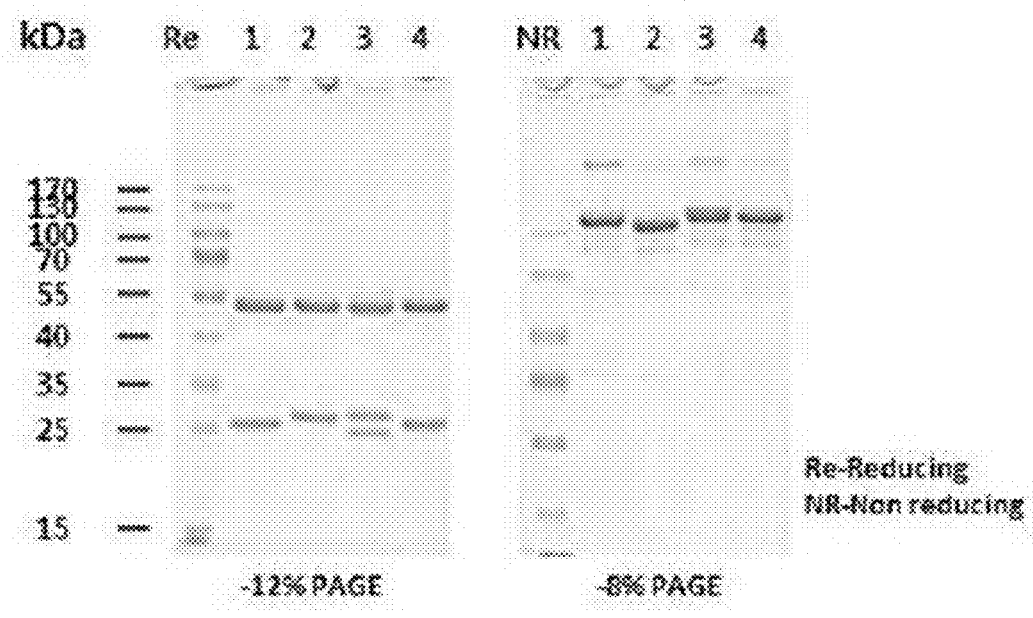
-20ul loading(3ug)

[FIG. 30]
-Purified Protein
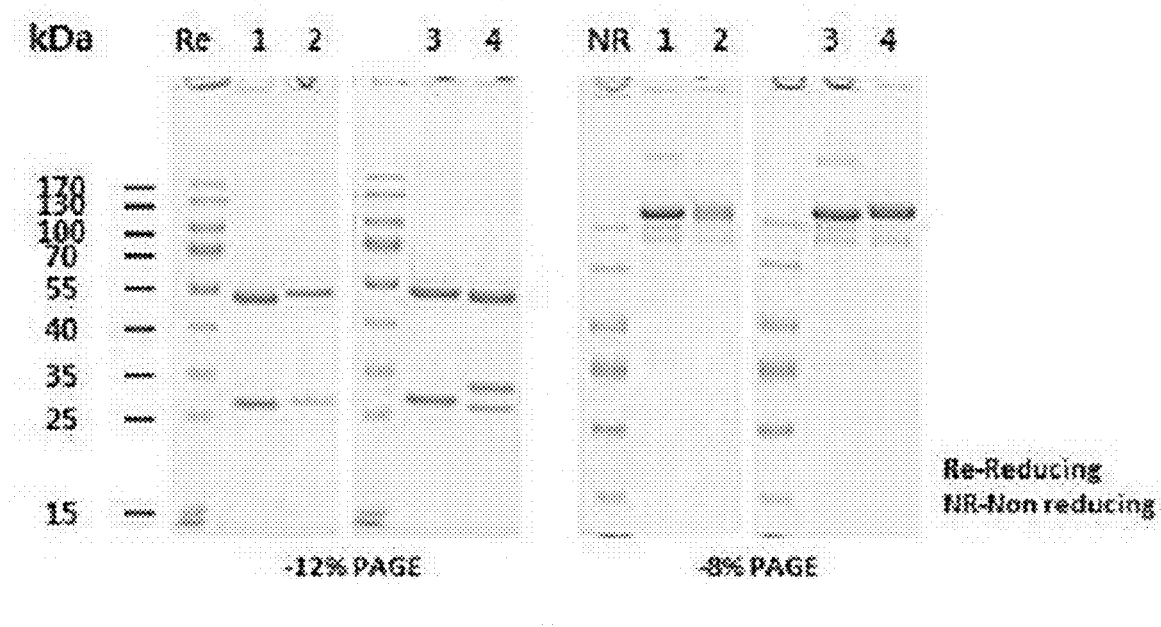
| | | |
|---|---|---|
| 1 | PU05950 | A56-11B10 |
| 2 | PU05951 | A56-11C04 |
| 3 | PU05952 | A56-15A01 |
| 4 | PU05953 | A56-16E02 |
-20ul loading(3ug)

[FIG. 31]
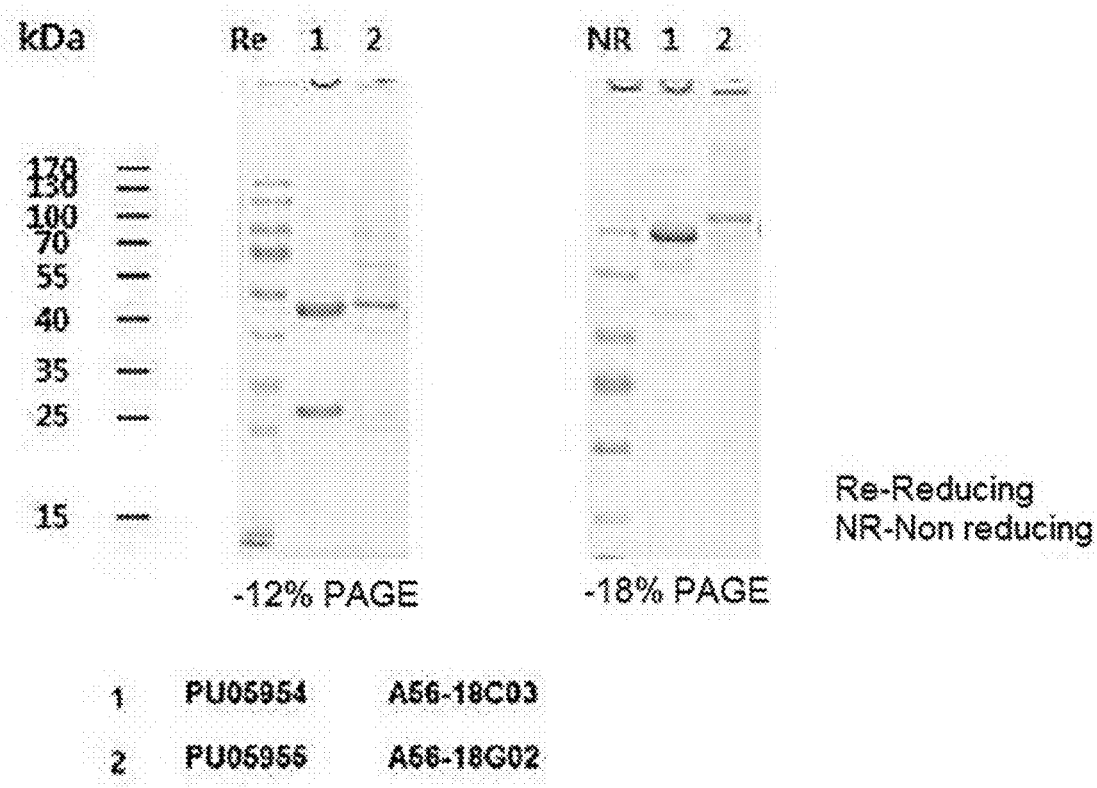

[FIG. 32]
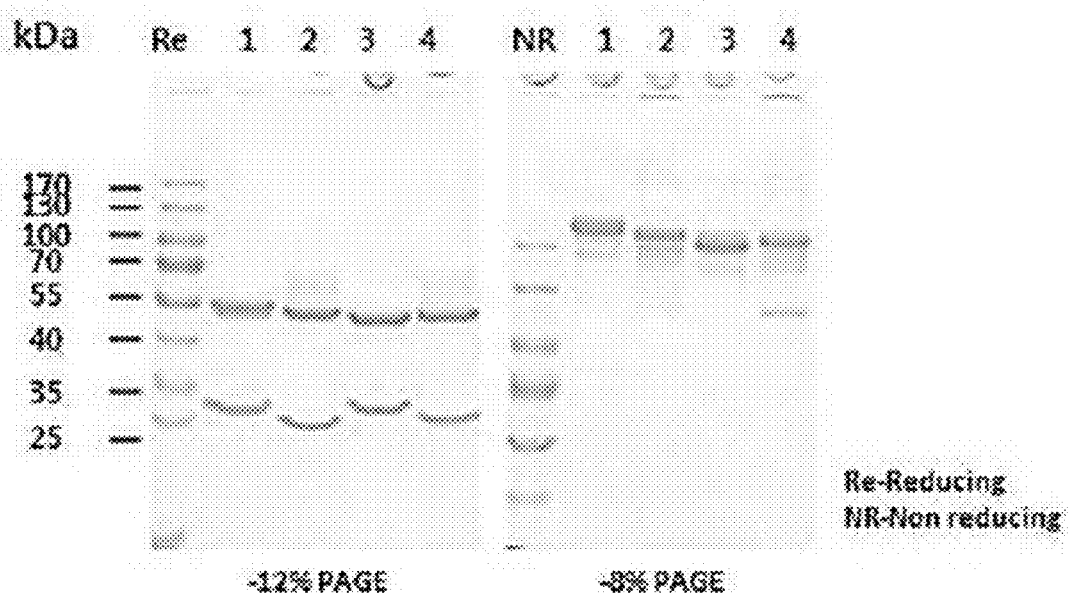
-Purified Protein
| | | |
|---|---|---|
| 1 | PU06956 | A66-20A05 |
| 2 | PU06957 | A66-20G03 |
| 3 | PU06958 | A66-20G12 |
| 4 | PU06959 | A66-21B10 |
-20ul loading(3ug)

[FIG. 33]
-Purified Protein
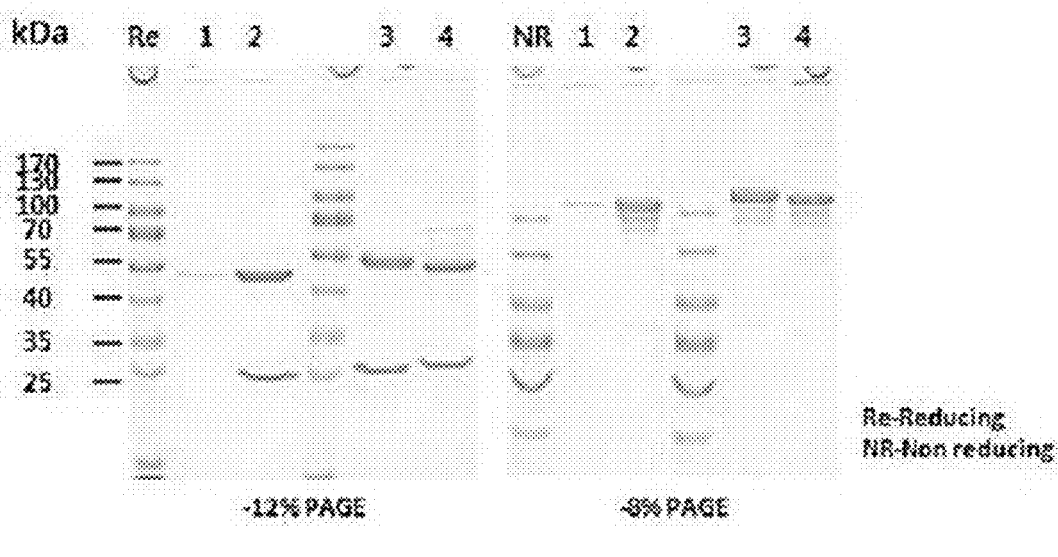
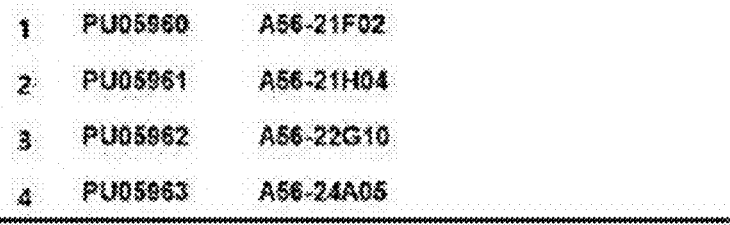
-20ul loading(3ug)

[FIG. 34]
-Purified Protein
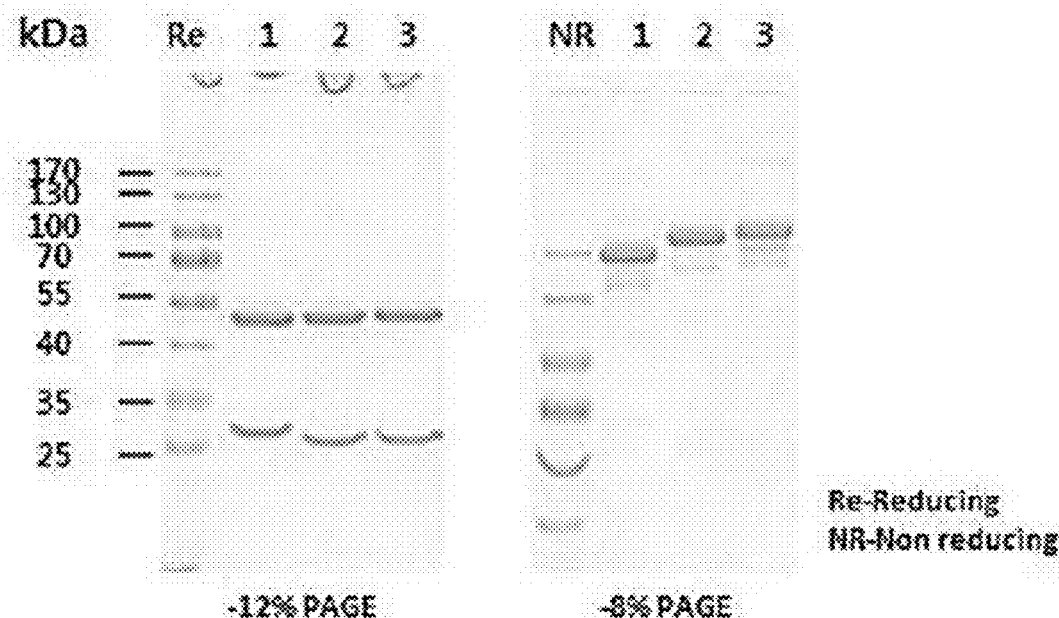
| | | |
|---|---|---|
| 1 | PU05964 | A66-30H01 |
| 2 | PU05965 | A66-32H08 |
| 3 | PU05966 | A66-35A06 |
-20ul loading(3ug)

[FIG. 35]
-Purified Protein
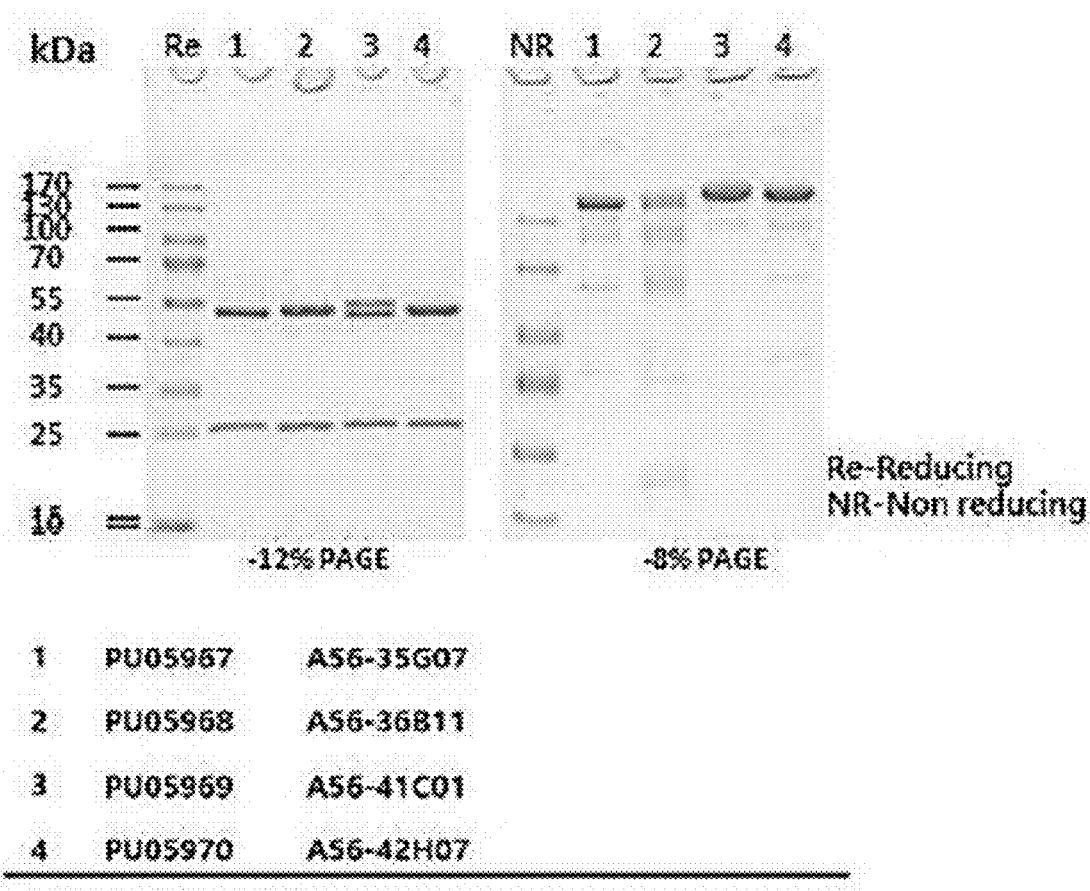
| | | |
|---|---|---|
| 1 | PU05967 | A56-35G07 |
| 2 | PU05968 | A56-36B11 |
| 3 | PU05969 | A56-41C01 |
| 4 | PU05970 | A56-42H07 |
-20ul loading(3ug)

[FIG. 36]
-Purified Protein
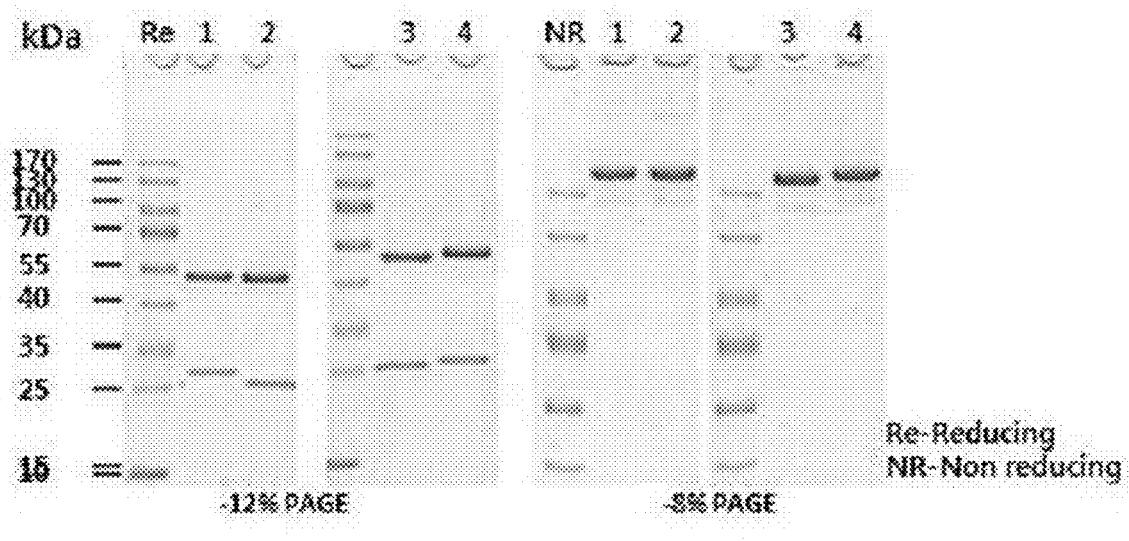
|   |          |            |
|---|----------|------------|
| 1 | PU05971  | A56-44G01  |
| 2 | PU05972  | A56-46A07  |
| 3 | PU05973  | A56-50A09  |
| 4 | PU05974  | A56-50A11  |
-20ul loading(3ug)

[FIG. 37]
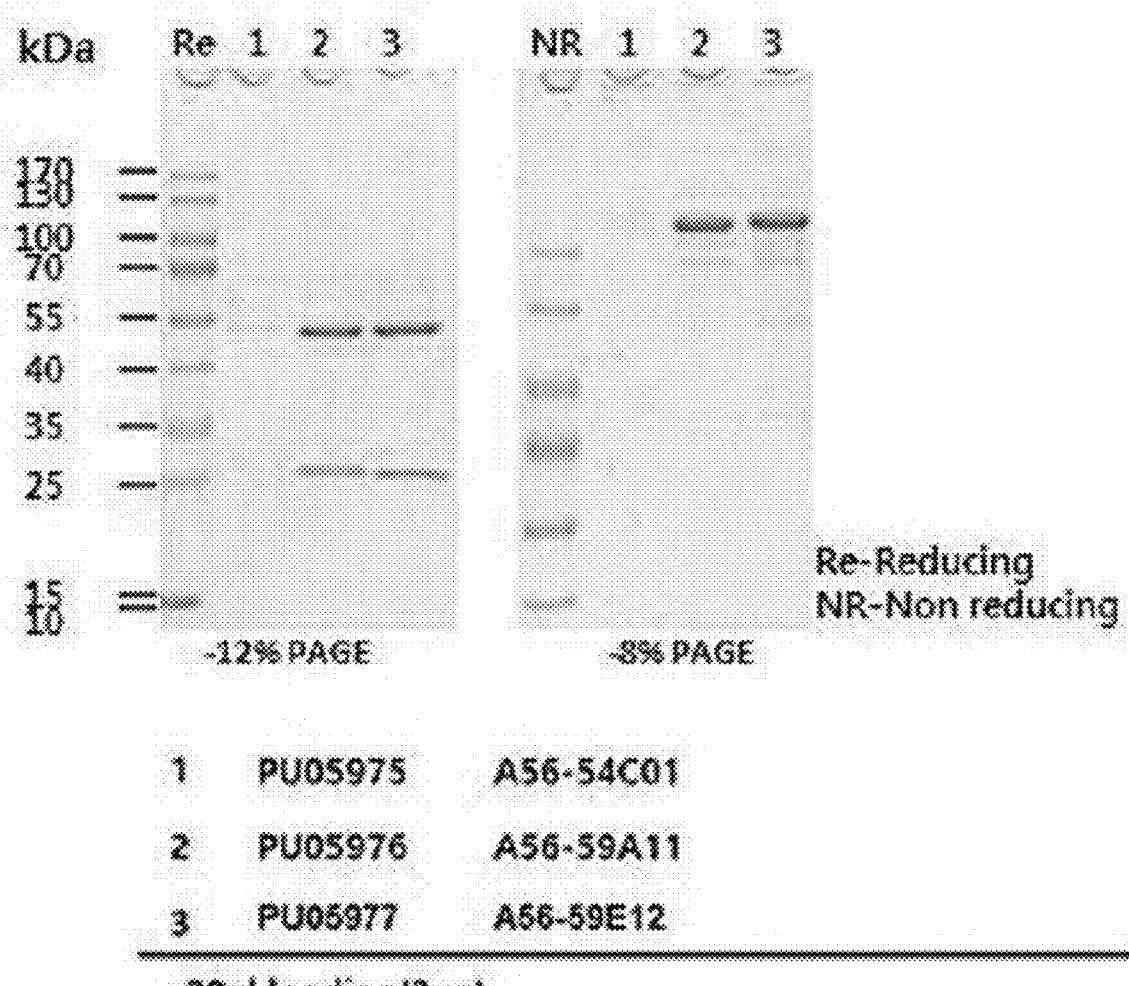
-Purified Protein
| 1 | PU05975 | A56-54C01 |
| 2 | PU05976 | A56-59A11 |
| 3 | PU05977 | A56-59E12 |
-20ul loading(3ug)

[FIG. 38]
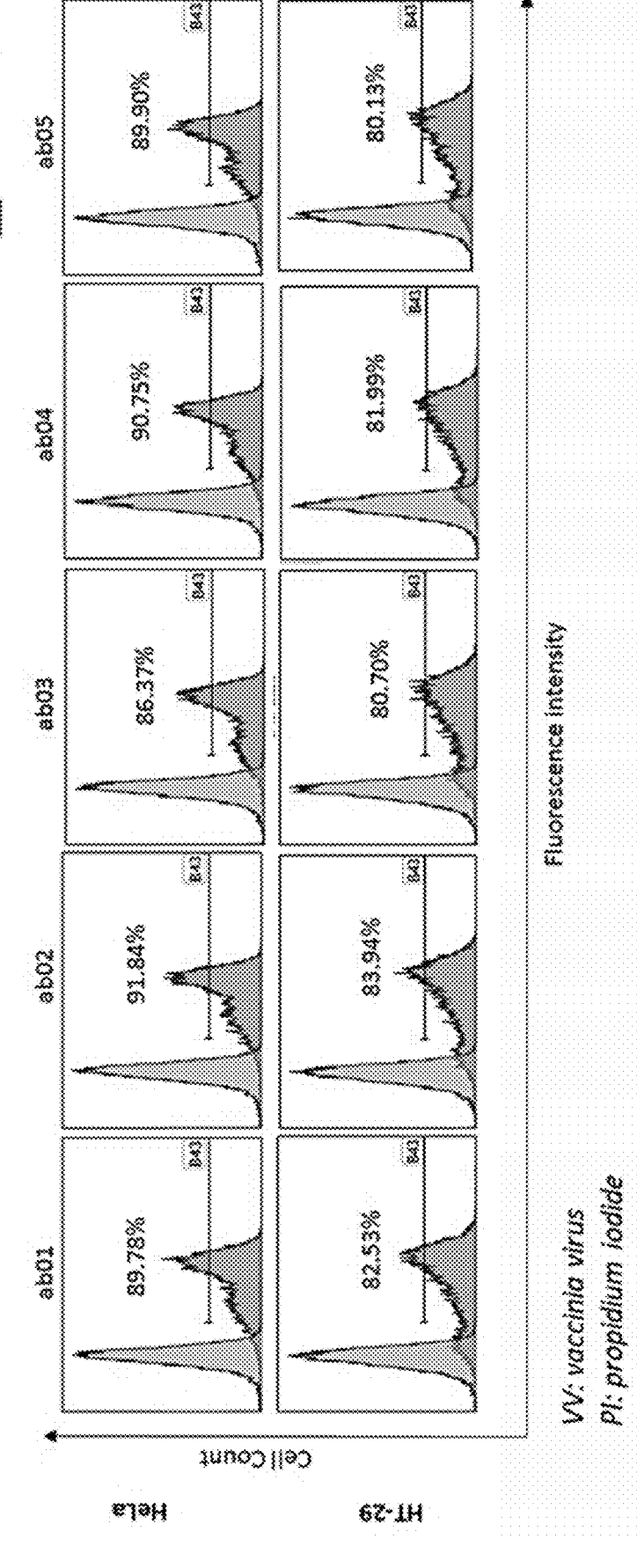

[FIG. 39]
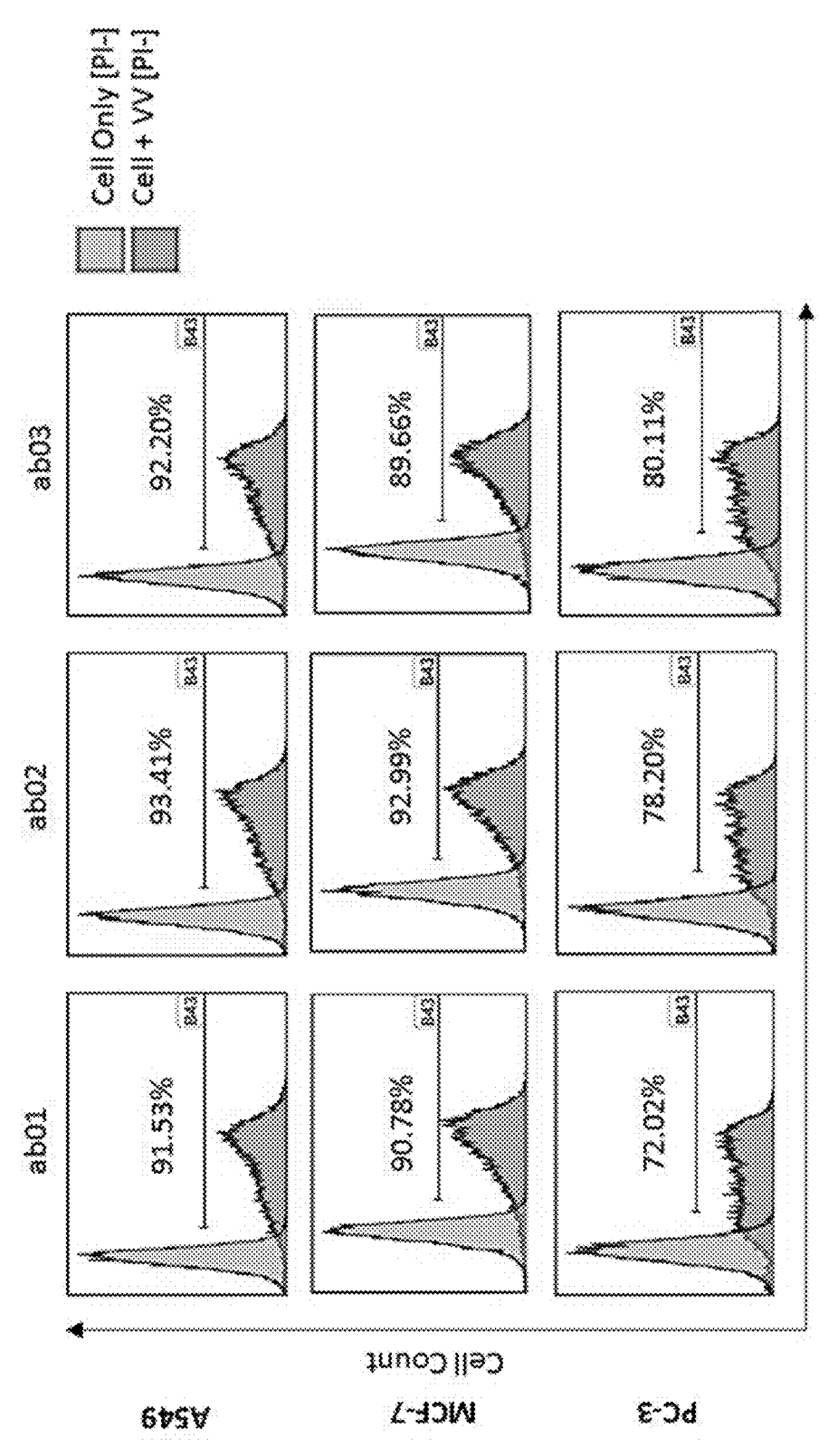

Positive control
(antibodies-online)
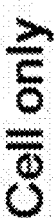
Cell only
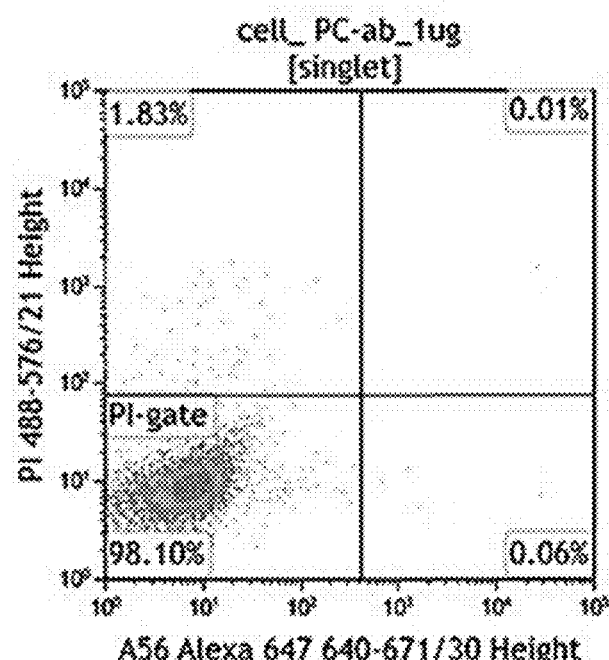
Cell+OV
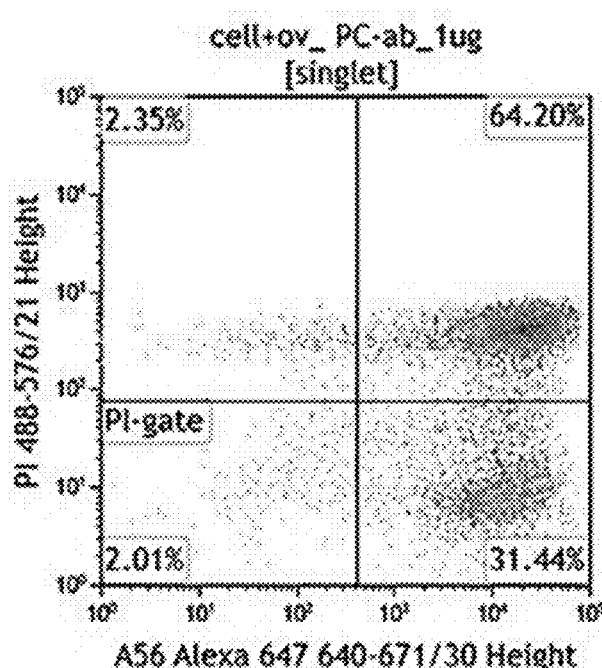
[FIG. 40]

[FIG. 41]
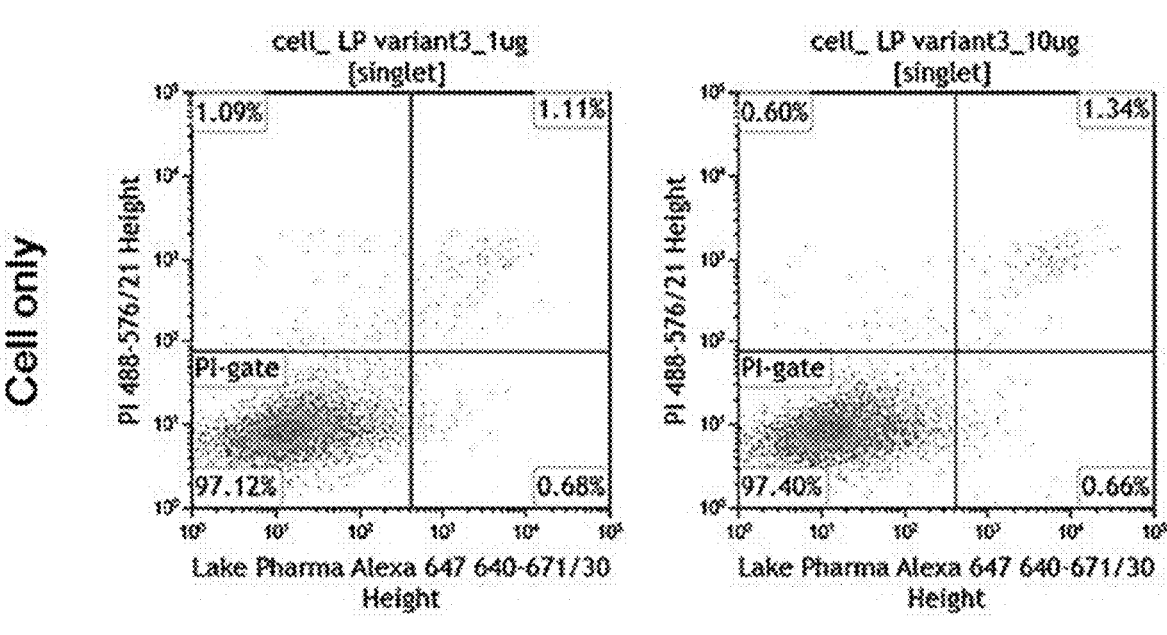
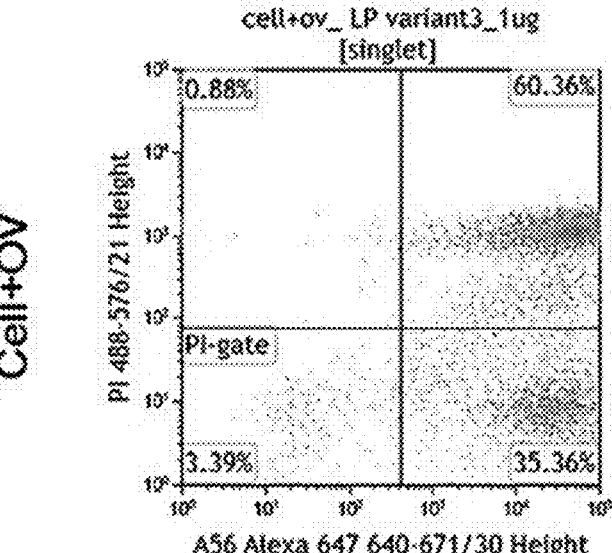

[FIG. 42]
LakePharma variant4
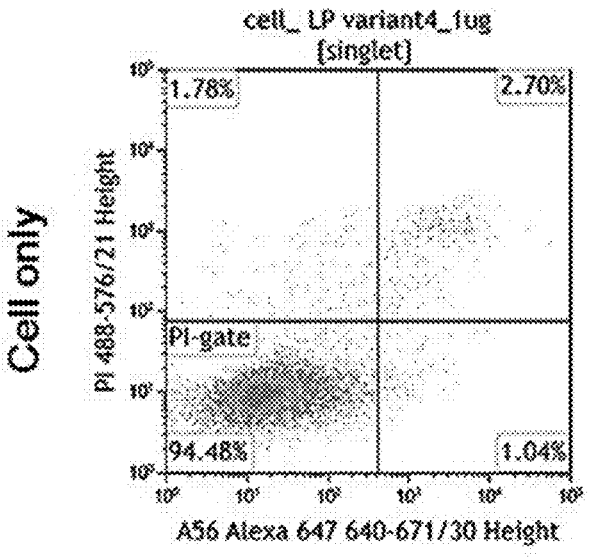
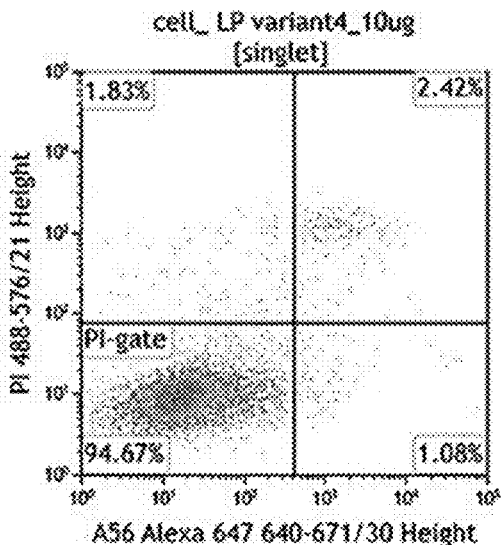
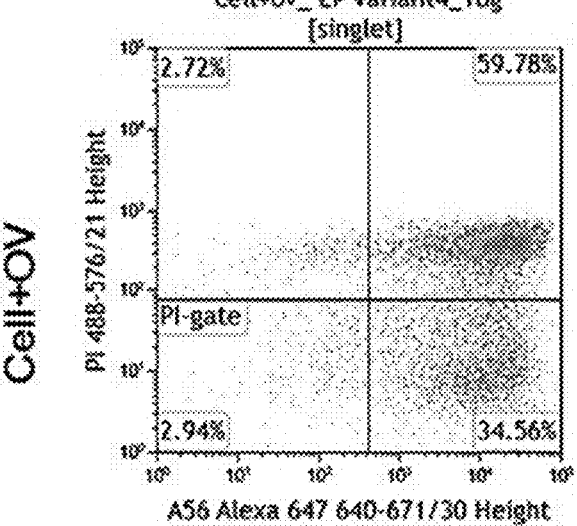
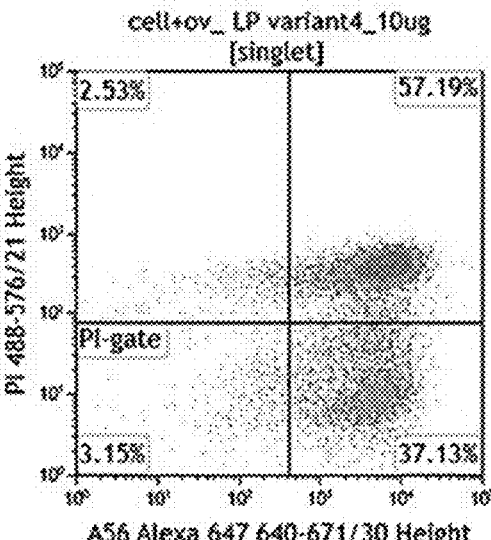

[FIG. 43]
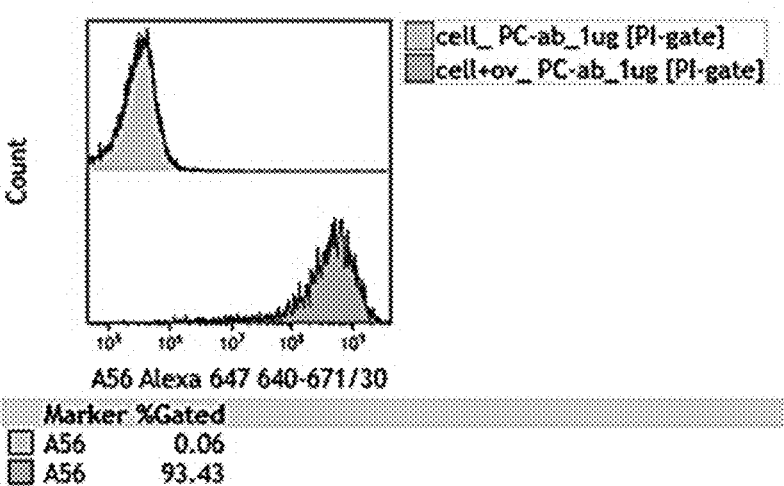
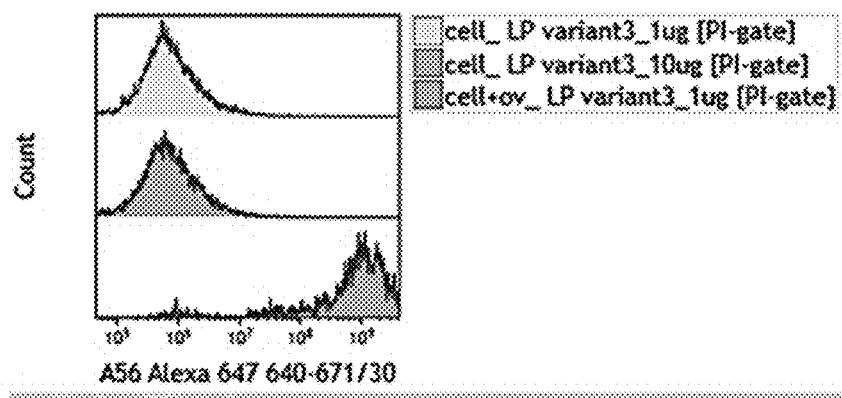
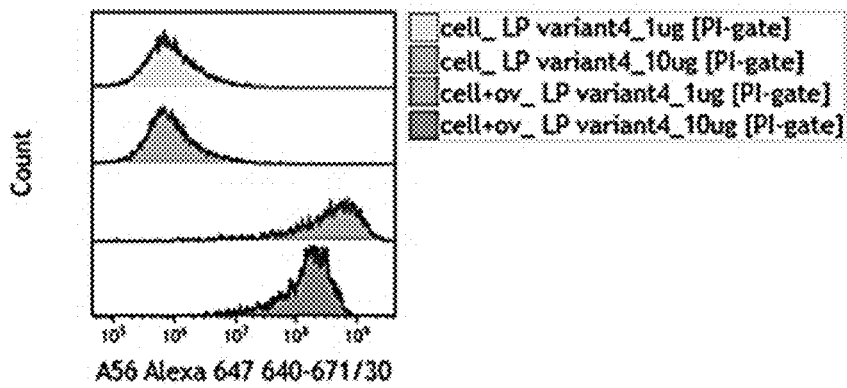

[FIG. 44]
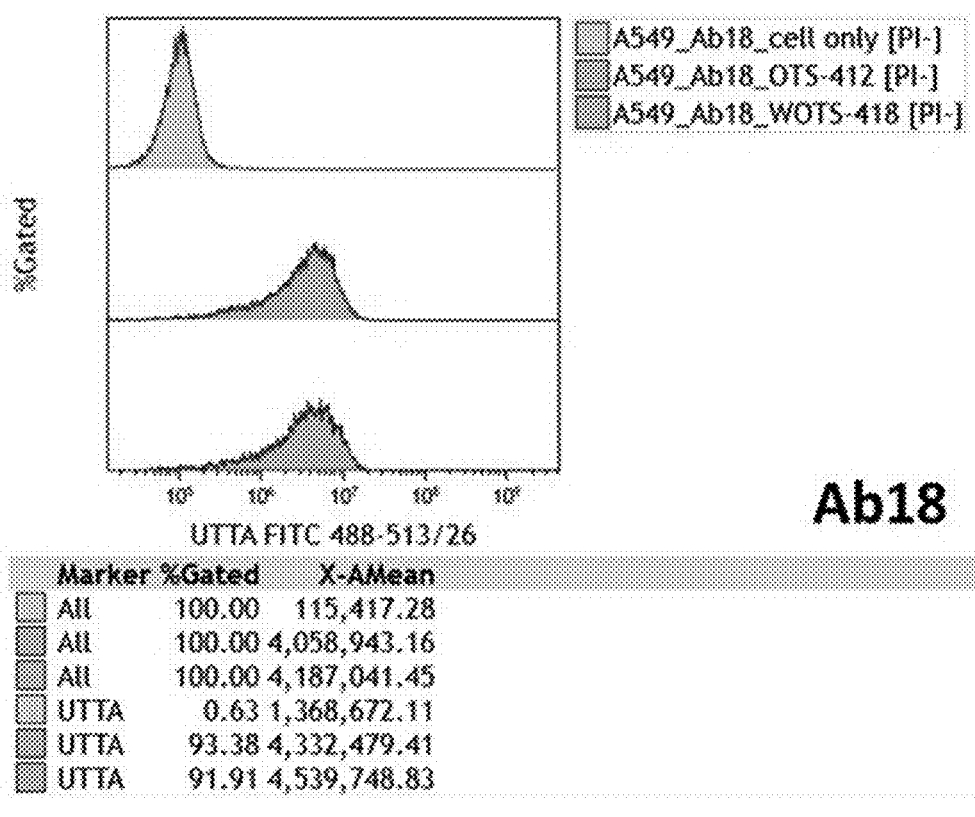
Ab18
| Marker | %Gated | X-AMean |
|--------|--------|---------|
| All | 100.00 | 115,417.28 |
| All | 100.00 | 4,058,943.16 |
| All | 100.00 | 4,187,041.45 |
| UTTA | 0.63 | 1,368,672.11 |
| UTTA | 93.38 | 4,332,479.41 |
| UTTA | 91.91 | 4,539,748.83 |
[FIG. 45]
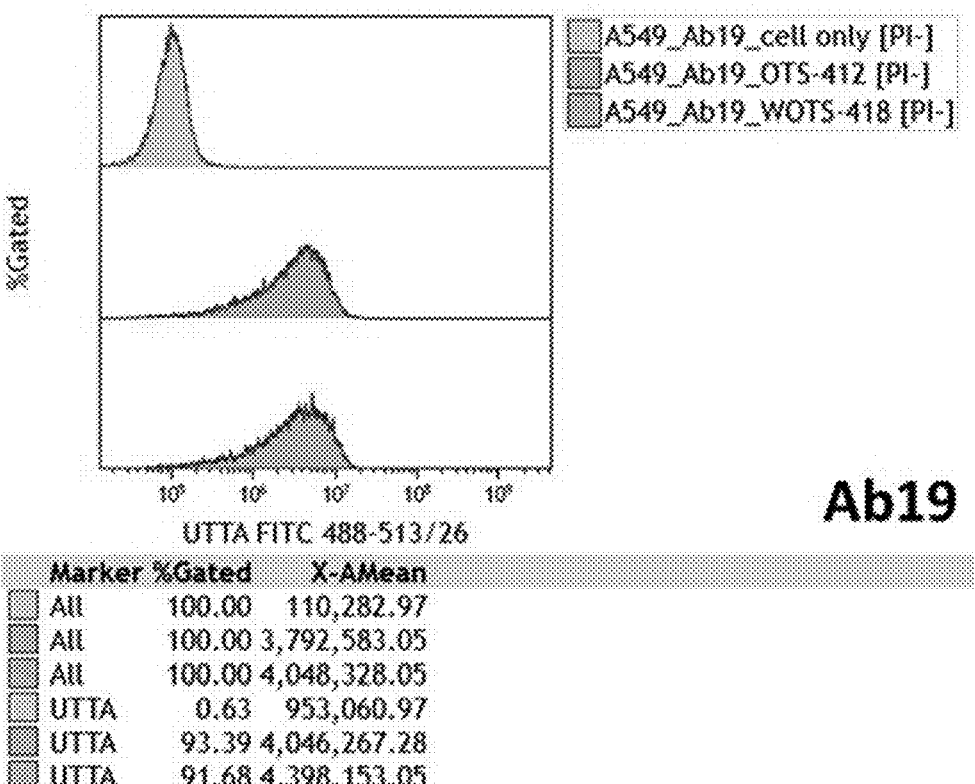
Ab19
| Marker | %Gated | X-AMean |
|--------|--------|---------|
| All | 100.00 | 110,282.97 |
| All | 100.00 | 3,792,583.05 |
| All | 100.00 | 4,048,328.05 |
| UTTA | 0.63 | 953,060.97 |
| UTTA | 93.39 | 4,046,267.28 |
| UTTA | 91.68 | 4,398,153.05 |

[FIG. 46]
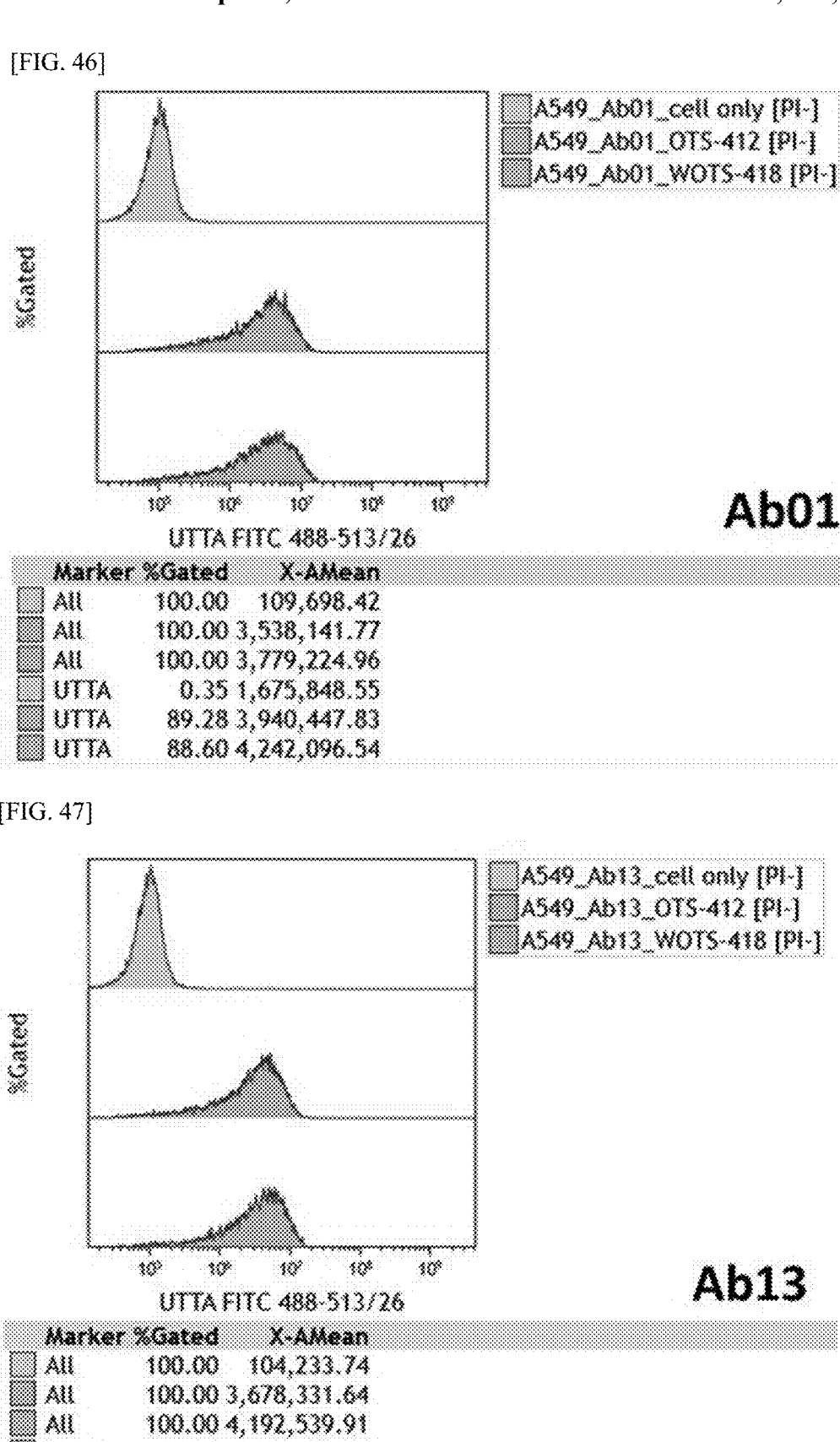

[FIG. 48]
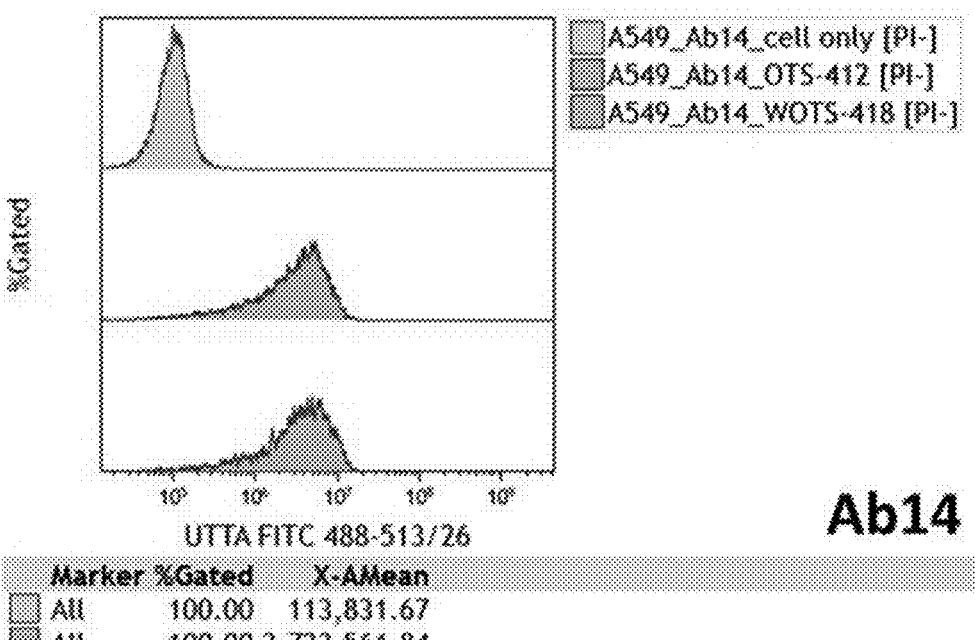
| Marker | %Gated | X-AMean |
|---|---|---|
| All | 100.00 | 113,831.67 |
| All | 100.00 | 3,723,561.84 |
| All | 100.00 | 4,206,088.63 |
| UTTA | 0.59 | 1,267,182.67 |
| UTTA | 91.40 | 4,056,062.57 |
| UTTA | 92.82 | 4,517,490.57 |
[FIG. 49]
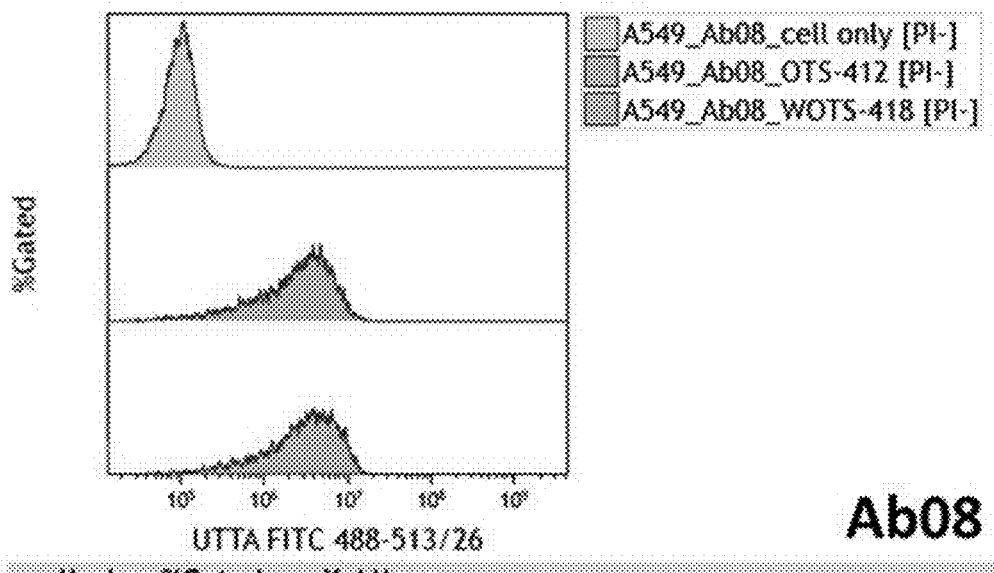
| Marker | %Gated | X-AMean |
|---|---|---|
| All | 100.00 | 107,850.50 |
| All | 100.00 | 3,294,754.96 |
| All | 100.00 | 3,873,356.90 |
| UTTA | 0.27 | 2,261,967.22 |
| UTTA | 90.27 | 3,628,716.04 |
| UTTA | 91.77 | 4,203,948.40 |

[FIG. 50]
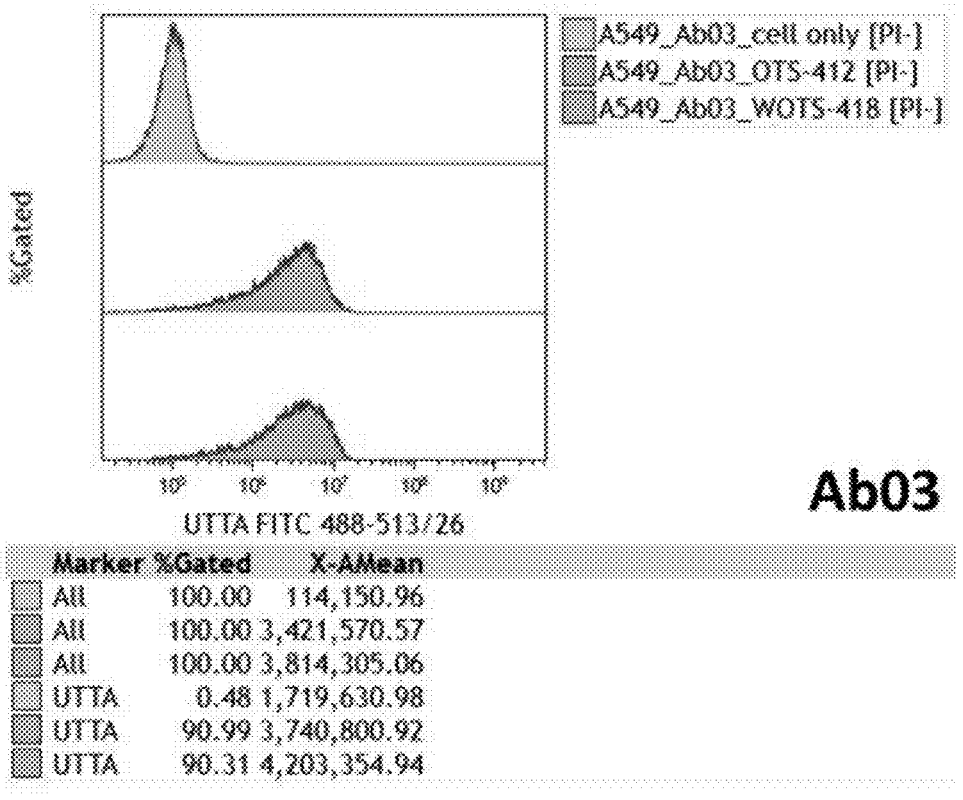
| Marker | %Gated | X-AMean |
|--------|--------|---------|
| All | 100.00 | 114,150.96 |
| All | 100.00 | 3,421,570.57 |
| All | 100.00 | 3,814,305.06 |
| UTTA | 0.48 | 1,719,630.98 |
| UTTA | 90.99 | 3,740,800.92 |
| UTTA | 90.31 | 4,203,354.94 |
[FIG. 51]
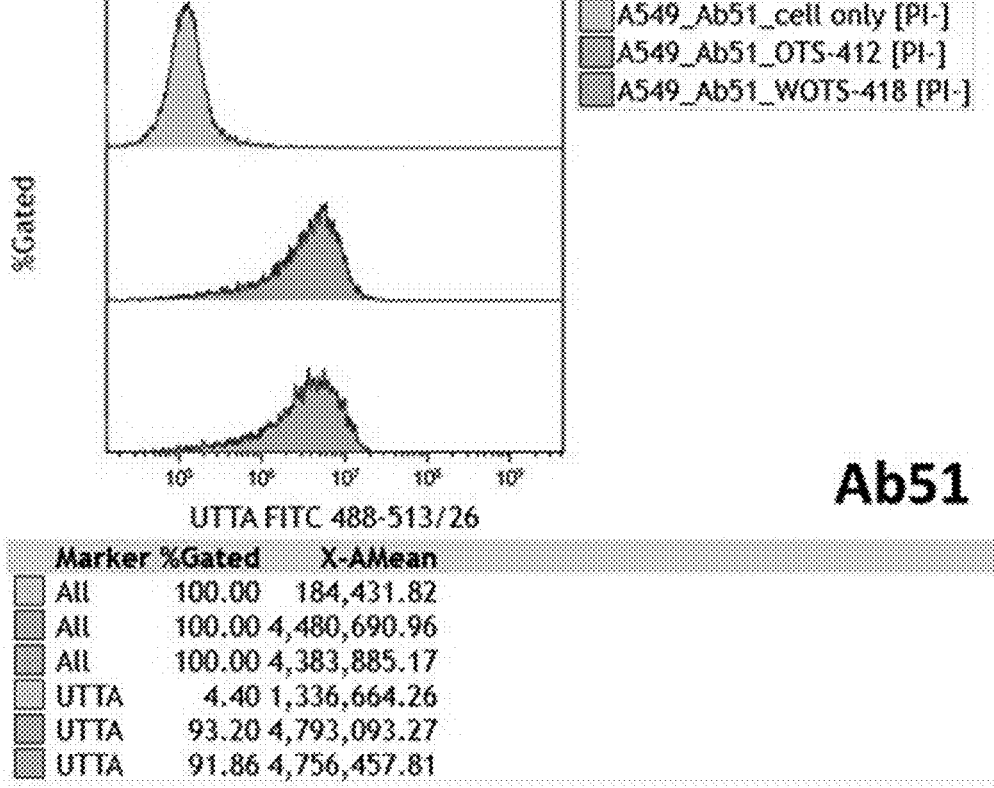
| Marker | %Gated | X-AMean |
|--------|--------|---------|
| All | 100.00 | 184,431.82 |
| All | 100.00 | 4,480,690.96 |
| All | 100.00 | 4,383,885.17 |
| UTTA | 4.40 | 1,336,664.26 |
| UTTA | 93.20 | 4,793,093.27 |
| UTTA | 91.86 | 4,756,457.81 |

[FIG. 52]
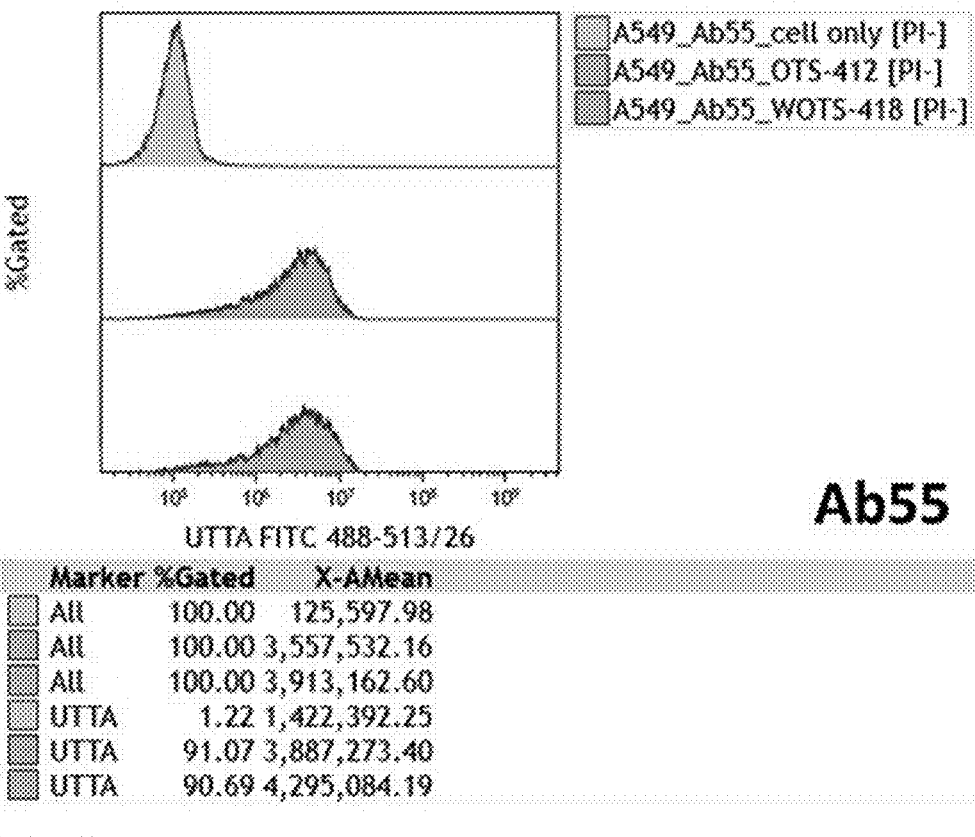
| Marker | %Gated | X-AMean |
|---|---|---|
| All | 100.00 | 125,597.98 |
| All | 100.00 | 3,557,532.16 |
| All | 100.00 | 3,913,162.60 |
| UTTA | 1.22 | 1,422,392.25 |
| UTTA | 91.07 | 3,887,273.40 |
| UTTA | 90.69 | 4,295,084.19 |
[FIG. 53]
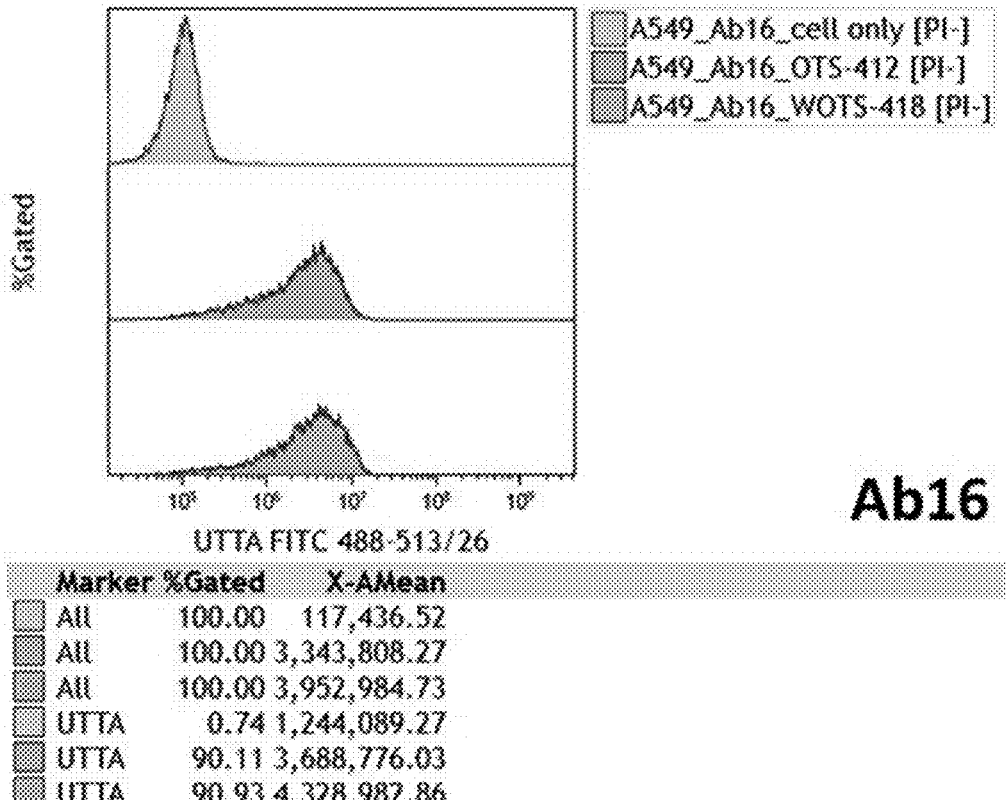
| Marker | %Gated | X-AMean |
|---|---|---|
| All | 100.00 | 117,436.52 |
| All | 100.00 | 3,343,808.27 |
| All | 100.00 | 3,952,984.73 |
| UTTA | 0.74 | 1,244,089.27 |
| UTTA | 90.11 | 3,688,776.03 |
| UTTA | 90.93 | 4,328,982.86 |

[FIG. 54]
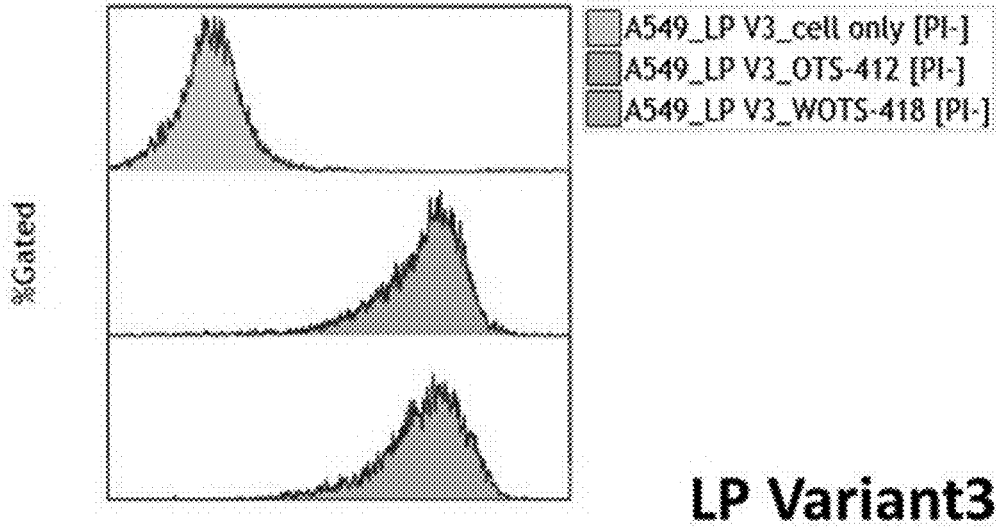
LP Variant3
| Marker | %Gated | X-AMean |
|--------|--------|---------------|
| All | 100.00 | 16,487,942.24 |
| All | 100.00 | 162,846,057.72 |
| All | 100.00 | 177,280,094.79 |
| UTTA | 1.53 | 1,054,008,503.34 |
| UTTA | 94.71 | 171,707,469.19 |
| UTTA | 93.83 | 188,625,930.16 |
[FIG. 55]
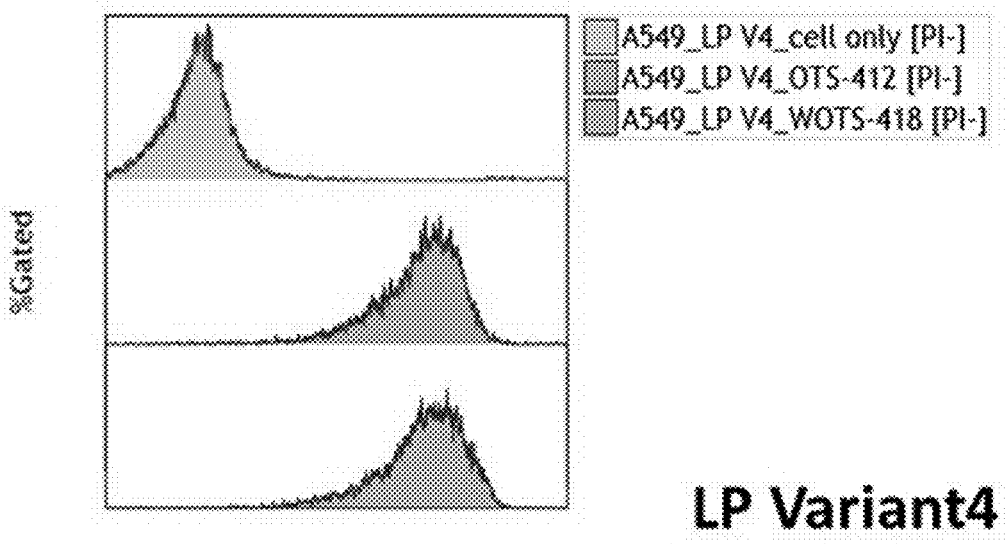
LP Variant4
| Marker | %Gated | X-AMean |
|--------|--------|---------------|
| All | 100.00 | 26,292,486.75 |
| All | 100.00 | 164,629,951.77 |
| All | 100.00 | 182,723,508.83 |
| UTTA | 1.97 | 1,318,852,181.71 |
| UTTA | 94.83 | 173,372,283.93 |
| UTTA | 94.19 | 193,703,387.35 |

[FIG. 56]
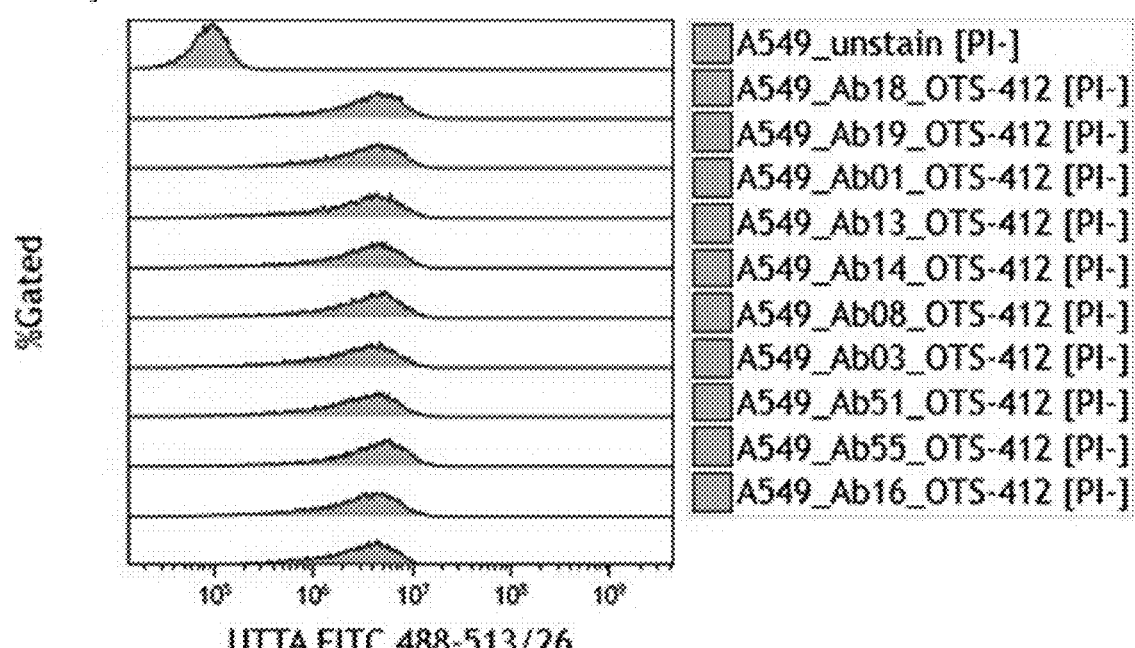
| Marker | %Gated | X-AMean |
|--------|--------|---------|
| All | 100.00 | 94,680.72 |
| All | 100.00 | 4,058,943.16 |
| All | 100.00 | 3,792,583.05 |
| All | 100.00 | 3,538,141.77 |
| All | 100.00 | 3,678,331.64 |
| All | 100.00 | 3,723,561.84 |
| All | 100.00 | 3,294,754.96 |
| All | 100.00 | 3,421,570.57 |
| All | 100.00 | 4,480,690.96 |
| All | 100.00 | 3,557,532.16 |
| All | 100.00 | 3,343,808.27 |
| UTTA | 0.30 | 1,246,060.44 |
| UTTA | 95.65 | 4,237,150.69 |
| UTTA | 95.83 | 3,951,662.69 |
| UTTA | 92.18 | 3,826,554.15 |
| UTTA | 93.18 | 3,938,259.65 |
| UTTA | 93.82 | 3,959,893.08 |
| UTTA | 93.25 | 3,523,234.51 |
| UTTA | 93.81 | 3,638,321.54 |
| UTTA | 95.31 | 4,694,460.90 |
| UTTA | 93.67 | 3,788,317.07 |
| UTTA | 93.16 | 3,578,679.08 |
OTS-412

[FIG. 57]
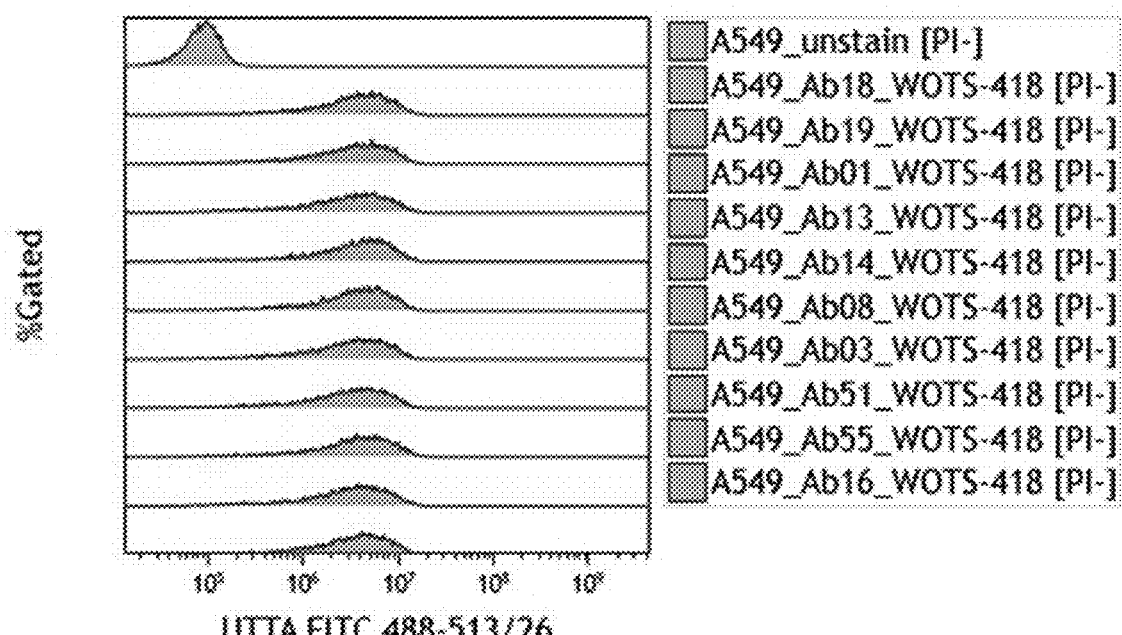
| Marker | %Gated | X-AMean |
|---|---|---|
| All | 100.00 | 94,680.72 |
| All | 100.00 | 4,187,041.45 |
| All | 100.00 | 4,048,328.05 |
| All | 100.00 | 3,779,224.96 |
| All | 100.00 | 4,192,539.91 |
| All | 100.00 | 4,206,088.63 |
| All | 100.00 | 3,873,356.90 |
| All | 100.00 | 3,814,305.06 |
| All | 100.00 | 4,383,885.17 |
| All | 100.00 | 3,913,162.60 |
| All | 100.00 | 3,952,984.73 |
| UTTA | 0.30 | 1,246,060.44 |
| UTTA | 94.05 | 4,444,133.90 |
| UTTA | 94.10 | 4,293,457.96 |
| UTTA | 91.30 | 4,126,413.57 |
| UTTA | 93.90 | 4,456,875.39 |
| UTTA | 94.56 | 4,440,283.71 |
| UTTA | 94.22 | 4,102,930.86 |
| UTTA | 93.01 | 4,090,754.47 |
| UTTA | 93.98 | 4,656,312.82 |
| UTTA | 93.10 | 4,192,458.74 |
| UTTA | 93.27 | 4,228,253.51 |
WOTS-418

[FIG. 58]
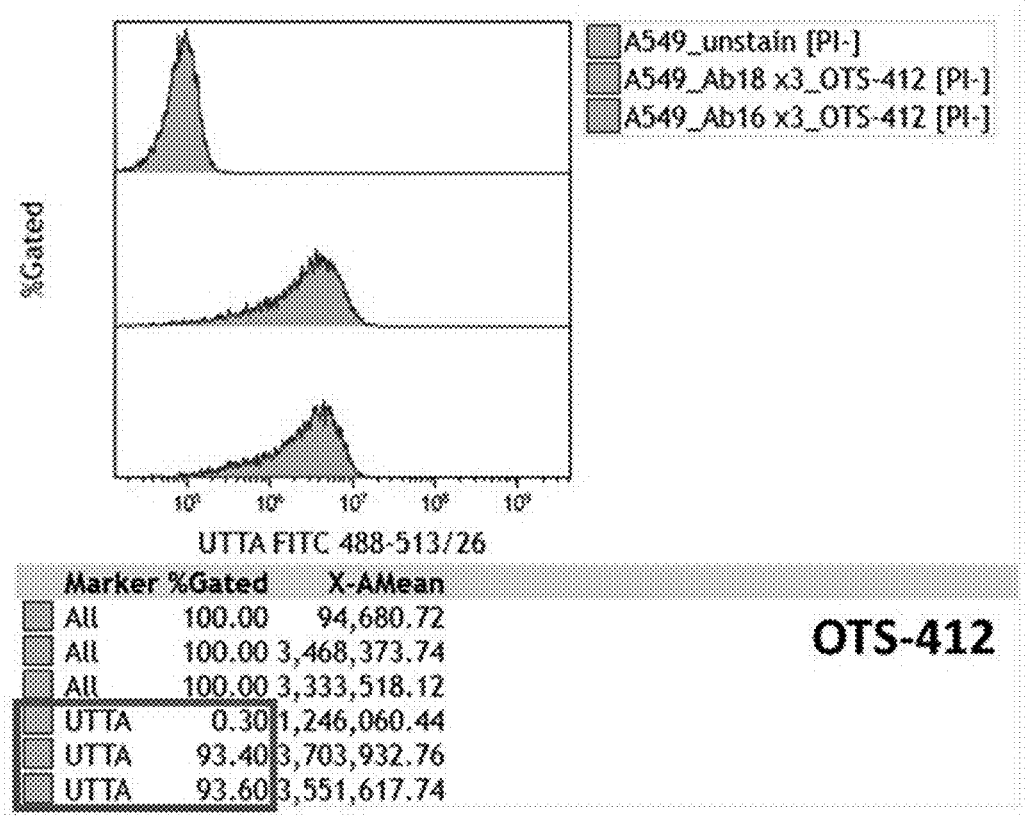
[FIG. 59]
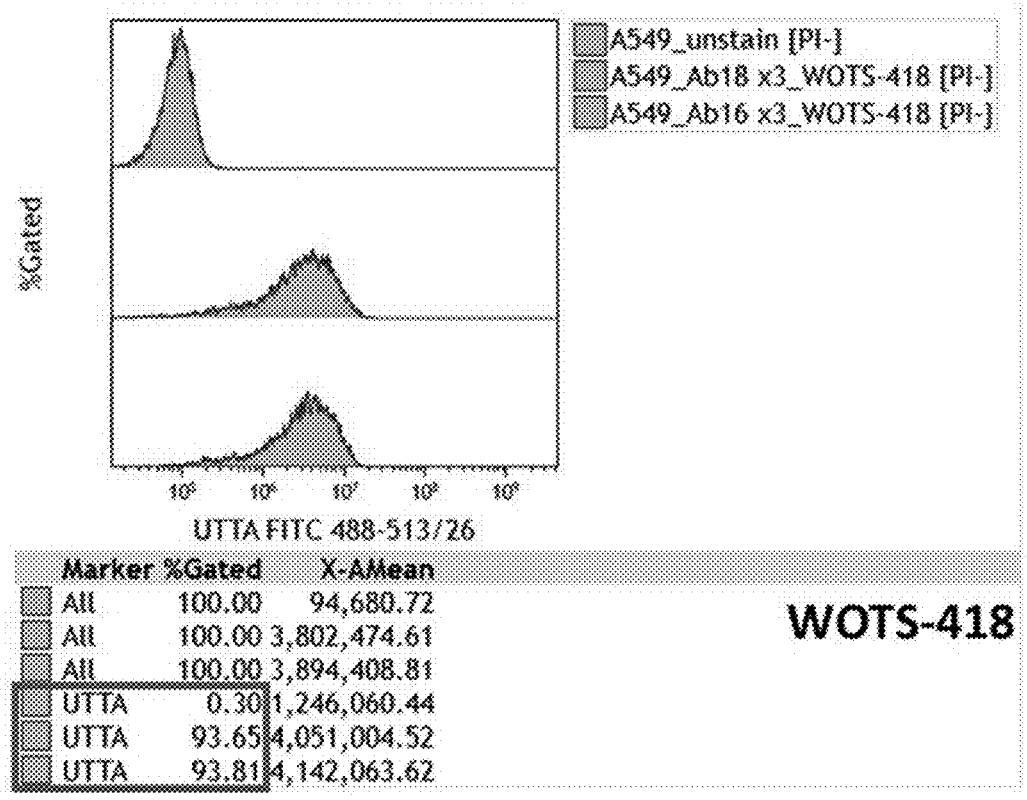

[FIG. 60]
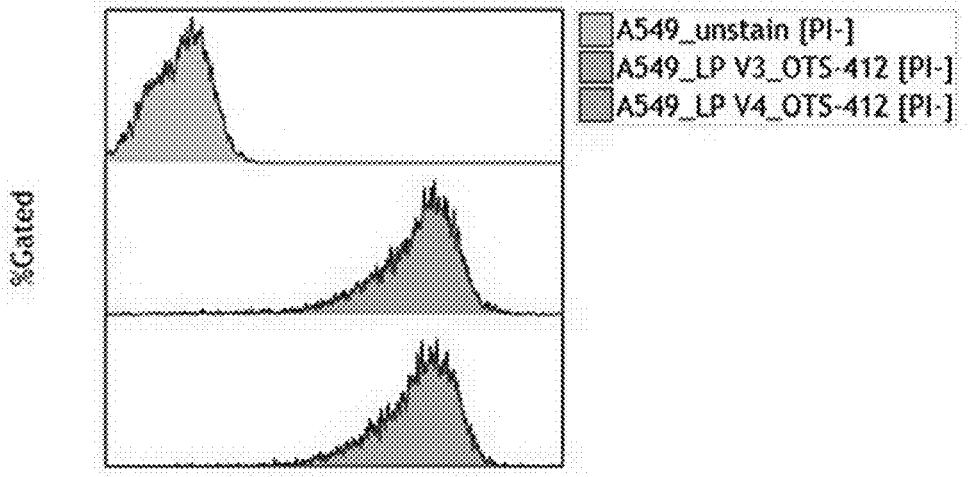
OTS-412
[FIG. 61]
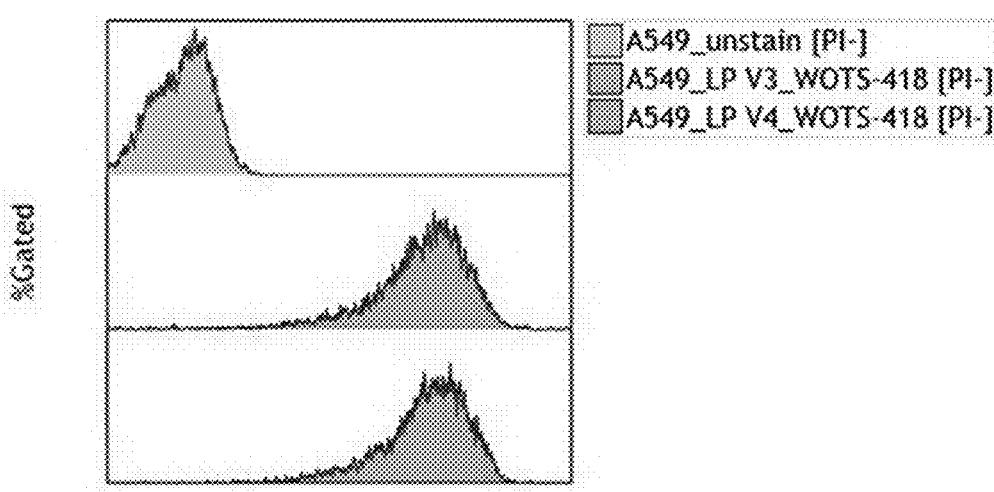
WOTS-418

[FIG. 62]
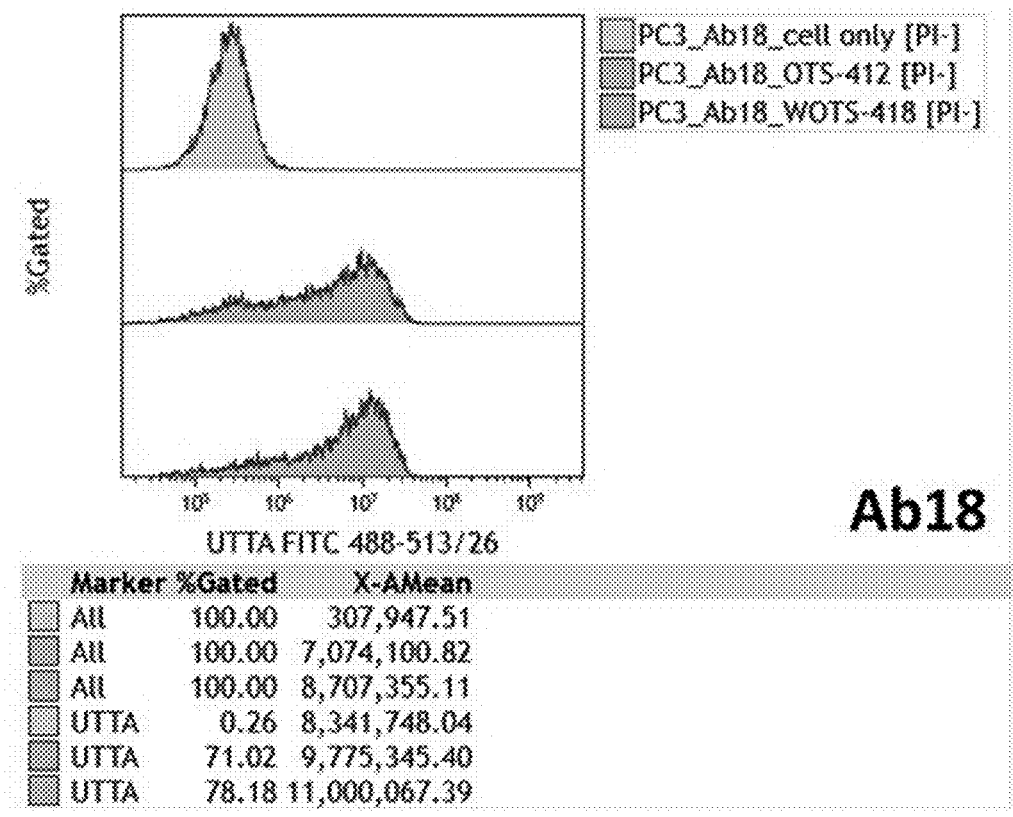
[FIG. 63]
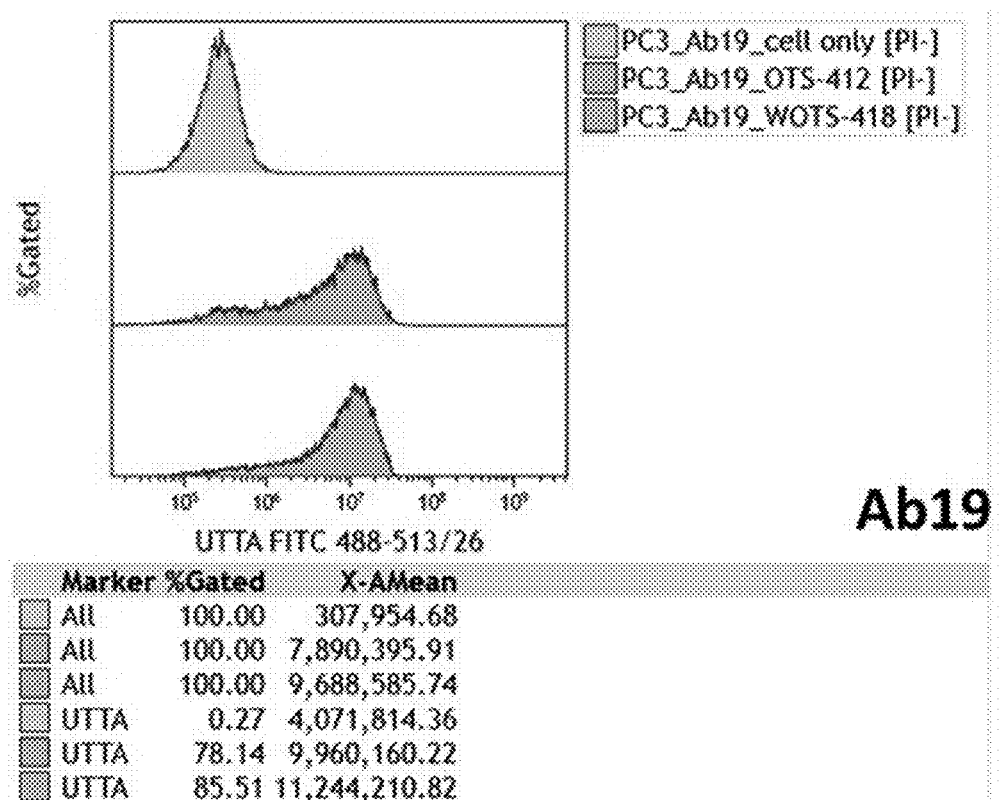

[FIG. 64]
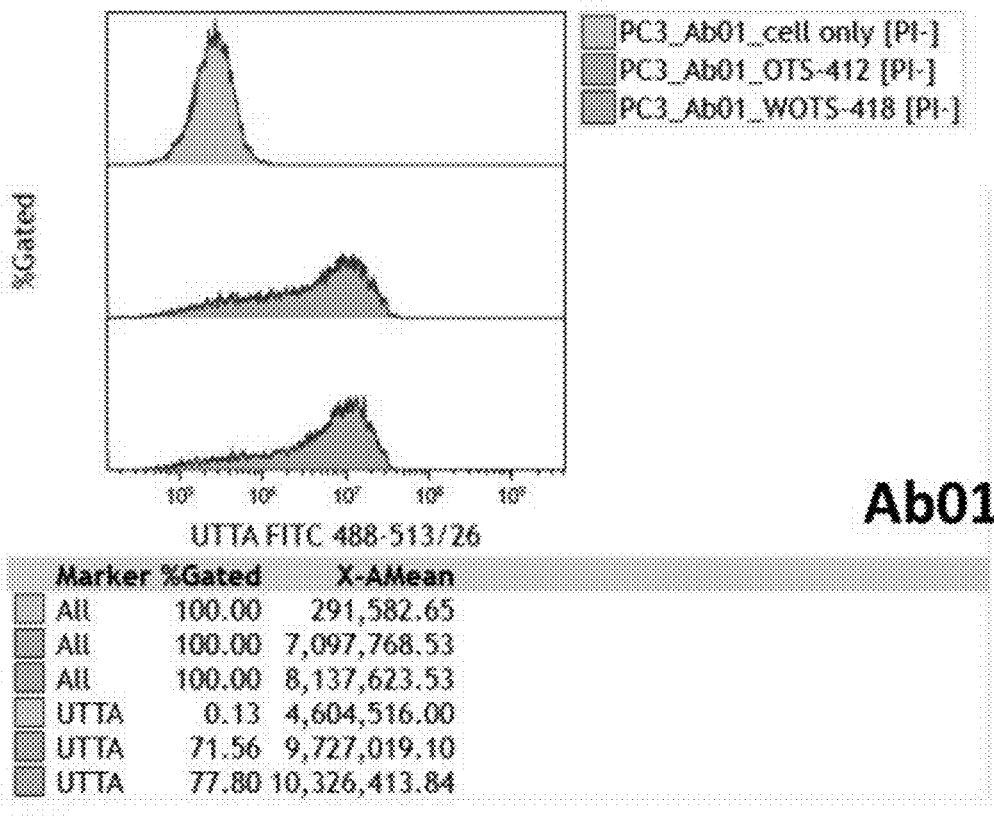
[FIG. 65]
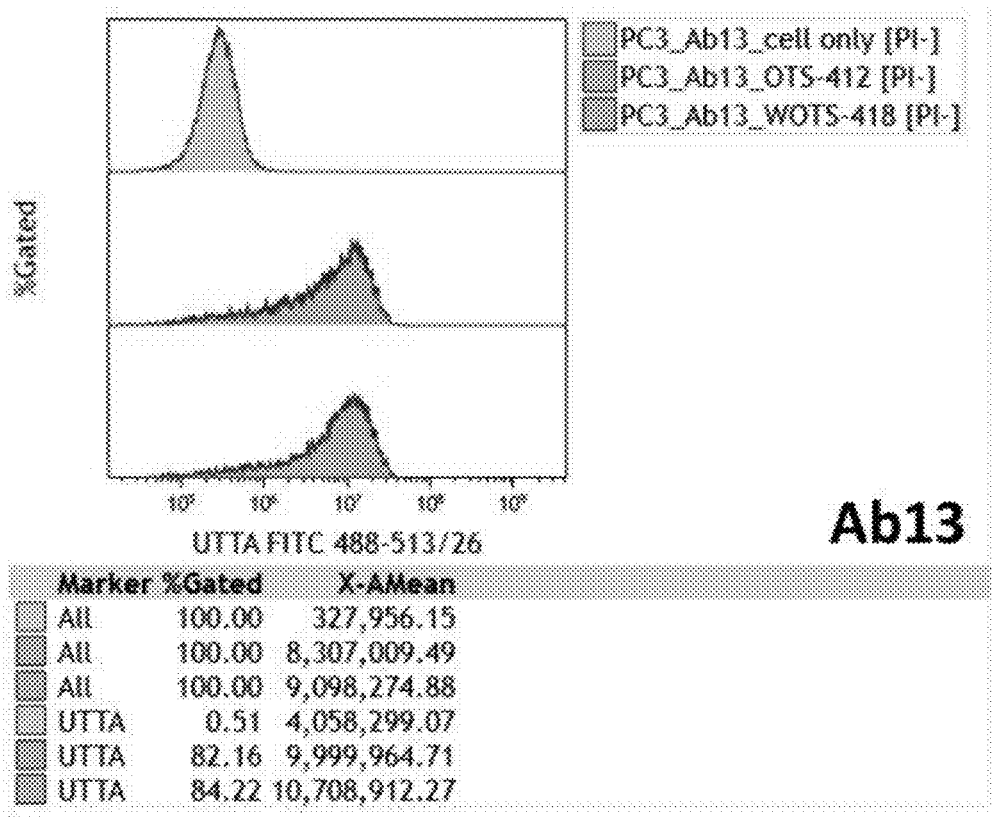

[FIG. 66]
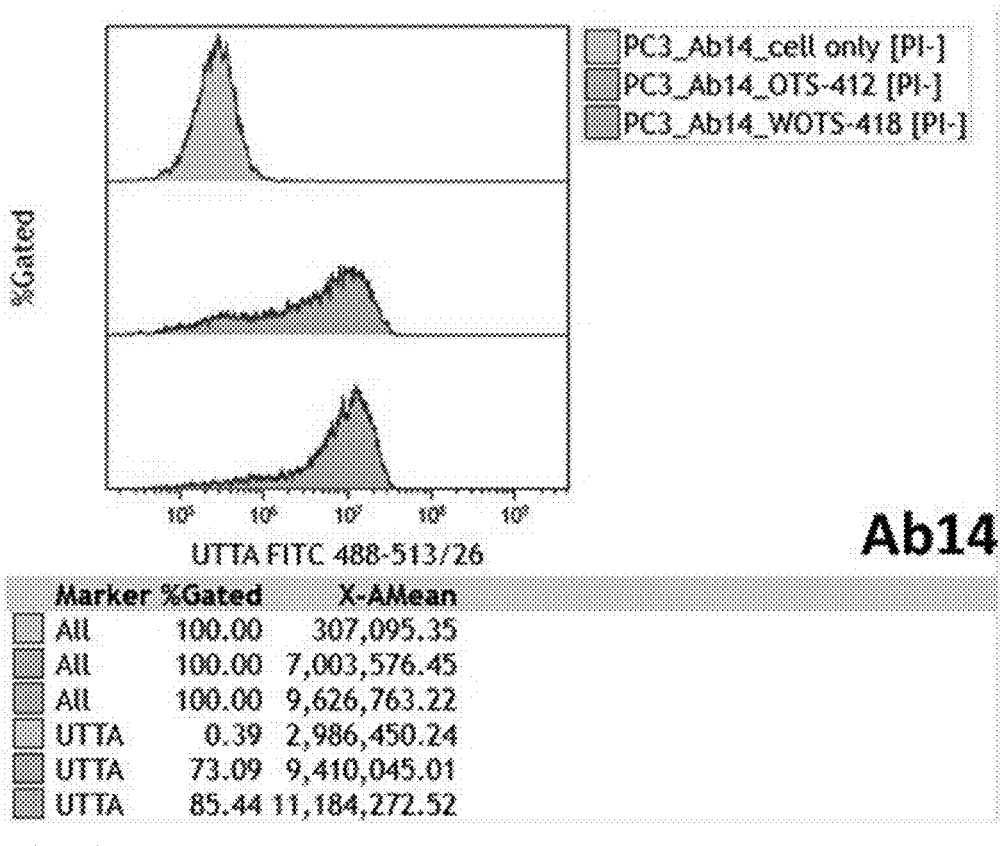
| Marker | %Gated | X-AMean |
|--------|--------|---------|
| All | 100.00 | 307,095.35 |
| All | 100.00 | 7,003,576.45 |
| All | 100.00 | 9,626,763.22 |
| UTTA | 0.39 | 2,986,450.24 |
| UTTA | 73.09 | 9,410,045.01 |
| UTTA | 85.44 | 11,184,272.52 |
[FIG. 67]
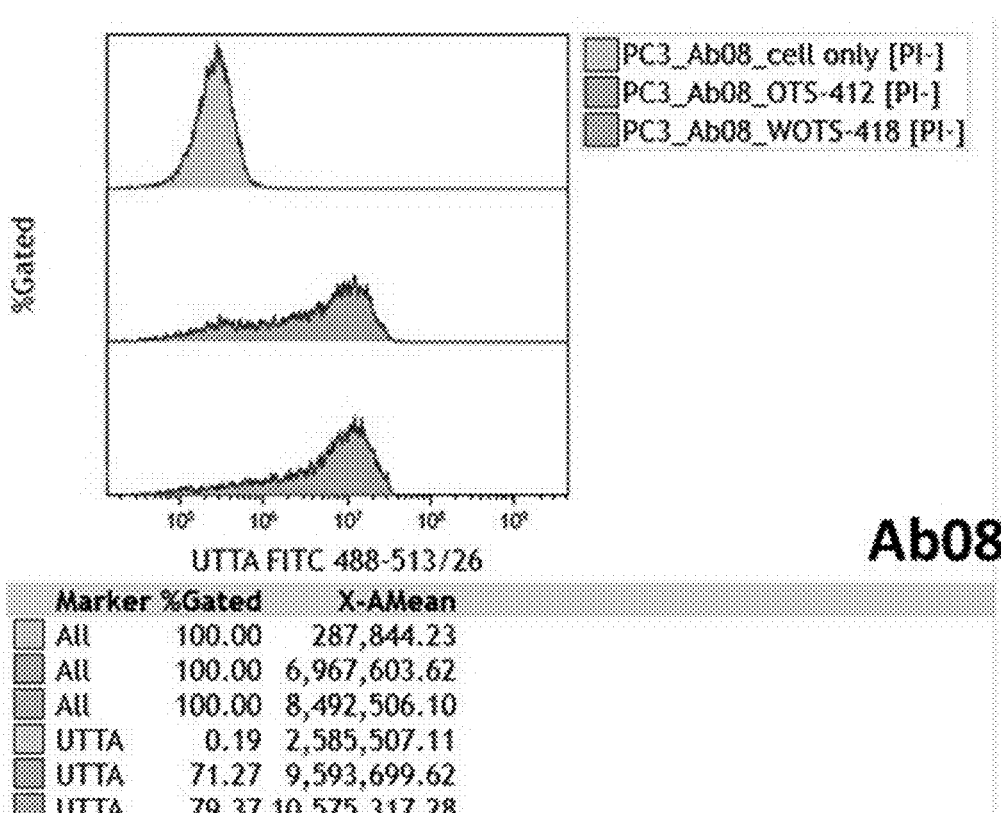
| Marker | %Gated | X-AMean |
|--------|--------|---------|
| All | 100.00 | 287,844.23 |
| All | 100.00 | 6,967,603.62 |
| All | 100.00 | 8,492,506.10 |
| UTTA | 0.19 | 2,585,507.11 |
| UTTA | 71.27 | 9,593,699.62 |
| UTTA | 79.37 | 10,575,317.28 |

[FIG. 68]
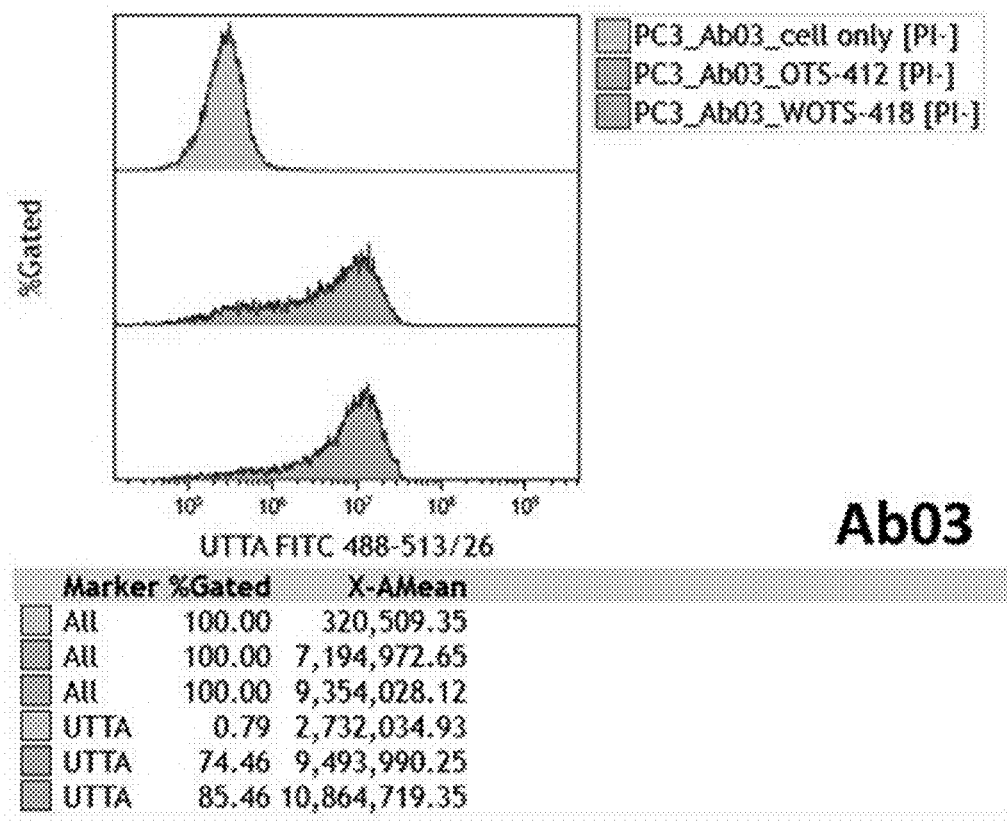
| Marker | %Gated | X-AMean |
|--------|--------|---------|
| All | 100.00 | 320,509.35 |
| All | 100.00 | 7,194,972.65 |
| All | 100.00 | 9,354,028.12 |
| UTTA | 0.79 | 2,732,034.93 |
| UTTA | 74.46 | 9,493,990.25 |
| UTTA | 85.46 | 10,864,719.35 |
[FIG. 69]
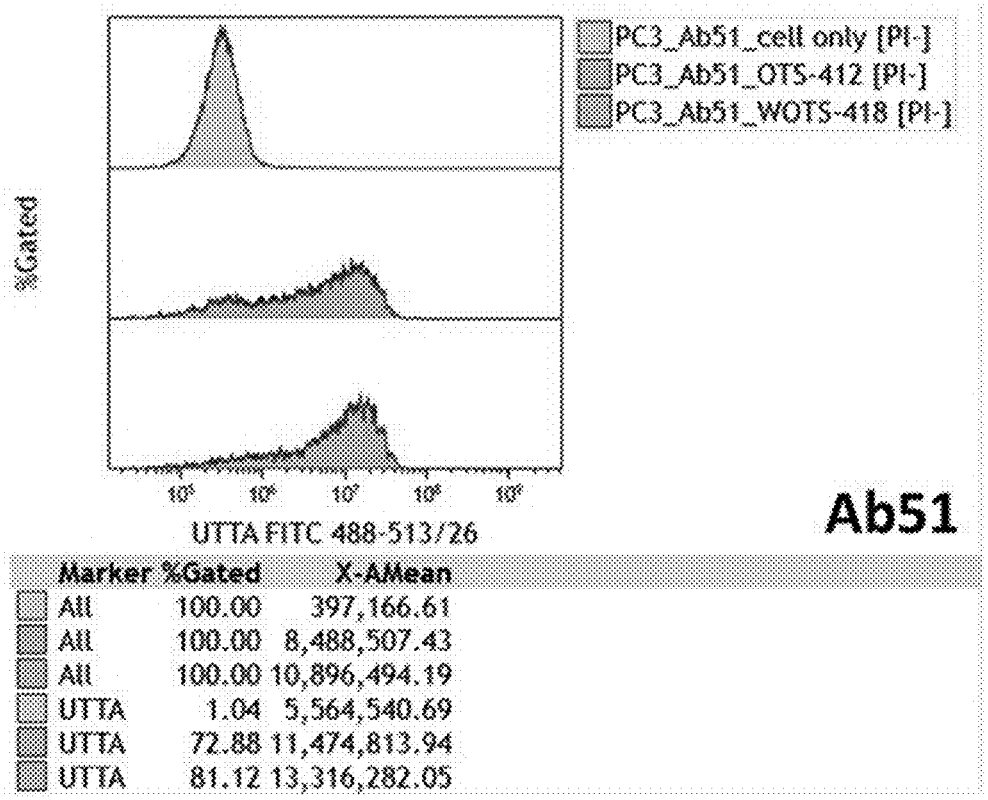
| Marker | %Gated | X-AMean |
|--------|--------|---------|
| All | 100.00 | 397,166.61 |
| All | 100.00 | 8,488,507.43 |
| All | 100.00 | 10,896,494.19 |
| UTTA | 1.04 | 5,564,540.69 |
| UTTA | 72.88 | 11,474,813.94 |
| UTTA | 81.12 | 13,316,282.05 |

[FIG. 70]
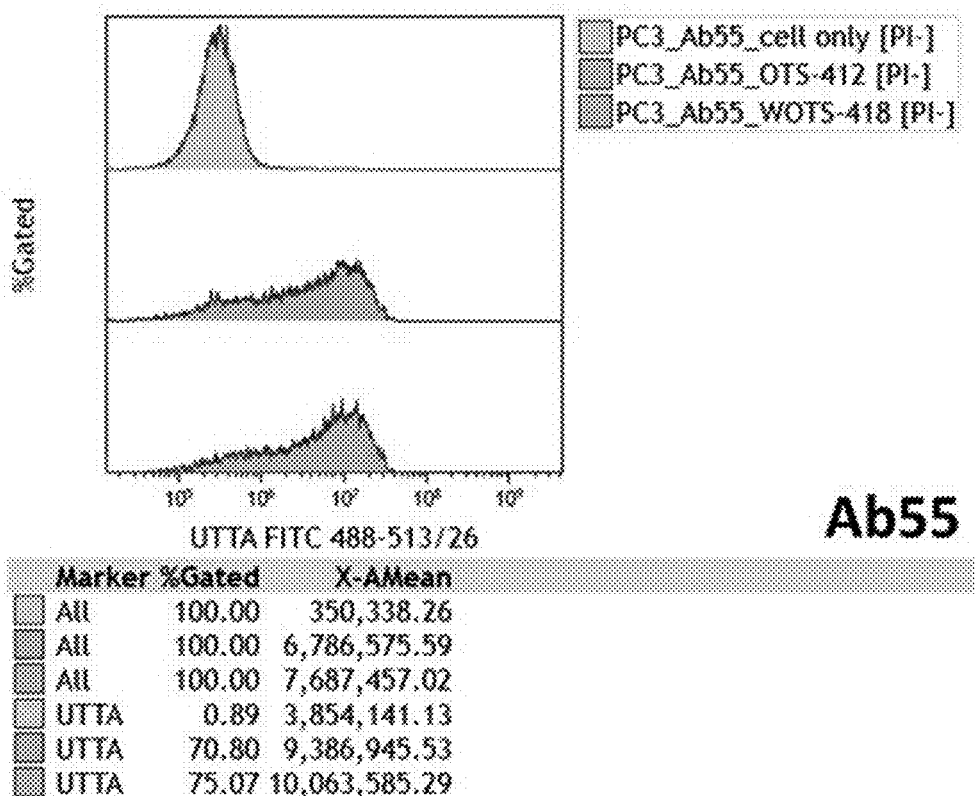
| Marker | %Gated | X-AMean |
|---|---|---|
| All | 100.00 | 350,338.26 |
| All | 100.00 | 6,786,575.59 |
| All | 100.00 | 7,687,457.02 |
| UTTA | 0.89 | 3,854,141.13 |
| UTTA | 70.80 | 9,386,945.53 |
| UTTA | 75.07 | 10,063,585.29 |
[FIG. 71]
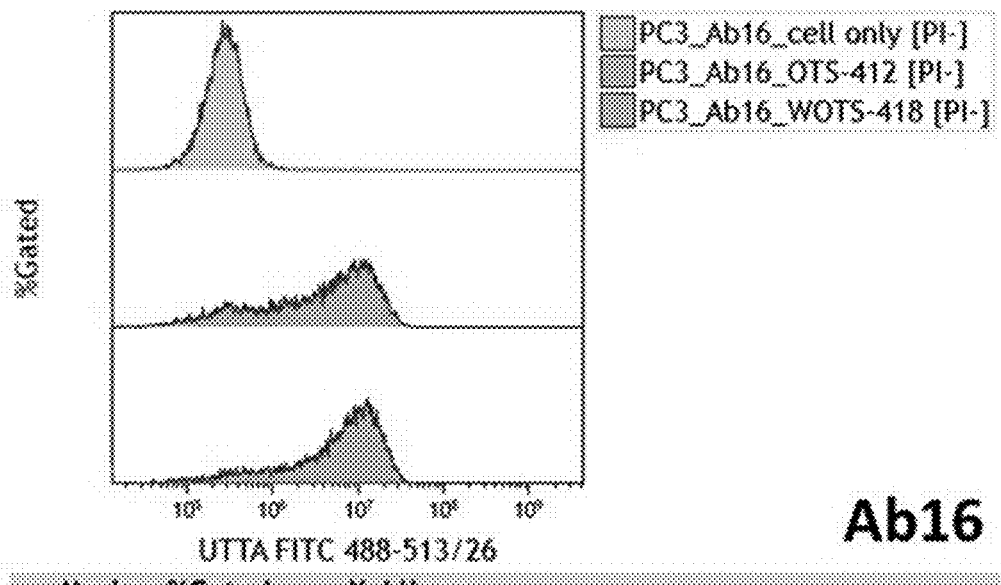
| Marker | %Gated | X-AMean |
|---|---|---|
| All | 100.00 | 313,689.41 |
| All | 100.00 | 6,795,696.42 |
| All | 100.00 | 8,476,396.00 |
| UTTA | 0.39 | 3,128,176.92 |
| UTTA | 72.72 | 9,169,673.91 |
| UTTA | 81.43 | 10,298,874.54 |

[FIG. 72]
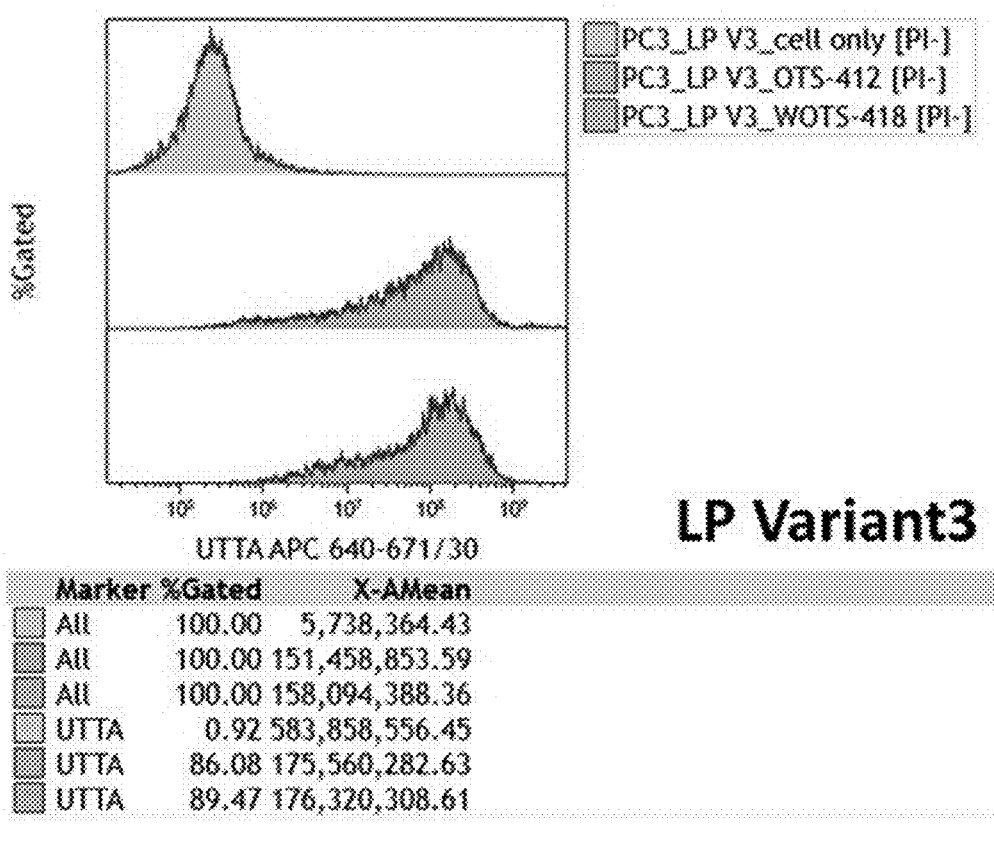
| Marker | %Gated | X-AMean |
|---|---|---|
| All | 100.00 | 5,738,364.43 |
| All | 100.00 | 151,458,853.59 |
| All | 100.00 | 158,094,388.36 |
| UTTA | 0.92 | 583,858,556.45 |
| UTTA | 86.08 | 175,560,282.63 |
| UTTA | 89.47 | 176,320,308.61 |
[FIG. 73]
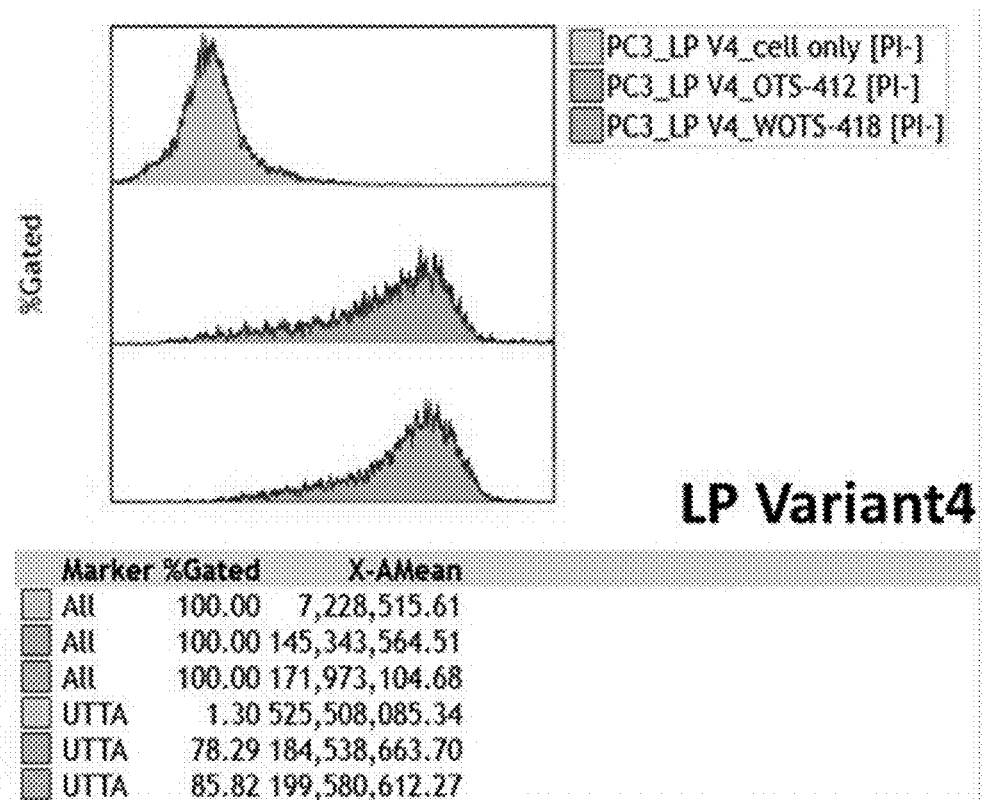
| Marker | %Gated | X-AMean |
|---|---|---|
| All | 100.00 | 7,228,515.61 |
| All | 100.00 | 145,343,564.51 |
| All | 100.00 | 171,973,104.68 |
| UTTA | 1.30 | 525,508,085.34 |
| UTTA | 78.29 | 184,538,663.70 |
| UTTA | 85.82 | 199,580,612.27 |

[FIG. 74]
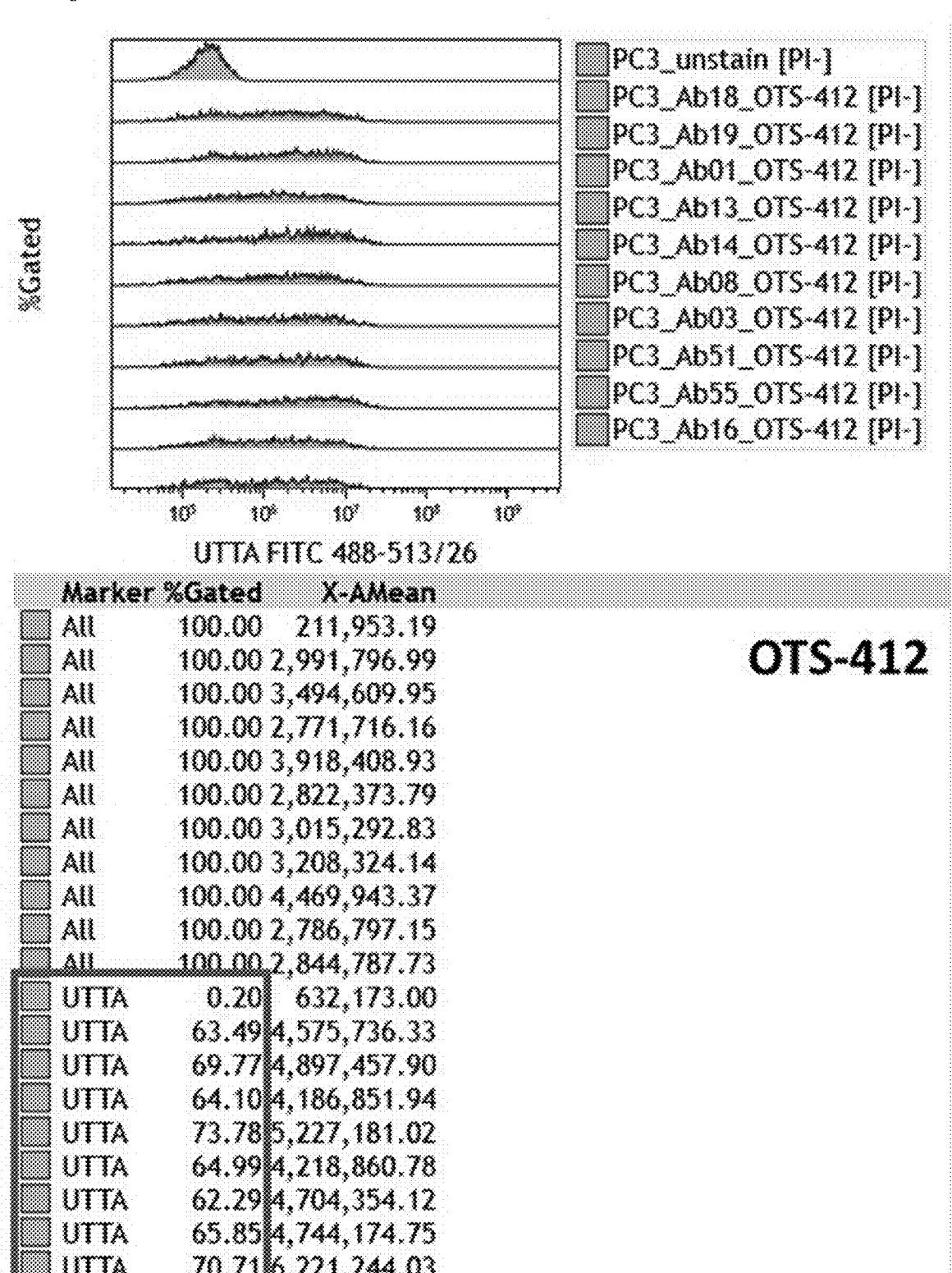

[FIG. 75]
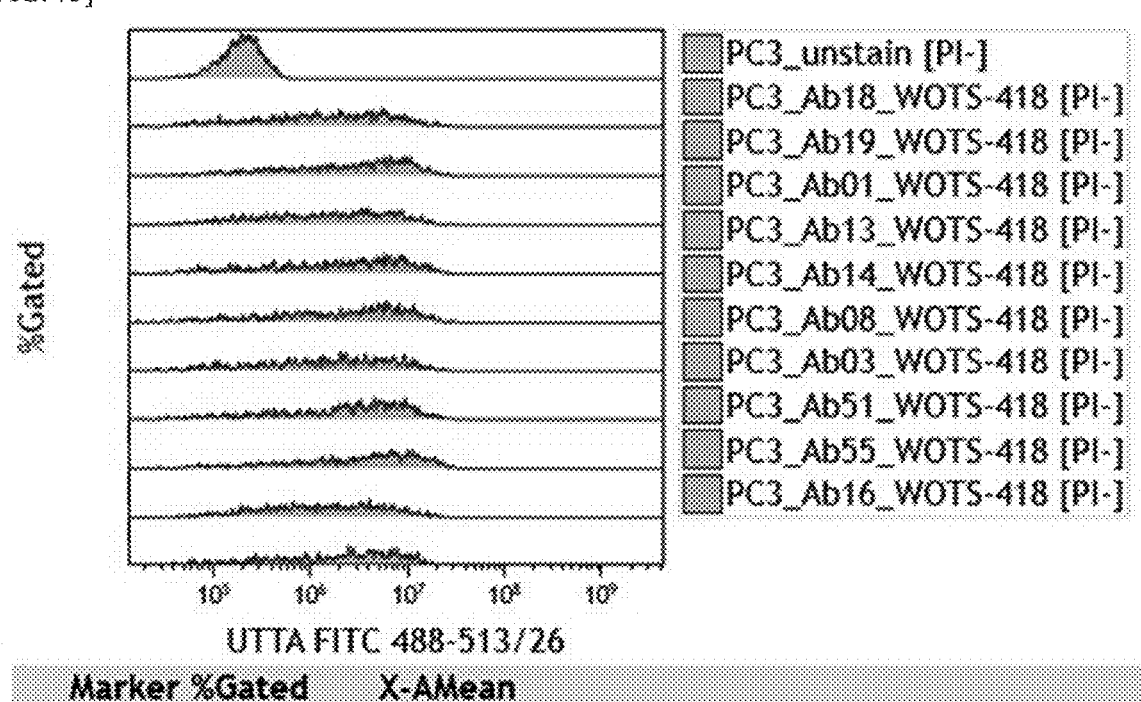
| Marker | %Gated | X-AMean |
|---|---|---|
| All | 100.00 | 211,953.19 |
| All | 100.00 | 3,232,710.07 |
| All | 100.00 | 4,556,788.51 |
| All | 100.00 | 3,282,326.12 |
| All | 100.00 | 4,127,059.90 |
| All | 100.00 | 4,242,583.51 |
| All | 100.00 | 3,360,473.88 |
| All | 100.00 | 4,386,922.77 |
| All | 100.00 | 5,861,633.44 |
| All | 100.00 | 3,039,592.41 |
| All | 100.00 | 3,737,512.37 |
| UTTA | 0.20 | 632,173.00 |
| UTTA | 69.05 | 4,574,047.39 |
| UTTA | 75.36 | 5,961,139.37 |
| UTTA | 68.09 | 4,704,578.12 |
| UTTA | 73.24 | 5,549,383.61 |
| UTTA | 74.26 | 5,630,628.24 |
| UTTA | 68.50 | 4,802,816.91 |
| UTTA | 75.18 | 5,756,497.77 |
| UTTA | 78.61 | 7,391,313.84 |
| UTTA | 67.57 | 4,368,078.29 |
| UTTA | 70.14 | 5,227,619.95 |
WOTS-418

[FIG. 76]
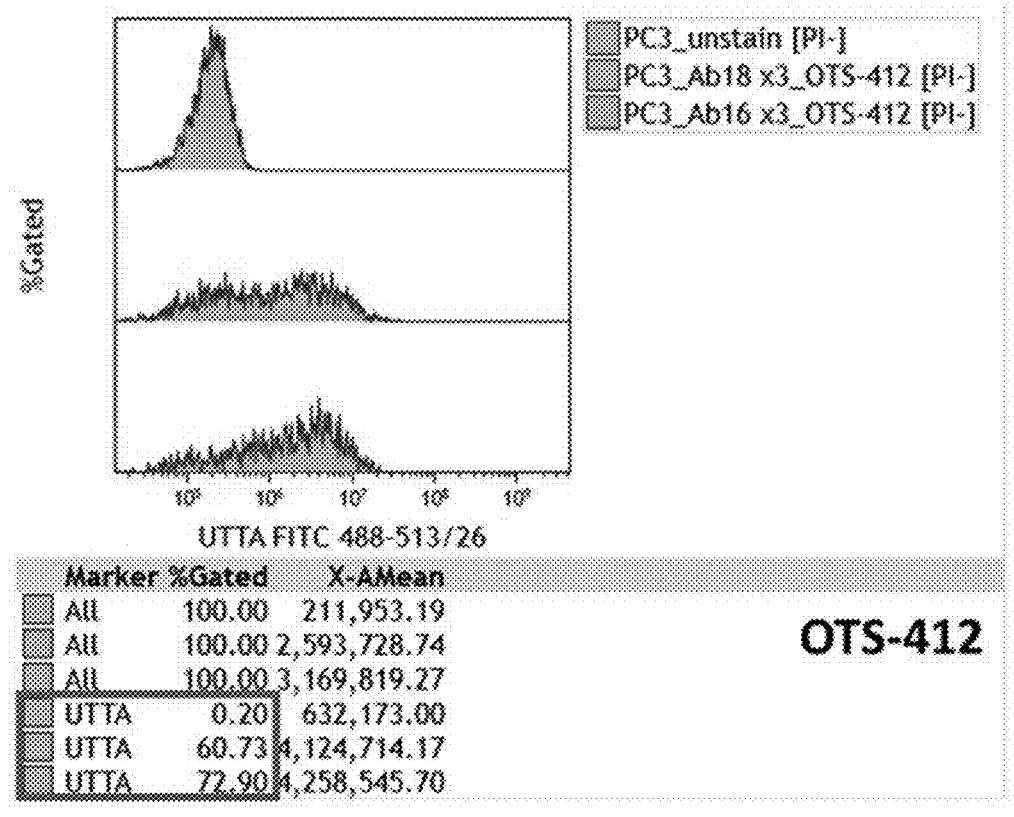
| Marker | %Gated | X-AMean |
|---|---|---|
| All | 100.00 | 211,953.19 |
| All | 100.00 | 2,593,728.74 |
| All | 100.00 | 3,169,819.27 |
| UTTA | 0.20 | 632,173.00 |
| UTTA | 60.73 | 4,124,714.17 |
| UTTA | 72.90 | 4,258,545.70 |
OTS-412
[FIG. 77]
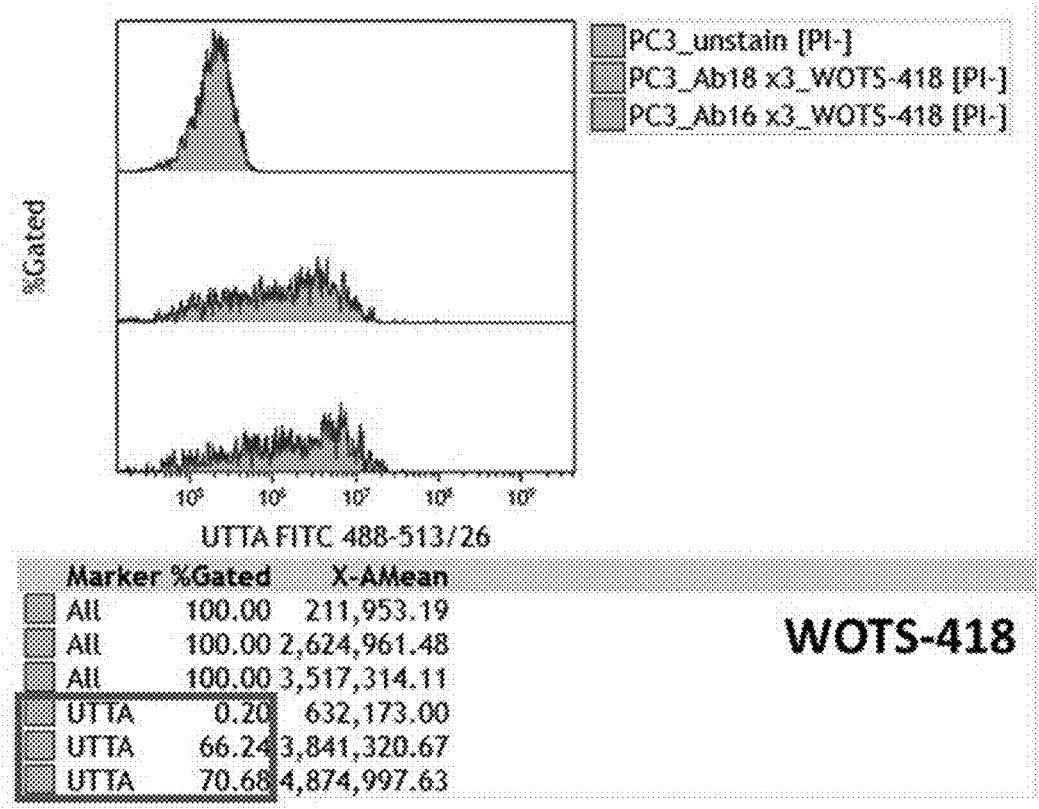
| Marker | %Gated | X-AMean |
|---|---|---|
| All | 100.00 | 211,953.19 |
| All | 100.00 | 2,624,961.48 |
| All | 100.00 | 3,517,314.11 |
| UTTA | 0.20 | 632,173.00 |
| UTTA | 66.24 | 3,841,320.67 |
| UTTA | 70.68 | 4,874,997.63 |
WOTS-418

[FIG. 78]
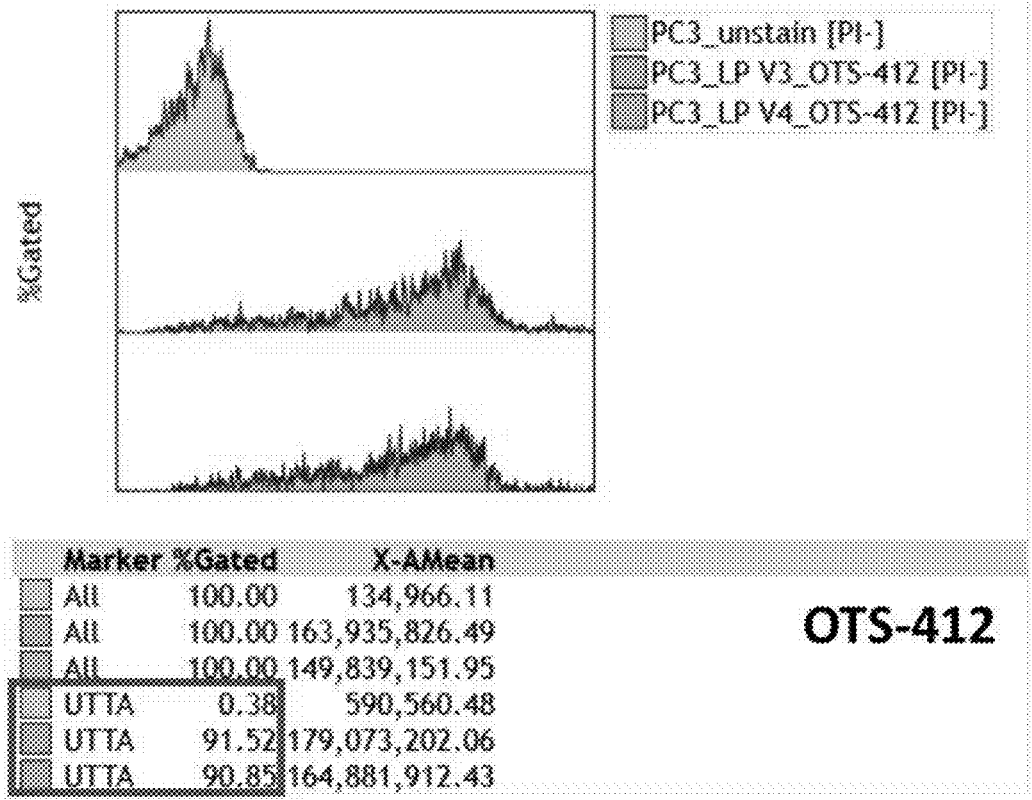
OTS-412
[FIG. 79]
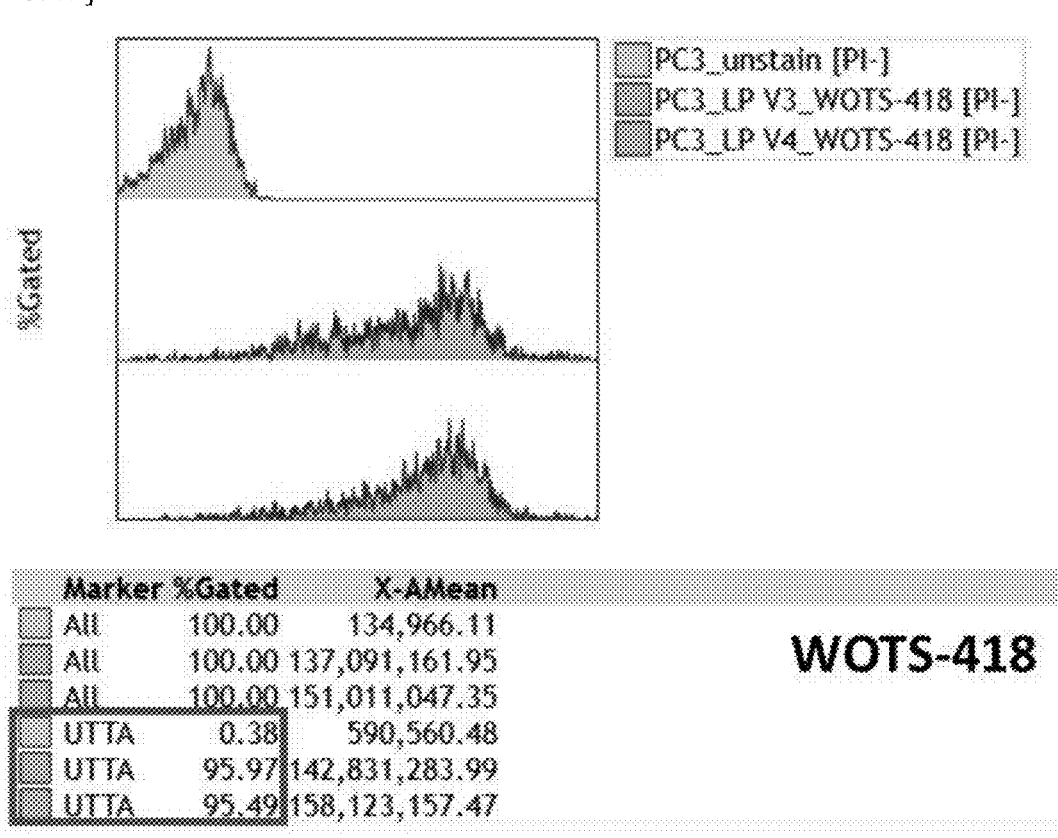
WOTS-418

[FIG. 80]
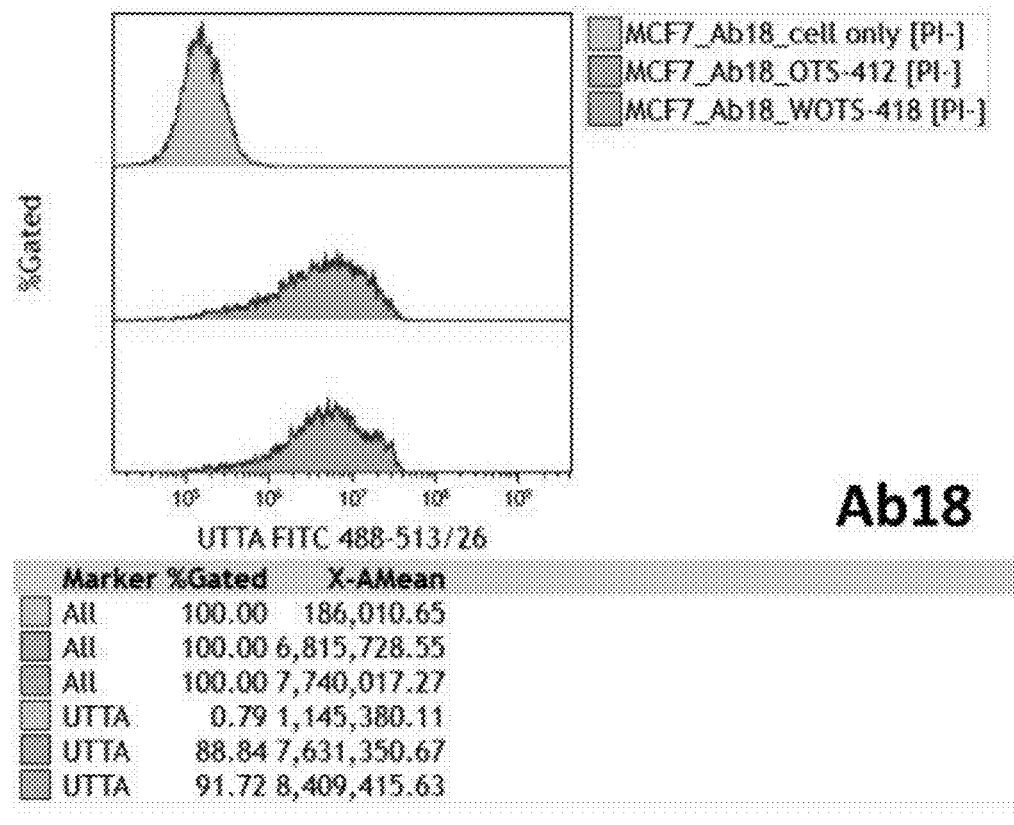
| Marker | %Gated | X-AMean |
|--------|--------|---------|
| All | 100.00 | 186,010.65 |
| All | 100.00 | 6,815,728.55 |
| All | 100.00 | 7,740,017.27 |
| UTTA | 0.79 | 1,145,380.11 |
| UTTA | 88.84 | 7,631,350.67 |
| UTTA | 91.72 | 8,409,415.63 |
[FIG. 81]
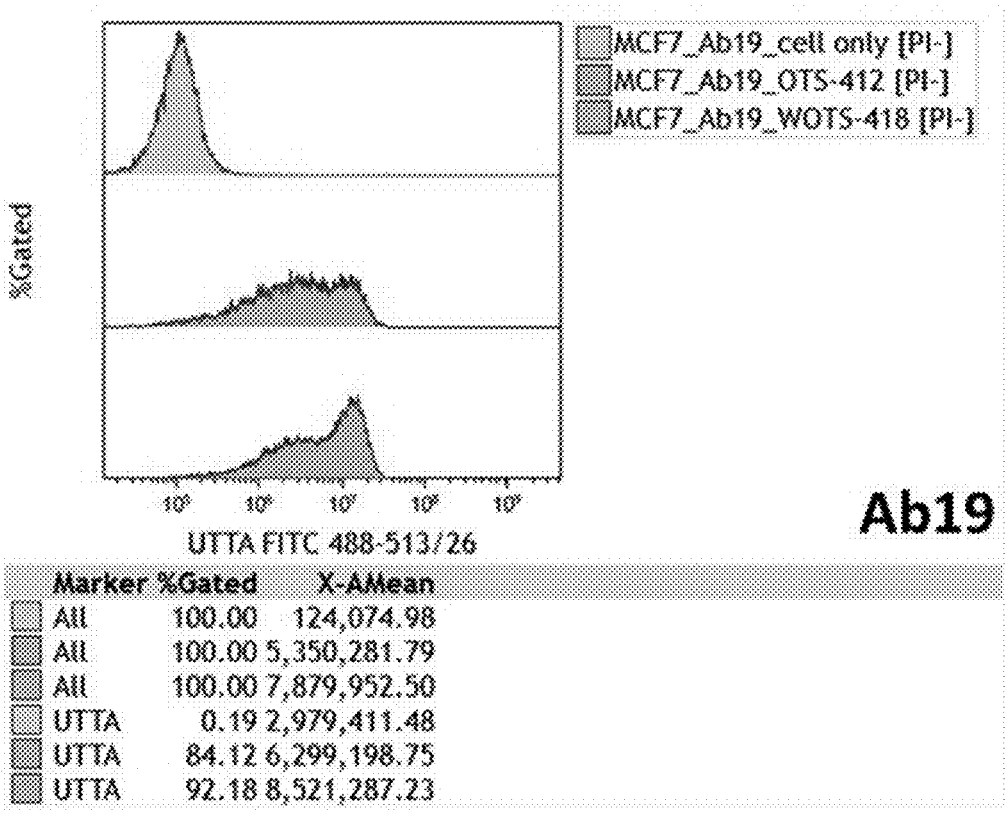
| Marker | %Gated | X-AMean |
|--------|--------|---------|
| All | 100.00 | 124,074.98 |
| All | 100.00 | 5,350,281.79 |
| All | 100.00 | 7,879,952.50 |
| UTTA | 0.19 | 2,979,411.48 |
| UTTA | 84.12 | 6,299,198.75 |
| UTTA | 92.18 | 8,521,287.23 |

[FIG. 82]
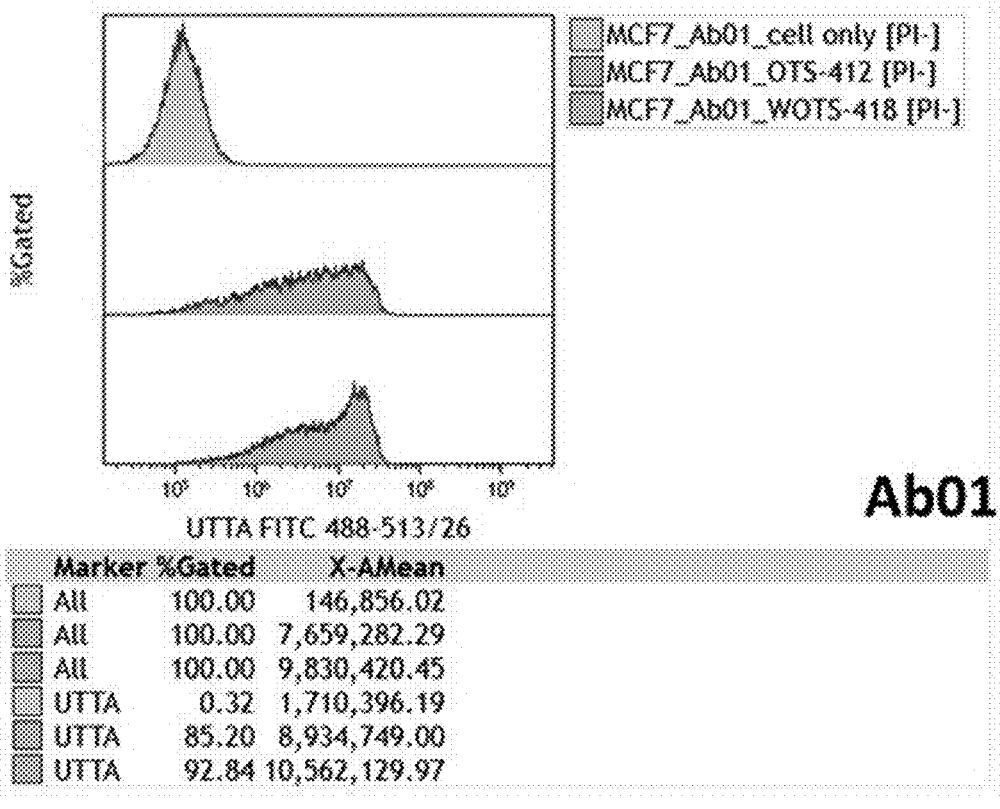
Ab01
| Marker | %Gated | X-AMean |
|--------|--------|---------|
| All | 100.00 | 146,856.02 |
| All | 100.00 | 7,659,282.29 |
| All | 100.00 | 9,830,420.45 |
| UTTA | 0.32 | 1,710,396.19 |
| UTTA | 85.20 | 8,934,749.00 |
| UTTA | 92.84 | 10,562,129.97 |
[FIG. 83]
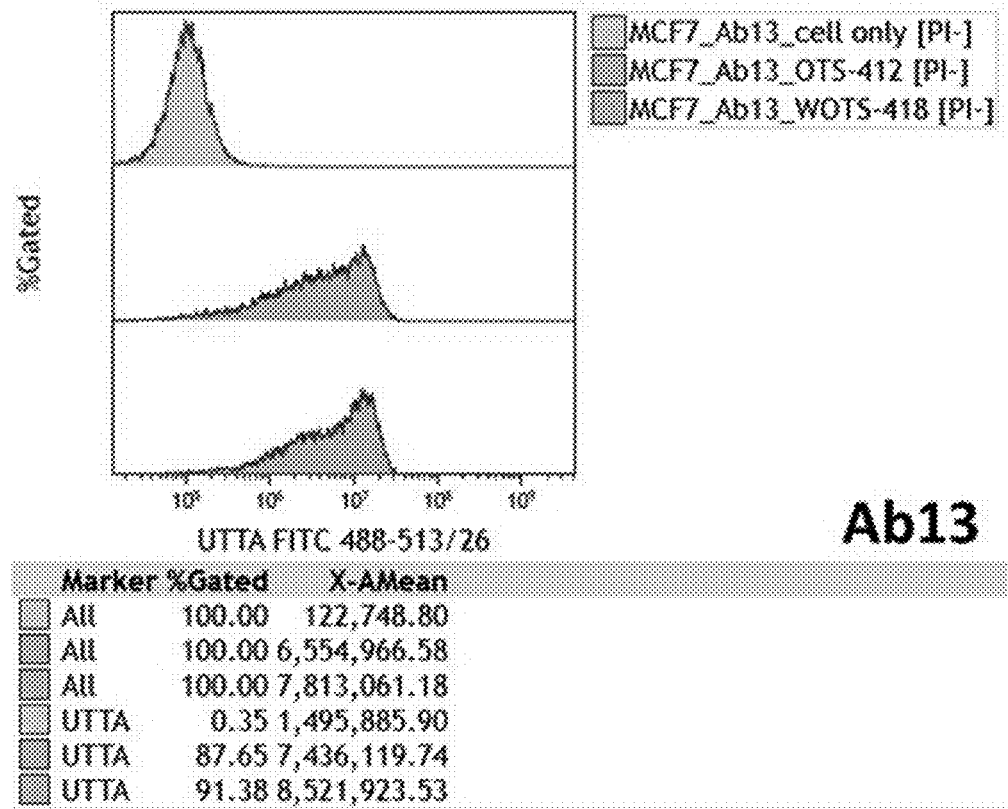
Ab13
| Marker | %Gated | X-AMean |
|--------|--------|---------|
| All | 100.00 | 122,748.80 |
| All | 100.00 | 6,554,966.58 |
| All | 100.00 | 7,813,061.18 |
| UTTA | 0.35 | 1,495,885.90 |
| UTTA | 87.65 | 7,436,119.74 |
| UTTA | 91.38 | 8,521,923.53 |

[FIG. 84]
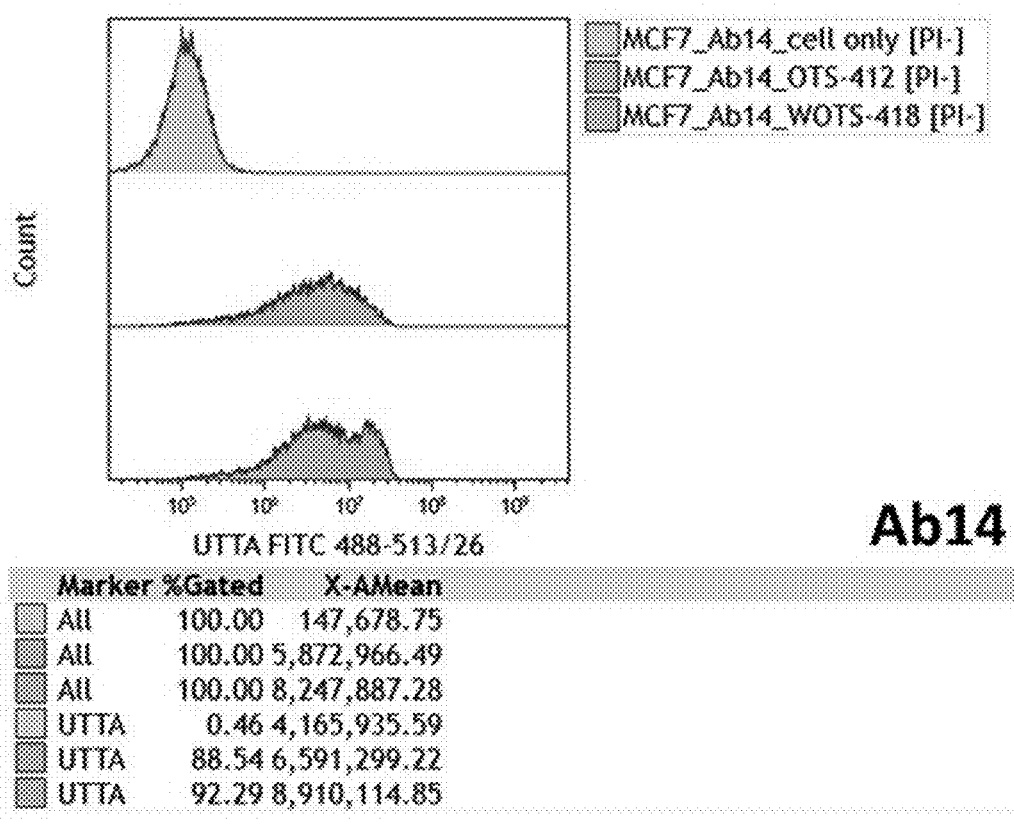
| Marker | %Gated | X-AMean |
|---|---|---|
| All | 100.00 | 147,678.75 |
| All | 100.00 | 5,872,966.49 |
| All | 100.00 | 8,247,887.28 |
| UTTA | 0.46 | 4,165,935.59 |
| UTTA | 88.54 | 6,591,299.22 |
| UTTA | 92.29 | 8,910,114.85 |
[FIG. 85]
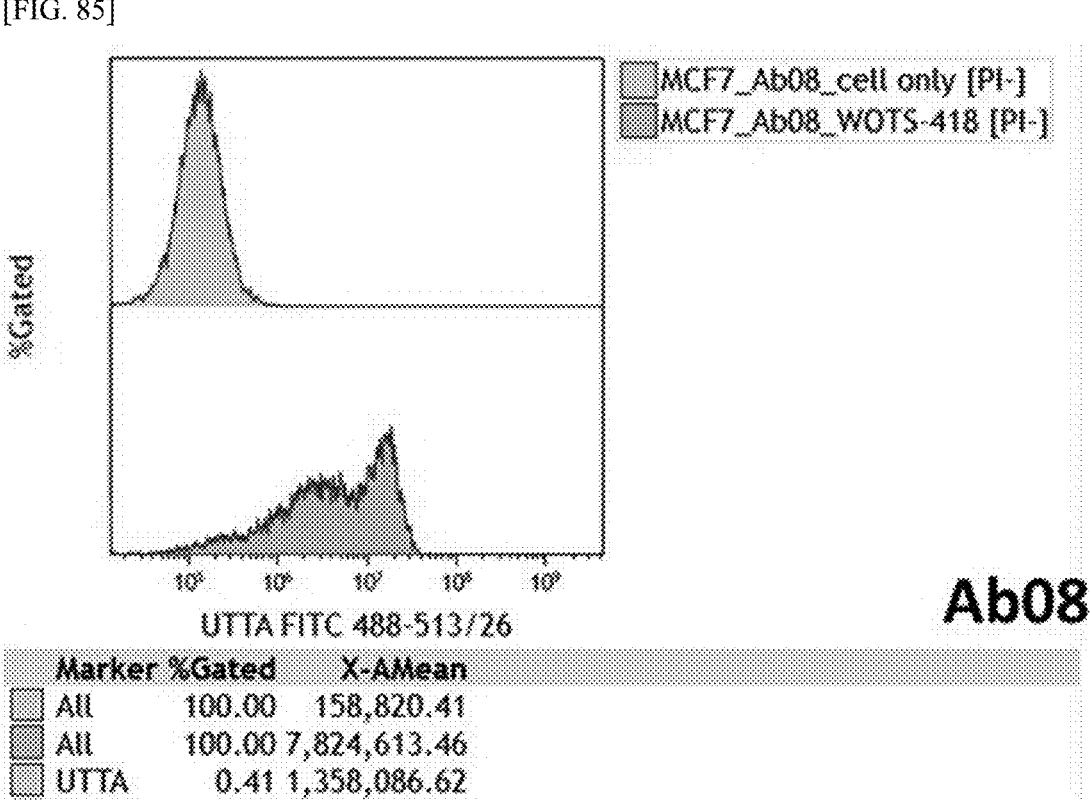
| Marker | %Gated | X-AMean |
|---|---|---|
| All | 100.00 | 158,820.41 |
| All | 100.00 | 7,824,613.46 |
| UTTA | 0.41 | 1,358,086.62 |
| UTTA | 87.28 | 8,921,588.08 |

[FIG. 86]
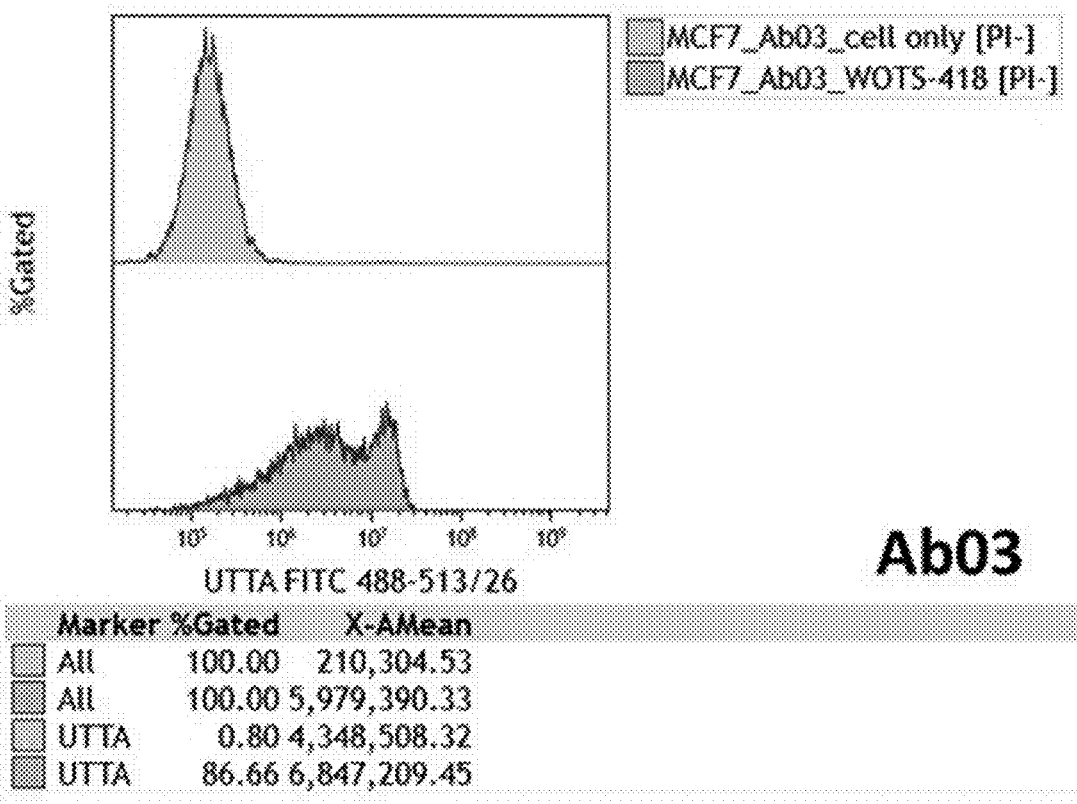
| Marker | %Gated | X-AMean |
|--------|--------|---------|
| All | 100.00 | 210,304.53 |
| All | 100.00 | 5,979,390.33 |
| UTTA | 0.80 | 4,348,508.32 |
| UTTA | 86.66 | 6,847,209.45 |
[FIG. 87]
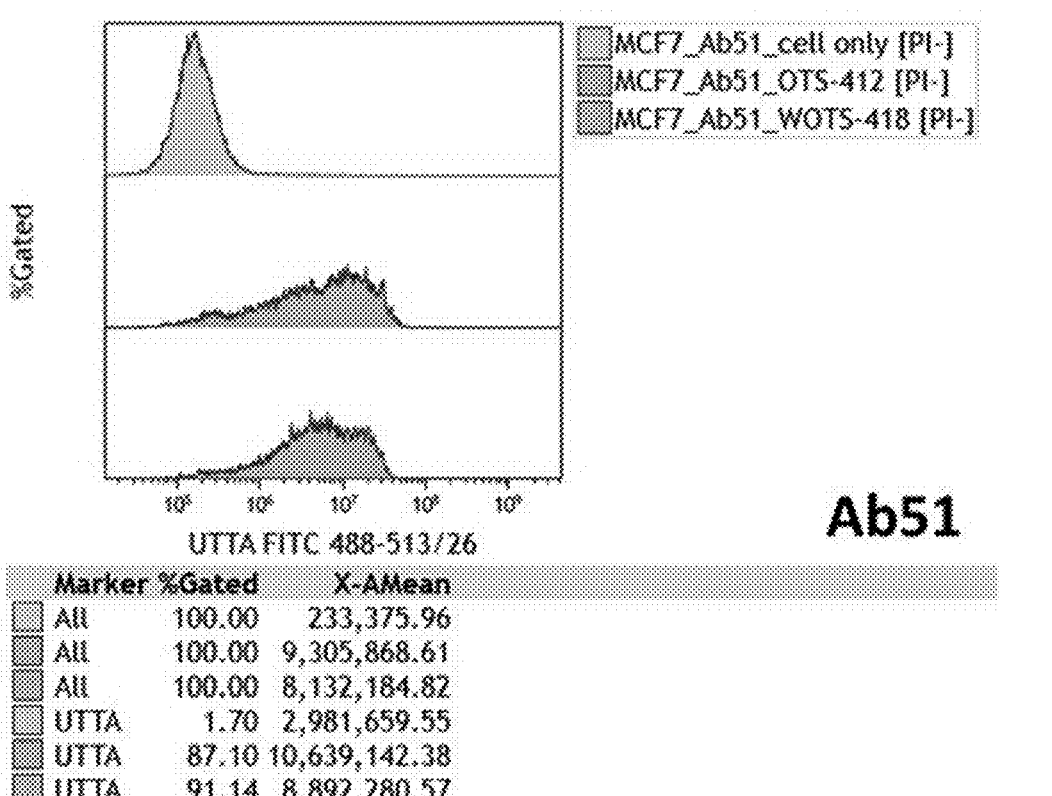
| Marker | %Gated | X-AMean |
|--------|--------|---------|
| All | 100.00 | 233,375.96 |
| All | 100.00 | 9,305,868.61 |
| All | 100.00 | 8,132,184.82 |
| UTTA | 1.70 | 2,981,659.55 |
| UTTA | 87.10 | 10,639,142.38 |
| UTTA | 91.14 | 8,892,280.57 |

[FIG. 88]
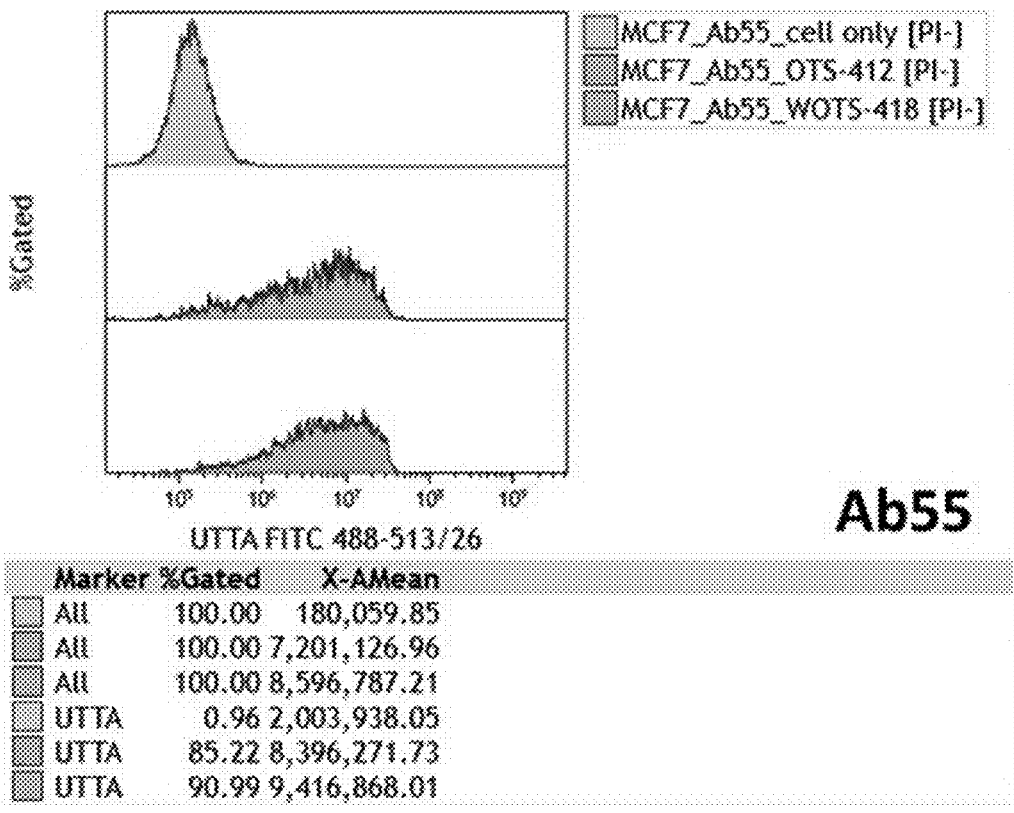
| Marker | %Gated | X-AMean |
|--------|--------|---------|
| All | 100.00 | 180,059.85 |
| All | 100.00 | 7,201,126.96 |
| All | 100.00 | 8,596,787.21 |
| UTTA | 0.96 | 2,003,938.05 |
| UTTA | 85.22 | 8,396,271.73 |
| UTTA | 90.99 | 9,416,868.01 |
[FIG. 89]
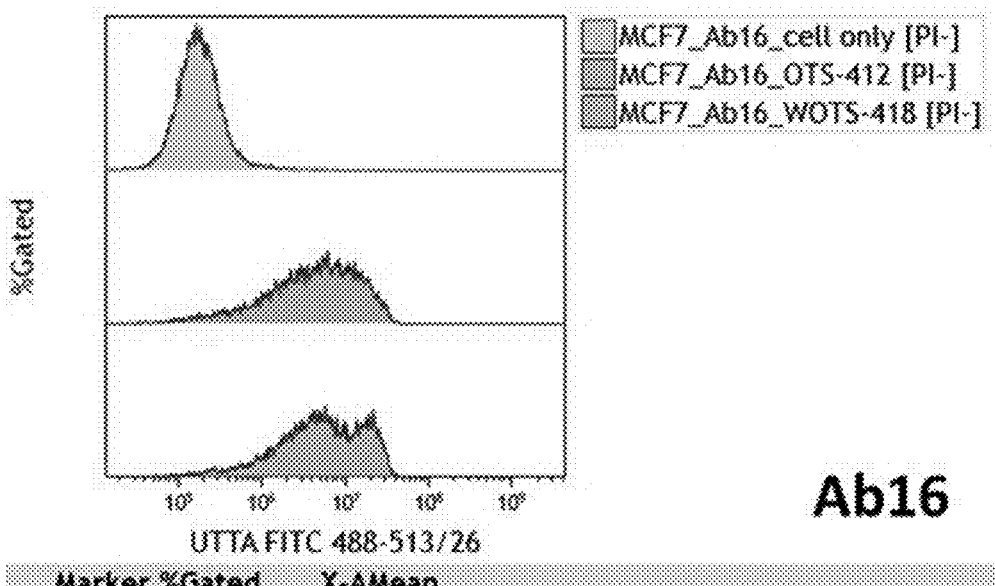
| Marker | %Gated | X-AMean |
|--------|--------|---------|
| All | 100.00 | 235,532.02 |
| All | 100.00 | 7,092,418.02 |
| All | 100.00 | 8,404,848.48 |
| UTTA | 2.79 | 1,606,107.31 |
| UTTA | 89.49 | 7,887,606.49 |
| UTTA | 92.11 | 9,097,710.40 |

[FIG. 90]
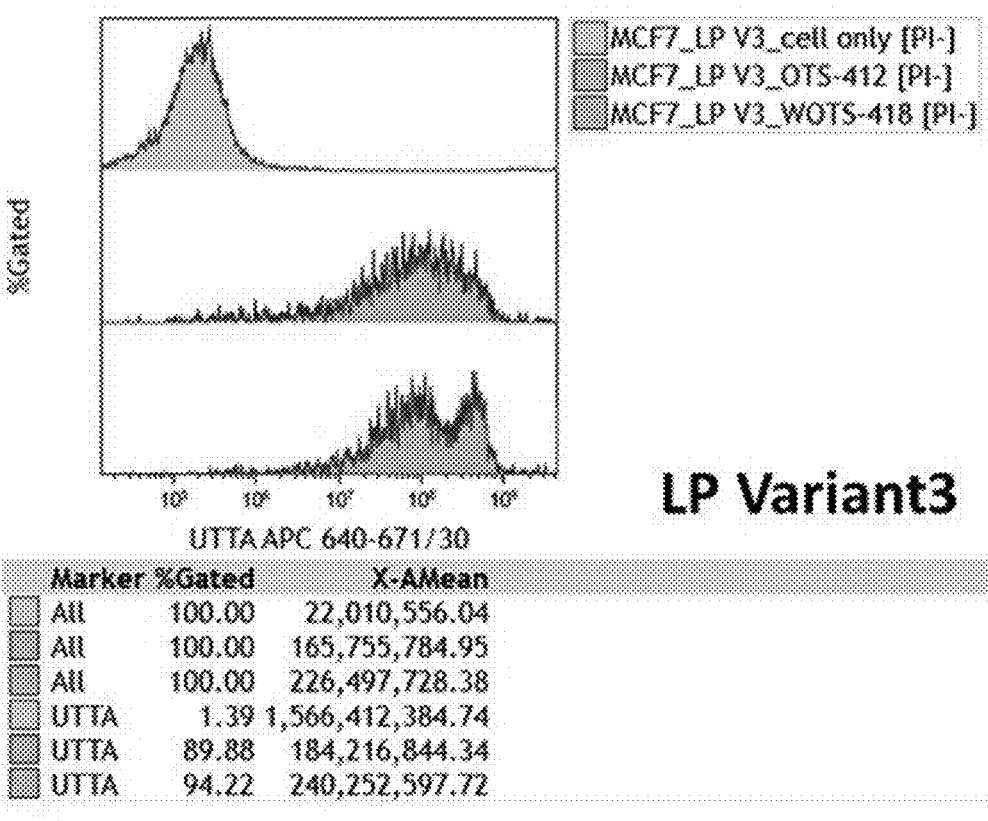
| Marker | %Gated | X-AMean |
|--------|--------|---------|
| All | 100.00 | 22,010,556.04 |
| All | 100.00 | 165,755,784.95 |
| All | 100.00 | 226,497,728.38 |
| UTTA | 1.39 | 1,566,412,384.74 |
| UTTA | 89.88 | 184,216,844.34 |
| UTTA | 94.22 | 240,252,597.72 |
[FIG. 91]
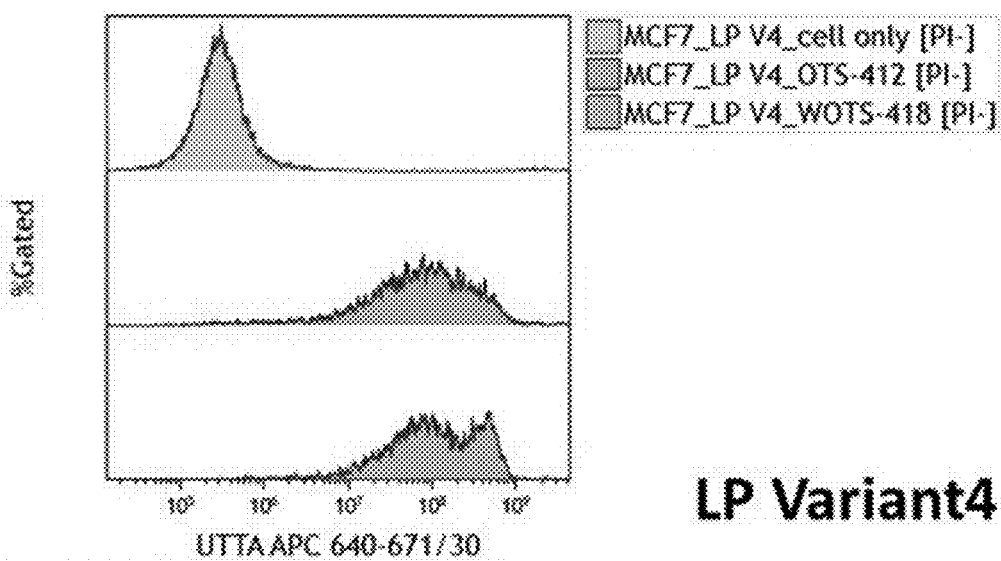
| Marker | %Gated | X-AMean |
|--------|--------|---------|
| All | 100.00 | 32,537,118.12 |
| All | 100.00 | 180,630,796.61 |
| All | 100.00 | 212,145,681.63 |
| UTTA | 2.11 | 1,527,208,536.72 |
| UTTA | 92.53 | 195,061,165.66 |
| UTTA | 95.10 | 222,971,636.86 |

[FIG. 92]
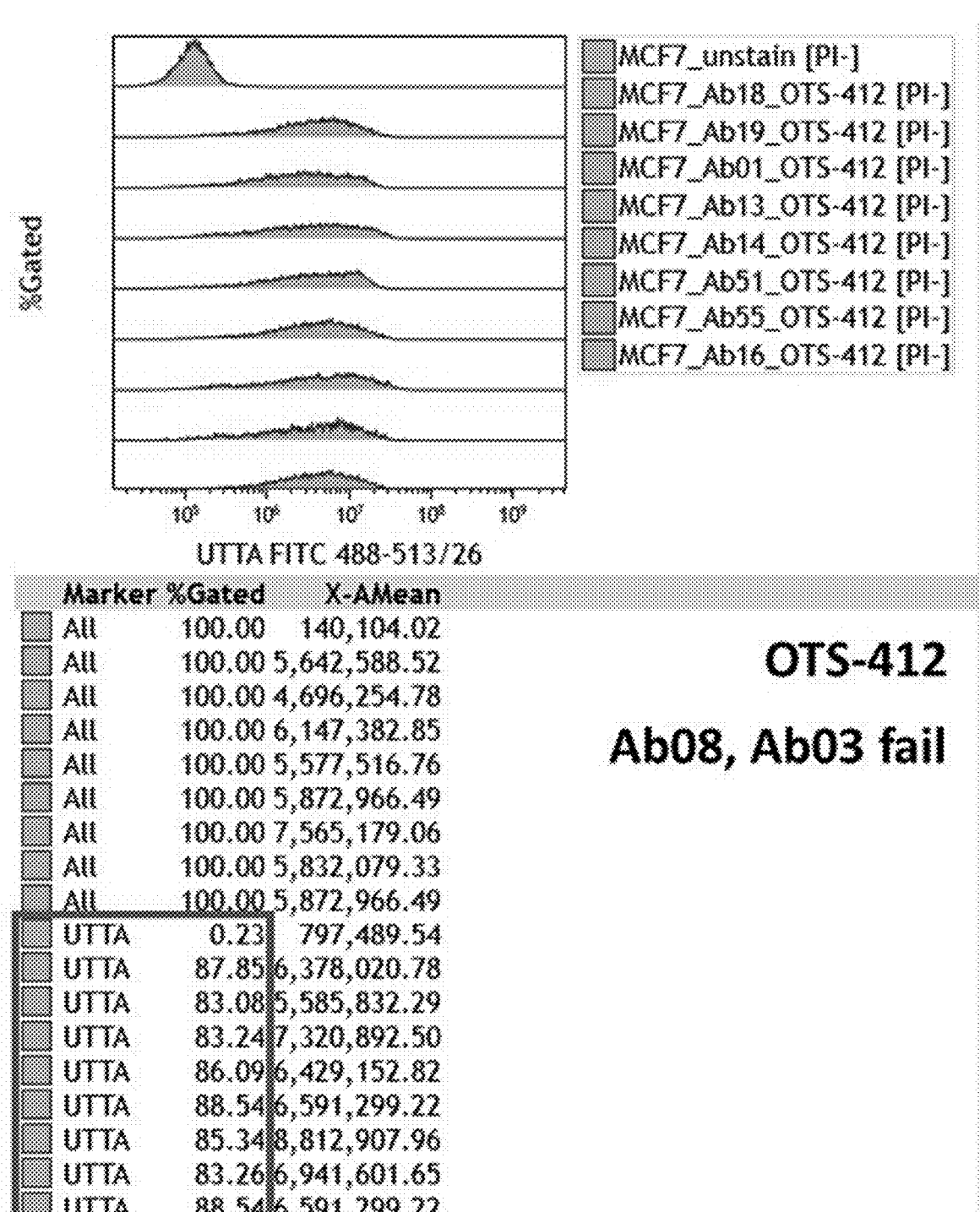

[FIG. 93]
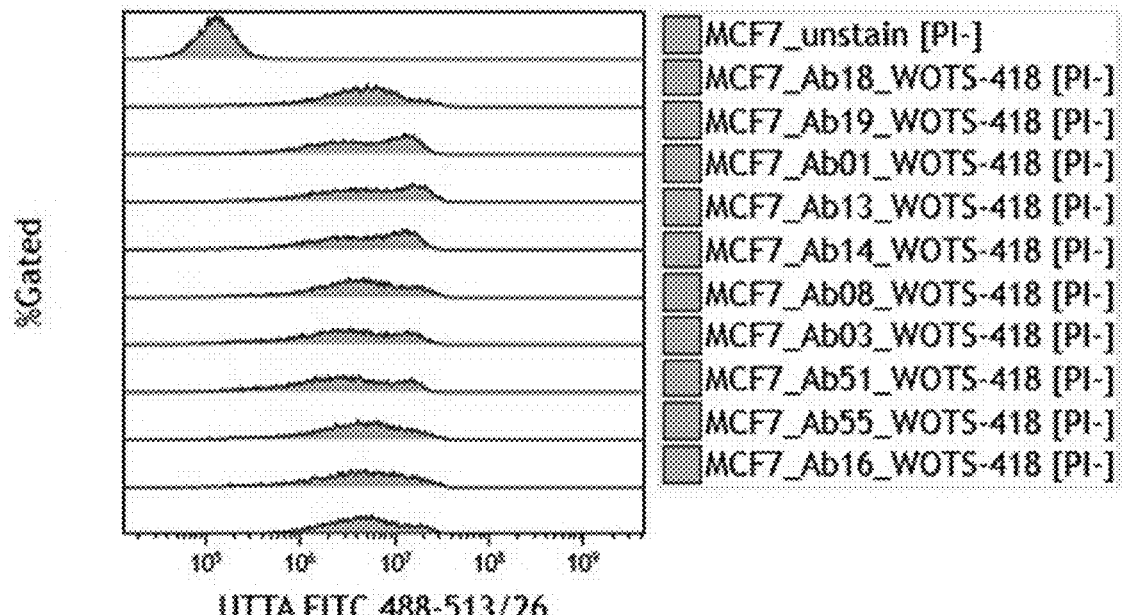
| Marker | %Gated | X-AMean |
|---|---|---|
| All | 100.00 | 140,104.02 |
| All | 100.00 | 6,240,046.38 |
| All | 100.00 | 6,891,989.64 |
| All | 100.00 | 8,073,504.40 |
| All | 100.00 | 6,744,501.35 |
| All | 100.00 | 6,627,527.68 |
| All | 100.00 | 5,486,730.91 |
| All | 100.00 | 4,939,059.27 |
| All | 100.00 | 6,409,509.46 |
| All | 100.00 | 6,657,359.34 |
| All | 100.00 | 6,596,791.91 |
| UTTA | 0.23 | 797,489.54 |
| UTTA | 90.79 | 6,840,117.08 |
| UTTA | 91.04 | 7,538,491.18 |
| UTTA | 91.25 | 8,814,836.93 |
| UTTA | 89.84 | 7,473,552.55 |
| UTTA | 91.46 | 7,216,856.73 |
| UTTA | 84.37 | 6,446,922.81 |
| UTTA | 85.21 | 5,736,979.51 |
| UTTA | 89.49 | 7,126,076.77 |
| UTTA | 89.39 | 7,410,450.25 |
| UTTA | 90.90 | 7,225,533.88 |
WOTS-418

[FIG. 94]
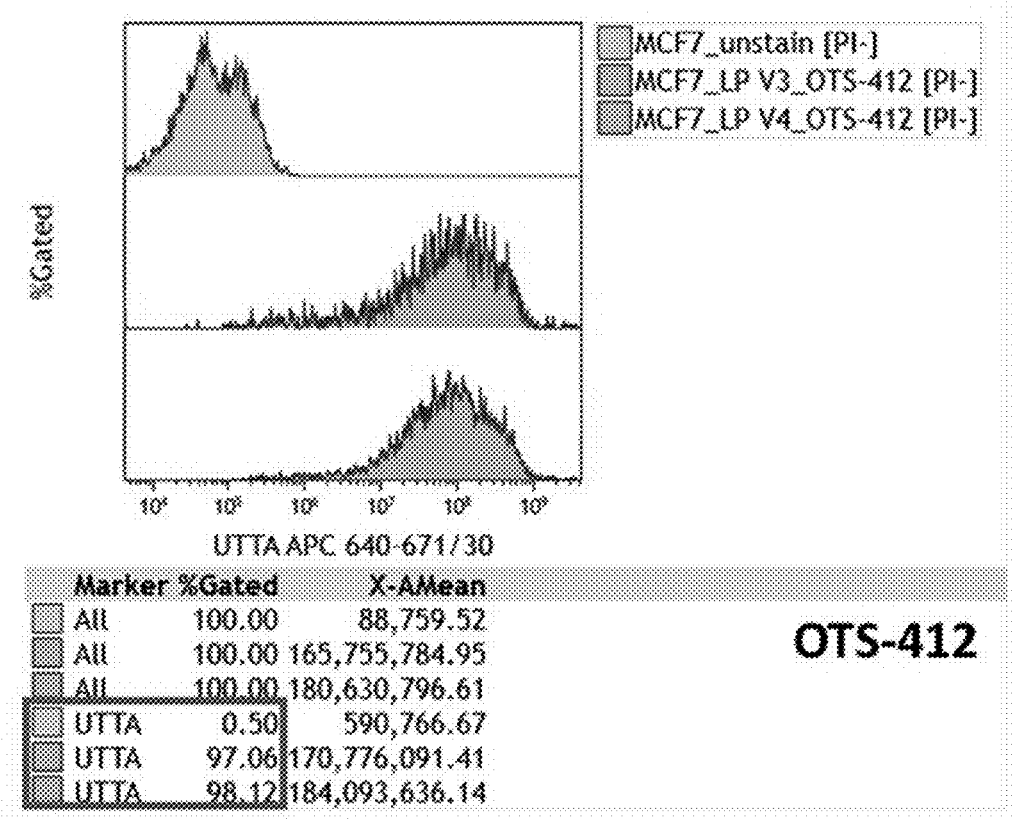
[FIG. 95]
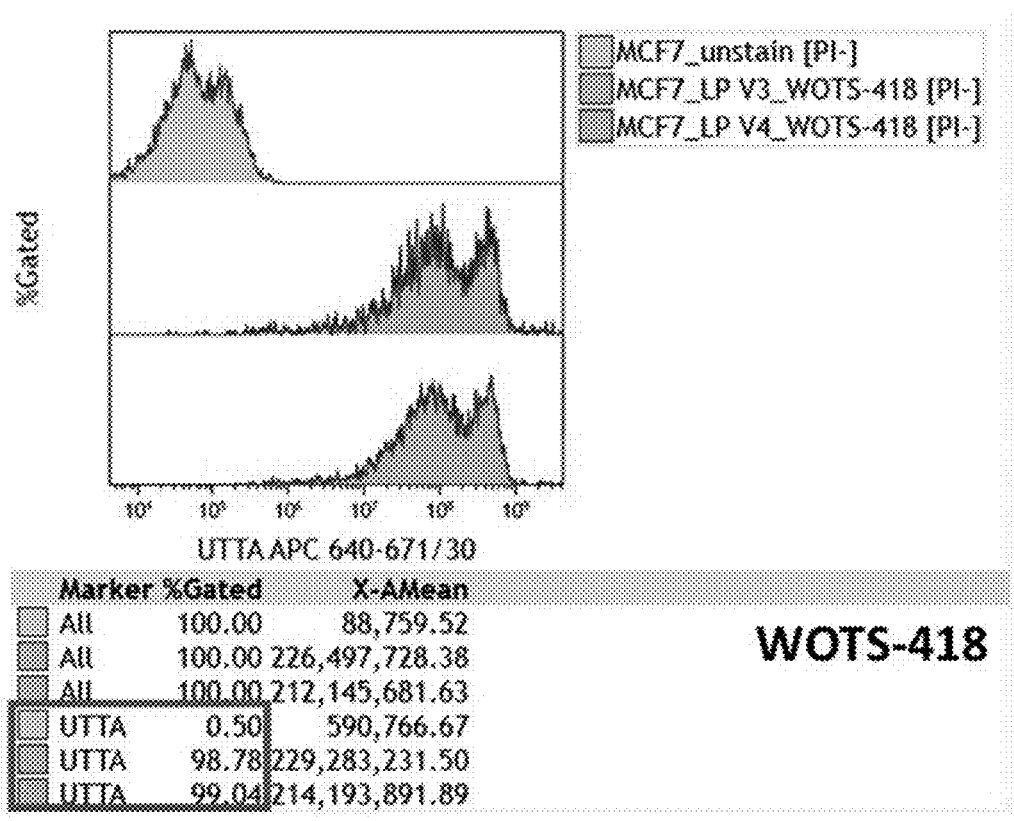

[FIG. 96]

* Performing additional ELISA (Signal-X)

[FIG. 97]
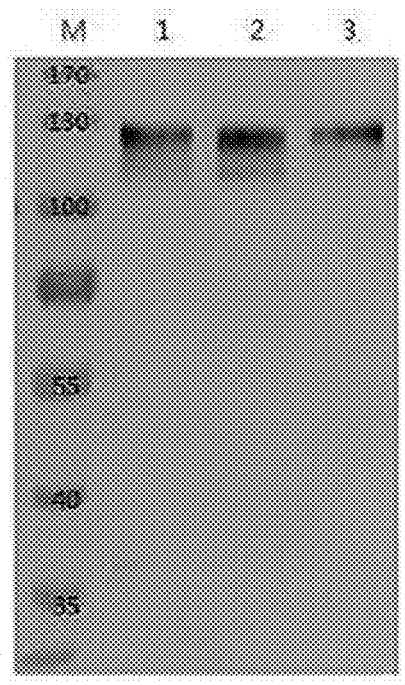
| 1 | A56-C-Fc |
| 2 | A56-Fc (ΔDFVE) OTS-412 |
| 3 | A56-Fc (ΔDFVE+DLYDT) |
—Sup
| HEK 293F TRANSFECTION |
| 8 ml / 50 ml tube/ 7 DAYS CULTURE |
| SAMPLING<br>-Sup : Sup 160 ul + 5X sample buffer 40 ul |
| LOADING - 20 ul |
| WB - anti-hFc-HRP (1:4000) |

[FIG. 98]
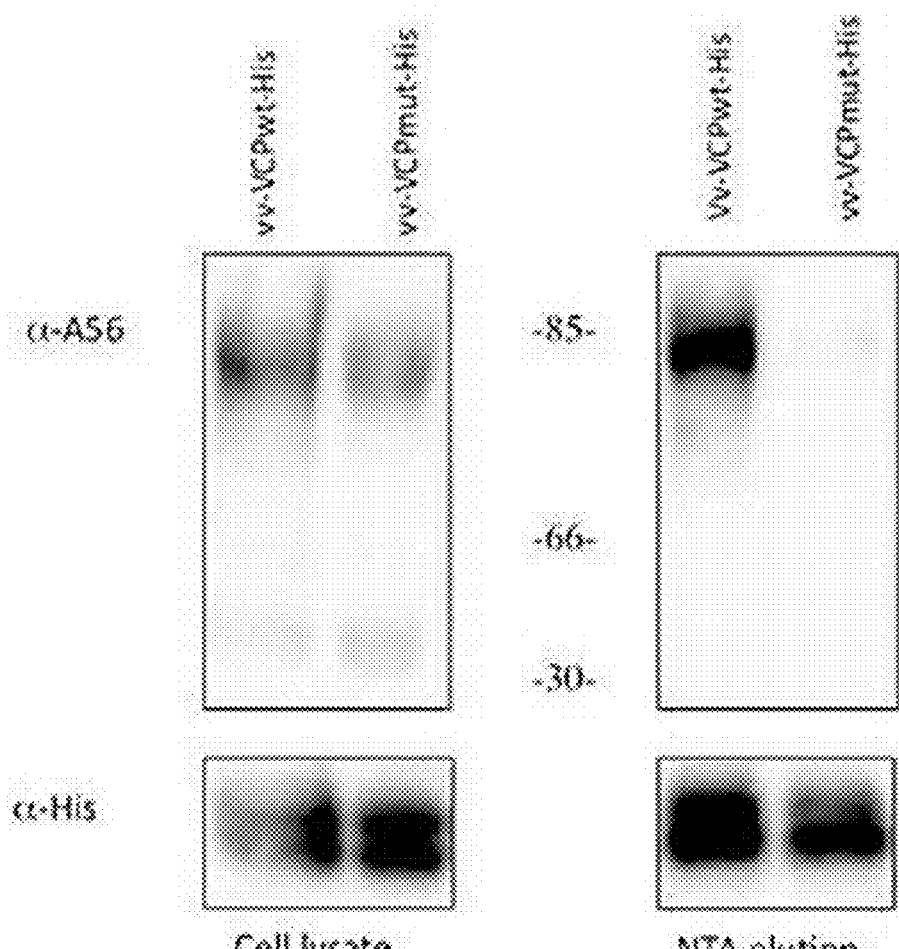

TUMOR-TARGETING A56 PROTEIN OR FRAGMENT THEREOF, ANTIBODY BINDING TO A56 PROTEIN, AND USE THEREOF

CROSS REFERENCE TO RELATED APPLICATIONS

This application is a National Stage of International Application No. PCT/KR2020/013485, filed Oct. 5, 2020, claiming priority to Korean Patent Application No. 10-2019-0122076, filed Oct. 2, 2019.

SEQUENCE LISTING

The content of the electronically submitted sequence listing, file name: Q272864_SEQ_LIST_ST25.txt; size: 455,128 bytes; and date of creation: Oct. 4, 2025, filed herewith, is incorporated herein by reference in its entirety.

TECHNICAL FIELD

The present invention relates to a tumor-targeting protein or a fragment thereof, an antibody binding thereto, and uses thereof. More particularly, the present invention relates to a vector that contains a nucleic acid encoding a fragment of protein A56, and uses thereof. In addition, the present invention relates to an antibody that specifically binds to protein A56 or a fragment thereof, and uses thereof.

BACKGROUND ART

Cancer is also called a tumor, and refers to cells that have grown abnormally due to autonomous overgrowth of body tissue. Cancer incidence continues to increase due to aging population, increased smoking population, increase in alcohol consumption, westernized eating habits, and environmental pollution in modern society.

Methods for treating cancer include surgery, radiation therapy, chemotherapy, and the like. Specifically, surgery is a therapeutic method that removes cancerous tissue from the body, and is very effective for early cancer or cancer in which lesions are restricted to a certain location. However, it is difficult to remove cancer that has invaded tissue around the lesion or has metastasized to the lymph node, and such cancer has a high probability of recurrence. In this case, radiation therapy or chemotherapy is used in combination with surgery. Radiation therapy or chemotherapy is used mainly for the treatment of advanced or terminal cancer; however, this therapy also affects normal cells, and thus causes serious adverse effects.

Recently, immune cell therapy has been actively studied as a cancer therapeutic method. The immune cell therapy is different from existing therapeutic methods in that it uses the patient's immune cells to kill cancer cells. Specifically, the immune cell therapy is a method in which immune cells are obtained from a patient, activated to specifically attack proliferating cells or cancer cells, and then returned back to the patient's body; and this method maximizes an anticancer effect while minimizing drug-induced adverse effects.

In addition, over the past 5 years, immune checkpoint inhibitors have been actively studied for immunotherapy for treating cancer. In particular, inhibitors against immune checkpoints, such as cytotoxic T-lymphocyte-associated protein 4 (CTLA-4), programmed cell death protein 1 (PD-1), and PD-L1, have been studied. Immune checkpoint inhibitors, such as ipilimumab (anti-CTLA-4), nivolumab (anti-PD-1), and pembrolizumab (anti-PD-1), have been approved by regulatory agencies for the treatment of several types of cancer. However, the immune checkpoint inhibitors are limitedly used for the treatment of patients with certain types of cancer, such as melanoma, lung cancer, head and neck cancer, kidney cancer, and bladder cancer.

Therefore, there is a need for continuous research and development on cancer cell-targeting methods that are safe and capable of effectively targeting even solid cancer.

DISCLOSURE OF INVENTION

Technical Problem

Accordingly, as a resulting of conducting studies to develop a method for safely and effectively targeting cancer cells, the present inventors have found that in a case where cancer cells are treated by injection of a vector that contains a nucleic acid encoding protein A56 or a fragment thereof, the protein A56 is expressed on the cancer cell surface. In addition, the present inventors have found that an antibody, which binds to the protein A56 or a fragment thereof, binds to the protein A56 expressed on the cancer cell surface, thereby completing the present invention.

Solution to Problem

In an aspect of the present invention, there is provided an anticancer agent, comprising, as an active ingredient, an antibody or a fragment thereof which specifically binds to protein A56 or a fragment thereof.

In another aspect of the present invention, there is provided an oncolytic virus, comprising a nucleic acid encoding protein A56 or a fragment thereof.

In yet another aspect of the present invention, there is provided an antibody or fragment thereof which binds to protein A56 or a fragment thereof.

In still yet another aspect of the present invention, there is provided a cancer-targeting polypeptide or a fragment thereof, the polypeptide including an amino acid sequence represented by SEQ ID NO: 1038, 1040, 1042, 1044, 1046, 1048, 1050, 1052, 1054, 1056, 1058, 1060, 1073, 1075, 1077, or 1079.

In still yet another aspect of the present invention, there is provided an isolated nucleic acid encoding the cancer-targeting polypeptide or a fragment thereof.

In still yet another aspect of the present invention, there is provided a kit for treating cancer, comprising the oncolytic virus and the antibody or a fragment thereof.

In still yet another aspect of the present invention, there is provided a pharmaceutical composition for targeting cancer, comprising the oncolytic virus.

Advantageous Effects of Invention

The oncolytic virus, which contains a nucleic acid encoding protein A56 or a fragment or variant thereof, of the present invention primarily kills only cancer cells in a specific manner in a case of being used as a vector and administered to an individual. In addition, cancer cells, which have survived even infection with the oncolytic virus, express protein A56 on the cell surface, and this enables targeting for secondary anticancer therapy. Accordingly, cancer can be effectively treated in a case of using the vector, which contains a nucleic acid encoding protein A56 or a fragment or variant thereof, and the antibody, which binds protein A56 or a fragment thereof, each of which is an embodiment of the present invention.

BRIEF DESCRIPTION OF DRAWINGS

FIG. 1 illustrates a diagram showing a process of targeting tumor cells using an oncolytic virus that contains a nucleic acid encoding protein A56 or a fragment thereof.

FIG. 2 illustrates results obtained by subjecting a human lung cancer cell line (A549) to infection with an oncolytic virus, which contains a nucleic acid encoding protein A56, and then identifying, with immunofluorescence staining, whether the protein A56 is expressed on the surface of the infected A549 cancer cell line.

FIG. 3 illustrates results obtained by subjecting a human colorectal cancer cell line (HCT-116) to infection with an oncolytic virus, which contains a nucleic acid encoding protein A56, and then identifying, with immunofluorescence staining, whether the protein A56 is expressed on the surface of the infected HC-116 cell line.

FIG. 4 illustrates results obtained by subjecting human colorectal cancer cell line (HT-29)-transplanted mice to intraperitoneal administration of an oncolytic virus, which contains a nucleic acid encoding protein A56, and then identifying expression of the protein A56 on the surface of each tissue.

FIG. 5 illustrates results obtained by subjecting normal rabbits to intraperitoneal administration of an oncolytic virus, which contains a nucleic acid encoding protein A56, and then identifying expression of the protein A56 on the surface of each tissue.

FIG. 6 illustrates results obtained by subjecting mouse renal cancer cell line (Renca)-transplanted mice to intratumoral administration of an oncolytic virus, which contains a nucleic acid encoding protein A56, and then identifying expression of the protein A56 on the surface of tumor tissue on days 7, 10, and 14.

Figures 7, 8, 9:
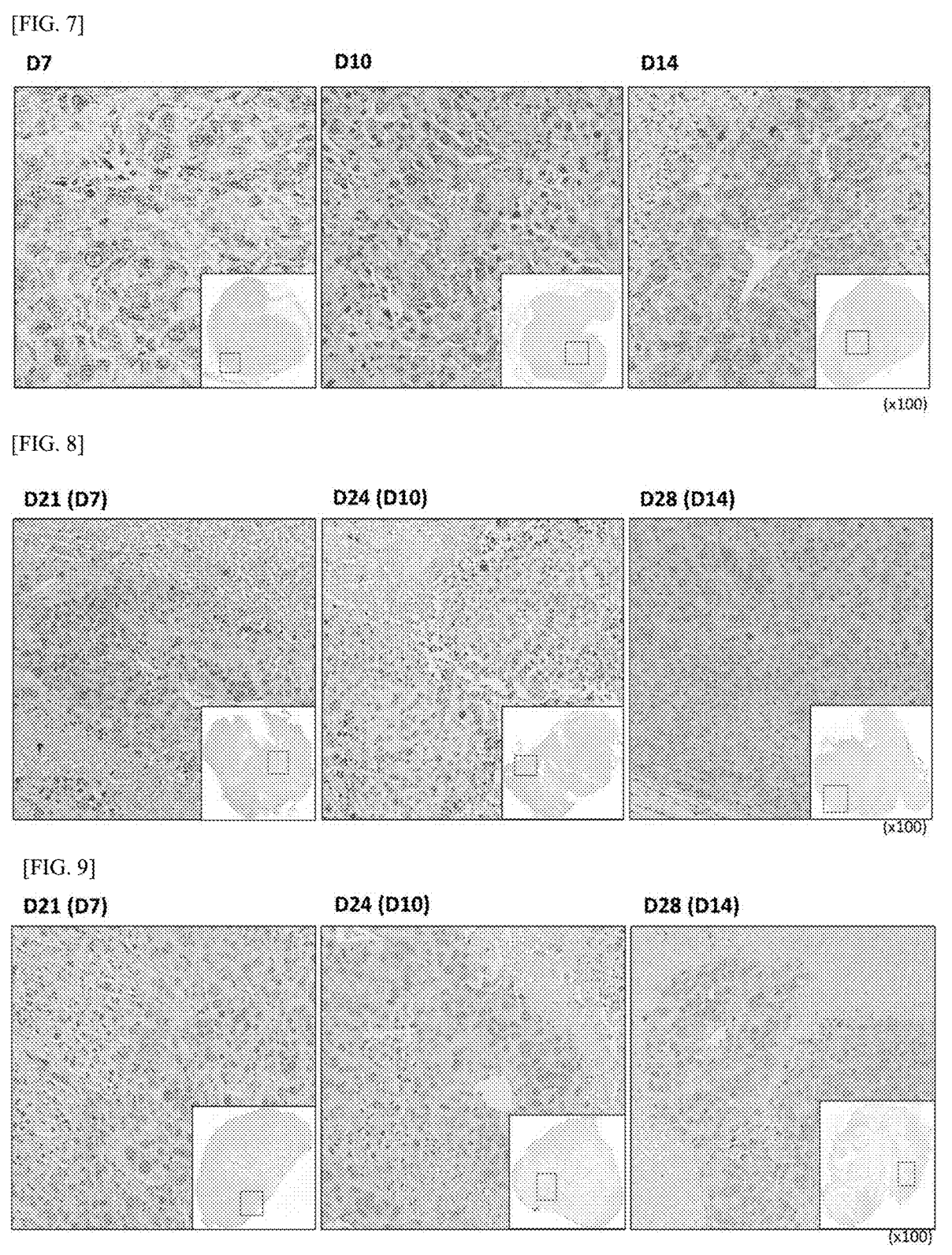

FIG. 7 illustrates results obtained by subjecting mouse renal cancer cell line (Renca)-transplanted mice to intratumoral administration of an oncolytic virus, which contains a nucleic acid encoding protein A56, and hydroxyurea, and then identifying expression of the protein A56 on the surface of tumor tissue on days 7, 10, and 14.

FIG. 8 illustrates results obtained by subjecting the mouse renal cancer cell line (Renca)-transplanted mice to secondary administration of the oncolytic virus, which contains a nucleic acid encoding protein A56, and then identifying expression of the protein A56 on the surface of tumor tissue on days 21, 24, and 28.

FIG. 9 illustrates results obtained by subjecting the mouse renal cancer cell line (Renca)-transplanted mice to secondary administration of the oncolytic virus, which contains a nucleic acid encoding protein A56, and hydroxyurea, and then identifying expression of the protein A56 on the surface of tumor tissue on days 21, 24, and 28.

FIG. 10 illustrates results obtained by subjecting mouse renal cancer cell line (Renca)-transplanted mice to administration of an oncolytic virus, which contains a nucleic acid encoding protein A56, and hydroxyurea, and then measuring mouse tumor volumes.

FIG. 11 illustrates results obtained by subjecting mouse renal cancer cell line (Renca)-transplanted mice to administration of an oncolytic virus, which contains a nucleic acid encoding protein A56, and hydroxyurea, and then measuring mouse body weights.

FIG. 12 illustrates a diagram showing an embodiment for protein A56 and fragments thereof.

4

Figure 99:
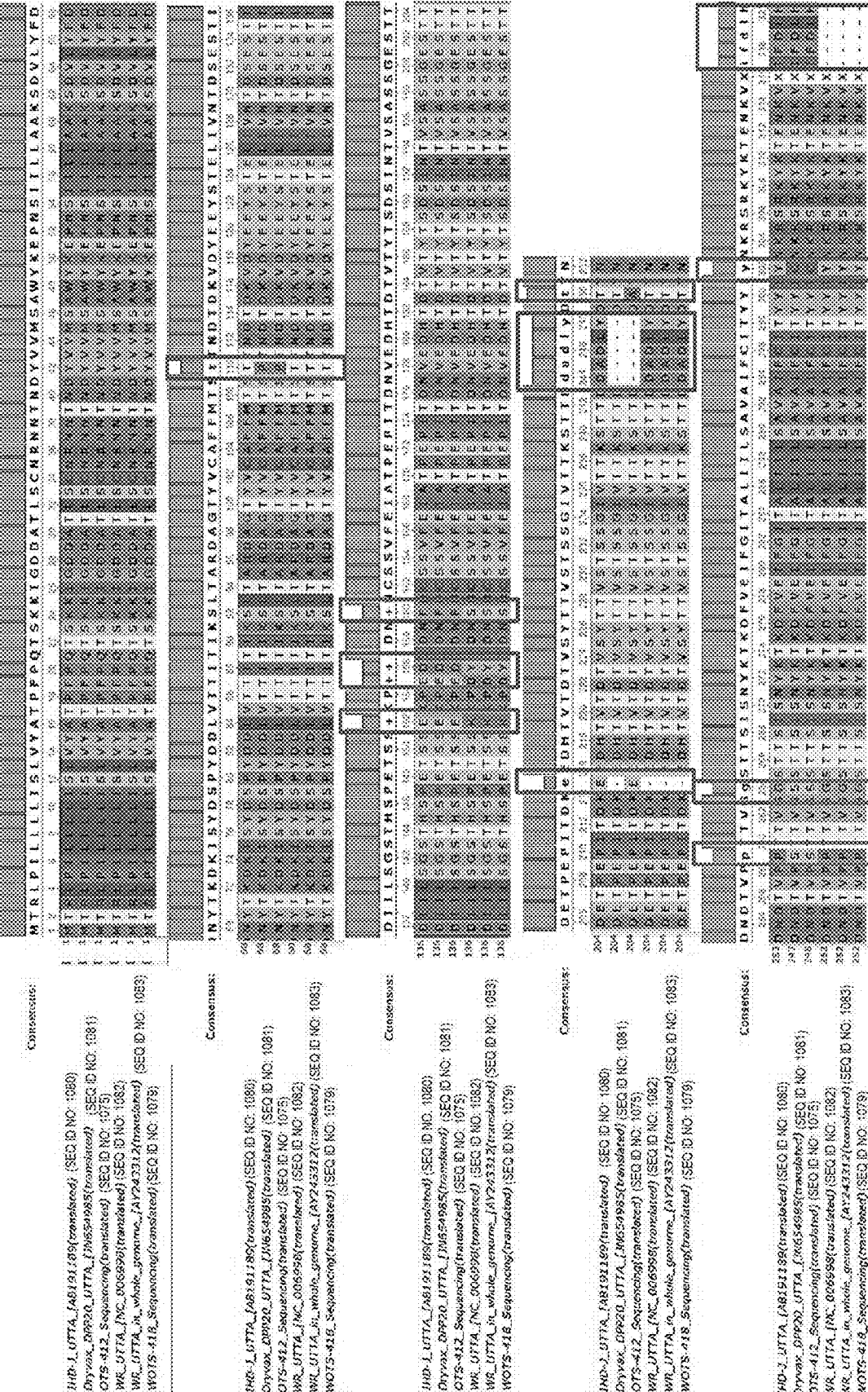

FIG. 13 illustrates results obtained by identifying expression of the protein A56 and fragments thereof on the cell surface.

Figure 14:
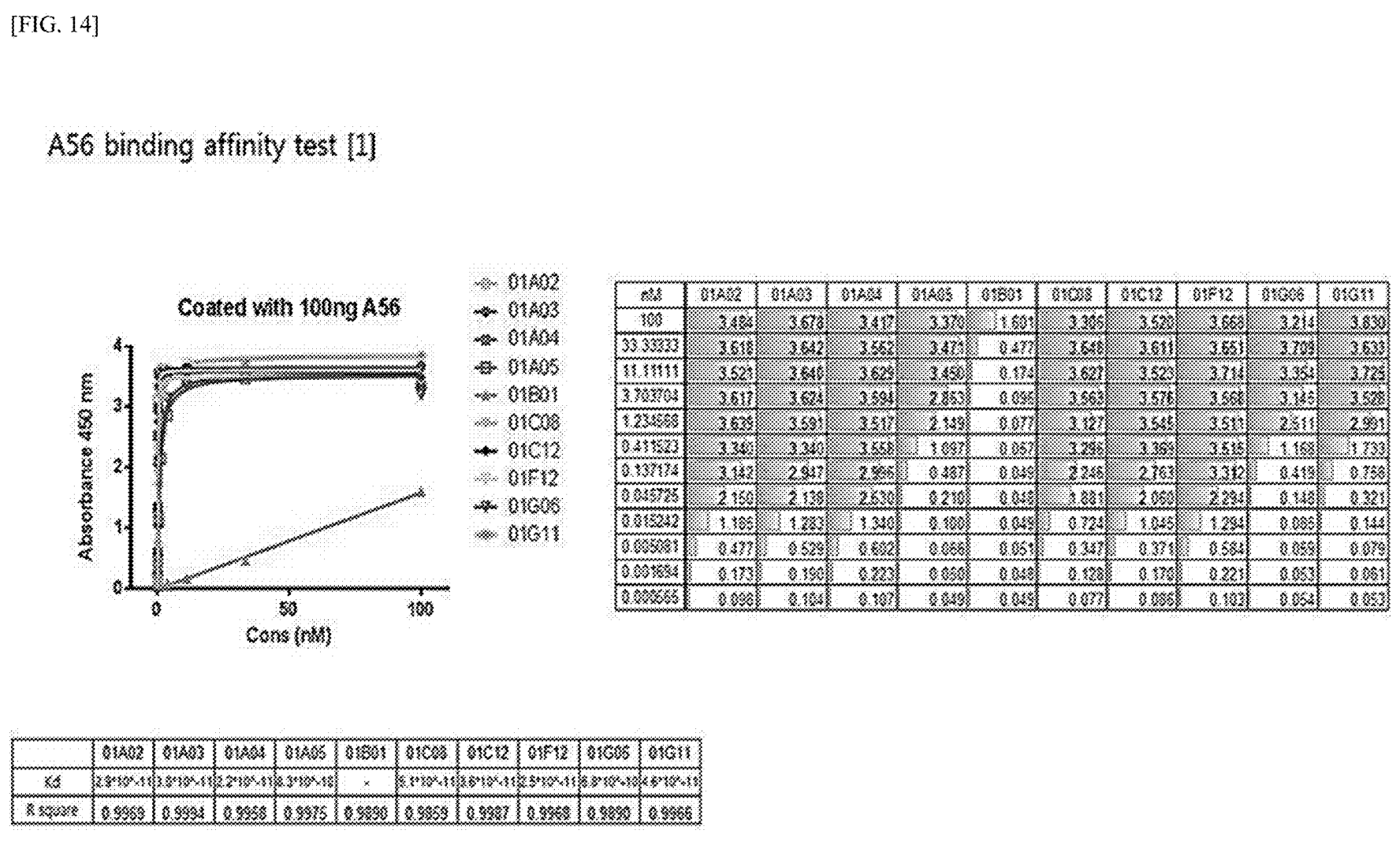
Figure 15:
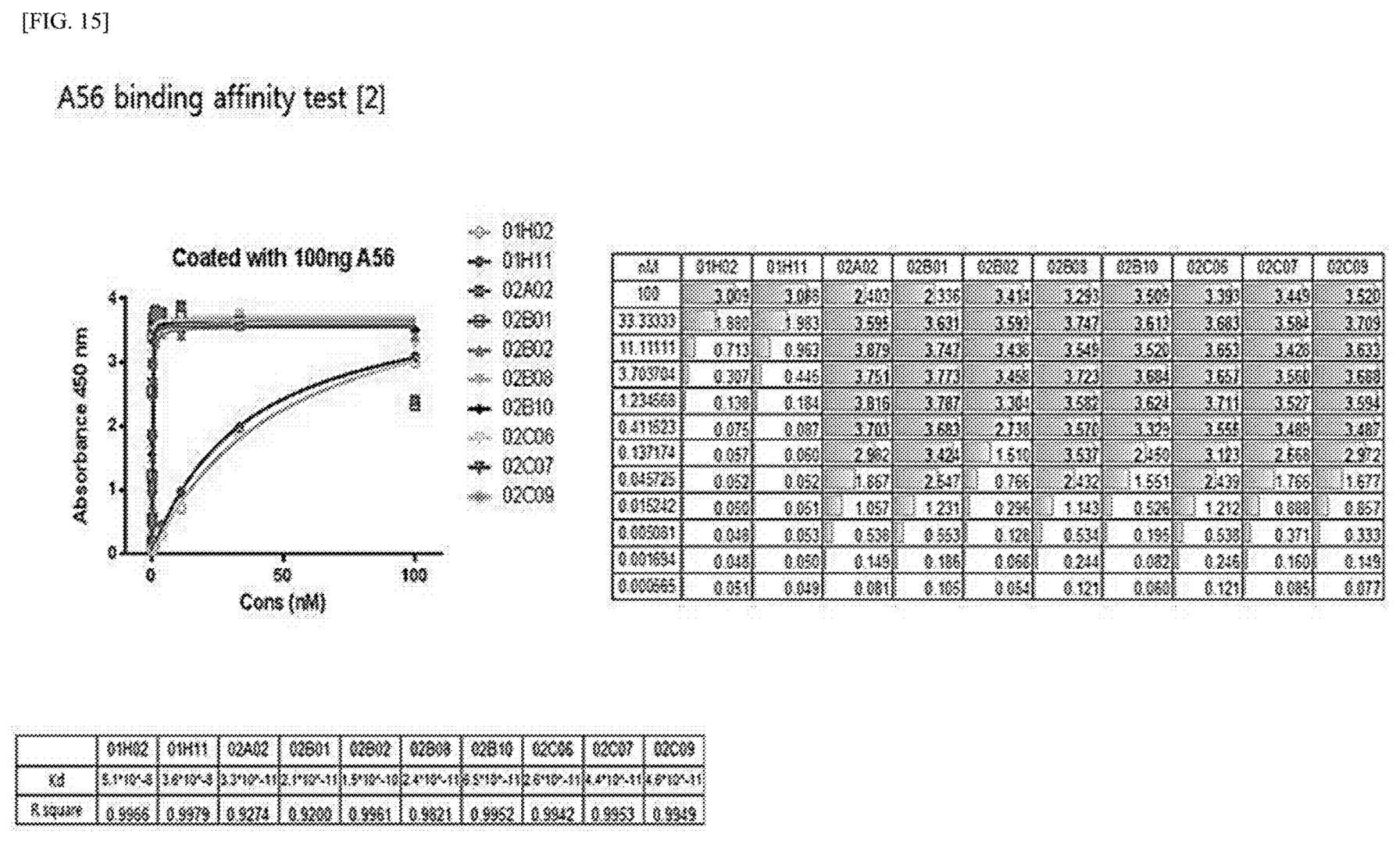
Figure 16:
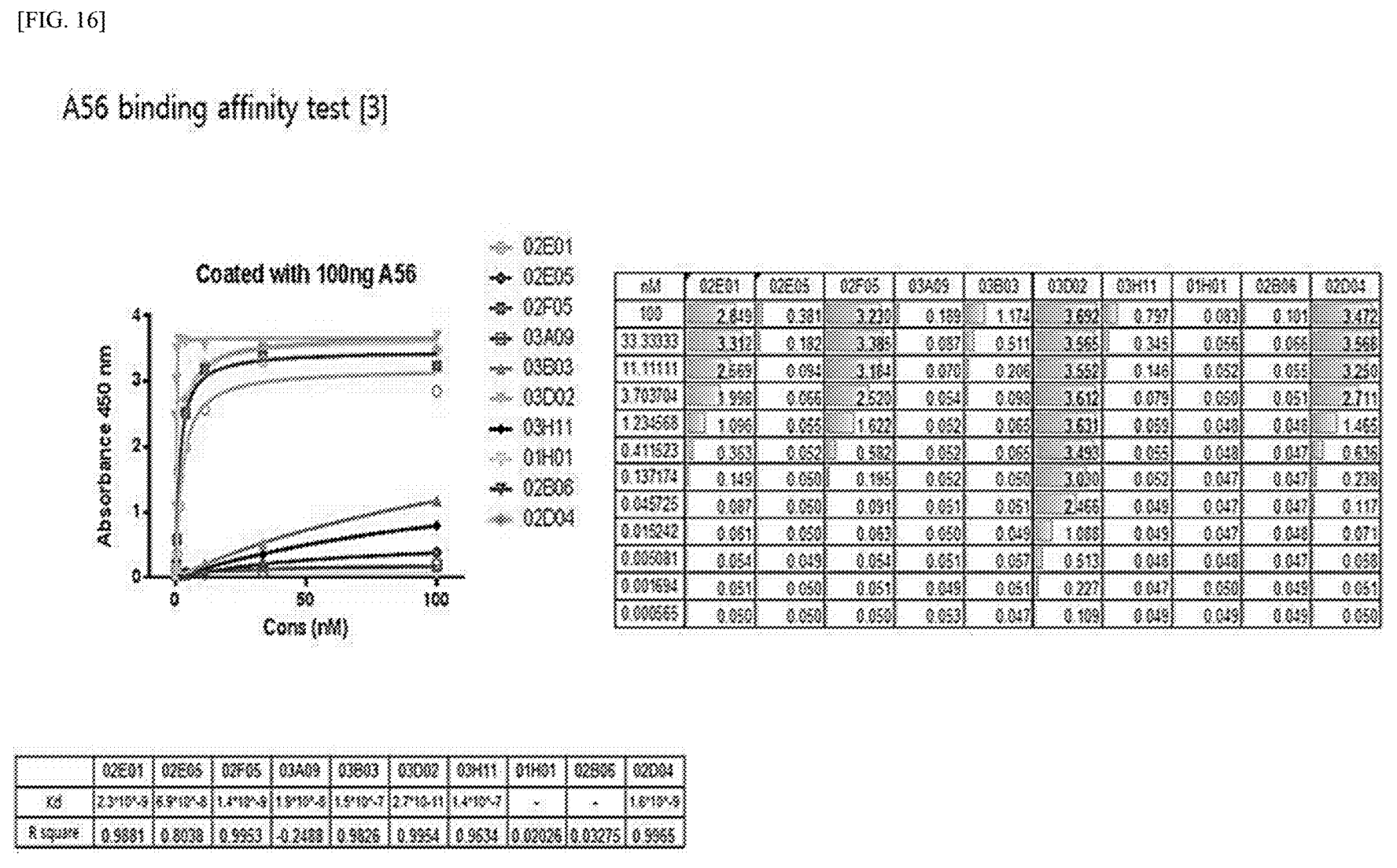
Figure 18:
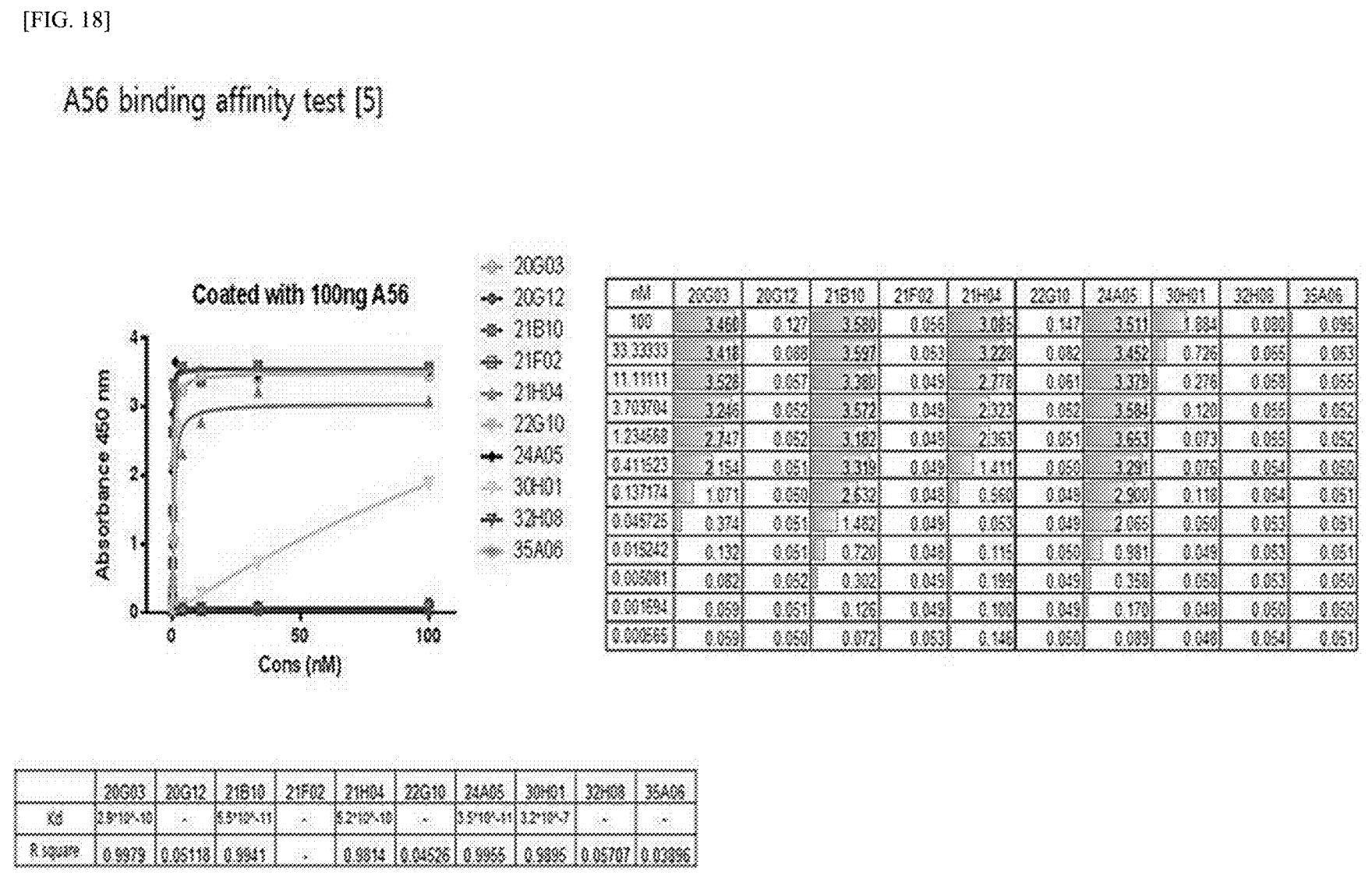
Figure 19:
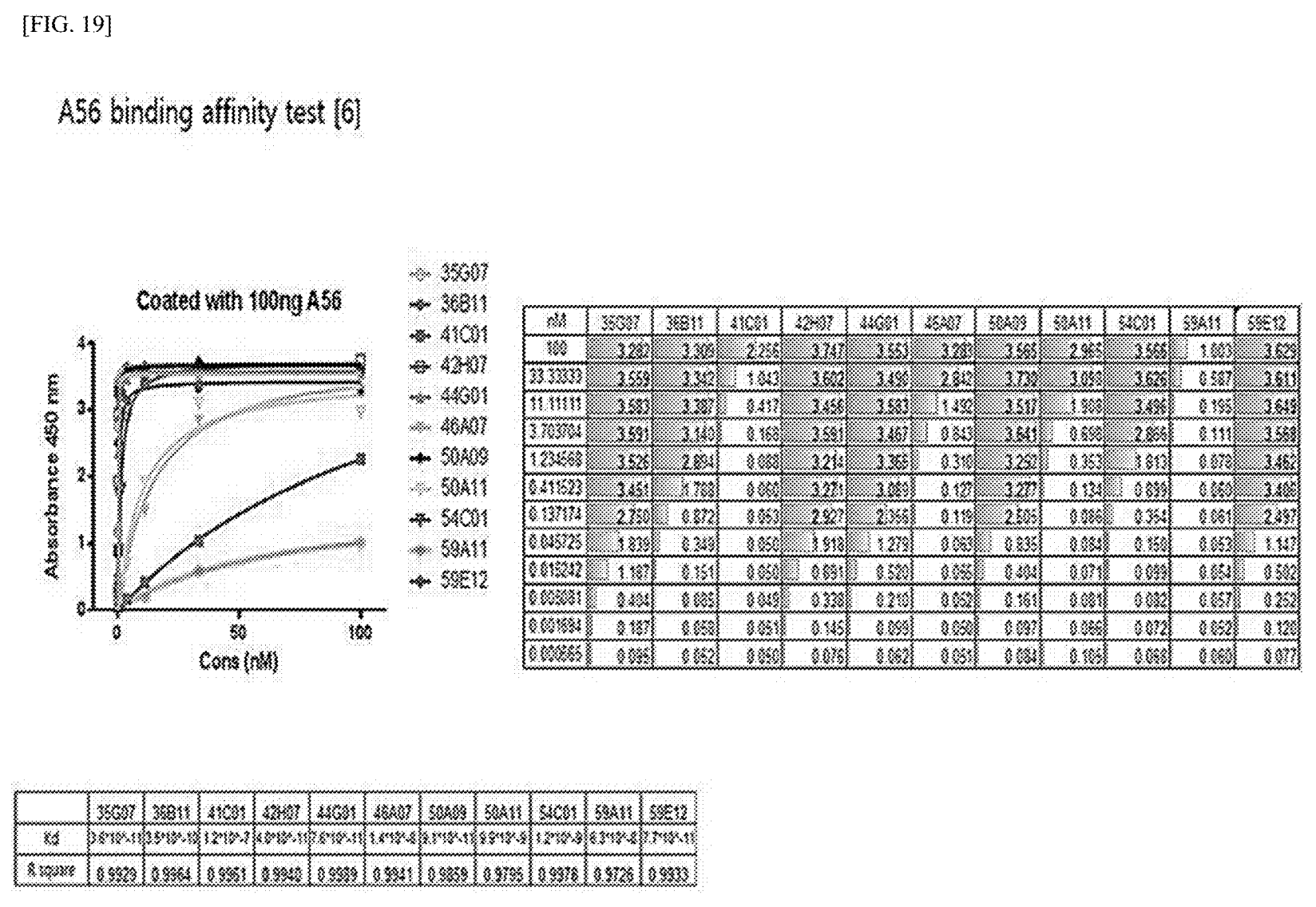

FIGS. 14 to 19 illustrate results obtained by measuring affinity between the produced anti-A56 antibodies and the protein A56.

FIG. 20A illustrates results obtained by identifying productivity of the antibodies A56-01A02 to A56-02B06.

FIG. 20B illustrates a graph showing productivity of the antibodies A56-01A02 to A56-02B06.

FIG. 20C illustrates results obtained by identifying productivity of the antibodies A56-02D04 to A56-59E12.

FIGS. 21 to 37 illustrate results obtained by purifying the produced anti-A56 antibodies, and then identifying these antibodies through SDS-PAGE.

FIG. 38 illustrates results obtained by subjecting HeLa or HT-29 cell line, which has been treated or not treated with the oncolytic virus, to treatment with each of five anti-A56 antibodies, and then performing measurements with flow cytometry.

FIG. 39 illustrates results obtained by subjecting A549, MCF-7, or PC-3 cell line, which has been treated or not treated with the oncolytic virus, to treatment with each of three anti-A56 antibodies, and then performing measurements with flow cytometry.

FIG. 40 illustrates results obtained by subjecting HeLa cell line, which has been treated or not treated with the oncolytic virus, to treatment with an anti-A56 antibody (Antibodies-Online), and then performing FACS analysis.

FIG. 41 illustrates results obtained by subjecting HeLa cell line, which has been treated or not treated with the oncolytic virus, to treatment with an anti-A56 antibody (LakePharma variant3), and then performing FACS analysis.

FIG. 42 illustrates results obtained by subjecting HeLa cell line, which has been treated or not treated with the oncolytic virus, to treatment with an anti-A56 antibody (LakePharma variant4), and then performing FACS analysis.

FIG. 43 illustrates results obtained by subjecting HeLa cell line, which has been treated or not treated with the oncolytic virus, to treatment with an anti-A56 antibody (Antibodies-Online, LakePharma variant3, or LakePharma variant4), and then performing FACS analysis.

FIG. 44 illustrates results obtained by subjecting A549 cancer cell line, which has been treated or not treated with an oncolytic virus (OTS-412, WOTS-418), to treatment with an anti-A56 antibody (Ab18), and then performing measurements with flow cytometry.

FIG. 45 illustrates results obtained by subjecting A549 cancer cell line, which has been treated or not treated with an oncolytic virus (OTS-412, WOTS-418), to treatment with an anti-A56 antibody (Ab19), and then performing measurements with flow cytometry.

FIG. 46 illustrates results obtained by subjecting A549 cancer cell line, which has been treated or not treated with an oncolytic virus (OTS-412, WOTS-418), to treatment with an anti-A56 antibody (Ab101), and then performing measurements with flow cytometry.

FIG. 47 illustrates results obtained by subjecting A549 cancer cell line, which has been treated or not treated with an oncolytic virus (OTS-412, WOTS-418), to treatment with an anti-A56 antibody (Ab13), and then performing measurements with flow cytometry.

FIG. 48 illustrates results obtained by subjecting A549 cancer cell line, which has been treated or not treated with an oncolytic virus (OTS-412, WOTS-418), to treatment with an anti-A56 antibody (Ab14), and then performing measurements with flow cytometry.

FIG. 49 illustrates results obtained by subjecting A549 cancer cell line, which has been treated or not treated with an oncolytic virus (OTS-412, WOTS-418), to treatment with an anti-A56 antibody (Ab08), and then performing measurements with flow cytometry.

FIG. 50 illustrates results obtained by subjecting A549 cancer cell line, which has been treated or not treated with an oncolytic virus (OTS-412, WOTS-418), to treatment with an anti-A56 antibody (Ab03), and then performing measurements with flow cytometry.

FIG. 51 illustrates results obtained by subjecting A549 cancer cell line, which has been treated or not treated with an oncolytic virus (OTS-412, WOTS-418), to treatment with an anti-A56 antibody (Ab51), and then performing measurements with flow cytometry.

FIG. 52 illustrates results obtained by subjecting A549 cancer cell line, which has been treated or not treated with an oncolytic virus (OTS-412, WOTS-418), to treatment with an anti-A56 antibody (Ab55), and then performing measurements with flow cytometry.

FIG. 53 illustrates results obtained by subjecting A549 cancer cell line, which has been treated or not treated with an oncolytic virus (OTS-412, WOTS-418), to treatment with an anti-A56 antibody (Ab16), and then performing measurements with flow cytometry.

FIG. 54 illustrates results obtained by subjecting A549 cancer cell line, which has been treated or not treated with an oncolytic virus (OTS-412, WOTS-418), to treatment with an anti-A56 antibody (LP variant3), and then performing measurements with flow cytometry.

FIG. 55 illustrates results obtained by subjecting A549 cancer cell line, which has been treated or not treated with an oncolytic virus (OTS-412, WOTS-418), to treatment with an anti-A56 antibody (LP variant4), and then performing measurements with flow cytometry.

FIG. 56 illustrates results obtained by subjecting A549 cancer cell line, which has been treated or not treated with an oncolytic virus (OTS-412), to treatment with an anti-A56 antibody (Ab18, Ab19, Ab01, Ab13, Ab14, Ab08, Ab03, Ab51, Ab55, Ab16), and then performing measurements with flow cytometry.

FIG. 57 illustrates results obtained by subjecting A549 cancer cell line, which has been treated or not treated with an oncolytic virus (WOTS-418), to treatment with an anti-A56 antibody (Ab18, Ab19, Ab01, Ab13, Ab14, Ab08, Ab03, Ab51, Ab55, Ab16), and then performing measurements with flow cytometry.

FIG. 58 illustrates results obtained by subjecting A549 cancer cell line, which has been treated or not treated with an oncolytic virus (OTS-412), to treatment with an anti-A56 antibody (Ab18, Ab16), and then performing measurements with flow cytometry.

FIG. 59 illustrates results obtained by subjecting A549 cancer cell line, which has been treated or not treated with an oncolytic virus (WOTS-418), to treatment with an anti-A56 antibody (Ab18, Ab16), and then performing measurements with flow cytometry.

FIG. 60 illustrates results obtained by subjecting A549 cancer cell line, which has been treated or not treated with an oncolytic virus (OTS-412), to treatment with LakePharma variant3 or LakePharma variant4, and then performing measurements with flow cytometry.

FIG. 61 illustrates results obtained by subjecting A549 cancer cell line, which has been treated or not treated with an oncolytic virus (WOTS-418), to treatment with LakePharma variant3 or LakePharma variant4, and then performing measurements with flow cytometry.

FIG. 62 illustrates results obtained by subjecting PC3 cancer cell line, which has been treated or not treated with an oncolytic virus (OTS-412, WOTS-418), to treatment with an anti-A56 antibody (Ab18), and then performing measurements with flow cytometry.

FIG. 63 illustrates results obtained by subjecting PC3 cancer cell line, which has been treated or not treated with an oncolytic virus (OTS-412, WOTS-418), to treatment with an anti-A56 antibody (Ab19), and then performing measurements with flow cytometry.

FIG. 64 illustrates results obtained by subjecting PC3 cancer cell line, which has been treated or not treated with an oncolytic virus (OTS-412, WOTS-418), to treatment with an anti-A56 antibody (Ab01), and then performing measurements with flow cytometry.

FIG. 65 illustrates results obtained by subjecting PC3 cancer cell line, which has been treated or not treated with an oncolytic virus (OTS-412, WOTS-418), to treatment with an anti-A56 antibody (Ab13), and then performing measurements with flow cytometry.

FIG. 66 illustrates results obtained by subjecting PC3 cancer cell line, which has been treated or not treated with an oncolytic virus (OTS-412, WOTS-418), to treatment with an anti-A56 antibody (Ab14), and then performing measurements with flow cytometry.

FIG. 67 illustrates results obtained by subjecting PC3 cancer cell line, which has been treated or not treated with an oncolytic virus (OTS-412, WOTS-418), to treatment with an anti-A56 antibody (Ab08), and then performing measurements with flow cytometry.

FIG. 68 illustrates results obtained by subjecting PC3 cancer cell line, which has been treated or not treated with an oncolytic virus (OTS-412, WOTS-418), to treatment with an anti-A56 antibody (Ab03), and then performing measurements with flow cytometry.

FIG. 69 illustrates results obtained by subjecting PC3 cancer cell line, which has been treated or not treated with an oncolytic virus (OTS-412, WOTS-418), to treatment with an anti-A56 antibody (Ab51), and then performing measurements with flow cytometry.

FIG. 70 illustrates results obtained by subjecting PC3 cancer cell line, which has been treated or not treated with an oncolytic virus (OTS-412, WOTS-418), to treatment with an anti-A56 antibody (Ab55), and then performing measurements with flow cytometry.

FIG. 71 illustrates results obtained by subjecting PC3 cancer cell line, which has been treated or not treated with an oncolytic virus (OTS-412, WOTS-418), to treatment with an anti-A56 antibody (Ab16), and then performing measurements with flow cytometry.

FIG. 72 illustrates results obtained by subjecting PC3 cancer cell line, which has been treated or not treated with an oncolytic virus (OTS-412, WOTS-418), to treatment with an anti-A56 antibody (LP variant3), and then performing measurements with flow cytometry.

FIG. 73 illustrates results obtained by subjecting PC3 cancer cell line, which has been treated or not treated with an oncolytic virus (OTS-412, WOTS-418), to treatment with an anti-A56 antibody (LP variant4), and then performing measurements with flow cytometry.

FIG. 74 illustrates results obtained by subjecting PC3 cancer cell line, which has been treated or not treated with an oncolytic virus (OTS-412), to treatment with an anti-A56 antibody (Ab18, Ab19, Ab01, Ab13, Ab14, Ab08, Ab03, Ab51, Ab55, Ab16), and then performing measurements with flow cytometry.

FIG. 75 illustrates results obtained by subjecting PC3 cancer cell line, which has been treated or not treated with an oncolytic virus (WOTS-418), to treatment with an anti-A56 antibody (Ab18, Ab19, Ab01, Ab13, Ab14, Ab08, Ab03, Ab51, Ab55, Ab16), and then performing measurements with flow cytometry.

FIG. 76 illustrates results obtained by subjecting PC3 cancer cell line, which has been treated or not treated with an oncolytic virus (OTS-412), to treatment with an anti-A56 antibody (Ab18, Ab16), and then performing measurements with flow cytometry.

FIG. 77 illustrates results obtained by subjecting PC3 cancer cell line, which has been treated or not treated with an oncolytic virus (WOTS-418), to treatment with an anti-A56 antibody (Ab18, Ab16), and then performing measurements with flow cytometry.

FIG. 78 illustrates results obtained by subjecting PC3 cancer cell line, which has been treated or not treated with an oncolytic virus (OTS-412), to treatment with LakePharma variant3 or LakePharma variant4, and then performing measurements with flow cytometry.

FIG. 79 illustrates results obtained by subjecting PC3 cancer cell line, which has been treated or not treated with an oncolytic virus (WOTS-418), to treatment with LakePharma variant3 or LakePharma variant4, and then performing measurements with flow cytometry.

FIG. 80 illustrates results obtained by subjecting MCF7 cancer cell line, which has been treated or not treated with an oncolytic virus (OTS-412, WOTS-418), to treatment with an anti-A56 antibody (Ab18), and then performing measurements with flow cytometry.

FIG. 81 illustrates results obtained by subjecting MCF7 cancer cell line, which has been treated or not treated with an oncolytic virus (OTS-412, WOTS-418), to treatment with an anti-A56 antibody (Ab19), and then performing measurements with flow cytometry.

FIG. 82 illustrates results obtained by subjecting MCF7 cancer cell line, which has been treated or not treated with an oncolytic virus (OTS-412, WOTS-418), to treatment with an anti-A56 antibody (Ab01), and then performing measurements with flow cytometry.

FIG. 83 illustrates results obtained by subjecting MCF7 cancer cell line, which has been treated or not treated with an oncolytic virus (OTS-412, WOTS-418), to treatment with an anti-A56 antibody (Ab13), and then performing measurements with flow cytometry.

FIG. 84 illustrates results obtained by subjecting MCF7 cancer cell line, which has been treated or not treated with an oncolytic virus (OTS-412, WOTS-418), to treatment with an anti-A56 antibody (Ab14), and then performing measurements with flow cytometry.

FIG. 85 illustrates results obtained by subjecting MCF7 cancer cell line, which has been treated or not treated with an oncolytic virus (OTS-412, WOTS-418), to treatment with an anti-A56 antibody (Ab08), and then performing measurements with flow cytometry.

FIG. 86 illustrates results obtained by subjecting MCF7 cancer cell line, which has been treated or not treated with an oncolytic virus (OTS-412, WOTS-418), to treatment with an anti-A56 antibody (Ab03), and then performing measurements with flow cytometry.

FIG. 87 illustrates results obtained by subjecting MCF7 cancer cell line, which has been treated or not treated with an oncolytic virus (OTS-412, WOTS-418), to treatment with an anti-A56 antibody (Ab51), and then performing measurements with flow cytometry.

FIG. 88 illustrates results obtained by subjecting MCF7 cancer cell line, which has been treated or not treated with an oncolytic virus (OTS-412, WOTS-418), to treatment with an anti-A56 antibody (Ab55), and then performing measurements with flow cytometry.

FIG. 89 illustrates results obtained by subjecting MCF7 cancer cell line, which has been treated or not treated with an oncolytic virus (OTS-412, WOTS-418), to treatment with an anti-A56 antibody (Ab16), and then performing measurements with flow cytometry.

FIG. 90 illustrates results obtained by subjecting MCF7 cancer cell line, which has been treated or not treated with an oncolytic virus (OTS-412, WOTS-418), to treatment with an anti-A56 antibody (LP variant3), and then performing measurements with flow cytometry.

FIG. 91 illustrates results obtained by subjecting MCF7 cancer cell line, which has been treated or not treated with an oncolytic virus (OTS-412, WOTS-418), to treatment with an anti-A56 antibody (LP variant4), and then performing measurements with flow cytometry.

FIG. 92 illustrates results obtained by subjecting MCF7 cancer cell line, which has been treated or not treated with an oncolytic virus (OTS-412), to treatment with an anti-A56 antibody (Ab18, Ab19, Ab01, Ab13, Ab14, Ab08, Ab03, Ab51, Ab55, Ab16), and then performing measurements with flow cytometry.

FIG. 93 illustrates results obtained by subjecting MCF7 cancer cell line, which has been treated or not treated with an oncolytic virus (WOTS-418), to treatment with an anti-A56 antibody (Ab18, Ab19, Ab01, Ab13, Ab14, Ab08, Ab03, Ab51, Ab55, Ab16), and then performing measurements with flow cytometry.

FIG. 94 illustrates results obtained by subjecting MCF7 cancer cell line, which has been treated or not treated with an oncolytic virus (OTS-412), to treatment with LakePharma variant3 or LakePharma variant4, and then performing measurements with flow cytometry.

FIG. 95 illustrates results obtained by subjecting MCF7 cancer cell line, which has been treated or not treated with an oncolytic virus (WOTS-418), to treatment with LakePharma variant3 or LakePharma variant4, and then performing measurements with flow cytometry.

Figure 96:
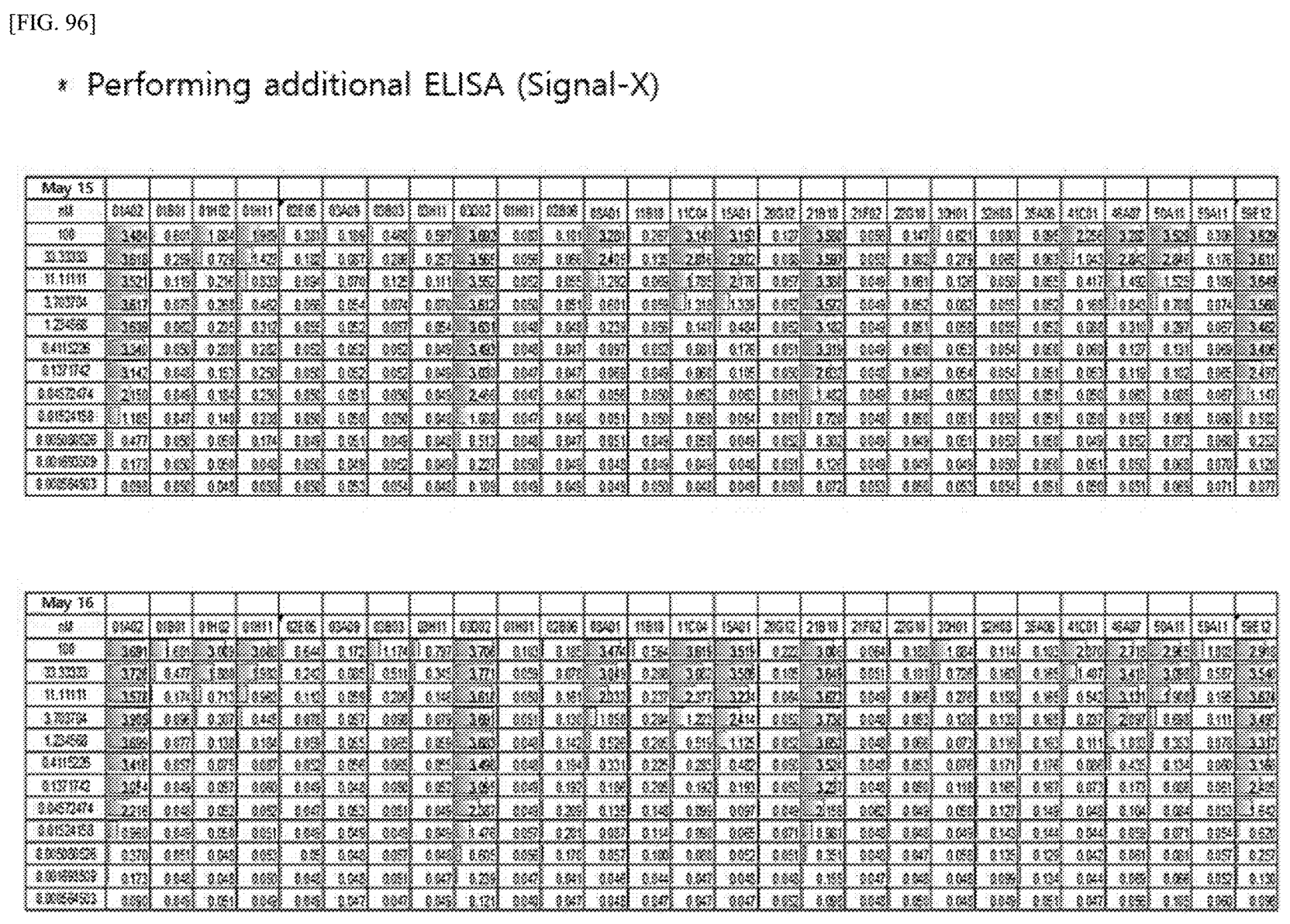

FIG. 96 illustrates results obtained by performing ELISA using the produced antibodies.

FIG. 97 illustrates results obtained by identifying expression levels of Fc-fused A56 fusion proteins.

FIG. 98 illustrates results obtained by identifying expression levels of the produced A56 fragments.

FIG. 99 illustrates results obtained by analyzing sequence homology with respect to the protein A56s in oncolytic viruses (OTS-412 and WOTS-418).

BEST MODE FOR CARRYING OUT THE INVENTION

Hereinafter, the present invention will be described in detail.

In an aspect of the present invention, there is provided an anticancer agent, comprising, as an active ingredient, an antibody or a fragment thereof which specifically binds to protein A56 or a fragment thereof.

As used herein, the term "protein A56" refers to a protein translated from a gene (for example, GeneID: 3707652) represented by A56, A56R, or HA, which is encoded in the gene of a poxviridae family virus after a host cell is infected with the virus. The protein A56 or a fragment thereof may include an amino acid sequence represented by SEQ ID NO: 1038, 1040, 1042, 1044, 1046, 1048, 1050, 1052, 1054, 1056, 1058, 1060, 1073, 1075, 1077, or 1079. The nucleic acid encoding the protein A56 or a fragment thereof may include a nucleotide sequence represented by SEQ ID NO: 1039, 1041, 1043, 1045, 1047, 1049, 1051, 1053, 1055, 1057, 1059, 1061, 1072, 1074, 1076, or 1078.

Specifically, the protein A56 may be wild-type protein A56 or a variant thereof. The wild-type protein A56 may have an amino acid sequence represented by SEQ ID NO: 1038 or 1073. In addition, the nucleic acid encoding the wild-type protein A56 may be a nucleotide sequence represented by SEQ ID NO: 1039 or 1072.

In addition, the protein A56 variant may have undergone substitution, deletion, or addition of one or more amino acids as long as the variant can be located on the cancer cell surface like the protein A56. The nucleotide sequence encoding the protein A56 variant may be a nucleotide sequence that encodes an amino acid sequence having a sequence homology of at least 60%, at least 70%, at least 80%, or at least 90% to an amino acid sequence represented by SEQ ID NO: 1038 or 1073, and may be most preferably a nucleotide sequence that encodes an amino acid sequence having a sequence homology of at least 95% thereto. Specifically, the protein A56 variant may include an amino acid sequence represented by SEQ ID NO: 1075 or 1079. The nucleic acid encoding the protein A56 variant may include a nucleotide sequence represented by SEQ ID NO: 1074 or 1078.

The protein A56 fragment may be a polypeptide including an amino acid sequence represented by SEQ ID NO: 1040, 1042, 1044, 1046, 1048, 1050, 1052, 1054, 1056, 1058, 1060, or 1077. In addition, the nucleic acid encoding the fragment may be a nucleotide sequence encoding a polypeptide represented by SEQ ID NO: 1040, 1042, 1044, 1046, 1048, 1050, 1052, 1054, 1056, 1058, 1060, or 1076. Specifically, the nucleotide sequence encoding the polypeptide represented by SEQ ID NO: 1040, 1042, 1044, 1046, 1048, 1050, 1052, 1054, 1056, 1058, 1060, or 1077 may be represented by SEQ ID NO: 1041, 1043, 1045, 1047, 1049, 1051, 1053, 1055, 1057, 1059, 1061, or 1076, respectively, in the order mentioned.

In addition, the nucleotide sequence encoding the protein A56 fragment may be a nucleotide sequence that encodes an amino acid sequence having a sequence homology of at least 60%, at least 70%, at least 80%, or at least 90% to an amino acid sequence represented by SEQ ID NO: 1040, 1042, 1044, 1046, 1048, 1050, 1052, 1054, 1056, 1058, 1060, or 1077, and may be most preferably a nucleotide sequence that encodes an amino acid sequence having sequence homology of at least 95% thereto.

As used herein, the term "antibody" refers to an immune protein that binds to an antigen and interferes with the action thereof, or removes the antigen. There are five types of antibodies: IgM, IgD, IgG, IgA, and IgE, each of which contains a heavy chain produced from the heavy chain constant region gene μ, δ, γ, α, or ε. In antibody techniques, IgG is mainly used. IgG includes four isotypes of IgG1, IgG2, IgG3, and IgG4, each of which may have different structural and functional properties.

The IgG forms a very stable Y-shaped structure (molecular weight: about 150 kDa) made of two heavy chain (about 50 kDa) proteins and two light chain (about 25 kDa) proteins. An antibody has a light chain and a heavy chain, and each chain is divided into a variable region whose amino acid sequence differs from antibody to antibody, and a constant region whose amino acid sequence is the same among antibodies. The heavy chain constant region includes CH1, H (hinge), CH2, CH3 domains. Each of the domains consists of two β-sheets, and these domains are linked by intramolecular disulfide bonds. The two variable regions in the heavy and light chains associate together to form an antigen-binding site. The site exists in each of the two arms on the Y-shape. In the Y-shape, the part capable of binding to an antigen is called an antibody binding fragment (Fab), and the part that does not bind to an antigen is called a crystalizable fragment (Fc). Fab and Fc are connected by a flexible hinge region.

As used herein, the term "CDR" refers to a site that binds to an antigen, the site being a hypervariable region present in heavy and light chain variable regions of an antibody and whose amino acid sequence differs from antibody to antibody. Looking at the three-dimensional structure of an antibody, CDR is in a loop shape on the antibody surface; and below the loop, there is a framework region (FR) that structurally supports CDR. Each of the heavy and light chains has three loop structures, and these six loop-region structures associate with each other to come in direct contact with an antigen. Antigen-binding sites on the six loop-region structures are referred to as CDR1, CDR2, CDR3, CDR4, CDR5, and CDR6, respectively, for convenience.

In addition, the antibody fragment may be any one selected from the group consisting of Fab, scFv, F (ab) 2, and Fv. The antibody fragments refer to antigen-binding domains, excluding the crystalizable region (Fc region) that has an effector function to transmit antigen-binding stimulation to cells, complements, or the like, and may include third-generation antibody fragments such as single domain antibody or minibody.

In addition, the antibody fragment has the following advantages: the antibody fragment is smaller in size than a fully-structured IgG, which results in improved penetration into tissues or tumors; and the antibody fragment can be produced in bacteria, which decreases production costs. In addition, the antibody fragment does not have Fc, and thus is used in a case where the function of transmitting antigen-binding stimulation to cells, complements, or the like is not desired. The antibody fragment has a short half-life in the human body, and thus is suitable for in vivo diagnostics; however, replacement of some basic, acidic, or neutral amino acids, which are in the amino acids constituting an antibody, may change a unique isoelectric point (pI) of the antibody. Such a change in the isoelectric point of the antibody may induce changes such as decreasing in vivo toxic side effects of the antibody or increasing water solubility of the antibody. Thus, for a therapeutic antibody, a fully-structured IgG can be used in consideration of affinity or structural form.

The antibody can be easily produced by known monoclonal antibody production techniques. A method for producing a monoclonal antibody may be performed by preparing a hybridoma using B lymphocytes obtained from an immunized animal, or may be performed by using a phage display technique. However, the present invention is not limited thereto.

The antibody or a fragment thereof may include:
a heavy chain variable region (VH), including a heavy chain CDR1 selected from the group consisting of SEQ ID NOs: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 919, 936, 953, 970, 987, 1004, 1021, 1062, and 1063;

a heavy chain CDR2 selected from the group consisting of SEQ ID NOs: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, and 1064; and a heavy chain CDR3 selected from the group consisting of SEQ ID NOs: 3, 20, 37, 54, 71, 88, 105, 122, 139, 156, 173, 190, 207, 224, 241, 258, 275, 292, 309, 326, 343, 360, 377, 394, 411, 428, 445, 462, 479, 496, 513, 530, 547, 564, 581, 598, 615, 632, 649, 666, 683, 700, 717, 734, 751, 768, 785, 802, 819, 836, 853, 870, 887, 904, 921, 938, 955, 972, 989, 1006, 1023, and 1065; and a light chain variable region (VL), including a light chain CDR1 selected from the group consisting of SEQ ID NOs: 4, 21, 38, 55, 72, 89, 106, 123, 140, 157, 174, 191, 208, 225, 242, 259, 276, 293, 310, 327, 344, 361, 378, 395, 412, 429, 446, 463, 480, 497, 514, 531, 548, 565, 582, 599, 616, 633, 650, 667, 684, 701, 718, 735, 752, 769, 786, 803, 820, 837, 854, 871, 888, 905, 922, 939, 956, 973, 990, 1007, 1024, and 1066;

a light chain CDR2 selected from the group consisting of SEQ ID NOs: 5, 22, 39, 56, 73, 90, 107, 124, 141, 158, 175, 192, 209, 226, 243, 260, 277, 294, 311, 328, 345, 362, 379, 396, 413, 430, 447, 464, 481, 498, 515, 532, 549, 566, 583, 600, 617, 634, 651, 668, 685, 702, 719, 736, 753, 770, 787, 804, 821, 838, 855, 872, 889, 906, 923, 940, 957, 974, 991, 1008, 1025, and 1067; and a light chain CDR3 selected from the group consisting of SEQ ID NOs: 6, 23, 40, 57, 74, 91, 108, 125, 142, 159, 176, 193, 210, 227, 244, 261, 278, 295, 312, 329, 346, 363, 380, 397, 414, 431, 448, 465, 482, 499, 516, 533, 550, 567, 584, 601, 618, 635, 652, 669, 686, 703, 720, 737, 754, 771, 788, 805, 822, 839, 856, 873, 890, 907, 924, 941, 958, 975, 992, 1009, 1026, and 1068.

The antibody or a fragment thereof may include:

a heavy chain variable region (VH), including a heavy chain CDR1 having an amino acid sequence of SEQ ID NO: 1, 35, 120, 222, 239, 290, 324, 341, 851, 919, 1062, or 1063;

a heavy chain CDR 2 having an amino acid sequence of SEQ ID NO: 2, 36, 121, 223, 240, 291, 325, 342, 852, 920, or 1064; and a heavy chain CDR3 having an amino acid sequence of SEQ ID NO: 3, 37, 122, 224, 241, 292, 326, 343, 853, 921, or 1065; and a light chain variable region (VL), including a light chain CDR1 having an amino acid sequence of SEQ ID NO: 4, 38, 123, 225, 242, 293, 327, 344, 854, 922, or 1066;

a light chain CDR2 having an amino acid sequence of SEQ ID NO: 5, 39, 124, 226, 243, 294, 328, 345, 855, 923 or 1067; and a light chain CDR3 having an amino acid sequence of SEQ ID NO: 6, 40, 125, 227, 244, 295, 329, 346, 856, 924, or 1068.

The antibody or a fragment thereof may include a heavy chain variable region (VH), including a heavy chain CDR1 having an amino acid sequence of SEQ ID NO: 1; a heavy chain CDR2 having an amino acid sequence of SEQ ID NO: 2; and a heavy chain CDR3 having an amino acid sequence of SEQ ID NO: 3; and a light chain variable region (VL), including a light chain CDR1 having an amino acid sequence of SEQ ID NO: 4; a light chain CDR2 having an amino acid sequence of SEQ ID NO: 5; and a light chain CDR3 having an amino acid sequence of SEQ ID NO: 6.

The antibody or a fragment thereof may include a heavy chain variable region (VH), including a heavy chain CDR1 having an amino acid sequence of SEQ ID NO: 35; a heavy chain CDR2 having an amino acid sequence of SEQ ID NO: 36; and a heavy chain CDR3 having an amino acid sequence of SEQ ID NO: 37; and a light chain variable region (VL), including a light chain CDR1 having an amino acid sequence of SEQ ID NO: 38; a light chain CDR2 having an amino acid sequence of SEQ ID NO: 39; and a light chain CDR3 having an amino acid sequence of SEQ ID NO: 40.

The antibody or a fragment thereof may include a heavy chain variable region (VH), including a heavy chain CDR1 having an amino acid sequence of SEQ ID NO: 120; a heavy chain CDR2 having an amino acid sequence of SEQ ID NO: 121; and a heavy chain CDR3 having an amino acid sequence of SEQ ID NO: 122; and a light chain variable region (VL), including a light chain CDR1 having an amino acid sequence of SEQ ID NO: 123; a light chain CDR2 having an amino acid sequence of SEQ ID NO: 124; and a light chain CDR3 having an amino acid sequence of SEQ ID NO: 125.

The antibody or a fragment thereof may include a heavy chain variable region (VH), including a heavy chain CDR1 having an amino acid sequence of SEQ ID NO: 222; a heavy chain CDR2 having an amino acid sequence of SEQ ID NO: 223; and a heavy chain CDR3 having an amino acid sequence of SEQ ID NO: 224; and a light chain variable region (VL), including a light chain CDR1 having an amino acid sequence of SEQ ID NO: 225; a light chain CDR2 having an amino acid sequence of SEQ ID NO: 226; and a light chain CDR3 having an amino acid sequence of SEQ ID NO: 227.

The antibody or a fragment thereof may include a heavy chain variable region (VH), including a heavy chain CDR1 having an amino acid sequence of SEQ ID NO: 239; a heavy chain CDR2 having an amino acid sequence of SEQ ID NO: 240; and a heavy chain CDR3 having an amino acid sequence of SEQ ID NO: 241; and a light chain variable region (VL), including a light chain CDR1 having an amino acid sequence of SEQ ID NO: 242; a light chain CDR2 having an amino acid sequence of SEQ ID NO: 243; and a light chain CDR3 having an amino acid sequence of SEQ ID NO: 244.

The antibody or a fragment thereof may include a heavy chain variable region (VH), including a heavy chain CDR1 having an amino acid sequence of SEQ ID NO: 290; a heavy chain CDR2 having an amino acid sequence of SEQ ID NO: 291; and a heavy chain CDR3 having an amino acid sequence of SEQ ID NO: 292; and a light chain variable region (VL), including a light chain CDR1 having an amino acid sequence of SEQ ID NO: 293; a light chain CDR2 having an amino acid sequence of SEQ ID NO: 294; and a light chain CDR3 having an amino acid sequence of SEQ ID NO: 295.

The antibody or a fragment thereof may include a heavy chain variable region (VH), including a heavy chain CDR1 having an amino acid sequence of SEQ ID NO: 324; a heavy chain CDR2 having an amino acid sequence of SEQ ID NO: 325; and a heavy chain CDR3 having an amino acid sequence of SEQ ID NO: 326; and a light chain variable region (VL), including a light chain CDR1 having an amino acid sequence of SEQ ID NO: 327; a light chain CDR2 having an amino acid sequence of SEQ ID NO: 328; and a light chain CDR3 having an amino acid sequence of SEQ ID NO: 329.

The antibody or a fragment thereof may include a heavy chain variable region (VH), including a heavy chain CDR1 having an amino acid sequence of SEQ ID NO: 341; a heavy chain CDR2 having an amino acid sequence of SEQ ID NO: 342; and a heavy chain CDR3 having an amino acid sequence of SEQ ID NO: 343; and a light chain variable region (VL), including a light chain CDR1 having an amino acid sequence of SEQ ID NO: 344; a light chain CDR2 having an amino acid sequence of SEQ ID NO: 345; and a light chain CDR3 having an amino acid sequence of SEQ ID NO: 346.

The antibody or a fragment thereof may include a heavy chain variable region (VH), including a heavy chain CDR1 having an amino acid sequence of SEQ ID NO: 851; a heavy chain CDR2 having an amino acid sequence of SEQ ID NO: 852; and a heavy chain CDR3 having an amino acid sequence of SEQ ID NO: 853; and a light chain variable region (VL), including a light chain CDR1 having an amino acid sequence of SEQ ID NO: 854; a light chain CDR2 having an amino acid sequence of SEQ ID NO: 855; and a light chain CDR3 having an amino acid sequence of SEQ ID NO: 856.

The antibody or a fragment thereof may include a heavy chain variable region (VH), including a heavy chain CDR1 having an amino acid sequence of SEQ ID NO: 919; a heavy chain CDR2 having an amino acid sequence of SEQ ID NO: 920; and a heavy chain CDR3 having an amino acid sequence of SEQ ID NO: 921; and a light chain variable region (VL), including a light chain CDR1 having an amino acid sequence of SEQ ID NO: 922; a light chain CDR2 having an amino acid sequence of SEQ ID NO: 923; and a light chain CDR3 having an amino acid sequence of SEQ ID NO: 924.

The antibody or a fragment thereof may include a heavy chain variable region (VH), including a heavy chain CDR1 having an amino acid sequence of SEQ ID NO: 1062 or 1063; a heavy chain CDR2 having an amino acid sequence of SEQ ID NO: 1064; and a heavy chain CDR3 having an amino acid sequence of SEQ ID NO: 1065; and a light chain variable region (VL), including a light chain CDR1 having an amino acid sequence of SEQ ID NO: 1066; a light chain CDR2 having an amino acid sequence of SEQ ID NO: 1067; and a light chain CDR3 having an amino acid sequence of SEQ ID NO: 1068.

In an embodiment, the antibody or a fragment thereof may include the following combinations of CDRs:

TABLE 1

| Antibody | H-CDR1 (SEQ ID NO) | H-CDR2 (SEQ ID NO) | CDR3 (SEQ ID NO) | CDR1 (SEQ ID NO) | CDR2 (SEQ ID NO) | L-CDR3 (SEQ ID NO) |
|---|---|---|---|---|---|---|
| A56-01A02 (Ab01) | 1 | 2 | 3 | 4 | 5 | 6 |
| A56-01A03 | 18 | 19 | 20 | 21 | 22 | 23 |
| A56-01A04 (Ab03) | 35 | 36 | 37 | 38 | 39 | 40 |
| A56-01A05 | 52 | 53 | 54 | 55 | 56 | 57 |
| A56-01B01 | 69 | 70 | 71 | 72 | 73 | 74 |
| A56-01C08 | 86 | 87 | 88 | 89 | 90 | 91 |
| A56-01C12 | 103 | 104 | 105 | 106 | 107 | 108 |
| A56-01F12 (Ab08) | 120 | 121 | 122 | 123 | 124 | 125 |
| A56-01G06 | 137 | 138 | 139 | 140 | 141 | 142 |
| A56-01G11 | 154 | 155 | 156 | 157 | 158 | 159 |
| A56-01H01 | 171 | 172 | 173 | 174 | 175 | 176 |
| A56-01H02 | 188 | 189 | 190 | 191 | 192 | 193 |
| A56-01H11 | 205 | 206 | 207 | 208 | 209 | 210 |
| A56-02A02 (Ab13) | 222 | 223 | 224 | 225 | 226 | 227 |
| A56-02B01 (Ab14) | 239 | 240 | 241 | 242 | 243 | 244 |
| A56-02B02 | 256 | 257 | 258 | 259 | 260 | 261 |
| A56-02B06 | 273 | 274 | 275 | 276 | 277 | 278 |
| A56-02B08 (Ab16) | 290 | 291 | 292 | 293 | 294 | 295 |
| A56-02B10 | 307 | 308 | 309 | 310 | 311 | 312 |
| A56-02C06 (Ab18) | 324 | 325 | 326 | 327 | 328 | 329 |
| A56-02C07 (Ab19) | 341 | 342 | 343 | 344 | 345 | 346 |
| A56-02C09 | 358 | 359 | 360 | 361 | 362 | 363 |
| A56-02D04 | 375 | 376 | 377 | 378 | 379 | 380 |
| A56-02E01 | 392 | 393 | 394 | 395 | 396 | 397 |
| A56-02E05 | 409 | 410 | 411 | 412 | 413 | 414 |
| A56-02F05 | 426 | 427 | 428 | 429 | 430 | 431 |
| A56-03A09 | 443 | 444 | 445 | 446 | 447 | 448 |
| A56-03B03 | 460 | 461 | 462 | 463 | 464 | 465 |
| A56-03D02 | 477 | 478 | 479 | 480 | 481 | 482 |
| A56-03H11 | 494 | 495 | 496 | 497 | 498 | 499 |
| A56-07A09 | 511 | 512 | 513 | 514 | 515 | 516 |
| A56-08A01 | 528 | 529 | 530 | 531 | 532 | 533 |
| A56-10A01 | 545 | 546 | 547 | 548 | 549 | 550 |
| A56-11B10 | 562 | 563 | 564 | 565 | 566 | 567 |
| A56-11C04 | 579 | 580 | 581 | 582 | 583 | 584 |
| A56-15A01 | 596 | 597 | 598 | 599 | 600 | 601 |
| A56-16E02 | 613 | 614 | 615 | 616 | 617 | 618 |
| A56-18C03 | 630 | 631 | 632 | 633 | 634 | 635 |
| A56-18G02 | 647 | 648 | 649 | 650 | 651 | 652 |

TABLE 1-continued

| Antibody | H-CDR1 (SEQ ID NO) | H-CDR2 (SEQ ID NO) | CDR3 (SEQ ID NO) | CDR1 (SEQ ID NO) | CDR2 (SEQ ID NO) | L-CDR3 (SEQ ID NO) |
|---|---|---|---|---|---|---|
| A56-20A05 | 664 | 665 | 666 | 667 | 668 | 669 |
| A56-20G03 | 681 | 682 | 683 | 684 | 685 | 686 |
| A56-20G12 | 698 | 699 | 700 | 701 | 702 | 703 |
| A56-21B10 | 715 | 716 | 717 | 718 | 719 | 720 |
| A56-21F02 | 732 | 733 | 734 | 735 | 736 | 737 |
| A56-21H04 | 749 | 750 | 751 | 752 | 753 | 754 |
| A56-22G10 | 766 | 767 | 768 | 769 | 770 | 771 |
| A56-24A05 | 783 | 784 | 785 | 786 | 787 | 788 |
| A56-30H01 | 800 | 801 | 802 | 803 | 804 | 805 |
| A56-32H08 | 817 | 818 | 819 | 820 | 821 | 822 |
| A56-35A06 | 834 | 835 | 836 | 837 | 838 | 839 |
| A56-35G07 (Ab51) | 851 | 852 | 853 | 854 | 855 | 856 |
| A56-36B11 | 868 | 869 | 870 | 871 | 872 | 873 |
| A56-41C01 | 885 | 886 | 887 | 888 | 889 | 890 |
| A56-42H07 | 902 | 903 | 904 | 905 | 906 | 907 |
| A56-44G01 (Ab55) | 919 | 920 | 921 | 922 | 923 | 924 |
| A56-46A07 | 936 | 937 | 938 | 939 | 940 | 941 |
| A56-50A09 | 953 | 954 | 955 | 956 | 957 | 958 |
| A56-50A11 | 970 | 971 | 972 | 973 | 974 | 975 |
| A56-54C01 | 987 | 988 | 989 | 990 | 991 | 992 |
| A56-59A11 | 1004 | 1005 | 1006 | 1007 | 1008 | 1009 |
| A56-59E12 | 1021 | 1022 | 1023 | 1024 | 1025 | 1026 |
| LakePharma variant3 | 1062 | 1064 | 1065 | 1066 | 1067 | 1068 |
| LakePharma variant4 | 1063 | | | | | |

In particular, the antibody or a fragment thereof may include a heavy chain variable region having any one amino acid sequence selected from the group consisting of SEQ ID NOs: 8, 25, 42, 59, 76, 93, 110, 127, 144, 161, 178, 195, 212, 229, 246, 263, 280, 297, 314, 331, 348, 365, 382, 399, 416, 433, 450, 467, 484, 501, 518, 535, 552, 569, 586, 603, 620, 637, 654, 671, 688, 705, 722, 739, 756, 773, 790, 807, 824, 841, 858, 875, 892, 909, 926, 943, 960, 977, 994, 1011, 1028, 1069, and 1070.

Specifically, the antibody or a fragment thereof may include a heavy chain variable region having any one amino acid sequence selected from the group consisting of SEQ ID NOs: 8, 42, 127, 229, 246, 297, 331, 348, 858, 926, 1069, and 1070.

In addition, the antibody or a fragment thereof may include a light chain variable region having any one amino acid sequence selected from the group consisting of SEQ ID NOs: SEQ ID NO: 9, 26, 43, 60, 77, 94, 111, 128, 145, 162, 179, 196, 213, 230, 247, 264, 281, 298, 315, 332, 349, 366, 383, 400, 417, 434, 451, 468, 485, 502, 519, 536, 553, 570, 587, 604, 621, 638, 655, 672, 689, 706, 723, 740, 757, 774, 791, 808, 825, 842, 859, 876, 893, 910, 927, 944, 961, 978, 995, 1012, 1029, and 1071.

Specifically, the antibody or a fragment thereof may include a light chain variable region having any one amino acid sequence selected from the group consisting of SEQ ID NOs: 9, 43, 128, 230, 247, 298, 332, 349, 859, 927, and 1071.

The antibody or a fragment thereof may include a heavy chain variable region having any one amino acid sequence selected from the group consisting of SEQ ID NOs: 8, 25, 42, 59, 76, 93, 110, 127, 144, 161, 178, 195, 212, 229, 246, 263, 280, 297, 314, 331, 348, 365, 382, 399, 416, 433, 450, 467, 484, 501, 518, 535, 552, 569, 586, 603, 620, 637, 654, 671, 688, 705, 722, 739, 756, 773, 790, 807, 824, 841, 858, 875, 892, 909, 926, 943, 960, 977, 994, 1011, 1028, 1069, and 1070; and a light chain variable region having any one amino acid sequence selected from the group consisting of SEQ ID NOs: 9, 26, 43, 60, 77, 94, 111, 128, 145, 162, 179, 196, 213, 230, 247, 264, 281, 298, 315, 332, 349, 366, 383, 400, 417, 434, 451, 468, 485, 502, 519, 536, 553, 570, 587, 604, 621, 638, 655, 672, 689, 706, 723, 740, 757, 774, 791, 808, 825, 842, 859, 876, 893, 910, 927, 944, 961, 978, 995, 1012, 1029, and 1071.

Specifically, the antibody or a fragment thereof may include a heavy chain variable region having any one amino acid sequence selected from the group consisting of SEQ ID NOs: 8, 42, 127, 229, 246, 297, 331, 348, 858, 926, 1069, and 1070; and a light chain variable region having any one amino acid sequence selected from the group consisting of SEQ ID NOs: 9, 43, 128, 230, 247, 298, 332, 349, 859, 927, and 1071.

The anticancer agent may target cancer cells infected with an oncolytic virus. Specifically, the oncolytic virus may be an oncolytic vaccinia virus. The oncolytic virus may contain a nucleic acid encoding protein A56 or a fragment thereof.

The protein A56 or a fragment thereof is as described above. The protein A56 may be wild-type protein A56 or a variant of the protein A56. The nucleic acid encoding the protein A56 or a fragment thereof may be a nucleic acid encoding wild-type protein A56 or a variant of the protein A56.

The nucleic acid encoding the protein A56 or a fragment thereof may include a nucleotide sequence represented by SEQ ID NO: 1039, 1041, 1043, 1045, 1047, 1049, 1051, 1053, 1055, 1057, 1059, 1061, 1072, 1074, 1076, or 1078.

The vaccinia virus may be, but is not limited to, one of the following vaccinia virus strains: Western Reserve (WR), New York vaccinia virus (NYVAC), Wyeth (The New York City Board of Health; NYCBOH), LC16m8, Lister, Copenhagen, Tian Tan, USSR, TashKent, Evans, International Health Division-J (IHD-J), and International Health Division-White (IHD-W).

The oncolytic virus may be one in which thymidine kinase (TK) gene is deleted. Specifically, the oncolytic virus may be a recombinant vaccinia virus in which a thymidine kinase gene is deleted.

As used herein, the term "thymidine kinase (TK)" refers to an enzyme that is called thymidine kinase and involved in nucleotide biosynthesis. The TK is an enzyme used for nucleotide biosynthesis in both cells and viruses. Here, for the cells, normal cells do not divide anymore, and thus no TK exists therein; and even for rapidly dividing cells such as hair follicle cells, TK is not present in an amount sufficient for viruses to utilize. From these viewpoints, a virus is allowed to proliferate only in the presence of cancer cells, in which TK is present, by deleting TK gene, so that the cancer cells can be selectively killed.

The anticancer agent may further comprise a physiologically acceptable carrier. In addition, the anticancer agent may further comprise suitable excipients and diluents commonly used in the preparation of pharmaceutical compositions. In addition, the anticancer agent may be formulated in the form of oral preparations such as powders, granules, tablets, capsules, suspensions, emulsions, syrups, and aerosols, external preparations, suppositories, or injections according to conventional methods, and used. Specifically, the anticancer agent may be in the form of an injection. Suitable formulations known in the art may be those disclosed in the literature (Remington's Pharmaceutical Science, 1985).

The anticancer agent may be intended for preventing or treating cancer selected from the group consisting of lung cancer, colorectal cancer, prostate cancer, thyroid cancer, breast cancer, brain cancer, head and neck cancer, esophageal cancer, skin cancer, thymus cancer, gastric cancer, colon cancer, liver cancer, ovarian cancer, uterine cancer, bladder cancer, rectal cancer, gallbladder cancer, biliary tract cancer, pancreatic cancer, lymphoma, acute leukemia, multiple myeloma, and combinations thereof. In addition, for the anticancer agent, examples of the carrier, the excipient, and the diluent may include sodium chloride, lactose, dextrose, sucrose, sorbitol, mannitol, xylitol, erythritol, maltitol, starch, gum acacia, alginate, gelatin, calcium phosphate, calcium silicate, cellulose, methylcellulose, microcrystalline cellulose, polyvinyl pyrrolidone, water, methyhydroxybenzoate, propylhydroxybenzoate, talc, magnesium stearate, mineral oil, and the like. In a case where the anticancer agent is formulated, preparation thereof may be made using diluents or excipients such as fillers, extenders, binders, wetting agents, disintegrants, and surfactants which are commonly used.

Preparations for parenteral administration may include sterile aqueous solutions, non-aqueous solvents, suspensions, emulsions, lyophilized preparations, suppositories, and the like. For the non-aqueous solvents and the suspensions, propylene glycol, polyethylene glycol, vegetable oil such as olive oil, injectable ester such as ethyl oleate, and the like may be used. As bases of the suppositories, Witepsol, macrogol, Tween 61, cacao fat, laurin fat, glycerogelatin, and the like may be used.

The cancer may be solid cancer or blood cancer. Specifically, the solid cancer may be any one selected from the group consisting of lung cancer, colorectal cancer, prostate cancer, thyroid cancer, breast cancer, brain cancer, head and neck cancer, esophageal cancer, skin cancer, thymic cancer, gastric cancer, colon cancer, liver cancer, ovarian cancer, uterine cancer, bladder cancer, rectal cancer, gallbladder cancer, biliary tract cancer, pancreatic cancer, and combinations thereof. In addition, the blood cancer may be any one selected from the group consisting of lymphoma, acute leukemia, multiple myeloma, and combinations thereof.

A dosage of the anticancer agent may be preferably determined in consideration of the patient's age, sex, condition, absorption of active ingredient(s) in the body, inactivation rate thereof, and drug(s) used in combination; and the anticancer agent may be administered at 0.0001 mg/kg (body weight) to 100 mg/kg (body weight) based on the antibody or a fragment thereof.

In another aspect of the present invention, there is provided an oncolytic virus, comprising a nucleic acid encoding protein A56 or a fragment thereof.

In yet another aspect of the present invention, there is provided a composition for targeting cancer cells, comprising, as an active ingredient, the oncolytic virus that contains a nucleic acid encoding protein A56 or a fragment thereof. The oncolytic virus is as described above for the anticancer agent.

The cancer cells may be cells of solid cancer or blood cancer. Specifically, the solid cancer may be, but is not limited to, any one selected from the group consisting of lung cancer, colorectal cancer, prostate cancer, thyroid cancer, breast cancer, brain cancer, head and neck cancer, esophageal cancer, skin cancer, thymus cancer, gastric cancer, colon cancer, liver cancer, ovarian cancer, uterine cancer, bladder cancer, rectal cancer, gallbladder cancer, biliary tract cancer, pancreatic cancer, kidney cancer, fibrosarcoma, testicular cancer, brain metastasis, liver metastasis, and combinations thereof.

In addition, the blood cancer may be, but is not limited to, any one selected from the group consisting of lymphoma, acute leukemia, multiple myeloma, and combinations thereof.

In still yet another aspect of the present invention, there is provided a method for targeting cancer cells, comprising a step of administering the oncolytic virus to an individual.

The individual may be a mammal including a human, and may be a non-human animal. The term "non-human animal" refers to any vertebrate and may include mammals and non-mammals, such as non-human primates, sheep, dogs, cats, horses, cattle, chickens, amphibians, and reptiles. In addition, the individual means an individual who is suffering from a cancer disease or a disease in a state that can be alleviated, inhibited, or treated by administering the oncolytic virus.

A dosage of the oncolytic virus varies depending on the individual's condition and body weight, the severity of disease, the type of drug, the route and period of administration, and can be appropriately selected by a person skilled in the art. The dosage may be such that a patient receives an oncolytic virus at $1\times10^5$ to $1\times10^{18}$ of virus particles, infectious virus units ($TCID_{50}$), or plaque forming units (pfu). Specifically, the dosage may be such that a patient receives an oncolytic virus at $1\times10^5$, $2\times10^5$, $5\times10^5$, $1\times10^6$, $2\times10^6$, $5\times10^6$, $1\times10^7$, $2\times10^7$, $5\times10^7$, $1\times10^8$, $2\times10^8$, $5\times10^8$, $1\times10^9$, $2\times10^9$, $5\times10^9$, $1\times10^{10}$, $5\times10^{10}$, $1\times10^{11}$, $5\times10^{11}$, $1\times10^{12}$, $1\times10^{13}$, $1\times10^{14}$, $1\times10^{15}$, $1\times10^{16}$, $1\times10^{17}$, or higher of virus particles, infectious virus units, or plaque forming units, and various numerical values and ranges between the above-mentioned numerical values may also be included therein. Preferably, the oncolytic virus may be administered at a dose of $1\times10^5$ to $1\times10^{10}$ pfu. More preferably, the oncolytic virus may be administered at a dose of equal to or greater than $1\times10^5$ and lower than $1\times10^9$ pfu.

The oncolytic virus may be administered parenterally, and such administration may be performed by any suitable method, such as intratumoral, intraperitoneal, subcutaneous, intradermal, intranodal, or intravenous administration. Among these, intratumoral, intraperitoneal, or intravenous administration may be preferred.

Regarding the administration route, dosage, and frequency of administration, the oncolytic virus may be administered to a patient in a variety of ways and amounts depending on the patient's condition and the presence or absence of side effects; and the optimal administration route, dosage, and frequency of administration therefor may be selected by a person skilled in the art within a suitable range. In addition, the oncolytic virus may be administered in combination with another drug or physiologically active substance whose therapeutic effect is known for the disease to be treated, or may be formulated in the form of a combination preparation with the other drug. Specifically, the oncolytic virus may be provided in the form of an injection.

In still yet another aspect of the present invention, there is provided an antibody or a fragment thereof which binds to protein A56 or a fragment thereof. The antibody or a fragment thereof is as described above for the anticancer agent.

The antibody may be produced by a method for producing an antibody, comprising steps of: i) administering protein A56 or a fragment thereof to an individual; ii) obtaining B cells from the individual; and iii) culturing the B cells to obtain a recombinant anti-protein A56 antibody.

In addition, the protein A56 or a fragment thereof may be produced by a method for producing a protein, comprising steps of: i) transfecting the vector of the present invention into a host cell; ii) culturing the transfected host cell; and iii) obtaining recombinant protein A56 from the culture.

The host cell may be a prokaryotic cell or a eukaryotic cell. Specifically, the prokaryotic cells may be *E. coli* or yeast cells. The eukaryotic cells may be NS/0 myeloma cells, 293 cells, Chinese hamster ovary cells (CHO cells), Hela cells, CapT cells (human amniotic fluid-derived cells), or COS cells.

The transfection may be performed via transient transfection, microinjection, transduction, cell fusion, calcium phosphate precipitation, liposome-mediated transfection, DEAE-dextran-mediated transfection, polybrene-mediated transfection, electroporation, or gene gun.

In still yet another aspect of the present invention, there is provided a cancer-targeting polypeptide or a fragment thereof, the polypeptide including an amino acid sequence represented by SEQ ID NO: 1038, 1040, 1042, 1044, 1046, 1048, 1050, 1052, 1054, 1056, 1058, 1060, 1073, 1075, 1077, or 1079. The polypeptide, which includes an amino acid sequence represented by SEQ ID NO: 1038, 1040, 1042, 1044, 1046, 1048, 1050, 1052, 1054, 1056, 1058, 1060, 1073, 1075, 1077, or 1079, or a fragment thereof is as described above for the anticancer agent.

In still yet another aspect of the present invention, there is provided an isolated nucleic acid encoding the cancer-targeting polypeptide or a fragment thereof. The nucleic acid may include a nucleotide sequence represented by SEQ ID NO: 1039, 1041, 1043, 1045, 1047, 1049, 1051, 1053, 1055, 1057, 1059, 1061, 1072, 1074, 1076, or 1078.

In still yet another aspect of the present invention, there is provided a kit for treating cancer, comprising the oncolytic virus and the antibody or a fragment thereof.

The oncolytic virus and the antibody or a fragment thereof are as described above for the anticancer agent.

The individual means an individual who has or is suffering from a disease in a state that can be alleviated, inhibited, or treated by administering the oncolytic virus and the antibody or a fragment thereof. The individual may be a mammal including a human, and may be a non-human animal. The term "non-human animal" refers to any vertebrate and may include mammals and non-mammals, such as non-human primates, sheep, dogs, cats, horses, cattle, chickens, amphibians, and reptiles. The oncolytic virus primarily can kill only cancer cells in a specific manner in a case of being included in a first composition for cancer cell killing and targeting and administered to an individual; and cancer cells, which have survived the oncolytic virus, express protein A56 on the cell surface, and this enables targeting for secondary anticancer therapy.

The antibody or a fragment thereof secondarily can kill only cancer cells, which express protein A56 on the cell surface, in a case of being included in a second composition for secondary anticancer therapy and administered to the individual.

The first composition and the second composition may be administered in pharmaceutically effective amounts to treat cancer cells or metastasis thereof, or to inhibit cancer growth. The pharmaceutically effective amount may vary depending on various factors such as type of cancer, the patient's age and weight, nature and severity of symptoms, type of current treatment, number of treatments, dosage form, and route, and may be easily determined by experts in the relevant field.

The first composition and the second composition may be administered parenterally, and such administration may be performed by any suitable method, such as intratumoral, intraperitoneal, subcutaneous, intradermal, intranodal, or intravenous administration. Among these, intratumoral, intraperitoneal, or intravenous administration may be preferred. On the other hand, a dosage of the pharmaceutical composition may be determined depending on administration schedule, dosage, the patient's health condition, and the like.

In still yet another aspect of the present invention, there is provided a pharmaceutical composition for targeting cancer, comprising the oncolytic virus. The oncolytic virus is as described for the anticancer agent.

In still yet another aspect of the present invention, there is provided a use of the oncolytic virus for the targeting of cancer. In still yet another aspect of the present invention, there is provided a method for targeting cancer, comprising a step of administering the oncolytic virus to an individual. The oncolytic virus is as described above for the anticancer agent.

In still yet another aspect of the present invention, there is provided a use of the oncolytic virus and the antibody or a fragment thereof, for the treatment of cancer. The oncolytic virus and the antibody or a fragment thereof are as described above for the anticancer agent.

In still yet another aspect of the present invention, there is provided a method for treating cancer, comprising steps of: i) administering the oncolytic virus to an individual; and ii) administering the antibody or a fragment thereof to the individual. The oncolytic virus and the antibody or a fragment thereof are as described above for the anticancer agent.

MODE FOR THE INVENTION

Hereinafter, the present invention will be described in more detail by way of the following examples. However, the following examples are for illustrative purposes only, and the scope of the present invention is not limited thereto.

I. Production of Oncolytic Virus that Contains Nucleic Acid Encoding Protein A56 or Fragment Thereof, and Identification of Expression Thereof on Tumor Cell Surface

Preparation 1.1. Preparation and Identification of Protein A56 Variants

Wild-type vaccinia virus (NYC Department of Health strain, VR-1536) was purchased from the American Type Culture Collection (ATCC). For recombination, pUC57amp+ (GENEWIZ, USA) with HSV1-TK gene (pSE/L promoter) and firefly luciferase reporter (p7.5 promoter) gene was used as a shuttle plasmid vector.

To obtain recombinant viruses, HeLa cells (ATCC) were seeded in 6-well plates at $4\times10^5$ cells per well, and then prepared in EMEM medium containing 10% fetal bovine serum. Treatment with the wild-type vaccinia virus was performed at an MOI of 0.05. After 2 hours, the medium was replaced with EMEM medium containing 2% fetal bovine serum, and then 4 µg of the shuttle plasmid vector, which had been linearized, was transferred into the cells using Xfect™ polymer (Clonetech 631317, USA). Culture was performed for 4 hours. Subsequently, the medium was replaced with EMEM medium containing 2% fetal bovine serum, and then the cells were further cultured for 72 hours. The recombinant vaccinia viruses containing HSV1-TK gene were obtained by checking luciferase activity in the Hela cells.

Then, mutations in HSV1-TK were induced by performing 10 consecutive subcultures in a state where a biochemical environment (TK-selection pressure) is applied which allows for selection of cells lacking TK function in the presence of BrdU (thymidine analogue, 15 µg/ml) in TK-osteosarcoma (143 TK-) cell line. A request for amino acid sequencing of the mutated vaccinia virus was made to Macrogen (Seoul, Korea). As a result, it was identified that the codon (caa) encoding glutamine (Gln), which is an amino acid at position 46 at the C-terminus of HSV1-TK of the mutated vaccinia virus, was point mutated to a stop codon. In addition, it was identified that for the HSV1-TK of the mutated vaccinia virus, amino acid residues following position 46 at the C-terminus were deleted. Finally, a mutated vaccinia virus (OTS-412) was obtained which expresses an HSV1-TK fragment with genetic stability.

In addition, the most reported mutations in HSV-TKs are frameshift mutations caused by insertion or deletion of bases which occur in the nucleotide sequence sections at positions 430 to 436 (7 Gs) and at positions 548 to 583 (6 Cs). After the wild-type HSV-TK was inserted into vaccinia viruses, 98% or higher of the mutations occurred in these sections. Accordingly, in order to cause a silent mutation in the nucleotide sequence sections, GGGGGGG, which is a nucleotide sequence at positions 430 to 436, was changed to GGTGGTG, and CCCCCC, which is a nucleotide sequence at positions 548 to 583, was changed to CCCCTC. In addition, the HSV-TK variant gene, which had been adapted such that alanine at position 167 in the amino acid sequence of HSV-TK is encoded as tyrosine, was used as a shuttle vector. Then, a recombinant vaccinia virus was produced in the same manner as OTS-412 using the shuttle vector and Western Reserve strain (WOTS-418) vaccinia virus.

A request for gene sequencing of the protein A56s in OTS-412 and WOTS-418 was made to Macrogen. Regarding the respective sequences for the protein A56s in OTS-412 and WOTS-418, alignment was performed through NCBI Blast and Uniprot. As a result, 100% identical sequences were not found; and in particular, it was identified that the amino acids at positions 245 to 250 were deleted. Comparison was performed with 4 other strains having high sequence homology (FIG. 99).

Preparation 1.2. Construction of Oncolytic Virus Vector that Contains Nucleic Acid Encoding Protein A56 or Fragment Thereof Wild-type pox virus (New York City Department of Health Laboratories) was purchased from the American Type Culture Collection (ATCC; VR-1536). In the virus, thymidine kinase gene was knocked out by homologous recombination, and substituted with a reporter gene and a gene (SEQ ID NO: 1039, 1041, 1043, 1045, 1047, 1049, 1051, 1053, 1055, 1057, 1059 or 1061, 1072, 1074 (OTS-412-A56), 1076, 1078 (WOTS-418-A56) that encodes protein A56 or a fragment thereof.

Preparation Example 1.3. Production of Oncolytic Virus that Contains Nucleic Acid Encoding Protein A56 or Fragment Thereof In order to produce oncolytic viruses containing protein A56, HeLaS3 (ATCC) cell line was seeded in 6-well plates at $4\times10^5$ cells per well, and then prepared in EMEM medium containing 10% fetal bovine serum. Treatment with the wild-type vaccinia virus was performed at an MOI of 0.05. After 2 hours, the medium was replaced with EMEM medium containing 2% fetal bovine serum, and then 4 µg of the oncolytic virus vector, which had been constructed in Preparation Example 1.2, was transfected into the cells using Xfect reagent buffer. Culture was performed for 4 hours. Subsequently, the medium was replaced with EMEM medium containing 2% fetal bovine serum, and then the cells were further cultured for 72 hours. Finally, the infected cells were collected, and then freezing and thawing were repeated 3 times. The cells were lysed by sonication, and a sucrose cushion method was used to obtain free oncolytic viruses that contain a nucleic acid encoding the protein A56 or a fragment thereof.

Experimental Example 1. Expression of Protein A56 on Cancer Cell Surface

The oncolytic virus that contains a nucleic acid encoding protein A56 or a fragment thereof, which was produced in Preparation Example 1.3, was used to infect a human lung cancer cell line (A549) or a human colorectal cancer cell line (HCT-116), to identify whether the protein A56 was expressed on the cancer cell surface.

Specifically, A549 (lung carcinoma, ATCC, USA) or HCT-116 (colorectal carcinoma, Korea Cell Line Bank) cell line was seeded on a cover glass in a 12-well-plate at $3.5\times10^4$ cells per well. Subsequently, the cells were infected with the oncolytic virus at an MOI of 0.1, and then incubated for 30 hours at a condition of 37° C. and 5% $CO_2$. Each of the incubated cell lines was harvested. Then, treatment with 4% (v/v) paraformaldehyde (PFA), 1% (v/v) BSA, anti-A56 primary antibody (cat no. ABIN1606294, Antibodies-Online), which was diluted at a ratio of 1:500, and secondary antibody (Alexa 594, cat no. A21205, Invitrogen), which was diluted at a ratio of 1:200, was performed. DAPI staining was performed. Then, a sample of each cell line was placed on a slide glass and observed using a confocal microscope (Olympus, FV1000).

As a result, it was identified that the protein A56 was expressed on the cell surface of the A549 and HCT-116 cell lines infected with the oncolytic virus (FIGS. 2 and 3).

Experimental Example 2. Identification of Expression of Protein A56 on Surface of Mouse Tumor Tissue (I)

A cancer-induced mouse model was subjected to intraperitoneal administration of the oncolytic virus that contains a nucleic acid encoding protein A56 or a fragment thereof, which was produced in Preparation Example 1.3, to identify whether the protein A56 was expressed on the tissue surface.

Specifically, BALB/c nude mice were subcutaneously transplanted with HT-29 colorectal cancer cell line (Korea Cell Line Bank, KCLB) at $6.3\times10^6$ cells to induce cancer. When the average tumor volume reached 150 mm$^3$ to 200 mm$^3$, the mice were subjected to intraperitoneal administration of the oncolytic virus, which was produced in Preparation Example 1.3, at a dose of $2\times10^7$ pfu. Then, on day 4, the mice were sacrificed, and tumor tissues, and brain, heart, lung, muscle, kidney, liver, and spleen tissues were collected therefrom.

Immunofluorescence staining for protein A56 was performed in the same manner as in Experimental Example 1. DAPI staining was performed. Then, a sample of each tissue was placed on a slide glass and observed using a fluorescence microscope.

As a result, it was identified that the protein A56 was expressed on the surface of the tumor tissue in the mice administered with the oncolytic virus. On the other hand, it was identified that the protein A56 was not expressed in the brain, heart, lung, muscle, kidney, liver, and spleen tissues (FIG. 4). From these results, it was identified that in a case where an antibody is produced which targets protein A56 expressed on the tumor tissue surface following administration of the oncolytic virus, this antibody can be utilized as anticancer immunotherapy.

Experimental Example 3. Identification of Expression of Protein A56 on Tissue Surface in Rabbits Normal rabbits were subjected to intravenous administration of the oncolytic virus that contains a nucleic acid encoding protein A56 or a fragment thereof, which was produced in Preparation Example 1.3, to identify whether the protein A56 was expressed on the tissue surface.

Specifically, New Zealand rabbits were subjected to intravenous administration of the oncolytic virus produced in Preparation Example 1.3 at a dose of $1\times10^8$ pfu or $1\times10^9$ pfu. Then, on week 3 or 8, the rabbits were sacrificed, and brain, heart, lung, muscle, kidney, liver, and spleen tissues were collected therefrom.

Immunofluorescence staining for protein A56 was performed in the same manner as in Experimental Example 1. DAPI staining was performed. Then, a sample of each tissue was placed on a slide glass and observed using a fluorescence microscope.

As a result, it was identified that the protein A56 was not expressed in the heart, lung, muscle, kidney, liver, and spleen tissues of the rabbits administered with the oncolytic virus.

On the other hand, a fluorescence reaction was detected in the brain tissue of the rabbits administered with the oncolytic virus. To identify whether the detected fluorescence reaction is a non-specific reaction of an anti-A56 antibody, the brain tissue of normal rabbits, which were not administered with the oncolytic virus, was subjected to immunofluorescence staining in the same manner as above, and then a fluorescence reaction therein was checked using a fluorescence microscope.

As a result, a fluorescence reaction was detected even in the brain tissue of rabbits that were not administered with the oncolytic virus. From this result, it was identified that such a fluorescence reaction was a non-specific reaction (FIG. 5).

In addition, in a case where brain tissue (Pusan National University Yangsan Hospital, Korea) of normal humans, who were not administered with the oncolytic virus, was subjected to immunofluorescence staining in the same manner as above, a weak fluorescence reaction was detected using a fluorescence microscope. However, from the viewpoint that an antibody does not cross the blood brain barrier, it is determined that an anti-A56 antibody will not cause a non-specific reaction unless the antibody is administered directly into the ventricle.

Experimental Example 4. Identification of Expression of Protein A56 on Surface of Mouse Tumor Tissue (II)

A cancer-induced mouse model was subjected to co-administration of the oncolytic virus that contains a nucleic acid encoding protein A56 or a fragment thereof, which was produced in Preparation Example 1.3, and hydroxyurea, to identify whether the protein A56 was expressed on the tissue surface.

Specifically, BALB/c nude mice were subcutaneously transplanted with Renca cancer cell line (Korea Cell Line Bank) at $6.3\times10^6$ cells to induce cancer. When the average tumor volume reached 150 mm$^3$ to 200 mm$^3$, the mice were subjected to intratumoral administration of the oncolytic virus, which was produced in Preparation Example 1.3, at a dose of $2\times10^7$ pfu, and to administration of hydroxyurea at a dose of 30 mg/kg.

The produced renal cancer cell-transplanted mice were divided into three groups (n=4). The group receiving intratumoral administration of saline was set as a control group, and the group receiving administration of the oncolytic virus $(1\times10^7$ pfu) alone and the group receiving co-administration of the oncolytic virus $(1\times10^7$ pfu) and hydroxyurea (30 mg/kg) were set as experimental groups. The oncolytic virus was intratumorally administered twice on days 0 and 14, and the hydroxyurea was intraperitoneally administered 6 times per week from 1 day before administration of the oncolytic virus to day 21 after administration of the oncolytic virus, except for the day when the oncolytic virus was administered.

The mice were sacrificed on days 7, 10, and 14 after first administration of the oncolytic virus, and tumor tissues were collected therefrom. Also, the mice were sacrificed on days 21, 24, and 28 after second administration of the oncolytic virus, and tumor tissues were collected therefrom. Immunofluorescence staining for protein A56 was performed in the same manner as in Experimental Example 1. DAPI staining was performed. Then, a sample of each tissue was placed on a slide glass and observed using a fluorescence microscope.

As a result, it was identified that the protein A56 was clearly expressed on the tumor surface of the mice of the group having received administration of only the oncolytic virus and the group having received co-administration of the oncolytic virus and the hydroxyurea, until days 7, 10, and 14 after first administration of the oncolytic virus (FIGS. 6 and 7).

In addition, it was identified that in a case where second administration of the oncolytic virus was performed on day 14 after first administration of the oncolytic virus, the protein A56 was expressed on the tumor surface until days 7, 10, and 14 after the second administration (FIGS. 8 and 9). In particular, it was identified that the protein A56 was expressed in both dead and living cells on day 24 (D10).

Furthermore, it was identified that the tumor volume was significantly decreased in both the mice of the group having received administration of the oncolytic virus alone and the mice of the group having received co-administration of the oncolytic virus and the hydroxyurea, as compared with the mice of the group having received administration of only saline (FIG. 10). In addition, body weights were measured for the mice of the three groups on days 3, 7, 14, 18, and 21. As a result, no significant weight loss was observed in all groups (FIG. 11).

Experimental Example 5. Expression of Protein A56 or Fragment Thereof On Cell Surface The oncolytic virus that contains a nucleic acid encoding protein A56 or a fragment thereof, which was produced in Preparation Example 1.3, was used to treat A549 cancer cell line, to identify whether the protein A56 was expressed on the cell surface.

Specifically, A549 (lung carcinoma, ATCC, USA) cell line was seeded on a cover glass in a 12-well-plate at $3.5 \times 10^4$ cells per well. Subsequently, the cells were infected with the oncolytic virus at an MOI of 0.1, and then incubated for 30 hours at a condition of 37° C. and 5% $CO_2$. Each incubated cell line was harvested. Then, treatment with 4% (v/v) paraformaldehyde (PFA), 1% (v/v) BSA, anti-A56 antibody (cat no. ABIN1606294, Antibodies-Online), which was diluted at a ratio of 1:500, and secondary antibody (Alexa 594, cat no. A21205, Invitrogen), which was diluted at a ratio of 1:200, was performed. The nucleus was stained with DAPI, and the Golgi apparatus was stained with a fluorescent dye. Thereafter, a sample of the cell line was placed on a slide glass and observed using a confocal microscope (Olympus, FV1000). The results are shown in FIGS. 12 and 13, and Table 2.

TABLE 2

| | Nucleus | Golgi Apparatus | ER | Cytosol(broad) | Plasma Membrane |
|---|---|---|---|---|---|
| A56-G | — | + | + | + | +++ |
| A56-121 | — | ++ | + | + | + |
| A56-17 | — | — | +++ | — | — |
| A56-121S | | + | + | + | — |
| A56-170 | — | — | + | ++ | — |
| A56-240 | — | — | ++ | + | — |
| A56-276 | — | — | ++ | + | — |
| BNX A56-LTC | — | + | ++ | + | — |

Wild-type A56 (A56-G) and fragments of A56 obtained by partial truncation of six regions of A56 were allowed to be expressed on the cell surface. As a result, it was identified that only wild-type A56 (A56-G) and A56-121, in which the IgV-like domain is truncated, reached the cell surface and were expressed thereon. It was identified that among the A56 variants in which the IgV-like domain is excluded, variants, in which signal peptides, transmembrane domain, stalk region, and tandem repeats regions are truncated individually or in combination, were not expressed on the plasma membrane. In addition, it was identified that in a case of including the IgV-like domain, even a variant including only the transmembrane domain was not expressed on the plasma membrane. That is, it was identified that variants, in which the IgV-like domain is excluded and which include five regions, were expressed on the plasma membrane.

II. Production of Antibody Binding to Protein A56 or Fragment Thereof

Preparation Example 2. Preparation of Protein A56 and Fragment Thereof

Primers were prepared to remove specific regions from the wild-type protein A56, and overlapping PCR was performed by forming a region overlapping with GFP.

Specifically, vector DNA (N293F-A56-C-HIS) was amplified, introduced into HEK293F cells, and overexpressed therein. Subsequently, primary purification was performed by affinity chromatography (Ni-NTA), and then secondary purification was performed by cation exchange chromatography (CEX). In this way, A56-C-HIS protein was finally produced (FIGS. 97 and 98).

Preparation Example 3. Production of Antibody Binding to Protein A56 or Fragment Thereof (I)

A request for production of anti-A56 antibodies, which specifically bind to the protein A56, or a variant or fragment thereof, was made to Ybiologics. 61 antibodies were produced using phage library techniques and CDRs thereof were analyzed. Phage libraries were added to a tube coated with A56 antigen, and biopanning was performed to find binding hits. Phages having specific binding were selected by performing washing 3 times on average. Three panning processes were performed. Then, affinity tests were performed, and colonies showing high affinity were picked at small amounts to identify whether the colonies exhibit affinity with the actual antigen. Sets with a relatively high number of hits were chosen, and an automated system was used for picking and hit selection.

Affinity between each of the thus-produced anti-A56 antibodies and the protein A56 was measured. The results are illustrated in FIGS. 14 to 19. In addition, productivity of each anti-A56 antibody was illustrated in FIGS. 20A to 20C. In addition, FIGS. 21 to 37 illustrate the results obtained by identifying each of the produced anti-A56 antibodies through SDS-PAGE.

Experimental Example 6. Affinity Measurement for Anti-A56 Antibody

Each well of an immuno-tube was coated with protein A56, and then a blocking process was performed. After the blocking process, each well was allowed to react with an antibody, which was subjected to three-fold serial dilution starting from 100 nM, at room temperature for a predetermined time. Thereafter, washing with PBS was performed three times, and then treatment with a secondary antibody was also performed at room temperature for a predetermined time. Subsequently, affinity between each anti-A56 antibody and the protein A56 was measured at respective concentrations.

Experimental Example 7. Identification of Binding
Between Protein A56 Expressed on Tumor Cell
Surface and Anti-A56 Antibody (I)

The oncolytic virus produced in Preparation Example 1.3
was used to infect each of HeLa, HT-29, A549, MCF-7, and
PC-3 cell lines at an MOI of 1. After 24 hours, each cell line
infected with the oncolytic virus was treated with each of the
five anti-A56 antibodies (ab01, ab02, ab03, ab04, ab05)
produced in Preparation Example 3, and then reaction was
allowed to proceed at 4° C. for 1 hour. Then, washing with
PBS was performed 3 times, and then treatment with anti-
hIgG antibody (FITC, Abcam) was performed. Subse-
quently, reaction was allowed to proceed at a temperature of
4° C. for 1 hour. After 1 hour, staining was performed using
a PI staining kit (BD Annexin V Kit) according to the
manufacturer's manual, and then analysis was performed
with flow cytometry (Moflo Astrios EQ, Backman Coulter).

As illustrated in FIGS. 38 and 39, comparison with the
analysis results (blue regions) for the cancer cell line (Cell
Only) that was not treated with the oncolytic virus shows
that the cancer cell line (Cell+VV) treated with the oncolytic
virus bound to the anti-A56 antibody, thereby causing shift-
ing towards the red region. From these results, it was
identified that the anti-A56 antibody bound to the protein
A56 expressed on the tumor cell surface.

Preparation Example 4. Production of Antibody
Binding to Protein A56 or Fragment Thereof (II)

In addition, a request for production of antibodies based
on anti-A56 antibody (cat no. ABIN1606294, Antibodies-
Online) was made to LakePharma, and the antibodies were
produced through reverse coding engineering. The thus
produced two antibodies were designated as "LakePharma
variant3" and "LakePharma variant4".

Experimental Example 8. Identification of Binding
Between Protein A56 Expressed on Tumor Cell
Surface and Anti-A56 Antibody (II)

The oncolytic virus produced in Preparation Example 1.3
was used to infect HeLa cell line at an MOI of 1. After 24
hours, the HeLa cell line infected with the oncolytic virus
was treated with an anti-A56 antibody (cat no.
ABIN1606294, Antibodies-Online) and the two anti-A56
antibodies (LakePharma variant3, 4) produced in Prepara-
tion Example 4, respectively, and then reaction was allowed
to proceed at 4° C. for 1 hour. Then, washing with PBS was
performed 3 times, and then treatment with anti-hlgG anti-
body (FITC, Abcam) was performed. Subsequently, reaction
was allowed to proceed at a temperature of 4° C. for 1 hour.
After 1 hour, staining was performed using a PI staining kit
(BD Annexin V Kit) according to the manufacturer's
manual, and then analysis was performed with flow cytom-
etry (Moflo Astrios EQ, Backman Coulter).

As a result, it was identified that in a case where treatment
with an anti-A56 antibody (cat no. ABIN1606294, Antibod-
ies-Online) was performed, which is a positive control
(Cell+OV), the anti-A56 antibody bound to A56, which was
expressed on the cell surface of the HeLa cell line due to
treatment with the oncolytic virus, thereby causing shifting
towards the right, as compared with a case (Cell Only)
where treatment with only HeLa cell line was performed
(FIG. 40).

In addition, in a case where treatment with each of the two
anti-A56 antibodies (LakePharma variant3, 4) was performed, which is an experimental group (Cell+OV), the
anti-A56 antibody bound to A56, which was expressed on
the cell surface of the HeLa cell line due to treatment with
the oncolytic virus, thereby causing shifting towards the
right, as compared with a case (Cell Only) where treatment
with only HeLa cell line was performed (FIGS. 41 and 42).
From these results, it was identified that the two anti-A56
antibodies (LakePharma variant3, 4) produced in Prepara-
tion Example 4 specifically bound to the A56 expressed on
the cell surface (FIG. 43).

Experimental Example 9. Identification of Binding
Between Protein A56 Expressed on Tumor Cell
Surface and Anti-A56 Antibody: A549 Cancer Cell
Line (I)

A549 cancer cell line was treated with the oncolytic virus
(OTS-412 or WOTS-418), which encodes the protein A56 of
SEQ ID NO: 1074 or 1078 and was produced in Preparation
Example 1.3, so that the protein A56 was expressed in the
cell line. Then, it was identified whether anti-A56 antibodies
(ten human anti-A56 antibodies and two mouse anti-A56
antibodies) bound to the protein A56.

The A549 cancer cell line was treated with each oncolytic
virus at an MOI of 1. After 24 hours, treatment with the ten
antibodies (binding affinity top 10, that is, Ab18, Ab19,
Ab01, Ab13, Ab14, Ab08, Ab03, Ab51, Ab55, Ab16), which
were produced in Production Example 3 and use human
scFv as a binding domain, and the two antibodies (LPvari-
ant03 and LPvariant04) produced in Preparation Example 4
was performed. After 1 hour, secondary antibodies (Goat
anti-human IgG FC, Goat anti-mouse IgG H&L) were added
thereto. After 1 hour, washing was performed, and the A549
cancer cell line was stained with propidium iodide (PI) and
analyzed with flow cytometry.

As a result, it was identified that the ten human antibodies
and the two mouse antibodies exhibited binding signals,
which are 90% or higher similar, for the oncolytic virus-
treated A549 cancer cell line (FIGS. 44 to 55). In addition,
it was identified that there was a slight difference between
the 10 human antibodies in terms of the peak observed in the
oncolytic virus-treated A549 cancer cell line, and the dif-
ference was not significant (FIGS. 56 and 57).

Experimental Example 10. Identification of Binding
Between Protein A56 Expressed on Tumor Cell
Surface and Anti-A56 Antibody: A549 Cancer Cell
Line (II)

A549 cancer cell line was treated with the oncolytic virus
(OTS-412 or WOTS-418), which encodes the protein A56 of
SEQ ID NO: 1074 or 1078 and was produced in Preparation
Example 1.3, so that the protein A56 was expressed in the
cell line. Then, it was identified whether the anti-A56
antibodies (Ybiologics: Ab18 and Ab16, LakePharma:
LakePharma variant3, 4), which were produced in Prepara-
tion Examples 3 and 4, bound to the protein A56.

The A549 cancer cell line was treated with the oncolytic
virus and the anti-A56 antibody in the same manner as in
Experimental Example 9. The A549 cancer cell line was
stained with propidium iodide (PI), and analysis was per-
formed with flow cytometry (Moflo Astrios EQ, Backman
Coulter).

As a result, it was identified that the respective anti-A56
antibodies produced by Ybiologics and LakePharma exhibited binding signals, which are 93% or higher similar, for the oncolytic virus-treated A549 cancer cell line (FIGS. 58 to 61).

Experimental Example 11. Identification of Binding Between Protein A56 Expressed on Tumor Cell Surface and Anti-A56 Antibody: PC3 Cancer Cell Line (I)

PC3 cancer cell line was treated with the oncolytic virus (OTS-412 or WOTS-418), which encodes the protein A56 of SEQ ID NO: 1074 or 1078 and was produced in Preparation Example 1.3, so that the protein A56 was expressed in the cell line. Then, it was identified whether anti-A56 antibodies (ten human anti-A56 antibodies and two mouse anti-A56 antibodies) bound to the protein A56.

In the same manner as in Experimental Example 9, the PC3 cancer cell line was treated with each oncolytic virus, and the ten antibodies (binding affinity top 10, that is, Ab18, Ab19, Ab01, Ab13, Ab14, Ab08, Ab03, Ab51, Ab55, Ab16), which were produced in Production Example 3 and use human scFv as a binding domain, and the two antibodies (LPvariant03 and LPvariant04) produced in Preparation Example 4. The PC3 cancer cell line was stained with PI, and analysis was performed with flow cytometry (Moflo Astrios EQ, Backman Coulter).

As a result, it was identified that the ten human antibodies and the two mouse antibodies exhibited binding signals, which are 90% or higher similar, for the oncolytic virus-treated PC3 cancer cell line (FIGS. 62 to 73). In addition, it was identified that while there was a slight difference between the 10 human antibodies in terms of the peak observed in the oncolytic virus-treated PC3 cancer cell line, the signals were 60% or higher, in which the anti-A56 antibody Ab51 exhibited the highest binding signals of 70.71% and 78.61%, respectively (FIGS. 74 and 75).

Experimental Example 12. Identification of Binding Between Protein A56 Expressed on Tumor Cell Surface and Anti-A56 Antibody: PC3 Cancer Cell Line (II)

PC3 cancer cell line was treated with the oncolytic virus (OTS-412 or WOTS-418), which encodes the protein A56 of SEQ ID NO: 1074 or 1078 and was produced in Preparation Example 1, so that the protein A56 was expressed in the cell line. Then, it was identified whether the anti-A56 antibodies (Ybiologics: Ab18 and Ab16, LakePharma: LakePharma variant3, 4), which were produced in Preparation Examples 3 and 4, bound to the protein A56.

The PC3 cancer cell line was treated with the oncolytic virus and the anti-A56 antibody in the same manner as in Experimental Example 9. The PC3 cancer cell line was stained with PI, and analysis was performed with flow cytometry (Moflo Astrios EQ, Backman Coulter).

As a result, it was identified that the respective anti-A56 antibodies (Ab18 and Ab16) produced by Ybiologics exhibited binding signals of 60% or higher and 70% or higher, respectively, for the oncolytic virus-treated PC3 cancer cell line (FIGS. 76 and 77). In addition, it was identified that the respective anti-A56 antibodies (LakePharma variant3, 4) produced by LakePharma all exhibited a binding signal of 90% or higher (FIGS. 78 and 79).

Experimental Example 13. Identification of Binding Between Protein A56 Expressed on Tumor Cell Surface and Anti-A56 Antibody: MCF7 Cancer Cell Line (I)

MCF7 cancer cell line was treated with the oncolytic virus (OTS-412 or WOTS-418), which encodes the protein A56 of SEQ ID NO: 1074 or 1078 and was produced in Preparation Example 1, so that the protein A56 was expressed in the cell line. Then, it was identified whether anti-A56 antibodies (ten human anti-A56 antibodies and two mouse anti-A56 antibodies) bound to the protein A56.

In the same manner as in Experimental Example 9, the MCF7 cancer cell line was treated with each oncolytic virus, and the ten antibodies (binding affinity top 10, that is, Ab18, Ab19, Ab01, Ab13, Ab14, Ab08, Ab03, Ab51, Ab55, Ab16), which were produced in Production Example 3 and use human scFv as a binding domain, and the two antibodies (LPvariant03 and LPvariant04) produced in Preparation Example 4. The MCF7 cancer cell line was stained with PI, and analysis was performed with flow cytometry (Moflo Astrios EQ, Backman Coulter).

As a result, it was identified that the ten human antibodies and the two mouse antibodies exhibited binding signals, which are 80% or higher similar, for the oncolytic virus-treated MCF7 cancer cell line (FIGS. 80 to 91). In addition, it was identified that while there was a slight difference between the 10 human antibodies in terms of the peak observed in the oncolytic virus-treated MCF7 cancer cell line, the signals were 80% or higher (FIGS. 92 and 93).

Experimental Example 14. Identification of Binding Between Protein A56 Expressed on Tumor Cell Surface and Anti-A56 Antibody: MCF7 Cancer Cell Line (II)

MCF7 cancer cell line was treated with the oncolytic virus (OTS-412 or WOTS-418), which encodes the protein A56 of SEQ ID NO: 1074 or 1078 and was produced in Preparation Example 1, so that the protein A56 was expressed in the cell line. Then, it was identified whether the anti-A56 antibodies (LakePharma: LakePharma variant3, 4), which were produced in Preparation Example 4, bound to the protein A56.

The MCF7 cancer cell line was treated with the oncolytic virus and the anti-A56 antibody in the same manner as in Experimental Example 9. The MCF7 cancer cell line was stained with PI, and analysis was performed with flow cytometry (Moflo Astrios EQ, Backman Coulter).

As a result, it was identified that the respective anti-A56 antibodies (LakePharma variant3, 4) produced by LakePharma all exhibited a binding signal of 97% or higher for the oncolytic virus-treated MCF7 cancer cell line (FIGS. 94 and 95).

III. Identification of Anticancer Effect Using Oncolytic Virus and Antibody

Experimental Example 15. Identification of Anticancer Effect Using Oncolytic Virus and Antibody The cancer-induced mice, which were produced in the same manner as in Experimental Example 2, were subjected to administration of the oncolytic virus produced in Preparation Example 1.3. After a predetermined time elapsed, the cancer-induced mice set as a control group received physiological saline, and the cancer-induced mice set as an experimental group received the antibody produced in Preparation Example 3. As a result, cancer cells, which were not killed by the oncolytic virus, remained in the tumor tissue of the control group, whereas cancer cells were completely killed in the tumor tissue of the experimental group.

Experimental Example 16. Identification of
Anticancer Effect Using Oncolytic Virus and
Immune Cells The cancer-induced mice, which were produced in the
same manner as in Experimental Example 2, were subjected
to administration of the oncolytic virus produced in Prepa-
ration Example 1.3. After a predetermined time elapsed, the
cancer-induced mice set as a control group received physi-
ological saline, and the cancer-induced mice set as an
experimental group received the produced immune cells. As
a result, cancer cells, which were not killed by the oncolytic
virus, remained in the tumor tissue of the control group,
whereas cancer cells were completely killed in the tumor
tissue of the experimental group.

The invention claimed is:

1. An anticancer agent for targeting cancer cells infected with an oncolytic virus, comprising, as an active ingredient:

an antibody or an antigen-binding fragment thereof, which specifically binds to protein A56 or a fragment thereof, wherein the oncolytic virus comprises a nucleic acid encoding the protein A56 or the fragment thereof, and wherein the antibody is an antibody comprising a heavy chain CDR1 of SEQ ID NO: 1, a heavy chain CDR2 of SEQ ID NO: 2, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6;

an antibody comprising a heavy chain CDR1 of SEQ ID NO: 18, a heavy chain CDR2 of SEQ ID NO: 19, a heavy chain CDR3 of SEQ ID NO: 20, a light chain CDR1 of SEQ ID NO: 21, a light chain CDR2 of SEQ ID NO: 22, and a light chain CDR3 of SEQ ID NO: 23;

an antibody comprising a heavy chain CDR1 of SEQ ID NO: 35, a heavy chain CDR2 of SEQ ID NO: 36, a heavy chain CDR3 of SEQ ID NO: 37, a light chain CDR1 of SEQ ID NO: 38, a light chain CDR2 of SEQ ID NO: 39, and a light chain CDR3 of SEQ ID NO: 40;

an antibody comprising a heavy chain CDR1 of SEQ ID NO: 52, a heavy chain CDR2 of SEQ ID NO: 53, a heavy chain CDR3 of SEQ ID NO: 54, a light chain CDR1 of SEQ ID NO: 55, a light chain CDR2 of SEQ ID NO: 56, and a light chain CDR3 of SEQ ID NO: 57;

an antibody comprising a heavy chain CDR1 of SEQ ID NO: 69, a heavy chain CDR2 of SEQ ID NO: 70, a heavy chain CDR3 of SEQ ID NO: 71, a light chain CDR1 of SEQ ID NO: 72, a light chain CDR2 of SEQ ID NO: 73, and a light chain CDR3 of SEQ ID NO: 74;

an antibody comprising a heavy chain CDR1 of SEQ ID NO: 86, a heavy chain CDR2 of SEQ ID NO: 87, a heavy chain CDR3 of SEQ ID NO: 88, a light chain CDR1 of SEQ ID NO: 89, a light chain CDR2 of SEQ ID NO: 90, and a light chain CDR3 of SEQ ID NO: 91;

an antibody comprising a heavy chain CDR1 of SEQ ID NO: 103, a heavy chain CDR2 of SEQ ID NO: 104, a heavy chain CDR3 of SEQ ID NO: 105, a light chain CDR1 of SEQ ID NO: 106, a light chain CDR2 of SEQ ID NO: 107, and a light chain CDR3 of SEQ ID NO: 108;

an antibody comprising a heavy chain CDR1 of SEQ ID NO: 120, a heavy chain CDR2 of SEQ ID NO: 121, a heavy chain CDR3 of SEQ ID NO: 122, a light chain CDR1 of SEQ ID NO: 123, a light chain CDR2 of SEQ ID NO: 124, and a light chain CDR3 of SEQ ID NO: 125;

an antibody comprising a heavy chain CDR1 of SEQ ID NO: 137, a heavy chain CDR2 of SEQ ID NO: 138, a heavy chain CDR3 of SEQ ID NO: 139, a light chain CDR1 of SEQ ID NO: 140, a light chain CDR2 of SEQ ID NO: 141, and a light chain CDR3 of SEQ ID NO: 142;

an antibody comprising a heavy chain CDR1 of SEQ ID NO: 154, a heavy chain CDR2 of SEQ ID NO: 155, a heavy chain CDR3 of SEQ ID NO: 156, a light chain CDR1 of SEQ ID NO: 157, a light chain CDR2 of SEQ ID NO: 158, and a light chain CDR3 of SEQ ID NO: 159;

an antibody comprising a heavy chain CDR1 of SEQ ID NO: 171, a heavy chain CDR2 of SEQ ID NO: 172, a heavy chain CDR3 of SEQ ID NO: 173, a light chain CDR1 of SEQ ID NO: 174, a light chain CDR2 of SEQ ID NO: 175, and a light chain CDR3 of SEQ ID NO: 176;

an antibody comprising a heavy chain CDR1 of SEQ ID NO: 188, a heavy chain CDR2 of SEQ ID NO: 189, a heavy chain CDR3 of SEQ ID NO: 190, a light chain CDR1 of SEQ ID NO: 191, a light chain CDR2 of SEQ ID NO: 192, and a light chain CDR3 of SEQ ID NO: 193;

an antibody comprising a heavy chain CDR1 of SEQ ID NO: 205, a heavy chain CDR2 of SEQ ID NO: 206, a heavy chain CDR3 of SEQ ID NO: 207, a light chain CDR1 of SEQ ID NO: 208, a light chain CDR2 of SEQ ID NO: 209, and a light chain CDR3 of SEQ ID NO: 210;

an antibody comprising a heavy chain CDR1 of SEQ ID NO: 222, a heavy chain CDR2 of SEQ ID NO: 223, a heavy chain CDR3 of SEQ ID NO: 224, a light chain CDR1 of SEQ ID NO: 225, a light chain CDR2 of SEQ ID NO: 226, and a light chain CDR3 of SEQ ID NO: 227;

an antibody comprising a heavy chain CDR1 of SEQ ID NO: 239, a heavy chain CDR2 of SEQ ID NO: 240, a heavy chain CDR3 of SEQ ID NO: 241, a light chain CDR1 of SEQ ID NO: 242, a light chain CDR2 of SEQ ID NO: 243, and a light chain CDR3 of SEQ ID NO: 244;

an antibody comprising a heavy chain CDR1 of SEQ ID NO: 256, a heavy chain CDR2 of SEQ ID NO: 257, a heavy chain CDR3 of SEQ ID NO: 258 a light chain CDR1 of SEQ ID NO: 259, a light chain CDR2 of SEQ ID NO: 260, and a light chain CDR3 of SEQ ID NO: 261;

an antibody comprising a heavy chain CDR1 of SEQ ID NO: 273, a heavy chain CDR2 of SEQ ID NO: 274, a heavy chain CDR3 of SEQ ID NO: 275, a light chain CDR1 of SEQ ID NO: 276, a light chain CDR2 of SEQ ID NO: 277, and a light chain CDR3 of SEQ ID NO: 278;

an antibody comprising a heavy chain CDR1 of SEQ ID NO: 290, a heavy chain CDR2 of SEQ ID NO: 291, a heavy chain CDR3 of SEQ ID NO: 292, a light chain CDR1 of SEQ ID NO: 293, a light chain CDR2 of SEQ ID NO: 294, and a light chain CDR3 of SEQ ID NO: 295;

an antibody comprising a heavy chain CDR1 of SEQ ID NO: 307, a heavy chain CDR2 of SEQ ID NO: 308, a heavy chain CDR3 of SEQ ID NO: 309, a light chain CDR1 of SEQ ID NO: 310, a light chain CDR2 of SEQ ID NO: 311, and a light chain CDR3 of SEQ ID NO: 312;

an antibody comprising a heavy chain CDR1 of SEQ ID NO: 324, a heavy chain CDR2 of SEQ ID NO: 325, a heavy chain CDR3 of SEQ ID NO: 326, a light chain CDR1 of SEQ ID NO: 327, a light chain CDR2 of SEQ ID NO: 328, and a light chain CDR3 of SEQ ID NO: 329;

an antibody comprising a heavy chain CDR1 of SEQ ID NO: 341, a heavy chain CDR2 of SEQ ID NO: 342, a heavy chain CDR3 of SEQ ID NO: 343, a light chain CDR1 of SEQ ID NO: 344, a light chain CDR2 of SEQ ID NO: 345, and a light chain CDR3 of SEQ ID NO: 346;

an antibody comprising a heavy chain CDR1 of SEQ ID NO: 358, a heavy chain CDR2 of SEQ ID NO: 359, a heavy chain CDR3 of SEQ ID NO: 360, a light chain CDR1 of SEQ ID NO: 361, a light chain CDR2 of SEQ ID NO: 362, and a light chain CDR3 of SEQ ID NO: 363;

an antibody comprising a heavy chain CDR1 of SEQ ID NO: 375, a heavy chain CDR2 of SEQ ID NO: 376, a heavy chain CDR3 of SEQ ID NO: 377, a light chain CDR1 of SEQ ID NO: 378, a light chain CDR2 of SEQ ID NO: 379, and a light chain CDR3 of SEQ ID NO: 380;

an antibody comprising a heavy chain CDR1 of SEQ ID NO: 392, a heavy chain CDR2 of SEQ ID NO: 393, a heavy chain CDR3 of SEQ ID NO: 394, a light chain CDR1 of SEQ ID NO: 395, a light chain CDR2 of SEQ ID NO: 396, and a light chain CDR3 of SEQ ID NO: 397;

an antibody comprising a heavy chain CDR1 of SEQ ID NO: 409, a heavy chain CDR2 of SEQ ID NO: 410, a heavy chain CDR3 of SEQ ID NO: 411, a light chain CDR1 of SEQ ID NO: 412, a light chain CDR2 of SEQ ID NO: 413, and a light chain CDR3 of SEQ ID NO: 414;

an antibody comprising a heavy chain CDR1 of SEQ ID NO: 426, a heavy chain CDR2 of SEQ ID NO: 427, a heavy chain CDR3 of SEQ ID NO: 428, a light chain CDR1 of SEQ ID NO: 429, a light chain CDR2 of SEQ ID NO: 430, and a light chain CDR3 of SEQ ID NO: 431;

an antibody comprising a heavy chain CDR1 of SEQ ID NO: 443, a heavy chain CDR2 of SEQ ID NO: 444, a heavy chain CDR3 of SEQ ID NO: 445, a light chain CDR1 of SEQ ID NO: 446, a light chain CDR2 of SEQ ID NO: 447, and a light chain CDR3 of SEQ ID NO: 448;

an antibody comprising a heavy chain CDR1 of SEQ ID NO: 460, a heavy chain CDR2 of SEQ ID NO: 461, a heavy chain CDR3 of SEQ ID NO: 462, a light chain CDR1 of SEQ ID NO: 463, a light chain CDR2 of SEQ ID NO: 464, and a light chain CDR3 of SEQ ID NO: 465;

an antibody comprising a heavy chain CDR1 of SEQ ID NO: 477, a heavy chain CDR2 of SEQ ID NO: 478, a heavy chain CDR3 of SEQ ID NO: 479, a light chain CDR1 of SEQ ID NO: 480, a light chain CDR2 of SEQ ID NO: 481, and a light chain CDR3 of SEQ ID NO: 482;

an antibody comprising a heavy chain CDR1 of SEQ ID NO: 494, a heavy chain CDR2 of SEQ ID NO: 495, a heavy chain CDR3 of SEQ ID NO: 496, a light chain CDR1 of SEQ ID NO: 497, a light chain CDR2 of SEQ ID NO: 498, and a light chain CDR3 of SEQ ID NO: 499;

an antibody comprising a heavy chain CDR1 of SEQ ID NO: 511, a heavy chain CDR2 of SEQ ID NO: 512, a heavy chain CDR3 of SEQ ID NO: 513, a light chain CDR1 of SEQ ID NO: 514, a light chain CDR2 of SEQ ID NO: 515, and a light chain CDR3 of SEQ ID NO: 516;

an antibody comprising a heavy chain CDR1 of SEQ ID NO: 528, a heavy chain CDR2 of SEQ ID NO: 529, a heavy chain CDR3 of SEQ ID NO: 530, a light chain CDR1 of SEQ ID NO: 531, a light chain CDR2 of SEQ ID NO: 532, and a light chain CDR3 of SEQ ID NO: 533;

an antibody comprising a heavy chain CDR1 of SEQ ID NO: 545, a heavy chain CDR2 of SEQ ID NO: 546, a heavy chain CDR3 of SEQ ID NO: 547, a light chain CDR1 of SEQ ID NO: 548, a light chain CDR2 of SEQ ID NO: 549, and a light chain CDR3 of SEQ ID NO: 550;

an antibody comprising a heavy chain CDR1 of SEQ ID NO: 562, a heavy chain CDR2 of SEQ ID NO: 563, a heavy chain CDR3 of SEQ ID NO: 564, a light chain CDR1 of SEQ ID NO: 565, a light chain CDR2 of SEQ ID NO: 566, and a light chain CDR3 of SEQ ID NO: 567;

an antibody comprising a heavy chain CDR1 of SEQ ID NO: 579, a heavy chain CDR2 of SEQ ID NO: 580, a heavy chain CDR3 of SEQ ID NO: 581, a light chain CDR1 of SEQ ID NO: 582, a light chain CDR2 of SEQ ID NO: 583, and a light chain CDR3 of SEQ ID NO: 584;

an antibody comprising a heavy chain CDR1 of SEQ ID NO: 596, a heavy chain CDR2 of SEQ ID NO: 597, a heavy chain CDR3 of SEQ ID NO: 598, a light chain CDR1 of SEQ ID NO: 599, a light chain CDR2 of SEQ ID NO: 600, and a light chain CDR3 of SEQ ID NO: 601;

an antibody comprising a heavy chain CDR1 of SEQ ID NO: 613, a heavy chain CDR2 of SEQ ID NO: 614, a heavy chain CDR3 of SEQ ID NO: 615, a light chain CDR1 of SEQ ID NO: 616, a light chain CDR2 of SEQ ID NO: 617, and a light chain CDR3 of SEQ ID NO: 618;

an antibody comprising a heavy chain CDR1 of SEQ ID NO: 630, a heavy chain CDR2 of SEQ ID NO: 631, a heavy chain CDR3 of SEQ ID NO: 632, a light chain CDR1 of SEQ ID NO: 633, a light chain CDR2 of SEQ ID NO: 634, and a light chain CDR3 of SEQ ID NO: 635;

an antibody comprising a heavy chain CDR1 of SEQ ID NO: 647, a heavy chain CDR2 of SEQ ID NO: 648, a heavy chain CDR3 of SEQ ID NO: 649, a light chain CDR1 of SEQ ID NO: 650, a light chain CDR2 of SEQ ID NO: 651, and a light chain CDR3 of SEQ ID NO: 652;

an antibody comprising a heavy chain CDR1 of SEQ ID NO: 664, a heavy chain CDR2 of SEQ ID NO: 665, a heavy chain CDR3 of SEQ ID NO: 666, a light chain CDR1 of SEQ ID NO: 667, a light chain CDR2 of SEQ ID NO: 668, and a light chain CDR3 of SEQ ID NO: 669;

an antibody comprising a heavy chain CDR1 of SEQ ID NO: 681, a heavy chain CDR2 of SEQ ID NO: 682, a heavy chain CDR3 of SEQ ID NO: 683, a light chain CDR1 of SEQ ID NO: 684, a light chain CDR2 of SEQ ID NO: 685, and a light chain CDR3 of SEQ ID NO: 686;

an antibody comprising a heavy chain CDR1 of SEQ ID NO: 698, a heavy chain CDR2 of SEQ ID NO: 699, a heavy chain CDR3 of SEQ ID NO: 700, a light chain CDR1 of SEQ ID NO: 701, a light chain CDR2 of SEQ ID NO: 702, and a light chain CDR3 of SEQ ID NO: 703;

an antibody comprising a heavy chain CDR1 of SEQ ID NO: 715, a heavy chain CDR2 of SEQ ID NO: 716, a heavy chain CDR3 of SEQ ID NO: 717, a light chain CDR1 of SEQ ID NO: 718, a light chain CDR2 of SEQ ID NO: 719, and a light chain CDR3 of SEQ ID NO: 720;

an antibody comprising a heavy chain CDR1 of SEQ ID NO: 732, a heavy chain CDR2 of SEQ ID NO: 733, a heavy chain CDR3 of SEQ ID NO: 734, a light chain CDR1 of SEQ ID NO: 735, a light chain CDR2 of SEQ ID NO: 736, and a light chain CDR3 of SEQ ID NO: 737;

an antibody comprising a heavy chain CDR1 of SEQ ID NO: 749, a heavy chain CDR2 of SEQ ID NO: 750, a heavy chain CDR3 of SEQ ID NO: 751, a light chain CDR1 of SEQ ID NO: 752, a light chain CDR2 of SEQ ID NO: 753, and a light chain CDR3 of SEQ ID NO: 754;

an antibody comprising a heavy chain CDR1 of SEQ ID NO: 766, a heavy chain CDR2 of SEQ ID NO: 767, a heavy chain CDR3 of SEQ ID NO: 768, a light chain CDR1 of SEQ ID NO: 769, a light chain CDR2 of SEQ ID NO: 770, and a light chain CDR3 of SEQ ID NO: 771;

an antibody comprising a heavy chain CDR1 of SEQ ID NO: 783, a heavy chain CDR2 of SEQ ID NO: 784, a heavy chain CDR3 of SEQ ID NO: 785, a light chain CDR1 of SEQ ID NO: 786, a light chain CDR2 of SEQ ID NO: 787, and a light chain CDR3 of SEQ ID NO: 788;

an antibody comprising a heavy chain CDR1 of SEQ ID NO: 800, a heavy chain CDR2 of SEQ ID NO: 801, a heavy chain CDR3 of SEQ ID NO: 802, a light chain CDR1 of SEQ ID NO: 803, a light chain CDR2 of SEQ ID NO: 804, and a light chain CDR3 of SEQ ID NO: 805;

an antibody comprising a heavy chain CDR1 of SEQ ID NO: 817, a heavy chain CDR2 of SEQ ID NO: 818, a heavy chain CDR3 of SEQ ID NO: 819, a light chain CDR1 of SEQ ID NO: 820, a light chain CDR2 of SEQ ID NO: 821, and a light chain CDR3 of SEQ ID NO: 822;

an antibody comprising a heavy chain CDR1 of SEQ ID NO: 834, a heavy chain CDR2 of SEQ ID NO: 835, a heavy chain CDR3 of SEQ ID NO: 836, a light chain CDR1 of SEQ ID NO: 837, a light chain CDR2 of SEQ ID NO: 838, and a light chain CDR3 of SEQ ID NO: 839;

an antibody comprising a heavy chain CDR1 of SEQ ID NO: 851, a heavy chain CDR2 of SEQ ID NO: 852, a heavy chain CDR3 of SEQ ID NO: 853, a light chain CDR1 of SEQ ID NO: 854, a light chain CDR2 of SEQ ID NO: 855, and a light chain CDR3 of SEQ ID NO: 856;

an antibody comprising a heavy chain CDR1 of SEQ ID NO: 868, a heavy chain CDR2 of SEQ ID NO: 869, a heavy chain CDR3 of SEQ ID NO: 870, a light chain CDR1 of SEQ ID NO: 871, a light chain CDR2 of SEQ ID NO: 872, and a light chain CDR3 of SEQ ID NO: 873;

an antibody comprising a heavy chain CDR1 of SEQ ID NO: 885, a heavy chain CDR2 of SEQ ID NO: 886, a heavy chain CDR3 of SEQ ID NO: 887, a light chain CDR1 of SEQ ID NO: 888, a light chain CDR2 of SEQ ID NO: 889, and a light chain CDR3 of SEQ ID NO: 890;

an antibody comprising a heavy chain CDR1 of SEQ ID NO: 902, a heavy chain CDR2 of SEQ ID NO: 903, a heavy chain CDR3 of SEQ ID NO: 904, a light chain CDR1 of SEQ ID NO: 905, a light chain CDR2 of SEQ ID NO: 906, and a light chain CDR3 of SEQ ID NO: 907;

an antibody comprising a heavy chain CDR1 of SEQ ID NO: 919, a heavy chain CDR2 of SEQ ID NO: 920, a heavy chain CDR3 of SEQ ID NO: 921, a light chain CDR1 of SEQ ID NO: 922, a light chain CDR2 of SEQ ID NO: 923, and a light chain CDR3 of SEQ ID NO: 924;

an antibody comprising a heavy chain CDR1 of SEQ ID NO: 936, a heavy chain CDR2 of SEQ ID NO: 937, a heavy chain CDR3 of SEQ ID NO: 938, a light chain CDR1 of SEQ ID NO: 939, a light chain CDR2 of SEQ ID NO: 940, and a light chain CDR3 of SEQ ID NO: 941;

an antibody comprising a heavy chain CDR1 of SEQ ID NO: 953, a heavy chain CDR2 of SEQ ID NO: 954, a heavy chain CDR3 of SEQ ID NO: 955, a light chain CDR1 of SEQ ID NO: 956, a light chain CDR2 of SEQ ID NO: 957, and a light chain CDR3 of SEQ ID NO: 958;

an antibody comprising a heavy chain CDR1 of SEQ ID NO: 970, a heavy chain CDR2 of SEQ ID NO: 971, a heavy chain CDR3 of SEQ ID NO: 972, a light chain CDR1 of SEQ ID NO: 973, a light chain CDR2 of SEQ ID NO: 974, and a light chain CDR3 of SEQ ID NO: 975;

an antibody comprising a heavy chain CDR1 of SEQ ID NO: 987, a heavy chain CDR2 of SEQ ID NO: 988, a heavy chain CDR3 of SEQ ID NO: 989, a light chain CDR1 of SEQ ID NO: 990, a light chain CDR2 of SEQ ID NO: 991, and a light chain CDR3 of SEQ ID NO: 992;

an antibody comprising a heavy chain CDR1 of SEQ ID NO: 1004, a heavy chain CDR2 of SEQ ID NO: 1005, a heavy chain CDR3 of SEQ ID NO: 1006, a light chain CDR1 of SEQ ID NO: 1007, a light chain CDR2 of SEQ ID NO: 1008, and a light chain CDR3 of SEQ ID NO: 1009;

an antibody comprising a heavy chain CDR1 of SEQ ID NO: 1021, a heavy chain CDR2 of SEQ ID NO: 1022, a heavy chain CDR3 of SEQ ID NO: 1023, a light chain CDR1 of SEQ ID NO: 1024, a light chain CDR2 of SEQ ID NO: 1025, and a light chain CDR3 of SEQ ID NO: 1026;

an antibody comprising a heavy chain CDR1 of SEQ ID NO: 1062, a heavy chain CDR2 of SEQ ID NO: 1064, a heavy chain CDR3 of SEQ ID NO: 1065, a light chain CDR1 of SEQ ID NO: 1066, a light chain CDR2 of SEQ ID NO: 1067, and a light chain CDR3 of SEQ ID NO: 1068; or an antibody comprising a heavy chain CDR1 of SEQ ID NO: 1063, a heavy chain CDR2 of SEQ ID NO: 1064, a heavy chain CDR3 of SEQ ID NO: 1065, a light chain CDR1 of SEQ ID NO: 1066, a light chain CDR2 of SEQ ID NO: 1067, and a light chain CDR3 of SEQ ID NO: 1068.

2. The anticancer agent of claim 1, wherein the oncolytic virus is a vaccinia virus.

3. The anticancer agent of claim 1, wherein the protein A56 is wild-type protein A56 or a variant of the protein A56.

4. The anticancer agent of claim 1, wherein the protein A56 or the fragment thereof comprises the amino acid sequence of SEQ ID NO: 1038, 1040, 1042, 1044, 1046, 1048, 1050, 1052, 1054, 1056, 1058, 1060, 1073, 1075, 1077, or 1079.

5. The anticancer agent of claim 1, wherein the nucleic acid encoding the protein A56 or the fragment thereof comprises the nucleotide sequence of SEQ ID NO: 1039, 1041, 1043, 1045, 1047, 1049, 1051, 1053, 1055, 1057, 1059, 1061, 1072, 1074, 1076, or 1078.

6. A recombinant antibody or an antigen-binding fragment thereof for targeting cancer cells infected with an oncolytic virus, wherein the recombinant antibody or the antigen-binding fragment thereof binds to protein A56 or a fragment thereof, wherein the oncolytic virus comprises a nucleic acid encoding the protein A56 or the fragment thereof, and wherein the antibody is an antibody comprising a heavy chain CDR1 of SEQ ID NO: 1, a heavy chain CDR2 of SEQ ID NO: 2, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6;

an antibody comprising a heavy chain CDR1 of SEQ ID NO: 18, a heavy chain CDR2 of SEQ ID NO: 19, a heavy chain CDR3 of SEQ ID NO: 20, a light chain CDR1 of SEQ ID NO: 21, a light chain CDR2 of SEQ ID NO: 22, and a light chain CDR3 of SEQ ID NO: 23;

an antibody comprising a heavy chain CDR1 of SEQ ID NO: 35, a heavy chain CDR2 of SEQ ID NO: 36, a heavy chain CDR3 of SEQ ID NO: 37, a light chain CDR1 of SEQ ID NO: 38, a light chain CDR2 of SEQ ID NO: 39, and a light chain CDR3 of SEQ ID NO: 40;

an antibody comprising a heavy chain CDR1 of SEQ ID NO: 52, a heavy chain CDR2 of SEQ ID NO: 53, a heavy chain CDR3 of SEQ ID NO: 54, a light chain CDR1 of SEQ ID NO: 55, a light chain CDR2 of SEQ ID NO: 56, and a light chain CDR3 of SEQ ID NO: 57;

an antibody comprising a heavy chain CDR1 of SEQ ID NO: 69, a heavy chain CDR2 of SEQ ID NO: 70, a heavy chain CDR3 of SEQ ID NO: 71, a light chain CDR1 of SEQ ID NO: 72, a light chain CDR2 of SEQ ID NO: 73, and a light chain CDR3 of SEQ ID NO: 74;

an antibody comprising a heavy chain CDR1 of SEQ ID NO: 86, a heavy chain CDR2 of SEQ ID NO: 87, a heavy chain CDR3 of SEQ ID NO: 88, a light chain CDR1 of SEQ ID NO: 89, a light chain CDR2 of SEQ ID NO: 90, and a light chain CDR3 of SEQ ID NO: 91;

an antibody comprising a heavy chain CDR1 of SEQ ID NO: 103, a heavy chain CDR2 of SEQ ID NO: 104, a heavy chain CDR3 of SEQ ID NO: 105, a light chain CDR1 of SEQ ID NO: 106, a light chain CDR2 of SEQ ID NO: 107, and a light chain CDR3 of SEQ ID NO: 108;

an antibody comprising a heavy chain CDR1 of SEQ ID NO: 120, a heavy chain CDR2 of SEQ ID NO: 121, a heavy chain CDR3 of SEQ ID NO: 122, a light chain CDR1 of SEQ ID NO: 123, a light chain CDR2 of SEQ ID NO: 124, and a light chain CDR3 of SEQ ID NO: 125;

an antibody comprising a heavy chain CDR1 of SEQ ID NO: 137, a heavy chain CDR2 of SEQ ID NO: 138, a heavy chain CDR3 of SEQ ID NO: 139, a light chain CDR1 of SEQ ID NO: 140, a light chain CDR2 of SEQ ID NO: 141, and a light chain CDR3 of SEQ ID NO: 142;

an antibody comprising a heavy chain CDR1 of SEQ ID NO: 154, a heavy chain CDR2 of SEQ ID NO: 155, a heavy chain CDR3 of SEQ ID NO: 156, a light chain CDR1 of SEQ ID NO: 157, a light chain CDR2 of SEQ ID NO: 158, and a light chain CDR3 of SEQ ID NO: 159;

an antibody comprising a heavy chain CDR1 of SEQ ID NO: 171, a heavy chain CDR2 of SEQ ID NO: 172, a heavy chain CDR3 of SEQ ID NO: 173, a light chain CDR1 of SEQ ID NO: 174, a light chain CDR2 of SEQ ID NO: 175, and a light chain CDR3 of SEQ ID NO: 176;

an antibody comprising a heavy chain CDR1 of SEQ ID NO: 188, a heavy chain CDR2 of SEQ ID NO: 189, a heavy chain CDR3 of SEQ ID NO: 190, a light chain CDR1 of SEQ ID NO: 191, a light chain CDR2 of SEQ ID NO: 192, and a light chain CDR3 of SEQ ID NO: 193;

an antibody comprising a heavy chain CDR1 of SEQ ID NO: 205, a heavy chain CDR2 of SEQ ID NO: 206, a heavy chain CDR3 of SEQ ID NO: 207, a light chain CDR1 of SEQ ID NO: 208, a light chain CDR2 of SEQ ID NO: 209, and a light chain CDR3 of SEQ ID NO: 210;

an antibody comprising a heavy chain CDR1 of SEQ ID NO: 222, a heavy chain CDR2 of SEQ ID NO: 223, a heavy chain CDR3 of SEQ ID NO: 224, a light chain CDR1 of SEQ ID NO: 225, a light chain CDR2 of SEQ ID NO: 226, and a light chain CDR3 of SEQ ID NO: 227;

an antibody comprising a heavy chain CDR1 of SEQ ID NO: 239, a heavy chain CDR2 of SEQ ID NO: 240, a heavy chain CDR3 of SEQ ID NO: 241, a light chain CDR1 of SEQ ID NO: 242, a light chain CDR2 of SEQ ID NO: 243, and a light chain CDR3 of SEQ ID NO: 244;

an antibody comprising a heavy chain CDR1 of SEQ ID NO: 256, a heavy chain CDR2 of SEQ ID NO: 257, a heavy chain CDR3 of SEQ ID NO: 258 a light chain CDR1 of SEQ ID NO: 259, a light chain CDR2 of SEQ ID NO: 260, and a light chain CDR3 of SEQ ID NO: 261;

an antibody comprising a heavy chain CDR1 of SEQ ID NO: 273, a heavy chain CDR2 of SEQ ID NO: 274, a heavy chain CDR3 of SEQ ID NO: 275, a light chain CDR1 of SEQ ID NO: 276, a light chain CDR2 of SEQ ID NO: 277, and a light chain CDR3 of SEQ ID NO: 278;

an antibody comprising a heavy chain CDR1 of SEQ ID NO: 290, a heavy chain CDR2 of SEQ ID NO: 291, a heavy chain CDR3 of SEQ ID NO: 292, a light chain CDR1 of SEQ ID NO: 293, a light chain CDR2 of SEQ ID NO: 294, and a light chain CDR3 of SEQ ID NO: 295;

an antibody comprising a heavy chain CDR1 of SEQ ID NO: 307, a heavy chain CDR2 of SEQ ID NO: 308, a heavy chain CDR3 of SEQ ID NO: 309, a light chain CDR1 of SEQ ID NO: 310, a light chain CDR2 of SEQ ID NO: 311, and a light chain CDR3 of SEQ ID NO: 312;

an antibody comprising a heavy chain CDR1 of SEQ ID NO: 324, a heavy chain CDR2 of SEQ ID NO: 325, a heavy chain CDR3 of SEQ ID NO: 326, a light chain CDR1 of SEQ ID NO: 327, a light chain CDR2 of SEQ ID NO: 328, and a light chain CDR3 of SEQ ID NO: 329;

an antibody comprising a heavy chain CDR1 of SEQ ID NO: 341, a heavy chain CDR2 of SEQ ID NO: 342, a heavy chain CDR3 of SEQ ID NO: 343, a light chain CDR1 of SEQ ID NO: 344, a light chain CDR2 of SEQ ID NO: 345, and a light chain CDR3 of SEQ ID NO: 346;

an antibody comprising a heavy chain CDR1 of SEQ ID NO: 358, a heavy chain CDR2 of SEQ ID NO: 359, a heavy chain CDR3 of SEQ ID NO: 360, a light chain CDR1 of SEQ ID NO: 361, a light chain CDR2 of SEQ ID NO: 362, and a light chain CDR3 of SEQ ID NO: 363;

an antibody comprising a heavy chain CDR1 of SEQ ID NO: 375, a heavy chain CDR2 of SEQ ID NO: 376, a heavy chain CDR3 of SEQ ID NO: 377, a light chain CDR1 of SEQ ID NO: 378, a light chain CDR2 of SEQ ID NO: 379, and a light chain CDR3 of SEQ ID NO: 380;

an antibody comprising a heavy chain CDR1 of SEQ ID NO: 392, a heavy chain CDR2 of SEQ ID NO: 393, a heavy chain CDR3 of SEQ ID NO: 394, a light chain CDR1 of SEQ ID NO: 395, a light chain CDR2 of SEQ ID NO: 396, and a light chain CDR3 of SEQ ID NO: 397;

an antibody comprising a heavy chain CDR1 of SEQ ID NO: 409, a heavy chain CDR2 of SEQ ID NO: 410, a heavy chain CDR3 of SEQ ID NO: 411, a light chain CDR1 of SEQ ID NO: 412, a light chain CDR2 of SEQ ID NO: 413, and a light chain CDR3 of SEQ ID NO: 414;

an antibody comprising a heavy chain CDR1 of SEQ ID NO: 426, a heavy chain CDR2 of SEQ ID NO: 427, a heavy chain CDR3 of SEQ ID NO: 428, a light chain CDR1 of SEQ ID NO: 429, a light chain CDR2 of SEQ ID NO: 430, and a light chain CDR3 of SEQ ID NO: 431;

an antibody comprising a heavy chain CDR1 of SEQ ID NO: 443, a heavy chain CDR2 of SEQ ID NO: 444, a heavy chain CDR3 of SEQ ID NO: 445, a light chain CDR1 of SEQ ID NO: 446, a light chain CDR2 of SEQ ID NO: 447, and a light chain CDR3 of SEQ ID NO: 448;

an antibody comprising a heavy chain CDR1 of SEQ ID NO: 460, a heavy chain CDR2 of SEQ ID NO: 461, a heavy chain CDR3 of SEQ ID NO: 462, a light chain CDR1 of SEQ ID NO: 463, a light chain CDR2 of SEQ ID NO: 464, and a light chain CDR3 of SEQ ID NO: 465;

an antibody comprising a heavy chain CDR1 of SEQ ID NO: 477, a heavy chain CDR2 of SEQ ID NO: 478, a heavy chain CDR3 of SEQ ID NO: 479, a light chain CDR1 of SEQ ID NO: 480, a light chain CDR2 of SEQ ID NO: 481, and a light chain CDR3 of SEQ ID NO: 482;

an antibody comprising a heavy chain CDR1 of SEQ ID NO: 494, a heavy chain CDR2 of SEQ ID NO: 495, a heavy chain CDR3 of SEQ ID NO: 496, a light chain CDR1 of SEQ ID NO: 497, a light chain CDR2 of SEQ ID NO: 498, and a light chain CDR3 of SEQ ID NO: 499;

an antibody comprising a heavy chain CDR1 of SEQ ID NO: 511, a heavy chain CDR2 of SEQ ID NO: 512, a heavy chain CDR3 of SEQ ID NO: 513, a light chain CDR1 of SEQ ID NO: 514, a light chain CDR2 of SEQ ID NO: 515, and a light chain CDR3 of SEQ ID NO: 516;

an antibody comprising a heavy chain CDR1 of SEQ ID NO: 528, a heavy chain CDR2 of SEQ ID NO: 529, a heavy chain CDR3 of SEQ ID NO: 530, a light chain CDR1 of SEQ ID NO: 531, a light chain CDR2 of SEQ ID NO: 532, and a light chain CDR3 of SEQ ID NO: 533;

an antibody comprising a heavy chain CDR1 of SEQ ID NO: 545, a heavy chain CDR2 of SEQ ID NO: 546, a heavy chain CDR3 of SEQ ID NO: 547, a light chain CDR1 of SEQ ID NO: 548, a light chain CDR2 of SEQ ID NO: 549, and a light chain CDR3 of SEQ ID NO: 550;

an antibody comprising a heavy chain CDR1 of SEQ ID NO: 562, a heavy chain CDR2 of SEQ ID NO: 563, a heavy chain CDR3 of SEQ ID NO: 564, a light chain CDR1 of SEQ ID NO: 565, a light chain CDR2 of SEQ ID NO: 566, and a light chain CDR3 of SEQ ID NO: 567;

an antibody comprising a heavy chain CDR1 of SEQ ID NO: 579, a heavy chain CDR2 of SEQ ID NO: 580, a heavy chain CDR3 of SEQ ID NO: 581, a light chain CDR1 of SEQ ID NO: 582, a light chain CDR2 of SEQ ID NO: 583, and a light chain CDR3 of SEQ ID NO: 584;

an antibody comprising a heavy chain CDR1 of SEQ ID NO: 596, a heavy chain CDR2 of SEQ ID NO: 597, a heavy chain CDR3 of SEQ ID NO: 598, a light chain CDR1 of SEQ ID NO: 599, a light chain CDR2 of SEQ ID NO: 600, and a light chain CDR3 of SEQ ID NO: 601;

an antibody comprising a heavy chain CDR1 of SEQ ID NO: 613, a heavy chain CDR2 of SEQ ID NO: 614, a heavy chain CDR3 of SEQ ID NO: 615, a light chain CDR1 of SEQ ID NO: 616, a light chain CDR2 of SEQ ID NO: 617, and a light chain CDR3 of SEQ ID NO: 618;

an antibody comprising a heavy chain CDR1 of SEQ ID NO: 630, a heavy chain CDR2 of SEQ ID NO: 631, a heavy chain CDR3 of SEQ ID NO: 632, a light chain CDR1 of SEQ ID NO: 633, a light chain CDR2 of SEQ ID NO: 634, and a light chain CDR3 of SEQ ID NO: 635;

an antibody comprising a heavy chain CDR1 of SEQ ID NO: 647, a heavy chain CDR2 of SEQ ID NO: 648, a heavy chain CDR3 of SEQ ID NO: 649, a light chain CDR1 of SEQ ID NO: 650, a light chain CDR2 of SEQ ID NO: 651, and a light chain CDR3 of SEQ ID NO: 652;

an antibody comprising a heavy chain CDR1 of SEQ ID NO: 664, a heavy chain CDR2 of SEQ ID NO: 665, a heavy chain CDR3 of SEQ ID NO: 666, a light chain CDR1 of SEQ ID NO: 667, a light chain CDR2 of SEQ ID NO: 668, and a light chain CDR3 of SEQ ID NO: 669;

an antibody comprising a heavy chain CDR1 of SEQ ID NO: 681, a heavy chain CDR2 of SEQ ID NO: 682, a heavy chain CDR3 of SEQ ID NO: 683, a light chain CDR1 of SEQ ID NO: 684, a light chain CDR2 of SEQ ID NO: 685, and a light chain CDR3 of SEQ ID NO: 686;

an antibody comprising a heavy chain CDR1 of SEQ ID NO: 698, a heavy chain CDR2 of SEQ ID NO: 699, a heavy chain CDR3 of SEQ ID NO: 700, a light chain CDR1 of SEQ ID NO: 701, a light chain CDR2 of SEQ ID NO: 702, and a light chain CDR3 of SEQ ID NO: 703;

an antibody comprising a heavy chain CDR1 of SEQ ID NO: 715, a heavy chain CDR2 of SEQ ID NO: 716, a heavy chain CDR3 of SEQ ID NO: 717, a light chain CDR1 of SEQ ID NO: 718, a light chain CDR2 of SEQ ID NO: 719, and a light chain CDR3 of SEQ ID NO: 720;

an antibody comprising a heavy chain CDR1 of SEQ ID NO: 732, a heavy chain CDR2 of SEQ ID NO: 733, a heavy chain CDR3 of SEQ ID NO: 734, a light chain CDR1 of SEQ ID NO: 735, a light chain CDR2 of SEQ ID NO: 736, and a light chain CDR3 of SEQ ID NO: 737;

an antibody comprising a heavy chain CDR1 of SEQ ID NO: 749, a heavy chain CDR2 of SEQ ID NO: 750, a heavy chain CDR3 of SEQ ID NO: 751, a light chain CDR1 of SEQ ID NO: 752, a light chain CDR2 of SEQ ID NO: 753, and a light chain CDR3 of SEQ ID NO: 754;

an antibody comprising a heavy chain CDR1 of SEQ ID NO: 766, a heavy chain CDR2 of SEQ ID NO: 767, a heavy chain CDR3 of SEQ ID NO: 768, a light chain CDR1 of SEQ ID NO: 769, a light chain CDR2 of SEQ ID NO: 770, and a light chain CDR3 of SEQ ID NO: 771;

an antibody comprising a heavy chain CDR1 of SEQ ID NO: 783, a heavy chain CDR2 of SEQ ID NO: 784, a heavy chain CDR3 of SEQ ID NO: 785, a light chain CDR1 of SEQ ID NO: 786, a light chain CDR2 of SEQ ID NO: 787, and a light chain CDR3 of SEQ ID NO: 788;

an antibody comprising a heavy chain CDR1 of SEQ ID NO: 800, a heavy chain CDR2 of SEQ ID NO: 801, a heavy chain CDR3 of SEQ ID NO: 802, a light chain CDR1 of SEQ ID NO: 803, a light chain CDR2 of SEQ ID NO: 804, and a light chain CDR3 of SEQ ID NO: 805;

an antibody comprising a heavy chain CDR1 of SEQ ID NO: 817, a heavy chain CDR2 of SEQ ID NO: 818, a heavy chain CDR3 of SEQ ID NO: 819, a light chain CDR1 of SEQ ID NO: 820, a light chain CDR2 of SEQ ID NO: 821, and a light chain CDR3 of SEQ ID NO: 822;

an antibody comprising a heavy chain CDR1 of SEQ ID NO: 834, a heavy chain CDR2 of SEQ ID NO: 835, a heavy chain CDR3 of SEQ ID NO: 836, a light chain CDR1 of SEQ ID NO: 837, a light chain CDR2 of SEQ ID NO: 838, and a light chain CDR3 of SEQ ID NO: 839;

an antibody comprising a heavy chain CDR1 of SEQ ID NO: 851, a heavy chain CDR2 of SEQ ID NO: 852, a heavy chain CDR3 of SEQ ID NO: 853, a light chain CDR1 of SEQ ID NO: 854, a light chain CDR2 of SEQ ID NO: 855, and a light chain CDR3 of SEQ ID NO: 856;

an antibody comprising a heavy chain CDR1 of SEQ ID NO: 868, a heavy chain CDR2 of SEQ ID NO: 869, a heavy chain CDR3 of SEQ ID NO: 870, a light chain CDR1 of SEQ ID NO: 871, a light chain CDR2 of SEQ ID NO: 872, and a light chain CDR3 of SEQ ID NO: 873;

an antibody comprising a heavy chain CDR1 of SEQ ID NO: 885, a heavy chain CDR2 of SEQ ID NO: 886, a heavy chain CDR3 of SEQ ID NO: 887, a light chain CDR1 of SEQ ID NO: 888, a light chain CDR2 of SEQ ID NO: 889, and a light chain CDR3 of SEQ ID NO: 890;

an antibody comprising a heavy chain CDR1 of SEQ ID NO: 902, a heavy chain CDR2 of SEQ ID NO: 903, a heavy chain CDR3 of SEQ ID NO: 904, a light chain CDR1 of SEQ ID NO: 905, a light chain CDR2 of SEQ ID NO: 906, and a light chain CDR3 of SEQ ID NO: 907;

an antibody comprising a heavy chain CDR1 of SEQ ID NO: 919, a heavy chain CDR2 of SEQ ID NO:

920, a heavy chain CDR3 of SEQ ID NO: 921, a light chain CDR1 of SEQ ID NO: 922, a light chain CDR2 of SEQ ID NO: 923, and a light chain CDR3 of SEQ ID NO: 924;

an antibody comprising a heavy chain CDR1 of SEQ ID NO: 936, a heavy chain CDR2 of SEQ ID NO: 937, a heavy chain CDR3 of SEQ ID NO: 938, a light chain CDR1 of SEQ ID NO: 939, a light chain CDR2 of SEQ ID NO: 940, and a light chain CDR3 of SEQ ID NO: 941;

an antibody comprising a heavy chain CDR1 of SEQ ID NO: 953, a heavy chain CDR2 of SEQ ID NO: 954, a heavy chain CDR3 of SEQ ID NO: 955, a light chain CDR1 of SEQ ID NO: 956, a light chain CDR2 of SEQ ID NO: 957, and a light chain CDR3 of SEQ ID NO: 958;

an antibody comprising a heavy chain CDR1 of SEQ ID NO: 970, a heavy chain CDR2 of SEQ ID NO: 971, a heavy chain CDR3 of SEQ ID NO: 972, a light chain CDR1 of SEQ ID NO: 973, a light chain CDR2 of SEQ ID NO: 974, and a light chain CDR3 of SEQ ID NO: 975;

an antibody comprising a heavy chain CDR1 of SEQ ID NO: 987, a heavy chain CDR2 of SEQ ID NO: 988, a heavy chain CDR3 of SEQ ID NO: 989, a light chain CDR1 of SEQ ID NO: 990, a light chain CDR2 of SEQ ID NO: 991, and a light chain CDR3 of SEQ ID NO: 992;

an antibody comprising a heavy chain CDR1 of SEQ ID NO: 1004, a heavy chain CDR2 of SEQ ID NO: 1005, a heavy chain CDR3 of SEQ ID NO: 1006, a light chain CDR1 of SEQ ID NO: 1007, a light chain CDR2 of SEQ ID NO: 1008, and a light chain CDR3 of SEQ ID NO: 1009;

an antibody comprising a heavy chain CDR1 of SEQ ID NO: 1021, a heavy chain CDR2 of SEQ ID NO: 1022, a heavy chain CDR3 of SEQ ID NO: 1023, a light chain CDR1 of SEQ ID NO: 1024, a light chain CDR2 of SEQ ID NO: 1025, and a light chain CDR3 of SEQ ID NO: 1026;

an antibody comprising a heavy chain CDR1 of SEQ ID NO: 1062, a heavy chain CDR2 of SEQ ID NO: 1064, a heavy chain CDR3 of SEQ ID NO: 1065, a light chain CDR1 of SEQ ID NO: 1066, a light chain CDR2 of SEQ ID NO: 1067, and a light chain CDR3 of SEQ ID NO: 1068; or an antibody comprising a heavy chain CDR1 of SEQ ID NO: 1063, a heavy chain CDR2 of SEQ ID NO: 1064, a heavy chain CDR3 of SEQ ID NO: 1065, a light chain CDR1 of SEQ ID NO: 1066, a light chain CDR2 of SEQ ID NO: 1067, and a light chain CDR3 of SEQ ID NO: 1068.

* * * * *

SEQUENCE LISTING

```
<160> NUMBER OF SEQ ID NOS: 1083

<210> SEQ ID NO 1
<211> LENGTH: 8
<212> TYPE: PRT
<213> ORGANISM: Artificial Sequence
<220> FEATURE:
<223> OTHER INFORMATION: H-CDR1 of A56-01A02

<400> SEQUENCE: 1

Gly Gly Thr Phe Ser Ser Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: H-CDR2 of A56-01A02

<400> SEQUENCE: 2

Ile Ile Pro Ile Phe Gly Thr Ala
1               5

<210> SEQ ID NO 3
<211> LENGTH: 13
<212> TYPE: PRT
<213> ORGANISM: Artificial Sequence
<220> FEATURE:
<223> OTHER INFORMATION: H-CDR3 of A56-01A02

<400> SEQUENCE: 3

Ala Arg Phe Val Phe Gly Ser Gly Thr Tyr Leu Asp Ser
1               5                   10

<210> SEQ ID NO 4
<211> LENGTH: 11
<212> TYPE: PRT
<213> ORGANISM: Artificial Sequence
<220> FEATURE:
<223> OTHER INFORMATION: L-CDR1 of A56-01A02

<400> SEQUENCE: 4

Gln Ser Leu Leu Tyr Ser Asn Gly Asn Asn Tyr
1               5                   10

<210> SEQ ID NO 5
<211> LENGTH: 3
<212> TYPE: PRT
<213> ORGANISM: Artificial Sequence
<220> FEATURE:
```

<223> OTHER INFORMATION: L-CDR2 of A56-01A02

<400> SEQUENCE: 5

Leu Gly Ser
1

<210> SEQ ID NO 6
<211> LENGTH: 9
<212> TYPE: PRT
<213> ORGANISM: Artificial Sequence
<220> FEATURE:
<223> OTHER INFORMATION: L-CDR3 of A56-01A02

<400> SEQUENCE: 6

Met Gln Ala Leu Gln Thr Pro Leu Thr
1               5

<210> SEQ ID NO 7
<211> LENGTH: 255
<212> TYPE: DNA
<213> ORGANISM: Artificial Sequence
<220> FEATURE:
<223> OTHER INFORMATION: SCFV of A56-01A02

<400> SEQUENCE: 7
cagatgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcaccatg accagggaca cgtccacgag cacagtctac    240
atggagctga gcagc                                                     255

<210> SEQ ID NO 8
<211> LENGTH: 120
<212> TYPE: PRT
<213> ORGANISM: Artificial Sequence
<220> FEATURE:
<223> OTHER INFORMATION: VH2 of A56-01A02

<400> SEQUENCE: 8

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Lys Ser Glu Asp Thr Ala Val Tyr Tyr Cys
                85                  90                  95

Ala Arg Phe Val Phe Gly Ser Gly Thr Tyr Leu Asp Ser Trp Gly Gln
            100                 105                 110

Gly Thr Leu Val Thr Val Ser Ser
        115                 120

<210> SEQ ID NO 9
<211> LENGTH: 112
<212> TYPE: PRT
<213> ORGANISM: Artificial Sequence -continued

```
<220> FEATURE:
<223> OTHER INFORMATION: VL2 of A56-01A02

<400> SEQUENCE: 9

Asp Ile Val Met Thr Gln Thr Pro Leu Ser Leu Pro Val Thr Pro Gly
1               5                   10                  15

Glu Ser Ala Ser Ile Ser Cys Arg Ser Ser Gln Ser Leu Leu Tyr Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Asp Ile Lys
            100                 105                 110

<210> SEQ ID NO 10
<211> LENGTH: 25
<212> TYPE: PRT
<213> ORGANISM: Artificial Sequence
<220> FEATURE:
<223> OTHER INFORMATION: H-FR1 of A56-01A02

<400> SEQUENCE: 10

Gln Met Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 11
<211> LENGTH: 17
<212> TYPE: PRT
<213> ORGANISM: Artificial Sequence
<220> FEATURE:
<223> OTHER INFORMATION: H-FR2 of A56-01A02

<400> SEQUENCE: 11

Ile Ser Trp Val Arg Gln Ala Pro Gly Gln Gly Leu Glu Trp Met Gly
1               5                   10                  15

Gly

<210> SEQ ID NO 12
<211> LENGTH: 38
<212> TYPE: PRT
<213> ORGANISM: Artificial Sequence
<220> FEATURE:
<223> OTHER INFORMATION: H-FR3 of A56-01A02

<400> SEQUENCE: 12

Asn Tyr Ala Gln Lys Phe Gln Gly Arg Val Thr Met Thr Arg Asp Thr
1               5                   10                  15

Ser Thr Ser Thr Val Tyr Met Glu Leu Ser Ser Leu Lys Ser Glu Asp
            20                  25                  30

Thr Ala Val Tyr Tyr Cys
            35

<210> SEQ ID NO 13
<211> LENGTH: 11
```

-continued

```
<212> TYPE: PRT
<213> ORGANISM: Artificial Sequence
<220> FEATURE:
<223> OTHER INFORMATION: H-FR4 of A56-01A02

<400> SEQUENCE: 13

Trp Gly Gln Gly Thr Leu Val Thr Val Ser Ser
1               5                   10

<210> SEQ ID NO 14
<211> LENGTH: 26
<212> TYPE: PRT
<213> ORGANISM: Artificial Sequence
<220> FEATURE:
<223> OTHER INFORMATION: L-FR1 of A56-01A02

<400> SEQUENCE: 14

Asp Ile Val Met Thr Gln Thr Pro Leu Ser Leu Pro Val Thr Pro Gly
1               5                   10                  15

Glu Ser Ala Ser Ile Ser Cys Arg Ser Ser
            20                  25

<210> SEQ ID NO 15
<211> LENGTH: 17
<212> TYPE: PRT
<213> ORGANISM: Artificial Sequence
<220> FEATURE:
<223> OTHER INFORMATION: L-FR2 of A56-01A02

<400> SEQUENCE: 15

Leu Asp Trp Tyr Leu Gln Lys Pro Gly Gln Ser Pro Gln Leu Leu Ile
1               5                   10                  15

Tyr

<210> SEQ ID NO 16
<211> LENGTH: 36
<212> TYPE: PRT
<213> ORGANISM: Artificial Sequence
<220> FEATURE:
<223> OTHER INFORMATION: L-FR3 of A56-01A02

<400> SEQUENCE: 16

Ile Tyr Leu Gly Ser Asn Arg Ala Ser Gly Val Pro Asp Arg Phe Ser
1               5                   10                  15

Gly Ser Gly Ser Gly Thr Asp Phe Thr Leu Lys Ile Ser Arg Val Glu
            20                  25                  30

Ala Glu Asp Val
        35

<210> SEQ ID NO 17
<211> LENGTH: 10
<212> TYPE: PRT
<213> ORGANISM: Artificial Sequence
<220> FEATURE:
<223> OTHER INFORMATION: L-FR4 of A56-01A02

<400> SEQUENCE: 17

Phe Gly Gly Gly Thr Lys Val Asp Ile Lys
1               5                   10

<210> SEQ ID NO 18
<211> LENGTH: 8
<212> TYPE: PRT
<213> ORGANISM: Artificial Sequence
<220> FEATURE:
```

<223> OTHER INFORMATION: H-CDR1 of A56-01A03

<400> SEQUENCE: 18

Gly Tyr Thr Phe Thr Pro Tyr Tyr
1               5

<210> SEQ ID NO 19
<211> LENGTH: 8
<212> TYPE: PRT
<213> ORGANISM: Artificial Sequence
<220> FEATURE:
<223> OTHER INFORMATION: H-CDR2 of A56-01A03

<400> SEQUENCE: 19

Ile Ile Pro Leu Leu Gly Lys Ala
1               5

<210> SEQ ID NO 20
<211> LENGTH: 14
<212> TYPE: PRT
<213> ORGANISM: Artificial Sequence
<220> FEATURE:
<223> OTHER INFORMATION: H-CDR3 of A56-01A03

<400> SEQUENCE: 20

Ala Arg Glu Ala Arg Gly Val Asn Tyr Tyr Gly Met Asp Val
1               5                   10

<210> SEQ ID NO 21
<211> LENGTH: 6
<212> TYPE: PRT
<213> ORGANISM: Artificial Sequence
<220> FEATURE:
<223> OTHER INFORMATION: L-CDR1 of A56-01A03

<400> SEQUENCE: 21

Gln Gly Ile Ser His Ser
1               5

<210> SEQ ID NO 22
<211> LENGTH: 3
<212> TYPE: PRT
<213> ORGANISM: Artificial Sequence
<220> FEATURE:
<223> OTHER INFORMATION: L-CDR2 of A56-01A03

<400> SEQUENCE: 22

Val Ala Ser
1

<210> SEQ ID NO 23
<211> LENGTH: 9
<212> TYPE: PRT
<213> ORGANISM: Artificial Sequence
<220> FEATURE:
<223> OTHER INFORMATION: L-CDR3 of A56-01A03

<400> SEQUENCE: 23

Gln Gln Thr Asn Asn Phe Pro Tyr Thr
1               5

<210> SEQ ID NO 24
<211> LENGTH: 255
<212> TYPE: DNA
<213> ORGANISM: Artificial Sequence
<220> FEATURE:
<223> OTHER INFORMATION: SCFV of A56-01A03

<400> SEQUENCE: 24
caggtgcagc tggtgcagtc tgggggctgag gttaggaagc ctgggggcctc cgtgaagatt          60 tcctgcatgg catctggata cacctttcacc ccctactata tccactgggt gcggcaggcc         120
cctggccaag ggcttgagtg gatgggaggg atcatccctc tccttggtaa agcgacctac         180
gcacagaagt tccagggcag aatcacggtt accgcggacg aatccacgag cacagcctac         240
atggaactga gcagt                                                            255

<210> SEQ ID NO 25
<211> LENGTH: 121
<212> TYPE: PRT
<213> ORGANISM: Artificial Sequence
<220> FEATURE:
<223> OTHER INFORMATION: VH2 of A56-01A03

<400> SEQUENCE: 25

Gln Val Gln Leu Val Gln Ser Gly Ala Glu Val Arg Lys Pro Gly Ala
1               5                   10                  15

Ser Val Lys Ile Ser Cys Met Ala Ser Gly Tyr Thr Phe Thr Pro Tyr
            20                  25                  30

Tyr Ile His Trp Val Arg Gln Ala Pro Gly Gln Gly Leu Glu Trp Met
        35                  40                  45

Gly Gly Ile Ile Pro Leu Leu Gly Lys Ala Thr Tyr Ala Gln Lys Phe
    50                  55                  60

Gln Gly Arg Ile Thr Val Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Arg Gly Val Asn Tyr Tyr Gly Met Asp Val Trp Gly
            100                 105                 110

Gln Gly Thr Thr Val Thr Val Ser Ser
        115                 120

<210> SEQ ID NO 26
<211> LENGTH: 107
<212> TYPE: PRT
<213> ORGANISM: Artificial Sequence
<220> FEATURE:
<223> OTHER INFORMATION: VL2 of A56-01A03

<400> SEQUENCE: 26

Asp Ile Gln Met Thr Gln Ser Pro Ser Ser Val Ser Ala Ser Val Gly
1               5                   10                  15

Asp Arg Val Thr Ile Ser Cys Arg Ala Ser Gln Gly Ile Ser His Ser
            20                  25                  30

Leu Ala Trp Tyr Gln Gln Lys Pro Gly Lys Ala Pro Lys Leu Leu Ile
        35                  40                  45

Asp Val Ala Ser Arg Leu Gln Ser Gly Val Pro Leu Arg Phe Ser Gly
    50                  55                  60

Ser Gly Ser Gly Thr Asp Phe Thr Leu Thr Ile Asn Ser Leu Gln Pro
65                  70                  75                  80

Glu Asp Ser Ala Thr Tyr Tyr Cys Gln Gln Thr Asn Asn Phe Pro Tyr
                85                  90                  95

Thr Phe Gly Gln Gly Thr Lys Leu Glu Ile Lys
            100                 105

-continued

```
<210> SEQ ID NO 27
<211> LENGTH: 25
<212> TYPE: PRT
<213> ORGANISM: Artificial Sequence
<220> FEATURE:
<223> OTHER INFORMATION: H-FR1 of A56-01A03

<400> SEQUENCE: 27

Gln Val Gln Leu Val Gln Ser Gly Ala Glu Val Arg Lys Pro Gly Ala
1               5                   10                  15

Ser Val Lys Ile Ser Cys Met Ala Ser
            20                  25

<210> SEQ ID NO 28
<211> LENGTH: 17
<212> TYPE: PRT
<213> ORGANISM: Artificial Sequence
<220> FEATURE:
<223> OTHER INFORMATION: H-FR2 of A56-01A03

<400> SEQUENCE: 28

Ile His Trp Val Arg Gln Ala Pro Gly Gln Gly Leu Glu Trp Met Gly
1               5                   10                  15

Gly

<210> SEQ ID NO 29
<211> LENGTH: 38
<212> TYPE: PRT
<213> ORGANISM: Artificial Sequence
<220> FEATURE:
<223> OTHER INFORMATION: H-FR3 of A56-01A03

<400> SEQUENCE: 29

Thr Tyr Ala Gln Lys Phe Gln Gly Arg Ile Thr Val Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
            35

<210> SEQ ID NO 30
<211> LENGTH: 11
<212> TYPE: PRT
<213> ORGANISM: Artificial Sequence
<220> FEATURE:
<223> OTHER INFORMATION: H-FR4 of A56-01A03

<400> SEQUENCE: 30

Trp Gly Gln Gly Thr Thr Val Thr Val Ser Ser
1               5                   10

<210> SEQ ID NO 31
<211> LENGTH: 26
<212> TYPE: PRT
<213> ORGANISM: Artificial Sequence
<220> FEATURE:
<223> OTHER INFORMATION: L-FR1 of A56-01A03

<400> SEQUENCE: 31

Asp Ile Gln Met Thr Gln Ser Pro Ser Ser Val Ser Ala Ser Val Gly
1               5                   10                  15

Asp Arg Val Thr Ile Ser Cys Arg Ala Ser
            20                  25
```

-continued

```
<210> SEQ ID NO 32
<211> LENGTH: 17
<212> TYPE: PRT
<213> ORGANISM: Artificial Sequence
<220> FEATURE:
<223> OTHER INFORMATION: L-FR2 of A56-01A03

<400> SEQUENCE: 32

Leu Ala Trp Tyr Gln Gln Lys Pro Gly Lys Ala Pro Lys Leu Leu Ile
1               5                   10                  15

Asp

<210> SEQ ID NO 33
<211> LENGTH: 36
<212> TYPE: PRT
<213> ORGANISM: Artificial Sequence
<220> FEATURE:
<223> OTHER INFORMATION: L-FR3 of A56-01A03

<400> SEQUENCE: 33

Ile Asp Val Ala Ser Arg Leu Gln Ser Gly Val Pro Leu Arg Phe Ser
1               5                   10                  15

Gly Ser Gly Ser Gly Thr Asp Phe Thr Leu Thr Ile Asn Ser Leu Gln
            20                  25                  30

Pro Glu Asp Ser
        35

<210> SEQ ID NO 34
<211> LENGTH: 10
<212> TYPE: PRT
<213> ORGANISM: Artificial Sequence
<220> FEATURE:
<223> OTHER INFORMATION: L-FR4 of A56-01A03

<400> SEQUENCE: 34

Phe Gly Gln Gly Thr Lys Leu Glu Ile Lys
1               5                   10

<210> SEQ ID NO 35
<211> LENGTH: 8
<212> TYPE: PRT
<213> ORGANISM: Artificial Sequence
<220> FEATURE:
<223> OTHER INFORMATION: H-CDR1 of A56-01A04

<400> SEQUENCE: 35

Gly Gly Thr Phe Ser Tyr Arg Tyr
1               5

<210> SEQ ID NO 36
<211> LENGTH: 8
<212> TYPE: PRT
<213> ORGANISM: Artificial Sequence
<220> FEATURE:
<223> OTHER INFORMATION: H-CDR2 of A56-01A04

<400> SEQUENCE: 36

Ile Thr Pro Phe Asn Gly Tyr Thr
1               5

<210> SEQ ID NO 37
<211> LENGTH: 11
<212> TYPE: PRT
<213> ORGANISM: Artificial Sequence
<220> FEATURE:
<223> OTHER INFORMATION: H-CDR3 of A56-01A04
```

-continued

<400> SEQUENCE: 37

Val Thr Gly Leu Gly Lys Thr Asn Leu Asp Ser
1               5                   10

<210> SEQ ID NO 38
<211> LENGTH: 11
<212> TYPE: PRT
<213> ORGANISM: Artificial Sequence
<220> FEATURE:
<223> OTHER INFORMATION: L-CDR1 of A56-01A04

<400> SEQUENCE: 38

Gln Ser Leu Val His Ser Asn Gly Asn Thr Tyr
1               5                   10

<210> SEQ ID NO 39
<211> LENGTH: 3
<212> TYPE: PRT
<213> ORGANISM: Artificial Sequence
<220> FEATURE:
<223> OTHER INFORMATION: L-CDR2 of A56-01A04

<400> SEQUENCE: 39

Gln Ile Ser
1

<210> SEQ ID NO 40
<211> LENGTH: 9
<212> TYPE: PRT
<213> ORGANISM: Artificial Sequence
<220> FEATURE:
<223> OTHER INFORMATION: L-CDR3 of A56-01A04

<400> SEQUENCE: 40

Met Gln Leu Thr Gln Phe Pro Leu Thr
1               5

<210> SEQ ID NO 41
<211> LENGTH: 255
<212> TYPE: DNA
<213> ORGANISM: Artificial Sequence
<220> FEATURE:
<223> OTHER INFORMATION: SCFV of A56-01A04

<400> SEQUENCE: 41
caggtgcagc tggtggagtc tgggggctgag gtgaagaagc ctgggtcctc ggtgaaggtc          60
tcctgcaagg cttctggagg caccttcagt taccgctacc tgcactgggt gcgacaggcc         120
tccggacagg cgcttgagtg gatggggtgg atcacacctt tcaatggtta caccaactac         180
gcacagaaat tccaggacag agtcaccatt accagggaca ggtctatgag cacagcctac         240
atggagctga gcagc                                                          255

<210> SEQ ID NO 42
<211> LENGTH: 118
<212> TYPE: PRT
<213> ORGANISM: Artificial Sequence
<220> FEATURE:
<223> OTHER INFORMATION: VH2 of A56-01A04

<400> SEQUENCE: 42

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Tyr Arg

-continued

```
                20              25              30

Tyr Leu His Trp Val Arg Gln Ala Ser Gly Gln Ala Leu Glu Trp Met
        35              40              45

Gly Trp Ile Thr Pro Phe Asn Gly Tyr Thr Asn Tyr Ala Gln Lys Phe
    50              55              60

Gln Asp Arg Val Thr Ile Thr Arg Asp Arg Ser Met Ser Thr Ala Tyr
65              70              75              80

Met Glu Leu Ser Ser Leu Arg Ser Glu Asp Thr Ala Val Tyr Tyr Cys
            85              90              95

Val Thr Gly Leu Gly Lys Thr Asn Leu Asp Ser Trp Gly Gln Gly Thr
        100             105             110

Leu Val Thr Val Ser Ser
        115

<210> SEQ ID NO 43
<211> LENGTH: 112
<212> TYPE: PRT
<213> ORGANISM: Artificial Sequence
<220> FEATURE:
<223> OTHER INFORMATION: VL2 of A56-01A04

<400> SEQUENCE: 43

Asp Ile Val Met Thr Gln Thr Pro Leu Ser Ser Pro Val Thr Leu Gly
1               5               10              15

Gln Pro Ala Ser Ile Ser Cys Arg Ser Ser Gln Ser Leu Val His Ser
            20              25              30

Asn Gly Asn Thr Tyr Leu Ser Trp Leu Gln Gln Arg Pro Gly Gln Pro
        35              40              45

Pro Arg Leu Leu Ile Tyr Gln Ile Ser Lys Arg Phe Ser Gly Val Pro
    50              55              60

Asp Arg Phe Ser Gly Ser Gly Ala Gly Thr Asp Phe Thr Leu Lys Ile
65              70              75              80

Ser Arg Val Glu Ala Glu Asp Val Gly Val Tyr Tyr Cys Met Gln Leu
            85              90              95

Thr Gln Phe Pro Leu Thr Phe Gly Gly Gly Thr Lys Val Glu Ile Lys
        100             105             110

<210> SEQ ID NO 44
<211> LENGTH: 25
<212> TYPE: PRT
<213> ORGANISM: Artificial Sequence
<220> FEATURE:
<223> OTHER INFORMATION: H-FR1 of A56-01A04

<400> SEQUENCE: 44

Gln Val Gln Leu Val Glu Ser Gly Ala Glu Val Lys Lys Pro Gly Ser
1               5               10              15

Ser Val Lys Val Ser Cys Lys Ala Ser
            20              25

<210> SEQ ID NO 45
<211> LENGTH: 17
<212> TYPE: PRT
<213> ORGANISM: Artificial Sequence
<220> FEATURE:
<223> OTHER INFORMATION: H-FR2 of A56-01A04

<400> SEQUENCE: 45

Leu His Trp Val Arg Gln Ala Ser Gly Gln Ala Leu Glu Trp Met Gly
1               5               10              15
```

-continued

Trp

```
<210> SEQ ID NO 46
<211> LENGTH: 38
<212> TYPE: PRT
<213> ORGANISM: Artificial Sequence
<220> FEATURE:
<223> OTHER INFORMATION: H-FR3 of A56-01A04

<400> SEQUENCE: 46

Asn Tyr Ala Gln Lys Phe Gln Asp Arg Val Thr Ile Thr Arg Asp Arg
1               5                   10                  15

Ser Met Ser Thr Ala Tyr Met Glu Leu Ser Ser Leu Arg Ser Glu Asp
            20                  25                  30

Thr Ala Val Tyr Tyr Cys
        35

<210> SEQ ID NO 47
<211> LENGTH: 11
<212> TYPE: PRT
<213> ORGANISM: Artificial Sequence
<220> FEATURE:
<223> OTHER INFORMATION: H-FR4 of A56-01A04

<400> SEQUENCE: 47

Trp Gly Gln Gly Thr Leu Val Thr Val Ser Ser
1               5                   10

<210> SEQ ID NO 48
<211> LENGTH: 26
<212> TYPE: PRT
<213> ORGANISM: Artificial Sequence
<220> FEATURE:
<223> OTHER INFORMATION: L-FR1 of A56-01A04

<400> SEQUENCE: 48

Asp Ile Val Met Thr Gln Thr Pro Leu Ser Ser Pro Val Thr Leu Gly
1               5                   10                  15

Gln Pro Ala Ser Ile Ser Cys Arg Ser Ser
            20                  25

<210> SEQ ID NO 49
<211> LENGTH: 17
<212> TYPE: PRT
<213> ORGANISM: Artificial Sequence
<220> FEATURE:
<223> OTHER INFORMATION: L-FR2 of A56-01A04

<400> SEQUENCE: 49

Leu Ser Trp Leu Gln Gln Arg Pro Gly Gln Pro Arg Leu Leu Ile
1               5                   10                  15

Tyr

<210> SEQ ID NO 50
<211> LENGTH: 36
<212> TYPE: PRT
<213> ORGANISM: Artificial Sequence
<220> FEATURE:
<223> OTHER INFORMATION: L-FR3 of A56-01A04

<400> SEQUENCE: 50

Ile Tyr Gln Ile Ser Lys Arg Phe Ser Gly Val Pro Asp Arg Phe Ser
1               5                   10                  15
```

```
Gly Ser Gly Ala Gly Thr Asp Phe Thr Leu Lys Ile Ser Arg Val Glu
        20                  25                  30

Ala Glu Asp Val
        35

<210> SEQ ID NO 51
<211> LENGTH: 10
<212> TYPE: PRT
<213> ORGANISM: Artificial Sequence
<220> FEATURE:
<223> OTHER INFORMATION: L-FR4 of A56-01A04

<400> SEQUENCE: 51

Phe Gly Gly Gly Thr Lys Val Glu Ile Lys
1               5                   10

<210> SEQ ID NO 52
<211> LENGTH: 8
<212> TYPE: PRT
<213> ORGANISM: Artificial Sequence
<220> FEATURE:
<223> OTHER INFORMATION: H-CDR1 of A56-01A05

<400> SEQUENCE: 52

Gly Asp Thr Leu Thr Tyr Arg Phe
1               5

<210> SEQ ID NO 53
<211> LENGTH: 8
<212> TYPE: PRT
<213> ORGANISM: Artificial Sequence
<220> FEATURE:
<223> OTHER INFORMATION: H-CDR2 of A56-01A05

<400> SEQUENCE: 53

Ile Thr Pro Phe Asn Gly Asn Thr
1               5

<210> SEQ ID NO 54
<211> LENGTH: 13
<212> TYPE: PRT
<213> ORGANISM: Artificial Sequence
<220> FEATURE:
<223> OTHER INFORMATION: H-CDR3 of A56-01A05

<400> SEQUENCE: 54

Ala Thr Gly Gly Gly Asn Asn Tyr Tyr Gly Met Glu Val
1               5                   10

<210> SEQ ID NO 55
<211> LENGTH: 6
<212> TYPE: PRT
<213> ORGANISM: Artificial Sequence
<220> FEATURE:
<223> OTHER INFORMATION: L-CDR1 of A56-01A05

<400> SEQUENCE: 55

Gln Gly Ile Gly Ser Trp
1               5

<210> SEQ ID NO 56
<211> LENGTH: 3
<212> TYPE: PRT
<213> ORGANISM: Artificial Sequence
<220> FEATURE:
<223> OTHER INFORMATION: L-CDR2 of A56-01A05
```

<400> SEQUENCE: 56

Gly Ala Ser
1

<210> SEQ ID NO 57
<211> LENGTH: 9
<212> TYPE: PRT
<213> ORGANISM: Artificial Sequence
<220> FEATURE:
<223> OTHER INFORMATION: L-CDR3 of A56-01A05

<400> SEQUENCE: 57

Gln Lys Ala Asn Asn Phe Pro Tyr Thr
1               5

<210> SEQ ID NO 58
<211> LENGTH: 255
<212> TYPE: DNA
<213> ORGANISM: Artificial Sequence
<220> FEATURE:
<223> OTHER INFORMATION: SCFV of A56-01A05

<400> SEQUENCE: 58
caggtgcagc tggtacagtc tggggctgag gtgaagaaga ctgggtcctc agtgaaggtt        60
tcgtgcaagg cttccggaga cacccttacc taccgcttcc tgcactgggt gcgacaggcc       120
cccggacaag cgcctgagtg gattggatgg atcacacctt tcaatggtaa caccaactac       180
gcacagaaat tccaggacag agtcaccatt accagggaca ggtctatgag cacagcctac       240
atggagctga gcagc                                                        255

<210> SEQ ID NO 59
<211> LENGTH: 120
<212> TYPE: PRT
<213> ORGANISM: Artificial Sequence
<220> FEATURE:
<223> OTHER INFORMATION: VH2 of A56-01A05

<400> SEQUENCE: 59

Gln Val Gln Leu Val Gln Ser Gly Ala Glu Val Lys Lys Thr Gly Ser
1               5                   10                  15

Ser Val Lys Val Ser Cys Lys Ala Ser Gly Asp Thr Leu Thr Tyr Arg
            20                  25                  30

Phe Leu His Trp Val Arg Gln Ala Pro Gly Gln Ala Pro Glu Trp Ile
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Gly Asn Asn Tyr Tyr Gly Met Glu Val Trp Gly Gln
            100                 105                 110

Gly Thr Pro Ile Thr Val Ser Ser
        115                 120

<210> SEQ ID NO 60
<211> LENGTH: 107
<212> TYPE: PRT
<213> ORGANISM: Artificial Sequence
<220> FEATURE:
<223> OTHER INFORMATION: VL2 of A56-01A05

<400> SEQUENCE: 60

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Gly Ser Trp
            20                  25                  30

Leu Ala Trp Tyr Gln Gln Lys Pro Gly Glu Ala Pro Asn Leu Leu Ile
        35                  40                  45

Tyr Gly Ala Ser Asn Leu Ala Ser Gly Val Pro Ser Arg Phe Ser Gly
    50                  55                  60

Gly Gly Ser Gly Thr Asp Phe Ser Leu Thr Ile Ser Ser Leu Gln Pro
65                  70                  75                  80

Glu Asp Phe Ala Thr Tyr Tyr Cys Gln Lys Ala Asn Asn Phe Pro Tyr
                85                  90                  95

Thr Phe Gly Gln Gly Thr Lys Leu Asp Ile Lys
            100                 105

<210> SEQ ID NO 61
<211> LENGTH: 25
<212> TYPE: PRT
<213> ORGANISM: Artificial Sequence
<220> FEATURE:
<223> OTHER INFORMATION: H-FR1 of A56-01A05

<400> SEQUENCE: 61

Gln Val Gln Leu Val Gln Ser Gly Ala Glu Val Lys Lys Thr Gly Ser
1               5                   10                  15

Ser Val Lys Val Ser Cys Lys Ala Ser
            20                  25

<210> SEQ ID NO 62
<211> LENGTH: 17
<212> TYPE: PRT
<213> ORGANISM: Artificial Sequence
<220> FEATURE:
<223> OTHER INFORMATION: H-FR2 of A56-01A05

<400> SEQUENCE: 62

Leu His Trp Val Arg Gln Ala Pro Gly Gln Ala Pro Glu Trp Ile Gly
1               5                   10                  15

Trp

<210> SEQ ID NO 63
<211> LENGTH: 38
<212> TYPE: PRT
<213> ORGANISM: Artificial Sequence
<220> FEATURE:
<223> OTHER INFORMATION: H-FR3 of A56-01A05

<400> SEQUENCE: 63

Asn Tyr Ala Gln Lys Phe Gln Asp Arg Val Thr Ile Thr Arg Asp Arg
1               5                   10                  15

Ser Met Ser Thr Ala Tyr Met Glu Leu Ser Ser Leu Arg Ser Glu Asp
            20                  25                  30

Thr Ala Val Tyr Tyr Cys
        35

<210> SEQ ID NO 64
<211> LENGTH: 11
<212> TYPE: PRT
<213> ORGANISM: Artificial Sequence

```
<220> FEATURE:
<223> OTHER INFORMATION: H-FR4 of A56-01A05

<400> SEQUENCE: 64

Trp Gly Gln Gly Thr Pro Ile Thr Val Ser Ser
1               5                   10

<210> SEQ ID NO 65
<211> LENGTH: 26
<212> TYPE: PRT
<213> ORGANISM: Artificial Sequence
<220> FEATURE:
<223> OTHER INFORMATION: L-FR1 of A56-01A05

<400> SEQUENCE: 65

Asp Ile Gln Met Thr Gln Ser Pro Ser Ser Val Ser Ala Ser Val Gly
1               5                   10                  15

Asp Arg Val Thr Ile Thr Cys Arg Ala Ser
            20                  25

<210> SEQ ID NO 66
<211> LENGTH: 17
<212> TYPE: PRT
<213> ORGANISM: Artificial Sequence
<220> FEATURE:
<223> OTHER INFORMATION: L-FR2 of A56-01A05

<400> SEQUENCE: 66

Leu Ala Trp Tyr Gln Gln Lys Pro Gly Glu Ala Pro Asn Leu Leu Ile
1               5                   10                  15

Tyr

<210> SEQ ID NO 67
<211> LENGTH: 36
<212> TYPE: PRT
<213> ORGANISM: Artificial Sequence
<220> FEATURE:
<223> OTHER INFORMATION: L-FR3 of A56-01A05

<400> SEQUENCE: 67

Ile Tyr Gly Ala Ser Asn Leu Ala Ser Gly Val Pro Ser Arg Phe Ser
1               5                   10                  15

Gly Gly Gly Ser Gly Thr Asp Phe Ser Leu Thr Ile Ser Ser Leu Gln
            20                  25                  30

Pro Glu Asp Phe
        35

<210> SEQ ID NO 68
<211> LENGTH: 10
<212> TYPE: PRT
<213> ORGANISM: Artificial Sequence
<220> FEATURE:
<223> OTHER INFORMATION: L-FR4 of A56-01A05

<400> SEQUENCE: 68

Phe Gly Gln Gly Thr Lys Leu Asp Ile Lys
1               5                   10

<210> SEQ ID NO 69
<211> LENGTH: 8
<212> TYPE: PRT
<213> ORGANISM: Artificial Sequence
<220> FEATURE:
<223> OTHER INFORMATION: H-CDR1 of A56-01B01
```

```
<400> SEQUENCE: 69

Gly Phe Thr Ile Ser Asn Tyr Ala
1               5

<210> SEQ ID NO 70
<211> LENGTH: 8
<212> TYPE: PRT
<213> ORGANISM: Artificial Sequence
<220> FEATURE:
<223> OTHER INFORMATION: H-CDR2 of A56-01B01

<400> SEQUENCE: 70

Val Ser Gly Ser Gly Val Thr Thr
1               5

<210> SEQ ID NO 71
<211> LENGTH: 8
<212> TYPE: PRT
<213> ORGANISM: Artificial Sequence
<220> FEATURE:
<223> OTHER INFORMATION: H-CDR3 of A56-01B01

<400> SEQUENCE: 71

Val Arg Met Thr Gly Gly Pro Leu
1               5

<210> SEQ ID NO 72
<211> LENGTH: 6
<212> TYPE: PRT
<213> ORGANISM: Artificial Sequence
<220> FEATURE:
<223> OTHER INFORMATION: L-CDR1 of A56-01B01

<400> SEQUENCE: 72

Gln Gly Val Arg Asn Asp
1               5

<210> SEQ ID NO 73
<211> LENGTH: 3
<212> TYPE: PRT
<213> ORGANISM: Artificial Sequence
<220> FEATURE:
<223> OTHER INFORMATION: L-CDR2 of A56-01B01

<400> SEQUENCE: 73

Gly Ala Ser
1

<210> SEQ ID NO 74
<211> LENGTH: 9
<212> TYPE: PRT
<213> ORGANISM: Artificial Sequence
<220> FEATURE:
<223> OTHER INFORMATION: L-CDR3 of A56-01B01

<400> SEQUENCE: 74

Leu Gln Asp Phe Ile Tyr Pro Tyr Thr
1               5

<210> SEQ ID NO 75
<211> LENGTH: 255
<212> TYPE: DNA
<213> ORGANISM: Artificial Sequence
<220> FEATURE:
<223> OTHER INFORMATION: SCFV of A56-01B01

<400> SEQUENCE: 75
```

```
cagatgcagc tggtggagtc tggggaggc ttggtccagc ctggggggtc cctgagactc        60
tcctgtacag cctctggatt caccattagc aactacgcca tgagctgggt ccgccaggct       120
ccagggaagg ggctggagtg ggtcgcaact gttagtggta gtggtgttac cacacactac       180
gcagcctccg tgaaggaccg gttcaccgtc tccagtgaca gttccaagaa cacacttttt       240
ctgcaaatga acagt                                                        255
```

<210> SEQ ID NO 76
<211> LENGTH: 115
<212> TYPE: PRT
<213> ORGANISM: Artificial Sequence
<220> FEATURE:
<223> OTHER INFORMATION: VH2 of A56-01B01

<400> SEQUENCE: 76

```
Gln Met Gln Leu Val Glu Ser Gly Gly Gly Leu Val Gln Pro Gly Gly
1               5                   10                  15

Ser Leu Arg Leu Ser Cys Thr Ala Ser Gly Phe Thr Ile Ser Asn Tyr
            20                  25                  30

Ala Met Ser Trp Val Arg Gln Ala Pro Gly Lys Gly Leu Glu Trp Val
        35                  40                  45

Ala Thr Val Ser Gly Ser Gly Val Thr Thr His Tyr Ala Ala Ser Val
    50                  55                  60

Lys Asp Arg Phe Thr Val Ser Ser Asp Ser Ser Lys Asn Thr Leu Phe
65                  70                  75                  80

Leu Gln Met Asn Ser Leu Arg Ala Glu Asp Thr Ala Val Tyr Tyr Cys
                85                  90                  95

Val Arg Met Thr Gly Gly Pro Leu Trp Gly Gln Gly Thr Leu Ile Thr
            100                 105                 110

Val Ser Ser
        115
```

<210> SEQ ID NO 77
<211> LENGTH: 107
<212> TYPE: PRT
<213> ORGANISM: Artificial Sequence
<220> FEATURE:
<223> OTHER INFORMATION: VL2 of A56-01B01

<400> SEQUENCE: 77

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Arg Asn Asp
            20                  25                  30

Leu Gly Trp Tyr Gln Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Ile Tyr Pro Tyr
                85                  90                  95

Thr Phe Gly Gln Gly Thr Lys Leu Glu Ile Lys
            100                 105
```

<210> SEQ ID NO 78
<211> LENGTH: 25

<212> TYPE: PRT
<213> ORGANISM: Artificial Sequence
<220> FEATURE:
<223> OTHER INFORMATION: H-FR1 of A56-01B01

<400> SEQUENCE: 78

Gln Met Gln Leu Val Glu Ser Gly Gly Gly Leu Val Gln Pro Gly Gly
1               5                   10                  15

Ser Leu Arg Leu Ser Cys Thr Ala Ser
            20                  25

<210> SEQ ID NO 79
<211> LENGTH: 17
<212> TYPE: PRT
<213> ORGANISM: Artificial Sequence
<220> FEATURE:
<223> OTHER INFORMATION: H-FR2 of A56-01B01

<400> SEQUENCE: 79

Met Ser Trp Val Arg Gln Ala Pro Gly Lys Gly Leu Glu Trp Val Ala
1               5                   10                  15

Thr

<210> SEQ ID NO 80
<211> LENGTH: 38
<212> TYPE: PRT
<213> ORGANISM: Artificial Sequence
<220> FEATURE:
<223> OTHER INFORMATION: H-FR3 of A56-01B01

<400> SEQUENCE: 80

His Tyr Ala Ala Ser Val Lys Asp Arg Phe Thr Val Ser Ser Asp Ser
1               5                   10                  15

Ser Lys Asn Thr Leu Phe Leu Gln Met Asn Ser Leu Arg Ala Glu Asp
            20                  25                  30

Thr Ala Val Tyr Tyr Cys
        35

<210> SEQ ID NO 81
<211> LENGTH: 11
<212> TYPE: PRT
<213> ORGANISM: Artificial Sequence
<220> FEATURE:
<223> OTHER INFORMATION: H-FR4 of A56-01B01

<400> SEQUENCE: 81

Trp Gly Gln Gly Thr Leu Ile Thr Val Ser Ser
1               5                   10

<210> SEQ ID NO 82
<211> LENGTH: 26
<212> TYPE: PRT
<213> ORGANISM: Artificial Sequence
<220> FEATURE:
<223> OTHER INFORMATION: L-FR1 of A56-01B01

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 83
<211> LENGTH: 17

```
<212> TYPE: PRT
<213> ORGANISM: Artificial Sequence
<220> FEATURE:
<223> OTHER INFORMATION: L-FR2 of A56-01B01

<400> SEQUENCE: 83

Leu Gly Trp Tyr Gln Gln Lys Pro Gly Lys Ala Pro Lys Leu Leu Ile
1               5                   10                  15

Tyr

<210> SEQ ID NO 84
<211> LENGTH: 36
<212> TYPE: PRT
<213> ORGANISM: Artificial Sequence
<220> FEATURE:
<223> OTHER INFORMATION: L-FR3 of A56-01B01

<400> SEQUENCE: 84

Ile Tyr Gly Ala Ser Thr Leu Gln Ser Gly Val Pro Ser Arg Phe Ser
1               5                   10                  15

Gly Ser Gly Ser Gly Thr Asp Phe Thr Leu Thr Ile Ser Ser Leu Gln
            20                  25                  30

Pro Glu Asp Phe
        35

<210> SEQ ID NO 85
<211> LENGTH: 10
<212> TYPE: PRT
<213> ORGANISM: Artificial Sequence
<220> FEATURE:
<223> OTHER INFORMATION: L-FR4 of A56-01B01

<400> SEQUENCE: 85

Phe Gly Gln Gly Thr Lys Leu Glu Ile Lys
1               5                   10

<210> SEQ ID NO 86
<211> LENGTH: 8
<212> TYPE: PRT
<213> ORGANISM: Artificial Sequence
<220> FEATURE:
<223> OTHER INFORMATION: H-CDR1 of A56-01C08

<400> SEQUENCE: 86

Gly Phe Thr Phe Ser Asn Asn Trp
1               5

<210> SEQ ID NO 87
<211> LENGTH: 8
<212> TYPE: PRT
<213> ORGANISM: Artificial Sequence
<220> FEATURE:
<223> OTHER INFORMATION: H-CDR2 of A56-01C08

<400> SEQUENCE: 87

Ile Asn Arg Asp Gly Ser Glu Arg
1               5

<210> SEQ ID NO 88
<211> LENGTH: 21
<212> TYPE: PRT
<213> ORGANISM: Artificial Sequence
<220> FEATURE:
<223> OTHER INFORMATION: H-CDR3 of A56-01C08

<400> SEQUENCE: 88
```

Val Arg Asp Ser Leu Ile Ile Tyr Asp Asn Ser Trp Tyr Pro Tyr Tyr
1               5                   10                  15

His Gly Met Ala Val
            20

<210> SEQ ID NO 89
<211> LENGTH: 6
<212> TYPE: PRT
<213> ORGANISM: Artificial Sequence
<220> FEATURE:
<223> OTHER INFORMATION: L-CDR1 of A56-01C08

<400> SEQUENCE: 89

Ser Leu Arg Lys Tyr His
1               5

<210> SEQ ID NO 90
<211> LENGTH: 3
<212> TYPE: PRT
<213> ORGANISM: Artificial Sequence
<220> FEATURE:
<223> OTHER INFORMATION: L-CDR2 of A56-01C08

<400> SEQUENCE: 90

Gly Lys Asn
1

<210> SEQ ID NO 91
<211> LENGTH: 11
<212> TYPE: PRT
<213> ORGANISM: Artificial Sequence
<220> FEATURE:
<223> OTHER INFORMATION: L-CDR3 of A56-01C08

<400> SEQUENCE: 91

Asn Ser Arg Asp Ser Ser Pro Asn His Leu Val
1               5                   10

<210> SEQ ID NO 92
<211> LENGTH: 255
<212> TYPE: DNA
<213> ORGANISM: Artificial Sequence
<220> FEATURE:
<223> OTHER INFORMATION: SCFV of A56-01C08

<400> SEQUENCE: 92
caggtgcagc tggtagagtc tggggggacgg ttggtccagc ctgggggatc cctgagactc      60
tcctgcgtaa cttctggatt cactttttagt aacaattgga tgacttgggt ccgccaggct     120
ccagggaagg ggctggagtg ggtggccacc ataaaccgag atggaagtga gaggtattat     180
gtggactctg tgaaggaccg gttcaccatc tccagagaaa acagcaaaaa ctccctgtat     240
ctgcaaatga acagt                                                       255

<210> SEQ ID NO 93
<211> LENGTH: 128
<212> TYPE: PRT
<213> ORGANISM: Artificial Sequence
<220> FEATURE:
<223> OTHER INFORMATION: VH2 of A56-01C08

<400> SEQUENCE: 93

Gln Val Gln Leu Val Glu Ser Gly Gly Arg Leu Val Gln Pro Gly Gly
1               5                   10                  15

```
Ser Leu Arg Leu Ser Cys Val Thr Ser Gly Phe Thr Phe Ser Asn Asn
            20                  25                  30

Trp Met Thr Trp Val Arg Gln Ala Pro Gly Lys Gly Leu Glu Trp Val
        35                  40                  45

Ala Thr Ile Asn Arg Asp Gly Ser Glu Arg Tyr Tyr Val Asp Ser Val
        50                  55                  60

Lys Asp Arg Phe Thr Ile Ser Arg Glu Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Ser Leu Ile Ile Tyr Asp Asn Ser Trp Tyr Pro Tyr Tyr
            100                 105                 110

His Gly Met Ala Val Trp Gly Gln Gly Thr Thr Val Thr Val Ser Ser
        115                 120                 125
```

```
<210> SEQ ID NO 94
<211> LENGTH: 108
<212> TYPE: PRT
<213> ORGANISM: Artificial Sequence
<220> FEATURE:
<223> OTHER INFORMATION: VL2 of A56-01C08

<400> SEQUENCE: 94

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Lys Tyr His Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Gly Arg Phe Ser Gly Ser
        50                  55                  60

Ser Ser Gly Asn Thr Ala Ser Leu Thr Ile Thr Glu Ala Gln Ala Glu
65                  70                  75                  80

Asp Glu Ala Asp Tyr Tyr Cys Asn Ser Arg Asp Ser Ser Pro Asn His
                85                  90                  95

Leu Val Phe Gly Gly Gly Thr Lys Leu Thr Val Leu
            100                 105
```

```
<210> SEQ ID NO 95
<211> LENGTH: 25
<212> TYPE: PRT
<213> ORGANISM: Artificial Sequence
<220> FEATURE:
<223> OTHER INFORMATION: H-FR1 of A56-01C08

<400> SEQUENCE: 95

Gln Val Gln Leu Val Glu Ser Gly Gly Arg Leu Val Gln Pro Gly Gly
1               5                   10                  15

Ser Leu Arg Leu Ser Cys Val Thr Ser
            20                  25
```

```
<210> SEQ ID NO 96
<211> LENGTH: 17
<212> TYPE: PRT
<213> ORGANISM: Artificial Sequence
<220> FEATURE:
<223> OTHER INFORMATION: H-FR2 of A56-01C08

<400> SEQUENCE: 96

Met Thr Trp Val Arg Gln Ala Pro Gly Lys Gly Leu Glu Trp Val Ala
```

-continued

```
1               5               10              15

Thr

<210> SEQ ID NO 97
<211> LENGTH: 38
<212> TYPE: PRT
<213> ORGANISM: Artificial Sequence
<220> FEATURE:
<223> OTHER INFORMATION: H-FR3 of A56-01C08

<400> SEQUENCE: 97

Tyr Tyr Val Asp Ser Val Lys Asp Arg Phe Thr Ile Ser Arg Glu Asn
1               5               10              15

Ser Lys Asn Ser Leu Tyr Leu Gln Met Asn Ser Leu Arg Ala Glu Asp
            20              25              30

Thr Ala Val Tyr Tyr Cys
        35

<210> SEQ ID NO 98
<211> LENGTH: 11
<212> TYPE: PRT
<213> ORGANISM: Artificial Sequence
<220> FEATURE:
<223> OTHER INFORMATION: H-FR4 of A56-01C08

<400> SEQUENCE: 98

Trp Gly Gln Gly Thr Thr Val Thr Val Ser Ser
1               5               10

<210> SEQ ID NO 99
<211> LENGTH: 25
<212> TYPE: PRT
<213> ORGANISM: Artificial Sequence
<220> FEATURE:
<223> OTHER INFORMATION: L-FR1 of A56-01C08

<400> SEQUENCE: 99

Ser Tyr Glu Leu Thr Gln Asp Pro Ala Val Ser Val Ala Leu Gly Gln
1               5               10              15

Thr Val Arg Ile Thr Cys Gln Gly Asp
            20              25

<210> SEQ ID NO 100
<211> LENGTH: 17
<212> TYPE: PRT
<213> ORGANISM: Artificial Sequence
<220> FEATURE:
<223> OTHER INFORMATION: L-FR2 of A56-01C08

<400> SEQUENCE: 100

Ala Ser Trp Tyr Gln Gln Lys Pro Gly Gln Ala Pro Val Leu Val Ile
1               5               10              15

Tyr

<210> SEQ ID NO 101
<211> LENGTH: 36
<212> TYPE: PRT
<213> ORGANISM: Artificial Sequence
<220> FEATURE:
<223> OTHER INFORMATION: L-FR3 of A56-01C08

<400> SEQUENCE: 101

Ile Tyr Gly Lys Asn Asn Arg Pro Ser Gly Ile Pro Gly Arg Phe Ser
1               5               10              15
```

Gly Ser Ser Ser Gly Asn Thr Ala Ser Leu Thr Ile Thr Glu Ala Gln
            20                  25                  30

Ala Glu Asp Glu
        35

<210> SEQ ID NO 102
<211> LENGTH: 10
<212> TYPE: PRT
<213> ORGANISM: Artificial Sequence
<220> FEATURE:
<223> OTHER INFORMATION: L-FR4 of A56-01C08

<400> SEQUENCE: 102

Phe Gly Gly Gly Thr Lys Leu Thr Val Leu
1               5                   10

<210> SEQ ID NO 103
<211> LENGTH: 8
<212> TYPE: PRT
<213> ORGANISM: Artificial Sequence
<220> FEATURE:
<223> OTHER INFORMATION: H-CDR1 of A56-01C12

<400> SEQUENCE: 103

Gly Phe Arg Ser Ser Thr Phe Trp
1               5

<210> SEQ ID NO 104
<211> LENGTH: 8
<212> TYPE: PRT
<213> ORGANISM: Artificial Sequence
<220> FEATURE:
<223> OTHER INFORMATION: H-CDR2 of A56-01C12

<400> SEQUENCE: 104

Ile Lys Gln Asp Gly Ser Glu Ile
1               5

<210> SEQ ID NO 105
<211> LENGTH: 17
<212> TYPE: PRT
<213> ORGANISM: Artificial Sequence
<220> FEATURE:
<223> OTHER INFORMATION: H-CDR3 of A56-01C12

<400> SEQUENCE: 105

Ala Arg Thr Arg Gly Ala Thr Ile Tyr Asp His Tyr Tyr Gly Met Asp
1               5                   10                  15

Val

<210> SEQ ID NO 106
<211> LENGTH: 8
<212> TYPE: PRT
<213> ORGANISM: Artificial Sequence
<220> FEATURE:
<223> OTHER INFORMATION: L-CDR1 of A56-01C12

<400> SEQUENCE: 106

Ser Ser Asn Ile Gly Ser Tyr Ser
1               5

<210> SEQ ID NO 107
<211> LENGTH: 3
<212> TYPE: PRT
<213> ORGANISM: Artificial Sequence -continued
<220> FEATURE:
<223> OTHER INFORMATION: L-CDR2 of A56-01C12

<400> SEQUENCE: 107

Gly His Asn
1

<210> SEQ ID NO 108
<211> LENGTH: 11
<212> TYPE: PRT
<213> ORGANISM: Artificial Sequence
<220> FEATURE:
<223> OTHER INFORMATION: L-CDR3 of A56-01C12

<400> SEQUENCE: 108

Ala Ala Trp Asp Asp Ser Val Asp Gly Trp Val
1               5                   10

<210> SEQ ID NO 109
<211> LENGTH: 255
<212> TYPE: DNA
<213> ORGANISM: Artificial Sequence
<220> FEATURE:
<223> OTHER INFORMATION: SCFV of A56-01C12

<400> SEQUENCE: 109
caggtgcagc tggtggagtc tgggggaggc ttggtccagc ctggggggtc cctgagactc        60
tcctgtgtag cctctggatt caggtctagt acttttggga tgagttggat ccgccaggct       120
ccagggaagg ggctggagtg ggtggcccac ataaagcaag atggaagtga gatatactat       180
gtggactctg tgaagggccg attcaccatc tccagagaca acagcaaaaa ctccctgtat       240
ctgcaaatga acagt                                                        255

<210> SEQ ID NO 110
<211> LENGTH: 124
<212> TYPE: PRT
<213> ORGANISM: Artificial Sequence
<220> FEATURE:
<223> OTHER INFORMATION: VH2 of A56-01C12

<400> SEQUENCE: 110

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Arg Ser Ser Thr Phe
                20                  25                  30

Trp Met Ser Trp Ile Arg Gln Ala Pro Gly Lys Gly Leu Glu Trp Val
            35                  40                  45

Ala His Ile Lys Gln Asp Gly Ser Glu Ile Tyr Tyr Val Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Thr Arg Gly Ala Thr Ile Tyr Asp His Tyr Tyr Gly Met Asp
            100                 105                 110

Val Trp Gly Gln Gly Thr Ala Val Thr Val Ser Ser
        115                 120

<210> SEQ ID NO 111
<211> LENGTH: 110
<212> TYPE: PRT

```
<213> ORGANISM: Artificial Sequence
<220> FEATURE:
<223> OTHER INFORMATION: VL2 of A56-01C12

<400> SEQUENCE: 111

Gln Ser Ala Leu Thr Gln Pro Pro Ser Arg Ser Val Thr Pro Gly Gln
1               5                   10                  15

Arg Val Thr Ile Ser Cys Ser Gly Ser Ser Ser Asn Ile Gly Ser Tyr
                20                  25                  30

Ser Val Asn Trp Tyr Gln Gln Leu Pro Gly Thr Ala Pro Lys Leu Leu
            35                  40                  45

Ile Tyr Gly His Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Ala Asp Glu Gly Asp Tyr Tyr Cys Ala Ala Trp Asp Asp Ser Val
                85                  90                  95

Asp Gly Trp Val Phe Gly Gly Gly Thr Lys Leu Thr Val Leu
                100                 105                 110

<210> SEQ ID NO 112
<211> LENGTH: 25
<212> TYPE: PRT
<213> ORGANISM: Artificial Sequence
<220> FEATURE:
<223> OTHER INFORMATION: H-FR1 of A56-01C12

<400> SEQUENCE: 112

Gln Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 113
<211> LENGTH: 17
<212> TYPE: PRT
<213> ORGANISM: Artificial Sequence
<220> FEATURE:
<223> OTHER INFORMATION: H-FR2 of A56-01C12

<400> SEQUENCE: 113

Met Ser Trp Ile Arg Gln Ala Pro Gly Lys Gly Leu Glu Trp Val Ala
1               5                   10                  15

His

<210> SEQ ID NO 114
<211> LENGTH: 38
<212> TYPE: PRT
<213> ORGANISM: Artificial Sequence
<220> FEATURE:
<223> OTHER INFORMATION: H-FR3 of A56-01C12

<400> SEQUENCE: 114

Tyr Tyr Val Asp Ser Val Lys Gly Arg Phe Thr Ile Ser Arg Asp Asn
1               5                   10                  15

Ser Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 115
```

-continued

```
<211> LENGTH: 11
<212> TYPE: PRT
<213> ORGANISM: Artificial Sequence
<220> FEATURE:
<223> OTHER INFORMATION: H-FR4 of A56-01C12

<400> SEQUENCE: 115

Trp Gly Gln Gly Thr Ala Val Thr Val Ser Ser
1               5                   10

<210> SEQ ID NO 116
<211> LENGTH: 25
<212> TYPE: PRT
<213> ORGANISM: Artificial Sequence
<220> FEATURE:
<223> OTHER INFORMATION: L-FR1 of A56-01C12

<400> SEQUENCE: 116

Gln Ser Ala Leu Thr Gln Pro Pro Ser Arg Ser Val Thr Pro Gly Gln
1               5                   10                  15

Arg Val Thr Ile Ser Cys Ser Gly Ser
            20                  25

<210> SEQ ID NO 117
<211> LENGTH: 17
<212> TYPE: PRT
<213> ORGANISM: Artificial Sequence
<220> FEATURE:
<223> OTHER INFORMATION: L-FR2 of A56-01C12

<400> SEQUENCE: 117

Val Asn Trp Tyr Gln Gln Leu Pro Gly Thr Ala Pro Lys Leu Leu Ile
1               5                   10                  15

Tyr

<210> SEQ ID NO 118
<211> LENGTH: 36
<212> TYPE: PRT
<213> ORGANISM: Artificial Sequence
<220> FEATURE:
<223> OTHER INFORMATION: L-FR3 of A56-01C12

<400> SEQUENCE: 118

Ile Tyr Gly His Asn Gln Arg Pro Ser Gly Val Pro Asp Arg Phe Ser
1               5                   10                  15

Gly Ser Lys Ser Gly Thr Ser Ala Ser Leu Ala Ile Ser Gly Leu Gln
            20                  25                  30

Ser Ala Asp Glu
        35

<210> SEQ ID NO 119
<211> LENGTH: 10
<212> TYPE: PRT
<213> ORGANISM: Artificial Sequence
<220> FEATURE:
<223> OTHER INFORMATION: L-FR4 of A56-01C12

<400> SEQUENCE: 119

Phe Gly Gly Gly Thr Lys Leu Thr Val Leu
1               5                   10

<210> SEQ ID NO 120
<211> LENGTH: 8
<212> TYPE: PRT
<213> ORGANISM: Artificial Sequence
```

-continued

```
<220> FEATURE:
<223> OTHER INFORMATION: H-CDR1 of A56-01F12

<400> SEQUENCE: 120

Gly Gly Ser Phe Ser Thr Tyr Ala
1               5

<210> SEQ ID NO 121
<211> LENGTH: 8
<212> TYPE: PRT
<213> ORGANISM: Artificial Sequence
<220> FEATURE:
<223> OTHER INFORMATION: H-CDR2 of A56-01F12

<400> SEQUENCE: 121

Ile Ile Pro Ile Ser Asp Ile Arg
1               5

<210> SEQ ID NO 122
<211> LENGTH: 13
<212> TYPE: PRT
<213> ORGANISM: Artificial Sequence
<220> FEATURE:
<223> OTHER INFORMATION: H-CDR3 of A56-01F12

<400> SEQUENCE: 122

Ala Lys Gly Gly Arg Leu Leu Ser Thr His Phe Asp Tyr
1               5                   10

<210> SEQ ID NO 123
<211> LENGTH: 8
<212> TYPE: PRT
<213> ORGANISM: Artificial Sequence
<220> FEATURE:
<223> OTHER INFORMATION: L-CDR1 of A56-01F12

<400> SEQUENCE: 123

Ser Ser Asn Ile Gly Asn Asn Tyr
1               5

<210> SEQ ID NO 124
<211> LENGTH: 3
<212> TYPE: PRT
<213> ORGANISM: Artificial Sequence
<220> FEATURE:
<223> OTHER INFORMATION: L-CDR2 of A56-01F12

<400> SEQUENCE: 124

Asp Asp Asp
1

<210> SEQ ID NO 125
<211> LENGTH: 12
<212> TYPE: PRT
<213> ORGANISM: Artificial Sequence
<220> FEATURE:
<223> OTHER INFORMATION: L-CDR3 of A56-01F12

<400> SEQUENCE: 125

Gly Thr Trp His Ser Gly Leu Ser Ala Gly Val Val
1               5                   10

<210> SEQ ID NO 126
<211> LENGTH: 255
<212> TYPE: DNA
<213> ORGANISM: Artificial Sequence
<220> FEATURE:
```

<223> OTHER INFORMATION: SCFV of A56-01F12

<400> SEQUENCE: 126
caggtgcagc tggtggagtc tggggggtgag gtgaagaagc ctgggtcctc ggtgaaggtc        60
tcctgcaagg cttctggagg cagcttcagc acctatgcta tcagctgggt gcgacaggcc       120
cctggacaag ggcttgagtg gatgggaagg atcatcccca tctctgatat cagaaactac       180
gcacagaaat tccagggcag agtcacgtta accgcggaca gagccacgag cacagcctac       240
atggagctga gcagc                                                         255

<210> SEQ ID NO 127
<211> LENGTH: 120
<212> TYPE: PRT
<213> ORGANISM: Artificial Sequence
<220> FEATURE:
<223> OTHER INFORMATION: VH2 of A56-01F12

<400> SEQUENCE: 127

Gln Val Gln Leu Val Glu Ser Gly Gly Glu Val Lys Lys Pro Gly Ser
1               5                   10                  15

Ser Val Lys Val Ser Cys Lys Ala Ser Gly Gly Ser Phe Ser Thr Tyr
                20                  25                  30

Ala Ile Ser Trp Val Arg Gln Ala Pro Gly Gln Gly Leu Glu Trp Met
            35                  40                  45

Gly Arg Ile Ile Pro Ile Ser Asp Ile Arg Asn Tyr Ala Gln Lys Phe
        50                  55                  60

Gln Gly Arg Val Thr Leu Thr Ala Asp Arg Ala Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Gly Arg Leu Leu Ser Thr His Phe Asp Tyr Trp Gly Gln
            100                 105                 110

Gly Thr Leu Val Thr Val Ser Ser
        115                 120

<210> SEQ ID NO 128
<211> LENGTH: 111
<212> TYPE: PRT
<213> ORGANISM: Artificial Sequence
<220> FEATURE:
<223> OTHER INFORMATION: VL2 of A56-01F12

<400> SEQUENCE: 128

Gln Leu Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asp Asp Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp His Ser Gly Leu
                85                  90                  95

Ser Ala Gly Val Val Phe Gly Gly Gly Thr Lys Leu Thr Val Leu
            100                 105                 110

-continued

```
<210> SEQ ID NO 129
<211> LENGTH: 25
<212> TYPE: PRT
<213> ORGANISM: Artificial Sequence
<220> FEATURE:
<223> OTHER INFORMATION: H-FR1 of A56-01F12

<400> SEQUENCE: 129

Gln Val Gln Leu Val Glu Ser Gly Gly Glu Val Lys Lys Pro Gly Ser
1               5                   10                  15

Ser Val Lys Val Ser Cys Lys Ala Ser
            20                  25

<210> SEQ ID NO 130
<211> LENGTH: 17
<212> TYPE: PRT
<213> ORGANISM: Artificial Sequence
<220> FEATURE:
<223> OTHER INFORMATION: H-FR2 of A56-01F12

<400> SEQUENCE: 130

Ile Ser Trp Val Arg Gln Ala Pro Gly Gln Gly Leu Glu Trp Met Gly
1               5                   10                  15

Arg

<210> SEQ ID NO 131
<211> LENGTH: 38
<212> TYPE: PRT
<213> ORGANISM: Artificial Sequence
<220> FEATURE:
<223> OTHER INFORMATION: H-FR3 of A56-01F12

<400> SEQUENCE: 131

Asn Tyr Ala Gln Lys Phe Gln Gly Arg Val Thr Leu Thr Ala Asp Arg
1               5                   10                  15

Ala Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 132
<211> LENGTH: 11
<212> TYPE: PRT
<213> ORGANISM: Artificial Sequence
<220> FEATURE:
<223> OTHER INFORMATION: H-FR4 of A56-01F12

<400> SEQUENCE: 132

Trp Gly Gln Gly Thr Leu Val Thr Val Ser Ser
1               5                   10

<210> SEQ ID NO 133
<211> LENGTH: 25
<212> TYPE: PRT
<213> ORGANISM: Artificial Sequence
<220> FEATURE:
<223> OTHER INFORMATION: L-FR1 of A56-01F12

<400> SEQUENCE: 133

Gln Leu Val Leu Thr Gln Pro Pro Ser Val Ser Ala Ala Pro Gly Gln
1               5                   10                  15

Lys Val Thr Ile Ser Cys Ser Gly Ser
            20                  25
```

-continued

<210> SEQ ID NO 134
<211> LENGTH: 17
<212> TYPE: PRT
<213> ORGANISM: Artificial Sequence
<220> FEATURE:
<223> OTHER INFORMATION: L-FR2 of A56-01F12

<400> SEQUENCE: 134

Val Ser Trp Tyr Gln Gln Leu Pro Gly Thr Ala Pro Lys Leu Leu Ile
1               5                   10                  15

Tyr

<210> SEQ ID NO 135
<211> LENGTH: 36
<212> TYPE: PRT
<213> ORGANISM: Artificial Sequence
<220> FEATURE:
<223> OTHER INFORMATION: L-FR3 of A56-01F12

<400> SEQUENCE: 135

Ile Tyr Asp Asp Asp Lys Arg Pro Ser Gly Ile Pro Asp Arg Phe Ser
1               5                   10                  15

Gly Ser Lys Ser Gly Thr Ser Ala Thr Leu Gly Ile Thr Gly Leu Gln
            20                  25                  30

Thr Gly Asp Glu
        35

<210> SEQ ID NO 136
<211> LENGTH: 10
<212> TYPE: PRT
<213> ORGANISM: Artificial Sequence
<220> FEATURE:
<223> OTHER INFORMATION: L-FR4 of A56-01F12

<400> SEQUENCE: 136

Phe Gly Gly Gly Thr Lys Leu Thr Val Leu
1               5                   10

<210> SEQ ID NO 137
<211> LENGTH: 8
<212> TYPE: PRT
<213> ORGANISM: Artificial Sequence
<220> FEATURE:
<223> OTHER INFORMATION: H-CDR1 of A56-01G06

<400> SEQUENCE: 137

Gly Gly Thr Leu Ser Ser Tyr Pro
1               5

<210> SEQ ID NO 138
<211> LENGTH: 8
<212> TYPE: PRT
<213> ORGANISM: Artificial Sequence
<220> FEATURE:
<223> OTHER INFORMATION: H-CDR2 of A56-01G06

<400> SEQUENCE: 138

Ile Ile Pro Ile Val Gly Arg Ala
1               5

<210> SEQ ID NO 139
<211> LENGTH: 15
<212> TYPE: PRT
<213> ORGANISM: Artificial Sequence
<220> FEATURE:

<223> OTHER INFORMATION: H-CDR3 of A56-01G06

<400> SEQUENCE: 139

Ala Arg Glu Asn Pro Ser Ser Tyr Ala Pro Phe Ala Leu Asp Ile
1               5                   10                  15

<210> SEQ ID NO 140
<211> LENGTH: 9
<212> TYPE: PRT
<213> ORGANISM: Artificial Sequence
<220> FEATURE:
<223> OTHER INFORMATION: L-CDR1 of A56-01G06

<400> SEQUENCE: 140

Ser Ser Asp Val Gly Gly Tyr Asn Tyr
1               5

<210> SEQ ID NO 141
<211> LENGTH: 3
<212> TYPE: PRT
<213> ORGANISM: Artificial Sequence
<220> FEATURE:
<223> OTHER INFORMATION: L-CDR2 of A56-01G06

<400> SEQUENCE: 141

Asp Val Thr
1

<210> SEQ ID NO 142
<211> LENGTH: 10
<212> TYPE: PRT
<213> ORGANISM: Artificial Sequence
<220> FEATURE:
<223> OTHER INFORMATION: L-CDR3 of A56-01G06

<400> SEQUENCE: 142

Ser Ser Tyr Ser Ser Ser Thr Phe Tyr Val
1               5                   10

<210> SEQ ID NO 143
<211> LENGTH: 255
<212> TYPE: DNA
<213> ORGANISM: Artificial Sequence
<220> FEATURE:
<223> OTHER INFORMATION: SCFV of A56-01G06

<400> SEQUENCE: 143
caggtgcagc tggtacagtc tgggggctgaa gtgaagaagc ctgggtcctc ggtgaaggtc     60
tcgtgcaagg cttctggagg caccctcagc agctatccca tcagctgggt gcgacaggcc    120
cctggacaag ggcttgagtg gatgggaagg atcattccta ttgttggtag agcaaactac    180
gcacagaagt tccagggcag agtcacgatt aacgcggaca catccacgaa cacagtccac    240
atggagttga gtagc                                                    255

<210> SEQ ID NO 144
<211> LENGTH: 122
<212> TYPE: PRT
<213> ORGANISM: Artificial Sequence
<220> FEATURE:
<223> OTHER INFORMATION: VH2 of A56-01G06

<400> SEQUENCE: 144

Gln Val Gln Leu Val Gln Ser Gly Ala Glu Val Lys Lys Pro Gly Ser
1               5                   10                  15

-continued

```
Ser Val Lys Val Ser Cys Lys Ala Ser Gly Gly Thr Leu Ser Ser Tyr
            20                  25                  30

Pro Ile Ser Trp Val Arg Gln Ala Pro Gly Gln Gly Leu Glu Trp Met
            35                  40                  45

Gly Arg Ile Ile Pro Ile Val Gly Arg Ala Asn Tyr Ala Gln Lys Phe
    50                  55                  60

Gln Gly Arg Val Thr Ile Asn Ala Asp Thr Ser Thr Asn Thr Val His
65                  70                  75                  80

Met Glu Leu Ser Ser Leu Arg Ser Glu Asp Thr Ala Val Tyr Tyr Cys
                85                  90                  95

Ala Arg Glu Asn Pro Ser Ser Tyr Ala Pro Phe Ala Leu Asp Ile Trp
                100                 105                 110

Gly Gln Gly Thr Ala Val Thr Val Ser Ser
        115                 120
```

<210> SEQ ID NO 145
<211> LENGTH: 110
<212> TYPE: PRT
<213> ORGANISM: Artificial Sequence
<220> FEATURE:
<223> OTHER INFORMATION: VL2 of A56-01G06

<400> SEQUENCE: 145

```
Asn Phe Met Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Gln Gly Lys Ala Pro Gln Leu
            35                  40                  45

Ile Ile Tyr Asp Val Thr Lys Arg Pro Ser Gly Val Ser Asn Arg Phe
    50                  55                  60

Ser Gly Ser Lys Ser Gly Asn Ser Ala Ser Leu Thr Ile Ser Gly Leu
65                  70                  75                  80

Gln Ala Glu Asp Glu Ala Asp Tyr Tyr Cys Ser Ser Tyr Ser Ser Ser
                85                  90                  95

Thr Phe Tyr Val Phe Gly Thr Gly Thr Lys Val Thr Val Leu
                100                 105                 110
```

<210> SEQ ID NO 146
<211> LENGTH: 25
<212> TYPE: PRT
<213> ORGANISM: Artificial Sequence
<220> FEATURE:
<223> OTHER INFORMATION: H-FR1 of A56-01G06

<400> SEQUENCE: 146

```
Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

<210> SEQ ID NO 147
<211> LENGTH: 17
<212> TYPE: PRT
<213> ORGANISM: Artificial Sequence
<220> FEATURE:
<223> OTHER INFORMATION: H-FR2 of A56-01G06

<400> SEQUENCE: 147

```
Ile Ser Trp Val Arg Gln Ala Pro Gly Gln Gly Leu Glu Trp Met Gly
```

-continued

```
1               5               10              15

Arg

<210> SEQ ID NO 148
<211> LENGTH: 38
<212> TYPE: PRT
<213> ORGANISM: Artificial Sequence
<220> FEATURE:
<223> OTHER INFORMATION: H-FR3 of A56-01G06

<400> SEQUENCE: 148

Asn Tyr Ala Gln Lys Phe Gln Gly Arg Val Thr Ile Asn Ala Asp Thr
1               5               10              15

Ser Thr Asn Thr Val His Met Glu Leu Ser Ser Leu Arg Ser Glu Asp
            20              25              30

Thr Ala Val Tyr Tyr Cys
        35

<210> SEQ ID NO 149
<211> LENGTH: 11
<212> TYPE: PRT
<213> ORGANISM: Artificial Sequence
<220> FEATURE:
<223> OTHER INFORMATION: H-FR4 of A56-01G06

<400> SEQUENCE: 149

Trp Gly Gln Gly Thr Ala Val Thr Val Ser Ser
1               5               10

<210> SEQ ID NO 150
<211> LENGTH: 25
<212> TYPE: PRT
<213> ORGANISM: Artificial Sequence
<220> FEATURE:
<223> OTHER INFORMATION: L-FR1 of A56-01G06

<400> SEQUENCE: 150

Asn Phe Met Leu Thr Gln Pro Ala Ser Val Ser Gly Ser Pro Gly Gln
1               5               10              15

Ser Ile Thr Ile Ser Cys Thr Gly Ser
            20              25

<210> SEQ ID NO 151
<211> LENGTH: 17
<212> TYPE: PRT
<213> ORGANISM: Artificial Sequence
<220> FEATURE:
<223> OTHER INFORMATION: L-FR2 of A56-01G06

<400> SEQUENCE: 151

Val Ser Trp Tyr Gln Gln His Gln Gly Lys Ala Pro Gln Leu Ile Ile
1               5               10              15

Tyr

<210> SEQ ID NO 152
<211> LENGTH: 36
<212> TYPE: PRT
<213> ORGANISM: Artificial Sequence
<220> FEATURE:
<223> OTHER INFORMATION: L-FR3 of A56-01G06

<400> SEQUENCE: 152

Ile Tyr Asp Val Thr Lys Arg Pro Ser Gly Val Ser Asn Arg Phe Ser
1               5               10              15
```

```
Gly Ser Lys Ser Gly Asn Ser Ala Ser Leu Thr Ile Ser Gly Leu Gln
            20                  25                  30

Ala Glu Asp Glu
        35

<210> SEQ ID NO 153
<211> LENGTH: 10
<212> TYPE: PRT
<213> ORGANISM: Artificial Sequence
<220> FEATURE:
<223> OTHER INFORMATION: L-FR4 of A56-01G06

<400> SEQUENCE: 153

Phe Gly Thr Gly Thr Lys Val Thr Val Leu
1               5                   10

<210> SEQ ID NO 154
<211> LENGTH: 8
<212> TYPE: PRT
<213> ORGANISM: Artificial Sequence
<220> FEATURE:
<223> OTHER INFORMATION: H-CDR1 of A56-01G11

<400> SEQUENCE: 154

Gly Phe Asn Phe Asp Asp His Ala
1               5

<210> SEQ ID NO 155
<211> LENGTH: 8
<212> TYPE: PRT
<213> ORGANISM: Artificial Sequence
<220> FEATURE:
<223> OTHER INFORMATION: H-CDR2 of A56-01G11

<400> SEQUENCE: 155

Ile Ser Trp Asn Gly Arg Ser Ile
1               5

<210> SEQ ID NO 156
<211> LENGTH: 18
<212> TYPE: PRT
<213> ORGANISM: Artificial Sequence
<220> FEATURE:
<223> OTHER INFORMATION: H-CDR3 of A56-01G11

<400> SEQUENCE: 156

Ala Arg Asp Leu Ala His Ala Ser Gly Ser Leu Arg Arg Pro Phe Phe
1               5                   10                  15

Asp Tyr

<210> SEQ ID NO 157
<211> LENGTH: 6
<212> TYPE: PRT
<213> ORGANISM: Artificial Sequence
<220> FEATURE:
<223> OTHER INFORMATION: L-CDR1 of A56-01G11

<400> SEQUENCE: 157

Gln Asp Ile Ser Thr Tyr
1               5

<210> SEQ ID NO 158
<211> LENGTH: 3
<212> TYPE: PRT
<213> ORGANISM: Artificial Sequence
```

-continued

```
<220> FEATURE:
<223> OTHER INFORMATION: L-CDR2 of A56-01G11

<400> SEQUENCE: 158

Ser Thr Ser
1

<210> SEQ ID NO 159
<211> LENGTH: 10
<212> TYPE: PRT
<213> ORGANISM: Artificial Sequence
<220> FEATURE:
<223> OTHER INFORMATION: L-CDR3 of A56-01G11

<400> SEQUENCE: 159

Gln Gln Leu Lys Ser Tyr Pro Arg Phe Thr
1               5                   10

<210> SEQ ID NO 160
<211> LENGTH: 255
<212> TYPE: DNA
<213> ORGANISM: Artificial Sequence
<220> FEATURE:
<223> OTHER INFORMATION: SCFV of A56-01G11

<400> SEQUENCE: 160
caggtgcagc tggtggagtc tggaggaggc ttgatccagc ctggggggtc cctgagactc        60
tcctgtgcag cctccggatt caactttgat gatcatgcca tgcactgggt ccggcaagct       120
ccagggaagg gcctggagtg gtctccggt attagttgga atggacgtag catatactat       180
gcggactctg tgaggggccg attcaccatc tccagagaca cgccaggaa ctccctgcat        240 ctgcaaatga acagt                                                        255

<210> SEQ ID NO 161
<211> LENGTH: 125
<212> TYPE: PRT
<213> ORGANISM: Artificial Sequence
<220> FEATURE:
<223> OTHER INFORMATION: VH2 of A56-01G11

<400> SEQUENCE: 161

Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Asn Phe Asp Asp His
            20                  25                  30

Ala Met His Trp Val Arg Gln Ala Pro Gly Lys Gly Leu Glu Trp Val
        35                  40                  45

Ser Gly Ile Ser Trp Asn Gly Arg Ser Ile Tyr Tyr Ala Asp Ser Val
    50                  55                  60

Arg Gly Arg Phe Thr Ile Ser Arg Asp Asn Ala Arg Asn Ser Leu His
65                  70                  75                  80

Leu Gln Met Asn Ser Leu Arg Ala Glu Asp Thr Ala Val Tyr Tyr Cys
                85                  90                  95

Ala Arg Asp Leu Ala His Ala Ser Gly Ser Leu Arg Arg Pro Phe Phe
            100                 105                 110

Asp Tyr Trp Gly Gln Gly Thr Leu Val Thr Val Ser Ser
        115                 120                 125

<210> SEQ ID NO 162
<211> LENGTH: 108
<212> TYPE: PRT
```

-continued

<213> ORGANISM: Artificial Sequence
<220> FEATURE:
<223> OTHER INFORMATION: VL2 of A56-01G11

<400> SEQUENCE: 162

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Ser Thr Ser Thr Leu Glu Ser Gly Val Pro Ser Arg Phe Ser Gly
    50                  55                  60

Ser Gly Ser Gly Thr Asn Phe Thr Leu Thr Ile Asn Asn Leu Gln Pro
65                  70                  75                  80

Glu Asp Phe Ala Thr Tyr Tyr Cys Gln Gln Leu Lys Ser Tyr Pro Arg
                85                  90                  95

Phe Thr Phe Gly Pro Gly Thr Lys Val Asp Ile Lys
            100                 105

<210> SEQ ID NO 163
<211> LENGTH: 25
<212> TYPE: PRT
<213> ORGANISM: Artificial Sequence
<220> FEATURE:
<223> OTHER INFORMATION: H-FR1 of A56-01G11

<400> SEQUENCE: 163

Gln Val Gln Leu Val Glu Ser Gly Gly Gly Leu Ile Gln Pro Gly Gly
1               5                   10                  15

Ser Leu Arg Leu Ser Cys Ala Ala Ser
            20                  25

<210> SEQ ID NO 164
<211> LENGTH: 17
<212> TYPE: PRT
<213> ORGANISM: Artificial Sequence
<220> FEATURE:
<223> OTHER INFORMATION: H-FR2 of A56-01G11

<400> SEQUENCE: 164

Met His Trp Val Arg Gln Ala Pro Gly Lys Gly Leu Glu Trp Val Ser
1               5                   10                  15

Gly

<210> SEQ ID NO 165
<211> LENGTH: 38
<212> TYPE: PRT
<213> ORGANISM: Artificial Sequence
<220> FEATURE:
<223> OTHER INFORMATION: H-FR3 of A56-01G11

<400> SEQUENCE: 165

Tyr Tyr Ala Asp Ser Val Arg Gly Arg Phe Thr Ile Ser Arg Asp Asn
1               5                   10                  15

Ala Arg Asn Ser Leu His Leu Gln Met Asn Ser Leu Arg Ala Glu Asp
            20                  25                  30

Thr Ala Val Tyr Tyr Cys
        35

<210> SEQ ID NO 166

```
<211> LENGTH: 11
<212> TYPE: PRT
<213> ORGANISM: Artificial Sequence
<220> FEATURE:
<223> OTHER INFORMATION: H-FR4 of A56-01G11

<400> SEQUENCE: 166

Trp Gly Gln Gly Thr Leu Val Thr Val Ser Ser
1               5                   10

<210> SEQ ID NO 167
<211> LENGTH: 26
<212> TYPE: PRT
<213> ORGANISM: Artificial Sequence
<220> FEATURE:
<223> OTHER INFORMATION: L-FR1 of A56-01G11

<400> SEQUENCE: 167

Asp Ile Gln Met Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 168
<211> LENGTH: 17
<212> TYPE: PRT
<213> ORGANISM: Artificial Sequence
<220> FEATURE:
<223> OTHER INFORMATION: L-FR2 of A56-01G11

<400> SEQUENCE: 168

Leu Asn Trp Tyr Gln Gln Lys Pro Gly Lys Ala Pro Lys Leu Leu Ile
1               5                   10                  15

Tyr

<210> SEQ ID NO 169
<211> LENGTH: 36
<212> TYPE: PRT
<213> ORGANISM: Artificial Sequence
<220> FEATURE:
<223> OTHER INFORMATION: L-FR3 of A56-01G11

<400> SEQUENCE: 169

Ile Tyr Ser Thr Ser Thr Leu Glu Ser Gly Val Pro Ser Arg Phe Ser
1               5                   10                  15

Gly Ser Gly Ser Gly Thr Asn Phe Thr Leu Thr Ile Asn Asn Leu Gln
            20                  25                  30

Pro Glu Asp Phe
        35

<210> SEQ ID NO 170
<211> LENGTH: 10
<212> TYPE: PRT
<213> ORGANISM: Artificial Sequence
<220> FEATURE:
<223> OTHER INFORMATION: L-FR4 of A56-01G11

<400> SEQUENCE: 170

Phe Gly Pro Gly Thr Lys Val Asp Ile Lys
1               5                   10

<210> SEQ ID NO 171
<211> LENGTH: 8
<212> TYPE: PRT
<213> ORGANISM: Artificial Sequence
```

```
<220> FEATURE:
<223> OTHER INFORMATION: H-CDR1 of A56-01H01

<400> SEQUENCE: 171

Gly Phe Lys Phe Glu Asp His Ala
1               5

<210> SEQ ID NO 172
<211> LENGTH: 8
<212> TYPE: PRT
<213> ORGANISM: Artificial Sequence
<220> FEATURE:
<223> OTHER INFORMATION: H-CDR2 of A56-01H01

<400> SEQUENCE: 172

Ile Ser Gly Asn Gly Asp Asp Thr
1               5

<210> SEQ ID NO 173
<211> LENGTH: 7
<212> TYPE: PRT
<213> ORGANISM: Artificial Sequence
<220> FEATURE:
<223> OTHER INFORMATION: H-CDR3 of A56-01H01

<400> SEQUENCE: 173

Ala Arg Asp Arg Gly Pro Gly
1               5

<210> SEQ ID NO 174
<211> LENGTH: 12
<212> TYPE: PRT
<213> ORGANISM: Artificial Sequence
<220> FEATURE:
<223> OTHER INFORMATION: L-CDR1 of A56-01H01

<400> SEQUENCE: 174

Gln Ser Val Leu Ser Ser Ser Asn Asn Lys Asn Tyr
1               5                   10

<210> SEQ ID NO 175
<211> LENGTH: 3
<212> TYPE: PRT
<213> ORGANISM: Artificial Sequence
<220> FEATURE:
<223> OTHER INFORMATION: L-CDR2 of A56-01H01

<400> SEQUENCE: 175

Trp Ala Ser
1

<210> SEQ ID NO 176
<211> LENGTH: 9
<212> TYPE: PRT
<213> ORGANISM: Artificial Sequence
<220> FEATURE:
<223> OTHER INFORMATION: L-CDR3 of A56-01H01

<400> SEQUENCE: 176

Gln Gln Tyr Tyr Ser Thr Pro Ser Thr
1               5

<210> SEQ ID NO 177
<211> LENGTH: 255
<212> TYPE: DNA
<213> ORGANISM: Artificial Sequence
<220> FEATURE:
```

<223> OTHER INFORMATION: SCFV of A56-01H01

<400> SEQUENCE: 177
caggtgcagc tggtggagtc tggggggaggc gtggtacagc ctgggggggtc cctgagactc        60 acctgtgtgg gctctggatt caagttcgaa gatcacgcca tccactgggt ccgtcaacgt       120
ccagggaagg gtctggagtg ggtctccgtt ataagtggca atggcgatga cacatactat       180
gcagattctg cgaagggccg attcaccatt tccagagaca acagcaaaaa ctccctgtat       240
ctgcaaatga acagt                                                        255

<210> SEQ ID NO 178
<211> LENGTH: 114
<212> TYPE: PRT
<213> ORGANISM: Artificial Sequence
<220> FEATURE:
<223> OTHER INFORMATION: VH2 of A56-01H01

<400> SEQUENCE: 178

Gln Val Gln Leu Val Glu Ser Gly Gly Gly Val Val Gln Pro Gly Gly
1               5                   10                  15

Ser Leu Arg Leu Thr Cys Val Gly Ser Gly Phe Lys Phe Glu Asp His
            20                  25                  30

Ala Ile His Trp Val Arg Gln Arg Pro Gly Lys Gly Leu Glu Trp Val
        35                  40                  45

Ser Val Ile Ser Gly Asn Gly Asp Asp Thr Tyr Tyr Ala Asp Ser Ala
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Pro Gly Leu Gly Gln Gly Thr Leu Val Thr Val
                100                 105                 110

Ser Ser

<210> SEQ ID NO 179
<211> LENGTH: 113
<212> TYPE: PRT
<213> ORGANISM: Artificial Sequence
<220> FEATURE:
<223> OTHER INFORMATION: VL2 of A56-01H01

<400> SEQUENCE: 179

Asp Ile Gln Met Thr Gln Ser Pro Ser Ser Leu Ala Val Ser Leu Gly
1               5                   10                  15

Glu Arg Ala Thr Ile Asn Cys Lys Ser Ser Gln Ser Val Leu Ser Ser
            20                  25                  30

Ser Asn Asn Lys Asn Tyr Leu Ala Trp Tyr Gln Gln Arg Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Ser Thr Pro Ser Thr Phe Gly Gln Gly Thr Lys Val Glu Ile
                100                 105                 110

Lys

-continued

```
<210> SEQ ID NO 180
<211> LENGTH: 25
<212> TYPE: PRT
<213> ORGANISM: Artificial Sequence
<220> FEATURE:
<223> OTHER INFORMATION: H-FR1 of A56-01H01

<400> SEQUENCE: 180

Gln Val Gln Leu Val Glu Ser Gly Gly Gly Val Val Gln Pro Gly Gly
1               5                   10                  15

Ser Leu Arg Leu Thr Cys Val Gly Ser
            20                  25

<210> SEQ ID NO 181
<211> LENGTH: 17
<212> TYPE: PRT
<213> ORGANISM: Artificial Sequence
<220> FEATURE:
<223> OTHER INFORMATION: H-FR2 of A56-01H01

<400> SEQUENCE: 181

Ile His Trp Val Arg Gln Arg Pro Gly Lys Gly Leu Glu Trp Val Ser
1               5                   10                  15

Val

<210> SEQ ID NO 182
<211> LENGTH: 38
<212> TYPE: PRT
<213> ORGANISM: Artificial Sequence
<220> FEATURE:
<223> OTHER INFORMATION: H-FR3 of A56-01H01

<400> SEQUENCE: 182

Tyr Tyr Ala Asp Ser Ala Lys Gly Arg Phe Thr Ile Ser Arg Asp Asn
1               5                   10                  15

Ser Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 183
<211> LENGTH: 11
<212> TYPE: PRT
<213> ORGANISM: Artificial Sequence
<220> FEATURE:
<223> OTHER INFORMATION: H-FR4 of A56-01H01

<400> SEQUENCE: 183

Leu Gly Gln Gly Thr Leu Val Thr Val Ser Ser
1               5                   10

<210> SEQ ID NO 184
<211> LENGTH: 26
<212> TYPE: PRT
<213> ORGANISM: Artificial Sequence
<220> FEATURE:
<223> OTHER INFORMATION: L-FR1 of A56-01H01

<400> SEQUENCE: 184

Asp Ile Gln Met Thr Gln Ser Pro Ser Ser Leu Ala Val Ser Leu Gly
1               5                   10                  15

Glu Arg Ala Thr Ile Asn Cys Lys Ser Ser
            20                  25
```

<210> SEQ ID NO 185
<211> LENGTH: 17
<212> TYPE: PRT
<213> ORGANISM: Artificial Sequence
<220> FEATURE:
<223> OTHER INFORMATION: L-FR2 of A56-01H01

<400> SEQUENCE: 185

Leu Ala Trp Tyr Gln Gln Arg Pro Gly Gln Ser Pro Lys Leu Leu Ile
1               5                   10                  15

Tyr

<210> SEQ ID NO 186
<211> LENGTH: 36
<212> TYPE: PRT
<213> ORGANISM: Artificial Sequence
<220> FEATURE:
<223> OTHER INFORMATION: L-FR3 of A56-01H01

<400> SEQUENCE: 186

Ile Tyr Trp Ala Ser Thr Arg Glu Ser Gly Val Pro Asp Arg Phe Ser
1               5                   10                  15

Gly Ser Gly Ser Gly Thr Asp Phe Thr Leu Thr Ile Asn Ser Leu Gln
            20                  25                  30

Ala Glu Asp Val
        35

<210> SEQ ID NO 187
<211> LENGTH: 10
<212> TYPE: PRT
<213> ORGANISM: Artificial Sequence
<220> FEATURE:
<223> OTHER INFORMATION: L-FR4 of A56-01H01

<400> SEQUENCE: 187

Phe Gly Gln Gly Thr Lys Val Glu Ile Lys
1               5                   10

<210> SEQ ID NO 188
<211> LENGTH: 8
<212> TYPE: PRT
<213> ORGANISM: Artificial Sequence
<220> FEATURE:
<223> OTHER INFORMATION: H-CDR1 of A56-01H02

<400> SEQUENCE: 188

Gly Phe Thr Phe Gly Asp Tyr Ala
1               5

<210> SEQ ID NO 189
<211> LENGTH: 10
<212> TYPE: PRT
<213> ORGANISM: Artificial Sequence
<220> FEATURE:
<223> OTHER INFORMATION: H-CDR2 of A56-01H02

<400> SEQUENCE: 189

Ile Arg Ser Lys Ala Tyr Gly Gly Thr Thr
1               5                   10

<210> SEQ ID NO 190
<211> LENGTH: 15
<212> TYPE: PRT
<213> ORGANISM: Artificial Sequence
<220> FEATURE:
<223> OTHER INFORMATION: H-CDR3 of A56-01H02

<400> SEQUENCE: 190

Ala Arg Asp Pro Ala Lys Glu Arg Ser Arg Asn Trp Phe Ala Pro
1               5                   10                  15

<210> SEQ ID NO 191
<211> LENGTH: 6
<212> TYPE: PRT
<213> ORGANISM: Artificial Sequence
<220> FEATURE:
<223> OTHER INFORMATION: L-CDR1 of A56-01H02

<400> SEQUENCE: 191

Gln Ser Ile Gly Ser Trp
1               5

<210> SEQ ID NO 192
<211> LENGTH: 3
<212> TYPE: PRT
<213> ORGANISM: Artificial Sequence
<220> FEATURE:
<223> OTHER INFORMATION: L-CDR2 of A56-01H02

<400> SEQUENCE: 192

Lys Ala Ser
1

<210> SEQ ID NO 193
<211> LENGTH: 9
<212> TYPE: PRT
<213> ORGANISM: Artificial Sequence
<220> FEATURE:
<223> OTHER INFORMATION: L-CDR3 of A56-01H02

<400> SEQUENCE: 193

Gln Gln Tyr Lys Leu Tyr Pro Trp Thr
1               5

<210> SEQ ID NO 194
<211> LENGTH: 255
<212> TYPE: DNA
<213> ORGANISM: Artificial Sequence
<220> FEATURE:
<223> OTHER INFORMATION: SCFV of A56-01H02

<400> SEQUENCE: 194
caggtgcagc tggtgcagtc tgggggaggc ttggtaaagc cagggcggtc cctgagactc        60
tcctgtacag cttctggatt cacctttggt gattatgcta tgagctggtt ccgccaggct       120
ccagggaagg ggctggagtg ggtaggtttc attagaagca aagcttatgg tgggacaaca       180
gaatacgccg cgtctgtgaa aggcagattc accatctcaa gagatgattc caaaagcatc       240
gcctatctgc aaatg                                                        255

<210> SEQ ID NO 195
<211> LENGTH: 124
<212> TYPE: PRT
<213> ORGANISM: Artificial Sequence
<220> FEATURE:
<223> OTHER INFORMATION: VH2 of A56-01H02

<400> SEQUENCE: 195

Gln Val Gln Leu Val Gln Ser Gly Gly Gly Leu Val Lys Pro Gly Arg
1               5                   10                  15

```
Ser Leu Arg Leu Ser Cys Thr Ala Ser Gly Phe Thr Phe Gly Asp Tyr
        20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Arg Ala Glu Asp Thr Ala Val Tyr
                85                  90                  95

Tyr Cys Ala Arg Asp Pro Ala Lys Glu Arg Ser Arg Asn Trp Phe Ala
            100                 105                 110

Pro Trp Gly Gln Gly Thr Leu Val Thr Val Ser Ser
        115                 120
```

```
<210> SEQ ID NO 196
<211> LENGTH: 107
<212> TYPE: PRT
<213> ORGANISM: Artificial Sequence
<220> FEATURE:
<223> OTHER INFORMATION: VL2 of A56-01H02

<400> SEQUENCE: 196
```

```
Asp Ile Gln Met Thr Gln Ser Pro Ser Thr Leu Ser Ala Ser Val Gly
1                   5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Leu Tyr Pro Trp
                85                  90                  95

Thr Phe Gly Gln Gly Thr Lys Val Asp Ile Lys
            100                 105
```

```
<210> SEQ ID NO 197
<211> LENGTH: 25
<212> TYPE: PRT
<213> ORGANISM: Artificial Sequence
<220> FEATURE:
<223> OTHER INFORMATION: H-FR1 of A56-01H02

<400> SEQUENCE: 197
```

```
Gln Val Gln Leu Val Gln Ser Gly Gly Gly Leu Val Lys Pro Gly Arg
1                   5                   10                  15

Ser Leu Arg Leu Ser Cys Thr Ala Ser
            20                  25
```

```
<210> SEQ ID NO 198
<211> LENGTH: 17
<212> TYPE: PRT
<213> ORGANISM: Artificial Sequence
<220> FEATURE:
<223> OTHER INFORMATION: H-FR2 of A56-01H02

<400> SEQUENCE: 198
```

```
Met Ser Trp Phe Arg Gln Ala Pro Gly Lys Gly Leu Glu Trp Val Gly
1               5                   10                  15

Phe

<210> SEQ ID NO 199
<211> LENGTH: 38
<212> TYPE: PRT
<213> ORGANISM: Artificial Sequence
<220> FEATURE:
<223> OTHER INFORMATION: H-FR3 of A56-01H02

<400> SEQUENCE: 199

Glu Tyr Ala Ala Ser Val Lys Gly Arg Phe Thr Ile Ser Arg Asp Asp
1               5                   10                  15

Ser Lys Ser Ile Ala Tyr Leu Gln Met Asn Ser Leu Arg Ala Glu Asp
            20                  25                  30

Thr Ala Val Tyr Tyr Cys
        35

<210> SEQ ID NO 200
<211> LENGTH: 11
<212> TYPE: PRT
<213> ORGANISM: Artificial Sequence
<220> FEATURE:
<223> OTHER INFORMATION: H-FR4 of A56-01H02

<400> SEQUENCE: 200

Trp Gly Gln Gly Thr Leu Val Thr Val Ser Ser
1               5                   10

<210> SEQ ID NO 201
<211> LENGTH: 26
<212> TYPE: PRT
<213> ORGANISM: Artificial Sequence
<220> FEATURE:
<223> OTHER INFORMATION: L-FR1 of A56-01H02

<400> SEQUENCE: 201

Asp Ile Gln Met Thr Gln Ser Pro Ser Thr Leu Ser Ala Ser Val Gly
1               5                   10                  15

Asp Arg Val Thr Ile Thr Cys Arg Ala Ser
            20                  25

<210> SEQ ID NO 202
<211> LENGTH: 17
<212> TYPE: PRT
<213> ORGANISM: Artificial Sequence
<220> FEATURE:
<223> OTHER INFORMATION: L-FR2 of A56-01H02

<400> SEQUENCE: 202

Leu Ala Trp Tyr Gln Gln Lys Pro Gly Lys Ala Pro Lys Leu Leu Ile
1               5                   10                  15

Tyr

<210> SEQ ID NO 203
<211> LENGTH: 36
<212> TYPE: PRT
<213> ORGANISM: Artificial Sequence
<220> FEATURE:
<223> OTHER INFORMATION: L-FR3 of A56-01H02

<400> SEQUENCE: 203

Ile Tyr Lys Ala Ser Ser Leu Glu Ser Gly Val Pro Ser Arg Phe Ser
```

-continued

```
1               5                   10                  15
Gly Ser Gly Ser Gly Thr Glu Phe Thr Leu Thr Ile Ser Ser Leu Gln
            20                  25                  30

Pro Asp Asp Phe
        35

<210> SEQ ID NO 204
<211> LENGTH: 10
<212> TYPE: PRT
<213> ORGANISM: Artificial Sequence
<220> FEATURE:
<223> OTHER INFORMATION: L-FR4 of A56-01H02

<400> SEQUENCE: 204

Phe Gly Gln Gly Thr Lys Val Asp Ile Lys
1               5                   10

<210> SEQ ID NO 205
<211> LENGTH: 8
<212> TYPE: PRT
<213> ORGANISM: Artificial Sequence
<220> FEATURE:
<223> OTHER INFORMATION: H-CDR1 of A56-01H11

<400> SEQUENCE: 205

Gly Tyr Thr Phe Ser Arg His Trp
1               5

<210> SEQ ID NO 206
<211> LENGTH: 8
<212> TYPE: PRT
<213> ORGANISM: Artificial Sequence
<220> FEATURE:
<223> OTHER INFORMATION: H-CDR2 of A56-01H11

<400> SEQUENCE: 206

Ile His Pro Ala Asp Ser Asp Thr
1               5

<210> SEQ ID NO 207
<211> LENGTH: 9
<212> TYPE: PRT
<213> ORGANISM: Artificial Sequence
<220> FEATURE:
<223> OTHER INFORMATION: H-CDR3 of A56-01H11

<400> SEQUENCE: 207

Ile Thr Glu Asp Ser Gly Arg Phe Asn
1               5

<210> SEQ ID NO 208
<211> LENGTH: 6
<212> TYPE: PRT
<213> ORGANISM: Artificial Sequence
<220> FEATURE:
<223> OTHER INFORMATION: L-CDR1 of A56-01H11

<400> SEQUENCE: 208

Gln Ser Ile Gly Asn Tyr
1               5

<210> SEQ ID NO 209
<211> LENGTH: 3
<212> TYPE: PRT
<213> ORGANISM: Artificial Sequence
<220> FEATURE:
```

-continued

<223> OTHER INFORMATION: L-CDR2 of A56-01H11

<400> SEQUENCE: 209

Ala Ser Ser
1

<210> SEQ ID NO 210
<211> LENGTH: 10
<212> TYPE: PRT
<213> ORGANISM: Artificial Sequence
<220> FEATURE:
<223> OTHER INFORMATION: L-CDR3 of A56-01H11

<400> SEQUENCE: 210

Gln Gln Thr Tyr Asn Thr Pro Pro Ile Thr
1               5                   10

<210> SEQ ID NO 211
<211> LENGTH: 255
<212> TYPE: DNA
<213> ORGANISM: Artificial Sequence
<220> FEATURE:
<223> OTHER INFORMATION: SCFV of A56-01H11

<400> SEQUENCE: 211
caggtgcagc tggtgcagtc tggagcagaa gtgaaaaagc ccggtgactc tctgaaaatc      60
tcttgtgagg cttctggcta cacgtttagt aggcattgga tcgtttgggt gcgccagatg     120
cccggaaaag gcctggagtg gatggggatg atccaccctg ctgactctga caccagatat     180
agcccgtcat tcggaggcca ggtcaccatg tcagtcgaca gtcagccac caccgcctac      240 ctgcagtgga gcagc                                                     255

<210> SEQ ID NO 212
<211> LENGTH: 116
<212> TYPE: PRT
<213> ORGANISM: Artificial Sequence
<220> FEATURE:
<223> OTHER INFORMATION: VH2 of A56-01H11

<400> SEQUENCE: 212

Gln Val Gln Leu Val Gln Ser Gly Ala Glu Val Lys Lys Pro Gly Asp
1               5                   10                  15

Ser Leu Lys Ile Ser Cys Glu Ala Ser Gly Tyr Thr Phe Ser Arg His
            20                  25                  30

Trp Ile Val Trp Val Arg Gln Met Pro Gly Lys Gly Leu Glu Trp Met
        35                  40                  45

Gly Met Ile His Pro Ala Asp Ser Asp Thr Arg Tyr Ser Pro Ser Phe
    50                  55                  60

Gly Gly Gln Val Thr Met Ser Val Asp Lys Ser Ala Thr Thr Ala Tyr
65                  70                  75                  80

Leu Gln Trp Ser Ser Leu Lys Ala Ser Asp Thr Ala Met Tyr Tyr Cys
                85                  90                  95

Ile Thr Glu Asp Ser Gly Arg Phe Asn Trp Gly Gln Gly Thr Leu Val
            100                 105                 110

Thr Val Ser Ser
        115

<210> SEQ ID NO 213
<211> LENGTH: 108
<212> TYPE: PRT
<213> ORGANISM: Artificial Sequence
<220> FEATURE:
<223> OTHER INFORMATION: VL2 of A56-01H11

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Asn Tyr
            20                  25                  30

Leu Asn Trp Tyr Gln Gln Lys Pro Gly Lys Ser Pro Lys Leu Leu Ile
        35                  40                  45

Tyr Ala Ser Ser Ser Leu Gln Ser Gly Ile Pro Ser Arg Phe Ser Gly
    50                  55                  60

Ser Gly Ser Gly Thr Asp Phe Asn Leu Thr Ile Ser Asn Leu Gln Pro
65                  70                  75                  80

Glu Asp Phe Gly Thr Tyr Tyr Cys Gln Gln Thr Tyr Asn Thr Pro Pro
                85                  90                  95

Ile Thr Phe Gly Gln Gly Thr Arg Leu Glu Ile Lys
            100                 105

<210> SEQ ID NO 214
<211> LENGTH: 25
<212> TYPE: PRT
<213> ORGANISM: Artificial Sequence
<220> FEATURE:
<223> OTHER INFORMATION: H-FR1 of A56-01H11

<400> SEQUENCE: 214

Gln Val Gln Leu Val Gln Ser Gly Ala Glu Val Lys Lys Pro Gly Asp
1               5                   10                  15

Ser Leu Lys Ile Ser Cys Glu Ala Ser
            20                  25

<210> SEQ ID NO 215
<211> LENGTH: 17
<212> TYPE: PRT
<213> ORGANISM: Artificial Sequence
<220> FEATURE:
<223> OTHER INFORMATION: H-FR2 of A56-01H11

<400> SEQUENCE: 215

Ile Val Trp Val Arg Gln Met Pro Gly Lys Gly Leu Glu Trp Met Gly
1               5                   10                  15

Met

<210> SEQ ID NO 216
<211> LENGTH: 38
<212> TYPE: PRT
<213> ORGANISM: Artificial Sequence
<220> FEATURE:
<223> OTHER INFORMATION: H-FR3 of A56-01H11

<400> SEQUENCE: 216

Arg Tyr Ser Pro Ser Phe Gly Gly Gln Val Thr Met Ser Val Asp Lys
1               5                   10                  15

Ser Ala Thr Thr Ala Tyr Leu Gln Trp Ser Ser Leu Lys Ala Ser Asp
            20                  25                  30

Thr Ala Met Tyr Tyr Cys
            35

<210> SEQ ID NO 217
<211> LENGTH: 11

```
<212> TYPE: PRT
<213> ORGANISM: Artificial Sequence
<220> FEATURE:
<223> OTHER INFORMATION: H-FR4 of A56-01H11

<400> SEQUENCE: 217

Trp Gly Gln Gly Thr Leu Val Thr Val Ser Ser
1               5                   10

<210> SEQ ID NO 218
<211> LENGTH: 26
<212> TYPE: PRT
<213> ORGANISM: Artificial Sequence
<220> FEATURE:
<223> OTHER INFORMATION: L-FR1 of A56-01H11

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 219
<211> LENGTH: 17
<212> TYPE: PRT
<213> ORGANISM: Artificial Sequence
<220> FEATURE:
<223> OTHER INFORMATION: L-FR2 of A56-01H11

<400> SEQUENCE: 219

Leu Asn Trp Tyr Gln Gln Lys Pro Gly Lys Ser Pro Lys Leu Leu Ile
1               5                   10                  15

Tyr

<210> SEQ ID NO 220
<211> LENGTH: 36
<212> TYPE: PRT
<213> ORGANISM: Artificial Sequence
<220> FEATURE:
<223> OTHER INFORMATION: L-FR3 of A56-01H11

<400> SEQUENCE: 220

Ile Tyr Ala Ser Ser Ser Leu Gln Ser Gly Ile Pro Ser Arg Phe Ser
1               5                   10                  15

Gly Ser Gly Ser Gly Thr Asp Phe Asn Leu Thr Ile Ser Asn Leu Gln
            20                  25                  30

Pro Glu Asp Phe
        35

<210> SEQ ID NO 221
<211> LENGTH: 10
<212> TYPE: PRT
<213> ORGANISM: Artificial Sequence
<220> FEATURE:
<223> OTHER INFORMATION: L-FR4 of A56-01H11

<400> SEQUENCE: 221

Phe Gly Gln Gly Thr Arg Leu Glu Ile Lys
1               5                   10

<210> SEQ ID NO 222
<211> LENGTH: 8
<212> TYPE: PRT
<213> ORGANISM: Artificial Sequence
<220> FEATURE:
```

<223> OTHER INFORMATION: H-CDR1 of A56-02A02

<400> SEQUENCE: 222

Gly Asp Thr Leu Thr Tyr Arg Phe
1               5

<210> SEQ ID NO 223
<211> LENGTH: 8
<212> TYPE: PRT
<213> ORGANISM: Artificial Sequence
<220> FEATURE:
<223> OTHER INFORMATION: H-CDR2 of A56-02A02

<400> SEQUENCE: 223

Ile Thr Pro Phe Asn Asp Asn Thr
1               5

<210> SEQ ID NO 224
<211> LENGTH: 13
<212> TYPE: PRT
<213> ORGANISM: Artificial Sequence
<220> FEATURE:
<223> OTHER INFORMATION: H-CDR3 of A56-02A02

<400> SEQUENCE: 224

Ala Thr Gly Gly Gly Asn Asn Tyr Tyr Gly Met Glu Val
1               5                   10

<210> SEQ ID NO 225
<211> LENGTH: 6
<212> TYPE: PRT
<213> ORGANISM: Artificial Sequence
<220> FEATURE:
<223> OTHER INFORMATION: L-CDR1 of A56-02A02

<400> SEQUENCE: 225

Lys Leu Gly Asp Lys Phe
1               5

<210> SEQ ID NO 226
<211> LENGTH: 3
<212> TYPE: PRT
<213> ORGANISM: Artificial Sequence
<220> FEATURE:
<223> OTHER INFORMATION: L-CDR2 of A56-02A02

<400> SEQUENCE: 226

Gln Asp Ala
1

<210> SEQ ID NO 227
<211> LENGTH: 9
<212> TYPE: PRT
<213> ORGANISM: Artificial Sequence
<220> FEATURE:
<223> OTHER INFORMATION: L-CDR3 of A56-02A02

<400> SEQUENCE: 227

Gln Ala Trp Asp Ser Ser Ser Val Val
1               5

<210> SEQ ID NO 228
<211> LENGTH: 255
<212> TYPE: DNA
<213> ORGANISM: Artificial Sequence
<220> FEATURE:
<223> OTHER INFORMATION: SCFV of A56-02A02

<400> SEQUENCE: 228
cagatgcagc tggtggagtc tggggctgag gtgaagaaga ctgggtcctc agtgaaggtt      60
tcctgcaagg cttccggaga caccctcacc taccgcttcc tgcactgggt gcgacaggcc     120
cccggacaag cgcctgagtg gatgggatgg atcacacctt caatgataa caccaactac      180 gcacagaaat tccaggacag agtcaccatt accagggaca ggtctatgag cacagcctac     240
atggagctga gcagc                                                      255

<210> SEQ ID NO 229
<211> LENGTH: 120
<212> TYPE: PRT
<213> ORGANISM: Artificial Sequence
<220> FEATURE:
<223> OTHER INFORMATION: VH2 of A56-02A02

<400> SEQUENCE: 229

Gln Met Gln Leu Val Glu Ser Gly Ala Glu Val Lys Lys Thr Gly Ser
1               5                   10                  15

Ser Val Lys Val Ser Cys Lys Ala Ser Gly Asp Thr Leu Thr Tyr Arg
            20                  25                  30

Phe Leu His Trp Val Arg Gln Ala Pro Gly Gln Ala Pro Glu Trp Met
        35                  40                  45

Gly Trp Ile Thr Pro Phe Asn Asp Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Gly Asn Asn Tyr Tyr Gly Met Glu Val Trp Gly Gln
            100                 105                 110

Gly Thr Pro Ile Thr Val Ser Ser
        115                 120

<210> SEQ ID NO 230
<211> LENGTH: 106
<212> TYPE: PRT
<213> ORGANISM: Artificial Sequence
<220> FEATURE:
<223> OTHER INFORMATION: VL2 of A56-02A02

<400> SEQUENCE: 230

Ser Tyr Glu Leu Thr Gln Pro Leu Ser Leu Ser Val Ser Pro Gly Gln
1               5                   10                  15

Thr Ala Ser Ile Thr Cys Ser Gly Asp Lys Leu Gly Asp Lys Phe Thr
            20                  25                  30

Ser Trp Tyr Gln Gln Gln Pro Gly Gln Ser Pro Val Leu Val Ile Tyr
        35                  40                  45

Gln Asp Ala Lys Arg Pro Ser Gly Ile Pro Glu Arg Phe Ser Gly Ser
    50                  55                  60

Asn Ser Gly Ser Thr Ala Thr Leu Thr Ile Ser Gly Thr Gln Ser Met
65                  70                  75                  80

Asp Glu Ala Asp Tyr Tyr Cys Gln Ala Trp Asp Ser Ser Ser Val Val
                85                  90                  95

Phe Gly Gly Gly Thr Lys Leu Thr Val Leu
            100                 105

-continued

```
<210> SEQ ID NO 231
<211> LENGTH: 25
<212> TYPE: PRT
<213> ORGANISM: Artificial Sequence
<220> FEATURE:
<223> OTHER INFORMATION: H-FR1 of A56-02A02

<400> SEQUENCE: 231

Gln Met Gln Leu Val Glu Ser Gly Ala Glu Val Lys Lys Thr Gly Ser
1               5                   10                  15

Ser Val Lys Val Ser Cys Lys Ala Ser
            20                  25

<210> SEQ ID NO 232
<211> LENGTH: 17
<212> TYPE: PRT
<213> ORGANISM: Artificial Sequence
<220> FEATURE:
<223> OTHER INFORMATION: H-FR2 of A56-02A02

<400> SEQUENCE: 232

Leu His Trp Val Arg Gln Ala Pro Gly Gln Ala Pro Glu Trp Met Gly
1               5                   10                  15

Trp

<210> SEQ ID NO 233
<211> LENGTH: 38
<212> TYPE: PRT
<213> ORGANISM: Artificial Sequence
<220> FEATURE:
<223> OTHER INFORMATION: H-FR3 of A56-02A02

<400> SEQUENCE: 233

Asn Tyr Ala Gln Lys Phe Gln Asp Arg Val Thr Ile Thr Arg Asp Arg
1               5                   10                  15

Ser Met Ser Thr Ala Tyr Met Glu Leu Ser Ser Leu Arg Ser Glu Asp
            20                  25                  30

Thr Ala Val Tyr Tyr Cys
        35

<210> SEQ ID NO 234
<211> LENGTH: 11
<212> TYPE: PRT
<213> ORGANISM: Artificial Sequence
<220> FEATURE:
<223> OTHER INFORMATION: H-FR4 of A56-02A02

<400> SEQUENCE: 234

Trp Gly Gln Gly Thr Pro Ile Thr Val Ser Ser
1               5                   10

<210> SEQ ID NO 235
<211> LENGTH: 25
<212> TYPE: PRT
<213> ORGANISM: Artificial Sequence
<220> FEATURE:
<223> OTHER INFORMATION: L-FR1 of A56-02A02

<400> SEQUENCE: 235

Ser Tyr Glu Leu Thr Gln Pro Leu Ser Leu Ser Val Ser Pro Gly Gln
1               5                   10                  15

Thr Ala Ser Ile Thr Cys Ser Gly Asp
            20                  25
```

```
<210> SEQ ID NO 236
<211> LENGTH: 17
<212> TYPE: PRT
<213> ORGANISM: Artificial Sequence
<220> FEATURE:
<223> OTHER INFORMATION: L-FR2 of A56-02A02

<400> SEQUENCE: 236

Thr Ser Trp Tyr Gln Gln Gln Pro Gly Gln Ser Pro Val Leu Val Ile
1               5                   10                  15

Tyr

<210> SEQ ID NO 237
<211> LENGTH: 36
<212> TYPE: PRT
<213> ORGANISM: Artificial Sequence
<220> FEATURE:
<223> OTHER INFORMATION: L-FR3 of A56-02A02

<400> SEQUENCE: 237

Ile Tyr Gln Asp Ala Lys Arg Pro Ser Gly Ile Pro Glu Arg Phe Ser
1               5                   10                  15

Gly Ser Asn Ser Gly Ser Thr Ala Thr Leu Thr Ile Ser Gly Thr Gln
            20                  25                  30

Ser Met Asp Glu
        35

<210> SEQ ID NO 238
<211> LENGTH: 10
<212> TYPE: PRT
<213> ORGANISM: Artificial Sequence
<220> FEATURE:
<223> OTHER INFORMATION: L-FR4 of A56-02A02

<400> SEQUENCE: 238

Phe Gly Gly Gly Thr Lys Leu Thr Val Leu
1               5                   10

<210> SEQ ID NO 239
<211> LENGTH: 8
<212> TYPE: PRT
<213> ORGANISM: Artificial Sequence
<220> FEATURE:
<223> OTHER INFORMATION: H-CDR1 of A56-02B01

<400> SEQUENCE: 239

Gly Phe Thr Phe Ser Asn Tyr Gly
1               5

<210> SEQ ID NO 240
<211> LENGTH: 8
<212> TYPE: PRT
<213> ORGANISM: Artificial Sequence
<220> FEATURE:
<223> OTHER INFORMATION: H-CDR2 of A56-02B01

<400> SEQUENCE: 240

Ile Trp Phe Asp Gly Ser Asn Lys
1               5

<210> SEQ ID NO 241
<211> LENGTH: 12
<212> TYPE: PRT
<213> ORGANISM: Artificial Sequence
<220> FEATURE:
<223> OTHER INFORMATION: H-CDR3 of A56-02B01
```

<400> SEQUENCE: 241

Ala Lys Ala Ala His Leu Trp Gly Ala Phe Asp Ile
1               5                   10

<210> SEQ ID NO 242
<211> LENGTH: 6
<212> TYPE: PRT
<213> ORGANISM: Artificial Sequence
<220> FEATURE:
<223> OTHER INFORMATION: L-CDR1 of A56-02B01

<400> SEQUENCE: 242

Gln Ser Val Ser Ser Tyr
1               5

<210> SEQ ID NO 243
<211> LENGTH: 3
<212> TYPE: PRT
<213> ORGANISM: Artificial Sequence
<220> FEATURE:
<223> OTHER INFORMATION: L-CDR2 of A56-02B01

<400> SEQUENCE: 243

Gly Ala Ser
1

<210> SEQ ID NO 244
<211> LENGTH: 9
<212> TYPE: PRT
<213> ORGANISM: Artificial Sequence
<220> FEATURE:
<223> OTHER INFORMATION: L-CDR3 of A56-02B01

<400> SEQUENCE: 244

Gln Gln Tyr Ala Thr Ser Pro Leu Ser
1               5

<210> SEQ ID NO 245
<211> LENGTH: 255
<212> TYPE: DNA
<213> ORGANISM: Artificial Sequence
<220> FEATURE:
<223> OTHER INFORMATION: SCFV of A56-02B01

<400> SEQUENCE: 245
caggtgcagc tggtgcagtc tgggggaggt gtggtccagc ctgggaggtc cctgagactc      60
tcctgtgcag cgtctggatt caccttcagt aactatggca tgcactgggt ccgccaggct     120
ccaggcaagg ggctggaatg gatggcattt atatggtttg atggaagtaa taaattctat     180
gcagactccg tgaagggccg attcaccgtc tccagagaca attccaagaa caccctgttt     240
ctgcaaatga acagt                                                      255

<210> SEQ ID NO 246
<211> LENGTH: 119
<212> TYPE: PRT
<213> ORGANISM: Artificial Sequence
<220> FEATURE:
<223> OTHER INFORMATION: VH2 of A56-02B01

<400> SEQUENCE: 246

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr

-continued

```
              20               25               30

Gly Met His Trp Val Arg Gln Ala Pro Gly Lys Gly Leu Glu Trp Met
        35               40               45

Ala Phe Ile Trp Phe Asp Gly Ser Asn Lys Phe Tyr Ala Asp Ser Val
    50               55               60

Lys Gly Arg Phe Thr Val Ser Arg Asp Asn Ser Lys Asn Thr Leu Phe
65               70               75               80

Leu Gln Met Asn Ser Leu Arg Ala Glu Asp Thr Ala Val Tyr Tyr Cys
                85               90               95

Ala Lys Ala Ala His Leu Trp Gly Ala Phe Asp Ile Trp Gly Gln Gly
            100              105              110

Thr Met Val Thr Val Ser Ser
        115

<210> SEQ ID NO 247
<211> LENGTH: 107
<212> TYPE: PRT
<213> ORGANISM: Artificial Sequence
<220> FEATURE:
<223> OTHER INFORMATION: VL2 of A56-02B01

<400> SEQUENCE: 247

Asp Ile Gln Met Thr Gln Ser Pro Asp Thr Leu Ser Leu Ser Pro Gly
1               5               10               15

Glu Arg Ala Thr Leu Ser Cys Arg Ala Ser Gln Ser Val Ser Ser Tyr
            20               25               30

Leu Ala Trp Tyr Gln Gln Lys Pro Gly Gln Ala Pro Arg Leu Leu Ile
        35               40               45

Tyr Gly Ala Ser Asn Arg Ala Thr Gly Ile Pro Ala Arg Phe Ser Gly
        50               55               60

Ser Gly Ser Gly Thr Asp Phe Ala Leu Thr Ile Gly Arg Leu Glu Pro
65               70               75               80

Glu Asp Phe Ala Val Tyr Tyr Cys Gln Gln Tyr Ala Thr Ser Pro Leu
                85               90               95

Ser Phe Gly Gly Gly Thr Lys Val Glu Ile Lys
            100              105

<210> SEQ ID NO 248
<211> LENGTH: 25
<212> TYPE: PRT
<213> ORGANISM: Artificial Sequence
<220> FEATURE:
<223> OTHER INFORMATION: H-FR1 of A56-02B01

<400> SEQUENCE: 248

Gln Val Gln Leu Val Gln Ser Gly Gly Gly Val Val Gln Pro Gly Arg
1               5               10               15

Ser Leu Arg Leu Ser Cys Ala Ala Ser
            20               25

<210> SEQ ID NO 249
<211> LENGTH: 17
<212> TYPE: PRT
<213> ORGANISM: Artificial Sequence
<220> FEATURE:
<223> OTHER INFORMATION: H-FR2 of A56-02B01

<400> SEQUENCE: 249

Met His Trp Val Arg Gln Ala Pro Gly Lys Gly Leu Glu Trp Met Ala
1               5               10               15
```

-continued

Phe

```
<210> SEQ ID NO 250
<211> LENGTH: 38
<212> TYPE: PRT
<213> ORGANISM: Artificial Sequence
<220> FEATURE:
<223> OTHER INFORMATION: H-FR3 of A56-02B01

<400> SEQUENCE: 250

Phe Tyr Ala Asp Ser Val Lys Gly Arg Phe Thr Val Ser Arg Asp Asn
1               5                   10                  15

Ser Lys Asn Thr Leu Phe Leu Gln Met Asn Ser Leu Arg Ala Glu Asp
            20                  25                  30

Thr Ala Val Tyr Tyr Cys
        35

<210> SEQ ID NO 251
<211> LENGTH: 11
<212> TYPE: PRT
<213> ORGANISM: Artificial Sequence
<220> FEATURE:
<223> OTHER INFORMATION: H-FR4 of A56-02B01

<400> SEQUENCE: 251

Trp Gly Gln Gly Thr Met Val Thr Val Ser Ser
1               5                   10

<210> SEQ ID NO 252
<211> LENGTH: 26
<212> TYPE: PRT
<213> ORGANISM: Artificial Sequence
<220> FEATURE:
<223> OTHER INFORMATION: L-FR1 of A56-02B01

<400> SEQUENCE: 252

Asp Ile Gln Met Thr Gln Ser Pro Asp Thr Leu Ser Leu Ser Pro Gly
1               5                   10                  15

Glu Arg Ala Thr Leu Ser Cys Arg Ala Ser
            20                  25

<210> SEQ ID NO 253
<211> LENGTH: 17
<212> TYPE: PRT
<213> ORGANISM: Artificial Sequence
<220> FEATURE:
<223> OTHER INFORMATION: L-FR2 of A56-02B01

<400> SEQUENCE: 253

Leu Ala Trp Tyr Gln Gln Lys Pro Gly Gln Ala Pro Arg Leu Leu Ile
1               5                   10                  15

Tyr

<210> SEQ ID NO 254
<211> LENGTH: 36
<212> TYPE: PRT
<213> ORGANISM: Artificial Sequence
<220> FEATURE:
<223> OTHER INFORMATION: L-FR3 of A56-02B01

<400> SEQUENCE: 254

Ile Tyr Gly Ala Ser Asn Arg Ala Thr Gly Ile Pro Ala Arg Phe Ser
1               5                   10                  15
```

```
Gly Ser Gly Ser Gly Thr Asp Phe Ala Leu Thr Ile Gly Arg Leu Glu
            20                  25                  30

Pro Glu Asp Phe
        35
```

```
<210> SEQ ID NO 255
<211> LENGTH: 10
<212> TYPE: PRT
<213> ORGANISM: Artificial Sequence
<220> FEATURE:
<223> OTHER INFORMATION: L-FR4 of A56-02B01

<400> SEQUENCE: 255

Phe Gly Gly Gly Thr Lys Val Glu Ile Lys
1               5                   10
```

```
<210> SEQ ID NO 256
<211> LENGTH: 8
<212> TYPE: PRT
<213> ORGANISM: Artificial Sequence
<220> FEATURE:
<223> OTHER INFORMATION: H-CDR1 of A56-02B02

<400> SEQUENCE: 256

Gly Phe Thr Phe Asn Arg His Val
1               5
```

```
<210> SEQ ID NO 257
<211> LENGTH: 8
<212> TYPE: PRT
<213> ORGANISM: Artificial Sequence
<220> FEATURE:
<223> OTHER INFORMATION: H-CDR2 of A56-02B02

<400> SEQUENCE: 257

Ile Ser Asn Asp Gly Ser Lys Gln
1               5
```

```
<210> SEQ ID NO 258
<211> LENGTH: 14
<212> TYPE: PRT
<213> ORGANISM: Artificial Sequence
<220> FEATURE:
<223> OTHER INFORMATION: H-CDR3 of A56-02B02

<400> SEQUENCE: 258

Ala Ser Asp Lys Arg Gly Trp Thr Leu Asn Gly Met Asp Val
1               5                   10
```

```
<210> SEQ ID NO 259
<211> LENGTH: 9
<212> TYPE: PRT
<213> ORGANISM: Artificial Sequence
<220> FEATURE:
<223> OTHER INFORMATION: L-CDR1 of A56-02B02

<400> SEQUENCE: 259

Ser Ser Asp Val Gly Ser Tyr Asn Leu
1               5
```

```
<210> SEQ ID NO 260
<211> LENGTH: 3
<212> TYPE: PRT
<213> ORGANISM: Artificial Sequence
<220> FEATURE:
<223> OTHER INFORMATION: L-CDR2 of A56-02B02
```

-continued

```
<400> SEQUENCE: 260

Glu Val Thr
1

<210> SEQ ID NO 261
<211> LENGTH: 9
<212> TYPE: PRT
<213> ORGANISM: Artificial Sequence
<220> FEATURE:
<223> OTHER INFORMATION: L-CDR3 of A56-02B02

<400> SEQUENCE: 261

Phe Ser Tyr Ala Gly Arg Gly Val Val
1               5

<210> SEQ ID NO 262
<211> LENGTH: 255
<212> TYPE: DNA
<213> ORGANISM: Artificial Sequence
<220> FEATURE:
<223> OTHER INFORMATION: SCFV of A56-02B02

<400> SEQUENCE: 262
caggtgcagc tggtagagtc tgggggaggc gtggtccagc ctgggaagtc cctgagactc      60
tcatgtgaag tcgctggatt caccttcaat agacatgtta tgcactgggt ccgccaggct     120
ccaggcaagg ggctggagtg gatggctttt atttcaaatg atggaagtaa gcaagtctac     180
gcagactccg tgaagggacg cttcaccatc tccagagaca attccaagaa cactctgtat     240
ctgcagatga ccgac                                                      255

<210> SEQ ID NO 263
<211> LENGTH: 121
<212> TYPE: PRT
<213> ORGANISM: Artificial Sequence
<220> FEATURE:
<223> OTHER INFORMATION: VH2 of A56-02B02

<400> SEQUENCE: 263

Gln Val Gln Leu Val Glu Ser Gly Gly Gly Val Val Gln Pro Gly Lys
1               5                   10                  15

Ser Leu Arg Leu Ser Cys Glu Val Ala Gly Phe Thr Phe Asn Arg His
            20                  25                  30

Val Met His Trp Val Arg Gln Ala Pro Gly Lys Gly Leu Glu Trp Met
        35                  40                  45

Ala Phe Ile Ser Asn Asp Gly Ser Lys Gln Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Thr Asp Leu Arg Ser Glu Asp Thr Ala Val Tyr Tyr Cys
                85                  90                  95

Ala Ser Asp Lys Arg Gly Trp Thr Leu Asn Gly Met Asp Val Trp Gly
            100                 105                 110

Gln Gly Thr Thr Val Thr Val Ser Ser
        115                 120

<210> SEQ ID NO 264
<211> LENGTH: 109
<212> TYPE: PRT
<213> ORGANISM: Artificial Sequence
<220> FEATURE:
<223> OTHER INFORMATION: VL2 of A56-02B02
```

```
<400> SEQUENCE: 264

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Ile Ile Tyr Glu Val Thr Lys Arg Pro Ser Gly Val Ser Asp Arg Phe
        50                  55                  60

Ser Ala Ser Lys Ser Ala Asn Thr Ala Ser Leu Thr Ile Ser Gly Leu
65                  70                  75                  80

Gln Val Glu Asp Glu Ala Asp Tyr Tyr Cys Phe Ser Tyr Ala Gly Arg
                85                  90                  95

Gly Val Val Phe Gly Gly Gly Thr Lys Leu Thr Val Leu
                100                 105

<210> SEQ ID NO 265
<211> LENGTH: 25
<212> TYPE: PRT
<213> ORGANISM: Artificial Sequence
<220> FEATURE:
<223> OTHER INFORMATION: H-FR1 of A56-02B02

<400> SEQUENCE: 265

Gln Val Gln Leu Val Glu Ser Gly Gly Gly Val Val Gln Pro Gly Lys
1               5                   10                  15

Ser Leu Arg Leu Ser Cys Glu Val Ala
            20                  25

<210> SEQ ID NO 266
<211> LENGTH: 17
<212> TYPE: PRT
<213> ORGANISM: Artificial Sequence
<220> FEATURE:
<223> OTHER INFORMATION: H-FR2 of A56-02B02

<400> SEQUENCE: 266

Met His Trp Val Arg Gln Ala Pro Gly Lys Gly Leu Glu Trp Met Ala
1               5                   10                  15

Phe

<210> SEQ ID NO 267
<211> LENGTH: 38
<212> TYPE: PRT
<213> ORGANISM: Artificial Sequence
<220> FEATURE:
<223> OTHER INFORMATION: H-FR3 of A56-02B02

<400> SEQUENCE: 267

Val Tyr Ala Asp Ser Val Lys Gly Arg Phe Thr Ile Ser Arg Asp Asn
1               5                   10                  15

Ser Lys Asn Thr Leu Tyr Leu Gln Met Thr Asp Leu Arg Ser Glu Asp
            20                  25                  30

Thr Ala Val Tyr Tyr Cys
        35

<210> SEQ ID NO 268
<211> LENGTH: 11
<212> TYPE: PRT
<213> ORGANISM: Artificial Sequence
```

```
<220> FEATURE:
<223> OTHER INFORMATION: H-FR4 of A56-02B02

<400> SEQUENCE: 268

Trp Gly Gln Gly Thr Thr Val Thr Val Ser Ser
1               5                   10

<210> SEQ ID NO 269
<211> LENGTH: 25
<212> TYPE: PRT
<213> ORGANISM: Artificial Sequence
<220> FEATURE:
<223> OTHER INFORMATION: L-FR1 of A56-02B02

<400> SEQUENCE: 269

Gln Ser Ala Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 270
<211> LENGTH: 17
<212> TYPE: PRT
<213> ORGANISM: Artificial Sequence
<220> FEATURE:
<223> OTHER INFORMATION: L-FR2 of A56-02B02

<400> SEQUENCE: 270

Val Ser Trp Tyr Gln Gln His Pro Gly Lys Ala Pro Lys Leu Ile Ile
1               5                   10                  15

Tyr

<210> SEQ ID NO 271
<211> LENGTH: 36
<212> TYPE: PRT
<213> ORGANISM: Artificial Sequence
<220> FEATURE:
<223> OTHER INFORMATION: L-FR3 of A56-02B02

<400> SEQUENCE: 271

Ile Tyr Glu Val Thr Lys Arg Pro Ser Gly Val Ser Asp Arg Phe Ser
1               5                   10                  15

Ala Ser Lys Ser Ala Asn Thr Ala Ser Leu Thr Ile Ser Gly Leu Gln
            20                  25                  30

Val Glu Asp Glu
        35

<210> SEQ ID NO 272
<211> LENGTH: 10
<212> TYPE: PRT
<213> ORGANISM: Artificial Sequence
<220> FEATURE:
<223> OTHER INFORMATION: L-FR4 of A56-02B02

<400> SEQUENCE: 272

Phe Gly Gly Gly Thr Lys Leu Thr Val Leu
1               5                   10

<210> SEQ ID NO 273
<211> LENGTH: 8
<212> TYPE: PRT
<213> ORGANISM: Artificial Sequence
<220> FEATURE:
<223> OTHER INFORMATION: H-CDR1 of A56-02B06
```

```
<400> SEQUENCE: 273

Gly Phe Thr Phe Ser Ser Tyr Ala
1               5

<210> SEQ ID NO 274
<211> LENGTH: 8
<212> TYPE: PRT
<213> ORGANISM: Artificial Sequence
<220> FEATURE:
<223> OTHER INFORMATION: H-CDR2 of A56-02B06

<400> SEQUENCE: 274

Ile Ser Tyr Asp Gly Ser Asn Lys
1               5

<210> SEQ ID NO 275
<211> LENGTH: 11
<212> TYPE: PRT
<213> ORGANISM: Artificial Sequence
<220> FEATURE:
<223> OTHER INFORMATION: H-CDR3 of A56-02B06

<400> SEQUENCE: 275

Met Arg Asp Arg Ser Thr Gly Glu Ile Pro His
1               5                   10

<210> SEQ ID NO 276
<211> LENGTH: 12
<212> TYPE: PRT
<213> ORGANISM: Artificial Sequence
<220> FEATURE:
<223> OTHER INFORMATION: L-CDR1 of A56-02B06

<400> SEQUENCE: 276

Gln Thr Val Leu Asn Ser Phe Asn Asn Lys Asn Tyr
1               5                   10

<210> SEQ ID NO 277
<211> LENGTH: 3
<212> TYPE: PRT
<213> ORGANISM: Artificial Sequence
<220> FEATURE:
<223> OTHER INFORMATION: L-CDR2 of A56-02B06

<400> SEQUENCE: 277

Trp Ala Ser
1

<210> SEQ ID NO 278
<211> LENGTH: 10
<212> TYPE: PRT
<213> ORGANISM: Artificial Sequence
<220> FEATURE:
<223> OTHER INFORMATION: L-CDR3 of A56-02B06

<400> SEQUENCE: 278

Gln Gln Tyr Ser Ser Thr Pro Pro Ile Thr
1               5                   10

<210> SEQ ID NO 279
<211> LENGTH: 255
<212> TYPE: DNA
<213> ORGANISM: Artificial Sequence
<220> FEATURE:
<223> OTHER INFORMATION: SCFV of A56-02B06

<400> SEQUENCE: 279
```

```
caggtgcagc tggtacagtc tggggggaggc gtggtccagc ctgggaggtc cctgagactc        60
tcctgtgcag cctctggatt caccttcagt agctatgcta tgcactgggt ccgccaggct       120
ccaggcaagg ggctggagtg ggtggcagtt atatcatatg atggaagcaa caaatactat       180
gcaaactccg tgaagggccg attcatcatc tccagagaca attccaacaa tacggtgtat       240
ctgcaaatga acgcc                                                        255
```

```
<210> SEQ ID NO 280
<211> LENGTH: 118
<212> TYPE: PRT
<213> ORGANISM: Artificial Sequence
<220> FEATURE:
<223> OTHER INFORMATION: VH2 of A56-02B06

<400> SEQUENCE: 280

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asn Ser Val
    50                  55                  60

Lys Gly Arg Phe Ile Ile Ser Arg Asp Asn Ser Asn Asn Thr Val Tyr
65                  70                  75                  80

Leu Gln Met Asn Ala Leu Arg Ser Glu Asp Thr Ala Val Tyr Tyr Cys
                85                  90                  95

Met Arg Asp Arg Ser Thr Gly Glu Ile Pro His Trp Gly Gln Gly Thr
            100                 105                 110

Leu Ile Thr Val Ser Ser
        115
```

```
<210> SEQ ID NO 281
<211> LENGTH: 114
<212> TYPE: PRT
<213> ORGANISM: Artificial Sequence
<220> FEATURE:
<223> OTHER INFORMATION: VL2 of A56-02B06

<400> SEQUENCE: 281

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Asn Ser
            20                  25                  30

Phe Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Thr Pro Pro Ile Thr Phe Gly Pro Gly Thr Arg Leu Glu
            100                 105                 110

Ile Lys
```

-continued

```
<210> SEQ ID NO 282
<211> LENGTH: 25
<212> TYPE: PRT
<213> ORGANISM: Artificial Sequence
<220> FEATURE:
<223> OTHER INFORMATION: H-FR1 of A56-02B06

<400> SEQUENCE: 282

Gln Val Gln Leu Val Gln Ser Gly Gly Gly Val Val Gln Pro Gly Arg
1               5                   10                  15

Ser Leu Arg Leu Ser Cys Ala Ala Ser
            20                  25

<210> SEQ ID NO 283
<211> LENGTH: 17
<212> TYPE: PRT
<213> ORGANISM: Artificial Sequence
<220> FEATURE:
<223> OTHER INFORMATION: H-FR2 of A56-02B06

<400> SEQUENCE: 283

Met His Trp Val Arg Gln Ala Pro Gly Lys Gly Leu Glu Trp Val Ala
1               5                   10                  15

Val

<210> SEQ ID NO 284
<211> LENGTH: 38
<212> TYPE: PRT
<213> ORGANISM: Artificial Sequence
<220> FEATURE:
<223> OTHER INFORMATION: H-FR3 of A56-02B06

<400> SEQUENCE: 284

Tyr Tyr Ala Asn Ser Val Lys Gly Arg Phe Ile Ile Ser Arg Asp Asn
1               5                   10                  15

Ser Asn Asn Thr Val Tyr Leu Gln Met Asn Ala Leu Arg Ser Glu Asp
            20                  25                  30

Thr Ala Val Tyr Tyr Cys
        35

<210> SEQ ID NO 285
<211> LENGTH: 11
<212> TYPE: PRT
<213> ORGANISM: Artificial Sequence
<220> FEATURE:
<223> OTHER INFORMATION: H-FR4 of A56-02B06

<400> SEQUENCE: 285

Trp Gly Gln Gly Thr Leu Ile Thr Val Ser Ser
1               5                   10

<210> SEQ ID NO 286
<211> LENGTH: 26
<212> TYPE: PRT
<213> ORGANISM: Artificial Sequence
<220> FEATURE:
<223> OTHER INFORMATION: L-FR1 of A56-02B06

<400> SEQUENCE: 286

Asp Ile Gln Met Thr Gln Ser Pro Asp Ser Leu Ala Val Ser Leu Gly
1               5                   10                  15

Glu Arg Ala Thr Ile Asn Cys Lys Ser Ser
            20                  25
```

```
<210> SEQ ID NO 287
<211> LENGTH: 17
<212> TYPE: PRT
<213> ORGANISM: Artificial Sequence
<220> FEATURE:
<223> OTHER INFORMATION: L-FR2 of A56-02B06

<400> SEQUENCE: 287

Leu Ala Trp Tyr Gln Gln Lys Pro Gly Gln Pro Pro Lys Leu Leu Ile
1               5                   10                  15

Tyr

<210> SEQ ID NO 288
<211> LENGTH: 36
<212> TYPE: PRT
<213> ORGANISM: Artificial Sequence
<220> FEATURE:
<223> OTHER INFORMATION: L-FR3 of A56-02B06

<400> SEQUENCE: 288

Ile Tyr Trp Ala Ser Thr Arg Glu Ser Gly Val Pro Asp Arg Phe Ser
1               5                   10                  15

Gly Ser Gly Ser Gly Thr Asp Phe Thr Leu Thr Ile Ser Ser Leu Gln
            20                  25                  30

Ala Glu Asp Val
        35

<210> SEQ ID NO 289
<211> LENGTH: 10
<212> TYPE: PRT
<213> ORGANISM: Artificial Sequence
<220> FEATURE:
<223> OTHER INFORMATION: L-FR4 of A56-02B06

<400> SEQUENCE: 289

Phe Gly Pro Gly Thr Arg Leu Glu Ile Lys
1               5                   10

<210> SEQ ID NO 290
<211> LENGTH: 10
<212> TYPE: PRT
<213> ORGANISM: Artificial Sequence
<220> FEATURE:
<223> OTHER INFORMATION: H-CDR1 of A56-02B08

<400> SEQUENCE: 290

Gly Asp Ser Val Ser Ser Asn Ser Ala Ala
1               5                   10

<210> SEQ ID NO 291
<211> LENGTH: 9
<212> TYPE: PRT
<213> ORGANISM: Artificial Sequence
<220> FEATURE:
<223> OTHER INFORMATION: H-CDR2 of A56-02B08

<400> SEQUENCE: 291

Thr Tyr Tyr Arg Ser Lys Trp Tyr Asn
1               5

<210> SEQ ID NO 292
<211> LENGTH: 17
<212> TYPE: PRT
<213> ORGANISM: Artificial Sequence
<220> FEATURE:
<223> OTHER INFORMATION: H-CDR3 of A56-02B08
```

-continued

<400> SEQUENCE: 292

Ala Lys Ser Tyr Ala Gly Pro Ile Ser Tyr Tyr Tyr Gly Leu Asp
1               5                   10                  15

Val

<210> SEQ ID NO 293
<211> LENGTH: 9
<212> TYPE: PRT
<213> ORGANISM: Artificial Sequence
<220> FEATURE:
<223> OTHER INFORMATION: L-CDR1 of A56-02B08

<400> SEQUENCE: 293

Ser Ser Asp Ile Gly Arg Tyr Asn Leu
1               5

<210> SEQ ID NO 294
<211> LENGTH: 3
<212> TYPE: PRT
<213> ORGANISM: Artificial Sequence
<220> FEATURE:
<223> OTHER INFORMATION: L-CDR2 of A56-02B08

<400> SEQUENCE: 294

Gly Gly Ser
1

<210> SEQ ID NO 295
<211> LENGTH: 11
<212> TYPE: PRT
<213> ORGANISM: Artificial Sequence
<220> FEATURE:
<223> OTHER INFORMATION: L-CDR3 of A56-02B08

<400> SEQUENCE: 295

Ser Ser Tyr Ala Ser Ser Ser Thr Pro Tyr Val
1               5                   10

<210> SEQ ID NO 296
<211> LENGTH: 255
<212> TYPE: DNA
<213> ORGANISM: Artificial Sequence
<220> FEATURE:
<223> OTHER INFORMATION: SCFV of A56-02B08

<400> SEQUENCE: 296
caggtgcagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcag                                                      255

<210> SEQ ID NO 297
<211> LENGTH: 127
<212> TYPE: PRT
<213> ORGANISM: Artificial Sequence
<220> FEATURE:
<223> OTHER INFORMATION: VH2 of A56-02B08

<400> SEQUENCE: 297

Gln Val Gln Leu Gln Gln Ser Gly Pro Gly Leu Val Lys Pro Ser Gln
1               5                   10                  15

-continued

```
Thr Leu Ser Leu Thr Cys Ala Ile Ser Gly Asp Ser Val Ser Ser Asn
         20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
         50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Ala Val Asp Thr Ala Val
                 85                  90                  95

Tyr Tyr Cys Ala Lys Ser Tyr Ala Gly Pro Ile Ser Tyr Tyr Tyr Tyr
             100                 105                 110

Gly Leu Asp Val Trp Gly Gln Gly Thr Thr Val Thr Val Ser Ser
         115                 120                 125
```

```
<210> SEQ ID NO 298
<211> LENGTH: 111
<212> TYPE: PRT
<213> ORGANISM: Artificial Sequence
<220> FEATURE:
<223> OTHER INFORMATION: VL2 of A56-02B08

<400> SEQUENCE: 298
```

```
Gln Ser Ala Leu Thr Gln Pro Ala Ser Val Ser Gly Ser Pro Gly Gln
1                5                  10                  15

Ser Val Thr Ile Ser Cys Thr Gly Thr Ser Ser Asp Ile Gly Arg Tyr
         20                  25                  30

Asn Leu Val Ser Trp Tyr Gln Gln His Pro Gly Lys Ala Pro Lys Leu
         35                  40                  45

Met Ile Tyr Gly Gly Ser Lys Arg Pro Ser Gly Val Ser Asn Arg Phe
         50                  55                  60

Ser Gly Ser Asn Ser Asp Asn Thr Ala Ser Leu Thr Ile Ser Gly Leu
65                  70                  75                  80

Arg Ala Glu Asp Glu Ala Asp Tyr Tyr Cys Ser Ser Tyr Ala Ser Ser
                 85                  90                  95

Ser Thr Pro Tyr Val Phe Gly Thr Gly Thr Lys Val Thr Val Leu
             100                 105                 110
```

```
<210> SEQ ID NO 299
<211> LENGTH: 25
<212> TYPE: PRT
<213> ORGANISM: Artificial Sequence
<220> FEATURE:
<223> OTHER INFORMATION: H-FR1 of A56-02B08

<400> SEQUENCE: 299
```

```
Gln Val Gln Leu Gln Gln Ser Gly Pro Gly Leu Val Lys Pro Ser Gln
1                5                  10                  15

Thr Leu Ser Leu Thr Cys Ala Ile Ser
         20                  25
```

```
<210> SEQ ID NO 300
<211> LENGTH: 17
<212> TYPE: PRT
<213> ORGANISM: Artificial Sequence
<220> FEATURE:
<223> OTHER INFORMATION: H-FR2 of A56-02B08

<400> SEQUENCE: 300
```

-continued

```
Trp Asn Trp Ile Arg Gln Ser Pro Ser Arg Gly Leu Glu Trp Leu Gly
1               5                   10                  15

Arg

<210> SEQ ID NO 301
<211> LENGTH: 38
<212> TYPE: PRT
<213> ORGANISM: Artificial Sequence
<220> FEATURE:
<223> OTHER INFORMATION: H-FR3 of A56-02B08

<400> SEQUENCE: 301

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Ala Val Asp
            20                  25                  30

Thr Ala Val Tyr Tyr Cys
        35

<210> SEQ ID NO 302
<211> LENGTH: 11
<212> TYPE: PRT
<213> ORGANISM: Artificial Sequence
<220> FEATURE:
<223> OTHER INFORMATION: H-FR4 of A56-02B08

<400> SEQUENCE: 302

Trp Gly Gln Gly Thr Thr Val Thr Val Ser Ser
1               5                   10

<210> SEQ ID NO 303
<211> LENGTH: 25
<212> TYPE: PRT
<213> ORGANISM: Artificial Sequence
<220> FEATURE:
<223> OTHER INFORMATION: L-FR1 of A56-02B08

<400> SEQUENCE: 303

Gln Ser Ala Leu Thr Gln Pro Ala Ser Val Ser Gly Ser Pro Gly Gln
1               5                   10                  15

Ser Val Thr Ile Ser Cys Thr Gly Thr
            20                  25

<210> SEQ ID NO 304
<211> LENGTH: 17
<212> TYPE: PRT
<213> ORGANISM: Artificial Sequence
<220> FEATURE:
<223> OTHER INFORMATION: L-FR2 of A56-02B08

<400> SEQUENCE: 304

Val Ser Trp Tyr Gln Gln His Pro Gly Lys Ala Pro Lys Leu Met Ile
1               5                   10                  15

Tyr

<210> SEQ ID NO 305
<211> LENGTH: 36
<212> TYPE: PRT
<213> ORGANISM: Artificial Sequence
<220> FEATURE:
<223> OTHER INFORMATION: L-FR3 of A56-02B08

<400> SEQUENCE: 305

Ile Tyr Gly Gly Ser Lys Arg Pro Ser Gly Val Ser Asn Arg Phe Ser
```

-continued

```
1               5                   10                  15

Gly Ser Asn Ser Asp Asn Thr Ala Ser Leu Thr Ile Ser Gly Leu Arg
            20                  25                  30

Ala Glu Asp Glu
        35

<210> SEQ ID NO 306
<211> LENGTH: 10
<212> TYPE: PRT
<213> ORGANISM: Artificial Sequence
<220> FEATURE:
<223> OTHER INFORMATION: L-FR4 of A56-02B08

<400> SEQUENCE: 306

Phe Gly Thr Gly Thr Lys Val Thr Val Leu
1               5                   10

<210> SEQ ID NO 307
<211> LENGTH: 8
<212> TYPE: PRT
<213> ORGANISM: Artificial Sequence
<220> FEATURE:
<223> OTHER INFORMATION: H-CDR1 of A56-02B10

<400> SEQUENCE: 307

Gly Gly Thr Phe Ser Arg Asn Thr
1               5

<210> SEQ ID NO 308
<211> LENGTH: 8
<212> TYPE: PRT
<213> ORGANISM: Artificial Sequence
<220> FEATURE:
<223> OTHER INFORMATION: H-CDR2 of A56-02B10

<400> SEQUENCE: 308

Ile Ile Pro Ile Phe His Ile Thr
1               5

<210> SEQ ID NO 309
<211> LENGTH: 13
<212> TYPE: PRT
<213> ORGANISM: Artificial Sequence
<220> FEATURE:
<223> OTHER INFORMATION: H-CDR3 of A56-02B10

<400> SEQUENCE: 309

Ala Arg Gly Ser Thr Thr Phe Pro Arg Tyr Phe Asp Tyr
1               5                   10

<210> SEQ ID NO 310
<211> LENGTH: 6
<212> TYPE: PRT
<213> ORGANISM: Artificial Sequence
<220> FEATURE:
<223> OTHER INFORMATION: L-CDR1 of A56-02B10

<400> SEQUENCE: 310

Gln Ser Val Gly Ser Tyr
1               5

<210> SEQ ID NO 311
<211> LENGTH: 3
<212> TYPE: PRT
<213> ORGANISM: Artificial Sequence
<220> FEATURE:
```

<223> OTHER INFORMATION: L-CDR2 of A56-02B10

<400> SEQUENCE: 311

Asp Ala Ser
1

<210> SEQ ID NO 312
<211> LENGTH: 9
<212> TYPE: PRT
<213> ORGANISM: Artificial Sequence
<220> FEATURE:
<223> OTHER INFORMATION: L-CDR3 of A56-02B10

<400> SEQUENCE: 312

Gln Gln Tyr Gly Arg Ser Pro Phe Thr
1                   5

<210> SEQ ID NO 313
<211> LENGTH: 255
<212> TYPE: DNA
<213> ORGANISM: Artificial Sequence
<220> FEATURE:
<223> OTHER INFORMATION: SCFV of A56-02B10

<400> SEQUENCE: 313
caggtgcagc tggtacagtc tggggctgag gtgaagaagc ctgggtcctc ggtgaaggtc       60
tcctgcaagg cttctggagg caccttcagc agaaatactt tcagctgggt gcgacaggcc      120
cctggacaag ggcttgagtg gatgggaggg atcatcccta tctttcatat aacaaattac      180
gcacagaaga tgcagggcag agtcacgatt ccgcggacg agtccacggg cacagtctag       240
atggagctga gcagg                                                       255

<210> SEQ ID NO 314
<211> LENGTH: 120
<212> TYPE: PRT
<213> ORGANISM: Artificial Sequence
<220> FEATURE:
<223> OTHER INFORMATION: VH2 of A56-02B10

<400> SEQUENCE: 314

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Asn
            20                  25                  30

Thr Phe Ser Trp Val Arg Gln Ala Pro Gly Gln Gly Leu Glu Trp Met
        35                  40                  45

Gly Gly Ile Ile Pro Ile Phe His Ile Thr Asn Tyr Ala Gln Lys Met
    50                  55                  60

Gln Gly Arg Val Thr Ile Ser Ala Asp Glu Ser Thr Gly Thr Val Tyr
65                  70                  75                  80

Met Glu Leu Ser Arg Leu Arg Ser Glu Asp Thr Ala Val Tyr Tyr Cys
                85                  90                  95

Ala Arg Gly Ser Thr Thr Phe Pro Arg Tyr Phe Asp Tyr Trp Gly Gln
            100                 105                 110

Gly Thr Leu Val Thr Val Ser Ser
        115                 120

<210> SEQ ID NO 315
<211> LENGTH: 107
<212> TYPE: PRT
<213> ORGANISM: Artificial Sequence
<220> FEATURE:
<223> OTHER INFORMATION: VL2 of A56-02B10

<400> SEQUENCE: 315

```
Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Arg Pro Gly Gln Pro Pro Arg Leu Leu Val
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Phe Cys Gln Gln Tyr Gly Arg Ser Pro Phe
                85                  90                  95

Thr Phe Gly Pro Gly Thr Lys Val Asp Ile Lys
            100                 105
```

<210> SEQ ID NO 316
<211> LENGTH: 25
<212> TYPE: PRT
<213> ORGANISM: Artificial Sequence
<220> FEATURE:
<223> OTHER INFORMATION: H-FR1 of A56-02B10

<400> SEQUENCE: 316

```
Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

<210> SEQ ID NO 317
<211> LENGTH: 17
<212> TYPE: PRT
<213> ORGANISM: Artificial Sequence
<220> FEATURE:
<223> OTHER INFORMATION: H-FR2 of A56-02B10

<400> SEQUENCE: 317

```
Phe Ser Trp Val Arg Gln Ala Pro Gly Gln Gly Leu Glu Trp Met Gly
1               5                   10                  15

Gly
```

<210> SEQ ID NO 318
<211> LENGTH: 38
<212> TYPE: PRT
<213> ORGANISM: Artificial Sequence
<220> FEATURE:
<223> OTHER INFORMATION: H-FR3 of A56-02B10

<400> SEQUENCE: 318

```
Asn Tyr Ala Gln Lys Met Gln Gly Arg Val Thr Ile Ser Ala Asp Glu
1               5                   10                  15

Ser Thr Gly Thr Val Tyr Met Glu Leu Ser Arg Leu Arg Ser Glu Asp
            20                  25                  30

Thr Ala Val Tyr Tyr Cys
        35
```

<210> SEQ ID NO 319
<211> LENGTH: 11

<212> TYPE: PRT
<213> ORGANISM: Artificial Sequence
<220> FEATURE:
<223> OTHER INFORMATION: H-FR4 of A56-02B10

<400> SEQUENCE: 319

Trp Gly Gln Gly Thr Leu Val Thr Val Ser Ser
1               5                   10

<210> SEQ ID NO 320
<211> LENGTH: 26
<212> TYPE: PRT
<213> ORGANISM: Artificial Sequence
<220> FEATURE:
<223> OTHER INFORMATION: L-FR1 of A56-02B10

<400> SEQUENCE: 320

Asp Ile Gln Met Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 321
<211> LENGTH: 17
<212> TYPE: PRT
<213> ORGANISM: Artificial Sequence
<220> FEATURE:
<223> OTHER INFORMATION: L-FR2 of A56-02B10

<400> SEQUENCE: 321

Leu Ala Trp Tyr Gln Gln Arg Pro Gly Gln Pro Pro Arg Leu Leu Val
1               5                   10                  15

Tyr

<210> SEQ ID NO 322
<211> LENGTH: 36
<212> TYPE: PRT
<213> ORGANISM: Artificial Sequence
<220> FEATURE:
<223> OTHER INFORMATION: L-FR3 of A56-02B10

<400> SEQUENCE: 322

Val Tyr Asp Ala Ser Asn Arg Ala Thr Gly Ile Pro Ala Arg Phe Ser
1               5                   10                  15

Gly Ser Gly Ser Gly Thr Asp Phe Thr Leu Thr Ile Ser Arg Leu Glu
            20                  25                  30

Pro Glu Asp Phe
        35

<210> SEQ ID NO 323
<211> LENGTH: 10
<212> TYPE: PRT
<213> ORGANISM: Artificial Sequence
<220> FEATURE:
<223> OTHER INFORMATION: L-FR4 of A56-02B10

<400> SEQUENCE: 323

Phe Gly Pro Gly Thr Lys Val Asp Ile Lys
1               5                   10

<210> SEQ ID NO 324
<211> LENGTH: 8
<212> TYPE: PRT
<213> ORGANISM: Artificial Sequence
<220> FEATURE:

<223> OTHER INFORMATION: H-CDR1 of A56-02C06

<400> SEQUENCE: 324

Gly Phe Thr Phe Ser Thr Tyr Gly
1               5

<210> SEQ ID NO 325
<211> LENGTH: 8
<212> TYPE: PRT
<213> ORGANISM: Artificial Sequence
<220> FEATURE:
<223> OTHER INFORMATION: H-CDR2 of A56-02C06

<400> SEQUENCE: 325

Ile Ser Gly Gly Gly Ser Ser Thr
1               5

<210> SEQ ID NO 326
<211> LENGTH: 11
<212> TYPE: PRT
<213> ORGANISM: Artificial Sequence
<220> FEATURE:
<223> OTHER INFORMATION: H-CDR3 of A56-02C06

<400> SEQUENCE: 326

Ala Arg Trp Gly Val Met Leu Ser Phe Asp Tyr
1               5                   10

<210> SEQ ID NO 327
<211> LENGTH: 6
<212> TYPE: PRT
<213> ORGANISM: Artificial Sequence
<220> FEATURE:
<223> OTHER INFORMATION: L-CDR1 of A56-02C06

<400> SEQUENCE: 327

Tyr Ser Val Ser Pro Trp
1               5

<210> SEQ ID NO 328
<211> LENGTH: 3
<212> TYPE: PRT
<213> ORGANISM: Artificial Sequence
<220> FEATURE:
<223> OTHER INFORMATION: L-CDR2 of A56-02C06

<400> SEQUENCE: 328

Lys Ala Ser
1

<210> SEQ ID NO 329
<211> LENGTH: 10
<212> TYPE: PRT
<213> ORGANISM: Artificial Sequence
<220> FEATURE:
<223> OTHER INFORMATION: L-CDR3 of A56-02C06

<400> SEQUENCE: 329

Gln Gln Phe Asn Ser Tyr Met Met Tyr Thr
1               5                   10

<210> SEQ ID NO 330
<211> LENGTH: 255
<212> TYPE: DNA
<213> ORGANISM: Artificial Sequence
<220> FEATURE:
<223> OTHER INFORMATION: SCFV of A56-02C06

<400> SEQUENCE: 330
caggtgcagc tggtggagtc tgggggaggc ttggtacagc ctgggaaatc cctgagactc          60
tcctgtgcag cctctggatt caccttcagc acctatggca tgacttgggt ccgccaggct         120
ccagggaagg ggctggagtg ggtctcaggg attagtggtg ggggttctag cacaaactac         180
gcagactccg tgaagggccg cttcatcatt tctagagaca actctaacaa cacgctgtat         240
ctgcaaatga acagt                                                           255

<210> SEQ ID NO 331
<211> LENGTH: 118
<212> TYPE: PRT
<213> ORGANISM: Artificial Sequence
<220> FEATURE:
<223> OTHER INFORMATION: VH2 of A56-02C06

<400> SEQUENCE: 331

Gln Val Gln Leu Val Glu Ser Gly Gly Gly Leu Val Gln Pro Gly Lys
1               5                   10                  15

Ser Leu Arg Leu Ser Cys Ala Ala Ser Gly Phe Thr Phe Ser Thr Tyr
            20                  25                  30

Gly Met Thr Trp Val Arg Gln Ala Pro Gly Lys Gly Leu Glu Trp Val
        35                  40                  45

Ser Gly Ile Ser Gly Gly Gly Ser Ser Thr Asn Tyr Ala Asp Ser Val
    50                  55                  60

Lys Gly Arg Phe Ile Ile Ser Arg Asp Asn Ser Asn Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Val Met Leu Ser Phe Asp Tyr Trp Gly Gln Gly Thr
            100                 105                 110

Pro Val Thr Val Ser Ser
        115

<210> SEQ ID NO 332
<211> LENGTH: 108
<212> TYPE: PRT
<213> ORGANISM: Artificial Sequence
<220> FEATURE:
<223> OTHER INFORMATION: VL2 of A56-02C06

<400> SEQUENCE: 332

Asp Ile Gln Met Thr Gln Ser Pro Ser Thr Leu Pro Ala Ser Val Gly
1               5                   10                  15

Asp Arg Val Thr Ile Thr Cys Arg Ala Ser Tyr Ser Val Ser Pro Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Asn Ser Tyr Met Met
                85                  90                  95

Tyr Thr Phe Gly Gln Gly Thr Lys Leu Glu Ile Lys
            100                 105

-continued

```
<210> SEQ ID NO 333
<211> LENGTH: 25
<212> TYPE: PRT
<213> ORGANISM: Artificial Sequence
<220> FEATURE:
<223> OTHER INFORMATION: H-FR1 of A56-02C06

<400> SEQUENCE: 333

Gln Val Gln Leu Val Glu Ser Gly Gly Gly Leu Val Gln Pro Gly Lys
1               5                   10                  15

Ser Leu Arg Leu Ser Cys Ala Ala Ser
            20                  25

<210> SEQ ID NO 334
<211> LENGTH: 17
<212> TYPE: PRT
<213> ORGANISM: Artificial Sequence
<220> FEATURE:
<223> OTHER INFORMATION: H-FR2 of A56-02C06

<400> SEQUENCE: 334

Met Thr Trp Val Arg Gln Ala Pro Gly Lys Gly Leu Glu Trp Val Ser
1               5                   10                  15

Gly

<210> SEQ ID NO 335
<211> LENGTH: 38
<212> TYPE: PRT
<213> ORGANISM: Artificial Sequence
<220> FEATURE:
<223> OTHER INFORMATION: H-FR3 of A56-02C06

<400> SEQUENCE: 335

Asn Tyr Ala Asp Ser Val Lys Gly Arg Phe Ile Ile Ser Arg Asp Asn
1               5                   10                  15

Ser Asn Asn Thr Leu Tyr Leu Gln Met Asn Ser Leu Arg Ala Glu Asp
            20                  25                  30

Thr Ala Val Tyr Tyr Cys
        35

<210> SEQ ID NO 336
<211> LENGTH: 11
<212> TYPE: PRT
<213> ORGANISM: Artificial Sequence
<220> FEATURE:
<223> OTHER INFORMATION: H-FR4 of A56-02C06

<400> SEQUENCE: 336

Trp Gly Gln Gly Thr Pro Val Thr Val Ser Ser
1               5                   10

<210> SEQ ID NO 337
<211> LENGTH: 26
<212> TYPE: PRT
<213> ORGANISM: Artificial Sequence
<220> FEATURE:
<223> OTHER INFORMATION: L-FR1 of A56-02C06

<400> SEQUENCE: 337

Asp Ile Gln Met Thr Gln Ser Pro Ser Thr Leu Pro Ala Ser Val Gly
1               5                   10                  15

Asp Arg Val Thr Ile Thr Cys Arg Ala Ser
            20                  25
```

-continued

```
<210> SEQ ID NO 338
<211> LENGTH: 17
<212> TYPE: PRT
<213> ORGANISM: Artificial Sequence
<220> FEATURE:
<223> OTHER INFORMATION: L-FR2 of A56-02C06

<400> SEQUENCE: 338

Leu Ala Trp Tyr Gln Gln Lys Pro Gly Lys Ala Pro Lys Leu Leu Ile
1               5                   10                  15

Tyr

<210> SEQ ID NO 339
<211> LENGTH: 36
<212> TYPE: PRT
<213> ORGANISM: Artificial Sequence
<220> FEATURE:
<223> OTHER INFORMATION: L-FR3 of A56-02C06

<400> SEQUENCE: 339

Ile Tyr Lys Ala Ser Thr Leu Glu Ser Gly Val Pro Ser Arg Phe Ser
1               5                   10                  15

Gly Ser Gly Ser Gly Thr Glu Phe Thr Leu Thr Ile Ser Ser Leu Gln
            20                  25                  30

Pro Asp Asp Phe
        35

<210> SEQ ID NO 340
<211> LENGTH: 10
<212> TYPE: PRT
<213> ORGANISM: Artificial Sequence
<220> FEATURE:
<223> OTHER INFORMATION: L-FR4 of A56-02C06

<400> SEQUENCE: 340

Phe Gly Gln Gly Thr Lys Leu Glu Ile Lys
1               5                   10

<210> SEQ ID NO 341
<211> LENGTH: 8
<212> TYPE: PRT
<213> ORGANISM: Artificial Sequence
<220> FEATURE:
<223> OTHER INFORMATION: H-CDR1 of A56-02C07

<400> SEQUENCE: 341

Gly Val Thr Phe Ser Gly Tyr Val
1               5

<210> SEQ ID NO 342
<211> LENGTH: 8
<212> TYPE: PRT
<213> ORGANISM: Artificial Sequence
<220> FEATURE:
<223> OTHER INFORMATION: H-CDR2 of A56-02C07

<400> SEQUENCE: 342

Ile Ile Pro Leu Ile Asp Val Glu
1               5

<210> SEQ ID NO 343
<211> LENGTH: 17
<212> TYPE: PRT
<213> ORGANISM: Artificial Sequence
<220> FEATURE:
<223> OTHER INFORMATION: H-CDR3 of A56-02C07
```

-continued

<400> SEQUENCE: 343

Ala Lys Ser Val Val Arg Gly Leu Asp Tyr Tyr Tyr Tyr Gly Phe Asp
1               5                   10                  15

Val

<210> SEQ ID NO 344
<211> LENGTH: 6
<212> TYPE: PRT
<213> ORGANISM: Artificial Sequence
<220> FEATURE:
<223> OTHER INFORMATION: L-CDR1 of A56-02C07

<400> SEQUENCE: 344

Asn Ile Gly Ser Lys Ser
1               5

<210> SEQ ID NO 345
<211> LENGTH: 3
<212> TYPE: PRT
<213> ORGANISM: Artificial Sequence
<220> FEATURE:
<223> OTHER INFORMATION: L-CDR2 of A56-02C07

<400> SEQUENCE: 345

Tyr Asp Gly
1

<210> SEQ ID NO 346
<211> LENGTH: 11
<212> TYPE: PRT
<213> ORGANISM: Artificial Sequence
<220> FEATURE:
<223> OTHER INFORMATION: L-CDR3 of A56-02C07

<400> SEQUENCE: 346

Gln Val Trp Asp Ser Ser Ser Asp Gln Gly Val
1               5                   10

<210> SEQ ID NO 347
<211> LENGTH: 255
<212> TYPE: DNA
<213> ORGANISM: Artificial Sequence
<220> FEATURE:
<223> OTHER INFORMATION: SCFV of A56-02C07

<400> SEQUENCE: 347
caggtgcagc tggtggagtc tgggggctgag gtgaggaggc ctgggtcctc ggtgaaggtc      60
tcctgcaaga cttcgggagt caccttcagc ggctatgttc tgagctgggt gcgacaggcc     120
cctggacacg gccttgagtg gatgggacgg atcatccctt taattgacgt ggaaaactat     180
gcacgggagt tccagggtag aatgaagatc accgcagaca agtccacgaa tacagtctac     240
atggaactga caaac                                                      255

<210> SEQ ID NO 348
<211> LENGTH: 124
<212> TYPE: PRT
<213> ORGANISM: Artificial Sequence
<220> FEATURE:
<223> OTHER INFORMATION: VH2 of A56-02C07

<400> SEQUENCE: 348

Gln Val Gln Leu Val Glu Ser Gly Ala Glu Val Arg Arg Pro Gly Ser
1               5                   10                  15

-continued

```
Ser Val Lys Val Ser Cys Lys Thr Ser Gly Val Thr Phe Ser Gly Tyr
            20                  25                  30

Val Leu Ser Trp Val Arg Gln Ala Pro Gly His Gly Leu Glu Trp Met
            35                  40                  45

Gly Arg Ile Ile Pro Leu Ile Asp Val Glu Asn Tyr Ala Arg Glu Phe
    50                  55                  60

Gln Gly Arg Met Lys Ile Thr Ala Asp Lys Ser Thr Asn Thr Val Tyr
65                  70                  75                  80

Met Glu Leu Asn Asn Leu Arg Ser Glu Asp Thr Ala Val Tyr Tyr Cys
                85                  90                  95

Ala Lys Ser Val Val Arg Gly Leu Asp Tyr Tyr Tyr Tyr Gly Phe Asp
            100                 105                 110

Val Trp Gly Gln Gly Thr Thr Val Thr Val Ser Ser
        115                 120
```

```
<210> SEQ ID NO 349
<211> LENGTH: 108
<212> TYPE: PRT
<213> ORGANISM: Artificial Sequence
<220> FEATURE:
<223> OTHER INFORMATION: VL2 of A56-02C07

<400> SEQUENCE: 349
```

```
Ser Tyr Glu Leu Thr Gln Pro Pro Ser Leu Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Arg Leu Val Thr Tyr
            35                  40                  45

Tyr Asp Gly Asn Arg Pro Ser Gly Ile Pro Glu Arg Phe Ser Gly Ser
    50                  55                  60

Asn Ser Gly Asn Thr Ala Thr Leu Ile Ile Ser Arg Val Glu Ala Gly
65                  70                  75                  80

Asp Glu Ala Asp Tyr Tyr Cys Gln Val Trp Asp Ser Ser Ser Asp Gln
                85                  90                  95

Gly Val Phe Gly Thr Gly Thr Lys Val Thr Val Leu
            100                 105
```

```
<210> SEQ ID NO 350
<211> LENGTH: 25
<212> TYPE: PRT
<213> ORGANISM: Artificial Sequence
<220> FEATURE:
<223> OTHER INFORMATION: H-FR1 of A56-02C07

<400> SEQUENCE: 350
```

```
Gln Val Gln Leu Val Glu Ser Gly Ala Glu Val Arg Arg Pro Gly Ser
1               5                   10                  15

Ser Val Lys Val Ser Cys Lys Thr Ser
            20                  25
```

```
<210> SEQ ID NO 351
<211> LENGTH: 17
<212> TYPE: PRT
<213> ORGANISM: Artificial Sequence
<220> FEATURE:
<223> OTHER INFORMATION: H-FR2 of A56-02C07

<400> SEQUENCE: 351
```

```
Leu Ser Trp Val Arg Gln Ala Pro Gly His Gly Leu Glu Trp Met Gly
1               5                  10                  15

Arg

<210> SEQ ID NO 352
<211> LENGTH: 38
<212> TYPE: PRT
<213> ORGANISM: Artificial Sequence
<220> FEATURE:
<223> OTHER INFORMATION: H-FR3 of A56-02C07

<400> SEQUENCE: 352

Asn Tyr Ala Arg Glu Phe Gln Gly Arg Met Lys Ile Thr Ala Asp Lys
1               5                  10                  15

Ser Thr Asn Thr Val Tyr Met Glu Leu Asn Asn Leu Arg Ser Glu Asp
            20                  25                  30

Thr Ala Val Tyr Tyr Cys
        35

<210> SEQ ID NO 353
<211> LENGTH: 11
<212> TYPE: PRT
<213> ORGANISM: Artificial Sequence
<220> FEATURE:
<223> OTHER INFORMATION: H-FR4 of A56-02C07

<400> SEQUENCE: 353

Trp Gly Gln Gly Thr Thr Val Thr Val Ser Ser
1               5                  10

<210> SEQ ID NO 354
<211> LENGTH: 25
<212> TYPE: PRT
<213> ORGANISM: Artificial Sequence
<220> FEATURE:
<223> OTHER INFORMATION: L-FR1 of A56-02C07

<400> SEQUENCE: 354

Ser Tyr Glu Leu Thr Gln Pro Pro Ser Leu Ser Val Ala Pro Gly Lys
1               5                  10                  15

Thr Ala Arg Ile Thr Cys Gly Gly Asn
            20                  25

<210> SEQ ID NO 355
<211> LENGTH: 17
<212> TYPE: PRT
<213> ORGANISM: Artificial Sequence
<220> FEATURE:
<223> OTHER INFORMATION: L-FR2 of A56-02C07

<400> SEQUENCE: 355

Val His Trp Tyr Gln Gln Lys Pro Gly Gln Ala Pro Arg Leu Val Thr
1               5                  10                  15

Tyr

<210> SEQ ID NO 356
<211> LENGTH: 36
<212> TYPE: PRT
<213> ORGANISM: Artificial Sequence
<220> FEATURE:
<223> OTHER INFORMATION: L-FR3 of A56-02C07

<400> SEQUENCE: 356

Thr Tyr Tyr Asp Gly Asn Arg Pro Ser Gly Ile Pro Glu Arg Phe Ser
```

-continued

```
1               5               10              15

Gly Ser Asn Ser Gly Asn Thr Ala Thr Leu Ile Ile Ser Arg Val Glu
            20              25              30

Ala Gly Asp Glu
        35

<210> SEQ ID NO 357
<211> LENGTH: 10
<212> TYPE: PRT
<213> ORGANISM: Artificial Sequence
<220> FEATURE:
<223> OTHER INFORMATION: L-FR4 of A56-02C07

<400> SEQUENCE: 357

Phe Gly Thr Gly Thr Lys Val Thr Val Leu
1               5               10

<210> SEQ ID NO 358
<211> LENGTH: 8
<212> TYPE: PRT
<213> ORGANISM: Artificial Sequence
<220> FEATURE:
<223> OTHER INFORMATION: H-CDR1 of A56-02C09

<400> SEQUENCE: 358

Gly Gly Thr Phe Ser Ser Tyr Thr
1               5

<210> SEQ ID NO 359
<211> LENGTH: 8
<212> TYPE: PRT
<213> ORGANISM: Artificial Sequence
<220> FEATURE:
<223> OTHER INFORMATION: H-CDR2 of A56-02C09

<400> SEQUENCE: 359

Ile Ile Pro Ile Leu Gly Ile Ala
1               5

<210> SEQ ID NO 360
<211> LENGTH: 18
<212> TYPE: PRT
<213> ORGANISM: Artificial Sequence
<220> FEATURE:
<223> OTHER INFORMATION: H-CDR3 of A56-02C09

<400> SEQUENCE: 360

Ala Lys Asp Met Val Arg Gly Phe Arg His Tyr Tyr Tyr Tyr Gly Met
1               5               10              15

Asp Val

<210> SEQ ID NO 361
<211> LENGTH: 9
<212> TYPE: PRT
<213> ORGANISM: Artificial Sequence
<220> FEATURE:
<223> OTHER INFORMATION: L-CDR1 of A56-02C09

<400> SEQUENCE: 361

Asn Ser Asp Val Gly Asp Tyr Asn Leu
1               5

<210> SEQ ID NO 362
<211> LENGTH: 3
<212> TYPE: PRT
```

-continued

```
<213> ORGANISM: Artificial Sequence
<220> FEATURE:
<223> OTHER INFORMATION: L-CDR2 of A56-02C09

<400> SEQUENCE: 362

Glu Val Thr
1

<210> SEQ ID NO 363
<211> LENGTH: 10
<212> TYPE: PRT
<213> ORGANISM: Artificial Sequence
<220> FEATURE:
<223> OTHER INFORMATION: L-CDR3 of A56-02C09

<400> SEQUENCE: 363

Ser Ser Tyr Thr Ser Ser Ser Thr Tyr Val
1               5               10

<210> SEQ ID NO 364
<211> LENGTH: 255
<212> TYPE: DNA
<213> ORGANISM: Artificial Sequence
<220> FEATURE:
<223> OTHER INFORMATION: SCFV of A56-02C09

<400> SEQUENCE: 364
caggtgcagc tggtgcagtc tggggctgag gtgaagaagc ctgggtcctc ggtgaaggtc      60
tcctgcaagg cttctggagg caccttcagc agctatacta tcagctgggt gcgacaggcc     120
cctggacaag gcttgagtg gatgggaagg atcatcccta tccttggtat agcaaactac      180
gcacagaagt tccagggcag agtcacgatt accgcggaca atccacgag cacagcctac       240 atggagctga gcagc                                                       255

<210> SEQ ID NO 365
<211> LENGTH: 125
<212> TYPE: PRT
<213> ORGANISM: Artificial Sequence
<220> FEATURE:
<223> OTHER INFORMATION: VH2 of A56-02C09

<400> SEQUENCE: 365

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Thr Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Met Val Arg Gly Phe Arg His Tyr Tyr Tyr Tyr Gly Met
            100                 105                 110

Asp Val Trp Gly Pro Gly Thr Lys Val Thr Val Ser Ser
            115                 120                 125

<210> SEQ ID NO 366
<211> LENGTH: 110
```

```
<212> TYPE: PRT
<213> ORGANISM: Artificial Sequence
<220> FEATURE:
<223> OTHER INFORMATION: VL2 of A56-02C09

<400> SEQUENCE: 366

Gln Ser Ala Leu Thr Gln Pro Ala Ser Val Ser Gly Ser Pro Gly Gln
1               5                   10                  15

Ser Ile Thr Ile Ser Cys Thr Gly Thr Asn Ser Asp Val Gly Asp Tyr
            20                  25                  30

Asn Leu Val Ser Trp Tyr Gln Gln His Pro Gly Lys Ala Pro Lys Leu
        35                  40                  45

Met Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Val Thr Val Leu
            100                 105                 110

<210> SEQ ID NO 367
<211> LENGTH: 25
<212> TYPE: PRT
<213> ORGANISM: Artificial Sequence
<220> FEATURE:
<223> OTHER INFORMATION: H-FR1 of A56-02C09

<400> SEQUENCE: 367

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 368
<211> LENGTH: 17
<212> TYPE: PRT
<213> ORGANISM: Artificial Sequence
<220> FEATURE:
<223> OTHER INFORMATION: H-FR2 of A56-02C09

<400> SEQUENCE: 368

Ile Ser Trp Val Arg Gln Ala Pro Gly Gln Gly Leu Glu Trp Met Gly
1               5                   10                  15

Arg

<210> SEQ ID NO 369
<211> LENGTH: 38
<212> TYPE: PRT
<213> ORGANISM: Artificial Sequence
<220> FEATURE:
<223> OTHER INFORMATION: H-FR3 of A56-02C09

<400> SEQUENCE: 369

Asn Tyr Ala Gln Lys Phe Gln Gly Arg Val Thr Ile Thr Ala Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys
            35
```

```
<210> SEQ ID NO 370
<211> LENGTH: 11
<212> TYPE: PRT
<213> ORGANISM: Artificial Sequence
<220> FEATURE:
<223> OTHER INFORMATION: H-FR4 of A56-02C09

<400> SEQUENCE: 370

Trp Gly Pro Gly Thr Lys Val Thr Val Ser Ser
1               5                   10

<210> SEQ ID NO 371
<211> LENGTH: 25
<212> TYPE: PRT
<213> ORGANISM: Artificial Sequence
<220> FEATURE:
<223> OTHER INFORMATION: L-FR1 of A56-02C09

<400> SEQUENCE: 371

Gln Ser Ala Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 372
<211> LENGTH: 17
<212> TYPE: PRT
<213> ORGANISM: Artificial Sequence
<220> FEATURE:
<223> OTHER INFORMATION: L-FR2 of A56-02C09

<400> SEQUENCE: 372

Val Ser Trp Tyr Gln Gln His Pro Gly Lys Ala Pro Lys Leu Met Ile
1               5                   10                  15

Tyr

<210> SEQ ID NO 373
<211> LENGTH: 36
<212> TYPE: PRT
<213> ORGANISM: Artificial Sequence
<220> FEATURE:
<223> OTHER INFORMATION: L-FR3 of A56-02C09

<400> SEQUENCE: 373

Ile Tyr Glu Val Thr Lys Arg Pro Ser Gly Val Ser Asn Arg Phe Ser
1               5                   10                  15

Gly Ser Lys Ser Gly Asn Thr Ala Ser Leu Thr Ile Ser Gly Leu Gln
            20                  25                  30

Ala Glu Asp Glu
        35

<210> SEQ ID NO 374
<211> LENGTH: 10
<212> TYPE: PRT
<213> ORGANISM: Artificial Sequence
<220> FEATURE:
<223> OTHER INFORMATION: L-FR4 of A56-02C09

<400> SEQUENCE: 374

Phe Gly Thr Gly Thr Lys Val Thr Val Leu
1               5                   10

<210> SEQ ID NO 375
<211> LENGTH: 8
<212> TYPE: PRT
```

```
<213> ORGANISM: Artificial Sequence
<220> FEATURE:
<223> OTHER INFORMATION: H-CDR1 of A56-02D04

<400> SEQUENCE: 375

Gly Phe Thr Phe Lys Asn Phe Ala
1               5

<210> SEQ ID NO 376
<211> LENGTH: 8
<212> TYPE: PRT
<213> ORGANISM: Artificial Sequence
<220> FEATURE:
<223> OTHER INFORMATION: H-CDR2 of A56-02D04

<400> SEQUENCE: 376

Ile Asn Gly Asp Gly Ser Asp Thr
1               5

<210> SEQ ID NO 377
<211> LENGTH: 14
<212> TYPE: PRT
<213> ORGANISM: Artificial Sequence
<220> FEATURE:
<223> OTHER INFORMATION: H-CDR3 of A56-02D04

<400> SEQUENCE: 377

Ala Lys Glu Ile Ala Glu Val Gly Arg Pro Asn Phe Asp Tyr
1               5                   10

<210> SEQ ID NO 378
<211> LENGTH: 7
<212> TYPE: PRT
<213> ORGANISM: Artificial Sequence
<220> FEATURE:
<223> OTHER INFORMATION: L-CDR1 of A56-02D04

<400> SEQUENCE: 378

Gln Ser Val Thr Ser Thr Tyr
1               5

<210> SEQ ID NO 379
<211> LENGTH: 3
<212> TYPE: PRT
<213> ORGANISM: Artificial Sequence
<220> FEATURE:
<223> OTHER INFORMATION: L-CDR2 of A56-02D04

<400> SEQUENCE: 379

Gly Ala Ser
1

<210> SEQ ID NO 380
<211> LENGTH: 9
<212> TYPE: PRT
<213> ORGANISM: Artificial Sequence
<220> FEATURE:
<223> OTHER INFORMATION: L-CDR3 of A56-02D04

<400> SEQUENCE: 380

Gln Gln Tyr Gly Ser Ser Pro Tyr Thr
1               5

<210> SEQ ID NO 381
<211> LENGTH: 255
<212> TYPE: DNA
<213> ORGANISM: Artificial Sequence
```

<220> FEATURE:
<223> OTHER INFORMATION: SCFV of A56-02D04

<400> SEQUENCE: 381
caggtgcagc tggtagagtc cggggggaggc ttagttgagc ctggggggtc cctgagactc          60
tcctgtgcag cctctggatt caccttcaaa aacttcgcga tgtactgggt ccgccaagct         120
ccagggaagg ggctggtgtg ggtctcacgt attaatggtg atgggagtga cacaacgtac         180
gcggagtccg tgaagggccg attcaccacc tccagagaca acgccaagaa cacagtgtat         240
ttgcaaatga acagt                                                         255

<210> SEQ ID NO 382
<211> LENGTH: 121
<212> TYPE: PRT
<213> ORGANISM: Artificial Sequence
<220> FEATURE:
<223> OTHER INFORMATION: VH2 of A56-02D04

<400> SEQUENCE: 382

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Lys Asn Phe
            20                  25                  30

Ala Met Tyr Trp Val Arg Gln Ala Pro Gly Lys Gly Leu Val Trp Val
        35                  40                  45

Ser Arg Ile Asn Gly Asp Gly Ser Asp Thr Thr Tyr Ala Glu Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Glu Ile Ala Glu Val Gly Arg Pro Asn Phe Asp Tyr Trp Gly
            100                 105                 110

Gln Gly Thr Leu Val Thr Val Ser Ser
        115                 120

<210> SEQ ID NO 383
<211> LENGTH: 108
<212> TYPE: PRT
<213> ORGANISM: Artificial Sequence
<220> FEATURE:
<223> OTHER INFORMATION: VL2 of A56-02D04

<400> SEQUENCE: 383

Asp Ile Gln Met Thr Gln Ser Pro Gly Thr Leu Ser Leu Ser Pro Gly
1               5                   10                  15

Asp Thr Ala Thr Leu Ser Cys Arg Ala Ser Gln Ser Val Thr Ser Thr
            20                  25                  30

Tyr Leu Ala Trp Tyr Gln Gln Lys Pro Gly Gln Ala Pro Arg Leu Leu
        35                  40                  45

Ile Ser Gly Ala Ser Ser Arg Ala Ala Gly Ile Pro Ala Arg Phe Thr
    50                  55                  60

Gly Ser Gly Ser Glu Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

-continued

```
<210> SEQ ID NO 384
<211> LENGTH: 25
<212> TYPE: PRT
<213> ORGANISM: Artificial Sequence
<220> FEATURE:
<223> OTHER INFORMATION: H-FR1 of A56-02D04

<400> SEQUENCE: 384

Gln Val Gln Leu Val Glu Ser Gly Gly Gly Leu Val Glu Pro Gly Gly
1               5                   10                  15

Ser Leu Arg Leu Ser Cys Ala Ala Ser
            20                  25

<210> SEQ ID NO 385
<211> LENGTH: 17
<212> TYPE: PRT
<213> ORGANISM: Artificial Sequence
<220> FEATURE:
<223> OTHER INFORMATION: H-FR2 of A56-02D04

<400> SEQUENCE: 385

Met Tyr Trp Val Arg Gln Ala Pro Gly Lys Gly Leu Val Trp Val Ser
1               5                   10                  15

Arg

<210> SEQ ID NO 386
<211> LENGTH: 38
<212> TYPE: PRT
<213> ORGANISM: Artificial Sequence
<220> FEATURE:
<223> OTHER INFORMATION: H-FR3 of A56-02D04

<400> SEQUENCE: 386

Thr Tyr Ala Glu Ser Val Lys Gly Arg Phe Thr Thr Ser Arg Asp Asn
1               5                   10                  15

Ala Lys Asn Thr Val Tyr Leu Gln Met Asn Ser Leu Arg Ala Glu Asp
            20                  25                  30

Thr Ala Val Tyr Tyr Cys
        35

<210> SEQ ID NO 387
<211> LENGTH: 11
<212> TYPE: PRT
<213> ORGANISM: Artificial Sequence
<220> FEATURE:
<223> OTHER INFORMATION: H-FR4 of A56-02D04

<400> SEQUENCE: 387

Trp Gly Gln Gly Thr Leu Val Thr Val Ser Ser
1               5                   10

<210> SEQ ID NO 388
<211> LENGTH: 26
<212> TYPE: PRT
<213> ORGANISM: Artificial Sequence
<220> FEATURE:
<223> OTHER INFORMATION: L-FR1 of A56-02D04

<400> SEQUENCE: 388

Asp Ile Gln Met Thr Gln Ser Pro Gly Thr Leu Ser Leu Ser Pro Gly
1               5                   10                  15

Asp Thr Ala Thr Leu Ser Cys Arg Ala Ser
            20                  25
```

-continued

```
<210> SEQ ID NO 389
<211> LENGTH: 17
<212> TYPE: PRT
<213> ORGANISM: Artificial Sequence
<220> FEATURE:
<223> OTHER INFORMATION: L-FR2 of A56-02D04

<400> SEQUENCE: 389

Leu Ala Trp Tyr Gln Gln Lys Pro Gly Gln Ala Pro Arg Leu Leu Ile
1               5                   10                  15

Ser

<210> SEQ ID NO 390
<211> LENGTH: 36
<212> TYPE: PRT
<213> ORGANISM: Artificial Sequence
<220> FEATURE:
<223> OTHER INFORMATION: L-FR3 of A56-02D04

<400> SEQUENCE: 390

Ile Ser Gly Ala Ser Ser Arg Ala Ala Gly Ile Pro Ala Arg Phe Thr
1               5                   10                  15

Gly Ser Gly Ser Glu Thr Asp Phe Thr Leu Thr Ile Ser Arg Leu Glu
            20                  25                  30

Pro Glu Asp Phe
        35

<210> SEQ ID NO 391
<211> LENGTH: 10
<212> TYPE: PRT
<213> ORGANISM: Artificial Sequence
<220> FEATURE:
<223> OTHER INFORMATION: L-FR4 of A56-02D04

<400> SEQUENCE: 391

Phe Gly Gln Gly Thr Lys Leu Glu Ile Lys
1               5                   10

<210> SEQ ID NO 392
<211> LENGTH: 8
<212> TYPE: PRT
<213> ORGANISM: Artificial Sequence
<220> FEATURE:
<223> OTHER INFORMATION: H-CDR1 of A56-02E01

<400> SEQUENCE: 392

Gly Gly Ser Ser Ser Asn Tyr Ala
1               5

<210> SEQ ID NO 393
<211> LENGTH: 8
<212> TYPE: PRT
<213> ORGANISM: Artificial Sequence
<220> FEATURE:
<223> OTHER INFORMATION: H-CDR2 of A56-02E01

<400> SEQUENCE: 393

Ile Thr Pro Phe Asn Gly Asn Thr
1               5

<210> SEQ ID NO 394
<211> LENGTH: 12
<212> TYPE: PRT
<213> ORGANISM: Artificial Sequence
```

<220> FEATURE:
<223> OTHER INFORMATION: H-CDR3 of A56-02E01

<400> SEQUENCE: 394

Ala Ser Ser Arg Gly Arg Phe Gln Trp Phe Asp Tyr
1               5                   10

<210> SEQ ID NO 395
<211> LENGTH: 7
<212> TYPE: PRT
<213> ORGANISM: Artificial Sequence
<220> FEATURE:
<223> OTHER INFORMATION: L-CDR1 of A56-02E01

<400> SEQUENCE: 395

Gln Ser Val Lys Asn Asn Asp
1               5

<210> SEQ ID NO 396
<211> LENGTH: 3
<212> TYPE: PRT
<213> ORGANISM: Artificial Sequence
<220> FEATURE:
<223> OTHER INFORMATION: L-CDR2 of A56-02E01

<400> SEQUENCE: 396

Gly Thr Ser
1

<210> SEQ ID NO 397
<211> LENGTH: 10
<212> TYPE: PRT
<213> ORGANISM: Artificial Sequence
<220> FEATURE:
<223> OTHER INFORMATION: L-CDR3 of A56-02E01

<400> SEQUENCE: 397

Gln Gln Phe Gly Gly Ser Pro Pro Trp Thr
1               5                   10

<210> SEQ ID NO 398
<211> LENGTH: 255
<212> TYPE: DNA
<213> ORGANISM: Artificial Sequence
<220> FEATURE:
<223> OTHER INFORMATION: SCFV of A56-02E01

<400> SEQUENCE: 398
caggtgcagc tggtgcagtc tggggctgag gtgaagaagc ctgggtcctc ggtgaaggtc      60
tcctgcaagg cttccggagg ctcctccagc aactatgcta tcagctgggt gcgacaggcc     120
cctggacaag gcttgagtg gatgggatgg atcacacctt tcaatggtaa caccagctac      180
gcgcagatat tccaggacag agtcaccatt accagggaca ggtctatgag cacagcctac     240
atggagctga gcagc                                                      255

<210> SEQ ID NO 399
<211> LENGTH: 119
<212> TYPE: PRT
<213> ORGANISM: Artificial Sequence
<220> FEATURE:
<223> OTHER INFORMATION: VH2 of A56-02E01

<400> SEQUENCE: 399

Gln Val Gln Leu Val Gln Ser Gly Ala Glu Val Lys Lys Pro Gly Ser
1               5                   10                  15

-continued

```
Ser Val Lys Val Ser Cys Lys Ala Ser Gly Gly Ser Ser Asn Tyr
        20              25              30

Ala Ile Ser Trp Val Arg Gln Ala Pro Gly Gln Gly Leu Glu Trp Met
        35              40              45

Gly Trp Ile Thr Pro Phe Asn Gly Asn Thr Ser Tyr Ala Gln Ile Phe
    50              55              60

Gln Asp Arg Val Thr Ile Thr Arg Asp Arg Ser Met Ser Thr Ala Tyr
65              70              75              80

Met Glu Leu Ser Ser Leu Arg Ser Glu Asp Thr Ala Val Tyr Tyr Cys
                85              90              95

Ala Ser Ser Arg Gly Arg Phe Gln Trp Phe Asp Tyr Trp Gly Pro Gly
        100             105             110

Thr Leu Val Thr Val Ser Ser
        115
```

```
<210> SEQ ID NO 400
<211> LENGTH: 109
<212> TYPE: PRT
<213> ORGANISM: Artificial Sequence
<220> FEATURE:
<223> OTHER INFORMATION: VL2 of A56-02E01

<400> SEQUENCE: 400
```

```
Asp Ile Gln Met Thr Gln Ser Pro Ala Thr Leu Ser Val Ser Pro Gly
1               5               10              15

Glu Arg Ala Thr Leu Ser Cys Arg Thr Ser Gln Ser Val Lys Asn Asn
        20              25              30

Asp Leu Ala Trp Tyr Gln Gln Lys Pro Gly Gln Ala Pro Arg Leu Leu
        35              40              45

Ile Tyr Gly Thr Ser Thr Arg Ala Thr Gly Ile Pro Asp Arg Phe Ser
    50              55              60

Gly Ser Gly Ser Gly Thr Asp Phe Thr Leu Thr Ile Ser Ser Leu Glu
65              70              75              80

Pro Glu Asp Phe Ala Val Tyr Tyr Cys Gln Gln Phe Gly Gly Ser Pro
                85              90              95

Pro Trp Thr Phe Gly Gln Gly Thr Lys Val Asp Ile Lys
        100             105
```

```
<210> SEQ ID NO 401
<211> LENGTH: 25
<212> TYPE: PRT
<213> ORGANISM: Artificial Sequence
<220> FEATURE:
<223> OTHER INFORMATION: H-FR1 of A56-02E01

<400> SEQUENCE: 401
```

```
Gln Val Gln Leu Val Gln Ser Gly Ala Glu Val Lys Lys Pro Gly Ser
1               5               10              15

Ser Val Lys Val Ser Cys Lys Ala Ser
        20              25
```

```
<210> SEQ ID NO 402
<211> LENGTH: 17
<212> TYPE: PRT
<213> ORGANISM: Artificial Sequence
<220> FEATURE:
<223> OTHER INFORMATION: H-FR2 of A56-02E01

<400> SEQUENCE: 402
```

```
Ile Ser Trp Val Arg Gln Ala Pro Gly Gln Gly Leu Glu Trp Met Gly
1               5                   10                  15

Trp

<210> SEQ ID NO 403
<211> LENGTH: 38
<212> TYPE: PRT
<213> ORGANISM: Artificial Sequence
<220> FEATURE:
<223> OTHER INFORMATION: H-FR3 of A56-02E01

<400> SEQUENCE: 403

Ser Tyr Ala Gln Ile Phe Gln Asp Arg Val Thr Ile Thr Arg Asp Arg
1               5                   10                  15

Ser Met Ser Thr Ala Tyr Met Glu Leu Ser Ser Leu Arg Ser Glu Asp
                20                  25                  30

Thr Ala Val Tyr Tyr Cys
        35

<210> SEQ ID NO 404
<211> LENGTH: 11
<212> TYPE: PRT
<213> ORGANISM: Artificial Sequence
<220> FEATURE:
<223> OTHER INFORMATION: H-FR4 of A56-02E01

<400> SEQUENCE: 404

Trp Gly Pro Gly Thr Leu Val Thr Val Ser Ser
1               5                   10

<210> SEQ ID NO 405
<211> LENGTH: 26
<212> TYPE: PRT
<213> ORGANISM: Artificial Sequence
<220> FEATURE:
<223> OTHER INFORMATION: L-FR1 of A56-02E01

<400> SEQUENCE: 405

Asp Ile Gln Met Thr Gln Ser Pro Ala Thr Leu Ser Val Ser Pro Gly
1               5                   10                  15

Glu Arg Ala Thr Leu Ser Cys Arg Thr Ser
                20                  25

<210> SEQ ID NO 406
<211> LENGTH: 17
<212> TYPE: PRT
<213> ORGANISM: Artificial Sequence
<220> FEATURE:
<223> OTHER INFORMATION: L-FR2 of A56-02E01

<400> SEQUENCE: 406

Leu Ala Trp Tyr Gln Gln Lys Pro Gly Gln Ala Pro Arg Leu Leu Ile
1               5                   10                  15

Tyr

<210> SEQ ID NO 407
<211> LENGTH: 36
<212> TYPE: PRT
<213> ORGANISM: Artificial Sequence
<220> FEATURE:
<223> OTHER INFORMATION: L-FR3 of A56-02E01

<400> SEQUENCE: 407

Ile Tyr Gly Thr Ser Thr Arg Ala Thr Gly Ile Pro Asp Arg Phe Ser
```

-continued

```
1               5              10              15

Gly Ser Gly Ser Gly Thr Asp Phe Thr Leu Thr Ile Ser Ser Leu Glu
            20              25              30

Pro Glu Asp Phe
        35

<210> SEQ ID NO 408
<211> LENGTH: 10
<212> TYPE: PRT
<213> ORGANISM: Artificial Sequence
<220> FEATURE:
<223> OTHER INFORMATION: L-FR4 of A56-02E01

<400> SEQUENCE: 408

Phe Gly Gln Gly Thr Lys Val Asp Ile Lys
1               5              10

<210> SEQ ID NO 409
<211> LENGTH: 8
<212> TYPE: PRT
<213> ORGANISM: Artificial Sequence
<220> FEATURE:
<223> OTHER INFORMATION: H-CDR1 of A56-02E05

<400> SEQUENCE: 409

Gly Phe Thr Ser Gly Asp Tyr Ala
1               5

<210> SEQ ID NO 410
<211> LENGTH: 10
<212> TYPE: PRT
<213> ORGANISM: Artificial Sequence
<220> FEATURE:
<223> OTHER INFORMATION: H-CDR2 of A56-02E05

<400> SEQUENCE: 410

Ile Gly Ser Ser Gly Tyr Gly Gly Pro Thr
1               5              10

<210> SEQ ID NO 411
<211> LENGTH: 17
<212> TYPE: PRT
<213> ORGANISM: Artificial Sequence
<220> FEATURE:
<223> OTHER INFORMATION: H-CDR3 of A56-02E05

<400> SEQUENCE: 411

Ala Arg Asp Leu Gly Phe Gly Tyr Ser Gly Tyr Arg Asn Ala Phe Asp
1               5              10              15

Ser

<210> SEQ ID NO 412
<211> LENGTH: 8
<212> TYPE: PRT
<213> ORGANISM: Artificial Sequence
<220> FEATURE:
<223> OTHER INFORMATION: L-CDR1 of A56-02E05

<400> SEQUENCE: 412

Gly Gly Thr Phe Ala Ser Asp Ser
1               5

<210> SEQ ID NO 413
<211> LENGTH: 3
<212> TYPE: PRT
```

-continued

```
<213> ORGANISM: Artificial Sequence
<220> FEATURE:
<223> OTHER INFORMATION: L-CDR2 of A56-02E05

<400> SEQUENCE: 413

Glu Gly Asp
1

<210> SEQ ID NO 414
<211> LENGTH: 9
<212> TYPE: PRT
<213> ORGANISM: Artificial Sequence
<220> FEATURE:
<223> OTHER INFORMATION: L-CDR3 of A56-02E05

<400> SEQUENCE: 414

Gln Ser Tyr Asp Ser Ser Asn Gln Val
1               5

<210> SEQ ID NO 415
<211> LENGTH: 255
<212> TYPE: DNA
<213> ORGANISM: Artificial Sequence
<220> FEATURE:
<223> OTHER INFORMATION: SCFV of A56-02E05

<400> SEQUENCE: 415
caggtgcagc tggtagagtc tgggggaggc tgggtacagc cagggcggtc cctgagactc       60
tcctgtacag tctctggatt cacgtctggt gattatgctg tgagttgggt ccgccaggct      120
ccagggaagg ggctggagtg ggtaggtgtc attggaagca gcggttatgg tgggccaaca      180
aaatatgctg cgtctgtgga aggcagattc accatctcaa gagatgattc caaagacatc      240
gcctatctgc aaatg                                                       255

<210> SEQ ID NO 416
<211> LENGTH: 126
<212> TYPE: PRT
<213> ORGANISM: Artificial Sequence
<220> FEATURE:
<223> OTHER INFORMATION: VH2 of A56-02E05

<400> SEQUENCE: 416

Gln Val Gln Leu Val Glu Ser Gly Gly Gly Trp Val Gln Pro Gly Arg
1               5                   10                  15

Ser Leu Arg Leu Ser Cys Thr Val Ser Gly Phe Thr Ser Gly Asp Tyr
            20                  25                  30

Ala Val Ser Trp Val Arg Gln Ala Pro Gly Lys Gly Leu Glu Trp Val
        35                  40                  45

Gly Val Ile Gly Ser Ser Gly Tyr Gly Gly Pro Thr Lys Tyr Ala Ala
    50                  55                  60

Ser Val Glu Gly Arg Phe Thr Ile Ser Arg Asp Asp Ser Lys Asp Ile
65                  70                  75                  80

Ala Tyr Leu Gln Met Asn Ser Leu Arg Ala Glu Asp Thr Ala Val Tyr
                85                  90                  95

Tyr Cys Ala Arg Asp Leu Gly Phe Gly Tyr Ser Gly Tyr Arg Asn Ala
            100                 105                 110

Phe Asp Ser Trp Gly Gln Gly Thr Met Val Thr Val Ser Ser
            115                 120                 125

<210> SEQ ID NO 417
<211> LENGTH: 110
```

-continued

<212> TYPE: PRT
<213> ORGANISM: Artificial Sequence
<220> FEATURE:
<223> OTHER INFORMATION: VL2 of A56-02E05

<400> SEQUENCE: 417

Gln Leu Val Leu Thr Gln Pro His Ser Val Ser Glu Ser Pro Gly Lys
1               5                   10                  15

Thr Val Thr Ile Ser Cys Thr Gly Ser Gly Gly Thr Phe Ala Ser Asp
            20                  25                  30

Ser Val Gln Trp Tyr Arg Gln Arg Pro Gly Ser Ala Pro Thr Thr Val
        35                  40                  45

Ile Tyr Glu Gly Asp Arg Arg Ala Ser Gly Val Pro Gly Arg Phe Ser
    50                  55                  60

Gly Ser Ile Asp Ser Ser Ser Asn Ser Ala Ser Leu Thr Ile Ser Gly
65                  70                  75                  80

Leu Lys Ala Glu Asp Glu Ala Asp Tyr Tyr Cys Gln Ser Tyr Asp Ser
                85                  90                  95

Ser Asn Gln Val Phe Gly Thr Gly Thr Lys Val Thr Val Leu
            100                 105                 110

<210> SEQ ID NO 418
<211> LENGTH: 25
<212> TYPE: PRT
<213> ORGANISM: Artificial Sequence
<220> FEATURE:
<223> OTHER INFORMATION: H-FR1 of A56-02E05

<400> SEQUENCE: 418

Gln Val Gln Leu Val Glu Ser Gly Gly Gly Trp Val Gln Pro Gly Arg
1               5                   10                  15

Ser Leu Arg Leu Ser Cys Thr Val Ser
            20                  25

<210> SEQ ID NO 419
<211> LENGTH: 17
<212> TYPE: PRT
<213> ORGANISM: Artificial Sequence
<220> FEATURE:
<223> OTHER INFORMATION: H-FR2 of A56-02E05

<400> SEQUENCE: 419

Val Ser Trp Val Arg Gln Ala Pro Gly Lys Gly Leu Glu Trp Val Gly
1               5                   10                  15

Val

<210> SEQ ID NO 420
<211> LENGTH: 38
<212> TYPE: PRT
<213> ORGANISM: Artificial Sequence
<220> FEATURE:
<223> OTHER INFORMATION: H-FR3 of A56-02E05

<400> SEQUENCE: 420

Lys Tyr Ala Ala Ser Val Glu Gly Arg Phe Thr Ile Ser Arg Asp Asp
1               5                   10                  15

Ser Lys Asp Ile Ala Tyr Leu Gln Met Asn Ser Leu Arg Ala Glu Asp
            20                  25                  30

Thr Ala Val Tyr Tyr Cys
        35

-continued

```
<210> SEQ ID NO 421
<211> LENGTH: 11
<212> TYPE: PRT
<213> ORGANISM: Artificial Sequence
<220> FEATURE:
<223> OTHER INFORMATION: H-FR4 of A56-02E05

<400> SEQUENCE: 421

Trp Gly Gln Gly Thr Met Val Thr Val Ser Ser
1               5               10

<210> SEQ ID NO 422
<211> LENGTH: 25
<212> TYPE: PRT
<213> ORGANISM: Artificial Sequence
<220> FEATURE:
<223> OTHER INFORMATION: L-FR1 of A56-02E05

<400> SEQUENCE: 422

Gln Leu Val Leu Thr Gln Pro His Ser Val Ser Glu Ser Pro Gly Lys
1               5               10              15

Thr Val Thr Ile Ser Cys Thr Gly Ser
            20              25

<210> SEQ ID NO 423
<211> LENGTH: 17
<212> TYPE: PRT
<213> ORGANISM: Artificial Sequence
<220> FEATURE:
<223> OTHER INFORMATION: L-FR2 of A56-02E05

<400> SEQUENCE: 423

Val Gln Trp Tyr Arg Gln Arg Pro Gly Ser Ala Pro Thr Thr Val Ile
1               5               10              15

Tyr

<210> SEQ ID NO 424
<211> LENGTH: 36
<212> TYPE: PRT
<213> ORGANISM: Artificial Sequence
<220> FEATURE:
<223> OTHER INFORMATION: L-FR3 of A56-02E05

<400> SEQUENCE: 424

Ile Tyr Glu Gly Asp Arg Arg Ala Ser Gly Val Pro Gly Arg Phe Ser
1               5               10              15

Gly Ser Ile Asp Ser Ser Ser Asn Ser Ala Ser Leu Thr Ile Ser Gly
            20              25              30

Leu Lys Ala Glu
        35

<210> SEQ ID NO 425
<211> LENGTH: 10
<212> TYPE: PRT
<213> ORGANISM: Artificial Sequence
<220> FEATURE:
<223> OTHER INFORMATION: L-FR4 of A56-02E05

<400> SEQUENCE: 425

Phe Gly Thr Gly Thr Lys Val Thr Val Leu
1               5               10

<210> SEQ ID NO 426
<211> LENGTH: 8
<212> TYPE: PRT
```

<213> ORGANISM: Artificial Sequence
<220> FEATURE:
<223> OTHER INFORMATION: H-CDR1 of A56-02F05

<400> SEQUENCE: 426

Gly Phe Ser Phe Ser Gly Tyr Ala
1               5

<210> SEQ ID NO 427
<211> LENGTH: 8
<212> TYPE: PRT
<213> ORGANISM: Artificial Sequence
<220> FEATURE:
<223> OTHER INFORMATION: H-CDR2 of A56-02F05

<400> SEQUENCE: 427

Ile Trp Phe Asp Gly Ser Thr Lys
1               5

<210> SEQ ID NO 428
<211> LENGTH: 10
<212> TYPE: PRT
<213> ORGANISM: Artificial Sequence
<220> FEATURE:
<223> OTHER INFORMATION: H-CDR3 of A56-02F05

<400> SEQUENCE: 428

Ala Arg Met Phe Arg Gly Ser Phe Asp Tyr
1               5                   10

<210> SEQ ID NO 429
<211> LENGTH: 11
<212> TYPE: PRT
<213> ORGANISM: Artificial Sequence
<220> FEATURE:
<223> OTHER INFORMATION: L-CDR1 of A56-02F05

<400> SEQUENCE: 429

Gln Ser Leu Val His Arg Asp Gly Asn Thr Tyr
1               5                   10

<210> SEQ ID NO 430
<211> LENGTH: 3
<212> TYPE: PRT
<213> ORGANISM: Artificial Sequence
<220> FEATURE:
<223> OTHER INFORMATION: L-CDR2 of A56-02F05

<400> SEQUENCE: 430

Lys Ile Ser
1

<210> SEQ ID NO 431
<211> LENGTH: 8
<212> TYPE: PRT
<213> ORGANISM: Artificial Sequence
<220> FEATURE:
<223> OTHER INFORMATION: L-CDR3 of A56-02F05

<400> SEQUENCE: 431

Met Gln Ala Thr Arg Leu Trp Thr
1               5

<210> SEQ ID NO 432
<211> LENGTH: 255
<212> TYPE: DNA
<213> ORGANISM: Artificial Sequence -continued

```
<220> FEATURE:
<223> OTHER INFORMATION: SCFV of A56-02F05

<400> SEQUENCE: 432
caggtgcagc tggtggagtc tgggggaggt gtggtccagc ctggggcgtc cctgaaactc      60
tcctgtgcag cgtccggatt cagcttcagt ggctatgcca tgcactgggt ccgccaggct     120
ccaggcatgg ggctggagtg ggtggcagtt atctggtttg atggaagtac taaatactat     180
gcagactccg tgaagggccg attcaccatc tcccgagaca attccaagaa tacactttt     240 ctgcaaatga acagt                                                       255

<210> SEQ ID NO 433
<211> LENGTH: 117
<212> TYPE: PRT
<213> ORGANISM: Artificial Sequence
<220> FEATURE:
<223> OTHER INFORMATION: VH2 of A56-02F05

<400> SEQUENCE: 433

Gln Val Gln Leu Val Glu Ser Gly Gly Gly Val Val Gln Pro Gly Ala
1               5                   10                  15

Ser Leu Lys Leu Ser Cys Ala Ala Ser Gly Phe Ser Phe Ser Gly Tyr
            20                  25                  30

Ala Met His Trp Val Arg Gln Ala Pro Gly Met Gly Leu Glu Trp Val
        35                  40                  45

Ala Val Ile Trp Phe Asp Gly Ser Thr Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Met Phe Arg Gly Ser Phe Asp Tyr Trp Gly Gln Gly Ala Leu
            100                 105                 110

Val Thr Val Ser Ser
        115

<210> SEQ ID NO 434
<211> LENGTH: 111
<212> TYPE: PRT
<213> ORGANISM: Artificial Sequence
<220> FEATURE:
<223> OTHER INFORMATION: VL2 of A56-02F05

<400> SEQUENCE: 434

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30

Asp Gly Asn Thr Tyr Leu Ser Trp Phe Gln Gln Arg Pro Gly Gln Ser
        35                  40                  45

Pro Arg Leu Leu Ile Ser Lys Ile Ser Asn Arg Ser Ser Glu Val Ser
    50                  55                  60

Asp Arg Phe Ser Gly Ser Gly Ala Gly Thr Glu Phe Thr Leu Lys Ile
65                  70                  75                  80

Ser Arg Val Glu Ala Glu Asp Val Gly Ile Tyr Tyr Cys Met Gln Ala
                85                  90                  95

Thr Arg Leu Trp Thr Phe Gly Gln Gly Thr Lys Val Glu Ile Lys
            100                 105                 110
```

```
<210> SEQ ID NO 435
<211> LENGTH: 25
<212> TYPE: PRT
<213> ORGANISM: Artificial Sequence
<220> FEATURE:
<223> OTHER INFORMATION: H-FR1 of A56-02F05

<400> SEQUENCE: 435

Gln Val Gln Leu Val Glu Ser Gly Gly Gly Val Val Gln Pro Gly Ala
1               5                   10                  15

Ser Leu Lys Leu Ser Cys Ala Ala Ser
            20                  25

<210> SEQ ID NO 436
<211> LENGTH: 17
<212> TYPE: PRT
<213> ORGANISM: Artificial Sequence
<220> FEATURE:
<223> OTHER INFORMATION: H-FR2 of A56-02F05

<400> SEQUENCE: 436

Met His Trp Val Arg Gln Ala Pro Gly Met Gly Leu Glu Trp Val Ala
1               5                   10                  15

Val

<210> SEQ ID NO 437
<211> LENGTH: 38
<212> TYPE: PRT
<213> ORGANISM: Artificial Sequence
<220> FEATURE:
<223> OTHER INFORMATION: H-FR3 of A56-02F05

<400> SEQUENCE: 437

Tyr Tyr Ala Asp Ser Val Lys Gly Arg Phe Thr Ile Ser Arg Asp Asn
1               5                   10                  15

Ser Lys Asn Thr Leu Phe Leu Gln Met Asn Ser Leu Arg Ala Glu Asp
            20                  25                  30

Thr Ala Val Tyr Tyr Cys
        35

<210> SEQ ID NO 438
<211> LENGTH: 11
<212> TYPE: PRT
<213> ORGANISM: Artificial Sequence
<220> FEATURE:
<223> OTHER INFORMATION: H-FR4 of A56-02F05

<400> SEQUENCE: 438

Trp Gly Gln Gly Ala Leu Val Thr Val Ser Ser
1               5                   10

<210> SEQ ID NO 439
<211> LENGTH: 26
<212> TYPE: PRT
<213> ORGANISM: Artificial Sequence
<220> FEATURE:
<223> OTHER INFORMATION: L-FR1 of A56-02F05

<400> SEQUENCE: 439

Asp Ile Val Met Thr Gln Thr Pro Leu Ser Ser Pro Val Thr Leu Gly
1               5                   10                  15

Gln Pro Ala Ser Ile Ser Cys Arg Ser Ser
            20                  25
```

```
<210> SEQ ID NO 440
<211> LENGTH: 17
<212> TYPE: PRT
<213> ORGANISM: Artificial Sequence
<220> FEATURE:
<223> OTHER INFORMATION: L-FR2 of A56-02F05

<400> SEQUENCE: 440

Leu Ser Trp Phe Gln Gln Arg Pro Gly Gln Ser Pro Arg Leu Leu Ile
1               5                   10                  15

Ser

<210> SEQ ID NO 441
<211> LENGTH: 36
<212> TYPE: PRT
<213> ORGANISM: Artificial Sequence
<220> FEATURE:
<223> OTHER INFORMATION: L-FR3 of A56-02F05

<400> SEQUENCE: 441

Ile Ser Lys Ile Ser Asn Arg Ser Ser Glu Val Ser Asp Arg Phe Ser
1               5                   10                  15

Gly Ser Gly Ala Gly Thr Glu Phe Thr Leu Lys Ile Ser Arg Val Glu
            20                  25                  30

Ala Glu Asp Val
        35

<210> SEQ ID NO 442
<211> LENGTH: 10
<212> TYPE: PRT
<213> ORGANISM: Artificial Sequence
<220> FEATURE:
<223> OTHER INFORMATION: L-FR4 of A56-02F05

<400> SEQUENCE: 442

Phe Gly Gln Gly Thr Lys Val Glu Ile Lys
1               5                   10

<210> SEQ ID NO 443
<211> LENGTH: 8
<212> TYPE: PRT
<213> ORGANISM: Artificial Sequence
<220> FEATURE:
<223> OTHER INFORMATION: H-CDR1 of A56-03A09

<400> SEQUENCE: 443

Gly Phe Thr Phe Ser Asp Tyr Ala
1               5

<210> SEQ ID NO 444
<211> LENGTH: 8
<212> TYPE: PRT
<213> ORGANISM: Artificial Sequence
<220> FEATURE:
<223> OTHER INFORMATION: H-CDR2 of A56-03A09

<400> SEQUENCE: 444

Ile Ser Ser Ser Gly Gly Ser Thr
1               5

<210> SEQ ID NO 445
<211> LENGTH: 14
<212> TYPE: PRT
<213> ORGANISM: Artificial Sequence
```

<220> FEATURE:
<223> OTHER INFORMATION: H-CDR3 of A56-03A09

<400> SEQUENCE: 445

Ala Arg Leu Arg Pro Phe Ser Lys Ala Asp Ser Phe Asp Tyr
1               5                   10

<210> SEQ ID NO 446
<211> LENGTH: 12
<212> TYPE: PRT
<213> ORGANISM: Artificial Sequence
<220> FEATURE:
<223> OTHER INFORMATION: L-CDR1 of A56-03A09

<400> SEQUENCE: 446

Gln Ser Val Leu Ser Ser Ser Ser Asn Lys Asn Phe
1               5                   10

<210> SEQ ID NO 447
<211> LENGTH: 3
<212> TYPE: PRT
<213> ORGANISM: Artificial Sequence
<220> FEATURE:
<223> OTHER INFORMATION: L-CDR2 of A56-03A09

<400> SEQUENCE: 447

Trp Ala Ser
1

<210> SEQ ID NO 448
<211> LENGTH: 9
<212> TYPE: PRT
<213> ORGANISM: Artificial Sequence
<220> FEATURE:
<223> OTHER INFORMATION: L-CDR3 of A56-03A09

<400> SEQUENCE: 448

Gln Gln Tyr Tyr Ser Ser Pro Leu Thr
1               5

<210> SEQ ID NO 449
<211> LENGTH: 255
<212> TYPE: DNA
<213> ORGANISM: Artificial Sequence
<220> FEATURE:
<223> OTHER INFORMATION: SCFV of A56-03A09

<400> SEQUENCE: 449
caggtgcagc tggtggagtc tggggggaggc ttggtacagc cggggggggtc cctgagactc      60 tcctgcagtg cctctggatt caccttagt gactatgcca tgagctgggt ccgccaggcc     120
ccagggaagc ggctggagtg ggtctcagcg attagtagta gtggtggtag cacacactac     180
gcagacttcg tgaagggccg gttcaccatt tccagagaca aatccaagaa cacactcttt     240
ctgcaaatga acagt                                                     255

<210> SEQ ID NO 450
<211> LENGTH: 121
<212> TYPE: PRT
<213> ORGANISM: Artificial Sequence
<220> FEATURE:
<223> OTHER INFORMATION: VH2 of A56-03A09

<400> SEQUENCE: 450

Gln Val Gln Leu Val Glu Ser Gly Gly Gly Leu Val Gln Pro Gly Gly
1               5                   10                  15

-continued

```
Ser Leu Arg Leu Ser Cys Ser Ala Ser Gly Phe Thr Phe Ser Asp Tyr
            20                  25                  30

Ala Met Ser Trp Val Arg Gln Ala Pro Gly Lys Arg Leu Glu Trp Val
            35                  40                  45

Ser Ala Ile Ser Ser Ser Gly Gly Ser Thr His Tyr Ala Asp Phe Val
        50                  55                  60

Lys Gly Arg Phe Thr Ile Ser Arg Asp Lys Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Leu Arg Pro Phe Ser Lys Ala Asp Ser Phe Asp Tyr Trp Gly
            100                 105                 110

Leu Gly Thr Leu Ile Thr Val Ser Ser
        115                 120

<210> SEQ ID NO 451
<211> LENGTH: 113
<212> TYPE: PRT
<213> ORGANISM: Artificial Sequence
<220> FEATURE:
<223> OTHER INFORMATION: VL2 of A56-03A09

<400> SEQUENCE: 451

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Ser
            20                  25                  30

Ser Ser Asn Lys Asn Phe Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Leu Thr Phe Gly Gly Gly Thr Lys Val Glu Ile
            100                 105                 110

Lys

<210> SEQ ID NO 452
<211> LENGTH: 25
<212> TYPE: PRT
<213> ORGANISM: Artificial Sequence
<220> FEATURE:
<223> OTHER INFORMATION: H-FR1 of A56-03A09

<400> SEQUENCE: 452

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 453
<211> LENGTH: 17
<212> TYPE: PRT
<213> ORGANISM: Artificial Sequence
<220> FEATURE:
<223> OTHER INFORMATION: H-FR2 of A56-03A09
```

-continued

<400> SEQUENCE: 453

```
Met Ser Trp Val Arg Gln Ala Pro Gly Lys Arg Leu Glu Trp Val Ser
1               5                   10                  15

Ala
```

<210> SEQ ID NO 454
<211> LENGTH: 38
<212> TYPE: PRT
<213> ORGANISM: Artificial Sequence
<220> FEATURE:
<223> OTHER INFORMATION: H-FR3 of A56-03A09

<400> SEQUENCE: 454

```
His Tyr Ala Asp Phe Val Lys Gly Arg Phe Thr Ile Ser Arg Asp Lys
1               5                   10                  15

Ser Lys Asn Thr Leu Phe Leu Gln Met Asn Ser Leu Arg Ala Glu Asp
            20                  25                  30

Thr Ala Val Tyr Tyr Cys
            35
```

<210> SEQ ID NO 455
<211> LENGTH: 11
<212> TYPE: PRT
<213> ORGANISM: Artificial Sequence
<220> FEATURE:
<223> OTHER INFORMATION: H-FR4 of A56-03A09

<400> SEQUENCE: 455

```
Trp Gly Leu Gly Thr Leu Ile Thr Val Ser Ser
1               5                   10
```

<210> SEQ ID NO 456
<211> LENGTH: 26
<212> TYPE: PRT
<213> ORGANISM: Artificial Sequence
<220> FEATURE:
<223> OTHER INFORMATION: L-FR1 of A56-03A09

<400> SEQUENCE: 456

```
Asp Ile Gln Met Thr Gln Ser Pro Asp Ser Leu Ala Val Ser Leu Gly
1               5                   10                  15

Glu Arg Ala Thr Ile Asn Cys Lys Ser Ser
            20                  25
```

<210> SEQ ID NO 457
<211> LENGTH: 17
<212> TYPE: PRT
<213> ORGANISM: Artificial Sequence
<220> FEATURE:
<223> OTHER INFORMATION: L-FR2 of A56-03A09

<400> SEQUENCE: 457

```
Leu Ala Trp Tyr Gln Gln Lys Pro Gly Gln Pro Pro Lys Leu Leu Ile
1               5                   10                  15

Tyr
```

<210> SEQ ID NO 458
<211> LENGTH: 36
<212> TYPE: PRT
<213> ORGANISM: Artificial Sequence
<220> FEATURE:
<223> OTHER INFORMATION: L-FR3 of A56-03A09

<400> SEQUENCE: 458

-continued

```
Ile Tyr Trp Ala Ser Ala Arg Glu Ser Gly Val Pro Asp Arg Phe Ser
1               5                  10                  15

Gly Ser Gly Ser Gly Thr Asp Phe Thr Leu Thr Ile Ser Ser Leu Gln
            20                  25                  30

Ala Glu Asp Val
        35

<210> SEQ ID NO 459
<211> LENGTH: 10
<212> TYPE: PRT
<213> ORGANISM: Artificial Sequence
<220> FEATURE:
<223> OTHER INFORMATION: L-FR4 of A56-03A09

<400> SEQUENCE: 459

Phe Gly Gly Gly Thr Lys Val Glu Ile Lys
1               5                  10

<210> SEQ ID NO 460
<211> LENGTH: 8
<212> TYPE: PRT
<213> ORGANISM: Artificial Sequence
<220> FEATURE:
<223> OTHER INFORMATION: H-CDR1 of A56-03B03

<400> SEQUENCE: 460

Gly Gly Asn Phe Asn Ser Tyr Ala
1               5

<210> SEQ ID NO 461
<211> LENGTH: 8
<212> TYPE: PRT
<213> ORGANISM: Artificial Sequence
<220> FEATURE:
<223> OTHER INFORMATION: H-CDR2 of A56-03B03

<400> SEQUENCE: 461

Ile Ile Pro Phe Phe Thr Thr Pro
1               5

<210> SEQ ID NO 462
<211> LENGTH: 5
<212> TYPE: PRT
<213> ORGANISM: Artificial Sequence
<220> FEATURE:
<223> OTHER INFORMATION: H-CDR3 of A56-03B03

<400> SEQUENCE: 462

Val Thr Arg Gly Ala
1               5

<210> SEQ ID NO 463
<211> LENGTH: 9
<212> TYPE: PRT
<213> ORGANISM: Artificial Sequence
<220> FEATURE:
<223> OTHER INFORMATION: L-CDR1 of A56-03B03

<400> SEQUENCE: 463

Ser Ser Asp Val Gly Gly Tyr Asn Tyr
1               5

<210> SEQ ID NO 464
<211> LENGTH: 3
<212> TYPE: PRT
```

-continued

```
<213> ORGANISM: Artificial Sequence
<220> FEATURE:
<223> OTHER INFORMATION: L-CDR2 of A56-03B03

<400> SEQUENCE: 464

Asp Val Thr
1

<210> SEQ ID NO 465
<211> LENGTH: 11
<212> TYPE: PRT
<213> ORGANISM: Artificial Sequence
<220> FEATURE:
<223> OTHER INFORMATION: L-CDR3 of A56-03B03

<400> SEQUENCE: 465

Gln Val Trp Asp Ser Ser Ser Asp His Tyr Val
1               5               10

<210> SEQ ID NO 466
<211> LENGTH: 255
<212> TYPE: DNA
<213> ORGANISM: Artificial Sequence
<220> FEATURE:
<223> OTHER INFORMATION: SCFV of A56-03B03

<400> SEQUENCE: 466
caggtgcagc tggtggagtc tgggggctgag gtgaagaagc ctgggtcctc ggttaaagtc     60
tcctgcaaga cttctggcgg caacttcaac agctatgcta tcaactgggt gcgacaggcc    120
cctggacaag ggcttgagtg gatgggaagc atcatcccat tctttactac accaaactac    180
gcacagaaat tccagggcag agtcacgatt accgcggacg aatccacgaa cacagccttc    240
atggaattga gcagt                                                      255

<210> SEQ ID NO 467
<211> LENGTH: 112
<212> TYPE: PRT
<213> ORGANISM: Artificial Sequence
<220> FEATURE:
<223> OTHER INFORMATION: VH2 of A56-03B03

<400> SEQUENCE: 467

Gln Val Gln Leu Val Glu Ser Gly Ala Glu Val Lys Lys Pro Gly Ser
1               5                   10                  15

Ser Val Lys Val Ser Cys Lys Thr Ser Gly Gly Asn Phe Asn Ser Tyr
                20                  25                  30

Ala Ile Asn Trp Val Arg Gln Ala Pro Gly Gln Gly Leu Glu Trp Met
            35                  40                  45

Gly Ser Ile Ile Pro Phe Phe Thr Thr Pro Asn Tyr Ala Gln Lys Phe
        50                  55                  60

Gln Gly Arg Val Thr Ile Thr Ala Asp Glu Ser Thr Asn Thr Ala Phe
65                  70                  75                  80

Met Glu Leu Ser Ser Leu Gly Ser Glu Asp Thr Ala Val Tyr Tyr Cys
                85                  90                  95

Val Thr Arg Gly Ala Gln Gly Arg Gly Thr Leu Val Thr Val Ser Ser
                100                 105                 110

<210> SEQ ID NO 468
<211> LENGTH: 111
<212> TYPE: PRT
<213> ORGANISM: Artificial Sequence
<220> FEATURE:
```

<223> OTHER INFORMATION: VL2 of A56-03B03

<400> SEQUENCE: 468

```
Asn Phe Met Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Gln Leu
        35                  40                  45

Ile Ile Tyr Asp Val Thr Lys Arg Pro Ser Gly Val Ser Asn Arg Phe
    50                  55                  60

Ser Gly Ser Asn Ser Gly Asn Thr Ala Thr Leu Thr Ile Ser Arg Val
65                  70                  75                  80

Glu Ala Gly Asp Glu Ala Asp Tyr Tyr Cys Gln Val Trp Asp Ser Ser
                85                  90                  95

Ser Asp His Tyr Val Phe Gly Thr Gly Thr Lys Val Thr Val Leu
            100                 105                 110
```

<210> SEQ ID NO 469
<211> LENGTH: 25
<212> TYPE: PRT
<213> ORGANISM: Artificial Sequence
<220> FEATURE:
<223> OTHER INFORMATION: H-FR1 of A56-03B03

<400> SEQUENCE: 469

```
Gln Val Gln Leu Val Glu Ser Gly Ala Glu Val Lys Lys Pro Gly Ser
1               5                   10                  15

Ser Val Lys Val Ser Cys Lys Thr Ser
            20                  25
```

<210> SEQ ID NO 470
<211> LENGTH: 17
<212> TYPE: PRT
<213> ORGANISM: Artificial Sequence
<220> FEATURE:
<223> OTHER INFORMATION: H-FR2 of A56-03B03

<400> SEQUENCE: 470

```
Ile Asn Trp Val Arg Gln Ala Pro Gly Gln Gly Leu Glu Trp Met Gly
1               5                   10                  15

Ser
```

<210> SEQ ID NO 471
<211> LENGTH: 38
<212> TYPE: PRT
<213> ORGANISM: Artificial Sequence
<220> FEATURE:
<223> OTHER INFORMATION: H-FR3 of A56-03B03

<400> SEQUENCE: 471

```
Asn Tyr Ala Gln Lys Phe Gln Gly Arg Val Thr Ile Thr Ala Asp Glu
1               5                   10                  15

Ser Thr Asn Thr Ala Phe Met Glu Leu Ser Ser Leu Gly Ser Glu Asp
            20                  25                  30

Thr Ala Val Tyr Tyr Cys
        35
```

<210> SEQ ID NO 472
<211> LENGTH: 11
<212> TYPE: PRT

-continued

```
<213> ORGANISM: Artificial Sequence
<220> FEATURE:
<223> OTHER INFORMATION: H-FR4 of A56-03B03

<400> SEQUENCE: 472

Gln Gly Arg Gly Thr Leu Val Thr Val Ser Ser
1               5                   10

<210> SEQ ID NO 473
<211> LENGTH: 25
<212> TYPE: PRT
<213> ORGANISM: Artificial Sequence
<220> FEATURE:
<223> OTHER INFORMATION: L-FR1 of A56-03B03

<400> SEQUENCE: 473

Asn Phe Met Leu Thr Gln Pro Ala Ser Val Ser Gly Ser Pro Gly Gln
1               5                   10                  15

Ser Ile Thr Ile Ser Cys Thr Gly Ser
            20                  25

<210> SEQ ID NO 474
<211> LENGTH: 17
<212> TYPE: PRT
<213> ORGANISM: Artificial Sequence
<220> FEATURE:
<223> OTHER INFORMATION: L-FR2 of A56-03B03

<400> SEQUENCE: 474

Val Ser Trp Tyr Gln Gln His Pro Gly Lys Ala Pro Gln Leu Ile Ile
1               5                   10                  15

Tyr

<210> SEQ ID NO 475
<211> LENGTH: 36
<212> TYPE: PRT
<213> ORGANISM: Artificial Sequence
<220> FEATURE:
<223> OTHER INFORMATION: L-FR3 of A56-03B03

<400> SEQUENCE: 475

Ile Tyr Asp Val Thr Lys Arg Pro Ser Gly Val Ser Asn Arg Phe Ser
1               5                   10                  15

Gly Ser Asn Ser Gly Asn Thr Ala Thr Leu Thr Ile Ser Arg Val Glu
            20                  25                  30

Ala Gly Asp Glu
        35

<210> SEQ ID NO 476
<211> LENGTH: 10
<212> TYPE: PRT
<213> ORGANISM: Artificial Sequence
<220> FEATURE:
<223> OTHER INFORMATION: L-FR4 of A56-03B03

<400> SEQUENCE: 476

Phe Gly Thr Gly Thr Lys Val Thr Val Leu
1               5                   10

<210> SEQ ID NO 477
<211> LENGTH: 8
<212> TYPE: PRT
<213> ORGANISM: Artificial Sequence
<220> FEATURE:
<223> OTHER INFORMATION: H-CDR1 of A56-03D02
```

<400> SEQUENCE: 477

Gly Phe Thr Phe Ser Ser Tyr Ala
1               5

<210> SEQ ID NO 478
<211> LENGTH: 8
<212> TYPE: PRT
<213> ORGANISM: Artificial Sequence
<220> FEATURE:
<223> OTHER INFORMATION: H-CDR2 of A56-03D02

<400> SEQUENCE: 478

Ile Ser Tyr Asp Gly Ser Asn Lys
1               5

<210> SEQ ID NO 479
<211> LENGTH: 15
<212> TYPE: PRT
<213> ORGANISM: Artificial Sequence
<220> FEATURE:
<223> OTHER INFORMATION: H-CDR3 of A56-03D02

<400> SEQUENCE: 479

Ala Arg Asp Ala Ala Ala Met Ile Ser Pro His Gly Met Asp Val
1               5                   10                  15

<210> SEQ ID NO 480
<211> LENGTH: 11
<212> TYPE: PRT
<213> ORGANISM: Artificial Sequence
<220> FEATURE:
<223> OTHER INFORMATION: L-CDR1 of A56-03D02

<400> SEQUENCE: 480

Gln Ser Leu Val His Ser Asp Gly Asn Ile Tyr
1               5                   10

<210> SEQ ID NO 481
<211> LENGTH: 3
<212> TYPE: PRT
<213> ORGANISM: Artificial Sequence
<220> FEATURE:
<223> OTHER INFORMATION: L-CDR2 of A56-03D02

<400> SEQUENCE: 481

Lys Val Ser
1

<210> SEQ ID NO 482
<211> LENGTH: 9
<212> TYPE: PRT
<213> ORGANISM: Artificial Sequence
<220> FEATURE:
<223> OTHER INFORMATION: L-CDR3 of A56-03D02

<400> SEQUENCE: 482

Met Gln Gly Thr Gln Trp Pro Pro Thr
1               5

<210> SEQ ID NO 483
<211> LENGTH: 255
<212> TYPE: DNA
<213> ORGANISM: Artificial Sequence
<220> FEATURE:
<223> OTHER INFORMATION: SCFV of A56-03D02

<400> SEQUENCE: 483
cagatgcagc tggtggagtc tggaggaggc gtggtccagc ctgggaggtc cctgagactc        60
tcctgtgcag cctctggatt caccttcagt agctatgcta tgcactgggt ccgccaggct       120
ccaggcaagg ggctggagtg ggtggcagtt atatcatatg atggaagtaa taaatactac       180
gcagactccg tgaagggccg attcaccatc tccagagaca attccaagaa cacgctgtat       240
ctgcaaatga acagc                                                        255

<210> SEQ ID NO 484
<211> LENGTH: 122
<212> TYPE: PRT
<213> ORGANISM: Artificial Sequence
<220> FEATURE:
<223> OTHER INFORMATION: VH2 of A56-03D02

<400> SEQUENCE: 484

Gln Met Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Arg Asp Ala Ala Ala Met Ile Ser Pro His Gly Met Asp Val Trp
            100                 105                 110

Gly Gln Gly Thr Thr Val Thr Val Ser Ser
            115                 120

<210> SEQ ID NO 485
<211> LENGTH: 112
<212> TYPE: PRT
<213> ORGANISM: Artificial Sequence
<220> FEATURE:
<223> OTHER INFORMATION: VL2 of A56-03D02

<400> SEQUENCE: 485

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Ile Tyr Leu Asn Trp Phe Gln Gln Arg Pro Gly Gln Ser
            35                  40                  45

Pro Arg Arg Leu Ile Tyr Lys Val Ser Asn Arg Gly Ser Gly Val Pro
        50                  55                  60

Asp Arg Phe Ser Gly Ser Gly Ser Gly Thr Asp Phe Thr Leu Glu Ile
65                  70                  75                  80

Ser Arg Val Glu Ala Glu Asp Val Ala Val Tyr Tyr Cys Met Gln Gly
                85                  90                  95

Thr Gln Trp Pro Pro Thr Phe Gly Gln Gly Thr Lys Leu Glu Ile Lys
            100                 105                 110

<210> SEQ ID NO 486

-continued

<211> LENGTH: 25
<212> TYPE: PRT
<213> ORGANISM: Artificial Sequence
<220> FEATURE:
<223> OTHER INFORMATION: H-FR1 of A56-03D02

<400> SEQUENCE: 486

Gln Met Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 487
<211> LENGTH: 17
<212> TYPE: PRT
<213> ORGANISM: Artificial Sequence
<220> FEATURE:
<223> OTHER INFORMATION: H-FR2 of A56-03D02

<400> SEQUENCE: 487

Met His Trp Val Arg Gln Ala Pro Gly Lys Gly Leu Glu Trp Val Ala
1               5                   10                  15

Val

<210> SEQ ID NO 488
<211> LENGTH: 38
<212> TYPE: PRT
<213> ORGANISM: Artificial Sequence
<220> FEATURE:
<223> OTHER INFORMATION: H-FR3 of A56-03D02

<400> SEQUENCE: 488

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ser Glu Asp
            20                  25                  30

Thr Ala Val Tyr Tyr Cys
        35

<210> SEQ ID NO 489
<211> LENGTH: 11
<212> TYPE: PRT
<213> ORGANISM: Artificial Sequence
<220> FEATURE:
<223> OTHER INFORMATION: H-FR4 of A56-03D02

<400> SEQUENCE: 489

Trp Gly Gln Gly Thr Thr Val Thr Val Ser Ser
1               5                   10

<210> SEQ ID NO 490
<211> LENGTH: 26
<212> TYPE: PRT
<213> ORGANISM: Artificial Sequence
<220> FEATURE:
<223> OTHER INFORMATION: L-FR1 of A56-03D02

<400> SEQUENCE: 490

Asp Ile Val Met Thr Gln Ser Pro Leu Ser Leu Pro Val Thr Leu Gly
1               5                   10                  15

Gln Pro Ala Ser Ile Ser Cys Arg Ser Ser
            20                  25

<210> SEQ ID NO 491

-continued

```
<211> LENGTH: 17
<212> TYPE: PRT
<213> ORGANISM: Artificial Sequence
<220> FEATURE:
<223> OTHER INFORMATION: L-FR2 of A56-03D02

<400> SEQUENCE: 491

Leu Asn Trp Phe Gln Gln Arg Pro Gly Gln Ser Pro Arg Arg Leu Ile
1               5                   10                  15

Tyr

<210> SEQ ID NO 492
<211> LENGTH: 36
<212> TYPE: PRT
<213> ORGANISM: Artificial Sequence
<220> FEATURE:
<223> OTHER INFORMATION: L-FR3 of A56-03D02

<400> SEQUENCE: 492

Ile Tyr Lys Val Ser Asn Arg Gly Ser Gly Val Pro Asp Arg Phe Ser
1               5                   10                  15

Gly Ser Gly Ser Gly Thr Asp Phe Thr Leu Glu Ile Ser Arg Val Glu
            20                  25                  30

Ala Glu Asp Val
        35

<210> SEQ ID NO 493
<211> LENGTH: 10
<212> TYPE: PRT
<213> ORGANISM: Artificial Sequence
<220> FEATURE:
<223> OTHER INFORMATION: L-FR4 of A56-03D02

<400> SEQUENCE: 493

Phe Gly Gln Gly Thr Lys Leu Glu Ile Lys
1               5                   10

<210> SEQ ID NO 494
<211> LENGTH: 8
<212> TYPE: PRT
<213> ORGANISM: Artificial Sequence
<220> FEATURE:
<223> OTHER INFORMATION: H-CDR1 of A56-03H11

<400> SEQUENCE: 494

Gly Phe Thr Phe Ser Ser Tyr Ala
1               5

<210> SEQ ID NO 495
<211> LENGTH: 8
<212> TYPE: PRT
<213> ORGANISM: Artificial Sequence
<220> FEATURE:
<223> OTHER INFORMATION: H-CDR2 of A56-03H11

<400> SEQUENCE: 495

Ile Ser Tyr Asp Gly Ser Asn Lys
1               5

<210> SEQ ID NO 496
<211> LENGTH: 16
<212> TYPE: PRT
<213> ORGANISM: Artificial Sequence
<220> FEATURE:
<223> OTHER INFORMATION: H-CDR3 of A56-03H11
```

-continued

```
<400> SEQUENCE: 496

Thr Pro Phe Gln His Asp Ser Val Pro Arg Arg Gly Ala Phe Asp Leu
1               5                   10                  15

<210> SEQ ID NO 497
<211> LENGTH: 12
<212> TYPE: PRT
<213> ORGANISM: Artificial Sequence
<220> FEATURE:
<223> OTHER INFORMATION: L-CDR1 of A56-03H11

<400> SEQUENCE: 497

Gln Ser Leu Leu Ser Ser Ser Asn Asn Lys Asn Tyr
1               5                   10

<210> SEQ ID NO 498
<211> LENGTH: 3
<212> TYPE: PRT
<213> ORGANISM: Artificial Sequence
<220> FEATURE:
<223> OTHER INFORMATION: L-CDR2 of A56-03H11

<400> SEQUENCE: 498

Trp Ala Ser
1

<210> SEQ ID NO 499
<211> LENGTH: 9
<212> TYPE: PRT
<213> ORGANISM: Artificial Sequence
<220> FEATURE:
<223> OTHER INFORMATION: L-CDR3 of A56-03H11

<400> SEQUENCE: 499

Gln Gln Tyr Tyr Thr Ser Pro Arg Thr
1               5

<210> SEQ ID NO 500
<211> LENGTH: 255
<212> TYPE: DNA
<213> ORGANISM: Artificial Sequence
<220> FEATURE:
<223> OTHER INFORMATION: SCFV of A56-03H11

<400> SEQUENCE: 500
caggtgcagc tggtggagtc tggggggaggc gtggtccagc ctggggaggtc cctgagactc      60 tcctgtgcag cctctggatt caccttcagt agctatgcta tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagt                                                      255

<210> SEQ ID NO 501
<211> LENGTH: 123
<212> TYPE: PRT
<213> ORGANISM: Artificial Sequence
<220> FEATURE:
<223> OTHER INFORMATION: VH2 of A56-03H11

<400> SEQUENCE: 501

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Pro Phe Gln His Asp Ser Val Pro Arg Arg Gly Ala Phe Asp Leu
            100                 105                 110

Trp Gly Gln Gly Thr Lys Ile Thr Val Ser Ser
        115                 120
```

```
<210> SEQ ID NO 502
<211> LENGTH: 113
<212> TYPE: PRT
<213> ORGANISM: Artificial Sequence
<220> FEATURE:
<223> OTHER INFORMATION: VL2 of A56-03H11

<400> SEQUENCE: 502

Asp Ile Gln Met Thr Gln Ser Pro Ser Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Ser Asn Asn Lys Asn Tyr Leu Ala Trp Tyr Gln His Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Ser Pro Arg Thr Phe Gly Gln Gly Thr Lys Val Glu Ile
            100                 105                 110

Lys
```

```
<210> SEQ ID NO 503
<211> LENGTH: 25
<212> TYPE: PRT
<213> ORGANISM: Artificial Sequence
<220> FEATURE:
<223> OTHER INFORMATION: H-FR1 of A56-03H11

<400> SEQUENCE: 503

Gln Val Gln Leu Val Glu Ser Gly Gly Gly Val Val Gln Pro Gly Arg
1               5                   10                  15

Ser Leu Arg Leu Ser Cys Ala Ala Ser
            20                  25
```

```
<210> SEQ ID NO 504
<211> LENGTH: 17
<212> TYPE: PRT
<213> ORGANISM: Artificial Sequence
<220> FEATURE:
<223> OTHER INFORMATION: H-FR2 of A56-03H11

<400> SEQUENCE: 504

Met His Trp Val Arg Gln Ala Pro Gly Lys Gly Leu Glu Trp Val Ala
```

-continued

```
1               5              10             15

Val

<210> SEQ ID NO 505
<211> LENGTH: 38
<212> TYPE: PRT
<213> ORGANISM: Artificial Sequence
<220> FEATURE:
<223> OTHER INFORMATION: H-FR3 of A56-03H11

<400> SEQUENCE: 505

Tyr Tyr Ala Asp Ser Val Lys Gly Arg Phe Thr Ile Ser Arg Asp Asn
1               5              10             15

Ser Lys Asn Thr Leu Tyr Leu Gln Met Asn Ser Leu Arg Ala Glu Asp
            20             25             30

Thr Ala Val Tyr Tyr Cys
        35

<210> SEQ ID NO 506
<211> LENGTH: 11
<212> TYPE: PRT
<213> ORGANISM: Artificial Sequence
<220> FEATURE:
<223> OTHER INFORMATION: H-FR4 of A56-03H11

<400> SEQUENCE: 506

Trp Gly Gln Gly Thr Lys Ile Thr Val Ser Ser
1               5              10

<210> SEQ ID NO 507
<211> LENGTH: 26
<212> TYPE: PRT
<213> ORGANISM: Artificial Sequence
<220> FEATURE:
<223> OTHER INFORMATION: L-FR1 of A56-03H11

<400> SEQUENCE: 507

Asp Ile Gln Met Thr Gln Ser Pro Ser Ser Leu Ala Val Ser Leu Gly
1               5              10             15

Glu Arg Ala Thr Ile Asn Cys Lys Ser Ser
            20             25

<210> SEQ ID NO 508
<211> LENGTH: 17
<212> TYPE: PRT
<213> ORGANISM: Artificial Sequence
<220> FEATURE:
<223> OTHER INFORMATION: L-FR2 of A56-03H11

<400> SEQUENCE: 508

Leu Ala Trp Tyr Gln His Lys Pro Gly Gln Pro Pro Lys Leu Leu Ile
1               5              10             15

Tyr

<210> SEQ ID NO 509
<211> LENGTH: 36
<212> TYPE: PRT
<213> ORGANISM: Artificial Sequence
<220> FEATURE:
<223> OTHER INFORMATION: L-FR3 of A56-03H11

<400> SEQUENCE: 509

Ile Tyr Trp Ala Ser Thr Arg Glu Ser Gly Val Pro Asp Arg Phe Ser
1               5              10             15
```

```
Gly Ser Gly Ser Gly Thr Asp Phe Thr Leu Thr Ile Ser Ser Leu Gln
            20                  25                  30

Ala Glu Asp Val
        35

<210> SEQ ID NO 510
<211> LENGTH: 10
<212> TYPE: PRT
<213> ORGANISM: Artificial Sequence
<220> FEATURE:
<223> OTHER INFORMATION: L-FR4 of A56-03H11

<400> SEQUENCE: 510

Phe Gly Gln Gly Thr Lys Val Glu Ile Lys
1               5                  10

<210> SEQ ID NO 511
<211> LENGTH: 8
<212> TYPE: PRT
<213> ORGANISM: Artificial Sequence
<220> FEATURE:
<223> OTHER INFORMATION: H-CDR1 of A56-07A09

<400> SEQUENCE: 511

Gly Gly Thr Phe Thr Arg Asp Ala
1               5

<210> SEQ ID NO 512
<211> LENGTH: 8
<212> TYPE: PRT
<213> ORGANISM: Artificial Sequence
<220> FEATURE:
<223> OTHER INFORMATION: H-CDR2 of A56-07A09

<400> SEQUENCE: 512

Ile Ile Pro Leu Ile Asp Thr Ala
1               5

<210> SEQ ID NO 513
<211> LENGTH: 17
<212> TYPE: PRT
<213> ORGANISM: Artificial Sequence
<220> FEATURE:
<223> OTHER INFORMATION: H-CDR3 of A56-07A09

<400> SEQUENCE: 513

Ala Arg Gly Glu Met Tyr Ser Arg Ser Trp Tyr Trp Gly Ala Phe Asp
1               5                  10                  15

Leu

<210> SEQ ID NO 514
<211> LENGTH: 9
<212> TYPE: PRT
<213> ORGANISM: Artificial Sequence
<220> FEATURE:
<223> OTHER INFORMATION: L-CDR1 of A56-07A09

<400> SEQUENCE: 514

Ser Ser Asp Val Gly Gly Tyr Asn Tyr
1               5

<210> SEQ ID NO 515
<211> LENGTH: 3
<212> TYPE: PRT
<213> ORGANISM: Artificial Sequence
```

```
<220> FEATURE:
<223> OTHER INFORMATION: L-CDR2 of A56-07A09

<400> SEQUENCE: 515

Asp Val Thr
1

<210> SEQ ID NO 516
<211> LENGTH: 10
<212> TYPE: PRT
<213> ORGANISM: Artificial Sequence
<220> FEATURE:
<223> OTHER INFORMATION: L-CDR3 of A56-07A09

<400> SEQUENCE: 516

Ser Ser Tyr Ser Ser Ser Thr Phe Tyr Val
1               5                   10

<210> SEQ ID NO 517
<211> LENGTH: 255
<212> TYPE: DNA
<213> ORGANISM: Artificial Sequence
<220> FEATURE:
<223> OTHER INFORMATION: SCFV of A56-07A09

<400> SEQUENCE: 517
caggtgcagc tggtagagtc tgggggctgag gtgaagaagc ctgggtcttc ggtgaaggtc      60
tcctgcaagg tttctggagg caccttcacc agggatgcta tcagttgggt gcgacaggcc     120
cctggacaag ggcttgagtg gatgggaagg atcatccctc tcattgatac agcaaattac     180
gcacagaagt tccagggcag agtcacgatt accgcggaca atccacgag cacagcctac      240 atgagtctaa gcagc                                                      255

<210> SEQ ID NO 518
<211> LENGTH: 124
<212> TYPE: PRT
<213> ORGANISM: Artificial Sequence
<220> FEATURE:
<223> OTHER INFORMATION: VH2 of A56-07A09

<400> SEQUENCE: 518

Gln Val Gln Leu Val Glu Ser Gly Ala Glu Val Lys Lys Pro Gly Ser
1               5                   10                  15

Ser Val Lys Val Ser Cys Lys Val Ser Gly Gly Thr Phe Thr Arg Asp
            20                  25                  30

Ala Ile Ser Trp Val Arg Gln Ala Pro Gly Gln Gly Leu Glu Trp Met
        35                  40                  45

Gly Arg Ile Ile Pro Leu Ile Asp Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Ser Leu Ser Ser Leu Gly Ser Glu Asp Thr Ala Val Tyr Tyr Cys
                85                  90                  95

Ala Arg Gly Glu Met Tyr Ser Arg Ser Trp Tyr Trp Gly Ala Phe Asp
            100                 105                 110

Leu Trp Gly Gln Gly Thr Met Val Thr Val Ser Ser
        115                 120

<210> SEQ ID NO 519
<211> LENGTH: 110
<212> TYPE: PRT
```

```
<213> ORGANISM: Artificial Sequence
<220> FEATURE:
<223> OTHER INFORMATION: VL2 of A56-07A09

<400> SEQUENCE: 519

Asn Phe Met Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Gln Leu
        35                  40                  45

Ile Ile Tyr Asp Val Thr Lys Arg Pro Ser Gly Val Ser Asn Arg Phe
    50                  55                  60

Ser Gly Ser Lys Ser Gly Asn Ser Ala Ser Leu Thr Ile Ser Gly Leu
65                  70                  75                  80

Gln Ala Glu Asp Glu Ala Asp Tyr Tyr Cys Ser Ser Tyr Ser Ser Ser
                85                  90                  95

Thr Phe Tyr Val Phe Gly Thr Gly Thr Lys Val Thr Val Leu
            100                 105                 110

<210> SEQ ID NO 520
<211> LENGTH: 25
<212> TYPE: PRT
<213> ORGANISM: Artificial Sequence
<220> FEATURE:
<223> OTHER INFORMATION: H-FR1 of A56-07A09

<400> SEQUENCE: 520

Gln Val Gln Leu Val Glu Ser Gly Ala Glu Val Lys Lys Pro Gly Ser
1               5                   10                  15

Ser Val Lys Val Ser Cys Lys Val Ser
            20                  25

<210> SEQ ID NO 521
<211> LENGTH: 17
<212> TYPE: PRT
<213> ORGANISM: Artificial Sequence
<220> FEATURE:
<223> OTHER INFORMATION: H-FR2 of A56-07A09

<400> SEQUENCE: 521

Ile Ser Trp Val Arg Gln Ala Pro Gly Gln Gly Leu Glu Trp Met Gly
1               5                   10                  15

Arg

<210> SEQ ID NO 522
<211> LENGTH: 38
<212> TYPE: PRT
<213> ORGANISM: Artificial Sequence
<220> FEATURE:
<223> OTHER INFORMATION: H-FR3 of A56-07A09

<400> SEQUENCE: 522

Asn Tyr Ala Gln Lys Phe Gln Gly Arg Val Thr Ile Thr Ala Asp Lys
1               5                   10                  15

Ser Thr Ser Thr Ala Tyr Met Ser Leu Ser Ser Leu Gly Ser Glu Asp
            20                  25                  30

Thr Ala Val Tyr Tyr Cys
        35

<210> SEQ ID NO 523
```

-continued

```
<211> LENGTH: 11
<212> TYPE: PRT
<213> ORGANISM: Artificial Sequence
<220> FEATURE:
<223> OTHER INFORMATION: H-FR4 of A56-07A09

<400> SEQUENCE: 523

Trp Gly Gln Gly Thr Met Val Thr Val Ser Ser
1               5                   10

<210> SEQ ID NO 524
<211> LENGTH: 25
<212> TYPE: PRT
<213> ORGANISM: Artificial Sequence
<220> FEATURE:
<223> OTHER INFORMATION: L-FR1 of A56-07A09

<400> SEQUENCE: 524

Asn Phe Met Leu Thr Gln Pro Ala Ser Val Ser Gly Ser Pro Gly Gln
1               5                   10                  15

Ser Ile Thr Ile Ser Cys Thr Gly Ser
            20                  25

<210> SEQ ID NO 525
<211> LENGTH: 17
<212> TYPE: PRT
<213> ORGANISM: Artificial Sequence
<220> FEATURE:
<223> OTHER INFORMATION: L-FR2 of A56-07A09

<400> SEQUENCE: 525

Val Ser Trp Tyr Gln Gln His Pro Gly Lys Ala Pro Gln Leu Ile Ile
1               5                   10                  15

Tyr

<210> SEQ ID NO 526
<211> LENGTH: 36
<212> TYPE: PRT
<213> ORGANISM: Artificial Sequence
<220> FEATURE:
<223> OTHER INFORMATION: L-FR3 of A56-07A09

<400> SEQUENCE: 526

Ile Tyr Asp Val Thr Lys Arg Pro Ser Gly Val Ser Asn Arg Phe Ser
1               5                   10                  15

Gly Ser Lys Ser Gly Asn Ser Ala Ser Leu Thr Ile Ser Gly Leu Gln
            20                  25                  30

Ala Glu Asp Glu
        35

<210> SEQ ID NO 527
<211> LENGTH: 10
<212> TYPE: PRT
<213> ORGANISM: Artificial Sequence
<220> FEATURE:
<223> OTHER INFORMATION: L-FR4 of A56-07A09

<400> SEQUENCE: 527

Phe Gly Thr Gly Thr Lys Val Thr Val Leu
1               5                   10

<210> SEQ ID NO 528
<211> LENGTH: 8
<212> TYPE: PRT
<213> ORGANISM: Artificial Sequence
```

-continued

```
<220> FEATURE:
<223> OTHER INFORMATION: H-CDR1 of A56-08A01

<400> SEQUENCE: 528

Gly Phe Ser Phe Ser Asn Tyr Gly
1               5

<210> SEQ ID NO 529
<211> LENGTH: 8
<212> TYPE: PRT
<213> ORGANISM: Artificial Sequence
<220> FEATURE:
<223> OTHER INFORMATION: H-CDR2 of A56-08A01

<400> SEQUENCE: 529

Val Ser Phe Asp Gly Ile Lys Lys
1               5

<210> SEQ ID NO 530
<211> LENGTH: 17
<212> TYPE: PRT
<213> ORGANISM: Artificial Sequence
<220> FEATURE:
<223> OTHER INFORMATION: H-CDR3 of A56-08A01

<400> SEQUENCE: 530

Ala Lys Ala Pro Val Tyr Cys Ser Gly Asp Cys Arg Phe Ala Phe Asp
1               5                   10                  15

Phe

<210> SEQ ID NO 531
<211> LENGTH: 11
<212> TYPE: PRT
<213> ORGANISM: Artificial Sequence
<220> FEATURE:
<223> OTHER INFORMATION: L-CDR1 of A56-08A01

<400> SEQUENCE: 531

Gln Ser Leu Leu His Ser Asp Gly Lys Thr Tyr
1               5                   10

<210> SEQ ID NO 532
<211> LENGTH: 3
<212> TYPE: PRT
<213> ORGANISM: Artificial Sequence
<220> FEATURE:
<223> OTHER INFORMATION: L-CDR2 of A56-08A01

<400> SEQUENCE: 532

Glu Val Ser
1

<210> SEQ ID NO 533
<211> LENGTH: 6
<212> TYPE: PRT
<213> ORGANISM: Artificial Sequence
<220> FEATURE:
<223> OTHER INFORMATION: L-CDR3 of A56-08A01

<400> SEQUENCE: 533

Met Gln Gly Ser Tyr Thr
1               5

<210> SEQ ID NO 534
<211> LENGTH: 255
<212> TYPE: DNA
```

-continued

<213> ORGANISM: Artificial Sequence
<220> FEATURE:
<223> OTHER INFORMATION: SCFV of A56-08A01

<400> SEQUENCE: 534
caggtgcagc tggtggagtc aggggggaggc gtggtccagc ctgggaggtc cctgagactc      60
tcctgtgcag cctctggatt cagtttcagt aattatggca tgcactgggt ccgccaggct     120
ccaggcaagg ggctgcagtg ggtggcaacc gtctcttttg atggaataaa aaaacattat     180
tcagactccg tgaagggccg tttcaccatc tccagagaca attccaagaa cacgctgtat     240
ctccaaatga acagt                                                      255

<210> SEQ ID NO 535
<211> LENGTH: 124
<212> TYPE: PRT
<213> ORGANISM: Artificial Sequence
<220> FEATURE:
<223> OTHER INFORMATION: VH2 of A56-08A01

<400> SEQUENCE: 535

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
                20                  25                  30

Gly Met His Trp Val Arg Gln Ala Pro Gly Lys Gly Leu Gln Trp Val
            35                  40                  45

Ala Thr Val Ser Phe Asp Gly Ile Lys Lys His Tyr Ser Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Val Tyr Cys Ser Gly Asp Cys Arg Phe Ala Phe Asp
            100                 105                 110

Phe Trp Gly Leu Gly Thr Thr Val Thr Val Ser Ser
        115                 120

<210> SEQ ID NO 536
<211> LENGTH: 109
<212> TYPE: PRT
<213> ORGANISM: Artificial Sequence
<220> FEATURE:
<223> OTHER INFORMATION: VL2 of A56-08A01

<400> SEQUENCE: 536

Asp Ile Val Met Thr Gln Thr Pro Leu Ser Leu Ser Val Thr Pro Gly
1               5                   10                  15

Gln Ser Ala Ser Ile Ser Cys Lys Ser Ser Gln Ser Leu Leu His Ser
                20                  25                  30

Asp Gly Lys Thr Tyr Leu Tyr Trp Tyr Leu Gln Arg Pro Gly Gln Ser
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Asn Ile
65                  70                  75                  80

Ser Arg Val Glu Ala Glu Asp Val Gly Ile Tyr Tyr Cys Met Gln Gly
                85                  90                  95

Ser Tyr Thr Phe Gly Gln Gly Thr Lys Val Asp Ile Lys

-continued

```
                100                 105

<210> SEQ ID NO 537
<211> LENGTH: 25
<212> TYPE: PRT
<213> ORGANISM: Artificial Sequence
<220> FEATURE:
<223> OTHER INFORMATION: H-FR1 of A56-08A01

<400> SEQUENCE: 537

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 538
<211> LENGTH: 17
<212> TYPE: PRT
<213> ORGANISM: Artificial Sequence
<220> FEATURE:
<223> OTHER INFORMATION: H-FR2 of A56-08A01

<400> SEQUENCE: 538

Met His Trp Val Arg Gln Ala Pro Gly Lys Gly Leu Gln Trp Val Ala
1               5                   10                  15

Thr

<210> SEQ ID NO 539
<211> LENGTH: 38
<212> TYPE: PRT
<213> ORGANISM: Artificial Sequence
<220> FEATURE:
<223> OTHER INFORMATION: H-FR3 of A56-08A01

<400> SEQUENCE: 539

His Tyr Ser Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 540
<211> LENGTH: 11
<212> TYPE: PRT
<213> ORGANISM: Artificial Sequence
<220> FEATURE:
<223> OTHER INFORMATION: H-FR4 of A56-08A01

<400> SEQUENCE: 540

Trp Gly Leu Gly Thr Thr Val Thr Val Ser Ser
1               5                   10

<210> SEQ ID NO 541
<211> LENGTH: 26
<212> TYPE: PRT
<213> ORGANISM: Artificial Sequence
<220> FEATURE:
<223> OTHER INFORMATION: L-FR1 of A56-08A01

<400> SEQUENCE: 541

Asp Ile Val Met Thr Gln Thr Pro Leu Ser Leu Ser Val Thr Pro Gly
1               5                   10                  15

Gln Ser Ala Ser Ile Ser Cys Lys Ser Ser
```

```
              20                  25

<210> SEQ ID NO 542
<211> LENGTH: 17
<212> TYPE: PRT
<213> ORGANISM: Artificial Sequence
<220> FEATURE:
<223> OTHER INFORMATION: L-FR2 of A56-08A01

<400> SEQUENCE: 542

Leu Tyr Trp Tyr Leu Gln Arg Pro Gly Gln Ser Pro Gln Leu Leu Ile
1               5                   10                  15

Tyr

<210> SEQ ID NO 543
<211> LENGTH: 36
<212> TYPE: PRT
<213> ORGANISM: Artificial Sequence
<220> FEATURE:
<223> OTHER INFORMATION: L-FR3 of A56-08A01

<400> SEQUENCE: 543

Ile Tyr Glu Val Ser Asn Arg Phe Ser Gly Val Pro Asp Arg Phe Ser
1               5                   10                  15

Gly Ser Gly Ser Gly Thr Asp Phe Thr Leu Asn Ile Ser Arg Val Glu
            20                  25                  30

Ala Glu Asp Val
        35

<210> SEQ ID NO 544
<211> LENGTH: 10
<212> TYPE: PRT
<213> ORGANISM: Artificial Sequence
<220> FEATURE:
<223> OTHER INFORMATION: L-FR4 of A56-08A01

<400> SEQUENCE: 544

Phe Gly Gln Gly Thr Lys Val Asp Ile Lys
1               5                   10

<210> SEQ ID NO 545
<211> LENGTH: 8
<212> TYPE: PRT
<213> ORGANISM: Artificial Sequence
<220> FEATURE:
<223> OTHER INFORMATION: H-CDR1 of A56-10A01

<400> SEQUENCE: 545

Gly Tyr Thr Phe Thr His Tyr Asp
1               5

<210> SEQ ID NO 546
<211> LENGTH: 8
<212> TYPE: PRT
<213> ORGANISM: Artificial Sequence
<220> FEATURE:
<223> OTHER INFORMATION: H-CDR2 of A56-10A01

<400> SEQUENCE: 546

Met Asn Pro Asn Lys Gly Asn Thr
1               5

<210> SEQ ID NO 547
<211> LENGTH: 20
<212> TYPE: PRT
```

<213> ORGANISM: Artificial Sequence
<220> FEATURE:
<223> OTHER INFORMATION: H-CDR3 of A56-10A01

<400> SEQUENCE: 547

Ala Arg Glu Arg Val Pro Asn Ala Met Val Gly Tyr Phe Ser Phe Tyr
1               5                   10                  15

Gly Met Asp Val
            20

<210> SEQ ID NO 548
<211> LENGTH: 6
<212> TYPE: PRT
<213> ORGANISM: Artificial Sequence
<220> FEATURE:
<223> OTHER INFORMATION: L-CDR1 of A56-10A01

<400> SEQUENCE: 548

Asp Ile Thr Arg Lys Ser
1               5

<210> SEQ ID NO 549
<211> LENGTH: 3
<212> TYPE: PRT
<213> ORGANISM: Artificial Sequence
<220> FEATURE:
<223> OTHER INFORMATION: L-CDR2 of A56-10A01

<400> SEQUENCE: 549

Tyr Asp Arg
1

<210> SEQ ID NO 550
<211> LENGTH: 9
<212> TYPE: PRT
<213> ORGANISM: Artificial Sequence
<220> FEATURE:
<223> OTHER INFORMATION: L-CDR3 of A56-10A01

<400> SEQUENCE: 550

Gln Val Trp Asp Thr Asn Ser Val Val
1               5

<210> SEQ ID NO 551
<211> LENGTH: 255
<212> TYPE: DNA
<213> ORGANISM: Artificial Sequence
<220> FEATURE:
<223> OTHER INFORMATION: SCFV of A56-10A01

<400> SEQUENCE: 551
caggtgcagc tggtgcagtc tggggctgag gtgaagaagc ctgggcctc agtgaaggtc        60 tcctgcaaga cctctggata caccttcacc cattatgata tcaactgggt gcgacaggcc       120
tctggacaag ggcttgagtg gatgggacgg atgaacccga ataagggaaa cacaggctat       180
gctcagaagt tccagggcag agtcaccatg accagggacg cctcgacaga cacagcctac       240
atggagctga gcagc                                                        255

<210> SEQ ID NO 552
<211> LENGTH: 127
<212> TYPE: PRT
<213> ORGANISM: Artificial Sequence
<220> FEATURE:
<223> OTHER INFORMATION: VH2 of A56-10A01

<400> SEQUENCE: 552

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr His Tyr
            20                  25                  30

Asp Ile Asn Trp Val Arg Gln Ala Ser Gly Gln Gly Leu Glu Trp Met
        35                  40                  45

Gly Arg Met Asn Pro Asn Lys Gly Asn Thr Gly Tyr Ala Gln Lys Phe
    50                  55                  60

Gln Gly Arg Val Thr Met Thr Arg Asp Ala Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Val Pro Asn Ala Met Val Gly Tyr Phe Ser Phe Tyr
            100                 105                 110

Gly Met Asp Val Trp Gly Gln Gly Thr Thr Val Thr Val Ser Ser
        115                 120                 125

<210> SEQ ID NO 553
<211> LENGTH: 106
<212> TYPE: PRT
<213> ORGANISM: Artificial Sequence
<220> FEATURE:
<223> OTHER INFORMATION: VL2 of A56-10A01

<400> SEQUENCE: 553

Ser Tyr Glu Leu Thr Gln Ala Pro Ser Leu Ser Val Ala Pro Gly Glu
1               5                   10                  15

Thr Ala Thr Ile Thr Cys Gly Gly Asn Asp Ile Thr Arg Lys Ser Val
            20                  25                  30

His Trp Tyr Gln Gln Arg Pro Gly Gln Ala Pro Val Leu Val Ile Tyr
        35                  40                  45

Tyr Asp Arg Ala Arg Pro Ser Gly Ile Pro Glu Arg Phe Ser Gly Ser
    50                  55                  60

Asn Ser Glu Asn Thr Ala Ser Leu Thr Ile Ser Arg Val Glu Ala Gly
65                  70                  75                  80

Asp Glu Ala Asp Tyr Tyr Cys Gln Val Trp Asp Thr Asn Ser Val Val
                85                  90                  95

Phe Gly Gly Gly Thr Lys Leu Thr Val Leu
            100                 105

<210> SEQ ID NO 554
<211> LENGTH: 25
<212> TYPE: PRT
<213> ORGANISM: Artificial Sequence
<220> FEATURE:
<223> OTHER INFORMATION: H-FR1 of A56-10A01

<400> SEQUENCE: 554

Gln Val Gln Leu Val Gln Ser Gly Ala Glu Val Lys Lys Pro Gly Ala
1               5                   10                  15

Ser Val Lys Val Ser Cys Lys Thr Ser
            20                  25

<210> SEQ ID NO 555
<211> LENGTH: 17
<212> TYPE: PRT
<213> ORGANISM: Artificial Sequence
<220> FEATURE:

-continued

```
<223> OTHER INFORMATION: H-FR2 of A56-10A01

<400> SEQUENCE: 555

Ile Asn Trp Val Arg Gln Ala Ser Gly Gln Gly Leu Glu Trp Met Gly
1               5                   10                  15

Arg

<210> SEQ ID NO 556
<211> LENGTH: 38
<212> TYPE: PRT
<213> ORGANISM: Artificial Sequence
<220> FEATURE:
<223> OTHER INFORMATION: H-FR3 of A56-10A01

<400> SEQUENCE: 556

Gly Tyr Ala Gln Lys Phe Gln Gly Arg Val Thr Met Thr Arg Asp Ala
1               5                   10                  15

Ser Thr Asp Thr Ala Tyr Met Glu Leu Ser Ser Leu Arg Ser Glu Asp
            20                  25                  30

Thr Ala Val Tyr Tyr Cys
        35

<210> SEQ ID NO 557
<211> LENGTH: 11
<212> TYPE: PRT
<213> ORGANISM: Artificial Sequence
<220> FEATURE:
<223> OTHER INFORMATION: H-FR4 of A56-10A01

<400> SEQUENCE: 557

Trp Gly Gln Gly Thr Thr Val Thr Val Ser Ser
1               5                   10

<210> SEQ ID NO 558
<211> LENGTH: 25
<212> TYPE: PRT
<213> ORGANISM: Artificial Sequence
<220> FEATURE:
<223> OTHER INFORMATION: L-FR1 of A56-10A01

<400> SEQUENCE: 558

Ser Tyr Glu Leu Thr Gln Ala Pro Ser Leu Ser Val Ala Pro Gly Glu
1               5                   10                  15

Thr Ala Thr Ile Thr Cys Gly Gly Asn
            20                  25

<210> SEQ ID NO 559
<211> LENGTH: 17
<212> TYPE: PRT
<213> ORGANISM: Artificial Sequence
<220> FEATURE:
<223> OTHER INFORMATION: L-FR2 of A56-10A01

<400> SEQUENCE: 559

Val His Trp Tyr Gln Gln Arg Pro Gly Gln Ala Pro Val Leu Val Ile
1               5                   10                  15

Tyr

<210> SEQ ID NO 560
<211> LENGTH: 36
<212> TYPE: PRT
<213> ORGANISM: Artificial Sequence
<220> FEATURE:
<223> OTHER INFORMATION: L-FR3 of A56-10A01
```

<400> SEQUENCE: 560

Ile Tyr Tyr Asp Arg Ala Arg Pro Ser Gly Ile Pro Glu Arg Phe Ser
1               5                   10                  15

Gly Ser Asn Ser Glu Asn Thr Ala Ser Leu Thr Ile Ser Arg Val Glu
            20                  25                  30

Ala Gly Asp Glu
        35

<210> SEQ ID NO 561
<211> LENGTH: 10
<212> TYPE: PRT
<213> ORGANISM: Artificial Sequence
<220> FEATURE:
<223> OTHER INFORMATION: L-FR4 of A56-10A01

<400> SEQUENCE: 561

Phe Gly Gly Gly Thr Lys Leu Thr Val Leu
1               5                   10

<210> SEQ ID NO 562
<211> LENGTH: 8
<212> TYPE: PRT
<213> ORGANISM: Artificial Sequence
<220> FEATURE:
<223> OTHER INFORMATION: H-CDR1 of A56-11B10

<400> SEQUENCE: 562

Gly Phe Thr Phe Ala Asn Ala Trp
1               5

<210> SEQ ID NO 563
<211> LENGTH: 10
<212> TYPE: PRT
<213> ORGANISM: Artificial Sequence
<220> FEATURE:
<223> OTHER INFORMATION: H-CDR2 of A56-11B10

<400> SEQUENCE: 563

Ile Tyr Ser Thr Ser Asp Gly Gly Ala Thr
1               5                   10

<210> SEQ ID NO 564
<211> LENGTH: 24
<212> TYPE: PRT
<213> ORGANISM: Artificial Sequence
<220> FEATURE:
<223> OTHER INFORMATION: H-CDR3 of A56-11B10

<400> SEQUENCE: 564

Ala Lys Asp Arg Gly Met Asp Asn Ile His Thr Gly Gln Asn Ser Gly
1               5                   10                  15

Trp Ser Phe Gly Trp Phe Asp Pro
            20

<210> SEQ ID NO 565
<211> LENGTH: 9
<212> TYPE: PRT
<213> ORGANISM: Artificial Sequence
<220> FEATURE:
<223> OTHER INFORMATION: L-CDR1 of A56-11B10

<400> SEQUENCE: 565

Ser Ser Asp Val Gly Gly Tyr Asn Tyr
1               5

-continued

```
<210> SEQ ID NO 566
<211> LENGTH: 3
<212> TYPE: PRT
<213> ORGANISM: Artificial Sequence
<220> FEATURE:
<223> OTHER INFORMATION: L-CDR2 of A56-11B10

<400> SEQUENCE: 566

Asp Val Thr
1

<210> SEQ ID NO 567
<211> LENGTH: 10
<212> TYPE: PRT
<213> ORGANISM: Artificial Sequence
<220> FEATURE:
<223> OTHER INFORMATION: L-CDR3 of A56-11B10

<400> SEQUENCE: 567

Ser Ser Tyr Ala Gly Ser Tyr Thr Ser Val
1               5                   10

<210> SEQ ID NO 568
<211> LENGTH: 255
<212> TYPE: DNA
<213> ORGANISM: Artificial Sequence
<220> FEATURE:
<223> OTHER INFORMATION: SCFV of A56-11B10

<400> SEQUENCE: 568
caggtgcagc tggtggagtc tgggggaggc ttggtaaagc ctggggagtc tcttagactc        60
tcctgtgaag cctctggttt cactttcgct aacgcctgga tgagttggtt ccgccaggcg       120
ccagggaagg ggctggagtg ggttggccgt atttatagca catctgatgg tggagccaca       180
gactacgctg ctcccgttga gggccgattt accatctcca gagatgactc aaaaaacacg       240
ctgtttctgc aaatg                                                        255

<210> SEQ ID NO 569
<211> LENGTH: 133
<212> TYPE: PRT
<213> ORGANISM: Artificial Sequence
<220> FEATURE:
<223> OTHER INFORMATION: VH2 of A56-11B10

<400> SEQUENCE: 569

Gln Val Gln Leu Val Glu Ser Gly Gly Gly Leu Val Lys Pro Gly Glu
1               5                   10                  15

Ser Leu Arg Leu Ser Cys Glu Ala Ser Gly Phe Thr Phe Ala Asn Ala
            20                  25                  30

Trp Met Ser Trp Phe Arg Gln Ala Pro Gly Lys Gly Leu Glu Trp Val
        35                  40                  45

Gly Arg Ile Tyr Ser Thr Ser Asp Gly Gly Ala Thr Asp Tyr Ala Ala
    50                  55                  60

Pro Val Glu Gly Arg Phe Thr Ile Ser Arg Asp Asp Ser Lys Asn Thr
65                  70                  75                  80

Leu Phe Leu Gln Met Asn Ser Leu Arg Ala Glu Asp Thr Ala Val Tyr
                85                  90                  95

Tyr Cys Ala Lys Asp Arg Gly Met Asp Asn Ile His Thr Gly Gln Asn
            100                 105                 110

Ser Gly Trp Ser Phe Gly Trp Phe Asp Pro Trp Gly Gln Gly Thr Leu
```

-continued

```
                115              120              125

Val Thr Val Ser Ser
    130

<210> SEQ ID NO 570
<211> LENGTH: 110
<212> TYPE: PRT
<213> ORGANISM: Artificial Sequence
<220> FEATURE:
<223> OTHER INFORMATION: VL2 of A56-11B10

<400> SEQUENCE: 570

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Tyr Thr Ser Val Phe Gly Thr Gly Thr Lys Val Thr Val Leu
            100                 105                 110

<210> SEQ ID NO 571
<211> LENGTH: 25
<212> TYPE: PRT
<213> ORGANISM: Artificial Sequence
<220> FEATURE:
<223> OTHER INFORMATION: H-FR1 of A56-11B10

<400> SEQUENCE: 571

Gln Val Gln Leu Val Glu Ser Gly Gly Gly Leu Val Lys Pro Gly Glu
1               5                   10                  15

Ser Leu Arg Leu Ser Cys Glu Ala Ser
            20                  25

<210> SEQ ID NO 572
<211> LENGTH: 17
<212> TYPE: PRT
<213> ORGANISM: Artificial Sequence
<220> FEATURE:
<223> OTHER INFORMATION: H-FR2 of A56-11B10

<400> SEQUENCE: 572

Met Ser Trp Phe Arg Gln Ala Pro Gly Lys Gly Leu Glu Trp Val Gly
1               5                   10                  15

Arg

<210> SEQ ID NO 573
<211> LENGTH: 38
<212> TYPE: PRT
<213> ORGANISM: Artificial Sequence
<220> FEATURE:
<223> OTHER INFORMATION: H-FR3 of A56-11B10

<400> SEQUENCE: 573

Asp Tyr Ala Ala Pro Val Glu Gly Arg Phe Thr Ile Ser Arg Asp Asp
1               5                   10                  15
```

-continued

Ser Lys Asn Thr Leu Phe Leu Gln Met Asn Ser Leu Arg Ala Glu Asp
            20                      25                  30

Thr Ala Val Tyr Tyr Cys
        35

<210> SEQ ID NO 574
<211> LENGTH: 11
<212> TYPE: PRT
<213> ORGANISM: Artificial Sequence
<220> FEATURE:
<223> OTHER INFORMATION: H-FR4 of A56-11B10

<400> SEQUENCE: 574

Trp Gly Gln Gly Thr Leu Val Thr Val Ser Ser
1                5                   10

<210> SEQ ID NO 575
<211> LENGTH: 25
<212> TYPE: PRT
<213> ORGANISM: Artificial Sequence
<220> FEATURE:
<223> OTHER INFORMATION: L-FR1 of A56-11B10

<400> SEQUENCE: 575

Gln Ser Ala Leu Thr Gln Pro Arg Ser Val Ser Gly Ser Pro Gly Gln
1                5                   10                  15

Ser Val Thr Ile Ser Cys Thr Gly Thr
            20                  25

<210> SEQ ID NO 576
<211> LENGTH: 17
<212> TYPE: PRT
<213> ORGANISM: Artificial Sequence
<220> FEATURE:
<223> OTHER INFORMATION: L-FR2 of A56-11B10

<400> SEQUENCE: 576

Val Ser Trp Tyr Gln Gln His Pro Gly Lys Ala Pro Lys Leu Met Ile
1                5                   10                  15

Tyr

<210> SEQ ID NO 577
<211> LENGTH: 36
<212> TYPE: PRT
<213> ORGANISM: Artificial Sequence
<220> FEATURE:
<223> OTHER INFORMATION: L-FR3 of A56-11B10

<400> SEQUENCE: 577

Ile Tyr Asp Val Thr Lys Arg Pro Ser Gly Val Pro Asp Arg Phe Ser
1                5                   10                  15

Gly Ser Lys Ser Gly Asn Thr Ala Ser Leu Thr Ile Ser Gly Leu Gln
            20                  25                  30

Ala Glu Asp Glu
        35

<210> SEQ ID NO 578
<211> LENGTH: 10
<212> TYPE: PRT
<213> ORGANISM: Artificial Sequence
<220> FEATURE:
<223> OTHER INFORMATION: L-FR4 of A56-11B10

<400> SEQUENCE: 578

```
Phe Gly Thr Gly Thr Lys Val Thr Val Leu
1               5                   10

<210> SEQ ID NO 579
<211> LENGTH: 8
<212> TYPE: PRT
<213> ORGANISM: Artificial Sequence
<220> FEATURE:
<223> OTHER INFORMATION: H-CDR1 of A56-11C04

<400> SEQUENCE: 579

Gly Phe Thr Val Ser Asn Ala Trp
1               5

<210> SEQ ID NO 580
<211> LENGTH: 10
<212> TYPE: PRT
<213> ORGANISM: Artificial Sequence
<220> FEATURE:
<223> OTHER INFORMATION: H-CDR2 of A56-11C04

<400> SEQUENCE: 580

Ile Lys Ser Lys Thr Asp Gly Gly Thr Thr
1               5                   10

<210> SEQ ID NO 581
<211> LENGTH: 11
<212> TYPE: PRT
<213> ORGANISM: Artificial Sequence
<220> FEATURE:
<223> OTHER INFORMATION: H-CDR3 of A56-11C04

<400> SEQUENCE: 581

Ala Lys Asp Pro Asp Ala Glu Asn Thr Gly Ala
1               5                   10

<210> SEQ ID NO 582
<211> LENGTH: 6
<212> TYPE: PRT
<213> ORGANISM: Artificial Sequence
<220> FEATURE:
<223> OTHER INFORMATION: L-CDR1 of A56-11C04

<400> SEQUENCE: 582

Asp Ile Gly Ser Lys Ser
1               5

<210> SEQ ID NO 583
<211> LENGTH: 3
<212> TYPE: PRT
<213> ORGANISM: Artificial Sequence
<220> FEATURE:
<223> OTHER INFORMATION: L-CDR2 of A56-11C04

<400> SEQUENCE: 583

Ser Asp Ser
1

<210> SEQ ID NO 584
<211> LENGTH: 12
<212> TYPE: PRT
<213> ORGANISM: Artificial Sequence
<220> FEATURE:
<223> OTHER INFORMATION: L-CDR3 of A56-11C04

<400> SEQUENCE: 584
```

-continued

```
Gln Val Trp Asp Asn Gly Ser Asp His Pro Gly Val
1               5                   10
```

<210> SEQ ID NO 585
<211> LENGTH: 255
<212> TYPE: DNA
<213> ORGANISM: Artificial Sequence
<220> FEATURE:
<223> OTHER INFORMATION: SCFV of A56-11C04

<400> SEQUENCE: 585

```
caggtgcagc tggtacagtc ggggggaggc ttggtaaagc ctggggggtc ccttagactc      60
tcctgtgcag tcagtggatt cactgtcagt aatgcctgga tgatgtggtt ccgccaggta     120
ccagggaagg ggctggagtg ggttggccgt attaaaagca aaactgatgg tgggacaaca     180
gagtacgctg cacccgtgaa aggcagattc agcatctcag agacgactc aaaaaacaca      240 ctgtatctcc aaatg                                                      255
```

<210> SEQ ID NO 586
<211> LENGTH: 120
<212> TYPE: PRT
<213> ORGANISM: Artificial Sequence
<220> FEATURE:
<223> OTHER INFORMATION: VH2 of A56-11C04

<400> SEQUENCE: 586

```
Gln Val Gln Leu Val Gln Ser Gly Gly Gly Leu Val Lys Pro Gly Gly
1               5                   10                  15

Ser Leu Arg Leu Ser Cys Ala Val Ser Gly Phe Thr Val Ser Asn Ala
            20                  25                  30

Trp Met Met Trp Phe Arg Gln Val Pro Gly Lys Gly Leu Glu Trp Val
        35                  40                  45

Gly Arg Ile Lys Ser Lys Thr Asp Gly Gly Thr Thr Glu Tyr Ala Ala
    50                  55                  60

Pro Val Lys Gly Arg Phe Ser Ile Ser Gly Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Pro Asp Ala Glu Asn Thr Gly Ala Leu Gly Gln
            100                 105                 110

Gly Thr Leu Val Thr Val Ser Ser
        115                 120
```

<210> SEQ ID NO 587
<211> LENGTH: 109
<212> TYPE: PRT
<213> ORGANISM: Artificial Sequence
<220> FEATURE:
<223> OTHER INFORMATION: VL2 of A56-11C04

<400> SEQUENCE: 587

```
Asn Phe Met Leu Thr Gln Pro Pro Ser Val Ser Val Ala Pro Gly Lys
1               5                   10                  15

Thr Ala Gly Ile Thr Cys Gly Gly Asp Asp Ile Gly Ser Lys Ser Val
            20                  25                  30

His Trp Tyr Gln Gln Arg Pro Gly Gln Ala Pro Val Leu Val Ile Ser
        35                  40                  45

Ser Asp Ser Asp Arg Pro Ser Gly Ile Pro Glu Arg Phe Ser Gly Ser
    50                  55                  60
```

```
Asn Ser Gly Asn Thr Ala Thr Leu Thr Ile Thr Arg Val Glu Asp Gly
65                  70                  75                  80

Asp Glu Ala Asp Tyr Tyr Cys Gln Val Trp Asp Asn Gly Ser Asp His
                85                  90                  95

Pro Gly Val Phe Gly Thr Gly Thr Lys Val Thr Val Leu
            100                 105
```

```
<210> SEQ ID NO 588
<211> LENGTH: 25
<212> TYPE: PRT
<213> ORGANISM: Artificial Sequence
<220> FEATURE:
<223> OTHER INFORMATION: H-FR1 of A56-11C04

<400> SEQUENCE: 588

Gln Val Gln Leu Val Gln Ser Gly Gly Gly Leu Val Lys Pro Gly Gly
1               5                   10                  15

Ser Leu Arg Leu Ser Cys Ala Val Ser
            20                  25
```

```
<210> SEQ ID NO 589
<211> LENGTH: 17
<212> TYPE: PRT
<213> ORGANISM: Artificial Sequence
<220> FEATURE:
<223> OTHER INFORMATION: H-FR2 of A56-11C04

<400> SEQUENCE: 589

Met Met Trp Phe Arg Gln Val Pro Gly Lys Gly Leu Glu Trp Val Gly
1               5                   10                  15

Arg
```

```
<210> SEQ ID NO 590
<211> LENGTH: 38
<212> TYPE: PRT
<213> ORGANISM: Artificial Sequence
<220> FEATURE:
<223> OTHER INFORMATION: H-FR3 of A56-11C04

<400> SEQUENCE: 590

Glu Tyr Ala Ala Pro Val Lys Gly Arg Phe Ser Ile Ser Gly Asp Asp
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35
```

```
<210> SEQ ID NO 591
<211> LENGTH: 11
<212> TYPE: PRT
<213> ORGANISM: Artificial Sequence
<220> FEATURE:
<223> OTHER INFORMATION: H-FR4 of A56-11C04

<400> SEQUENCE: 591

Leu Gly Gln Gly Thr Leu Val Thr Val Ser Ser
1               5                   10
```

```
<210> SEQ ID NO 592
<211> LENGTH: 25
<212> TYPE: PRT
<213> ORGANISM: Artificial Sequence
<220> FEATURE:
<223> OTHER INFORMATION: L-FR1 of A56-11C04
```

-continued

<400> SEQUENCE: 592

Asn Phe Met Leu Thr Gln Pro Pro Ser Val Ser Val Ala Pro Gly Lys
1               5                   10                  15

Thr Ala Gly Ile Thr Cys Gly Gly Asp
            20              25

<210> SEQ ID NO 593
<211> LENGTH: 17
<212> TYPE: PRT
<213> ORGANISM: Artificial Sequence
<220> FEATURE:
<223> OTHER INFORMATION: L-FR2 of A56-11C04

<400> SEQUENCE: 593

Val His Trp Tyr Gln Gln Arg Pro Gly Gln Ala Pro Val Leu Val Ile
1               5                   10                  15

Ser

<210> SEQ ID NO 594
<211> LENGTH: 36
<212> TYPE: PRT
<213> ORGANISM: Artificial Sequence
<220> FEATURE:
<223> OTHER INFORMATION: L-FR3 of A56-11C04

<400> SEQUENCE: 594

Ile Ser Ser Asp Ser Asp Arg Pro Ser Gly Ile Pro Glu Arg Phe Ser
1               5                   10                  15

Gly Ser Asn Ser Gly Asn Thr Ala Thr Leu Thr Ile Thr Arg Val Glu
            20                  25                  30

Asp Gly Asp Glu
        35

<210> SEQ ID NO 595
<211> LENGTH: 10
<212> TYPE: PRT
<213> ORGANISM: Artificial Sequence
<220> FEATURE:
<223> OTHER INFORMATION: L-FR4 of A56-11C04

<400> SEQUENCE: 595

Phe Gly Thr Gly Thr Lys Val Thr Val Leu
1               5                   10

<210> SEQ ID NO 596
<211> LENGTH: 8
<212> TYPE: PRT
<213> ORGANISM: Artificial Sequence
<220> FEATURE:
<223> OTHER INFORMATION: H-CDR1 of A56-15A01

<400> SEQUENCE: 596

Gly Phe Thr Phe Thr Lys Tyr Thr
1               5

<210> SEQ ID NO 597
<211> LENGTH: 8
<212> TYPE: PRT
<213> ORGANISM: Artificial Sequence
<220> FEATURE:
<223> OTHER INFORMATION: H-CDR2 of A56-15A01

<400> SEQUENCE: 597

Ile Ser Tyr Asp Gly Ser Asn Lys
1               5

<210> SEQ ID NO 598
<211> LENGTH: 16
<212> TYPE: PRT
<213> ORGANISM: Artificial Sequence
<220> FEATURE:
<223> OTHER INFORMATION: H-CDR3 of A56-15A01

<400> SEQUENCE: 598

Thr Pro Phe Gln His Asp Ser Val Pro Arg Arg Gly Ala Phe Asp Leu
1               5                   10                  15

<210> SEQ ID NO 599
<211> LENGTH: 9
<212> TYPE: PRT
<213> ORGANISM: Artificial Sequence
<220> FEATURE:
<223> OTHER INFORMATION: L-CDR1 of A56-15A01

<400> SEQUENCE: 599

Ser Ser Asp Val Gly Gly Tyr Asn Tyr
1               5

<210> SEQ ID NO 600
<211> LENGTH: 3
<212> TYPE: PRT
<213> ORGANISM: Artificial Sequence
<220> FEATURE:
<223> OTHER INFORMATION: L-CDR2 of A56-15A01

<400> SEQUENCE: 600

Asp Val Asp
1

<210> SEQ ID NO 601
<211> LENGTH: 11
<212> TYPE: PRT
<213> ORGANISM: Artificial Sequence
<220> FEATURE:
<223> OTHER INFORMATION: L-CDR3 of A56-15A01

<400> SEQUENCE: 601

Ser Ser Ser Arg Pro Ser Ser Thr Pro Arg Val
1               5                   10

<210> SEQ ID NO 602
<211> LENGTH: 255
<212> TYPE: DNA
<213> ORGANISM: Artificial Sequence
<220> FEATURE:
<223> OTHER INFORMATION: SCFV of A56-15A01

<400> SEQUENCE: 602
cagatgcagc tggtggagtc tggggggaggc gtggtccagc ctggggggtc cctgagactc      60
tcctgtgcag cctctggatt caccttcact aaatatacta tgctctgggt ccgccaggct     120
ccaggcaagg ggctggagtg ggtggcactt atatcatatg atggaagcaa caaaaattac     180
gcagattccg tgaagggccg attcaccatt tcccgagacg attccaagag cacgctattt     240
ctgcaaatga gcagc                                                       255

<210> SEQ ID NO 603
<211> LENGTH: 123
<212> TYPE: PRT

```
<213> ORGANISM: Artificial Sequence
<220> FEATURE:
<223> OTHER INFORMATION: VH2 of A56-15A01

<400> SEQUENCE: 603

Gln Met Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Lys Tyr
            20                  25                  30

Thr Met Leu Trp Val Arg Gln Ala Pro Gly Lys Gly Leu Glu Trp Val
        35                  40                  45

Ala Leu Ile Ser Tyr Asp Gly Ser Asn Lys Asn Tyr Ala Asp Ser Val
    50                  55                  60

Lys Gly Arg Phe Thr Ile Ser Arg Asp Asp Ser Lys Ser Thr Leu Phe
65                  70                  75                  80

Leu Gln Met Ser Ser Leu Arg Ser Glu Asp Thr Ala Val Tyr Tyr Cys
                85                  90                  95

Thr Pro Phe Gln His Asp Ser Val Pro Arg Arg Gly Ala Phe Asp Leu
            100                 105                 110

Trp Gly Gln Gly Thr Met Val Thr Val Ser Ser
        115                 120

<210> SEQ ID NO 604
<211> LENGTH: 111
<212> TYPE: PRT
<213> ORGANISM: Artificial Sequence
<220> FEATURE:
<223> OTHER INFORMATION: VL2 of A56-15A01

<400> SEQUENCE: 604

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Val Ile Tyr Asp Val Asp Lys Arg Pro Ser Gly Val Ser Asn Arg Phe
    50                  55                  60

Ser Gly Ser Lys Ser Ala Asn Thr Ala Ser Leu Thr Ile Ser Gly Leu
65                  70                  75                  80

Gln Ala Asp Asp Glu Ala Asp Tyr Tyr Cys Ser Ser Ser Arg Pro Ser
                85                  90                  95

Ser Thr Pro Arg Val Phe Gly Thr Gly Thr Lys Val Thr Val Leu
            100                 105                 110

<210> SEQ ID NO 605
<211> LENGTH: 25
<212> TYPE: PRT
<213> ORGANISM: Artificial Sequence
<220> FEATURE:
<223> OTHER INFORMATION: H-FR1 of A56-15A01

<400> SEQUENCE: 605

Gln Met Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 606
```

```
<211> LENGTH: 17
<212> TYPE: PRT
<213> ORGANISM: Artificial Sequence
<220> FEATURE:
<223> OTHER INFORMATION: H-FR2 of A56-15A01

<400> SEQUENCE: 606

Met Leu Trp Val Arg Gln Ala Pro Gly Lys Gly Leu Glu Trp Val Ala
1               5                   10                  15

Leu

<210> SEQ ID NO 607
<211> LENGTH: 38
<212> TYPE: PRT
<213> ORGANISM: Artificial Sequence
<220> FEATURE:
<223> OTHER INFORMATION: H-FR3 of A56-15A01

<400> SEQUENCE: 607

Asn Tyr Ala Asp Ser Val Lys Gly Arg Phe Thr Ile Ser Arg Asp Asp
1               5                   10                  15

Ser Lys Ser Thr Leu Phe Leu Gln Met Ser Ser Leu Arg Ser Glu Asp
            20                  25                  30

Thr Ala Val Tyr Tyr Cys
        35

<210> SEQ ID NO 608
<211> LENGTH: 11
<212> TYPE: PRT
<213> ORGANISM: Artificial Sequence
<220> FEATURE:
<223> OTHER INFORMATION: H-FR4 of A56-15A01

<400> SEQUENCE: 608

Trp Gly Gln Gly Thr Met Val Thr Val Ser Ser
1               5                   10

<210> SEQ ID NO 609
<211> LENGTH: 25
<212> TYPE: PRT
<213> ORGANISM: Artificial Sequence
<220> FEATURE:
<223> OTHER INFORMATION: L-FR1 of A56-15A01

<400> SEQUENCE: 609

Gln Ser Ala Leu Thr Gln Pro Ala Ser Val Ser Gly Ser Pro Gly Gln
1               5                   10                  15

Ser Ile Ala Ile Ser Cys Thr Gly Thr
            20                  25

<210> SEQ ID NO 610
<211> LENGTH: 17
<212> TYPE: PRT
<213> ORGANISM: Artificial Sequence
<220> FEATURE:
<223> OTHER INFORMATION: L-FR2 of A56-15A01

<400> SEQUENCE: 610

Val Ser Trp Tyr Gln Gln His Pro Gly Lys Ala Pro Lys Leu Val Ile
1               5                   10                  15

Tyr

<210> SEQ ID NO 611
<211> LENGTH: 36
```

-continued

```
<212> TYPE: PRT
<213> ORGANISM: Artificial Sequence
<220> FEATURE:
<223> OTHER INFORMATION: L-FR3 of A56-15A01

<400> SEQUENCE: 611

Ile Tyr Asp Val Asp Lys Arg Pro Ser Gly Val Ser Asn Arg Phe Ser
1               5                   10                  15

Gly Ser Lys Ser Ala Asn Thr Ala Ser Leu Thr Ile Ser Gly Leu Gln
            20                  25                  30

Ala Asp Asp Glu
        35

<210> SEQ ID NO 612
<211> LENGTH: 10
<212> TYPE: PRT
<213> ORGANISM: Artificial Sequence
<220> FEATURE:
<223> OTHER INFORMATION: L-FR4 of A56-15A01

<400> SEQUENCE: 612

Phe Gly Thr Gly Thr Lys Val Thr Val Leu
1               5                   10

<210> SEQ ID NO 613
<211> LENGTH: 8
<212> TYPE: PRT
<213> ORGANISM: Artificial Sequence
<220> FEATURE:
<223> OTHER INFORMATION: H-CDR1 of A56-16E02

<400> SEQUENCE: 613

Gly Ile Ala Phe Ser Arg Tyr Ala
1               5

<210> SEQ ID NO 614
<211> LENGTH: 7
<212> TYPE: PRT
<213> ORGANISM: Artificial Sequence
<220> FEATURE:
<223> OTHER INFORMATION: H-CDR2 of A56-16E02

<400> SEQUENCE: 614

Ile Gly Ser Thr Gly Thr Thr
1               5

<210> SEQ ID NO 615
<211> LENGTH: 9
<212> TYPE: PRT
<213> ORGANISM: Artificial Sequence
<220> FEATURE:
<223> OTHER INFORMATION: H-CDR3 of A56-16E02

<400> SEQUENCE: 615

Ala Thr His Phe Gly Phe Phe Ser Lys
1               5

<210> SEQ ID NO 616
<211> LENGTH: 11
<212> TYPE: PRT
<213> ORGANISM: Artificial Sequence
<220> FEATURE:
<223> OTHER INFORMATION: L-CDR1 of A56-16E02

<400> SEQUENCE: 616

Gln Ser Leu Leu His Arg Asn Gly Tyr Asn Tyr
```

-continued

```
1                5                10
```

<210> SEQ ID NO 617
<211> LENGTH: 3
<212> TYPE: PRT
<213> ORGANISM: Artificial Sequence
<220> FEATURE:
<223> OTHER INFORMATION: L-CDR2 of A56-16E02

<400> SEQUENCE: 617

Leu Gly Ser
1

<210> SEQ ID NO 618
<211> LENGTH: 9
<212> TYPE: PRT
<213> ORGANISM: Artificial Sequence
<220> FEATURE:
<223> OTHER INFORMATION: L-CDR3 of A56-16E02

<400> SEQUENCE: 618

Met Gln Ala Leu Glu Thr Arg Trp Thr
1               5

<210> SEQ ID NO 619
<211> LENGTH: 255
<212> TYPE: DNA
<213> ORGANISM: Artificial Sequence
<220> FEATURE:
<223> OTHER INFORMATION: SCFV of A56-16E02

<400> SEQUENCE: 619
caggtgcagc tggtggagtc tggggggagac ttggtacagc ctggggggtc cctgagactc       60
tcctgtgtag actctggaat cgcctttagc agatatgcca tgaactgggt ccgccaggct      120
ccagggaagg ggctggagtg ggtctcaagt attggtagta ctggtaccac atactacgca      180
gactccgtga aggccggtt caccatctcc agagacagat ccaagaacac gctgtatctg      240
caaatgaaca gtctg                                                        255

<210> SEQ ID NO 620
<211> LENGTH: 115
<212> TYPE: PRT
<213> ORGANISM: Artificial Sequence
<220> FEATURE:
<223> OTHER INFORMATION: VH2 of A56-16E02

<400> SEQUENCE: 620

Gln Val Gln Leu Val Glu Ser Gly Gly Asp Leu Val Gln Pro Gly Gly
1               5                   10                  15

Ser Leu Arg Leu Ser Cys Val Asp Ser Gly Ile Ala Phe Ser Arg Tyr
            20                  25                  30

Ala Met Asn Trp Val Arg Gln Ala Pro Gly Lys Gly Leu Glu Trp Val
        35                  40                  45

Ser Ser Ile Gly Ser Thr Gly Thr Thr Tyr Tyr Ala Asp Ser Val Lys
    50                  55                  60

Gly Arg Phe Thr Ile Ser Arg Asp Arg Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr His Phe Gly Phe Phe Ser Lys Trp Gly Gln Gly Thr Leu Val Thr
            100                 105                 110

```
Val Ser Ser
        115

<210> SEQ ID NO 621
<211> LENGTH: 112
<212> TYPE: PRT
<213> ORGANISM: Artificial Sequence
<220> FEATURE:
<223> OTHER INFORMATION: VL2 of A56-16E02

<400> SEQUENCE: 621

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Asn Ile
65                  70                  75                  80

Ser Arg Val Glu Ala Glu Asp Val Gly Val Tyr Tyr Cys Met Gln Ala
                85                  90                  95

Leu Glu Thr Arg Trp Thr Phe Gly Gln Gly Thr Lys Val Asp Ile Lys
            100                 105                 110

<210> SEQ ID NO 622
<211> LENGTH: 25
<212> TYPE: PRT
<213> ORGANISM: Artificial Sequence
<220> FEATURE:
<223> OTHER INFORMATION: H-FR1 of A56-16E02

<400> SEQUENCE: 622

Gln Val Gln Leu Val Glu Ser Gly Gly Asp Leu Val Gln Pro Gly Gly
1               5                   10                  15

Ser Leu Arg Leu Ser Cys Val Asp Ser
            20                  25

<210> SEQ ID NO 623
<211> LENGTH: 17
<212> TYPE: PRT
<213> ORGANISM: Artificial Sequence
<220> FEATURE:
<223> OTHER INFORMATION: H-FR2 of A56-16E02

<400> SEQUENCE: 623

Met Asn Trp Val Arg Gln Ala Pro Gly Lys Gly Leu Glu Trp Val Ser
1               5                   10                  15

Ser

<210> SEQ ID NO 624
<211> LENGTH: 38
<212> TYPE: PRT
<213> ORGANISM: Artificial Sequence
<220> FEATURE:
<223> OTHER INFORMATION: H-FR3 of A56-16E02

<400> SEQUENCE: 624

Tyr Tyr Ala Asp Ser Val Lys Gly Arg Phe Thr Ile Ser Arg Asp Arg
1               5                   10                  15

Ser Lys Asn Thr Leu Tyr Leu Gln Met Asn Ser Leu Arg Ala Glu Asp
```

-continued

```
                20                  25                  30

Thr Ala Val Tyr Tyr Cys
        35
```

```
<210> SEQ ID NO 625
<211> LENGTH: 11
<212> TYPE: PRT
<213> ORGANISM: Artificial Sequence
<220> FEATURE:
<223> OTHER INFORMATION: H-FR4 of A56-16E02

<400> SEQUENCE: 625

Trp Gly Gln Gly Thr Leu Val Thr Val Ser Ser
1               5                   10
```

```
<210> SEQ ID NO 626
<211> LENGTH: 26
<212> TYPE: PRT
<213> ORGANISM: Artificial Sequence
<220> FEATURE:
<223> OTHER INFORMATION: L-FR1 of A56-16E02

<400> SEQUENCE: 626

Asp Ile Val Met Thr Gln Thr Pro Leu Ser Leu Pro Val Thr Pro Gly
1               5                   10                  15

Glu Pro Ala Ser Ile Ser Cys Arg Ser Ser
            20                  25
```

```
<210> SEQ ID NO 627
<211> LENGTH: 17
<212> TYPE: PRT
<213> ORGANISM: Artificial Sequence
<220> FEATURE:
<223> OTHER INFORMATION: L-FR2 of A56-16E02

<400> SEQUENCE: 627

Leu Asp Trp Tyr Leu Gln Lys Pro Gly Gln Ser Pro Gln Leu Leu Ile
1               5                   10                  15

Tyr
```

```
<210> SEQ ID NO 628
<211> LENGTH: 36
<212> TYPE: PRT
<213> ORGANISM: Artificial Sequence
<220> FEATURE:
<223> OTHER INFORMATION: L-FR3 of A56-16E02

<400> SEQUENCE: 628

Ile Tyr Leu Gly Ser Asn Arg Ala Ser Gly Val Pro Asp Arg Phe Ser
1               5                   10                  15

Gly Ser Gly Ser Gly Thr Asp Phe Thr Leu Asn Ile Ser Arg Val Glu
            20                  25                  30

Ala Glu Asp Val
        35
```

```
<210> SEQ ID NO 629
<211> LENGTH: 10
<212> TYPE: PRT
<213> ORGANISM: Artificial Sequence
<220> FEATURE:
<223> OTHER INFORMATION: L-FR4 of A56-16E02

<400> SEQUENCE: 629

Phe Gly Gln Gly Thr Lys Val Asp Ile Lys
```

-continued

```
1               5                       10

<210> SEQ ID NO 630
<211> LENGTH: 8
<212> TYPE: PRT
<213> ORGANISM: Artificial Sequence
<220> FEATURE:
<223> OTHER INFORMATION: H-CDR1 of A56-18C03

<400> SEQUENCE: 630

Gly Gly Thr Leu Ser Ser Tyr Pro
1               5

<210> SEQ ID NO 631
<211> LENGTH: 8
<212> TYPE: PRT
<213> ORGANISM: Artificial Sequence
<220> FEATURE:
<223> OTHER INFORMATION: H-CDR2 of A56-18C03

<400> SEQUENCE: 631

Ile Asn Pro Asn Gly Gly Ala Thr
1               5

<210> SEQ ID NO 632
<211> LENGTH: 9
<212> TYPE: PRT
<213> ORGANISM: Artificial Sequence
<220> FEATURE:
<223> OTHER INFORMATION: H-CDR3 of A56-18C03

<400> SEQUENCE: 632

Ala Gln Leu Gly Ser Ser Gly Gly Gly
1               5

<210> SEQ ID NO 633
<211> LENGTH: 6
<212> TYPE: PRT
<213> ORGANISM: Artificial Sequence
<220> FEATURE:
<223> OTHER INFORMATION: L-CDR1 of A56-18C03

<400> SEQUENCE: 633

Ser Leu Arg Lys Tyr His
1               5

<210> SEQ ID NO 634
<211> LENGTH: 3
<212> TYPE: PRT
<213> ORGANISM: Artificial Sequence
<220> FEATURE:
<223> OTHER INFORMATION: L-CDR2 of A56-18C03

<400> SEQUENCE: 634

Gly Lys Asn
1

<210> SEQ ID NO 635
<211> LENGTH: 12
<212> TYPE: PRT
<213> ORGANISM: Artificial Sequence
<220> FEATURE:
<223> OTHER INFORMATION: L-CDR3 of A56-18C03

<400> SEQUENCE: 635

Asn Ser Arg Asp Ser Ser Gly Asn Asp Leu Arg Val
1               5                       10
```

<210> SEQ ID NO 636
<211> LENGTH: 255
<212> TYPE: DNA
<213> ORGANISM: Artificial Sequence
<220> FEATURE:
<223> OTHER INFORMATION: SCFV of A56-18C03

<400> SEQUENCE: 636
caggtgcagc tggtggagtc tgggggctgag gtgaagaagc ctgggtcctc ggtgaaggtc      60
tcctgcaaga cttctggagg cactttaagc agttatccca tcacctgggt gcgacaggcc     120
cctggacaag ggcctgagtg gatgggaatt atcaacccca atggtggcgc cacaaactac     180
gcacagaagt tccagggcag agtcaccatg accagggaca cgtccacggg cacagtctac     240
atggaactga gcagc                                                      255

<210> SEQ ID NO 637
<211> LENGTH: 116
<212> TYPE: PRT
<213> ORGANISM: Artificial Sequence
<220> FEATURE:
<223> OTHER INFORMATION: VH2 of A56-18C03

<400> SEQUENCE: 637

Gln Val Gln Leu Val Glu Ser Gly Ala Glu Val Lys Lys Pro Gly Ser
1               5                   10                  15

Ser Val Lys Val Ser Cys Lys Thr Ser Gly Gly Thr Leu Ser Ser Tyr
            20                  25                  30

Pro Ile Thr Trp Val Arg Gln Ala Pro Gly Gln Gly Pro Glu Trp Met
        35                  40                  45

Gly Ile Ile Asn Pro Asn Gly Gly Ala Thr Asn Tyr Ala Gln Lys Phe
    50                  55                  60

Gln Gly Arg Val Thr Met Thr Arg Asp Thr Ser Thr Gly Thr Val Tyr
65                  70                  75                  80

Met Glu Leu Ser Ser Leu Arg Ser Glu Asp Thr Ala Val Tyr Tyr Cys
                85                  90                  95

Ala Gln Leu Gly Ser Ser Gly Gly Gly Leu Gly Gln Gly Thr Leu Val
            100                 105                 110

Thr Val Ser Ser
        115

<210> SEQ ID NO 638
<211> LENGTH: 109
<212> TYPE: PRT
<213> ORGANISM: Artificial Sequence
<220> FEATURE:
<223> OTHER INFORMATION: VL2 of A56-18C03

<400> SEQUENCE: 638

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Lys Tyr His Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Gly Arg Phe Ser Gly Ser
    50                  55                  60

Ser Ser Gly Asn Thr Ala Ser Leu Thr Ile Thr Gly Ala Gln Ala Glu
65                  70                  75                  80

-continued

```
Asp Glu Ala Asp Tyr Tyr Cys Asn Ser Arg Asp Ser Ser Gly Asn Asp
                85                  90                  95

Leu Arg Val Phe Gly Gly Gly Thr Lys Leu Thr Val Leu
            100                 105

<210> SEQ ID NO 639
<211> LENGTH: 25
<212> TYPE: PRT
<213> ORGANISM: Artificial Sequence
<220> FEATURE:
<223> OTHER INFORMATION: H-FR1 of A56-18C03

<400> SEQUENCE: 639

Gln Val Gln Leu Val Glu Ser Gly Ala Glu Val Lys Lys Pro Gly Ser
1               5                  10                  15

Ser Val Lys Val Ser Cys Lys Thr Ser
            20                  25

<210> SEQ ID NO 640
<211> LENGTH: 17
<212> TYPE: PRT
<213> ORGANISM: Artificial Sequence
<220> FEATURE:
<223> OTHER INFORMATION: H-FR2 of A56-18C03

<400> SEQUENCE: 640

Ile Thr Trp Val Arg Gln Ala Pro Gly Gln Gly Pro Glu Trp Met Gly
1               5                  10                  15

Ile

<210> SEQ ID NO 641
<211> LENGTH: 38
<212> TYPE: PRT
<213> ORGANISM: Artificial Sequence
<220> FEATURE:
<223> OTHER INFORMATION: H-FR3 of A56-18C03

<400> SEQUENCE: 641

Asn Tyr Ala Gln Lys Phe Gln Gly Arg Val Thr Met Thr Arg Asp Thr
1               5                  10                  15

Ser Thr Gly Thr Val Tyr Met Glu Leu Ser Ser Leu Arg Ser Glu Asp
            20                  25                  30

Thr Ala Val Tyr Tyr Cys
        35

<210> SEQ ID NO 642
<211> LENGTH: 11
<212> TYPE: PRT
<213> ORGANISM: Artificial Sequence
<220> FEATURE:
<223> OTHER INFORMATION: H-FR4 of A56-18C03

<400> SEQUENCE: 642

Leu Gly Gln Gly Thr Leu Val Thr Val Ser Ser
1               5                  10

<210> SEQ ID NO 643
<211> LENGTH: 25
<212> TYPE: PRT
<213> ORGANISM: Artificial Sequence
<220> FEATURE:
<223> OTHER INFORMATION: L-FR1 of A56-18C03

<400> SEQUENCE: 643
```

-continued

Ser Tyr Glu Leu Thr Gln Asp Pro Ala Val Ser Val Ala Leu Gly Gln
1               5                   10                  15

Thr Val Arg Ile Thr Cys Gln Gly Asp
            20                  25

<210> SEQ ID NO 644
<211> LENGTH: 17
<212> TYPE: PRT
<213> ORGANISM: Artificial Sequence
<220> FEATURE:
<223> OTHER INFORMATION: L-FR2 of A56-18C03

<400> SEQUENCE: 644

Ala Ser Trp Tyr Gln Gln Lys Pro Gly Gln Ala Pro Val Leu Val Ile
1               5                   10                  15

Tyr

<210> SEQ ID NO 645
<211> LENGTH: 36
<212> TYPE: PRT
<213> ORGANISM: Artificial Sequence
<220> FEATURE:
<223> OTHER INFORMATION: L-FR3 of A56-18C03

<400> SEQUENCE: 645

Ile Tyr Gly Lys Asn Asn Arg Pro Ser Gly Ile Pro Gly Arg Phe Ser
1               5                   10                  15

Gly Ser Ser Ser Gly Asn Thr Ala Ser Leu Thr Ile Thr Gly Ala Gln
            20                  25                  30

Ala Glu Asp Glu
        35

<210> SEQ ID NO 646
<211> LENGTH: 10
<212> TYPE: PRT
<213> ORGANISM: Artificial Sequence
<220> FEATURE:
<223> OTHER INFORMATION: L-FR4 of A56-18C03

<400> SEQUENCE: 646

Phe Gly Gly Gly Thr Lys Leu Thr Val Leu
1               5                   10

<210> SEQ ID NO 647
<211> LENGTH: 8
<212> TYPE: PRT
<213> ORGANISM: Artificial Sequence
<220> FEATURE:
<223> OTHER INFORMATION: H-CDR1 of A56-18G02

<400> SEQUENCE: 647

Gly Phe Thr Phe Ser Ser Tyr Gly
1               5

<210> SEQ ID NO 648
<211> LENGTH: 8
<212> TYPE: PRT
<213> ORGANISM: Artificial Sequence
<220> FEATURE:
<223> OTHER INFORMATION: H-CDR2 of A56-18G02

<400> SEQUENCE: 648

Ile Ser Tyr Asp Gly Ser Asn Lys
1               5

<210> SEQ ID NO 649
<211> LENGTH: 15
<212> TYPE: PRT
<213> ORGANISM: Artificial Sequence
<220> FEATURE:
<223> OTHER INFORMATION: H-CDR3 of A56-18G02

<400> SEQUENCE: 649

Ala Arg Met Arg Trp Ala Val Ala Gly Met Gly Ala Phe Glu Ile
1               5                   10                  15

<210> SEQ ID NO 650
<211> LENGTH: 7
<212> TYPE: PRT
<213> ORGANISM: Artificial Sequence
<220> FEATURE:
<223> OTHER INFORMATION: L-CDR1 of A56-18G02

<400> SEQUENCE: 650

Gln Ser Val Thr Ser Ser Tyr
1               5

<210> SEQ ID NO 651
<211> LENGTH: 3
<212> TYPE: PRT
<213> ORGANISM: Artificial Sequence
<220> FEATURE:
<223> OTHER INFORMATION: L-CDR2 of A56-18G02

<400> SEQUENCE: 651

Gly Ala Ser
1

<210> SEQ ID NO 652
<211> LENGTH: 10
<212> TYPE: PRT
<213> ORGANISM: Artificial Sequence
<220> FEATURE:
<223> OTHER INFORMATION: L-CDR3 of A56-18G02

<400> SEQUENCE: 652

Gln Gln Arg Ser Ser Trp Pro Pro Leu Thr
1               5                   10

<210> SEQ ID NO 653
<211> LENGTH: 255
<212> TYPE: DNA
<213> ORGANISM: Artificial Sequence
<220> FEATURE:
<223> OTHER INFORMATION: SCFV of A56-18G02

<400> SEQUENCE: 653
cagatgcagc tggtgcagtc tggggggaggc gtggtccagc ctgggaggtc cctgagactc        60
tcctgtgcag cctctggatt caccttcagt agctatggca tgcactgggt ccgccaggct       120
ccaggcaagg ggctggagtg ggtggcagtt atatcatatg atggaagtaa taaatactat       180
gcagactccg tgaagggccg attcaccatc tccagagaca attccaagaa cacgctgtat       240
ctgcaaatga acagc                                                        255

<210> SEQ ID NO 654
<211> LENGTH: 122
<212> TYPE: PRT
<213> ORGANISM: Artificial Sequence
<220> FEATURE:

-continued

<223> OTHER INFORMATION: VH2 of A56-18G02

<400> SEQUENCE: 654

```
Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Arg Met Arg Trp Ala Val Ala Gly Met Gly Ala Phe Glu Ile Trp
            100                 105                 110

Gly Gln Gly Thr Thr Val Thr Val Ser Ser
        115                 120
```

<210> SEQ ID NO 655
<211> LENGTH: 109
<212> TYPE: PRT
<213> ORGANISM: Artificial Sequence
<220> FEATURE:
<223> OTHER INFORMATION: VL2 of A56-18G02

<400> SEQUENCE: 655

```
Asp Ile Gln Met Thr Gln Ser Pro Gly Thr Leu Ser Leu Ser Pro Gly
1               5                   10                  15

Glu Ser Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Lys Val Leu
        35                  40                  45

Ile Tyr Gly Ala Ser Gly Arg Ala Thr Gly Thr Pro Ala Arg Phe Ser
    50                  55                  60

Gly Gly Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Ser Trp Pro
                85                  90                  95

Pro Leu Thr Phe Gly Pro Gly Ser Lys Val Glu Ile Lys
            100                 105
```

<210> SEQ ID NO 656
<211> LENGTH: 25
<212> TYPE: PRT
<213> ORGANISM: Artificial Sequence
<220> FEATURE:
<223> OTHER INFORMATION: H-FR1 of A56-18G02

<400> SEQUENCE: 656

```
Gln Met Gln Leu Val Gln Ser Gly Gly Gly Val Val Gln Pro Gly Arg
1               5                   10                  15

Ser Leu Arg Leu Ser Cys Ala Ala Ser
            20                  25
```

<210> SEQ ID NO 657
<211> LENGTH: 17
<212> TYPE: PRT

-continued

```
<213> ORGANISM: Artificial Sequence
<220> FEATURE:
<223> OTHER INFORMATION: H-FR2 of A56-18G02

<400> SEQUENCE: 657

Met His Trp Val Arg Gln Ala Pro Gly Lys Gly Leu Glu Trp Val Ala
1               5                   10                  15

Val

<210> SEQ ID NO 658
<211> LENGTH: 38
<212> TYPE: PRT
<213> ORGANISM: Artificial Sequence
<220> FEATURE:
<223> OTHER INFORMATION: H-FR3 of A56-18G02

<400> SEQUENCE: 658

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ser Glu Asp
            20                  25                  30

Thr Ala Val Tyr Tyr Cys
        35

<210> SEQ ID NO 659
<211> LENGTH: 11
<212> TYPE: PRT
<213> ORGANISM: Artificial Sequence
<220> FEATURE:
<223> OTHER INFORMATION: H-FR4 of A56-18G02

<400> SEQUENCE: 659

Trp Gly Gln Gly Thr Thr Val Thr Val Ser Ser
1               5                   10

<210> SEQ ID NO 660
<211> LENGTH: 26
<212> TYPE: PRT
<213> ORGANISM: Artificial Sequence
<220> FEATURE:
<223> OTHER INFORMATION: L-FR1 of A56-18G02

<400> SEQUENCE: 660

Asp Ile Gln Met Thr Gln Ser Pro Gly Thr Leu Ser Leu Ser Pro Gly
1               5                   10                  15

Glu Ser Ala Thr Leu Ser Cys Arg Ala Ser
            20                  25

<210> SEQ ID NO 661
<211> LENGTH: 17
<212> TYPE: PRT
<213> ORGANISM: Artificial Sequence
<220> FEATURE:
<223> OTHER INFORMATION: L-FR2 of A56-18G02

<400> SEQUENCE: 661

Leu Ala Trp Tyr Gln Gln Lys Pro Gly Gln Ala Pro Lys Val Leu Ile
1               5                   10                  15

Tyr

<210> SEQ ID NO 662
<211> LENGTH: 36
<212> TYPE: PRT
<213> ORGANISM: Artificial Sequence
```

-continued

```
<220> FEATURE:
<223> OTHER INFORMATION: L-FR3 of A56-18G02

<400> SEQUENCE: 662

Ile Tyr Gly Ala Ser Gly Arg Ala Thr Gly Thr Pro Ala Arg Phe Ser
1               5                   10                  15

Gly Gly Gly Ser Gly Thr Asp Phe Thr Leu Thr Ile Ser Ser Leu Glu
            20                  25                  30

Pro Glu Asp Phe
        35

<210> SEQ ID NO 663
<211> LENGTH: 10
<212> TYPE: PRT
<213> ORGANISM: Artificial Sequence
<220> FEATURE:
<223> OTHER INFORMATION: L-FR4 of A56-18G02

<400> SEQUENCE: 663

Phe Gly Pro Gly Ser Lys Val Glu Ile Lys
1               5                   10

<210> SEQ ID NO 664
<211> LENGTH: 8
<212> TYPE: PRT
<213> ORGANISM: Artificial Sequence
<220> FEATURE:
<223> OTHER INFORMATION: H-CDR1 of A56-20A05

<400> SEQUENCE: 664

Gly Gly Ser Phe Arg Ser Asn Ala
1               5

<210> SEQ ID NO 665
<211> LENGTH: 8
<212> TYPE: PRT
<213> ORGANISM: Artificial Sequence
<220> FEATURE:
<223> OTHER INFORMATION: H-CDR2 of A56-20A05

<400> SEQUENCE: 665

Ile Ile Pro Leu Ala Asn Arg Ser
1               5

<210> SEQ ID NO 666
<211> LENGTH: 13
<212> TYPE: PRT
<213> ORGANISM: Artificial Sequence
<220> FEATURE:
<223> OTHER INFORMATION: H-CDR3 of A56-20A05

<400> SEQUENCE: 666

Ala Arg Leu Asp Asp Asn Val Ser Trp Gly Leu Asp Pro
1               5                   10

<210> SEQ ID NO 667
<211> LENGTH: 6
<212> TYPE: PRT
<213> ORGANISM: Artificial Sequence
<220> FEATURE:
<223> OTHER INFORMATION: L-CDR1 of A56-20A05

<400> SEQUENCE: 667

Gln Asp Ile Ser Arg Arg
1               5
```

<210> SEQ ID NO 668
<211> LENGTH: 3
<212> TYPE: PRT
<213> ORGANISM: Artificial Sequence
<220> FEATURE:
<223> OTHER INFORMATION: L-CDR2 of A56-20A05

<400> SEQUENCE: 668

Ala Ala Ser
1

<210> SEQ ID NO 669
<211> LENGTH: 9
<212> TYPE: PRT
<213> ORGANISM: Artificial Sequence
<220> FEATURE:
<223> OTHER INFORMATION: L-CDR3 of A56-20A05

<400> SEQUENCE: 669

Gln Gln Ser Ser Asn Val Pro Leu Thr
1               5

<210> SEQ ID NO 670
<211> LENGTH: 255
<212> TYPE: DNA
<213> ORGANISM: Artificial Sequence
<220> FEATURE:
<223> OTHER INFORMATION: SCFV of A56-20A05

<400> SEQUENCE: 670
caggtgcagc tggtgcagtc tggggctgag gtggtgaagc ccgggtcctc ggtgaaggtc      60
tcctgtaagg cttctggagg cagcttcaga agcaatgctg tcagctgggt gcgacaggcc     120
cctggacaag gtcttgagtg gataggaggc atcatccctc tggctaatag gtcagtctac     180
gcacagaagt tccagggcag actcaccatt accgcggaca atccacgggg tacagcctac     240
atggagttga gcagc                                                      255

<210> SEQ ID NO 671
<211> LENGTH: 120
<212> TYPE: PRT
<213> ORGANISM: Artificial Sequence
<220> FEATURE:
<223> OTHER INFORMATION: VH2 of A56-20A05

<400> SEQUENCE: 671

Gln Val Gln Leu Val Gln Ser Gly Ala Glu Val Val Lys Pro Gly Ser
1               5                   10                  15

Ser Val Lys Val Ser Cys Lys Ala Ser Gly Gly Ser Phe Arg Ser Asn
            20                  25                  30

Ala Val Ser Trp Val Arg Gln Ala Pro Gly Gln Gly Leu Glu Trp Ile
        35                  40                  45

Gly Gly Ile Ile Pro Leu Ala Asn Arg Ser Val Tyr Ala Gln Lys Phe
    50                  55                  60

Gln Gly Arg Leu Thr Ile Thr Ala Asp Lys Ser Thr Gly Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Asp Asp Asn Val Ser Trp Gly Leu Asp Pro Trp Gly Gln
            100                 105                 110

Gly Thr Leu Val Thr Val Ser Ser
        115                 120

```
<210> SEQ ID NO 672
<211> LENGTH: 107
<212> TYPE: PRT
<213> ORGANISM: Artificial Sequence
<220> FEATURE:
<223> OTHER INFORMATION: VL2 of A56-20A05

<400> SEQUENCE: 672

Asp Ile Gln Met Thr Gln Ser Pro Ser Phe Leu Ser Ala Ser Val Gly
1               5                   10                  15

Asp Arg Val Asn Ile Thr Cys Arg Ala Ser Gln Asp Ile Ser Arg Arg
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Asn Val Pro Leu
                85                  90                  95

Thr Phe Gly Gly Gly Thr Lys Val Glu Ile Lys
            100                 105

<210> SEQ ID NO 673
<211> LENGTH: 25
<212> TYPE: PRT
<213> ORGANISM: Artificial Sequence
<220> FEATURE:
<223> OTHER INFORMATION: H-FR1 of A56-20A05

<400> SEQUENCE: 673

Gln Val Gln Leu Val Gln Ser Gly Ala Glu Val Val Lys Pro Gly Ser
1               5                   10                  15

Ser Val Lys Val Ser Cys Lys Ala Ser
            20                  25

<210> SEQ ID NO 674
<211> LENGTH: 17
<212> TYPE: PRT
<213> ORGANISM: Artificial Sequence
<220> FEATURE:
<223> OTHER INFORMATION: H-FR2 of A56-20A05

<400> SEQUENCE: 674

Val Ser Trp Val Arg Gln Ala Pro Gly Gln Gly Leu Glu Trp Ile Gly
1               5                   10                  15

Gly

<210> SEQ ID NO 675
<211> LENGTH: 38
<212> TYPE: PRT
<213> ORGANISM: Artificial Sequence
<220> FEATURE:
<223> OTHER INFORMATION: H-FR3 of A56-20A05

<400> SEQUENCE: 675

Val Tyr Ala Gln Lys Phe Gln Gly Arg Leu Thr Ile Thr Ala Asp Lys
1               5                   10                  15

Ser Thr Gly Thr Ala Tyr Met Glu Leu Ser Ser Leu Arg Ser Glu Asp
            20                  25                  30
```

-continued

```
Thr Ala Val Tyr Tyr Cys
        35

<210> SEQ ID NO 676
<211> LENGTH: 11
<212> TYPE: PRT
<213> ORGANISM: Artificial Sequence
<220> FEATURE:
<223> OTHER INFORMATION: H-FR4 of A56-20A05

<400> SEQUENCE: 676

Trp Gly Gln Gly Thr Leu Val Thr Val Ser Ser
1               5                   10

<210> SEQ ID NO 677
<211> LENGTH: 26
<212> TYPE: PRT
<213> ORGANISM: Artificial Sequence
<220> FEATURE:
<223> OTHER INFORMATION: L-FR1 of A56-20A05

<400> SEQUENCE: 677

Asp Ile Gln Met Thr Gln Ser Pro Ser Phe Leu Ser Ala Ser Val Gly
1               5                   10                  15

Asp Arg Val Asn Ile Thr Cys Arg Ala Ser
            20                  25

<210> SEQ ID NO 678
<211> LENGTH: 17
<212> TYPE: PRT
<213> ORGANISM: Artificial Sequence
<220> FEATURE:
<223> OTHER INFORMATION: L-FR2 of A56-20A05

<400> SEQUENCE: 678

Leu Ala Trp Tyr Gln Gln Lys Pro Gly Lys Ala Pro Lys Leu Leu Ile
1               5                   10                  15

Ser

<210> SEQ ID NO 679
<211> LENGTH: 36
<212> TYPE: PRT
<213> ORGANISM: Artificial Sequence
<220> FEATURE:
<223> OTHER INFORMATION: L-FR3 of A56-20A05

<400> SEQUENCE: 679

Ile Ser Ala Ala Ser Ser Leu Gln Ser Gly Val Pro Ser Arg Phe Ser
1               5                   10                  15

Gly Ser Gly Ser Gly Thr Asp Phe Thr Leu Thr Ile Ser Ser Leu Gln
            20                  25                  30

Pro Glu Asp Phe
        35

<210> SEQ ID NO 680
<211> LENGTH: 10
<212> TYPE: PRT
<213> ORGANISM: Artificial Sequence
<220> FEATURE:
<223> OTHER INFORMATION: L-FR4 of A56-20A05

<400> SEQUENCE: 680

Phe Gly Gly Gly Thr Lys Val Glu Ile Lys
1               5                   10
```

<210> SEQ ID NO 681
<211> LENGTH: 8
<212> TYPE: PRT
<213> ORGANISM: Artificial Sequence
<220> FEATURE:
<223> OTHER INFORMATION: H-CDR1 of A56-20G03

<400> SEQUENCE: 681

Gly Gly Thr Phe Ser Ser Tyr Ala
1               5

<210> SEQ ID NO 682
<211> LENGTH: 8
<212> TYPE: PRT
<213> ORGANISM: Artificial Sequence
<220> FEATURE:
<223> OTHER INFORMATION: H-CDR2 of A56-20G03

<400> SEQUENCE: 682

Ile Ile Pro Ile Phe Gly Thr Ala
1               5

<210> SEQ ID NO 683
<211> LENGTH: 20
<212> TYPE: PRT
<213> ORGANISM: Artificial Sequence
<220> FEATURE:
<223> OTHER INFORMATION: H-CDR3 of A56-20G03

<400> SEQUENCE: 683

Ala Thr Lys Gly Gly Gly Asn Ser Arg Ser Phe Leu Arg Tyr Phe Tyr
1               5                   10                  15

Gly Leu Asp Val
            20

<210> SEQ ID NO 684
<211> LENGTH: 11
<212> TYPE: PRT
<213> ORGANISM: Artificial Sequence
<220> FEATURE:
<223> OTHER INFORMATION: L-CDR1 of A56-20G03

<400> SEQUENCE: 684

Gln Ser Leu Val His Ser Asp Gly Asn Thr Tyr
1               5                   10

<210> SEQ ID NO 685
<211> LENGTH: 3
<212> TYPE: PRT
<213> ORGANISM: Artificial Sequence
<220> FEATURE:
<223> OTHER INFORMATION: L-CDR2 of A56-20G03

<400> SEQUENCE: 685

Lys Val Ser
1

<210> SEQ ID NO 686
<211> LENGTH: 9
<212> TYPE: PRT
<213> ORGANISM: Artificial Sequence
<220> FEATURE:
<223> OTHER INFORMATION: L-CDR3 of A56-20G03

<400> SEQUENCE: 686

Met Gln Gly Thr His Trp Pro Trp Thr 1                5

<210> SEQ ID NO 687
<211> LENGTH: 255
<212> TYPE: DNA
<213> ORGANISM: Artificial Sequence
<220> FEATURE:
<223> OTHER INFORMATION: SCFV of A56-20G03

<400> SEQUENCE: 687
caggtgcagc tggtgcagtc tgggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgaa cacagcctac     240
atggagctga gcagc                                                      255

<210> SEQ ID NO 688
<211> LENGTH: 127
<212> TYPE: PRT
<213> ORGANISM: Artificial Sequence
<220> FEATURE:
<223> OTHER INFORMATION: VH2 of A56-20G03

<400> SEQUENCE: 688

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Thr Lys Gly Gly Gly Asn Ser Arg Ser Phe Leu Arg Tyr Phe Tyr
            100                 105                 110

Gly Leu Asp Val Trp Gly Gln Gly Thr Thr Val Thr Val Ser Ser
        115                 120                 125

<210> SEQ ID NO 689
<211> LENGTH: 112
<212> TYPE: PRT
<213> ORGANISM: Artificial Sequence
<220> FEATURE:
<223> OTHER INFORMATION: VL2 of A56-20G03

<400> SEQUENCE: 689

Asp Ile Val Met Thr Gln Thr Pro Leu Ser Leu Pro Val Ala Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile

-continued

```
65              70              75              80

Ser Arg Val Glu Ala Glu Asp Val Gly Val Tyr Tyr Cys Met Gln Gly
                85              90              95

Thr His Trp Pro Trp Thr Phe Gly Gln Gly Thr Lys Val Glu Ile Lys
            100             105             110

<210> SEQ ID NO 690
<211> LENGTH: 25
<212> TYPE: PRT
<213> ORGANISM: Artificial Sequence
<220> FEATURE:
<223> OTHER INFORMATION: H-FR1 of A56-20G03

<400> SEQUENCE: 690

Gln Val Gln Leu Val Gln Ser Gly Ala Glu Val Lys Lys Pro Gly Ser
1               5               10              15

Ser Val Lys Val Ser Cys Lys Ala Ser
            20              25

<210> SEQ ID NO 691
<211> LENGTH: 17
<212> TYPE: PRT
<213> ORGANISM: Artificial Sequence
<220> FEATURE:
<223> OTHER INFORMATION: H-FR2 of A56-20G03

<400> SEQUENCE: 691

Ile Ser Trp Val Arg Gln Ala Pro Gly Gln Gly Leu Glu Trp Met Gly
1               5               10              15

Gly

<210> SEQ ID NO 692
<211> LENGTH: 38
<212> TYPE: PRT
<213> ORGANISM: Artificial Sequence
<220> FEATURE:
<223> OTHER INFORMATION: H-FR3 of A56-20G03

<400> SEQUENCE: 692

Asn Tyr Ala Gln Lys Phe Gln Gly Arg Val Thr Ile Thr Ala Asp Glu
1               5               10              15

Ser Thr Asn Thr Ala Tyr Met Glu Leu Ser Ser Leu Arg Ser Glu Asp
            20              25              30

Thr Ala Val Tyr Tyr Cys
        35

<210> SEQ ID NO 693
<211> LENGTH: 11
<212> TYPE: PRT
<213> ORGANISM: Artificial Sequence
<220> FEATURE:
<223> OTHER INFORMATION: H-FR4 of A56-20G03

<400> SEQUENCE: 693

Trp Gly Gln Gly Thr Thr Val Thr Val Ser Ser
1               5               10

<210> SEQ ID NO 694
<211> LENGTH: 26
<212> TYPE: PRT
<213> ORGANISM: Artificial Sequence
<220> FEATURE:
<223> OTHER INFORMATION: L-FR1 of A56-20G03
```

-continued

<400> SEQUENCE: 694

Asp Ile Val Met Thr Gln Thr Pro Leu Ser Leu Pro Val Ala Leu Gly
1               5                   10                  15

Gln Pro Ala Ser Ile Ser Cys Arg Ser Ser
            20                  25

<210> SEQ ID NO 695
<211> LENGTH: 17
<212> TYPE: PRT
<213> ORGANISM: Artificial Sequence
<220> FEATURE:
<223> OTHER INFORMATION: L-FR2 of A56-20G03

<400> SEQUENCE: 695

Leu Asn Trp Phe Gln Gln Arg Pro Gly Gln Ser Pro Arg Arg Leu Ile
1               5                   10                  15

Tyr

<210> SEQ ID NO 696
<211> LENGTH: 36
<212> TYPE: PRT
<213> ORGANISM: Artificial Sequence
<220> FEATURE:
<223> OTHER INFORMATION: L-FR3 of A56-20G03

<400> SEQUENCE: 696

Ile Tyr Lys Val Ser Asn Arg Asp Ser Gly Val Pro Asp Arg Phe Ser
1               5                   10                  15

Gly Ser Gly Ser Gly Thr Asp Phe Thr Leu Lys Ile Ser Arg Val Glu
            20                  25                  30

Ala Glu Asp Val
        35

<210> SEQ ID NO 697
<211> LENGTH: 10
<212> TYPE: PRT
<213> ORGANISM: Artificial Sequence
<220> FEATURE:
<223> OTHER INFORMATION: L-FR4 of A56-20G03

<400> SEQUENCE: 697

Phe Gly Gln Gly Thr Lys Val Glu Ile Lys
1               5                   10

<210> SEQ ID NO 698
<211> LENGTH: 8
<212> TYPE: PRT
<213> ORGANISM: Artificial Sequence
<220> FEATURE:
<223> OTHER INFORMATION: H-CDR1 of A56-20G12

<400> SEQUENCE: 698

Gly Phe Asn Phe Asn Thr Tyr Ala
1               5

<210> SEQ ID NO 699
<211> LENGTH: 8
<212> TYPE: PRT
<213> ORGANISM: Artificial Sequence
<220> FEATURE:
<223> OTHER INFORMATION: H-CDR2 of A56-20G12

<400> SEQUENCE: 699

Ile Gly Gly Gly Gly Gly Asn Thr

-continued 1               5

<210> SEQ ID NO 700
<211> LENGTH: 10
<212> TYPE: PRT
<213> ORGANISM: Artificial Sequence
<220> FEATURE:
<223> OTHER INFORMATION: H-CDR3 of A56-20G12

<400> SEQUENCE: 700

Ala Thr Arg Gly Gly Trp Tyr Val Asn Asp
1               5                   10

<210> SEQ ID NO 701
<211> LENGTH: 9
<212> TYPE: PRT
<213> ORGANISM: Artificial Sequence
<220> FEATURE:
<223> OTHER INFORMATION: L-CDR1 of A56-20G12

<400> SEQUENCE: 701

Ser Ser Asn Ile Gly Ala Gly Tyr Ala
1               5

<210> SEQ ID NO 702
<211> LENGTH: 3
<212> TYPE: PRT
<213> ORGANISM: Artificial Sequence
<220> FEATURE:
<223> OTHER INFORMATION: L-CDR2 of A56-20G12

<400> SEQUENCE: 702

Ser Asn Thr
1

<210> SEQ ID NO 703
<211> LENGTH: 12
<212> TYPE: PRT
<213> ORGANISM: Artificial Sequence
<220> FEATURE:
<223> OTHER INFORMATION: L-CDR3 of A56-20G12

<400> SEQUENCE: 703

Gln Ser Tyr Asp Asn Ser Leu Ser Asp Ser Val Val
1               5                   10

<210> SEQ ID NO 704
<211> LENGTH: 255
<212> TYPE: DNA
<213> ORGANISM: Artificial Sequence
<220> FEATURE:
<223> OTHER INFORMATION: SCFV of A56-20G12

<400> SEQUENCE: 704
caggtgcagc tggtggagtc tgggggaggg ttggtacagc cggggggggtc cctgagactc      60 tcctgtacag cctctggatt caactttaat acctatgcca tgagctgggt ccgccagcct     120
ccagggaagg ggctggagtg ggtctcaact attgggggtg gtggtgggaa cacattttac     180
gcagattccg tgagggggccg gttcaccatc tccagagaca attccgagaa cacgctgtat     240
ctgcaaatga acagt                                                       255

<210> SEQ ID NO 705
<211> LENGTH: 117
<212> TYPE: PRT
<213> ORGANISM: Artificial Sequence -continued

```
<220> FEATURE:
<223> OTHER INFORMATION: VH2 of A56-20G12

<400> SEQUENCE: 705

Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Asn Phe Asn Thr Tyr
            20                  25                  30

Ala Met Ser Trp Val Arg Gln Pro Pro Gly Lys Gly Leu Glu Trp Val
        35                  40                  45

Ser Thr Ile Gly Gly Gly Gly Asn Thr Phe Tyr Ala Asp Ser Val
    50                  55                  60

Arg Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Arg Gly Gly Trp Tyr Val Asn Asp Trp Gly Arg Gly Thr Leu
            100                 105                 110

Val Thr Val Ser Ser
        115

<210> SEQ ID NO 706
<211> LENGTH: 112
<212> TYPE: PRT
<213> ORGANISM: Artificial Sequence
<220> FEATURE:
<223> OTHER INFORMATION: VL2 of A56-20G12

<400> SEQUENCE: 706

Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ala Val His Trp Tyr Gln Gln Ile Pro Gly Thr Ala Pro Lys Leu
        35                  40                  45

Leu Ile Tyr Ser Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Asp Ser Val Val Phe Gly Gly Gly Thr Lys Leu Thr Val Leu
            100                 105                 110

<210> SEQ ID NO 707
<211> LENGTH: 25
<212> TYPE: PRT
<213> ORGANISM: Artificial Sequence
<220> FEATURE:
<223> OTHER INFORMATION: H-FR1 of A56-20G12

<400> SEQUENCE: 707

Gln Val Gln Leu Val Glu Ser Gly Gly Gly Leu Val Gln Pro Gly Gly
1               5                   10                  15

Ser Leu Arg Leu Ser Cys Thr Ala Ser
            20                  25

<210> SEQ ID NO 708
<211> LENGTH: 17
```

```
<212> TYPE: PRT
<213> ORGANISM: Artificial Sequence
<220> FEATURE:
<223> OTHER INFORMATION: H-FR2 of A56-20G12

<400> SEQUENCE: 708

Met Ser Trp Val Arg Gln Pro Pro Gly Lys Gly Leu Glu Trp Val Ser
1               5                   10                  15

Thr

<210> SEQ ID NO 709
<211> LENGTH: 38
<212> TYPE: PRT
<213> ORGANISM: Artificial Sequence
<220> FEATURE:
<223> OTHER INFORMATION: H-FR3 of A56-20G12

<400> SEQUENCE: 709

Phe Tyr Ala Asp Ser Val Arg Gly Arg Phe Thr Ile Ser Arg Asp Asn
1               5                   10                  15

Ser Glu Asn Thr Leu Tyr Leu Gln Met Asn Ser Leu Arg Ala Glu Asp
                20                  25                  30

Thr Ala Val Tyr Tyr Cys
        35

<210> SEQ ID NO 710
<211> LENGTH: 11
<212> TYPE: PRT
<213> ORGANISM: Artificial Sequence
<220> FEATURE:
<223> OTHER INFORMATION: H-FR4 of A56-20G12

<400> SEQUENCE: 710

Trp Gly Arg Gly Thr Leu Val Thr Val Ser Ser
1               5                   10

<210> SEQ ID NO 711
<211> LENGTH: 25
<212> TYPE: PRT
<213> ORGANISM: Artificial Sequence
<220> FEATURE:
<223> OTHER INFORMATION: L-FR1 of A56-20G12

<400> SEQUENCE: 711

Gln Leu Val Leu Thr Gln Pro Pro Ser Val Ser Gly Ala Pro Gly Gln
1               5                   10                  15

Arg Val Thr Ile Ser Cys Thr Gly Ser
                20                  25

<210> SEQ ID NO 712
<211> LENGTH: 17
<212> TYPE: PRT
<213> ORGANISM: Artificial Sequence
<220> FEATURE:
<223> OTHER INFORMATION: L-FR2 of A56-20G12

<400> SEQUENCE: 712

Val His Trp Tyr Gln Gln Ile Pro Gly Thr Ala Pro Lys Leu Leu Ile
1               5                   10                  15

Tyr

<210> SEQ ID NO 713
<211> LENGTH: 36
<212> TYPE: PRT
```

-continued

```
<213> ORGANISM: Artificial Sequence
<220> FEATURE:
<223> OTHER INFORMATION: L-FR3 of A56-20G12

<400> SEQUENCE: 713

Ile Tyr Ser Asn Thr Asn Arg Pro Ser Gly Val Pro Asp Arg Phe Ser
1               5                   10                  15

Gly Ser Lys Ser Gly Thr Ser Ala Ser Leu Ala Ile Thr Gly Leu Gln
            20                  25                  30

Ala Glu Asp Glu
        35

<210> SEQ ID NO 714
<211> LENGTH: 10
<212> TYPE: PRT
<213> ORGANISM: Artificial Sequence
<220> FEATURE:
<223> OTHER INFORMATION: L-FR4 of A56-20G12

<400> SEQUENCE: 714

Phe Gly Gly Gly Thr Lys Leu Thr Val Leu
1               5                   10

<210> SEQ ID NO 715
<211> LENGTH: 8
<212> TYPE: PRT
<213> ORGANISM: Artificial Sequence
<220> FEATURE:
<223> OTHER INFORMATION: H-CDR1 of A56-21B10

<400> SEQUENCE: 715

Gly Asp Thr Phe Ser Thr Tyr Ala
1               5

<210> SEQ ID NO 716
<211> LENGTH: 8
<212> TYPE: PRT
<213> ORGANISM: Artificial Sequence
<220> FEATURE:
<223> OTHER INFORMATION: H-CDR2 of A56-21B10

<400> SEQUENCE: 716

Ile Ile Pro Arg Leu Gly Ile Ala
1               5

<210> SEQ ID NO 717
<211> LENGTH: 19
<212> TYPE: PRT
<213> ORGANISM: Artificial Sequence
<220> FEATURE:
<223> OTHER INFORMATION: H-CDR3 of A56-21B10

<400> SEQUENCE: 717

Ala Ala Asp Pro Leu Trp Phe Gly Asp Phe Ile Arg Gly Gly Arg Ala
1               5                   10                  15

Phe Asn Ile

<210> SEQ ID NO 718
<211> LENGTH: 6
<212> TYPE: PRT
<213> ORGANISM: Artificial Sequence
<220> FEATURE:
<223> OTHER INFORMATION: L-CDR1 of A56-21B10

<400> SEQUENCE: 718
```

```
Gln Ser Ile Ser Thr Trp
1               5

<210> SEQ ID NO 719
<211> LENGTH: 3
<212> TYPE: PRT
<213> ORGANISM: Artificial Sequence
<220> FEATURE:
<223> OTHER INFORMATION: L-CDR2 of A56-21B10

<400> SEQUENCE: 719

Lys Ala Ser
1

<210> SEQ ID NO 720
<211> LENGTH: 9
<212> TYPE: PRT
<213> ORGANISM: Artificial Sequence
<220> FEATURE:
<223> OTHER INFORMATION: L-CDR3 of A56-21B10

<400> SEQUENCE: 720

Gln Gln Tyr Tyr Asn Tyr Pro Tyr Thr
1               5

<210> SEQ ID NO 721
<211> LENGTH: 255
<212> TYPE: DNA
<213> ORGANISM: Artificial Sequence
<220> FEATURE:
<223> OTHER INFORMATION: SCFV of A56-21B10

<400> SEQUENCE: 721
cagatgcagc tggtgcagtc tggggctgag gtgagaaagc ctgggtcttc ggtgacggtc    60
tcctgcaagg ctcctggaga caccttcagt acttatgcta tcagttgggt gcgacaggcc   120
cctggacaag ggcttgactg gatggggagg atcatccctc gccttggtat tgcaaaaaat   180
gcaccggagt tccaggacag agtctcgatc accgcggaca atccacgaa tacagtgcat    240 atggagttga gaaac                                                    255

<210> SEQ ID NO 722
<211> LENGTH: 126
<212> TYPE: PRT
<213> ORGANISM: Artificial Sequence
<220> FEATURE:
<223> OTHER INFORMATION: VH2 of A56-21B10

<400> SEQUENCE: 722

Gln Met Gln Leu Val Gln Ser Gly Ala Glu Val Arg Lys Pro Gly Ser
1               5                   10                  15

Ser Val Thr Val Ser Cys Lys Ala Pro Gly Asp Thr Phe Ser Thr Tyr
            20                  25                  30

Ala Ile Ser Trp Val Arg Gln Ala Pro Gly Gln Gly Leu Asp Trp Met
        35                  40                  45

Gly Arg Ile Ile Pro Arg Leu Gly Ile Ala Lys Asn Ala Pro Glu Phe
    50                  55                  60

Gln Asp Arg Val Ser Ile Thr Ala Asp Lys Ser Thr Asn Thr Val His
65                  70                  75                  80

Met Glu Leu Arg Asn Leu Arg Ser Glu Asp Thr Ala Val Tyr Tyr Cys
                85                  90                  95

Ala Ala Asp Pro Leu Trp Phe Gly Asp Phe Ile Arg Gly Gly Arg Ala
            100                 105                 110
```

-continued

```
Phe Asn Ile Trp Gly Gln Gly Thr Met Ile Thr Val Ser Ser
        115                 120                 125
```

```
<210> SEQ ID NO 723
<211> LENGTH: 107
<212> TYPE: PRT
<213> ORGANISM: Artificial Sequence
<220> FEATURE:
<223> OTHER INFORMATION: VL2 of A56-21B10

<400> SEQUENCE: 723

Asp Ile Gln Met Thr Gln Ser Pro Ser Thr Leu Ser Ala Ser Ile Gly
1                   5                   10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Thr Ile Glu Ser Gly Val Pro Ser Arg Phe Ser Gly
    50                  55                  60

Ser Gly Ser Asp Thr Glu Phe Thr Leu Thr Ile Thr Asn Leu Gln Pro
65                  70                  75                  80

Asp Asp Ser Ala Thr Tyr Tyr Cys Gln Gln Tyr Tyr Asn Tyr Pro Tyr
                85                  90                  95

Thr Phe Gly Gln Gly Thr Lys Leu Glu Ile Lys
            100                 105
```

```
<210> SEQ ID NO 724
<211> LENGTH: 25
<212> TYPE: PRT
<213> ORGANISM: Artificial Sequence
<220> FEATURE:
<223> OTHER INFORMATION: H-FR1 of A56-21B10

<400> SEQUENCE: 724

Gln Met Gln Leu Val Gln Ser Gly Ala Glu Val Arg Lys Pro Gly Ser
1                   5                   10                  15

Ser Val Thr Val Ser Cys Lys Ala Pro
            20                  25
```

```
<210> SEQ ID NO 725
<211> LENGTH: 17
<212> TYPE: PRT
<213> ORGANISM: Artificial Sequence
<220> FEATURE:
<223> OTHER INFORMATION: H-FR2 of A56-21B10

<400> SEQUENCE: 725

Ile Ser Trp Val Arg Gln Ala Pro Gly Gln Gly Leu Asp Trp Met Gly
1                   5                   10                  15

Arg
```

```
<210> SEQ ID NO 726
<211> LENGTH: 38
<212> TYPE: PRT
<213> ORGANISM: Artificial Sequence
<220> FEATURE:
<223> OTHER INFORMATION: H-FR3 of A56-21B10

<400> SEQUENCE: 726

Lys Asn Ala Pro Glu Phe Gln Asp Arg Val Ser Ile Thr Ala Asp Lys
1                   5                   10                  15
```

-continued

```
Ser Thr Asn Thr Val His Met Glu Leu Arg Asn Leu Arg Ser Glu Asp
            20              25              30

Thr Ala Val Tyr Tyr Cys
        35

<210> SEQ ID NO 727
<211> LENGTH: 11
<212> TYPE: PRT
<213> ORGANISM: Artificial Sequence
<220> FEATURE:
<223> OTHER INFORMATION: H-FR4 of A56-21B10

<400> SEQUENCE: 727

Trp Gly Gln Gly Thr Met Ile Thr Val Ser Ser
1               5                   10

<210> SEQ ID NO 728
<211> LENGTH: 26
<212> TYPE: PRT
<213> ORGANISM: Artificial Sequence
<220> FEATURE:
<223> OTHER INFORMATION: L-FR1 of A56-21B10

<400> SEQUENCE: 728

Asp Ile Gln Met Thr Gln Ser Pro Ser Thr Leu Ser Ala Ser Ile Gly
1               5                   10                  15

Asp Arg Val Thr Ile Thr Cys Arg Ala Ser
            20              25

<210> SEQ ID NO 729
<211> LENGTH: 17
<212> TYPE: PRT
<213> ORGANISM: Artificial Sequence
<220> FEATURE:
<223> OTHER INFORMATION: L-FR2 of A56-21B10

<400> SEQUENCE: 729

Leu Ala Trp Tyr Gln Gln Lys Pro Gly Lys Ala Pro Lys Leu Leu Ile
1               5                   10                  15

Tyr

<210> SEQ ID NO 730
<211> LENGTH: 36
<212> TYPE: PRT
<213> ORGANISM: Artificial Sequence
<220> FEATURE:
<223> OTHER INFORMATION: L-FR3 of A56-21B10

<400> SEQUENCE: 730

Ile Tyr Lys Ala Ser Thr Ile Glu Ser Gly Val Pro Ser Arg Phe Ser
1               5                   10                  15

Gly Ser Gly Ser Asp Thr Glu Phe Thr Leu Thr Ile Thr Asn Leu Gln
            20              25              30

Pro Asp Asp Ser
        35

<210> SEQ ID NO 731
<211> LENGTH: 10
<212> TYPE: PRT
<213> ORGANISM: Artificial Sequence
<220> FEATURE:
<223> OTHER INFORMATION: L-FR4 of A56-21B10

<400> SEQUENCE: 731
```

-continued

```
Phe Gly Gln Gly Thr Lys Leu Glu Ile Lys
1               5                   10

<210> SEQ ID NO 732
<211> LENGTH: 8
<212> TYPE: PRT
<213> ORGANISM: Artificial Sequence
<220> FEATURE:
<223> OTHER INFORMATION: H-CDR1 of A56-21F02

<400> SEQUENCE: 732

Gly Phe Thr Phe Asp Tyr Ser Ala
1               5

<210> SEQ ID NO 733
<211> LENGTH: 8
<212> TYPE: PRT
<213> ORGANISM: Artificial Sequence
<220> FEATURE:
<223> OTHER INFORMATION: H-CDR2 of A56-21F02

<400> SEQUENCE: 733

Ile Ser Gly Asp Gly Gly Thr Ala
1               5

<210> SEQ ID NO 734
<211> LENGTH: 16
<212> TYPE: PRT
<213> ORGANISM: Artificial Sequence
<220> FEATURE:
<223> OTHER INFORMATION: H-CDR3 of A56-21F02

<400> SEQUENCE: 734

Ala Arg Asp Arg Trp Arg Trp Met Asp Asp Tyr Tyr Gly Met Asp Val
1               5                   10                  15

<210> SEQ ID NO 735
<211> LENGTH: 6
<212> TYPE: PRT
<213> ORGANISM: Artificial Sequence
<220> FEATURE:
<223> OTHER INFORMATION: L-CDR1 of A56-21F02

<400> SEQUENCE: 735

Gln Gly Ile Thr Gly Tyr
1               5

<210> SEQ ID NO 736
<211> LENGTH: 3
<212> TYPE: PRT
<213> ORGANISM: Artificial Sequence
<220> FEATURE:
<223> OTHER INFORMATION: L-CDR2 of A56-21F02

<400> SEQUENCE: 736

Lys Ser Ser
1

<210> SEQ ID NO 737
<211> LENGTH: 9
<212> TYPE: PRT
<213> ORGANISM: Artificial Sequence
<220> FEATURE:
<223> OTHER INFORMATION: L-CDR3 of A56-21F02

<400> SEQUENCE: 737

Gln Gln Tyr Asp Ser Tyr Pro Trp Thr
```

-continued

```
1                5
```

```
<210> SEQ ID NO 738
<211> LENGTH: 255
<212> TYPE: DNA
<213> ORGANISM: Artificial Sequence
<220> FEATURE:
<223> OTHER INFORMATION: SCFV of A56-21F02

<400> SEQUENCE: 738
cagatgcagc tggtgcagtc ggggggaacc gtggtacagc ctggggagtc cctgagactc      60
tcctgtgcaa cctctggatt cacctttgat tattctgcca tgcactgggt ccgtcaagct     120
ccagggaagg gtctggagtg ggtctctctc atcagtgggg atggtggtac cgcatattat     180
gcagactctg tgaagggccg attcaccgtc tccagagaca acagcaaaaa ctccctgtat     240
ctgcaaatga acagt                                                      255

<210> SEQ ID NO 739
<211> LENGTH: 123
<212> TYPE: PRT
<213> ORGANISM: Artificial Sequence
<220> FEATURE:
<223> OTHER INFORMATION: VH2 of A56-21F02

<400> SEQUENCE: 739

Gln Met Gln Leu Val Gln Ser Gly Gly Thr Val Val Gln Pro Gly Glu
1                5                  10                  15

Ser Leu Arg Leu Ser Cys Ala Thr Ser Gly Phe Thr Phe Asp Tyr Ser
            20                  25                  30

Ala Met His Trp Val Arg Gln Ala Pro Gly Lys Gly Leu Glu Trp Val
        35                  40                  45

Ser Leu Ile Ser Gly Asp Gly Gly Thr Ala Tyr Tyr Ala Asp Ser Val
    50                  55                  60

Lys Gly Arg Phe Thr Val Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Arg Trp Met Asp Asp Tyr Tyr Gly Met Asp Val
            100                 105                 110

Trp Gly Gln Gly Thr Thr Val Thr Val Ser Ser
        115                 120

<210> SEQ ID NO 740
<211> LENGTH: 107
<212> TYPE: PRT
<213> ORGANISM: Artificial Sequence
<220> FEATURE:
<223> OTHER INFORMATION: VL2 of A56-21F02

<400> SEQUENCE: 740

Asp Ile Gln Met Thr Gln Ser Pro Ser Ser Leu Ser Thr Ser Val Gly
1                5                  10                  15

Asp Arg Val Thr Ile Thr Cys Arg Ala Ser Gln Gly Ile Thr Gly Tyr
            20                  25                  30

Phe Ala Trp Tyr Gln Gln Lys Pro Gly Lys Ala Pro Asn Leu Leu Leu
        35                  40                  45

Tyr Lys Ser Ser Ile Leu Gln Ser Gly Val Pro Ser Arg Phe Ser Gly
    50                  55                  60

Ser Gly Ser Gly Thr Glu Phe Thr Leu Thr Ile Asn Ser Leu Gln Ala
```

-continued

```
65              70              75              80

Asp Asp Phe Ala Thr Tyr Tyr Cys Gln Gln Tyr Asp Ser Tyr Pro Trp
                85                  90                  95

Thr Phe Gly Gln Gly Thr Lys Val Asp Ile Lys
            100                 105

<210> SEQ ID NO 741
<211> LENGTH: 25
<212> TYPE: PRT
<213> ORGANISM: Artificial Sequence
<220> FEATURE:
<223> OTHER INFORMATION: H-FR1 of A56-21F02

<400> SEQUENCE: 741

Gln Met Gln Leu Val Gln Ser Gly Gly Thr Val Val Gln Pro Gly Glu
1               5                   10                  15

Ser Leu Arg Leu Ser Cys Ala Thr Ser
            20                  25

<210> SEQ ID NO 742
<211> LENGTH: 17
<212> TYPE: PRT
<213> ORGANISM: Artificial Sequence
<220> FEATURE:
<223> OTHER INFORMATION: H-FR2 of A56-21F02

<400> SEQUENCE: 742

Met His Trp Val Arg Gln Ala Pro Gly Lys Gly Leu Glu Trp Val Ser
1               5                   10                  15

Leu

<210> SEQ ID NO 743
<211> LENGTH: 38
<212> TYPE: PRT
<213> ORGANISM: Artificial Sequence
<220> FEATURE:
<223> OTHER INFORMATION: H-FR3 of A56-21F02

<400> SEQUENCE: 743

Tyr Tyr Ala Asp Ser Val Lys Gly Arg Phe Thr Val Ser Arg Asp Asn
1               5                   10                  15

Ser Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 744
<211> LENGTH: 11
<212> TYPE: PRT
<213> ORGANISM: Artificial Sequence
<220> FEATURE:
<223> OTHER INFORMATION: H-FR4 of A56-21F02

<400> SEQUENCE: 744

Trp Gly Gln Gly Thr Thr Val Thr Val Ser Ser
1               5                   10

<210> SEQ ID NO 745
<211> LENGTH: 26
<212> TYPE: PRT
<213> ORGANISM: Artificial Sequence
<220> FEATURE:
<223> OTHER INFORMATION: L-FR1 of A56-21F02
```

-continued

```
<400> SEQUENCE: 745

Asp Ile Gln Met Thr Gln Ser Pro Ser Ser Leu Ser Thr Ser Val Gly
1               5                   10                  15

Asp Arg Val Thr Ile Thr Cys Arg Ala Ser
            20                  25

<210> SEQ ID NO 746
<211> LENGTH: 17
<212> TYPE: PRT
<213> ORGANISM: Artificial Sequence
<220> FEATURE:
<223> OTHER INFORMATION: L-FR2 of A56-21F02

<400> SEQUENCE: 746

Phe Ala Trp Tyr Gln Gln Lys Pro Gly Lys Ala Pro Asn Leu Leu Leu
1               5                   10                  15

Tyr

<210> SEQ ID NO 747
<211> LENGTH: 36
<212> TYPE: PRT
<213> ORGANISM: Artificial Sequence
<220> FEATURE:
<223> OTHER INFORMATION: L-FR3 of A56-21F02

<400> SEQUENCE: 747

Leu Tyr Lys Ser Ser Ile Leu Gln Ser Gly Val Pro Ser Arg Phe Ser
1               5                   10                  15

Gly Ser Gly Ser Gly Thr Glu Phe Thr Leu Thr Ile Asn Ser Leu Gln
            20                  25                  30

Ala Asp Asp Phe
        35

<210> SEQ ID NO 748
<211> LENGTH: 10
<212> TYPE: PRT
<213> ORGANISM: Artificial Sequence
<220> FEATURE:
<223> OTHER INFORMATION: L-FR4 of A56-21F02

<400> SEQUENCE: 748

Phe Gly Gln Gly Thr Lys Val Asp Ile Lys
1               5                   10

<210> SEQ ID NO 749
<211> LENGTH: 8
<212> TYPE: PRT
<213> ORGANISM: Artificial Sequence
<220> FEATURE:
<223> OTHER INFORMATION: H-CDR1 of A56-21H04

<400> SEQUENCE: 749

Gly Phe Thr Phe Asn Phe Tyr Gly
1               5

<210> SEQ ID NO 750
<211> LENGTH: 8
<212> TYPE: PRT
<213> ORGANISM: Artificial Sequence
<220> FEATURE:
<223> OTHER INFORMATION: H-CDR2 of A56-21H04

<400> SEQUENCE: 750

Ile Ser Tyr Glu Gly Ser Lys Lys
```

```
1              5
```

```
<210> SEQ ID NO 751
<211> LENGTH: 20
<212> TYPE: PRT
<213> ORGANISM: Artificial Sequence
<220> FEATURE:
<223> OTHER INFORMATION: H-CDR3 of A56-21H04

<400> SEQUENCE: 751

Ala Arg Gly Phe Asp Pro Asp Tyr Leu Arg Gly Asn Asn Arg Tyr Phe
1               5                   10                  15

Gly Leu Asp Val
            20

<210> SEQ ID NO 752
<211> LENGTH: 6
<212> TYPE: PRT
<213> ORGANISM: Artificial Sequence
<220> FEATURE:
<223> OTHER INFORMATION: L-CDR1 of A56-21H04

<400> SEQUENCE: 752

Glu Asp Ile Ser Arg Gln
1               5

<210> SEQ ID NO 753
<211> LENGTH: 3
<212> TYPE: PRT
<213> ORGANISM: Artificial Sequence
<220> FEATURE:
<223> OTHER INFORMATION: L-CDR2 of A56-21H04

<400> SEQUENCE: 753

Gly Ala Ser
1

<210> SEQ ID NO 754
<211> LENGTH: 9
<212> TYPE: PRT
<213> ORGANISM: Artificial Sequence
<220> FEATURE:
<223> OTHER INFORMATION: L-CDR3 of A56-21H04

<400> SEQUENCE: 754

Gln Lys Ala Asn Asn Phe Pro Tyr Thr
1               5

<210> SEQ ID NO 755
<211> LENGTH: 255
<212> TYPE: DNA
<213> ORGANISM: Artificial Sequence
<220> FEATURE:
<223> OTHER INFORMATION: SCFV of A56-21H04

<400> SEQUENCE: 755
caggtgcagc tggtggagtc tgggggaggt gtggtccagc ctggggaggtc cctgagactc      60 tcctgtgcag cctctggatt caccttcaat ttctatggta tgcactgggt ccgccaggct     120
ccaggtaagg ggctagagtg gctggcagct atatcatatg aaggaagtaa gaagtactac     180
gcagactccg tgaagggccg attcaccatc tccagagaca attccaagaa cacgccggat     240
ctgcaaatga acagt                                                      255

<210> SEQ ID NO 756
```

-continued

```
<211> LENGTH: 127
<212> TYPE: PRT
<213> ORGANISM: Artificial Sequence
<220> FEATURE:
<223> OTHER INFORMATION: VH2 of A56-21H04

<400> SEQUENCE: 756

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Phe Tyr
            20                  25                  30

Gly Met His Trp Val Arg Gln Ala Pro Gly Lys Gly Leu Glu Trp Leu
        35                  40                  45

Ala Ala Ile Ser Tyr Glu Gly Ser Lys Lys Tyr Tyr Ala Asp Ser Val
    50                  55                  60

Lys Gly Arg Phe Thr Ile Ser Arg Asp Asn Ser Lys Asn Thr Pro Asp
65                  70                  75                  80

Leu Gln Met Asn Ser Leu Arg Ala Glu Asp Thr Ala Val Tyr Tyr Cys
                85                  90                  95

Ala Arg Gly Phe Asp Pro Asp Tyr Leu Arg Gly Asn Asn Arg Tyr Phe
            100                 105                 110

Gly Leu Asp Val Trp Gly Gln Gly Thr Thr Val Thr Val Ser Ser
        115                 120                 125

<210> SEQ ID NO 757
<211> LENGTH: 107
<212> TYPE: PRT
<213> ORGANISM: Artificial Sequence
<220> FEATURE:
<223> OTHER INFORMATION: VL2 of A56-21H04

<400> SEQUENCE: 757

Asp Ile Gln Met Thr Gln Ser Pro Ser Ser Val Ser Ala Ser Val Gly
1               5                   10                  15

Asp Arg Val Thr Ile Thr Cys Arg Ala Ser Glu Asp Ile Ser Arg Gln
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Phe Gly Thr Glu Phe Thr Leu Thr Ile Asn Ser Leu Gln Pro
65                  70                  75                  80

Glu Asp Phe Ala Thr Tyr Tyr Cys Gln Lys Ala Asn Asn Phe Pro Tyr
                85                  90                  95

Thr Phe Gly Gln Gly Thr Lys Val Asp Ile Lys
            100                 105

<210> SEQ ID NO 758
<211> LENGTH: 25
<212> TYPE: PRT
<213> ORGANISM: Artificial Sequence
<220> FEATURE:
<223> OTHER INFORMATION: H-FR1 of A56-21H04

<400> SEQUENCE: 758

Gln Val Gln Leu Val Glu Ser Gly Gly Gly Val Val Gln Pro Gly Arg
1               5                   10                  15

Ser Leu Arg Leu Ser Cys Ala Ala Ser
            20                  25
```

-continued

<210> SEQ ID NO 759
<211> LENGTH: 17
<212> TYPE: PRT
<213> ORGANISM: Artificial Sequence
<220> FEATURE:
<223> OTHER INFORMATION: H-FR2 of A56-21H04

<400> SEQUENCE: 759

Met His Trp Val Arg Gln Ala Pro Gly Lys Gly Leu Glu Trp Leu Ala
1               5                   10                  15

Ala

<210> SEQ ID NO 760
<211> LENGTH: 38
<212> TYPE: PRT
<213> ORGANISM: Artificial Sequence
<220> FEATURE:
<223> OTHER INFORMATION: H-FR3 of A56-21H04

<400> SEQUENCE: 760

Tyr Tyr Ala Asp Ser Val Lys Gly Arg Phe Thr Ile Ser Arg Asp Asn
1               5                   10                  15

Ser Lys Asn Thr Pro Asp Leu Gln Met Asn Ser Leu Arg Ala Glu Asp
            20                  25                  30

Thr Ala Val Tyr Tyr Cys
        35

<210> SEQ ID NO 761
<211> LENGTH: 11
<212> TYPE: PRT
<213> ORGANISM: Artificial Sequence
<220> FEATURE:
<223> OTHER INFORMATION: H-FR4 of A56-21H04

<400> SEQUENCE: 761

Trp Gly Gln Gly Thr Thr Val Thr Val Ser Ser
1               5                   10

<210> SEQ ID NO 762
<211> LENGTH: 26
<212> TYPE: PRT
<213> ORGANISM: Artificial Sequence
<220> FEATURE:
<223> OTHER INFORMATION: L-FR1 of A56-21H04

<400> SEQUENCE: 762

Asp Ile Gln Met Thr Gln Ser Pro Ser Ser Val Ser Ala Ser Val Gly
1               5                   10                  15

Asp Arg Val Thr Ile Thr Cys Arg Ala Ser
            20                  25

<210> SEQ ID NO 763
<211> LENGTH: 17
<212> TYPE: PRT
<213> ORGANISM: Artificial Sequence
<220> FEATURE:
<223> OTHER INFORMATION: L-FR2 of A56-21H04

<400> SEQUENCE: 763

Leu Ala Trp Tyr Gln Gln Lys Pro Gly Lys Ala Pro Lys Leu Leu Ile
1               5                   10                  15

Tyr

<210> SEQ ID NO 764
<211> LENGTH: 36
<212> TYPE: PRT
<213> ORGANISM: Artificial Sequence
<220> FEATURE:
<223> OTHER INFORMATION: L-FR3 of A56-21H04

<400> SEQUENCE: 764

Ile Tyr Gly Ala Ser Ser Leu Gln Ser Gly Val Pro Ser Arg Phe Ser
1               5                   10                  15

Gly Ser Gly Phe Gly Thr Glu Phe Thr Leu Thr Ile Asn Ser Leu Gln
            20                  25                  30

Pro Glu Asp Phe
        35

<210> SEQ ID NO 765
<211> LENGTH: 10
<212> TYPE: PRT
<213> ORGANISM: Artificial Sequence
<220> FEATURE:
<223> OTHER INFORMATION: L-FR4 of A56-21H04

<400> SEQUENCE: 765

Phe Gly Gln Gly Thr Lys Val Asp Ile Lys
1               5                   10

<210> SEQ ID NO 766
<211> LENGTH: 8
<212> TYPE: PRT
<213> ORGANISM: Artificial Sequence
<220> FEATURE:
<223> OTHER INFORMATION: H-CDR1 of A56-22G10

<400> SEQUENCE: 766

Gly Phe Met Phe Lys Asn Tyr Ala
1               5

<210> SEQ ID NO 767
<211> LENGTH: 8
<212> TYPE: PRT
<213> ORGANISM: Artificial Sequence
<220> FEATURE:
<223> OTHER INFORMATION: H-CDR2 of A56-22G10

<400> SEQUENCE: 767

Val Ser Gly Ser Gly Asp Thr Thr
1               5

<210> SEQ ID NO 768
<211> LENGTH: 12
<212> TYPE: PRT
<213> ORGANISM: Artificial Sequence
<220> FEATURE:
<223> OTHER INFORMATION: H-CDR3 of A56-22G10

<400> SEQUENCE: 768

Ala Lys Val Gly Val Ala Val Ala Gln Gly Asp Tyr
1               5                   10

<210> SEQ ID NO 769
<211> LENGTH: 12
<212> TYPE: PRT
<213> ORGANISM: Artificial Sequence
<220> FEATURE:
<223> OTHER INFORMATION: L-CDR1 of A56-22G10

<400> SEQUENCE: 769

-continued

Gln Ser Val Leu Ser Ser Ser Asn Asn Lys Asn Tyr
1               5                   10

<210> SEQ ID NO 770
<211> LENGTH: 3
<212> TYPE: PRT
<213> ORGANISM: Artificial Sequence
<220> FEATURE:
<223> OTHER INFORMATION: L-CDR2 of A56-22G10

<400> SEQUENCE: 770

Trp Ala Ser
1

<210> SEQ ID NO 771
<211> LENGTH: 9
<212> TYPE: PRT
<213> ORGANISM: Artificial Sequence
<220> FEATURE:
<223> OTHER INFORMATION: L-CDR3 of A56-22G10

<400> SEQUENCE: 771

Gln Gln Tyr Tyr Gly Thr Pro Leu Thr
1               5

<210> SEQ ID NO 772
<211> LENGTH: 255
<212> TYPE: DNA
<213> ORGANISM: Artificial Sequence
<220> FEATURE:
<223> OTHER INFORMATION: SCFV of A56-22G10

<400> SEQUENCE: 772
cagatgcagc tggtggagtc ggggggaggc ttcgtacagc ctggggggtc ccggagactc        60
tcctgtgcag gctctggatt catgtttaag aattatgcca tgacttggtt cgccaggct       120 ccagggaagg ggctggagtg ggtctcagct gtcagtggtt ctggtgacac cacatactac       180
acagactccg tgaagggccg gttcatcatc tccagagaca attccaacaa caccgtctat       240
ctgcaaatga acagt                                                        255

<210> SEQ ID NO 773
<211> LENGTH: 119
<212> TYPE: PRT
<213> ORGANISM: Artificial Sequence
<220> FEATURE:
<223> OTHER INFORMATION: VH2 of A56-22G10

<400> SEQUENCE: 773

Gln Met Gln Leu Val Glu Ser Gly Gly Gly Phe Val Gln Pro Gly Gly
1               5                   10                  15

Ser Arg Arg Leu Ser Cys Ala Gly Ser Gly Phe Met Phe Lys Asn Tyr
            20                  25                  30

Ala Met Thr Trp Phe Arg Gln Ala Pro Gly Lys Gly Leu Glu Trp Val
        35                  40                  45

Ser Ala Val Ser Gly Ser Gly Asp Thr Thr Tyr Tyr Thr Asp Ser Val
    50                  55                  60

Lys Gly Arg Phe Ile Ile Ser Arg Asp Asn Ser Asn Asn Thr Val Tyr
65                  70                  75                  80

Leu Gln Met Asn Ser Leu Arg Ala Glu Asp Thr Ala Val Tyr Tyr Cys
                85                  90                  95

Ala Lys Val Gly Val Ala Val Ala Gln Gly Asp Tyr Trp Gly Gln Gly

-continued

```
                100             105             110

Thr Leu Val Thr Val Ser Ser
        115

<210> SEQ ID NO 774
<211> LENGTH: 113
<212> TYPE: PRT
<213> ORGANISM: Artificial Sequence
<220> FEATURE:
<223> OTHER INFORMATION: VL2 of A56-22G10

<400> SEQUENCE: 774

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Thr Pro Leu Thr Phe Gly Gly Gly Thr Lys Val Glu Ile
            100                 105                 110

Lys

<210> SEQ ID NO 775
<211> LENGTH: 25
<212> TYPE: PRT
<213> ORGANISM: Artificial Sequence
<220> FEATURE:
<223> OTHER INFORMATION: H-FR1 of A56-22G10

<400> SEQUENCE: 775

Gln Met Gln Leu Val Glu Ser Gly Gly Gly Phe Val Gln Pro Gly Gly
1               5                   10                  15

Ser Arg Arg Leu Ser Cys Ala Gly Ser
            20                  25

<210> SEQ ID NO 776
<211> LENGTH: 17
<212> TYPE: PRT
<213> ORGANISM: Artificial Sequence
<220> FEATURE:
<223> OTHER INFORMATION: H-FR2 of A56-22G10

<400> SEQUENCE: 776

Met Thr Trp Phe Arg Gln Ala Pro Gly Lys Gly Leu Glu Trp Val Ser
1               5                   10                  15

Ala

<210> SEQ ID NO 777
<211> LENGTH: 38
<212> TYPE: PRT
<213> ORGANISM: Artificial Sequence
<220> FEATURE:
<223> OTHER INFORMATION: H-FR3 of A56-22G10

<400> SEQUENCE: 777
```

-continued

```
Tyr Tyr Thr Asp Ser Val Lys Gly Arg Phe Ile Ile Ser Arg Asp Asn
1               5                   10                  15

Ser Asn Asn Thr Val Tyr Leu Gln Met Asn Ser Leu Arg Ala Glu Asp
            20                  25                  30

Thr Ala Val Tyr Tyr Cys
            35

<210> SEQ ID NO 778
<211> LENGTH: 11
<212> TYPE: PRT
<213> ORGANISM: Artificial Sequence
<220> FEATURE:
<223> OTHER INFORMATION: H-FR4 of A56-22G10

<400> SEQUENCE: 778

Trp Gly Gln Gly Thr Leu Val Thr Val Ser Ser
1               5                   10

<210> SEQ ID NO 779
<211> LENGTH: 26
<212> TYPE: PRT
<213> ORGANISM: Artificial Sequence
<220> FEATURE:
<223> OTHER INFORMATION: L-FR1 of A56-22G10

<400> SEQUENCE: 779

Asp Ile Gln Met Thr Gln Ser Pro Asp Ser Leu Ala Val Ser Leu Gly
1               5                   10                  15

Glu Arg Ala Thr Ile Asn Cys Lys Ser Ser
            20                  25

<210> SEQ ID NO 780
<211> LENGTH: 17
<212> TYPE: PRT
<213> ORGANISM: Artificial Sequence
<220> FEATURE:
<223> OTHER INFORMATION: L-FR2 of A56-22G10

<400> SEQUENCE: 780

Leu Ala Trp Tyr Gln Gln Lys Pro Gly Gln Pro Pro Lys Leu Leu Ile
1               5                   10                  15

Tyr

<210> SEQ ID NO 781
<211> LENGTH: 36
<212> TYPE: PRT
<213> ORGANISM: Artificial Sequence
<220> FEATURE:
<223> OTHER INFORMATION: L-FR3 of A56-22G10

<400> SEQUENCE: 781

Ile Tyr Trp Ala Ser Thr Arg Glu Ser Gly Val Pro Asp Arg Phe Ser
1               5                   10                  15

Gly Ser Gly Ser Gly Thr Asp Phe Thr Leu Thr Ile Ser Ser Leu Gln
            20                  25                  30

Ala Glu Asp Val
            35

<210> SEQ ID NO 782
<211> LENGTH: 10
<212> TYPE: PRT
<213> ORGANISM: Artificial Sequence
<220> FEATURE:
<223> OTHER INFORMATION: L-FR4 of A56-22G10
```

<400> SEQUENCE: 782

Phe Gly Gly Gly Thr Lys Val Glu Ile Lys
1               5                   10

<210> SEQ ID NO 783
<211> LENGTH: 8
<212> TYPE: PRT
<213> ORGANISM: Artificial Sequence
<220> FEATURE:
<223> OTHER INFORMATION: H-CDR1 of A56-24A05

<400> SEQUENCE: 783

Arg Tyr Thr Phe Thr Tyr Arg Tyr
1               5

<210> SEQ ID NO 784
<211> LENGTH: 8
<212> TYPE: PRT
<213> ORGANISM: Artificial Sequence
<220> FEATURE:
<223> OTHER INFORMATION: H-CDR2 of A56-24A05

<400> SEQUENCE: 784

Ile Gln Pro Phe Asn Gly Asn Thr
1               5

<210> SEQ ID NO 785
<211> LENGTH: 16
<212> TYPE: PRT
<213> ORGANISM: Artificial Sequence
<220> FEATURE:
<223> OTHER INFORMATION: H-CDR3 of A56-24A05

<400> SEQUENCE: 785

Ala Lys Asp Ile Arg Ile Glu Asp Ile Val Val Val Pro Ala Ala Ile
1               5                   10                  15

<210> SEQ ID NO 786
<211> LENGTH: 9
<212> TYPE: PRT
<213> ORGANISM: Artificial Sequence
<220> FEATURE:
<223> OTHER INFORMATION: L-CDR1 of A56-24A05

<400> SEQUENCE: 786

Ser Ser Asp Val Gly Gly Tyr Asn Tyr
1               5

<210> SEQ ID NO 787
<211> LENGTH: 3
<212> TYPE: PRT
<213> ORGANISM: Artificial Sequence
<220> FEATURE:
<223> OTHER INFORMATION: L-CDR2 of A56-24A05

<400> SEQUENCE: 787

Glu Val Asn
1

<210> SEQ ID NO 788
<211> LENGTH: 10
<212> TYPE: PRT
<213> ORGANISM: Artificial Sequence
<220> FEATURE:
<223> OTHER INFORMATION: L-CDR3 of A56-24A05

-continued

<400> SEQUENCE: 788

Ser Ser Tyr Thr Ser Ser Ser Thr Phe Asp
1               5                   10

<210> SEQ ID NO 789
<211> LENGTH: 255
<212> TYPE: DNA
<213> ORGANISM: Artificial Sequence
<220> FEATURE:
<223> OTHER INFORMATION: SCFV of A56-24A05

<400> SEQUENCE: 789
caggtgcagc tggtgcagtc tggggctgag gtgaagaaga ctgggtcctc agtgaaagtt      60
tcctgcaaga cttccagata caccttcacc taccgttatc tgcactgggt gcgacaggcc     120
cccggacaag cgcttgagtg gttggggtgg atccaacctt tcaatggtaa taccaactac     180
gcacagaaat tccaagacag agtcaccatt acccgggaca ggtctatgag cacagcctac     240
atggagctga gcagc                                                      255

<210> SEQ ID NO 790
<211> LENGTH: 123
<212> TYPE: PRT
<213> ORGANISM: Artificial Sequence
<220> FEATURE:
<223> OTHER INFORMATION: VH2 of A56-24A05

<400> SEQUENCE: 790

Gln Val Gln Leu Val Gln Ser Gly Ala Glu Val Lys Lys Thr Gly Ser
1               5                   10                  15

Ser Val Lys Val Ser Cys Lys Thr Ser Arg Tyr Thr Phe Thr Tyr Arg
            20                  25                  30

Tyr Leu His Trp Val Arg Gln Ala Pro Gly Gln Ala Leu Glu Trp Leu
        35                  40                  45

Gly Trp Ile Gln Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Ile Arg Ile Glu Asp Ile Val Val Val Pro Ala Ala Ile
            100                 105                 110

Trp Gly Gln Gly Thr Leu Val Thr Val Ser Ser
        115                 120

<210> SEQ ID NO 791
<211> LENGTH: 110
<212> TYPE: PRT
<213> ORGANISM: Artificial Sequence
<220> FEATURE:
<223> OTHER INFORMATION: VL2 of A56-24A05

<400> SEQUENCE: 791

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Asn Lys Arg Pro Ser Gly Val Ser Asn Arg Phe

```
                 50              55                60

Ser Gly Ser Lys Ser Gly Asn Thr Ala Phe Leu Thr Ile Ser Gly Leu
65                  70              75                  80

Gln Ser Glu Asp Glu Ala Asp Tyr Tyr Cys Ser Ser Tyr Thr Ser Ser
                    85              90                  95

Ser Thr Phe Asp Phe Gly Thr Gly Thr Lys Val Thr Val Leu
            100             105             110
```

```
<210> SEQ ID NO 792
<211> LENGTH: 25
<212> TYPE: PRT
<213> ORGANISM: Artificial Sequence
<220> FEATURE:
<223> OTHER INFORMATION: H-FR1 of A56-24A05

<400> SEQUENCE: 792

Gln Val Gln Leu Val Gln Ser Gly Ala Glu Val Lys Lys Thr Gly Ser
1               5               10              15

Ser Val Lys Val Ser Cys Lys Thr Ser
            20              25
```

```
<210> SEQ ID NO 793
<211> LENGTH: 17
<212> TYPE: PRT
<213> ORGANISM: Artificial Sequence
<220> FEATURE:
<223> OTHER INFORMATION: H-FR2 of A56-24A05

<400> SEQUENCE: 793

Leu His Trp Val Arg Gln Ala Pro Gly Gln Ala Leu Glu Trp Leu Gly
1               5               10              15

Trp
```

```
<210> SEQ ID NO 794
<211> LENGTH: 38
<212> TYPE: PRT
<213> ORGANISM: Artificial Sequence
<220> FEATURE:
<223> OTHER INFORMATION: H-FR3 of A56-24A05

<400> SEQUENCE: 794

Asn Tyr Ala Gln Lys Phe Gln Asp Arg Val Thr Ile Thr Arg Asp Arg
1               5               10              15

Ser Met Ser Thr Ala Tyr Met Glu Leu Ser Ser Leu Arg Ser Glu Asp
            20              25              30

Thr Ala Val Tyr Tyr Cys
        35
```

```
<210> SEQ ID NO 795
<211> LENGTH: 11
<212> TYPE: PRT
<213> ORGANISM: Artificial Sequence
<220> FEATURE:
<223> OTHER INFORMATION: H-FR4 of A56-24A05

<400> SEQUENCE: 795

Trp Gly Gln Gly Thr Leu Val Thr Val Ser Ser
1               5               10
```

```
<210> SEQ ID NO 796
<211> LENGTH: 25
<212> TYPE: PRT
<213> ORGANISM: Artificial Sequence
```

<220> FEATURE:
<223> OTHER INFORMATION: L-FR1 of A56-24A05

<400> SEQUENCE: 796

Gln Ser Ala Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 797
<211> LENGTH: 17
<212> TYPE: PRT
<213> ORGANISM: Artificial Sequence
<220> FEATURE:
<223> OTHER INFORMATION: L-FR2 of A56-24A05

<400> SEQUENCE: 797

Val Ser Trp Tyr Gln Gln His Pro Gly Lys Ala Pro Lys Leu Met Ile
1               5                   10                  15

Tyr

<210> SEQ ID NO 798
<211> LENGTH: 36
<212> TYPE: PRT
<213> ORGANISM: Artificial Sequence
<220> FEATURE:
<223> OTHER INFORMATION: L-FR3 of A56-24A05

<400> SEQUENCE: 798

Ile Tyr Glu Val Asn Lys Arg Pro Ser Gly Val Ser Asn Arg Phe Ser
1               5                   10                  15

Gly Ser Lys Ser Gly Asn Thr Ala Phe Leu Thr Ile Ser Gly Leu Gln
            20                  25                  30

Ser Glu Asp Glu
        35

<210> SEQ ID NO 799
<211> LENGTH: 10
<212> TYPE: PRT
<213> ORGANISM: Artificial Sequence
<220> FEATURE:
<223> OTHER INFORMATION: L-FR4 of A56-24A05

<400> SEQUENCE: 799

Phe Gly Thr Gly Thr Lys Val Thr Val Leu
1               5                   10

<210> SEQ ID NO 800
<211> LENGTH: 8
<212> TYPE: PRT
<213> ORGANISM: Artificial Sequence
<220> FEATURE:
<223> OTHER INFORMATION: H-CDR1 of A56-30H01

<400> SEQUENCE: 800

Gly Phe Thr Phe Lys Thr Tyr Ser
1               5

<210> SEQ ID NO 801
<211> LENGTH: 8
<212> TYPE: PRT
<213> ORGANISM: Artificial Sequence
<220> FEATURE:
<223> OTHER INFORMATION: H-CDR2 of A56-30H01

```
<400> SEQUENCE: 801

Ile Asn Asn Asn Gly Asp Ala Thr
1               5

<210> SEQ ID NO 802
<211> LENGTH: 28
<212> TYPE: PRT
<213> ORGANISM: Artificial Sequence
<220> FEATURE:
<223> OTHER INFORMATION: H-CDR3 of A56-30H01

<400> SEQUENCE: 802

Ala Arg Asp Leu Ile Ala His Glu Gln Pro Lys Phe Ser Leu Arg Tyr
1               5                   10                  15

Phe Asp Trp Leu Ser Ser Arg Lys Gly Met Asp Val
            20              25

<210> SEQ ID NO 803
<211> LENGTH: 9
<212> TYPE: PRT
<213> ORGANISM: Artificial Sequence
<220> FEATURE:
<223> OTHER INFORMATION: L-CDR1 of A56-30H01

<400> SEQUENCE: 803

Ser Ser Asp Val Gly Gly Tyr Asn Tyr
1               5

<210> SEQ ID NO 804
<211> LENGTH: 3
<212> TYPE: PRT
<213> ORGANISM: Artificial Sequence
<220> FEATURE:
<223> OTHER INFORMATION: L-CDR2 of A56-30H01

<400> SEQUENCE: 804

Asp Val Thr
1

<210> SEQ ID NO 805
<211> LENGTH: 10
<212> TYPE: PRT
<213> ORGANISM: Artificial Sequence
<220> FEATURE:
<223> OTHER INFORMATION: L-CDR3 of A56-30H01

<400> SEQUENCE: 805

Ser Ser Tyr Ser Ser Ser Thr Phe Tyr Val
1               5                   10

<210> SEQ ID NO 806
<211> LENGTH: 255
<212> TYPE: DNA
<213> ORGANISM: Artificial Sequence
<220> FEATURE:
<223> OTHER INFORMATION: SCFV of A56-30H01

<400> SEQUENCE: 806
caggtgcagc tggtgcagtc tggggggaggc ttggtccagc ctggggggtc cctgaaactc      60
tcctgttcag cctctggatt caccttcaaa acctattcta tgcactgggt ccgccaggct     120
ccggggaagg gactggaata tgtttcagct attaataata tggggatgc cacatactac     180 gcagactccg tgaagggcag attcaccatc tccagagaca attccaagga cacgctgtat     240
cttcaaatga acagt                                                     255
```

-continued

<210> SEQ ID NO 807
<211> LENGTH: 135
<212> TYPE: PRT
<213> ORGANISM: Artificial Sequence
<220> FEATURE:
<223> OTHER INFORMATION: VH2 of A56-30H01

<400> SEQUENCE: 807

Gln Val Gln Leu Val Gln Ser Gly Gly Gly Leu Val Gln Pro Gly Gly
1               5                   10                  15

Ser Leu Lys Leu Ser Cys Ser Ala Ser Gly Phe Thr Phe Lys Thr Tyr
            20                  25                  30

Ser Met His Trp Val Arg Gln Ala Pro Gly Lys Gly Leu Glu Tyr Val
        35                  40                  45

Ser Ala Ile Asn Asn Asn Gly Asp Ala Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile Ala His Glu Gln Pro Lys Phe Ser Leu Arg Tyr
            100                 105                 110

Phe Asp Trp Leu Ser Ser Arg Lys Gly Met Asp Val Trp Gly Gln Gly
        115                 120                 125

Thr Thr Ile Thr Val Ser Ser
    130                 135

<210> SEQ ID NO 808
<211> LENGTH: 110
<212> TYPE: PRT
<213> ORGANISM: Artificial Sequence
<220> FEATURE:
<223> OTHER INFORMATION: VL2 of A56-30H01

<400> SEQUENCE: 808

Asn Phe Met Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Gln Leu
        35                  40                  45

Ile Ile Tyr Asp Val Thr Lys Arg Pro Ser Gly Val Ser Asn Arg Phe
    50                  55                  60

Ser Gly Ser Lys Ser Gly Asn Ser Ala Ser Leu Thr Ile Ser Gly Leu
65                  70                  75                  80

Gln Ala Glu Asp Glu Ala Asp Tyr Tyr Cys Ser Ser Tyr Ser Ser Ser
                85                  90                  95

Thr Phe Tyr Val Phe Gly Thr Gly Thr Lys Val Thr Val Leu
            100                 105                 110

<210> SEQ ID NO 809
<211> LENGTH: 25
<212> TYPE: PRT
<213> ORGANISM: Artificial Sequence
<220> FEATURE:
<223> OTHER INFORMATION: H-FR1 of A56-30H01

<400> SEQUENCE: 809

-continued

```
Gln Val Gln Leu Val Gln Ser Gly Gly Gly Leu Val Gln Pro Gly Gly
1               5                   10                  15

Ser Leu Lys Leu Ser Cys Ser Ala Ser
            20                  25

<210> SEQ ID NO 810
<211> LENGTH: 17
<212> TYPE: PRT
<213> ORGANISM: Artificial Sequence
<220> FEATURE:
<223> OTHER INFORMATION: H-FR2 of A56-30H01

<400> SEQUENCE: 810

Met His Trp Val Arg Gln Ala Pro Gly Lys Gly Leu Glu Tyr Val Ser
1               5                   10                  15

Ala

<210> SEQ ID NO 811
<211> LENGTH: 38
<212> TYPE: PRT
<213> ORGANISM: Artificial Sequence
<220> FEATURE:
<223> OTHER INFORMATION: H-FR3 of A56-30H01

<400> SEQUENCE: 811

Tyr Tyr Ala Asp Ser Val Lys Gly Arg Phe Thr Ile Ser Arg Asp Asn
1               5                   10                  15

Ser Lys Asp Thr Leu Tyr Leu Gln Met Asn Ser Leu Arg Ala Glu Asp
            20                  25                  30

Thr Ala Val Tyr Tyr Cys
            35

<210> SEQ ID NO 812
<211> LENGTH: 11
<212> TYPE: PRT
<213> ORGANISM: Artificial Sequence
<220> FEATURE:
<223> OTHER INFORMATION: H-FR4 of A56-30H01

<400> SEQUENCE: 812

Trp Gly Gln Gly Thr Thr Ile Thr Val Ser Ser
1               5                   10

<210> SEQ ID NO 813
<211> LENGTH: 25
<212> TYPE: PRT
<213> ORGANISM: Artificial Sequence
<220> FEATURE:
<223> OTHER INFORMATION: L-FR1 of A56-30H01

<400> SEQUENCE: 813

Asn Phe Met Leu Thr Gln Pro Ala Ser Val Ser Gly Ser Pro Gly Gln
1               5                   10                  15

Ser Ile Thr Ile Ser Cys Thr Gly Ser
            20                  25

<210> SEQ ID NO 814
<211> LENGTH: 17
<212> TYPE: PRT
<213> ORGANISM: Artificial Sequence
<220> FEATURE:
<223> OTHER INFORMATION: L-FR2 of A56-30H01

<400> SEQUENCE: 814
```

Val Ser Trp Tyr Gln Gln His Pro Gly Lys Ala Pro Gln Leu Ile Ile
1               5                   10                  15

Tyr

<210> SEQ ID NO 815
<211> LENGTH: 36
<212> TYPE: PRT
<213> ORGANISM: Artificial Sequence
<220> FEATURE:
<223> OTHER INFORMATION: L-FR3 of A56-30H01

<400> SEQUENCE: 815

Ile Tyr Asp Val Thr Lys Arg Pro Ser Gly Val Ser Asn Arg Phe Ser
1               5                   10                  15

Gly Ser Lys Ser Gly Asn Ser Ala Ser Leu Thr Ile Ser Gly Leu Gln
            20                  25                  30

Ala Glu Asp Glu
        35

<210> SEQ ID NO 816
<211> LENGTH: 10
<212> TYPE: PRT
<213> ORGANISM: Artificial Sequence
<220> FEATURE:
<223> OTHER INFORMATION: L-FR4 of A56-30H01

<400> SEQUENCE: 816

Phe Gly Thr Gly Thr Lys Val Thr Val Leu
1               5                   10

<210> SEQ ID NO 817
<211> LENGTH: 9
<212> TYPE: PRT
<213> ORGANISM: Artificial Sequence
<220> FEATURE:
<223> OTHER INFORMATION: H-CDR1 of A56-32H08

<400> SEQUENCE: 817

Ser Gly Phe Lys Phe Glu Asp His Ala
1               5

<210> SEQ ID NO 818
<211> LENGTH: 8
<212> TYPE: PRT
<213> ORGANISM: Artificial Sequence
<220> FEATURE:
<223> OTHER INFORMATION: H-CDR2 of A56-32H08

<400> SEQUENCE: 818

Ile Ser Gly Asn Gly Asp Asp Thr
1               5

<210> SEQ ID NO 819
<211> LENGTH: 5
<212> TYPE: PRT
<213> ORGANISM: Artificial Sequence
<220> FEATURE:
<223> OTHER INFORMATION: H-CDR3 of A56-32H08

<400> SEQUENCE: 819

Val Thr Arg Gly Ala
1               5

<210> SEQ ID NO 820
<211> LENGTH: 6

-continued

```
<212> TYPE: PRT
<213> ORGANISM: Artificial Sequence
<220> FEATURE:
<223> OTHER INFORMATION: L-CDR1 of A56-32H08

<400> SEQUENCE: 820

Gln Ser Val Gly Thr Trp
1               5

<210> SEQ ID NO 821
<211> LENGTH: 3
<212> TYPE: PRT
<213> ORGANISM: Artificial Sequence
<220> FEATURE:
<223> OTHER INFORMATION: L-CDR2 of A56-32H08

<400> SEQUENCE: 821

Ala Ala Ser
1

<210> SEQ ID NO 822
<211> LENGTH: 8
<212> TYPE: PRT
<213> ORGANISM: Artificial Sequence
<220> FEATURE:
<223> OTHER INFORMATION: L-CDR3 of A56-32H08

<400> SEQUENCE: 822

Gln Gln Ala Asp Ser Phe His Ser
1               5

<210> SEQ ID NO 823
<211> LENGTH: 255
<212> TYPE: DNA
<213> ORGANISM: Artificial Sequence
<220> FEATURE:
<223> OTHER INFORMATION: SCFV of A56-32H08

<400> SEQUENCE: 823
cagatgcagc tggtggagtc aggggggaggc gtggtacagc ctggggggtc cctaagactc        60
gcctgtgtag gctctggatt caagtttgaa gatcatgcca tacactgggt ccgtcaacgt       120
ccagggaagg gtctggagtg ggtcgccgtt ataagtggca atggcgatga cacatactat       180
gcagactctg cgaagggccg attcaccatt tccagagaca acagcaaaaa ctccctgtat       240
ctgcaaatga acagt                                                        255

<210> SEQ ID NO 824
<211> LENGTH: 112
<212> TYPE: PRT
<213> ORGANISM: Artificial Sequence
<220> FEATURE:
<223> OTHER INFORMATION: VH2 of A56-32H08

<400> SEQUENCE: 824

Gln Met Gln Leu Val Glu Ser Gly Gly Gly Val Val Gln Pro Gly Gly
1               5                   10                  15

Ser Leu Arg Leu Ala Cys Val Gly Ser Gly Phe Lys Phe Glu Asp His
            20                  25                  30

Ala Ile His Trp Val Arg Gln Arg Pro Gly Lys Gly Leu Glu Trp Val
        35                  40                  45

Ala Val Ile Ser Gly Asn Gly Asp Asp Thr Tyr Tyr Ala Asp Ser Ala
    50                  55                  60

Lys Gly Arg Phe Thr Ile Ser Arg Asp Asn Ser Lys Asn Ser Leu Tyr
```

-continued

```
65                70                75                80

Leu Gln Met Asn Ser Leu Arg Ala Glu Asp Thr Ala Val Tyr Tyr Cys
                 85                90                95

Val Thr Arg Gly Ala Gln Gly Arg Gly Thr Leu Val Thr Val Ser Ser
            100               105               110
```

<210> SEQ ID NO 825
<211> LENGTH: 106
<212> TYPE: PRT
<213> ORGANISM: Artificial Sequence
<220> FEATURE:
<223> OTHER INFORMATION: VL2 of A56-32H08

<400> SEQUENCE: 825

```
Asp Ile Gln Met Thr Gln Ser Pro Ser Ser Val Ser Ala Ser Val Gly
1                5                10                15

Asp Arg Val Thr Ile Thr Cys Arg Ala Ser Gln Ser Val Gly Thr Trp
            20                25                30

Leu Ala Trp Tyr Gln Gln Lys Pro Gly Arg Ala Pro Lys Leu Leu Ile
        35                40                45

Ser Ala Ala Ser Ser Leu His Pro Gly Val Pro Ser Arg Phe Ser Gly
        50                55                60

Ser Gly Ser Gly Thr Glu Phe Thr Leu Thr Ile Ser Ser Leu Gln Pro
65                70                75                80

Glu Asp Ile Ala Thr Tyr Tyr Cys Gln Gln Ala Asp Ser Phe His Ser
                 85                90                95

Phe Gly Pro Gly Thr Lys Val Asp Ile Lys
            100               105
```

<210> SEQ ID NO 826
<211> LENGTH: 24
<212> TYPE: PRT
<213> ORGANISM: Artificial Sequence
<220> FEATURE:
<223> OTHER INFORMATION: H-FR1 of A56-32H08

<400> SEQUENCE: 826

```
Gln Met Gln Leu Val Glu Ser Gly Gly Gly Val Val Gln Pro Gly Gly
1                5                10                15

Ser Leu Arg Leu Ala Cys Val Gly
            20
```

<210> SEQ ID NO 827
<211> LENGTH: 17
<212> TYPE: PRT
<213> ORGANISM: Artificial Sequence
<220> FEATURE:
<223> OTHER INFORMATION: H-FR2 of A56-32H08

<400> SEQUENCE: 827

```
Ile His Trp Val Arg Gln Arg Pro Gly Lys Gly Leu Glu Trp Val Ala
1                5                10                15

Val
```

<210> SEQ ID NO 828
<211> LENGTH: 38
<212> TYPE: PRT
<213> ORGANISM: Artificial Sequence
<220> FEATURE:
<223> OTHER INFORMATION: H-FR3 of A56-32H08

<400> SEQUENCE: 828

-continued

Tyr Tyr Ala Asp Ser Ala Lys Gly Arg Phe Thr Ile Ser Arg Asp Asn
1               5                   10                  15

Ser Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 829
<211> LENGTH: 11
<212> TYPE: PRT
<213> ORGANISM: Artificial Sequence
<220> FEATURE:
<223> OTHER INFORMATION: H-FR4 of A56-32H08

<400> SEQUENCE: 829

Gln Gly Arg Gly Thr Leu Val Thr Val Ser Ser
1               5                   10

<210> SEQ ID NO 830
<211> LENGTH: 26
<212> TYPE: PRT
<213> ORGANISM: Artificial Sequence
<220> FEATURE:
<223> OTHER INFORMATION: L-FR1 of A56-32H08

<400> SEQUENCE: 830

Asp Ile Gln Met Thr Gln Ser Pro Ser Ser Val Ser Ala Ser Val Gly
1               5                   10                  15

Asp Arg Val Thr Ile Thr Cys Arg Ala Ser
            20                  25

<210> SEQ ID NO 831
<211> LENGTH: 17
<212> TYPE: PRT
<213> ORGANISM: Artificial Sequence
<220> FEATURE:
<223> OTHER INFORMATION: L-FR2 of A56-32H08

<400> SEQUENCE: 831

Leu Ala Trp Tyr Gln Gln Lys Pro Gly Arg Ala Pro Lys Leu Leu Ile
1               5                   10                  15

Ser

<210> SEQ ID NO 832
<211> LENGTH: 36
<212> TYPE: PRT
<213> ORGANISM: Artificial Sequence
<220> FEATURE:
<223> OTHER INFORMATION: L-FR3 of A56-32H08

<400> SEQUENCE: 832

Ile Ser Ala Ala Ser Ser Leu His Pro Gly Val Pro Ser Arg Phe Ser
1               5                   10                  15

Gly Ser Gly Ser Gly Thr Glu Phe Thr Leu Thr Ile Ser Ser Leu Gln
            20                  25                  30

Pro Glu Asp Ile
        35

<210> SEQ ID NO 833
<211> LENGTH: 10
<212> TYPE: PRT
<213> ORGANISM: Artificial Sequence
<220> FEATURE:

-continued

```
<223> OTHER INFORMATION: L-FR4 of A56-32H08

<400> SEQUENCE: 833

Phe Gly Pro Gly Thr Lys Val Asp Ile Lys
1               5                   10

<210> SEQ ID NO 834
<211> LENGTH: 8
<212> TYPE: PRT
<213> ORGANISM: Artificial Sequence
<220> FEATURE:
<223> OTHER INFORMATION: H-CDR1 of A56-35A06

<400> SEQUENCE: 834

Gly Asp Thr Phe Arg Lys Phe Thr
1               5

<210> SEQ ID NO 835
<211> LENGTH: 8
<212> TYPE: PRT
<213> ORGANISM: Artificial Sequence
<220> FEATURE:
<223> OTHER INFORMATION: H-CDR2 of A56-35A06

<400> SEQUENCE: 835

Leu Ile Pro Ile Phe Gly Thr Pro
1               5

<210> SEQ ID NO 836
<211> LENGTH: 17
<212> TYPE: PRT
<213> ORGANISM: Artificial Sequence
<220> FEATURE:
<223> OTHER INFORMATION: H-CDR3 of A56-35A06

<400> SEQUENCE: 836

Val Arg Glu Asn Tyr Glu Phe Leu Thr Gly Ala Thr Arg Tyr Phe Asp
1               5                   10                  15

Leu

<210> SEQ ID NO 837
<211> LENGTH: 9
<212> TYPE: PRT
<213> ORGANISM: Artificial Sequence
<220> FEATURE:
<223> OTHER INFORMATION: L-CDR1 of A56-35A06

<400> SEQUENCE: 837

Ser Ser Asn Leu Gly Ala Pro Asn Asp
1               5

<210> SEQ ID NO 838
<211> LENGTH: 3
<212> TYPE: PRT
<213> ORGANISM: Artificial Sequence
<220> FEATURE:
<223> OTHER INFORMATION: L-CDR2 of A56-35A06

<400> SEQUENCE: 838

Gly Ser Thr
1

<210> SEQ ID NO 839
<211> LENGTH: 12
<212> TYPE: PRT
<213> ORGANISM: Artificial Sequence
```

-continued

<220> FEATURE:
<223> OTHER INFORMATION: L-CDR3 of A56-35A06

<400> SEQUENCE: 839

Gln Ser Tyr Asp Asn Arg Leu Ser Gly Phe Val Val
1               5               10

<210> SEQ ID NO 840
<211> LENGTH: 255
<212> TYPE: DNA
<213> ORGANISM: Artificial Sequence
<220> FEATURE:
<223> OTHER INFORMATION: SCFV of A56-35A06

<400> SEQUENCE: 840
caggtgcagc tggtgcagtc tggggctgag gtgaagaagc ctgggtcctc ggttacggtc      60
tcctgcaagg cctctggaga caccttcagg aagtttactt tcaactgggt gcgacaggcc     120
cctggacaag gcttgagtg gatgggaggg ctcatcccga tctttggtac acctaaatac     180
tcacagaagt tccaggacag attcacaata accgcggacg aatcaacgag cacagcctac     240
atggagctac gtcgc                                                     255

<210> SEQ ID NO 841
<211> LENGTH: 124
<212> TYPE: PRT
<213> ORGANISM: Artificial Sequence
<220> FEATURE:
<223> OTHER INFORMATION: VH2 of A56-35A06

<400> SEQUENCE: 841

Gln Val Gln Leu Val Gln Ser Gly Ala Glu Val Lys Lys Pro Gly Ser
1               5                   10                  15

Ser Val Thr Val Ser Cys Lys Ala Ser Gly Asp Thr Phe Arg Lys Phe
                20                  25                  30

Thr Phe Asn Trp Val Arg Gln Ala Pro Gly Gln Gly Leu Glu Trp Met
            35                  40                  45

Gly Gly Leu Ile Pro Ile Phe Gly Thr Pro Lys Tyr Ser Gln Lys Phe
        50                  55                  60

Gln Asp Arg Phe Thr Ile Thr Ala Asp Glu Ser Thr Ser Thr Ala Tyr
65                  70                  75                  80

Met Glu Leu Arg Arg Leu Gly Ser Glu Asp Thr Ala Val Tyr Tyr Cys
                85                  90                  95

Val Arg Glu Asn Tyr Glu Phe Leu Thr Gly Ala Thr Arg Tyr Phe Asp
                100                 105                 110

Leu Trp Gly Arg Gly Thr Leu Ile Thr Val Ser Ser
            115                 120

<210> SEQ ID NO 842
<211> LENGTH: 112
<212> TYPE: PRT
<213> ORGANISM: Artificial Sequence
<220> FEATURE:
<223> OTHER INFORMATION: VL2 of A56-35A06

<400> SEQUENCE: 842

Gln Phe Val Leu Thr Gln Pro Pro Ser Val Ser Gly Ala Pro Gly Gln
1               5                   10                  15

Gly Val Thr Ile Ser Cys Thr Gly Ser Ser Ser Asn Leu Gly Ala Pro
                20                  25                  30

Asn Asp Val His Trp Tyr Gln Gln Arg Pro Gly Thr Ala Pro Arg Leu

-continued

```
            35                  40                  45
Leu Ile Tyr Gly Ser Thr Asn Arg Pro Ser Gly Val Pro Asp Arg Phe
    50                  55                  60

Ser Gly Ser Met Ser Gly Ala Ser Ala Ser Leu Ala Ile Thr Gly Leu
65                  70                  75                  80

Leu Pro Glu Asp Glu Ala Asp Tyr Tyr Cys Gln Ser Tyr Asp Asn Arg
                85                  90                  95

Leu Ser Gly Phe Val Val Phe Gly Gly Gly Thr Lys Leu Thr Val Leu
            100                 105                 110

<210> SEQ ID NO 843
<211> LENGTH: 25
<212> TYPE: PRT
<213> ORGANISM: Artificial Sequence
<220> FEATURE:
<223> OTHER INFORMATION: H-FR1 of A56-35A06

<400> SEQUENCE: 843

Gln Val Gln Leu Val Gln Ser Gly Ala Glu Val Lys Lys Pro Gly Ser
1               5                   10                  15

Ser Val Thr Val Ser Cys Lys Ala Ser
            20                  25

<210> SEQ ID NO 844
<211> LENGTH: 17
<212> TYPE: PRT
<213> ORGANISM: Artificial Sequence
<220> FEATURE:
<223> OTHER INFORMATION: H-FR2 of A56-35A06

<400> SEQUENCE: 844

Phe Asn Trp Val Arg Gln Ala Pro Gly Gln Gly Leu Glu Trp Met Gly
1               5                   10                  15

Gly

<210> SEQ ID NO 845
<211> LENGTH: 38
<212> TYPE: PRT
<213> ORGANISM: Artificial Sequence
<220> FEATURE:
<223> OTHER INFORMATION: H-FR3 of A56-35A06

<400> SEQUENCE: 845

Lys Tyr Ser Gln Lys Phe Gln Asp Arg Phe Thr Ile Thr Ala Asp Glu
1               5                   10                  15

Ser Thr Ser Thr Ala Tyr Met Glu Leu Arg Arg Leu Gly Ser Glu Asp
            20                  25                  30

Thr Ala Val Tyr Tyr Cys
        35

<210> SEQ ID NO 846
<211> LENGTH: 11
<212> TYPE: PRT
<213> ORGANISM: Artificial Sequence
<220> FEATURE:
<223> OTHER INFORMATION: H-FR4 of A56-35A06

<400> SEQUENCE: 846

Trp Gly Arg Gly Thr Leu Ile Thr Val Ser Ser
1               5                   10

<210> SEQ ID NO 847
```

-continued

```
<211> LENGTH: 25
<212> TYPE: PRT
<213> ORGANISM: Artificial Sequence
<220> FEATURE:
<223> OTHER INFORMATION: L-FR1 of A56-35A06

<400> SEQUENCE: 847

Gln Phe Val Leu Thr Gln Pro Pro Ser Val Ser Gly Ala Pro Gly Gln
1               5                   10                  15

Gly Val Thr Ile Ser Cys Thr Gly Ser
            20                  25

<210> SEQ ID NO 848
<211> LENGTH: 17
<212> TYPE: PRT
<213> ORGANISM: Artificial Sequence
<220> FEATURE:
<223> OTHER INFORMATION: L-FR2 of A56-35A06

<400> SEQUENCE: 848

Val His Trp Tyr Gln Gln Arg Pro Gly Thr Ala Pro Arg Leu Leu Ile
1               5                   10                  15

Tyr

<210> SEQ ID NO 849
<211> LENGTH: 36
<212> TYPE: PRT
<213> ORGANISM: Artificial Sequence
<220> FEATURE:
<223> OTHER INFORMATION: L-FR3 of A56-35A06

<400> SEQUENCE: 849

Ile Tyr Gly Ser Thr Asn Arg Pro Ser Gly Val Pro Asp Arg Phe Ser
1               5                   10                  15

Gly Ser Met Ser Gly Ala Ser Ala Ser Leu Ala Ile Thr Gly Leu Leu
            20                  25                  30

Pro Glu Asp Glu
        35

<210> SEQ ID NO 850
<211> LENGTH: 10
<212> TYPE: PRT
<213> ORGANISM: Artificial Sequence
<220> FEATURE:
<223> OTHER INFORMATION: L-FR4 of A56-35A06

<400> SEQUENCE: 850

Phe Gly Gly Gly Thr Lys Leu Thr Val Leu
1               5                   10

<210> SEQ ID NO 851
<211> LENGTH: 8
<212> TYPE: PRT
<213> ORGANISM: Artificial Sequence
<220> FEATURE:
<223> OTHER INFORMATION: H-CDR1 of A56-35G07

<400> SEQUENCE: 851

Gly Asp Thr Phe Ser Ser Tyr Ala
1               5

<210> SEQ ID NO 852
<211> LENGTH: 8
<212> TYPE: PRT
<213> ORGANISM: Artificial Sequence
```

```
<220> FEATURE:
<223> OTHER INFORMATION: H-CDR2 of A56-35G07

<400> SEQUENCE: 852

Thr Ile Pro Arg Leu Gly Ala Thr
1               5

<210> SEQ ID NO 853
<211> LENGTH: 19
<212> TYPE: PRT
<213> ORGANISM: Artificial Sequence
<220> FEATURE:
<223> OTHER INFORMATION: H-CDR3 of A56-35G07

<400> SEQUENCE: 853

Ala Arg Tyr Ile Pro Leu Val Arg Gly Val Arg Gln Pro Arg Asp Asp
1               5               10              15

Phe Glu Ile

<210> SEQ ID NO 854
<211> LENGTH: 7
<212> TYPE: PRT
<213> ORGANISM: Artificial Sequence
<220> FEATURE:
<223> OTHER INFORMATION: L-CDR1 of A56-35G07

<400> SEQUENCE: 854

Gln Ser Val Ser Ser Ser Tyr
1               5

<210> SEQ ID NO 855
<211> LENGTH: 3
<212> TYPE: PRT
<213> ORGANISM: Artificial Sequence
<220> FEATURE:
<223> OTHER INFORMATION: L-CDR2 of A56-35G07

<400> SEQUENCE: 855

Gly Ala Ser
1

<210> SEQ ID NO 856
<211> LENGTH: 11
<212> TYPE: PRT
<213> ORGANISM: Artificial Sequence
<220> FEATURE:
<223> OTHER INFORMATION: L-CDR3 of A56-35G07

<400> SEQUENCE: 856

Gln His Arg Lys Ser Trp Pro Pro Gly Ala Thr
1               5               10

<210> SEQ ID NO 857
<211> LENGTH: 255
<212> TYPE: DNA
<213> ORGANISM: Artificial Sequence
<220> FEATURE:
<223> OTHER INFORMATION: SCFV of A56-35G07

<400> SEQUENCE: 857
cagatgcagc tggtgcagtc tggggctgag gtgaggaagc ctgggtcctc ggtgaaggtc      60
tcctgcaagg cttctggaga caccttcagc agctatgctg tcagctgggt gcgacaggcc     120
cctggactag ggcttgaatg gatgggaagg accatccctc gccttggggc aacaagctac     180
gcacagaact tccagggcag agtctcgatc actgcggaca atccacgaa tacagtgtac      240
```

-continued atggaactga gtggg                                                        255

<210> SEQ ID NO 858
<211> LENGTH: 126
<212> TYPE: PRT
<213> ORGANISM: Artificial Sequence
<220> FEATURE:
<223> OTHER INFORMATION: VH2 of A56-35G07

<400> SEQUENCE: 858

Gln Met Gln Leu Val Gln Ser Gly Ala Glu Val Arg Lys Pro Gly Ser
1               5                   10                  15

Ser Val Lys Val Ser Cys Lys Ala Ser Gly Asp Thr Phe Ser Ser Tyr
            20                  25                  30

Ala Val Ser Trp Val Arg Gln Ala Pro Gly Leu Gly Leu Glu Trp Met
        35                  40                  45

Gly Arg Thr Ile Pro Arg Leu Gly Ala Thr Ser Tyr Ala Gln Asn Phe
    50                  55                  60

Gln Gly Arg Val Ser Ile Thr Ala Asp Lys Ser Thr Asn Thr Val Tyr
65                  70                  75                  80

Met Glu Leu Ser Gly Leu Arg Ser Glu Asp Thr Ala Val Tyr Tyr Cys
                85                  90                  95

Ala Arg Tyr Ile Pro Leu Val Arg Gly Val Arg Gln Pro Arg Asp Asp
            100                 105                 110

Phe Glu Ile Trp Gly Pro Gly Thr Met Ile Thr Val Ser Ser
        115                 120                 125

<210> SEQ ID NO 859
<211> LENGTH: 110
<212> TYPE: PRT
<213> ORGANISM: Artificial Sequence
<220> FEATURE:
<223> OTHER INFORMATION: VL2 of A56-35G07

<400> SEQUENCE: 859

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln His Arg Lys Ser Trp Pro
                85                  90                  95

Pro Gly Ala Thr Phe Gly Gln Gly Thr Arg Leu Glu Ile Lys
            100                 105                 110

<210> SEQ ID NO 860
<211> LENGTH: 25
<212> TYPE: PRT
<213> ORGANISM: Artificial Sequence
<220> FEATURE:
<223> OTHER INFORMATION: H-FR1 of A56-35G07

<400> SEQUENCE: 860

Gln Met Gln Leu Val Gln Ser Gly Ala Glu Val Arg Lys Pro Gly Ser

-continued

```
1               5               10              15

Ser Val Lys Val Ser Cys Lys Ala Ser
            20              25

<210> SEQ ID NO 861
<211> LENGTH: 17
<212> TYPE: PRT
<213> ORGANISM: Artificial Sequence
<220> FEATURE:
<223> OTHER INFORMATION: H-FR2 of A56-35G07

<400> SEQUENCE: 861

Val Ser Trp Val Arg Gln Ala Pro Gly Leu Gly Leu Glu Trp Met Gly
1               5               10              15

Arg

<210> SEQ ID NO 862
<211> LENGTH: 38
<212> TYPE: PRT
<213> ORGANISM: Artificial Sequence
<220> FEATURE:
<223> OTHER INFORMATION: H-FR3 of A56-35G07

<400> SEQUENCE: 862

Ser Tyr Ala Gln Asn Phe Gln Gly Arg Val Ser Ile Thr Ala Asp Lys
1               5               10              15

Ser Thr Asn Thr Val Tyr Met Glu Leu Ser Gly Leu Arg Ser Glu Asp
            20              25              30

Thr Ala Val Tyr Tyr Cys
        35

<210> SEQ ID NO 863
<211> LENGTH: 11
<212> TYPE: PRT
<213> ORGANISM: Artificial Sequence
<220> FEATURE:
<223> OTHER INFORMATION: H-FR4 of A56-35G07

<400> SEQUENCE: 863

Trp Gly Pro Gly Thr Met Ile Thr Val Ser Ser
1               5               10

<210> SEQ ID NO 864
<211> LENGTH: 26
<212> TYPE: PRT
<213> ORGANISM: Artificial Sequence
<220> FEATURE:
<223> OTHER INFORMATION: L-FR1 of A56-35G07

<400> SEQUENCE: 864

Asp Ile Gln Met Thr Gln Ser Pro Gly Thr Leu Ser Leu Ser Pro Gly
1               5               10              15

Glu Arg Ala Thr Leu Ser Cys Arg Ala Ser
            20              25

<210> SEQ ID NO 865
<211> LENGTH: 17
<212> TYPE: PRT
<213> ORGANISM: Artificial Sequence
<220> FEATURE:
<223> OTHER INFORMATION: L-FR2 of A56-35G07

<400> SEQUENCE: 865

Leu Ala Trp Tyr Gln Gln Lys Pro Gly Gln Ala Pro Arg Leu Leu Ile
```

-continued

```
1               5               10              15

Tyr

<210> SEQ ID NO 866
<211> LENGTH: 36
<212> TYPE: PRT
<213> ORGANISM: Artificial Sequence
<220> FEATURE:
<223> OTHER INFORMATION: L-FR3 of A56-35G07

<400> SEQUENCE: 866

Ile Tyr Gly Ala Ser Ser Arg Ala Thr Gly Ile Pro Asp Arg Phe Ser
1               5               10              15

Gly Ser Gly Ser Gly Thr Asp Phe Thr Leu Thr Ile Ser Ser Leu Glu
            20              25              30

Pro Glu Asp Phe
        35

<210> SEQ ID NO 867
<211> LENGTH: 10
<212> TYPE: PRT
<213> ORGANISM: Artificial Sequence
<220> FEATURE:
<223> OTHER INFORMATION: L-FR4 of A56-35G07

<400> SEQUENCE: 867

Phe Gly Gln Gly Thr Arg Leu Glu Ile Lys
1               5               10

<210> SEQ ID NO 868
<211> LENGTH: 8
<212> TYPE: PRT
<213> ORGANISM: Artificial Sequence
<220> FEATURE:
<223> OTHER INFORMATION: H-CDR1 of A56-36B11

<400> SEQUENCE: 868

Gly Gly Asn Phe Asn Ala Tyr Ala
1               5

<210> SEQ ID NO 869
<211> LENGTH: 8
<212> TYPE: PRT
<213> ORGANISM: Artificial Sequence
<220> FEATURE:
<223> OTHER INFORMATION: H-CDR2 of A56-36B11

<400> SEQUENCE: 869

Ile Ile Pro Phe Phe Gly Ser Pro
1               5

<210> SEQ ID NO 870
<211> LENGTH: 10
<212> TYPE: PRT
<213> ORGANISM: Artificial Sequence
<220> FEATURE:
<223> OTHER INFORMATION: H-CDR3 of A56-36B11

<400> SEQUENCE: 870

Thr Arg Ser Arg Asp Tyr Gly Met Asp Val
1               5               10

<210> SEQ ID NO 871
<211> LENGTH: 11
<212> TYPE: PRT
```

<213> ORGANISM: Artificial Sequence
<220> FEATURE:
<223> OTHER INFORMATION: L-CDR1 of A56-36B11

<400> SEQUENCE: 871

Gln Ser Leu Val Asp Asn Asp Gly Asn Thr Tyr
1               5                   10

<210> SEQ ID NO 872
<211> LENGTH: 3
<212> TYPE: PRT
<213> ORGANISM: Artificial Sequence
<220> FEATURE:
<223> OTHER INFORMATION: L-CDR2 of A56-36B11

<400> SEQUENCE: 872

Arg Val Ser
1

<210> SEQ ID NO 873
<211> LENGTH: 9
<212> TYPE: PRT
<213> ORGANISM: Artificial Sequence
<220> FEATURE:
<223> OTHER INFORMATION: L-CDR3 of A56-36B11

<400> SEQUENCE: 873

Met Gln Thr Thr His Trp Pro Pro Leu
1               5

<210> SEQ ID NO 874
<211> LENGTH: 255
<212> TYPE: DNA
<213> ORGANISM: Artificial Sequence
<220> FEATURE:
<223> OTHER INFORMATION: SCFV of A56-36B11

<400> SEQUENCE: 874
caggtgcagc tggtacagtc tggggctgag gtgaggaggc ctgggtcctc ggttaaggtc      60
tcctgcgaga cttctggagg caacttcaac gcctatgcga tcaactgggt gcgacaggcc     120
cctggacagg gcttgaatg gatgggagga atcatccctt tctttggttc gccaaactac      180
gcacagaggt tccagggcag actcacgatc accgcggacg aatctacgag gacaacctac      240
atggaattga gcagt                                                      255

<210> SEQ ID NO 875
<211> LENGTH: 117
<212> TYPE: PRT
<213> ORGANISM: Artificial Sequence
<220> FEATURE:
<223> OTHER INFORMATION: VH2 of A56-36B11

<400> SEQUENCE: 875

Gln Val Gln Leu Val Gln Ser Gly Ala Glu Val Arg Arg Pro Gly Ser
1               5                   10                  15

Ser Val Lys Val Ser Cys Glu Thr Ser Gly Gly Asn Phe Asn Ala Tyr
            20                  25                  30

Ala Ile Asn Trp Val Arg Gln Ala Pro Gly Gln Gly Leu Glu Trp Met
        35                  40                  45

Gly Gly Ile Ile Pro Phe Phe Gly Ser Pro Asn Tyr Ala Gln Arg Phe
    50                  55                  60

Gln Gly Arg Leu Thr Ile Thr Ala Asp Glu Ser Thr Arg Thr Thr Tyr
65                  70                  75                  80

-continued

```
Met Glu Leu Ser Ser Leu Arg Ser Glu Asp Thr Ala Val Tyr Tyr Cys
                85                  90                  95

Thr Arg Ser Arg Asp Tyr Gly Met Asp Val Trp Gly Gln Gly Thr Thr
            100                 105                 110

Ile Thr Val Ser Ser
        115

<210> SEQ ID NO 876
<211> LENGTH: 112
<212> TYPE: PRT
<213> ORGANISM: Artificial Sequence
<220> FEATURE:
<223> OTHER INFORMATION: VL2 of A56-36B11

<400> SEQUENCE: 876

Asp Ile Val Met Thr Gln Thr Pro Leu Ser Leu Pro Val Ile Leu Gly
1               5                   10                  15

Gln Pro Ala Ser Val Ser Cys Arg Ser Ser Gln Ser Leu Val Asp Asn
            20                  25                  30

Asp Gly Asn Thr Tyr Leu His Trp Phe Gln Gln Arg Pro Gly Gln Ser
        35                  40                  45

Pro Arg Arg Leu Ile Tyr Arg Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr His Trp Pro Pro Leu Phe Gly Gly Gly Thr Lys Val Asp Ile Lys
            100                 105                 110

<210> SEQ ID NO 877
<211> LENGTH: 25
<212> TYPE: PRT
<213> ORGANISM: Artificial Sequence
<220> FEATURE:
<223> OTHER INFORMATION: H-FR1 of A56-36B11

<400> SEQUENCE: 877

Gln Val Gln Leu Val Gln Ser Gly Ala Glu Val Arg Arg Pro Gly Ser
1               5                   10                  15

Ser Val Lys Val Ser Cys Glu Thr Ser
            20                  25

<210> SEQ ID NO 878
<211> LENGTH: 17
<212> TYPE: PRT
<213> ORGANISM: Artificial Sequence
<220> FEATURE:
<223> OTHER INFORMATION: H-FR2 of A56-36B11

<400> SEQUENCE: 878

Ile Asn Trp Val Arg Gln Ala Pro Gly Gln Gly Leu Glu Trp Met Gly
1               5                   10                  15

Gly

<210> SEQ ID NO 879
<211> LENGTH: 38
<212> TYPE: PRT
<213> ORGANISM: Artificial Sequence
<220> FEATURE:
<223> OTHER INFORMATION: H-FR3 of A56-36B11
```

-continued

```
<400> SEQUENCE: 879

Asn Tyr Ala Gln Arg Phe Gln Gly Arg Leu Thr Ile Thr Ala Asp Glu
1               5                   10                  15

Ser Thr Arg Thr Thr Tyr Met Glu Leu Ser Ser Leu Arg Ser Glu Asp
            20                  25                  30

Thr Ala Val Tyr Tyr Cys
        35

<210> SEQ ID NO 880
<211> LENGTH: 11
<212> TYPE: PRT
<213> ORGANISM: Artificial Sequence
<220> FEATURE:
<223> OTHER INFORMATION: H-FR4 of A56-36B11

<400> SEQUENCE: 880

Trp Gly Gln Gly Thr Thr Ile Thr Val Ser Ser
1               5                   10

<210> SEQ ID NO 881
<211> LENGTH: 26
<212> TYPE: PRT
<213> ORGANISM: Artificial Sequence
<220> FEATURE:
<223> OTHER INFORMATION: L-FR1 of A56-36B11

<400> SEQUENCE: 881

Asp Ile Val Met Thr Gln Thr Pro Leu Ser Leu Pro Val Ile Leu Gly
1               5                   10                  15

Gln Pro Ala Ser Val Ser Cys Arg Ser Ser
            20                  25

<210> SEQ ID NO 882
<211> LENGTH: 17
<212> TYPE: PRT
<213> ORGANISM: Artificial Sequence
<220> FEATURE:
<223> OTHER INFORMATION: L-FR2 of A56-36B11

<400> SEQUENCE: 882

Leu His Trp Phe Gln Gln Arg Pro Gly Gln Ser Pro Arg Arg Leu Ile
1               5                   10                  15

Tyr

<210> SEQ ID NO 883
<211> LENGTH: 36
<212> TYPE: PRT
<213> ORGANISM: Artificial Sequence
<220> FEATURE:
<223> OTHER INFORMATION: L-FR3 of A56-36B11

<400> SEQUENCE: 883

Ile Tyr Arg Val Ser Asn Arg Asp Ser Gly Val Pro Asp Arg Phe Ser
1               5                   10                  15

Gly Ser Gly Ser Gly Thr Asp Phe Thr Leu Lys Ile Ser Arg Val Glu
            20                  25                  30

Ala Glu Asp Val
        35

<210> SEQ ID NO 884
<211> LENGTH: 10
<212> TYPE: PRT
```

```
<213> ORGANISM: Artificial Sequence
<220> FEATURE:
<223> OTHER INFORMATION: L-FR4 of A56-36B11

<400> SEQUENCE: 884

Phe Gly Gly Gly Thr Lys Val Asp Ile Lys
1               5                   10

<210> SEQ ID NO 885
<211> LENGTH: 8
<212> TYPE: PRT
<213> ORGANISM: Artificial Sequence
<220> FEATURE:
<223> OTHER INFORMATION: H-CDR1 of A56-41C01

<400> SEQUENCE: 885

Gly Gly Ser Ile Ser Ser His Tyr
1               5

<210> SEQ ID NO 886
<211> LENGTH: 7
<212> TYPE: PRT
<213> ORGANISM: Artificial Sequence
<220> FEATURE:
<223> OTHER INFORMATION: H-CDR2 of A56-41C01

<400> SEQUENCE: 886

Ile Ser Asn Ser Gly Asn Thr
1               5

<210> SEQ ID NO 887
<211> LENGTH: 11
<212> TYPE: PRT
<213> ORGANISM: Artificial Sequence
<220> FEATURE:
<223> OTHER INFORMATION: H-CDR3 of A56-41C01

<400> SEQUENCE: 887

Ala Ser Gln Arg Ser Asp Gly Ser Leu Asp Tyr
1               5                   10

<210> SEQ ID NO 888
<211> LENGTH: 12
<212> TYPE: PRT
<213> ORGANISM: Artificial Sequence
<220> FEATURE:
<223> OTHER INFORMATION: L-CDR1 of A56-41C01

<400> SEQUENCE: 888

Gln Ser Leu Leu Asp Ser Asp Asp Gly Asn Thr Tyr
1               5                   10

<210> SEQ ID NO 889
<211> LENGTH: 3
<212> TYPE: PRT
<213> ORGANISM: Artificial Sequence
<220> FEATURE:
<223> OTHER INFORMATION: L-CDR2 of A56-41C01

<400> SEQUENCE: 889

Glu Val Ser
1

<210> SEQ ID NO 890
<211> LENGTH: 9
<212> TYPE: PRT
<213> ORGANISM: Artificial Sequence
```

<220> FEATURE:
<223> OTHER INFORMATION: L-CDR3 of A56-41C01

<400> SEQUENCE: 890

Met Gln Arg Ile Glu Phe Pro Tyr Thr
1               5

<210> SEQ ID NO 891
<211> LENGTH: 255
<212> TYPE: DNA
<213> ORGANISM: Artificial Sequence
<220> FEATURE:
<223> OTHER INFORMATION: SCFV of A56-41C01

<400> SEQUENCE: 891
caggtgcagc tgcaggagtc gggcccagga ctggtgaagc cttcggagac cctgtccctc      60
acctgcactg tctccggtgg ctccatcagt agtcactact ggagctgggt ccggcagccc     120
ccagggaaga gaccggagtg gattgggtac atctctaaca gtgggaacac gatctacaac     180
ccctccctca gagtcgagt caccatatca ttaaacacgt ccaggaacca attctccctg     240
cagctgaggt ctgtg                                                       255

<210> SEQ ID NO 892
<211> LENGTH: 117
<212> TYPE: PRT
<213> ORGANISM: Artificial Sequence
<220> FEATURE:
<223> OTHER INFORMATION: VH2 of A56-41C01

<400> SEQUENCE: 892

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser His
            20                  25                  30

Tyr Trp Ser Trp Val Arg Gln Pro Pro Gly Lys Arg Pro Glu Trp Ile
        35                  40                  45

Gly Tyr Ile Ser Asn Ser Gly Asn Thr Ile Tyr Asn Pro Ser Leu Lys
    50                  55                  60

Ser Arg Val Thr Ile Ser Leu Asn Thr Ser Arg Asn Gln Phe Ser Leu
65                  70                  75                  80

Gln Leu Arg Ser Val Thr Ala Val Asp Thr Ala Val Tyr Tyr Cys Ala
                85                  90                  95

Ser Gln Arg Ser Asp Gly Ser Leu Asp Tyr Arg Gly Pro Gly Thr Leu
            100                 105                 110

Val Thr Val Ser Ser
        115

<210> SEQ ID NO 893
<211> LENGTH: 113
<212> TYPE: PRT
<213> ORGANISM: Artificial Sequence
<220> FEATURE:
<223> OTHER INFORMATION: VL2 of A56-41C01

<400> SEQUENCE: 893

Asp Ile Val Met Thr Gln Thr Pro Leu Ser Leu Pro Val Thr Pro Gly
1               5                   10                  15

Glu Ala Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln

-continued

```
          35                  40                  45

Pro Pro Gln Leu Leu Ile Tyr Glu Val Ser Asn Arg Phe Ser Gly Val
   50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                 85                  90                  95

Arg Ile Glu Phe Pro Tyr Thr Phe Gly Gln Gly Thr Lys Val Glu Ile
                100                 105                 110

Lys

<210> SEQ ID NO 894
<211> LENGTH: 25
<212> TYPE: PRT
<213> ORGANISM: Artificial Sequence
<220> FEATURE:
<223> OTHER INFORMATION: H-FR1 of A56-41C01

<400> SEQUENCE: 894

Gln Val Gln Leu Gln Glu Ser Gly Pro Gly Leu Val Lys Pro Ser Glu
1                   5                  10                  15

Thr Leu Ser Leu Thr Cys Thr Val Ser
             20                  25

<210> SEQ ID NO 895
<211> LENGTH: 17
<212> TYPE: PRT
<213> ORGANISM: Artificial Sequence
<220> FEATURE:
<223> OTHER INFORMATION: H-FR2 of A56-41C01

<400> SEQUENCE: 895

Trp Ser Trp Val Arg Gln Pro Pro Gly Lys Arg Pro Glu Trp Ile Gly
1                   5                  10                  15

Tyr

<210> SEQ ID NO 896
<211> LENGTH: 38
<212> TYPE: PRT
<213> ORGANISM: Artificial Sequence
<220> FEATURE:
<223> OTHER INFORMATION: H-FR3 of A56-41C01

<400> SEQUENCE: 896

Ile Tyr Asn Pro Ser Leu Lys Ser Arg Val Thr Ile Ser Leu Asn Thr
1                   5                  10                  15

Ser Arg Asn Gln Phe Ser Leu Gln Leu Arg Ser Val Thr Ala Val Asp
                 20                  25                  30

Thr Ala Val Tyr Tyr Cys
             35

<210> SEQ ID NO 897
<211> LENGTH: 11
<212> TYPE: PRT
<213> ORGANISM: Artificial Sequence
<220> FEATURE:
<223> OTHER INFORMATION: H-FR4 of A56-41C01

<400> SEQUENCE: 897

Arg Gly Pro Gly Thr Leu Val Thr Val Ser Ser
1                   5                  10
```

```
<210> SEQ ID NO 898
<211> LENGTH: 26
<212> TYPE: PRT
<213> ORGANISM: Artificial Sequence
<220> FEATURE:
<223> OTHER INFORMATION: L-FR1 of A56-41C01

<400> SEQUENCE: 898

Asp Ile Val Met Thr Gln Thr Pro Leu Ser Leu Pro Val Thr Pro Gly
1               5                   10                  15

Glu Ala Ala Ser Ile Ser Cys Arg Ser Ser
            20                  25

<210> SEQ ID NO 899
<211> LENGTH: 17
<212> TYPE: PRT
<213> ORGANISM: Artificial Sequence
<220> FEATURE:
<223> OTHER INFORMATION: L-FR2 of A56-41C01

<400> SEQUENCE: 899

Leu Asp Trp Tyr Leu Gln Lys Pro Gly Gln Pro Pro Gln Leu Leu Ile
1               5                   10                  15

Tyr

<210> SEQ ID NO 900
<211> LENGTH: 36
<212> TYPE: PRT
<213> ORGANISM: Artificial Sequence
<220> FEATURE:
<223> OTHER INFORMATION: L-FR3 of A56-41C01

<400> SEQUENCE: 900

Ile Tyr Glu Val Ser Asn Arg Phe Ser Gly Val Pro Asp Arg Phe Ser
1               5                   10                  15

Gly Ser Gly Ser Gly Thr Asp Phe Thr Leu Lys Ile Ser Arg Val Glu
            20                  25                  30

Ala Glu Asp Val
        35

<210> SEQ ID NO 901
<211> LENGTH: 10
<212> TYPE: PRT
<213> ORGANISM: Artificial Sequence
<220> FEATURE:
<223> OTHER INFORMATION: L-FR4 of A56-41C01

<400> SEQUENCE: 901

Phe Gly Gln Gly Thr Lys Val Glu Ile Lys
1               5                   10

<210> SEQ ID NO 902
<211> LENGTH: 8
<212> TYPE: PRT
<213> ORGANISM: Artificial Sequence
<220> FEATURE:
<223> OTHER INFORMATION: H-CDR1 of A56-42H07

<400> SEQUENCE: 902

Gly Asp Thr Phe Ser Arg Tyr Ala
1               5

<210> SEQ ID NO 903
<211> LENGTH: 8
```

<212> TYPE: PRT
<213> ORGANISM: Artificial Sequence
<220> FEATURE:
<223> OTHER INFORMATION: H-CDR2 of A56-42H07

<400> SEQUENCE: 903

Ile Ile Pro Val Leu Gly Ala Ala
1               5

<210> SEQ ID NO 904
<211> LENGTH: 16
<212> TYPE: PRT
<213> ORGANISM: Artificial Sequence
<220> FEATURE:
<223> OTHER INFORMATION: H-CDR3 of A56-42H07

<400> SEQUENCE: 904

Ala Arg Asp Leu Val Arg Gly Val Thr Pro His Tyr Gly Met Asp Val
1               5                   10                  15

<210> SEQ ID NO 905
<211> LENGTH: 11
<212> TYPE: PRT
<213> ORGANISM: Artificial Sequence
<220> FEATURE:
<223> OTHER INFORMATION: L-CDR1 of A56-42H07

<400> SEQUENCE: 905

Gln Ser Leu Leu His Ser Asn Gly Tyr Asn Tyr
1               5                   10

<210> SEQ ID NO 906
<211> LENGTH: 3
<212> TYPE: PRT
<213> ORGANISM: Artificial Sequence
<220> FEATURE:
<223> OTHER INFORMATION: L-CDR2 of A56-42H07

<400> SEQUENCE: 906

Leu Gly Ser
1

<210> SEQ ID NO 907
<211> LENGTH: 9
<212> TYPE: PRT
<213> ORGANISM: Artificial Sequence
<220> FEATURE:
<223> OTHER INFORMATION: L-CDR3 of A56-42H07

<400> SEQUENCE: 907

Met Gln Ala Arg Gln Thr Pro Leu Thr
1               5

<210> SEQ ID NO 908
<211> LENGTH: 255
<212> TYPE: DNA
<213> ORGANISM: Artificial Sequence
<220> FEATURE:
<223> OTHER INFORMATION: SCFV of A56-42H07

<400> SEQUENCE: 908
caggtgcagc tggtgcagtc tggggctgag gtgaagaagc ctgggtcctc ggtgaaggtc      60
tcctgcaagg cttctggaga cacgttcagc agatatgcta tcagctggat ccgacaggcc     120
cctggacaag ggcctgagtg gatgggaagg atcatccctg tccttggtgc agcaaattat     180
gcacggaagt tccaggacag agtcacgatc acagcggaca atccacgac tacagcctac      240

-continued

```
atggaactga ccagt                                                       255

<210> SEQ ID NO 909
<211> LENGTH: 123
<212> TYPE: PRT
<213> ORGANISM: Artificial Sequence
<220> FEATURE:
<223> OTHER INFORMATION: VH2 of A56-42H07

<400> SEQUENCE: 909

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Arg Tyr
            20                  25                  30

Ala Ile Ser Trp Ile Arg Gln Ala Pro Gly Gln Gly Pro Glu Trp Met
        35                  40                  45

Gly Arg Ile Ile Pro Val Leu Gly Ala Ala Asn Tyr Ala Arg Lys Phe
    50                  55                  60

Gln Asp Arg Val Thr Ile Thr Ala Asp Lys Ser Thr Thr Thr Ala Tyr
65                  70                  75                  80

Met Glu Leu Thr Ser Leu Arg Ser Glu Asp Thr Ala Val Tyr Tyr Cys
                85                  90                  95

Ala Arg Asp Leu Val Arg Gly Val Thr Pro His Tyr Gly Met Asp Val
            100                 105                 110

Trp Gly Gln Gly Thr Thr Val Thr Val Ser Ser
        115                 120

<210> SEQ ID NO 910
<211> LENGTH: 112
<212> TYPE: PRT
<213> ORGANISM: Artificial Sequence
<220> FEATURE:
<223> OTHER INFORMATION: VL2 of A56-42H07

<400> SEQUENCE: 910

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Leu Thr Phe Gly Gly Gly Thr Lys Val Glu Ile Lys
            100                 105                 110

<210> SEQ ID NO 911
<211> LENGTH: 25
<212> TYPE: PRT
<213> ORGANISM: Artificial Sequence
<220> FEATURE:
<223> OTHER INFORMATION: H-FR1 of A56-42H07

<400> SEQUENCE: 911

Gln Val Gln Leu Val Gln Ser Gly Ala Glu Val Lys Lys Pro Gly Ser
```

-continued

```
1               5               10              15

Ser Val Lys Val Ser Cys Lys Ala Ser
            20              25

<210> SEQ ID NO 912
<211> LENGTH: 17
<212> TYPE: PRT
<213> ORGANISM: Artificial Sequence
<220> FEATURE:
<223> OTHER INFORMATION: H-FR2 of A56-42H07

<400> SEQUENCE: 912

Ile Ser Trp Ile Arg Gln Ala Pro Gly Gln Gly Pro Glu Trp Met Gly
1               5               10              15

Arg

<210> SEQ ID NO 913
<211> LENGTH: 38
<212> TYPE: PRT
<213> ORGANISM: Artificial Sequence
<220> FEATURE:
<223> OTHER INFORMATION: H-FR3 of A56-42H07

<400> SEQUENCE: 913

Asn Tyr Ala Arg Lys Phe Gln Asp Arg Val Thr Ile Thr Ala Asp Lys
1               5               10              15

Ser Thr Thr Thr Ala Tyr Met Glu Leu Thr Ser Leu Arg Ser Glu Asp
            20              25              30

Thr Ala Val Tyr Tyr Cys
        35

<210> SEQ ID NO 914
<211> LENGTH: 11
<212> TYPE: PRT
<213> ORGANISM: Artificial Sequence
<220> FEATURE:
<223> OTHER INFORMATION: H-FR4 of A56-42H07

<400> SEQUENCE: 914

Trp Gly Gln Gly Thr Thr Val Thr Val Ser Ser
1               5               10

<210> SEQ ID NO 915
<211> LENGTH: 26
<212> TYPE: PRT
<213> ORGANISM: Artificial Sequence
<220> FEATURE:
<223> OTHER INFORMATION: L-FR1 of A56-42H07

<400> SEQUENCE: 915

Asp Ile Val Met Thr Gln Thr Pro Leu Ser Leu Pro Val Thr Pro Gly
1               5               10              15

Glu Pro Ala Ser Ile Ser Cys Arg Ser Ser
            20              25

<210> SEQ ID NO 916
<211> LENGTH: 17
<212> TYPE: PRT
<213> ORGANISM: Artificial Sequence
<220> FEATURE:
<223> OTHER INFORMATION: L-FR2 of A56-42H07

<400> SEQUENCE: 916

Leu Asp Trp Tyr Leu Gln Lys Pro Gly Gln Ser Pro Gln Leu Leu Ile
```

-continued

```
1               5               10              15

Tyr

<210> SEQ ID NO 917
<211> LENGTH: 36
<212> TYPE: PRT
<213> ORGANISM: Artificial Sequence
<220> FEATURE:
<223> OTHER INFORMATION: L-FR3 of A56-42H07

<400> SEQUENCE: 917

Ile Tyr Leu Gly Ser Ser Arg Ala Ser Gly Val Pro Asp Arg Phe Ser
1               5               10              15

Gly Ser Gly Ser Gly Thr Asp Phe Thr Leu Lys Ile Ser Arg Val Glu
            20              25              30

Ala Glu Asp Val
        35

<210> SEQ ID NO 918
<211> LENGTH: 10
<212> TYPE: PRT
<213> ORGANISM: Artificial Sequence
<220> FEATURE:
<223> OTHER INFORMATION: L-FR4 of A56-42H07

<400> SEQUENCE: 918

Phe Gly Gly Gly Thr Lys Val Glu Ile Lys
1               5               10

<210> SEQ ID NO 919
<211> LENGTH: 8
<212> TYPE: PRT
<213> ORGANISM: Artificial Sequence
<220> FEATURE:
<223> OTHER INFORMATION: H-CDR1 of A56-44G01

<400> SEQUENCE: 919

Gly Phe Thr Phe Ser Ser Tyr Ala
1               5

<210> SEQ ID NO 920
<211> LENGTH: 8
<212> TYPE: PRT
<213> ORGANISM: Artificial Sequence
<220> FEATURE:
<223> OTHER INFORMATION: H-CDR2 of A56-44G01

<400> SEQUENCE: 920

Ile Ser Tyr Asp Gly Ser Asn Lys
1               5

<210> SEQ ID NO 921
<211> LENGTH: 17
<212> TYPE: PRT
<213> ORGANISM: Artificial Sequence
<220> FEATURE:
<223> OTHER INFORMATION: H-CDR3 of A56-44G01

<400> SEQUENCE: 921

Ala Lys Asp Leu Trp Gly Arg Val Gly Ala Leu Val Gly Ala Leu Asp
1               5               10              15

Leu

<210> SEQ ID NO 922
```

<211> LENGTH: 6
<212> TYPE: PRT
<213> ORGANISM: Artificial Sequence
<220> FEATURE:
<223> OTHER INFORMATION: L-CDR1 of A56-44G01

<400> SEQUENCE: 922

Asn Leu Arg Thr Lys Tyr
1               5

<210> SEQ ID NO 923
<211> LENGTH: 3
<212> TYPE: PRT
<213> ORGANISM: Artificial Sequence
<220> FEATURE:
<223> OTHER INFORMATION: L-CDR2 of A56-44G01

<400> SEQUENCE: 923

Gln Asp Thr
1

<210> SEQ ID NO 924
<211> LENGTH: 9
<212> TYPE: PRT
<213> ORGANISM: Artificial Sequence
<220> FEATURE:
<223> OTHER INFORMATION: L-CDR3 of A56-44G01

<400> SEQUENCE: 924

Gln Ala Trp Asp Ser Gly Asn Tyr Val
1               5

<210> SEQ ID NO 925
<211> LENGTH: 255
<212> TYPE: DNA
<213> ORGANISM: Artificial Sequence
<220> FEATURE:
<223> OTHER INFORMATION: SCFV of A56-44G01

<400> SEQUENCE: 925
caggtgcagc tggtggagtc tgggggaggt gtggtccagc ctggagagtc cctgagactc      60
tcctgtgcag cctctggatt caccttcagt agctatgcta tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagt                                                      255

<210> SEQ ID NO 926
<211> LENGTH: 124
<212> TYPE: PRT
<213> ORGANISM: Artificial Sequence
<220> FEATURE:
<223> OTHER INFORMATION: VH2 of A56-44G01

<400> SEQUENCE: 926

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Trp Gly Arg Val Gly Ala Leu Val Gly Ala Leu Asp
            100                 105                 110

Leu Trp Gly Gln Gly Thr Met Ile Thr Val Ser Ser
        115                 120

<210> SEQ ID NO 927
<211> LENGTH: 106
<212> TYPE: PRT
<213> ORGANISM: Artificial Sequence
<220> FEATURE:
<223> OTHER INFORMATION: VL2 of A56-44G01

<400> SEQUENCE: 927

Ser Tyr Glu Leu Thr Gln Gly Pro Ser Leu Ser Val Ser Pro Gly Gln
1               5                   10                  15

Thr Ala Asn Ile Ile Cys Ser Gly Asp Asn Leu Arg Thr Lys Tyr Val
                20                  25                  30

Ser Trp Tyr Gln Gln Lys Pro Gly Gln Ser Pro Ile Leu Val Ile Tyr
        35                  40                  45

Gln Asp Thr Arg Arg Pro Ser Gly Ile Pro Ala Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Gly Asn Tyr Val
                85                  90                  95

Phe Gly Thr Gly Thr Lys Val Thr Val Leu
            100                 105

<210> SEQ ID NO 928
<211> LENGTH: 25
<212> TYPE: PRT
<213> ORGANISM: Artificial Sequence
<220> FEATURE:
<223> OTHER INFORMATION: H-FR1 of A56-44G01

<400> SEQUENCE: 928

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 929
<211> LENGTH: 17
<212> TYPE: PRT
<213> ORGANISM: Artificial Sequence
<220> FEATURE:
<223> OTHER INFORMATION: H-FR2 of A56-44G01

<400> SEQUENCE: 929

Met His Trp Val Arg Gln Ala Pro Gly Lys Gly Leu Glu Trp Val Ala
1               5                   10                  15

Val

<210> SEQ ID NO 930
<211> LENGTH: 38
<212> TYPE: PRT
<213> ORGANISM: Artificial Sequence

```
<220> FEATURE:
<223> OTHER INFORMATION: H-FR3 of A56-44G01

<400> SEQUENCE: 930

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 931
<211> LENGTH: 11
<212> TYPE: PRT
<213> ORGANISM: Artificial Sequence
<220> FEATURE:
<223> OTHER INFORMATION: H-FR4 of A56-44G01

<400> SEQUENCE: 931

Trp Gly Gln Gly Thr Met Ile Thr Val Ser Ser
1               5                   10

<210> SEQ ID NO 932
<211> LENGTH: 25
<212> TYPE: PRT
<213> ORGANISM: Artificial Sequence
<220> FEATURE:
<223> OTHER INFORMATION: L-FR1 of A56-44G01

<400> SEQUENCE: 932

Ser Tyr Glu Leu Thr Gln Gly Pro Ser Leu Ser Val Ser Pro Gly Gln
1               5                   10                  15

Thr Ala Asn Ile Ile Cys Ser Gly Asp
            20                  25

<210> SEQ ID NO 933
<211> LENGTH: 17
<212> TYPE: PRT
<213> ORGANISM: Artificial Sequence
<220> FEATURE:
<223> OTHER INFORMATION: L-FR2 of A56-44G01

<400> SEQUENCE: 933

Val Ser Trp Tyr Gln Gln Lys Pro Gly Gln Ser Pro Ile Leu Val Ile
1               5                   10                  15

Tyr

<210> SEQ ID NO 934
<211> LENGTH: 36
<212> TYPE: PRT
<213> ORGANISM: Artificial Sequence
<220> FEATURE:
<223> OTHER INFORMATION: L-FR3 of A56-44G01

<400> SEQUENCE: 934

Ile Tyr Gln Asp Thr Arg Arg Pro Ser Gly Ile Pro Ala Arg Phe Ser
1               5                   10                  15

Gly Ser Asn Ser Gly Asn Thr Ala Thr Leu Thr Ile Ser Gly Thr Gln
            20                  25                  30

Ala Met Asp Glu
        35

<210> SEQ ID NO 935
```

```
<211> LENGTH: 10
<212> TYPE: PRT
<213> ORGANISM: Artificial Sequence
<220> FEATURE:
<223> OTHER INFORMATION: L-FR4 of A56-44G01

<400> SEQUENCE: 935

Phe Gly Thr Gly Thr Lys Val Thr Val Leu
1               5                   10

<210> SEQ ID NO 936
<211> LENGTH: 8
<212> TYPE: PRT
<213> ORGANISM: Artificial Sequence
<220> FEATURE:
<223> OTHER INFORMATION: H-CDR1 of A56-46A07

<400> SEQUENCE: 936

Gly Phe Ile Phe Ser Asp Ser Pro
1               5

<210> SEQ ID NO 937
<211> LENGTH: 10
<212> TYPE: PRT
<213> ORGANISM: Artificial Sequence
<220> FEATURE:
<223> OTHER INFORMATION: H-CDR2 of A56-46A07

<400> SEQUENCE: 937

Ile Gly Thr Thr Ala Ser Thr Tyr Ala Thr
1               5                   10

<210> SEQ ID NO 938
<211> LENGTH: 11
<212> TYPE: PRT
<213> ORGANISM: Artificial Sequence
<220> FEATURE:
<223> OTHER INFORMATION: H-CDR3 of A56-46A07

<400> SEQUENCE: 938

Ala Arg Asp Arg Ser Gly Trp Ser Arg Asp Tyr
1               5                   10

<210> SEQ ID NO 939
<211> LENGTH: 6
<212> TYPE: PRT
<213> ORGANISM: Artificial Sequence
<220> FEATURE:
<223> OTHER INFORMATION: L-CDR1 of A56-46A07

<400> SEQUENCE: 939

Gln Gly Ile Gly Arg Ser
1               5

<210> SEQ ID NO 940
<211> LENGTH: 3
<212> TYPE: PRT
<213> ORGANISM: Artificial Sequence
<220> FEATURE:
<223> OTHER INFORMATION: L-CDR2 of A56-46A07

<400> SEQUENCE: 940

Ala Ala Ser
1

<210> SEQ ID NO 941
<211> LENGTH: 9
```

-continued

```
<212> TYPE: PRT
<213> ORGANISM: Artificial Sequence
<220> FEATURE:
<223> OTHER INFORMATION: L-CDR3 of A56-46A07

<400> SEQUENCE: 941

Gln Gln Val Tyr Ser Tyr Pro Tyr Ser
1               5

<210> SEQ ID NO 942
<211> LENGTH: 255
<212> TYPE: DNA
<213> ORGANISM: Artificial Sequence
<220> FEATURE:
<223> OTHER INFORMATION: SCFV of A56-46A07

<400> SEQUENCE: 942
caggtgcagc tggtggagtc tgggggaggc ttggtccagc cggggggggtc cctgaaactc      60 tcctgtgcag cctctgggtt catcttcagt gactctccta tgcactgggt ccgccaggct     120
tccgggaaag gcctggagtg ggttggccgc attggaacca cagcttccac ttacgcgaca     180
gtatatgctg cgtcggtgaa aggcaggttc accatctcca gagatgactc aaagaacacg     240
gcttatctgc aaatg                                                      255

<210> SEQ ID NO 943
<211> LENGTH: 120
<212> TYPE: PRT
<213> ORGANISM: Artificial Sequence
<220> FEATURE:
<223> OTHER INFORMATION: VH2 of A56-46A07

<400> SEQUENCE: 943

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asp Ser
            20                  25                  30

Pro Met His Trp Val Arg Gln Ala Ser Gly Lys Gly Leu Glu Trp Val
        35                  40                  45

Gly Arg Ile Gly Thr Thr Ala Ser Thr Tyr Ala Thr Val Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ala Arg Asp Arg Ser Gly Trp Ser Arg Asp Tyr Trp Gly Gln
            100                 105                 110

Gly Thr Leu Val Thr Val Ser Ser
        115                 120

<210> SEQ ID NO 944
<211> LENGTH: 107
<212> TYPE: PRT
<213> ORGANISM: Artificial Sequence
<220> FEATURE:
<223> OTHER INFORMATION: VL2 of A56-46A07

<400> SEQUENCE: 944

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Arg Ser
            20                  25                  30
```

```
Leu Ala Trp Tyr Gln Gln Lys Pro Gly Lys Ala Pro Thr Val Leu Ile
        35                  40                  45

Tyr Ala Ala Ser Thr Leu His Ser Gly Val Pro Ser Arg Phe Ser Gly
    50                  55                  60

Ala Gly Ser Gly Thr Asp Phe Ala Leu Thr Ile Ser Arg Leu Leu Pro
65                  70                  75                  80

Glu Asp Phe Ala Thr Tyr Tyr Cys Gln Gln Val Tyr Ser Tyr Pro Tyr
                85                  90                  95

Ser Phe Gly Leu Gly Thr Met Leu Glu Ile Lys
            100                 105
```

```
<210> SEQ ID NO 945
<211> LENGTH: 25
<212> TYPE: PRT
<213> ORGANISM: Artificial Sequence
<220> FEATURE:
<223> OTHER INFORMATION: H-FR1 of A56-46A07

<400> SEQUENCE: 945

Gln Val Gln Leu Val Glu Ser Gly Gly Gly Leu Val Gln Pro Gly Gly
1               5                   10                  15

Ser Leu Lys Leu Ser Cys Ala Ala Ser
            20                  25
```

```
<210> SEQ ID NO 946
<211> LENGTH: 17
<212> TYPE: PRT
<213> ORGANISM: Artificial Sequence
<220> FEATURE:
<223> OTHER INFORMATION: H-FR2 of A56-46A07

<400> SEQUENCE: 946

Met His Trp Val Arg Gln Ala Ser Gly Lys Gly Leu Glu Trp Val Gly
1               5                   10                  15

Arg
```

```
<210> SEQ ID NO 947
<211> LENGTH: 38
<212> TYPE: PRT
<213> ORGANISM: Artificial Sequence
<220> FEATURE:
<223> OTHER INFORMATION: H-FR3 of A56-46A07

<400> SEQUENCE: 947

Val Tyr Ala Ala Ser Val Lys Gly Arg Phe Thr Ile Ser Arg Asp Asp
1               5                   10                  15

Ser Lys Asn Thr Ala Tyr Leu Gln Met Asn Ser Leu Arg Ala Glu Asp
            20                  25                  30

Thr Ala Val Tyr Tyr Cys
            35
```

```
<210> SEQ ID NO 948
<211> LENGTH: 11
<212> TYPE: PRT
<213> ORGANISM: Artificial Sequence
<220> FEATURE:
<223> OTHER INFORMATION: H-FR4 of A56-46A07

<400> SEQUENCE: 948

Trp Gly Gln Gly Thr Leu Val Thr Val Ser Ser
1               5                   10
```

-continued

```
<210> SEQ ID NO 949
<211> LENGTH: 26
<212> TYPE: PRT
<213> ORGANISM: Artificial Sequence
<220> FEATURE:
<223> OTHER INFORMATION: L-FR1 of A56-46A07

<400> SEQUENCE: 949

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 950
<211> LENGTH: 17
<212> TYPE: PRT
<213> ORGANISM: Artificial Sequence
<220> FEATURE:
<223> OTHER INFORMATION: L-FR2 of A56-46A07

<400> SEQUENCE: 950

Leu Ala Trp Tyr Gln Gln Lys Pro Gly Lys Ala Pro Thr Val Leu Ile
1               5                   10                  15

Tyr

<210> SEQ ID NO 951
<211> LENGTH: 36
<212> TYPE: PRT
<213> ORGANISM: Artificial Sequence
<220> FEATURE:
<223> OTHER INFORMATION: L-FR3 of A56-46A07

<400> SEQUENCE: 951

Thr Leu His Ser Gly Val Pro Ser Arg Phe Ser Gly Ala Gly Ser Gly
1               5                   10                  15

Thr Asp Phe Ala Leu Thr Ile Ser Arg Leu Leu Pro Glu Asp Phe Ala
            20                  25                  30

Thr Tyr Tyr Cys
        35

<210> SEQ ID NO 952
<211> LENGTH: 10
<212> TYPE: PRT
<213> ORGANISM: Artificial Sequence
<220> FEATURE:
<223> OTHER INFORMATION: L-FR4 of A56-46A07

<400> SEQUENCE: 952

Phe Gly Leu Gly Thr Met Leu Glu Ile Lys
1               5                   10

<210> SEQ ID NO 953
<211> LENGTH: 8
<212> TYPE: PRT
<213> ORGANISM: Artificial Sequence
<220> FEATURE:
<223> OTHER INFORMATION: H-CDR1 of A56-50A09

<400> SEQUENCE: 953

Gly Phe Thr Phe Asp Asp Tyr Ala
1               5

<210> SEQ ID NO 954
<211> LENGTH: 8
```

```
<212> TYPE: PRT
<213> ORGANISM: Artificial Sequence
<220> FEATURE:
<223> OTHER INFORMATION: H-CDR2 of A56-50A09

<400> SEQUENCE: 954

Ile Ser Gly Asp Gly Gly Ser Thr
1               5

<210> SEQ ID NO 955
<211> LENGTH: 16
<212> TYPE: PRT
<213> ORGANISM: Artificial Sequence
<220> FEATURE:
<223> OTHER INFORMATION: H-CDR3 of A56-50A09

<400> SEQUENCE: 955

Ala Arg Val Phe Gln Tyr Tyr Gly Leu Pro Arg Gly Ala Phe Asp Ile
1               5                   10                  15

<210> SEQ ID NO 956
<211> LENGTH: 6
<212> TYPE: PRT
<213> ORGANISM: Artificial Sequence
<220> FEATURE:
<223> OTHER INFORMATION: L-CDR1 of A56-50A09

<400> SEQUENCE: 956

Gln Val Ile Asn Asn Tyr
1               5

<210> SEQ ID NO 957
<211> LENGTH: 3
<212> TYPE: PRT
<213> ORGANISM: Artificial Sequence
<220> FEATURE:
<223> OTHER INFORMATION: L-CDR2 of A56-50A09

<400> SEQUENCE: 957

Ala Ala Ser
1

<210> SEQ ID NO 958
<211> LENGTH: 9
<212> TYPE: PRT
<213> ORGANISM: Artificial Sequence
<220> FEATURE:
<223> OTHER INFORMATION: L-CDR3 of A56-50A09

<400> SEQUENCE: 958

Leu Gln His Lys Ser Tyr Pro Leu Thr
1               5

<210> SEQ ID NO 959
<211> LENGTH: 255
<212> TYPE: DNA
<213> ORGANISM: Artificial Sequence
<220> FEATURE:
<223> OTHER INFORMATION: SCFV of A56-50A09

<400> SEQUENCE: 959
caggtgcagc tggtgcagtc tgggggaggt gtggtacagc ctggggggtc cctgagactc      60
tcctgtgcag cctctggatt cacctttgat gattatgcca tgcactgggt ccgtcaagct     120
ccagggaagg gtctggagtg ggtctctctt attagtgggg atggtggtag cacatactat     180
gcagactctg tgaagggccg attcaccatc tccagagaca acagcaaaaa ctccctgtat     240
```

-continued ctgcaaatga acagt                                                           255

<210> SEQ ID NO 960
<211> LENGTH: 123
<212> TYPE: PRT
<213> ORGANISM: Artificial Sequence
<220> FEATURE:
<223> OTHER INFORMATION: VH2 of A56-50A09

<400> SEQUENCE: 960

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Leu Ile Ser Gly Asp Gly Gly Ser Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Phe Gln Tyr Tyr Gly Leu Pro Arg Gly Ala Phe Asp Ile
                100                 105                 110

Trp Gly Gln Gly Thr Met Ile Thr Val Ser Ser
        115                 120

<210> SEQ ID NO 961
<211> LENGTH: 107
<212> TYPE: PRT
<213> ORGANISM: Artificial Sequence
<220> FEATURE:
<223> OTHER INFORMATION: VL2 of A56-50A09

<400> SEQUENCE: 961

Asp Ile Gln Met Thr Gln Ser Pro Ser Ala Met Ser Ala Ser Ile Gly
1               5                   10                  15

Asp Arg Val Thr Ile Thr Cys Arg Ala Ser Gln Val Ile Asn Asn Tyr
                20                  25                  30

Leu Ile Trp Phe Gln Gln Lys Pro Gly Lys Val Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Pro Gly Thr Lys Val Glu Ile Lys
            100                 105

<210> SEQ ID NO 962
<211> LENGTH: 25
<212> TYPE: PRT
<213> ORGANISM: Artificial Sequence
<220> FEATURE:
<223> OTHER INFORMATION: H-FR1 of A56-50A09

<400> SEQUENCE: 962

Gln Val Gln Leu Val Gln Ser Gly Gly Gly Val Val Gln Pro Gly Gly

-continued

```
1               5               10              15

Ser Leu Arg Leu Ser Cys Ala Ala Ser
            20              25

<210> SEQ ID NO 963
<211> LENGTH: 17
<212> TYPE: PRT
<213> ORGANISM: Artificial Sequence
<220> FEATURE:
<223> OTHER INFORMATION: H-FR2 of A56-50A09

<400> SEQUENCE: 963

Met His Trp Val Arg Gln Ala Pro Gly Lys Gly Leu Glu Trp Val Ser
1               5               10              15

Leu

<210> SEQ ID NO 964
<211> LENGTH: 38
<212> TYPE: PRT
<213> ORGANISM: Artificial Sequence
<220> FEATURE:
<223> OTHER INFORMATION: H-FR3 of A56-50A09

<400> SEQUENCE: 964

Tyr Tyr Ala Asp Ser Val Lys Gly Arg Phe Thr Ile Ser Arg Asp Asn
1               5               10              15

Ser Lys Asn Ser Leu Tyr Leu Gln Met Asn Ser Leu Arg Ala Glu Asp
            20              25              30

Thr Ala Val Tyr Tyr Cys
        35

<210> SEQ ID NO 965
<211> LENGTH: 11
<212> TYPE: PRT
<213> ORGANISM: Artificial Sequence
<220> FEATURE:
<223> OTHER INFORMATION: H-FR4 of A56-50A09

<400> SEQUENCE: 965

Trp Gly Gln Gly Thr Met Ile Thr Val Ser Ser
1               5               10

<210> SEQ ID NO 966
<211> LENGTH: 26
<212> TYPE: PRT
<213> ORGANISM: Artificial Sequence
<220> FEATURE:
<223> OTHER INFORMATION: L-FR1 of A56-50A09

<400> SEQUENCE: 966

Asp Ile Gln Met Thr Gln Ser Pro Ser Ala Met Ser Ala Ser Ile Gly
1               5               10              15

Asp Arg Val Thr Ile Thr Cys Arg Ala Ser
            20              25

<210> SEQ ID NO 967
<211> LENGTH: 17
<212> TYPE: PRT
<213> ORGANISM: Artificial Sequence
<220> FEATURE:
<223> OTHER INFORMATION: L-FR2 of A56-50A09

<400> SEQUENCE: 967

Leu Ile Trp Phe Gln Gln Lys Pro Gly Lys Val Pro Lys Arg Leu Ile
```

-continued

```
1               5               10              15

Tyr

<210> SEQ ID NO 968
<211> LENGTH: 36
<212> TYPE: PRT
<213> ORGANISM: Artificial Sequence
<220> FEATURE:
<223> OTHER INFORMATION: L-FR3 of A56-50A09

<400> SEQUENCE: 968

Ile Tyr Ala Ala Ser Ser Leu Gln Ser Gly Val Pro Ser Arg Phe Ser
1               5               10              15

Gly Ser Gly Ser Gly Thr Glu Phe Thr Leu Thr Ile Ser Ser Leu Gln
            20              25              30

Pro Glu Asp Phe
        35

<210> SEQ ID NO 969
<211> LENGTH: 10
<212> TYPE: PRT
<213> ORGANISM: Artificial Sequence
<220> FEATURE:
<223> OTHER INFORMATION: L-FR4 of A56-50A09

<400> SEQUENCE: 969

Phe Gly Pro Gly Thr Lys Val Glu Ile Lys
1               5               10

<210> SEQ ID NO 970
<211> LENGTH: 10
<212> TYPE: PRT
<213> ORGANISM: Artificial Sequence
<220> FEATURE:
<223> OTHER INFORMATION: H-CDR1 of A56-50A11

<400> SEQUENCE: 970

Gly Phe Ser Leu Ser Asn Ala Arg Met Gly
1               5               10

<210> SEQ ID NO 971
<211> LENGTH: 7
<212> TYPE: PRT
<213> ORGANISM: Artificial Sequence
<220> FEATURE:
<223> OTHER INFORMATION: H-CDR2 of A56-50A11

<400> SEQUENCE: 971

Ile Phe Ser Ser Asp Glu Lys
1               5

<210> SEQ ID NO 972
<211> LENGTH: 15
<212> TYPE: PRT
<213> ORGANISM: Artificial Sequence
<220> FEATURE:
<223> OTHER INFORMATION: H-CDR3 of A56-50A11

<400> SEQUENCE: 972

Ala Arg Thr Ser Arg Ile Ser Pro Thr Gly Glu Ala Phe Asp Ile
1               5               10              15

<210> SEQ ID NO 973
<211> LENGTH: 6
<212> TYPE: PRT
```

<213> ORGANISM: Artificial Sequence
<220> FEATURE:
<223> OTHER INFORMATION: L-CDR1 of A56-50A11

<400> SEQUENCE: 973

Gln Asn Ile Gly Ser Ile
1               5

<210> SEQ ID NO 974
<211> LENGTH: 3
<212> TYPE: PRT
<213> ORGANISM: Artificial Sequence
<220> FEATURE:
<223> OTHER INFORMATION: L-CDR2 of A56-50A11

<400> SEQUENCE: 974

Tyr Ala Ser
1

<210> SEQ ID NO 975
<211> LENGTH: 9
<212> TYPE: PRT
<213> ORGANISM: Artificial Sequence
<220> FEATURE:
<223> OTHER INFORMATION: L-CDR3 of A56-50A11

<400> SEQUENCE: 975

His Gln Ser Arg Ser Leu Pro Gln Thr
1               5

<210> SEQ ID NO 976
<211> LENGTH: 255
<212> TYPE: DNA
<213> ORGANISM: Artificial Sequence
<220> FEATURE:
<223> OTHER INFORMATION: SCFV of A56-50A11

<400> SEQUENCE: 976
caggtcacct tgagggagtc tggtcctgtg ctggtgaaac ccacagagac cctcacgctg      60
acctgcaccg tctctggatt ctcactcagc aatgctagaa tgggtgtggg ctggatccgt     120
cagcccccag ggaaggccct ggagtggctc gcccacattt tttcgagcga cgaaaaatct     180
tttagggcat ctctgaagag caggctcacc atctccaagg acacctccaa aagccaggtg     240
gtccttacaa tgacc                                                      255

<210> SEQ ID NO 977
<211> LENGTH: 123
<212> TYPE: PRT
<213> ORGANISM: Artificial Sequence
<220> FEATURE:
<223> OTHER INFORMATION: VH2 of A56-50A11

<400> SEQUENCE: 977

Gln Val Thr Leu Arg Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Gly Trp Ile Arg Gln Pro Pro Gly Lys Ala Leu Glu
        35                  40                  45

Trp Leu Ala His Ile Phe Ser Ser Asp Glu Lys Ser Phe Arg Ala Ser
    50                  55                  60

Leu Lys Ser Arg Leu Thr Ile Ser Lys Asp Thr Ser Lys Ser Gln Val
65                  70                  75                  80

-continued

```
Val Leu Thr Met Thr Asn Met Asp Pro Val Asp Thr Ala Ile Tyr Tyr
            85                  90                  95

Cys Ala Arg Thr Ser Arg Ile Ser Pro Thr Gly Glu Ala Phe Asp Ile
            100                 105                 110

Trp Gly Gln Gly Thr Val Val Thr Val Ser Ser
        115                 120
```

```
<210> SEQ ID NO 978
<211> LENGTH: 107
<212> TYPE: PRT
<213> ORGANISM: Artificial Sequence
<220> FEATURE:
<223> OTHER INFORMATION: VL2 of A56-50A11

<400> SEQUENCE: 978

Asp Ile Val Met Thr Gln Thr Pro Asp Phe Arg Ser Val Ala Pro Ala
1               5                   10                  15

Glu Thr Val Thr Ile Thr Cys Arg Ala Ser Gln Asn Ile Gly Ser Ile
            20                  25                  30

Leu His Trp Tyr Gln Gln Lys Pro Asn Gln Ser Pro Val Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Glu Phe Thr Leu Thr Ile Tyr Ser Leu Glu Ala
65                  70                  75                  80

Glu Asp Ala Ala Thr Tyr Tyr Cys His Gln Ser Arg Ser Leu Pro Gln
            85                  90                  95

Thr Phe Gly Gln Gly Thr Lys Leu Glu Val Lys
            100                 105
```

```
<210> SEQ ID NO 979
<211> LENGTH: 25
<212> TYPE: PRT
<213> ORGANISM: Artificial Sequence
<220> FEATURE:
<223> OTHER INFORMATION: H-FR1 of A56-50A11

<400> SEQUENCE: 979

Gln Val Thr Leu Arg Glu Ser Gly Pro Val Leu Val Lys Pro Thr Glu
1               5                   10                  15

Thr Leu Thr Leu Thr Cys Thr Val Ser
            20                  25
```

```
<210> SEQ ID NO 980
<211> LENGTH: 17
<212> TYPE: PRT
<213> ORGANISM: Artificial Sequence
<220> FEATURE:
<223> OTHER INFORMATION: H-FR2 of A56-50A11

<400> SEQUENCE: 980

Val Gly Trp Ile Arg Gln Pro Pro Gly Lys Ala Leu Glu Trp Leu Ala
1               5                   10                  15

His
```

```
<210> SEQ ID NO 981
<211> LENGTH: 38
<212> TYPE: PRT
<213> ORGANISM: Artificial Sequence
<220> FEATURE:
<223> OTHER INFORMATION: H-FR3 of A56-50A11
```

<400> SEQUENCE: 981

Ser Phe Arg Ala Ser Leu Lys Ser Arg Leu Thr Ile Ser Lys Asp Thr
1               5                   10                  15

Ser Lys Ser Gln Val Val Leu Thr Met Thr Asn Met Asp Pro Val Asp
            20                  25                  30

Thr Ala Ile Tyr Tyr Cys
        35

<210> SEQ ID NO 982
<211> LENGTH: 11
<212> TYPE: PRT
<213> ORGANISM: Artificial Sequence
<220> FEATURE:
<223> OTHER INFORMATION: H-FR4 of A56-50A11

<400> SEQUENCE: 982

Trp Gly Gln Gly Thr Val Val Thr Val Ser Ser
1               5                   10

<210> SEQ ID NO 983
<211> LENGTH: 26
<212> TYPE: PRT
<213> ORGANISM: Artificial Sequence
<220> FEATURE:
<223> OTHER INFORMATION: L-FR1 of A56-50A11

<400> SEQUENCE: 983

Asp Ile Val Met Thr Gln Thr Pro Asp Phe Arg Ser Val Ala Pro Ala
1               5                   10                  15

Glu Thr Val Thr Ile Thr Cys Arg Ala Ser
            20                  25

<210> SEQ ID NO 984
<211> LENGTH: 17
<212> TYPE: PRT
<213> ORGANISM: Artificial Sequence
<220> FEATURE:
<223> OTHER INFORMATION: L-FR2 of A56-50A11

<400> SEQUENCE: 984

Leu His Trp Tyr Gln Gln Lys Pro Asn Gln Ser Pro Val Leu Leu Ile
1               5                   10                  15

Lys

<210> SEQ ID NO 985
<211> LENGTH: 36
<212> TYPE: PRT
<213> ORGANISM: Artificial Sequence
<220> FEATURE:
<223> OTHER INFORMATION: L-FR3 of A56-50A11

<400> SEQUENCE: 985

Ile Lys Tyr Ala Ser Gln Ser Ile Ser Gly Val Pro Ser Arg Phe Ser
1               5                   10                  15

Gly Ser Gly Ser Gly Thr Glu Phe Thr Leu Thr Ile Tyr Ser Leu Glu
            20                  25                  30

Ala Glu Asp Ala
        35

<210> SEQ ID NO 986
<211> LENGTH: 10
<212> TYPE: PRT

<213> ORGANISM: Artificial Sequence
<220> FEATURE:
<223> OTHER INFORMATION: L-FR4 of A56-50A11

<400> SEQUENCE: 986

Phe Gly Gln Gly Thr Lys Leu Glu Val Lys
1               5                   10

<210> SEQ ID NO 987
<211> LENGTH: 8
<212> TYPE: PRT
<213> ORGANISM: Artificial Sequence
<220> FEATURE:
<223> OTHER INFORMATION: H-CDR1 of A56-54C01

<400> SEQUENCE: 987

Gly Phe Thr Phe Val Val Phe Pro
1               5

<210> SEQ ID NO 988
<211> LENGTH: 8
<212> TYPE: PRT
<213> ORGANISM: Artificial Sequence
<220> FEATURE:
<223> OTHER INFORMATION: H-CDR2 of A56-54C01

<400> SEQUENCE: 988

Ile Ser Gly Ser Gly Gly Ser Thr
1               5

<210> SEQ ID NO 989
<211> LENGTH: 14
<212> TYPE: PRT
<213> ORGANISM: Artificial Sequence
<220> FEATURE:
<223> OTHER INFORMATION: H-CDR3 of A56-54C01

<400> SEQUENCE: 989

Ala Ile Gly Gly Pro Leu Thr Ser His Asn Trp Phe Asp Pro
1               5                   10

<210> SEQ ID NO 990
<211> LENGTH: 8
<212> TYPE: PRT
<213> ORGANISM: Artificial Sequence
<220> FEATURE:
<223> OTHER INFORMATION: L-CDR1 of A56-54C01

<400> SEQUENCE: 990

Ser Gly Ser Ile Gly Ser Ser Tyr
1               5

<210> SEQ ID NO 991
<211> LENGTH: 3
<212> TYPE: PRT
<213> ORGANISM: Artificial Sequence
<220> FEATURE:
<223> OTHER INFORMATION: L-CDR2 of A56-54C01

<400> SEQUENCE: 991

Glu Asp Ala
1

<210> SEQ ID NO 992
<211> LENGTH: 10
<212> TYPE: PRT
<213> ORGANISM: Artificial Sequence
<220> FEATURE:
<223> OTHER INFORMATION: L-CDR3 of A56-54C01

<400> SEQUENCE: 992

Gln Ser Tyr Asp Gly Ser Asn His Phe Val
1               5                   10

<210> SEQ ID NO 993
<211> LENGTH: 255
<212> TYPE: DNA
<213> ORGANISM: Artificial Sequence
<220> FEATURE:
<223> OTHER INFORMATION: SCFV of A56-54C01

<400> SEQUENCE: 993
caggtgcagc tggtagagtc ggggggaggc gtggtccagc ctggggggtc cctgaaactc     60
tcctgtgcag cctctggatt caccttcgtt gtctttccta tgcgctgggt ccgccaggct    120
ccagggaagg ggctggagtg ggtctcagct attagtggta gtggtggtag cacatactac    180
tcagactccg tgaagggccg gttcaccatc tccagagaca attccaagaa caccctgtat    240
ctgcaaatga acagt                                                      255

<210> SEQ ID NO 994
<211> LENGTH: 121
<212> TYPE: PRT
<213> ORGANISM: Artificial Sequence
<220> FEATURE:
<223> OTHER INFORMATION: VH2 of A56-54C01

<400> SEQUENCE: 994

Gln Val Gln Leu Val Glu Ser Gly Gly Gly Val Val Gln Pro Gly Gly
1               5                   10                  15

Ser Leu Lys Leu Ser Cys Ala Ala Ser Gly Phe Thr Phe Val Val Phe
                20                  25                  30

Pro Met Arg Trp Val Arg Gln Ala Pro Gly Lys Gly Leu Glu Trp Val
            35                  40                  45

Ser Ala Ile Ser Gly Ser Gly Gly Ser Thr Tyr Tyr Ser Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gly Gly Pro Leu Thr Ser His Asn Trp Phe Asp Pro Trp Gly
            100                 105                 110

Gln Gly Thr Leu Val Thr Val Ser Ser
        115                 120

<210> SEQ ID NO 995
<211> LENGTH: 111
<212> TYPE: PRT
<213> ORGANISM: Artificial Sequence
<220> FEATURE:
<223> OTHER INFORMATION: VL2 of A56-54C01

<400> SEQUENCE: 995

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Gly Ser Ser
                20                  25                  30

Tyr Ile Gln Trp Tyr Gln Gln Arg Pro Gly Ser Ala Pro Thr Thr Val

-continued

```
        35                  40                  45

Met Tyr Glu Asp Ala Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Gly
                85                  90                  95

Ser Asn His Phe Val Phe Gly Gly Gly Thr Lys Leu Thr Val Leu
            100                 105                 110
```

```
<210> SEQ ID NO 996
<211> LENGTH: 25
<212> TYPE: PRT
<213> ORGANISM: Artificial Sequence
<220> FEATURE:
<223> OTHER INFORMATION: H-FR1 of A56-54C01

<400> SEQUENCE: 996

Gln Val Gln Leu Val Glu Ser Gly Gly Gly Val Val Gln Pro Gly Gly
1               5                  10                  15

Ser Leu Lys Leu Ser Cys Ala Ala Ser
            20                  25
```

```
<210> SEQ ID NO 997
<211> LENGTH: 17
<212> TYPE: PRT
<213> ORGANISM: Artificial Sequence
<220> FEATURE:
<223> OTHER INFORMATION: H-FR2 of A56-54C01

<400> SEQUENCE: 997

Met Arg Trp Val Arg Gln Ala Pro Gly Lys Gly Leu Glu Trp Val Ser
1               5                  10                  15

Ala
```

```
<210> SEQ ID NO 998
<211> LENGTH: 38
<212> TYPE: PRT
<213> ORGANISM: Artificial Sequence
<220> FEATURE:
<223> OTHER INFORMATION: H-FR3 of A56-54C01

<400> SEQUENCE: 998

Tyr Tyr Ser Asp Ser Val Lys Gly Arg Phe Thr Ile Ser Arg Asp Asn
1               5                  10                  15

Ser Lys Asn Thr Leu Tyr Leu Gln Met Asn Ser Leu Arg Ala Glu Asp
            20                  25                  30

Thr Ala Val Tyr Tyr Cys
        35
```

```
<210> SEQ ID NO 999
<211> LENGTH: 11
<212> TYPE: PRT
<213> ORGANISM: Artificial Sequence
<220> FEATURE:
<223> OTHER INFORMATION: H-FR4 of A56-54C01

<400> SEQUENCE: 999

Trp Gly Gln Gly Thr Leu Val Thr Val Ser Ser
1               5                  10
```

```
<210> SEQ ID NO 1000
```

-continued

```
<211> LENGTH: 25
<212> TYPE: PRT
<213> ORGANISM: Artificial Sequence
<220> FEATURE:
<223> OTHER INFORMATION: L-FR1 of A56-54C01

<400> SEQUENCE: 1000

Asn Phe Met Leu Thr Gln Pro His Ser Val Ser Glu Ser Pro Gly Lys
1               5                   10                  15

Thr Val Thr Ile Ser Cys Thr Arg Ser
            20                  25

<210> SEQ ID NO 1001
<211> LENGTH: 17
<212> TYPE: PRT
<213> ORGANISM: Artificial Sequence
<220> FEATURE:
<223> OTHER INFORMATION: L-FR2 of A56-54C01

<400> SEQUENCE: 1001

Ile Gln Trp Tyr Gln Gln Arg Pro Gly Ser Ala Pro Thr Thr Val Met
1               5                   10                  15

Tyr

<210> SEQ ID NO 1002
<211> LENGTH: 36
<212> TYPE: PRT
<213> ORGANISM: Artificial Sequence
<220> FEATURE:
<223> OTHER INFORMATION: L-FR3 of A56-54C01

<400> SEQUENCE: 1002

Met Tyr Glu Asp Ala Glu Arg Pro Ser Gly Val Pro Asp Arg Phe Ser
1               5                   10                  15

Gly Ser Ile Asp Ser Ser Ser Asn Ser Ala Ser Leu Thr Ile Ser Gly
            20                  25                  30

Leu Lys Thr Glu
        35

<210> SEQ ID NO 1003
<211> LENGTH: 10
<212> TYPE: PRT
<213> ORGANISM: Artificial Sequence
<220> FEATURE:
<223> OTHER INFORMATION: L-FR4 of A56-54C01

<400> SEQUENCE: 1003

Phe Gly Gly Gly Thr Lys Leu Thr Val Leu
1               5                   10

<210> SEQ ID NO 1004
<211> LENGTH: 8
<212> TYPE: PRT
<213> ORGANISM: Artificial Sequence
<220> FEATURE:
<223> OTHER INFORMATION: H-CDR1 of A56-59A11

<400> SEQUENCE: 1004

Gly Phe Ser Leu Ser Asn Tyr Gly
1               5

<210> SEQ ID NO 1005
<211> LENGTH: 8
<212> TYPE: PRT
<213> ORGANISM: Artificial Sequence
```

```
<220> FEATURE:
<223> OTHER INFORMATION: H-CDR2 of A56-59A11

<400> SEQUENCE: 1005

Ile Ser Ala Ser Ser Ser Tyr Lys
1               5

<210> SEQ ID NO 1006
<211> LENGTH: 15
<212> TYPE: PRT
<213> ORGANISM: Artificial Sequence
<220> FEATURE:
<223> OTHER INFORMATION: H-CDR3 of A56-59A11

<400> SEQUENCE: 1006

Ala Arg Asp Arg Tyr Phe Tyr Gly Ser Gly Ser Tyr Pro Pro Ala
1               5                   10                  15

<210> SEQ ID NO 1007
<211> LENGTH: 11
<212> TYPE: PRT
<213> ORGANISM: Artificial Sequence
<220> FEATURE:
<223> OTHER INFORMATION: L-CDR1 of A56-59A11

<400> SEQUENCE: 1007

Gln Ser Leu Leu Gln Thr Asn Gly Tyr Asn Tyr
1               5                   10

<210> SEQ ID NO 1008
<211> LENGTH: 3
<212> TYPE: PRT
<213> ORGANISM: Artificial Sequence
<220> FEATURE:
<223> OTHER INFORMATION: L-CDR2 of A56-59A11

<400> SEQUENCE: 1008

Leu Gly Ser
1

<210> SEQ ID NO 1009
<211> LENGTH: 8
<212> TYPE: PRT
<213> ORGANISM: Artificial Sequence
<220> FEATURE:
<223> OTHER INFORMATION: L-CDR3 of A56-59A11

<400> SEQUENCE: 1009

Met His Ser Leu Gln Thr Pro Thr
1               5

<210> SEQ ID NO 1010
<211> LENGTH: 255
<212> TYPE: DNA
<213> ORGANISM: Artificial Sequence
<220> FEATURE:
<223> OTHER INFORMATION: SCFV of A56-59A11

<400> SEQUENCE: 1010
caggtgcagc tggtggagtc tgggggaggc gtggtccagc ctgggaggtc cctgagactc      60
tcctgtgcag cgtctggatt cagcctcagt aactatggca tgcactgggt ccgccaggct     120
ccaggcaagg ggctggagtg ggtatcatat attagtgcta gtagtagtta caagaagtac     180
gcagactcag tgaagggccg attcaccatc tccagagaca cgccaagaa ctccctgtat      240 ctgcaaatga acagt                                                      255
```

-continued

<210> SEQ ID NO 1011
<211> LENGTH: 122
<212> TYPE: PRT
<213> ORGANISM: Artificial Sequence
<220> FEATURE:
<223> OTHER INFORMATION: VH2 of A56-59A11

<400> SEQUENCE: 1011

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Ser Asn Tyr
                20                  25                  30

Gly Met His Trp Val Arg Gln Ala Pro Gly Lys Gly Leu Glu Trp Val
            35                  40                  45

Ser Tyr Ile Ser Ala Ser Ser Ser Tyr Lys Lys Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Phe Tyr Gly Ser Gly Ser Tyr Pro Pro Ala Leu
                100                 105                 110

Gly Arg Gly Thr Leu Val Thr Val Ser Ser
            115                 120

<210> SEQ ID NO 1012
<211> LENGTH: 111
<212> TYPE: PRT
<213> ORGANISM: Artificial Sequence
<220> FEATURE:
<223> OTHER INFORMATION: VL2 of A56-59A11

<400> SEQUENCE: 1012

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Gln Thr
                20                  25                  30

Asn Gly Tyr Asn Tyr Leu Asp Trp Tyr Leu Gln Lys Pro Gly Gln Thr
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met His Ser
                85                  90                  95

Leu Gln Thr Pro Thr Phe Gly Pro Gly Thr Lys Val Glu Ile Lys
                100                 105                 110

<210> SEQ ID NO 1013
<211> LENGTH: 25
<212> TYPE: PRT
<213> ORGANISM: Artificial Sequence
<220> FEATURE:
<223> OTHER INFORMATION: H-FR1 of A56-59A11

<400> SEQUENCE: 1013

Gln Val Gln Leu Val Glu Ser Gly Gly Gly Val Val Gln Pro Gly Arg
1               5                   10                  15

Ser Leu Arg Leu Ser Cys Ala Ala Ser
            20                        25

<210> SEQ ID NO 1014
<211> LENGTH: 17
<212> TYPE: PRT
<213> ORGANISM: Artificial Sequence
<220> FEATURE:
<223> OTHER INFORMATION: H-FR2 of A56-59A11

<400> SEQUENCE: 1014

Met His Trp Val Arg Gln Ala Pro Gly Lys Gly Leu Glu Trp Val Ser
1               5                   10                  15

Tyr

<210> SEQ ID NO 1015
<211> LENGTH: 38
<212> TYPE: PRT
<213> ORGANISM: Artificial Sequence
<220> FEATURE:
<223> OTHER INFORMATION: H-FR3 of A56-59A11

<400> SEQUENCE: 1015

Lys Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 1016
<211> LENGTH: 11
<212> TYPE: PRT
<213> ORGANISM: Artificial Sequence
<220> FEATURE:
<223> OTHER INFORMATION: H-FR4 of A56-59A11

<400> SEQUENCE: 1016

Leu Gly Arg Gly Thr Leu Val Thr Val Ser Ser
1               5                   10

<210> SEQ ID NO 1017
<211> LENGTH: 26
<212> TYPE: PRT
<213> ORGANISM: Artificial Sequence
<220> FEATURE:
<223> OTHER INFORMATION: L-FR1 of A56-59A11

<400> SEQUENCE: 1017

Asp Ile Val Met Thr Gln Thr Pro Leu Ser Leu Pro Val Thr Pro Gly
1               5                   10                  15

Glu Pro Ala Ser Ile Ser Cys Arg Ser Ser
            20                  25

<210> SEQ ID NO 1018
<211> LENGTH: 17
<212> TYPE: PRT
<213> ORGANISM: Artificial Sequence
<220> FEATURE:
<223> OTHER INFORMATION: L-FR2 of A56-59A11

<400> SEQUENCE: 1018

Leu Asp Trp Tyr Leu Gln Lys Pro Gly Gln Thr Pro Gln Leu Leu Ile
1               5                   10                  15

-continued

Tyr

<210> SEQ ID NO 1019
<211> LENGTH: 36
<212> TYPE: PRT
<213> ORGANISM: Artificial Sequence
<220> FEATURE:
<223> OTHER INFORMATION: L-FR3 of A56-59A11

<400> SEQUENCE: 1019

Ile Tyr Leu Gly Ser Asn Arg Ala Ser Gly Val Pro Asp Arg Phe Ser
1               5                   10                  15

Gly Ser Gly Ser Gly Thr Asp Phe Thr Leu Lys Ile Ser Arg Val Glu
            20                  25                  30

Ala Glu Asp Val
        35

<210> SEQ ID NO 1020
<211> LENGTH: 10
<212> TYPE: PRT
<213> ORGANISM: Artificial Sequence
<220> FEATURE:
<223> OTHER INFORMATION: L-FR4 of A56-59A11

<400> SEQUENCE: 1020

Phe Gly Pro Gly Thr Lys Val Glu Ile Lys
1               5                   10

<210> SEQ ID NO 1021
<211> LENGTH: 8
<212> TYPE: PRT
<213> ORGANISM: Artificial Sequence
<220> FEATURE:
<223> OTHER INFORMATION: H-CDR1 of A56-59E12

<400> SEQUENCE: 1021

Gly Phe Asn Phe Gly Asp Tyr Ala
1               5

<210> SEQ ID NO 1022
<211> LENGTH: 10
<212> TYPE: PRT
<213> ORGANISM: Artificial Sequence
<220> FEATURE:
<223> OTHER INFORMATION: H-CDR2 of A56-59E12

<400> SEQUENCE: 1022

Thr Ser Ser Lys His Tyr Gly Gly Thr Ile
1               5                   10

<210> SEQ ID NO 1023
<211> LENGTH: 14
<212> TYPE: PRT
<213> ORGANISM: Artificial Sequence
<220> FEATURE:
<223> OTHER INFORMATION: H-CDR3 of A56-59E12

<400> SEQUENCE: 1023

Ala Lys Gly Lys Trp Leu Arg Phe Asp Ser Pro Phe Asp Ser
1               5                   10

<210> SEQ ID NO 1024
<211> LENGTH: 11
<212> TYPE: PRT
<213> ORGANISM: Artificial Sequence
<220> FEATURE:

-continued

<223> OTHER INFORMATION: L-CDR1 of A56-59E12

<400> SEQUENCE: 1024

Gln Ser Leu Leu His Asn Asn Gly Asn Lys Phe
1               5                   10

<210> SEQ ID NO 1025
<211> LENGTH: 3
<212> TYPE: PRT
<213> ORGANISM: Artificial Sequence
<220> FEATURE:
<223> OTHER INFORMATION: L-CDR2 of A56-59E12

<400> SEQUENCE: 1025

Leu Gly Ser
1

<210> SEQ ID NO 1026
<211> LENGTH: 9
<212> TYPE: PRT
<213> ORGANISM: Artificial Sequence
<220> FEATURE:
<223> OTHER INFORMATION: L-CDR3 of A56-59E12

<400> SEQUENCE: 1026

Met Gln Ala Leu Arg Thr Pro Trp Thr
1               5

<210> SEQ ID NO 1027
<211> LENGTH: 255
<212> TYPE: DNA
<213> ORGANISM: Artificial Sequence
<220> FEATURE:
<223> OTHER INFORMATION: SCFV of A56-59E12

<400> SEQUENCE: 1027
caggtgcagc tggtgcagtc tggggggaggc ttggtaaagc cagggcggtc ccagagactc      60
tcctgtacag gttctggatt caactttggt gattatgcca tcagttggat ccgccaggct     120
ccagggaagg ggctggagtg ggtcggcttc actagcagca acattatgg tgggacaata     180 gactacgccg cgtctgtgaa aggcagattc atcatctcaa gagatgattc gaaaagcacc     240
gcctatctgc aaatg                                                      255

<210> SEQ ID NO 1028
<211> LENGTH: 123
<212> TYPE: PRT
<213> ORGANISM: Artificial Sequence
<220> FEATURE:
<223> OTHER INFORMATION: VH2 of A56-59E12

<400> SEQUENCE: 1028

Gln Val Gln Leu Val Gln Ser Gly Gly Gly Leu Val Lys Pro Gly Arg
1               5                   10                  15

Ser Gln Arg Leu Ser Cys Thr Gly Ser Gly Phe Asn Phe Gly Asp Tyr
            20                  25                  30

Ala Ile Ser Trp Ile Arg Gln Ala Pro Gly Lys Gly Leu Glu Trp Val
        35                  40                  45

Gly Phe Thr Ser Ser Lys His Tyr Gly Gly Thr Ile Asp Tyr Ala Ala
    50                  55                  60

Ser Val Lys Gly Arg Phe Ile Ile Ser Arg Asp Asp Ser Lys Ser Thr
65                  70                  75                  80

Ala Tyr Leu Gln Met Asn Ser Leu Arg Ala Glu Asp Thr Ala Val Tyr

-continued

```
                    85              90              95
Tyr Cys Ala Lys Gly Lys Trp Leu Arg Phe Asp Ser Pro Phe Asp Ser
            100             105             110

Trp Gly Gln Gly Thr Leu Val Thr Val Ser Ser
        115             120
```

<210> SEQ ID NO 1029
<211> LENGTH: 112
<212> TYPE: PRT
<213> ORGANISM: Artificial Sequence
<220> FEATURE:
<223> OTHER INFORMATION: VL2 of A56-59E12

<400> SEQUENCE: 1029

```
Asp Ile Val Met Thr Gln Thr Pro Leu Ser Leu Pro Val Thr Leu Gly
1               5               10              15

Glu Pro Ala Ser Ile Ser Cys Arg Ser Ser Gln Ser Leu Leu His Asn
            20              25              30

Asn Gly Asn Lys Phe Phe Asp Trp Tyr Leu Gln Lys Pro Gly Gln Ser
        35              40              45

Pro Gln Leu Leu Ile Tyr Leu Gly Ser Asn Arg Ala Ser Gly Val Pro
    50              55              60

Asp Arg Phe Ser Gly Ser Gly Ser Gly Thr Asp Phe Ala Leu Lys Ile
65              70              75              80

Ser Arg Val Glu Ala Glu Asp Val Gly Leu Tyr Tyr Cys Met Gln Ala
                85              90              95

Leu Arg Thr Pro Trp Thr Phe Gly Gln Gly Thr Lys Val Glu Ile Lys
            100             105             110
```

<210> SEQ ID NO 1030
<211> LENGTH: 25
<212> TYPE: PRT
<213> ORGANISM: Artificial Sequence
<220> FEATURE:
<223> OTHER INFORMATION: H-FR1 of A56-59E12

<400> SEQUENCE: 1030

```
Gln Val Gln Leu Val Gln Ser Gly Gly Gly Leu Val Lys Pro Gly Arg
1               5               10              15

Ser Gln Arg Leu Ser Cys Thr Gly Ser
            20              25
```

<210> SEQ ID NO 1031
<211> LENGTH: 17
<212> TYPE: PRT
<213> ORGANISM: Artificial Sequence
<220> FEATURE:
<223> OTHER INFORMATION: H-FR2 of A56-59E12

<400> SEQUENCE: 1031

```
Ile Ser Trp Ile Arg Gln Ala Pro Gly Lys Gly Leu Glu Trp Val Gly
1               5               10              15

Phe
```

<210> SEQ ID NO 1032
<211> LENGTH: 38
<212> TYPE: PRT
<213> ORGANISM: Artificial Sequence
<220> FEATURE:
<223> OTHER INFORMATION: H-FR3 of A56-59E12

<400> SEQUENCE: 1032

```
Asp Tyr Ala Ala Ser Val Lys Gly Arg Phe Ile Ile Ser Arg Asp Asp
1               5                   10                  15

Ser Lys Ser Thr Ala Tyr Leu Gln Met Asn Ser Leu Arg Ala Glu Asp
            20                  25                  30

Thr Ala Val Tyr Tyr Cys
        35

<210> SEQ ID NO 1033
<211> LENGTH: 11
<212> TYPE: PRT
<213> ORGANISM: Artificial Sequence
<220> FEATURE:
<223> OTHER INFORMATION: H-FR4 of A56-59E12

<400> SEQUENCE: 1033

Trp Gly Gln Gly Thr Leu Val Thr Val Ser Ser
1               5                   10

<210> SEQ ID NO 1034
<211> LENGTH: 26
<212> TYPE: PRT
<213> ORGANISM: Artificial Sequence
<220> FEATURE:
<223> OTHER INFORMATION: L-FR1 of A56-59E12

<400> SEQUENCE: 1034

Asp Ile Val Met Thr Gln Thr Pro Leu Ser Leu Pro Val Thr Leu Gly
1               5                   10                  15

Glu Pro Ala Ser Ile Ser Cys Arg Ser Ser
            20                  25

<210> SEQ ID NO 1035
<211> LENGTH: 17
<212> TYPE: PRT
<213> ORGANISM: Artificial Sequence
<220> FEATURE:
<223> OTHER INFORMATION: L-FR2 of A56-59E12

<400> SEQUENCE: 1035

Phe Asp Trp Tyr Leu Gln Lys Pro Gly Gln Ser Pro Gln Leu Leu Ile
1               5                   10                  15

Tyr

<210> SEQ ID NO 1036
<211> LENGTH: 36
<212> TYPE: PRT
<213> ORGANISM: Artificial Sequence
<220> FEATURE:
<223> OTHER INFORMATION: L-FR3 of A56-59E12

<400> SEQUENCE: 1036

Ile Tyr Leu Gly Ser Asn Arg Ala Ser Gly Val Pro Asp Arg Phe Ser
1               5                   10                  15

Gly Ser Gly Ser Gly Thr Asp Phe Ala Leu Lys Ile Ser Arg Val Glu
            20                  25                  30

Ala Glu Asp Val
        35

<210> SEQ ID NO 1037
<211> LENGTH: 10
<212> TYPE: PRT
<213> ORGANISM: Artificial Sequence
<220> FEATURE:
```

-continued

<223> OTHER INFORMATION: L-FR4 of A56-59E12

<400> SEQUENCE: 1037

Phe Gly Gln Gly Thr Lys Val Glu Ile Lys
1               5                   10

<210> SEQ ID NO 1038
<211> LENGTH: 310
<212> TYPE: PRT
<213> ORGANISM: Artificial Sequence
<220> FEATURE:
<223> OTHER INFORMATION: amino acid seqeunce for A56 protein

<400> SEQUENCE: 1038

Met Thr Arg Leu Pro Ile Leu Leu Leu Leu Ile Ser Leu Val Tyr Ala
1               5                   10                  15

Thr Pro Phe Pro Gln Thr Ser Lys Lys Ile Gly Asp Asp Ala Thr Leu
                20                  25                  30

Ser Cys Asn Arg Asn Asn Thr Asn Asp Tyr Val Val Met Ser Ala Trp
            35                  40                  45

Tyr Lys Glu Pro Asn Ser Ile Ile Leu Leu Ala Ala Lys Ser Asp Val
        50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Pro Thr Asn
                100                 105                 110

Asp Thr Asp Lys Val Asp Tyr Glu Glu Tyr Ser Thr Glu Leu Ile Val
            115                 120                 125

Asn Thr Asp Ser Glu Ser Thr Ile Asp Ile Ile Leu Ser Gly Ser Thr
        130                 135                 140

His Ser Pro Glu Thr Ser Ser Glu Lys Pro Glu Asp Ile Asp Asn Phe
145                 150                 155                 160

Asn Cys Ser Ser Val Phe Glu Ile Ala Thr Pro Glu Pro Ile Thr Asp
                165                 170                 175

Asn Val Glu Asp His Thr Asp Thr Val Thr Tyr Thr Ser Asp Ser Ile
            180                 185                 190

Asn Thr Val Ser Ala Ser Ser Gly Glu Ser Thr Thr Asp Glu Thr Pro
        195                 200                 205

Glu Pro Ile Thr Asp Lys Glu Glu Asp His Thr Val Thr Asp Thr Val
    210                 215                 220

Ser Tyr Thr Thr Val Ser Thr Ser Ser Gly Ile Val Thr Thr Lys Ser
225                 230                 235                 240

Thr Thr Asp Asp Ala Tyr Asn Asp Asn Asp Thr Val Pro Ser Thr Thr
                245                 250                 255

Val Gly Ser Ser Thr Thr Ser Ile Ser Asn Tyr Lys Thr Lys Asp Phe
            260                 265                 270

Val Glu Ile Phe Gly Ile Thr Ala Leu Ile Ile Leu Ser Ala Val Ala
        275                 280                 285

Ile Phe Cys Ile Thr Tyr Tyr Ile Cys Asn Lys Arg Ser Arg Lys Tyr
        290                 295                 300

Lys Thr Glu Asn Lys Pro
305                 310

<210> SEQ ID NO 1039

-continued

```
<211> LENGTH: 930
<212> TYPE: DNA
<213> ORGANISM: Artificial Sequence
<220> FEATURE:
<223> OTHER INFORMATION: nucleotide seqeunce of A56 protein

<400> SEQUENCE: 1039
atgacacgat taccaatact tttgttacta atatcattag tatacgctac accttttcct          60
cagacatcta aaaaaatagg tgatgatgca actctatcat gtaatcgaaa taatacaaat         120
gactacgttg ttatgagtgc ttggtataag gagcccaatt ccattattct tttagctgct         180
aaaagcgacg tcttgtattt tgataattat accaaggata aaatatctta cgactctcca         240
tacgatgatc tagttacaac tatcacaatt aaatcattga ctgctagaga tgccggtact         300
tatgtatgtg cattctttat gacatcacct acaaatgaca ctgataaagt agattatgaa         360
gaatactcca cagagttgat tgtaaataca gatagtgaat cgactataga cataatacta         420
tctggatcta cacattcacc agaaactagt tctgagaaac cagaggatat agataatttt         480
aattgctcgt cggtattcga aatcgcgact ccggaaccaa ttactgataa tgtagaagat         540
catacagaca ccgtcacata cactagtgat agcattaata cagtaagtgc atcatctgga         600
gaatccacaa cagacgagac tccggaacca attactgata agaagaaga tcatacagtc          660 acagacactg tctcatacac tacagtaagt acatcatctg gaattgtcac tactaaatca         720
accaccgatg atacgtacaa tgataatgat acagtaccac caactactgt aggcagtagt         780
acaacctcta ttagcaatta taaaaccaag gactttgtag aaatatttgg tattaccgca         840
ttaattatat tgtcggccgt ggcaatattc tgtattacgt attatatatg taataaacgt         900
tcacgtaaat acaaaacaga gaacaagccg                                         930

<210> SEQ ID NO 1040
<211> LENGTH: 270
<212> TYPE: PRT
<213> ORGANISM: Artificial Sequence
<220> FEATURE:
<223> OTHER INFORMATION: amino acid seqeunce for A56 protein fragment
      (BN-A56-S)

<400> SEQUENCE: 1040

Met Thr Arg Leu Pro Ile Leu Leu Leu Leu Ile Ser Leu Val Tyr Ala
1               5                   10                  15

Thr Pro Phe Pro Gln Thr Ser Lys Lys Ile Gly Asp Asp Ala Thr Leu
                20                  25                  30

Ser Cys Asn Arg Asn Asn Thr Asn Asp Tyr Val Val Met Ser Ala Trp
            35                  40                  45

Tyr Lys Glu Pro Asn Ser Ile Ile Leu Leu Ala Ala Lys Ser Asp Val
        50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Pro Thr Asn
            100                 105                 110

Asp Thr Asp Lys Val Asp Tyr Glu Glu Tyr Ser Thr Glu Leu Ile Val
        115                 120                 125

Asn Thr Asp Ser Glu Ser Thr Ile Asp Ile Ile Leu Ser Gly Ser Thr
    130                 135                 140

His Ser Pro Glu Thr Ser Ser Glu Lys Pro Glu Asp Ile Asp Asn Phe
```

-continued

```
145              150              155              160

Asn Cys Ser Ser Val Phe Glu Ile Ala Thr Pro Glu Pro Ile Thr Asp
                    165              170              175

Asn Val Glu Asp His Thr Asp Thr Val Thr Tyr Thr Ser Asp Ser Ile
                180              185              190

Asn Thr Val Ser Ala Ser Ser Gly Glu Ser Thr Thr Asp Glu Thr Pro
                195              200              205

Glu Pro Ile Thr Asp Lys Glu Glu Asp His Thr Val Thr Asp Thr Val
        210              215              220

Ser Tyr Thr Thr Val Ser Thr Ser Ser Gly Ile Val Thr Thr Lys Ser
225              230              235              240

Thr Thr Asp Asp Ala Tyr Asn Asp Asn Asp Thr Val Pro Ser Thr Thr
                245              250              255

Val Gly Ser Ser Thr Thr Ser Ile Ser Asn Tyr Lys Thr Lys
                260              265              270
```

```
<210> SEQ ID NO 1041
<211> LENGTH: 810
<212> TYPE: DNA
<213> ORGANISM: Artificial Sequence
<220> FEATURE:
<223> OTHER INFORMATION: nucleotide seqeunce of A56 protein fragment
      (BN-A56-S)

<400> SEQUENCE: 1041
atgacacgat taccaatact tttgttacta atatcattag tatacgctac acctttttcct      60 cagacatcta aaaaaatagg tgatgatgca actctatcat gtaatcgaaa taatacaaat     120
gactacgttg ttatgagtgc ttggtataag gagcccaatt ccattattct tttagctgct     180
aaaagcgacg tcttgtattt tgataattat accaaggata aaatatctta cgactctcca     240
tacgatgatc tagttacaac tatcacaatt aaatcattga ctgctagaga tgccggtact     300
tatgtatgtg cattctttat gacatcacct acaaatgaca ctgataaagt agattatgaa     360
gaatactcca cagagttgat tgtaaataca gatagtgaat cgactataga cataatacta     420
tctggatcta cacattcacc agaaactagt tctgagaaac cagaggatat agataatttt     480
aattgctcgt cggtattcga aatcgcgact ccggaaccaa ttactgataa tgtagaagat     540
catacagaca ccgtcacata cactagtgat agcattaata cagtaagtgc atcatctgga     600
gaatccacaa cagacgagac tccggaacca attactgata agaagaaga tcatacagtc     660 acagacactg tctcatacac tacagtaagt acatcatctg gaattgtcac tactaaatca     720
accaccgatg atacgtacaa tgataatgat acagtaccac caactactgt aggcagtagt     780
acaacctcta ttagcaatta taaaaccaag                                       810
```

```
<210> SEQ ID NO 1042
<211> LENGTH: 300
<212> TYPE: PRT
<213> ORGANISM: Artificial Sequence
<220> FEATURE:
<223> OTHER INFORMATION: amino acid sequence for A56 protein fragment
      (BN-A56-17)

<400> SEQUENCE: 1042

Thr Pro Phe Pro Gln Thr Ser Lys Lys Ile Gly Asp Asp Ala Thr Leu
1              5              10              15

Ser Cys Asn Arg Asn Asn Thr Asn Asp Tyr Val Val Met Ser Ala Trp
                20              25              30
```

-continued

```
Tyr Lys Glu Pro Asn Ser Ile Ile Leu Leu Ala Ala Lys Ser Asp Val
        35                  40                  45

Leu Tyr Phe Asp Asn Tyr Thr Lys Asp Lys Ile Ser Tyr Asp Ser Pro
    50                  55                  60

Tyr Asp Asp Leu Val Thr Thr Ile Thr Ile Lys Ser Leu Thr Ala Arg
65                  70                  75                  80

Asp Ala Gly Thr Tyr Val Cys Ala Phe Phe Met Thr Ser Pro Thr Asn
                85                  90                  95

Asp Thr Asp Lys Val Asp Tyr Glu Glu Gly Gly Gly Gly Gly Gly Tyr
            100                 105                 110

Ser Thr Glu Leu Ile Val Asn Thr Asp Ser Glu Ser Thr Ile Asp Ile
        115                 120                 125

Ile Leu Ser Gly Ser Thr His Ser Pro Glu Thr Ser Ser Glu Lys Pro
    130                 135                 140

Glu Asp Ile Asp Asn Phe Asn Cys Ser Ser Val Phe Glu Ile Ala Thr
145                 150                 155                 160

Pro Glu Pro Ile Thr Asp Asn Val Glu Asp His Thr Asp Thr Val Thr
                165                 170                 175

Tyr Thr Ser Asp Ser Ile Asn Thr Val Ser Ala Ser Ser Gly Glu Ser
            180                 185                 190

Thr Thr Asp Glu Thr Pro Glu Pro Ile Thr Asp Lys Glu Glu Asp His
        195                 200                 205

Thr Val Thr Asp Thr Val Ser Tyr Thr Thr Val Ser Thr Ser Ser Gly
    210                 215                 220

Ile Val Thr Thr Lys Ser Thr Thr Asp Asp Ala Tyr Asn Asp Asn Asp
225                 230                 235                 240

Thr Val Pro Ser Thr Thr Val Gly Ser Ser Thr Thr Ser Ile Ser Asn
                245                 250                 255

Tyr Lys Thr Lys Asp Phe Val Glu Ile Phe Gly Ile Thr Ala Leu Ile
            260                 265                 270

Ile Leu Ser Ala Val Ala Ile Phe Cys Ile Thr Tyr Tyr Ile Cys Asn
        275                 280                 285

Lys Arg Ser Arg Lys Tyr Lys Thr Glu Asn Lys Pro
    290                 295                 300
```

```
<210> SEQ ID NO 1043
<211> LENGTH: 900
<212> TYPE: DNA
<213> ORGANISM: Artificial Sequence
<220> FEATURE:
<223> OTHER INFORMATION: nucleotide sequence of A56 protein fragment
      (BN-A56-17)

<400> SEQUENCE: 1043
acaccttttc ctcagacatc taaaaaaata ggtgatgatg caactctatc atgtaatcga        60
aataatacaa atgactacgt tgttatgagt gcttggtata aggagcccaa ttccattatt       120
cttttagctg ctaaaagcga cgtcttgtat tttgataatt ataccaagga taaaatatct       180
tacgactctc catacgatga tctagttaca actatcacaa ttaaatcatt gactgctaga       240
gatgccggta cttatgtatg tgcattcttt atgacatcac ctacaaatga cactgataaa       300
gtagattatg aagaaggcgg cggcggcggc ggctactcca cagagttgat tgtaaataca       360
gatagtgaat cgactataga cataatacta tctggatcta cacattcacc agaaactagt       420
tctgagaaac cagaggatat agataatttt aattgctcgt cggtattcga aatcgcgact       480
ccggaaccaa ttactgataa tgtagaagat catacagaca ccgtcacata cactagtgat       540
```

```
agcattaata cagtaagtgc atcatctgga gaatccacaa cagacgagac tccggaacca      600
attactgata aagaagaaga tcatacagtc acagacactg tctcatacac tacagtaagt      660
acatcatctg gaattgtcac tactaaatca accaccgatg atacgtacaa tgataatgat      720
acagtaccac caactactgt aggcagtagt acaacctcta ttagcaatta taaaaccaag      780
gactttgtag aaatatttgg tattaccgca ttaattatat tgtcggccgt ggcaatattc      840
tgtattacgt attatatatg taataaacgt tcacgtaaat acaaaacaga gaacaagccg      900
```

```
<210> SEQ ID NO 1044
<211> LENGTH: 267
<212> TYPE: PRT
<213> ORGANISM: Artificial Sequence
<220> FEATURE:
<223> OTHER INFORMATION: amino acid sequence for A56 protein fragment
      (BN-A56-170)

<400> SEQUENCE: 1044

Met Thr Arg Leu Pro Ile Leu Leu Leu Ile Ser Leu Val Tyr Ala
1               5                   10                  15

Thr Pro Phe Pro Gln Thr Ser Lys Lys Ile Gly Asp Asp Ala Thr Leu
            20                  25                  30

Ser Cys Asn Arg Asn Asn Thr Asn Asp Tyr Val Val Met Ser Ala Trp
        35                  40                  45

Tyr Lys Glu Pro Asn Ser Ile Ile Leu Leu Ala Ala Lys Ser Asp Val
    50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Pro Thr Asn
            100                 105                 110

Asp Thr Asp Lys Val Asp Tyr Glu Glu Gly Gly Gly Gly Gly Gly Pro
        115                 120                 125

Glu Pro Ile Thr Asp Asn Val Glu Asp His Thr Asp Thr Val Thr Tyr
    130                 135                 140

Thr Ser Asp Ser Ile Asn Thr Val Ser Ala Ser Ser Gly Glu Ser Thr
145                 150                 155                 160

Thr Asp Glu Thr Pro Glu Pro Ile Thr Asp Lys Glu Glu Asp His Thr
                165                 170                 175

Val Thr Asp Thr Val Ser Tyr Thr Thr Val Ser Thr Ser Ser Gly Ile
            180                 185                 190

Val Thr Thr Lys Ser Thr Thr Asp Asp Ala Tyr Asn Asp Asn Asp Thr
        195                 200                 205

Val Pro Ser Thr Thr Val Gly Ser Ser Thr Thr Ser Ile Ser Asn Tyr
    210                 215                 220

Lys Thr Lys Asp Phe Val Glu Ile Phe Gly Ile Thr Ala Leu Ile Ile
225                 230                 235                 240

Leu Ser Ala Val Ala Ile Phe Cys Ile Thr Tyr Tyr Ile Cys Asn Lys
                245                 250                 255

Arg Ser Arg Lys Tyr Lys Thr Glu Asn Lys Pro
            260                 265
```

```
<210> SEQ ID NO 1045
<211> LENGTH: 801
<212> TYPE: DNA
```

-continued

```
<213> ORGANISM: Artificial Sequence
<220> FEATURE:
<223> OTHER INFORMATION: nucleotide sequence of A56 protein fragment
      (BN-A56-170)

<400> SEQUENCE: 1045
atgacacgat taccaatact tttgttacta atatcattag tatacgctac acctttctct      60
cagacatcta aaaaaatagg tgatgatgca actctatcat gtaatcgaaa taatacaaat     120
gactacgttg ttatgagtgc ttggtataag gagcccaatt ccattattct tttagctgct     180
aaaagcgacg tcttgtattt tgataattat accaaggata aaatatctta cgactctcca     240
tacgatgatc tagttacaac tatcacaatt aaatcattga ctgctagaga tgccggtact     300
tatgtatgtg cattctttat gacatcacct acaaatgaca ctgataaagt agattatgaa     360
gaaggcggcg gcggcggcgg cccggaacca attactgata atgtagaaga tcatacagac     420
accgtcacat acactagtga tagcattaat acagtaagtg catcatctgg agaatccaca     480
acagacgaga ctccggaacc aattactgat aaagaagaag atcatacagt cacagacact     540
gtctcataca ctacagtaag tacatcatct ggaattgtca ctactaaatc aaccaccgat     600
gatacgtaca atgataatga tacagtacca ccaactactg taggcagtag tacaacctct     660
attagcaatt ataaaaccaa ggactttgta gaaatatttg gtattaccgc attaattata     720
ttgtcggccg tggcaatatt ctgtattacg tattatatat gtaataaacg ttcacgtaaa     780
tacaaaacag agaacaagcc g                                               801

<210> SEQ ID NO 1046
<211> LENGTH: 197
<212> TYPE: PRT
<213> ORGANISM: Artificial Sequence
<220> FEATURE:
<223> OTHER INFORMATION: amino acid sequence for A56 protein fragment
      (BN-A56-240)

<400> SEQUENCE: 1046

Met Thr Arg Leu Pro Ile Leu Leu Leu Leu Ile Ser Leu Val Tyr Ala
1               5                   10                  15

Thr Pro Phe Pro Gln Thr Ser Lys Lys Ile Gly Asp Asp Ala Thr Leu
            20                  25                  30

Ser Cys Asn Arg Asn Asn Thr Asn Asp Tyr Val Val Met Ser Ala Trp
        35                  40                  45

Tyr Lys Glu Pro Asn Ser Ile Ile Leu Leu Ala Ala Lys Ser Asp Val
    50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Pro Thr Asn
            100                 105                 110

Asp Thr Asp Lys Val Asp Tyr Glu Glu Gly Gly Gly Gly Gly Gly Thr
            115                 120                 125

Thr Asp Asp Ala Tyr Asn Asp Asn Asp Thr Val Pro Ser Thr Thr Val
    130                 135                 140

Gly Ser Ser Thr Thr Ser Ile Ser Asn Tyr Lys Thr Lys Asp Phe Val
145                 150                 155                 160

Glu Ile Phe Gly Ile Thr Ala Leu Ile Ile Leu Ser Ala Val Ala Ile
                165                 170                 175
```

```
Phe Cys Ile Thr Tyr Tyr Ile Cys Asn Lys Arg Ser Arg Lys Tyr Lys
            180                 185                 190

Thr Glu Asn Lys Pro
        195

<210> SEQ ID NO 1047
<211> LENGTH: 591
<212> TYPE: DNA
<213> ORGANISM: Artificial Sequence
<220> FEATURE:
<223> OTHER INFORMATION: nucleotide sequence of A56 protein fragment
      (BN-A56-240)

<400> SEQUENCE: 1047
atgacacgat taccaatact tttgttacta atatcattag tatacgctac accttttcct        60
cagacatcta aaaaaatagg tgatgatgca actctatcat gtaatcgaaa taatacaaat       120
gactacgttg ttatgagtgc ttggtataag gagcccaatt ccattattct tttagctgct       180
aaaagcgacg tcttgtattt tgataattat accaaggata aaatatctta cgactctcca       240
tacgatgatc tagttacaac tatcacaatt aaatcattga ctgctagaga tgccggtact       300
tatgtatgtg cattctttat gacatcacct acaaatgaca ctgataaagt agattatgaa       360
gaaggcggcg gcggcggcgg caccaccgat gatacgtaca atgataatga tacagtacca       420
ccaactactg taggcagtag tacaacctct attagcaatt ataaaaccaa ggactttgta       480
gaaatatttg gtattaccgc attaattata ttgtcggccg tggcaatatt ctgtattacg       540
tattatatat gtaataaacg ttcacgtaaa tacaaaacag agaacaagcc g                591

<210> SEQ ID NO 1048
<211> LENGTH: 167
<212> TYPE: PRT
<213> ORGANISM: Artificial Sequence
<220> FEATURE:
<223> OTHER INFORMATION: amino acid sequence for A56 protein fragment
      (BN-A56-276)

<400> SEQUENCE: 1048

Met Thr Arg Leu Pro Ile Leu Leu Leu Leu Ile Ser Leu Val Tyr Ala
1               5                   10                  15

Thr Pro Phe Pro Gln Thr Ser Lys Lys Ile Gly Asp Asp Ala Thr Leu
            20                  25                  30

Ser Cys Asn Arg Asn Asn Thr Asn Asp Tyr Val Val Met Ser Ala Trp
        35                  40                  45

Tyr Lys Glu Pro Asn Ser Ile Ile Leu Leu Ala Ala Lys Ser Asp Val
    50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Pro Thr Asn
            100                 105                 110

Asp Thr Asp Lys Val Asp Tyr Glu Glu Gly Gly Gly Gly Gly Gly Asp
        115                 120                 125

Phe Val Glu Ile Phe Gly Ile Thr Ala Leu Ile Ile Leu Ser Ala Val
    130                 135                 140

Ala Ile Phe Cys Ile Thr Tyr Tyr Ile Cys Asn Lys Arg Ser Arg Lys
145                 150                 155                 160

Tyr Lys Thr Glu Asn Lys Pro
```

-continued

165

```
<210> SEQ ID NO 1049
<211> LENGTH: 501
<212> TYPE: DNA
<213> ORGANISM: Artificial Sequence
<220> FEATURE:
<223> OTHER INFORMATION: nucleotide sequence of A56 protein fragment
      (BN-A56-276)

<400> SEQUENCE: 1049
atgacacgat taccaatact tttgttacta atatcattag tatacgctac accttttcct       60
cagacatcta aaaaaatagg tgatgatgca actctatcat gtaatcgaaa taatacaaat      120
gactacgttg ttatgagtgc ttggtataag gagcccaatt ccattattct tttagctgct      180
aaaagcgacg tcttgtattt tgataattat accaaggata aaatatctta cgactctcca      240
tacgatgatc tagttacaac tatcacaatt aaatcattga ctgctagaga tgccggtact      300
tatgtatgtg cattctttat gacatcacct acaaatgaca ctgataaagt agattatgaa      360
gaaggcggcg gcggcggcgg cgactttgta gaaatatttg gtattaccgc attaattata      420
ttgtcggccg tggcaatatt ctgtattacg tattatatat gtaataaacg ttcacgtaaa      480
tacaaaacag agaacaagcc g                                                501

<210> SEQ ID NO 1050
<211> LENGTH: 205
<212> TYPE: PRT
<213> ORGANISM: Artificial Sequence
<220> FEATURE:
<223> OTHER INFORMATION: amino acid sequence for A56 protein fragment
      (A56-121)

<400> SEQUENCE: 1050

Met Thr Arg Leu Pro Ile Leu Leu Leu Ile Ser Leu Val Tyr Ala
1               5                   10                  15

Tyr Ser Thr Glu Leu Ile Val Asn Thr Asp Ser Glu Ser Thr Ile Asp
            20                  25                  30

Ile Ile Leu Ser Gly Ser Thr His Ser Pro Glu Thr Ser Ser Glu Lys
        35                  40                  45

Pro Glu Asp Ile Asp Asn Phe Asn Cys Ser Ser Val Phe Glu Ile Ala
    50                  55                  60

Thr Pro Glu Pro Ile Thr Asp Asn Val Glu Asp His Thr Asp Thr Val
65                  70                  75                  80

Thr Tyr Thr Ser Asp Ser Ile Asn Thr Val Ser Ala Ser Ser Gly Glu
                85                  90                  95

Ser Thr Thr Asp Glu Thr Pro Glu Pro Ile Thr Asp Lys Glu Glu Asp
            100                 105                 110

His Thr Val Thr Asp Thr Val Ser Tyr Thr Thr Val Ser Thr Ser Ser
        115                 120                 125

Gly Ile Val Thr Thr Lys Ser Thr Thr Asp Asp Ala Tyr Asn Asp Asn
    130                 135                 140

Asp Thr Val Pro Ser Thr Thr Val Gly Ser Ser Thr Thr Ser Ile Ser
145                 150                 155                 160

Asn Tyr Lys Thr Lys Asp Phe Val Glu Ile Phe Gly Ile Thr Ala Leu
                165                 170                 175

Ile Ile Leu Ser Ala Val Ala Ile Phe Cys Ile Thr Tyr Tyr Ile Cys
            180                 185                 190

Asn Lys Arg Ser Arg Lys Tyr Lys Thr Glu Asn Lys Pro
```

-continued

```
          195                 200                 205
```

<210> SEQ ID NO 1051
<211> LENGTH: 615
<212> TYPE: DNA
<213> ORGANISM: Artificial Sequence
<220> FEATURE:
<223> OTHER INFORMATION: nucleotide sequence of A56 protein fragment
      (A56-121)

<400> SEQUENCE: 1051

```
atgacacgat taccaatact tttgttacta atatcattag tatacgctta ctccacagag     60
ttgattgtaa atacagatag tgaatcgact atagacataa tactatctgg atctacacat    120
tcaccagaaa ctagttctga gaaaccagag gatatagata attttaattg ctcgtcggta    180
ttcgaaatcg cgactccgga accaattact gataatgtag aagatcatac agacaccgtc    240
acatacacta gtgatagcat taatacagta agtgcatcat ctggagaatc cacaacagac    300
gagactccgg aaccaattac tgataaagaa gaagatcata cagtcacaga cactgtctca    360
tacactacag taagtacatc atctggaatt gtcactacta aatcaaccac cgatgatacg    420
tacaatgata atgatacagt accaccaact actgtaggca gtagtacaac tctctattagc   480 aattataaaa ccaaggactt tgtagaaata tttggtatta ccgcattaat tatattgtcg    540
gccgtggcaa tattctgtat tacgtattat atatgtaata aacgttcacg taaatacaaa    600
acagagaaca agccg                                                     615
```

<210> SEQ ID NO 1052
<211> LENGTH: 189
<212> TYPE: PRT
<213> ORGANISM: Artificial Sequence
<220> FEATURE:
<223> OTHER INFORMATION: amino acid sequence for A56 protein fragment
      (A56-17)

<400> SEQUENCE: 1052

```
Tyr Ser Thr Glu Leu Ile Val Asn Thr Asp Ser Glu Ser Thr Ile Asp
1               5                  10                  15

Ile Ile Leu Ser Gly Ser Thr His Ser Pro Glu Thr Ser Ser Glu Lys
            20                  25                  30

Pro Glu Asp Ile Asp Asn Phe Asn Cys Ser Ser Val Phe Glu Ile Ala
        35                  40                  45

Thr Pro Glu Pro Ile Thr Asp Asn Val Glu Asp His Thr Asp Thr Val
    50                  55                  60

Thr Tyr Thr Ser Asp Ser Ile Asn Thr Val Ser Ala Ser Ser Gly Glu
65                  70                  75                  80

Ser Thr Thr Asp Glu Thr Pro Glu Pro Ile Thr Asp Lys Glu Glu Asp
                85                  90                  95

His Thr Val Thr Asp Thr Val Ser Tyr Thr Thr Val Ser Thr Ser Ser
            100                 105                 110

Gly Ile Val Thr Thr Lys Ser Thr Thr Asp Asp Ala Tyr Asn Asp Asn
        115                 120                 125

Asp Thr Val Pro Ser Thr Thr Val Gly Ser Ser Thr Thr Ser Ile Ser
    130                 135                 140

Asn Tyr Lys Thr Lys Asp Phe Val Glu Ile Phe Gly Ile Thr Ala Leu
145                 150                 155                 160

Ile Ile Leu Ser Ala Val Ala Ile Phe Cys Ile Thr Tyr Tyr Ile Cys
                165                 170                 175
```

Asn Lys Arg Ser Arg Lys Tyr Lys Thr Glu Asn Lys Pro
            180                 185

<210> SEQ ID NO 1053
<211> LENGTH: 567
<212> TYPE: DNA
<213> ORGANISM: Artificial Sequence
<220> FEATURE:
<223> OTHER INFORMATION: nucleotide sequence of A56 protein fragment
      (A56-17)

<400> SEQUENCE: 1053
tactccacag agttgattgt aaatacagat agtgaatcga ctatagacat aatactatct       60
ggatctacac attcaccaga aactagttct gagaaaccag aggatataga taattttaat      120
tgctcgtcgg tattcgaaat cgcgactccg gaaccaatta ctgataatgt agaagatcat      180
acagacaccg tcacatacac tagtgatagc attaatacag taagtgcatc atctggagaa      240
tccacaacag acgagactcc ggaaccaatt actgataaag aagaagatca tacagtcaca      300
gacactgtct catacactac agtaagtaca tcatctggaa ttgtcactac taaatcaacc      360
accgatgata cgtacaatga taatgataca gtaccaccaa ctactgtagg cagtagtaca      420
acctctatta gcaattataa aaccaaggac tttgtagaaa tatttggtat taccgcatta      480
attatattgt cggccgtggc aatattctgt attacgtatt atatatgtaa taaacgttca      540
cgtaaataca aaacagagaa caagccg                                          567

<210> SEQ ID NO 1054
<211> LENGTH: 165
<212> TYPE: PRT
<213> ORGANISM: Artificial Sequence
<220> FEATURE:
<223> OTHER INFORMATION: amino acid sequence for A56 protein fragment
      (A56-121S)

<400> SEQUENCE: 1054

Met Thr Arg Leu Pro Ile Leu Leu Leu Ile Ser Leu Val Tyr Ala
1               5                   10                  15

Tyr Ser Thr Glu Leu Ile Val Asn Thr Asp Ser Glu Ser Thr Ile Asp
            20                  25                  30

Ile Ile Leu Ser Gly Ser Thr His Ser Pro Glu Thr Ser Ser Glu Lys
        35                  40                  45

Pro Glu Asp Ile Asp Asn Phe Asn Cys Ser Ser Val Phe Glu Ile Ala
    50                  55                  60

Thr Pro Glu Pro Ile Thr Asp Asn Val Glu Asp His Thr Asp Thr Val
65                  70                  75                  80

Thr Tyr Thr Ser Asp Ser Ile Asn Thr Val Ser Ala Ser Ser Gly Glu
                85                  90                  95

Ser Thr Thr Asp Glu Thr Pro Glu Pro Ile Thr Asp Lys Glu Glu Asp
                100                 105                 110

His Thr Val Thr Asp Thr Val Ser Tyr Thr Thr Val Ser Thr Ser Ser
            115                 120                 125

Gly Ile Val Thr Thr Lys Ser Thr Thr Asp Asp Ala Tyr Asn Asp Asn
        130                 135                 140

Asp Thr Val Pro Ser Thr Thr Val Gly Ser Ser Thr Thr Ser Ile Ser
145                 150                 155                 160

Asn Tyr Lys Thr Lys
                165

-continued

```
<210> SEQ ID NO 1055
<211> LENGTH: 495
<212> TYPE: DNA
<213> ORGANISM: Artificial Sequence
<220> FEATURE:
<223> OTHER INFORMATION: nucleotide sequence of A56 protein fragment
      (A56-121S)

<400> SEQUENCE: 1055
atgacacgat taccaatact tttgttacta atatcattag tatacgctta ctccacagag        60
ttgattgtaa atacagatag tgaatcgact atagacataa tactatctgg atctacacat       120
tcaccagaaa ctagttctga gaaaccagag gatatagata attttaattg ctcgtcggta       180
ttcgaaatcg cgactccgga accaattact gataatgtag aagatcatac agacaccgtc       240
acatacacta gtgatagcat taatacagta agtgcatcat ctggagaatc cacaacagac       300
gagactccgg aaccaattac tgataaagaa gaagatcata cagtcacaga cactgtctca       360
tacactacag taagtacatc atctggaatt gtcactacta aatcaaccac cgatgatacg       420
tacaatgata atgatacagt accaccaact actgtaggca gtagtacaac ctctattagc       480
aattataaaa ccaag                                                       495

<210> SEQ ID NO 1056
<211> LENGTH: 156
<212> TYPE: PRT
<213> ORGANISM: Artificial Sequence
<220> FEATURE:
<223> OTHER INFORMATION: amino acid sequence for A56 protein fragment
      (A56-170)

<400> SEQUENCE: 1056

Met Thr Arg Leu Pro Ile Leu Leu Leu Leu Ile Ser Leu Val Tyr Ala
1               5                   10                  15

Pro Glu Pro Ile Thr Asp Asn Val Glu Asp His Thr Asp Thr Val Thr
                20                  25                  30

Tyr Thr Ser Asp Ser Ile Asn Thr Val Ser Ala Ser Ser Gly Glu Ser
            35                  40                  45

Thr Thr Asp Glu Thr Pro Glu Pro Ile Thr Asp Lys Glu Glu Asp His
        50                  55                  60

Thr Val Thr Asp Thr Val Ser Tyr Thr Thr Val Ser Thr Ser Ser Gly
65                  70                  75                  80

Ile Val Thr Thr Lys Ser Thr Thr Asp Asp Ala Tyr Asn Asp Asn Asp
                85                  90                  95

Thr Val Pro Ser Thr Thr Val Gly Ser Ser Thr Thr Ser Ile Ser Asn
            100                 105                 110

Tyr Lys Thr Lys Asp Phe Val Glu Ile Phe Gly Ile Thr Ala Leu Ile
        115                 120                 125

Ile Leu Ser Ala Val Ala Ile Phe Cys Ile Thr Tyr Tyr Ile Cys Asn
    130                 135                 140

Lys Arg Ser Arg Lys Tyr Lys Thr Glu Asn Lys Pro
145                 150                 155

<210> SEQ ID NO 1057
<211> LENGTH: 468
<212> TYPE: DNA
<213> ORGANISM: Artificial Sequence
<220> FEATURE:
<223> OTHER INFORMATION: nucleotide sequence of A56 protein fragment
      (A56-170)

<400> SEQUENCE: 1057
```

```
atgacacgat taccaatact tttgttacta atatcattag tatacgctcc ggaaccaatt        60
actgataatg tagaagatca tacagacacc gtcacataca ctagtgatag cattaataca       120
gtaagtgcat catctggaga atccacaaca gacgagactc cggaaccaat tactgataaa       180
gaagaagatc atacagtcac agacactgtc tcatacacta cagtaagtac atcatctgga       240
attgtcacta ctaaatcaac caccgatgat acgtacaatg ataatgatac agtaccacca       300
actactgtag gcagtagtac aacctctatt agcaattata aaaccaagga ctttgtagaa       360
atatttggta ttaccgcatt aattatattg tcggccgtgg caatattctg tattacgtat       420
tatatatgta ataaacgttc acgtaaatac aaaacagaga acaagccg                    468
```

```
<210> SEQ ID NO 1058
<211> LENGTH: 86
<212> TYPE: PRT
<213> ORGANISM: Artificial Sequence
<220> FEATURE:
<223> OTHER INFORMATION: amino acid sequence for A56 protein fragment
      (A56-240)

<400> SEQUENCE: 1058

Met Thr Arg Leu Pro Ile Leu Leu Leu Leu Ile Ser Leu Val Tyr Ala
1               5                   10                  15

Thr Thr Asp Asp Ala Tyr Asn Asp Asn Asp Thr Val Pro Ser Thr Thr
            20                  25                  30

Val Gly Ser Ser Thr Thr Ser Ile Ser Asn Tyr Lys Thr Lys Asp Phe
        35                  40                  45

Val Glu Ile Phe Gly Ile Thr Ala Leu Ile Ile Leu Ser Ala Val Ala
    50                  55                  60

Ile Phe Cys Ile Thr Tyr Tyr Ile Cys Asn Lys Arg Ser Arg Lys Tyr
65                  70                  75                  80

Lys Thr Glu Asn Lys Pro
                85
```

```
<210> SEQ ID NO 1059
<211> LENGTH: 258
<212> TYPE: DNA
<213> ORGANISM: Artificial Sequence
<220> FEATURE:
<223> OTHER INFORMATION: nucleotide sequence of A56 protein fragment
      (A56-240)

<400> SEQUENCE: 1059
atgacacgat taccaatact tttgttacta atatcattag tatacgctac caccgatgat        60
acgtacaatg ataatgatac agtaccacca actactgtag gcagtagtac aacctctatt       120
agcaattata aaaccaagga ctttgtagaa atatttggta ttaccgcatt aattatattg       180
tcggccgtgg caatattctg tattacgtat tatatatgta ataaacgttc acgtaaatac       240
aaaacagaga acaagccg                                                     258
```

```
<210> SEQ ID NO 1060
<211> LENGTH: 56
<212> TYPE: PRT
<213> ORGANISM: Artificial Sequence
<220> FEATURE:
<223> OTHER INFORMATION: amino acid sequence for A56 protein fragment
      (A56-276)

<400> SEQUENCE: 1060

Met Thr Arg Leu Pro Ile Leu Leu Leu Leu Ile Ser Leu Val Tyr Ala
```

-continued

```
1                5                 10                15

Asp Phe Val Glu Ile Phe Gly Ile Thr Ala Leu Ile Ile Leu Ser Ala
             20                 25                30

Val Ala Ile Phe Cys Ile Thr Tyr Tyr Ile Cys Asn Lys Arg Ser Arg
         35                 40                 45

Lys Tyr Lys Thr Glu Asn Lys Pro
     50                 55
```

```
<210> SEQ ID NO 1061
<211> LENGTH: 168
<212> TYPE: DNA
<213> ORGANISM: Artificial Sequence
<220> FEATURE:
<223> OTHER INFORMATION: nucleotide sequence of A56 protein fragment
      (A56-276)

<400> SEQUENCE: 1061
atgacacgat taccaatact tttgttacta atatcattag tatacgctga ctttgtagaa      60
atatttggta ttaccgcatt aattatattg tcggccgtgg caatattctg tattacgtat     120
tatatatgta ataaacgttc acgtaaatac aaaacagaga acaagccg                   168
```

```
<210> SEQ ID NO 1062
<211> LENGTH: 8
<212> TYPE: PRT
<213> ORGANISM: Artificial Sequence
<220> FEATURE:
<223> OTHER INFORMATION: VH-CDR1 (LakePharma variant3)

<400> SEQUENCE: 1062

Gly Tyr Ser Phe Thr Gly Tyr Thr
1               5
```

```
<210> SEQ ID NO 1063
<211> LENGTH: 8
<212> TYPE: PRT
<213> ORGANISM: Artificial Sequence
<220> FEATURE:
<223> OTHER INFORMATION: H-CDR1 of LakePharma variant4

<400> SEQUENCE: 1063

Gly Tyr Ser Phe Thr Gly Tyr Thr
1               5
```

```
<210> SEQ ID NO 1064
<211> LENGTH: 8
<212> TYPE: PRT
<213> ORGANISM: Artificial Sequence
<220> FEATURE:
<223> OTHER INFORMATION: H-CDR2 of LakePharma variant3

<400> SEQUENCE: 1064

Ile Asn Pro Tyr Asn Gly Gly Thr
1               5
```

```
<210> SEQ ID NO 1065
<211> LENGTH: 14
<212> TYPE: PRT
<213> ORGANISM: Artificial Sequence
<220> FEATURE:
<223> OTHER INFORMATION: H-CDR3 of LakePharma variant 3,4

<400> SEQUENCE: 1065

Ala Arg Ser His Tyr Arg Tyr Asp Tyr Trp Tyr Phe Asp Val
1               5                 10
```

```
<210> SEQ ID NO 1066
<211> LENGTH: 11
<212> TYPE: PRT
<213> ORGANISM: Artificial Sequence
<220> FEATURE:
<223> OTHER INFORMATION: L-CDR1 of LakePharma variant 3,4

<400> SEQUENCE: 1066

Gln Ser Leu Val His Ser Asn Gly Asn Thr Tyr
1               5                   10

<210> SEQ ID NO 1067
<211> LENGTH: 3
<212> TYPE: PRT
<213> ORGANISM: Artificial Sequence
<220> FEATURE:
<223> OTHER INFORMATION: L-CDR2 of LakePharma variant 3,4

<400> SEQUENCE: 1067

Lys Val Ser
1

<210> SEQ ID NO 1068
<211> LENGTH: 10
<212> TYPE: PRT
<213> ORGANISM: Artificial Sequence
<220> FEATURE:
<223> OTHER INFORMATION: L-CDR3 of LakePharma variant 3,4

<400> SEQUENCE: 1068

Ser Gln Ser Thr His Val Pro Pro Phe Thr
1               5                   10

<210> SEQ ID NO 1069
<211> LENGTH: 445
<212> TYPE: PRT
<213> ORGANISM: Artificial Sequence
<220> FEATURE:
<223> OTHER INFORMATION: VH of LakePharma variant 3,4

<400> SEQUENCE: 1069

Gln Val Gln Leu Gln Gln Ser Gly Pro Glu Leu Val Lys Pro Gly Ala
1               5                   10                  15

Ser Met Lys Leu Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser His Tyr Arg Tyr Asp Tyr Trp Tyr Phe Asp Val Trp Gly
            100                 105                 110

Ala Gly Thr Thr Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160
```

-continued

```
Thr Trp Asn Ser Gly Ser Leu Ser Ser Gly Val His Thr Phe Pro Ala
            165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
            210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                    245                 250                 255

Val Thr Cys Val Val Val Asp Ile Ser Lys Asp Asp Pro Glu Val Gln
                    260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
            290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                    325                 330                 335

Thr Lys Gly Arg Pro Lys Ala Pro Gln Val Tyr Thr Ile Pro Pro Pro
                    340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
            370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                    405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445
```

```
<210> SEQ ID NO 1070
<211> LENGTH: 445
<212> TYPE: PRT
<213> ORGANISM: Artificial Sequence
<220> FEATURE:
<223> OTHER INFORMATION: VH of LakePharma variant 4

<400> SEQUENCE: 1070

Glu Val Gln Leu Gln Gln Ser Gly Pro Glu Leu Val Lys Pro Gly Ala
1               5                   10                  15

Ser Met Lys Leu Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80
```

-continued

```
Met Glu Leu Leu Ser Leu Thr Ser Glu Asp Ser Ala Val Tyr Tyr Cys
                85                  90                  95

Ala Arg Ser His Tyr Arg Tyr Asp Tyr Trp Tyr Phe Asp Val Trp Gly
            100                 105                 110

Ala Gly Thr Thr Val Thr Val Ser Ser Ala Lys Thr Thr Pro Pro Ser
            115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
                420                 425                 430

His His Thr Glu Lys Ser Leu Ser His Ser Pro Gly Lys
                435                 440                 445
```

```
<210> SEQ ID NO 1071
<211> LENGTH: 220
<212> TYPE: PRT
<213> ORGANISM: Artificial Sequence
<220> FEATURE:
<223> OTHER INFORMATION: VL of LakePharma variant 3, 4

<400> SEQUENCE: 1071
```

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Phe Thr Phe Gly Ser Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
            195                 200                 205

Ser Pro Ile Val Lys Ser Phe Asn Arg Asn Glu Cys
    210                 215                 220
```

```
<210> SEQ ID NO 1072
<211> LENGTH: 945
<212> TYPE: DNA
<213> ORGANISM: Artificial Sequence
<220> FEATURE:
<223> OTHER INFORMATION: nucleotide sequence of A56 protein

<400> SEQUENCE: 1072
atgacacgat taccaatact tttgttacta atatcattag tatacgctac accttttcct       60
cagacatcta aaaaaatagg tgatgatgca actctatcat gtaatcgaaa taatacaaat      120
gactacgttg ttatgagtgc ttggtataag gagcccaatt ctattattct tttagctgct      180
aaaagcgacg tcttgtattt tgataattat accaaggata aaatatctta cgactctcca      240
tacgatgatc tagttacaac tatcacaatt aaatcattga ctgctagaga tgccggtact      300
tatgtatgtg cattctttat gacatcgcct acaaatgaca ctgataaagt agattatgaa      360
gaatactcca cagagttgat tgtaaataca gatagtgaat cgactattga cataatacta      420
tctggatcta cacattcacc ggaaactagt tctgagaaac cagaggatat agataatttt      480
aattgctcgt cggtattcga aatcgcgact ccggaaccaa ttactgataa tgtagaagat      540
catacagaca ccgtcacata cactagtgat agcattaata cagtaagtgc atcatctgga      600
gaatccacaa cagacgagac tccggaacca attactgata agaagaaga tcatacagtc      660 acagacactg tctcatacac tacagtaagt acatcatctg gaattgtcac tactaaatca      720
accaccgatg atgcggatct ttatgatacg tacaatgata atgatacagt accatcaact      780
```

-continued

```
actgtaggta gtagtacaac ctctattagc aattataaaa ccaaggactt tgtagaaata    840
tttggtatta ccgcattaat tatattgtcg gccgtggcaa tattctgtat tacgtattat    900
atatgtaata aacgttcacg taaatacaaa acagagaaca aagtc                     945

<210> SEQ ID NO 1073
<211> LENGTH: 315
<212> TYPE: PRT
<213> ORGANISM: Artificial Sequence
<220> FEATURE:
<223> OTHER INFORMATION: amino acid sequence for A56 protein

<400> SEQUENCE: 1073

Met Thr Arg Leu Pro Ile Leu Leu Leu Leu Ile Ser Leu Val Tyr Ala
1               5                   10                  15

Thr Pro Phe Pro Gln Thr Ser Lys Lys Ile Gly Asp Asp Ala Thr Leu
            20                  25                  30

Ser Cys Asn Arg Asn Asn Thr Asn Asp Tyr Val Val Met Ser Ala Trp
        35                  40                  45

Tyr Lys Glu Pro Asn Ser Ile Ile Leu Leu Ala Ala Lys Ser Asp Val
    50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Pro Thr Asn
            100                 105                 110

Asp Thr Asp Lys Val Asp Tyr Glu Glu Tyr Ser Thr Glu Leu Ile Val
            115                 120                 125

Asn Thr Asp Ser Glu Ser Thr Ile Asp Ile Ile Leu Ser Gly Ser Thr
        130                 135                 140

His Ser Pro Glu Thr Ser Ser Glu Lys Pro Glu Asp Ile Asp Asn Phe
145                 150                 155                 160

Asn Cys Ser Ser Val Phe Glu Ile Ala Thr Pro Glu Pro Ile Thr Asp
                165                 170                 175

Asn Val Glu Asp His Thr Asp Thr Val Thr Tyr Thr Ser Asp Ser Ile
            180                 185                 190

Asn Thr Val Ser Ala Ser Ser Gly Glu Ser Thr Thr Asp Glu Thr Pro
        195                 200                 205

Glu Pro Ile Thr Asp Lys Glu Glu Asp His Thr Val Thr Asp Thr Val
    210                 215                 220

Ser Tyr Thr Thr Val Ser Thr Ser Ser Gly Ile Val Thr Thr Lys Ser
225                 230                 235                 240

Thr Thr Asp Asp Ala Asp Leu Tyr Asp Thr Tyr Asn Asp Asn Asp Thr
                245                 250                 255

Val Pro Ser Thr Thr Val Gly Ser Ser Thr Thr Ser Ile Ser Asn Tyr
            260                 265                 270

Lys Thr Lys Asp Phe Val Glu Ile Phe Gly Ile Thr Ala Leu Ile Ile
        275                 280                 285

Leu Ser Ala Val Ala Ile Phe Cys Ile Thr Tyr Tyr Ile Cys Asn Lys
    290                 295                 300

Arg Ser Arg Lys Tyr Lys Thr Glu Asn Lys Val
305                 310                 315

<210> SEQ ID NO 1074
<211> LENGTH: 930
```

<212> TYPE: DNA
<213> ORGANISM: Artificial Sequence
<220> FEATURE:
<223> OTHER INFORMATION: nucleotide sequence of A56 protein
     (OTS-412-A56)

<400> SEQUENCE: 1074
atgacacgat taccaatact tttgttacta atatcattag tatacgctac accttttcct      60
cagacatcta aaaaaatagg tgatgatgca actctatcat gtaatcgaaa taatacaaat     120
gactacgttg ttatgagtgc ttggtataag gagcccaatt ctattattct tttagctgct     180
aaaagcgacg tcttgtattt tgataattat accaaggata aaatatctta cgactctcca     240
tacgatgatc tagttacaac tatcacaatt aaatcattga ctgctagaga tgccggtact     300
tatgtatgtg cattctttat gacatcgcct acaaatgaca ctgataaagt agattatgaa     360
gaatactcca cagagttgat tgtaaataca gatagtgaat cgactattga cataatacta     420
tctggatcta cacattcacc ggaaactagt tctgagaaac cagaggatat agataatttt     480
aattgctcgt cggtattcga aatcgcgact ccggaaccaa ttactgataa tgtagaagat     540
catacagaca ccgtcacata cactagtgat agcattaata cagtaagtgc atcatctgga     600
gaatccacaa cagacgagac tccggaacca attactgata agaagaaga tcatacagtc     660 acagacactg tctcatacac tacagtaagt acatcatctg gaattgtcac tactaaatca     720
accaccgatg atgcgtacaa tgataatgat acagtaccat caactactgt aggtagtagt     780
acaacctcta ttagcaatta taaaaccaag gactttgtag aaatatttgg tattaccgca     840
ttaattatat tgtcggccgt ggcaatattc tgtattacgt attatatatg taataaacgt     900
tcacgtaaat acaaaacaga gaacaaagtc                                       930

<210> SEQ ID NO 1075
<211> LENGTH: 310
<212> TYPE: PRT
<213> ORGANISM: Artificial Sequence
<220> FEATURE:
<223> OTHER INFORMATION: amino acid sequence of A56 protein
     (OTS-412-A56)

<400> SEQUENCE: 1075

Met Thr Arg Leu Pro Ile Leu Leu Leu Leu Ile Ser Leu Val Tyr Ala
1               5                   10                  15

Thr Pro Phe Pro Gln Thr Ser Lys Lys Ile Gly Asp Asp Ala Thr Leu
                20                  25                  30

Ser Cys Asn Arg Asn Asn Thr Asn Asp Tyr Val Val Met Ser Ala Trp
            35                  40                  45

Tyr Lys Glu Pro Asn Ser Ile Ile Leu Leu Ala Ala Lys Ser Asp Val
        50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Pro Thr Asn
            100                 105                 110

Asp Thr Asp Lys Val Asp Tyr Glu Glu Tyr Ser Thr Glu Leu Ile Val
        115                 120                 125

Asn Thr Asp Ser Glu Ser Thr Ile Asp Ile Ile Leu Ser Gly Ser Thr
    130                 135                 140

His Ser Pro Glu Thr Ser Ser Glu Lys Pro Glu Asp Ile Asp Asn Phe

-continued

```
145              150              155              160

Asn Cys Ser Ser Val Phe Glu Ile Ala Thr Pro Glu Pro Ile Thr Asp
                165              170              175

Asn Val Glu Asp His Thr Asp Thr Val Thr Tyr Thr Ser Asp Ser Ile
            180              185              190

Asn Thr Val Ser Ala Ser Ser Gly Glu Ser Thr Thr Asp Glu Thr Pro
        195              200              205

Glu Pro Ile Thr Asp Lys Glu Glu Asp His Thr Val Thr Asp Thr Val
    210              215              220

Ser Tyr Thr Thr Val Ser Thr Ser Ser Gly Ile Val Thr Thr Lys Ser
225              230              235              240

Thr Thr Asp Asp Ala Tyr Asn Asp Asn Asp Thr Val Pro Ser Thr Thr
                245              250              255

Val Gly Ser Ser Thr Thr Ser Ile Ser Asn Tyr Lys Thr Lys Asp Phe
            260              265              270

Val Glu Ile Phe Gly Ile Thr Ala Leu Ile Ile Leu Ser Ala Val Ala
        275              280              285

Ile Phe Cys Ile Thr Tyr Tyr Ile Cys Asn Lys Arg Ser Arg Lys Tyr
    290              295              300

Lys Thr Glu Asn Lys Val
305              310
```

<210> SEQ ID NO 1076
<211> LENGTH: 774
<212> TYPE: DNA
<213> ORGANISM: Artificial Sequence
<220> FEATURE:
<223> OTHER INFORMATION: amino acid sequence of A56 protein
    (WOTS-418-A56)

<400> SEQUENCE: 1076

```
acaccttttc ctcagacatc taaaaaaata ggtgatgatg caactctatc atgtaatcga      60
aataatacaa atgactacgt tgttatgagt gcttggtata aggagcccaa ttctattatt     120
cttttagctg ctaaaagcga cgtcttgtat tttgataatt ataccaagga taaaatatct     180
tacgactctc catacgatga tctagttaca actatcacaa ttaaatcatt gactgctaga     240
gatgccggta cttatgtatg tgcattcttt atgacatcgc ctacaaatga cactgataaa     300
gtagattatg aagaatactc cacagagttg attgtaaata cagatagtga atcgactatt     360
gacataatac tatctggatc tacacattca ccggaaacta gttctgagaa accagaggat     420
atagataatt ttaattgctc gtcggtattc gaaatcgcga ctccggaacc aattactgat     480
aatgtagaag atcatacaga caccgtcaca tacactagtg atagcattaa tacagtaagt     540
gcatcatctg gagaatccac aacagacgag actccggaac caattactga taaagaagaa     600
gatcatacag tcacagacac tgtctcatac actacagtaa gtacatcatc tggaattgtc     660
actactaaat caaccaccga tgatgcgtac aatgataatg atacagtacc atcaactact     720
gtaggtagta gtacaacctc tattagcaat tataaaacca aggactttgt agaa           774
```

<210> SEQ ID NO 1077
<211> LENGTH: 258
<212> TYPE: PRT
<213> ORGANISM: Artificial Sequence
<220> FEATURE:
<223> OTHER INFORMATION: amino acid sequence of A56 protein fragment
    (WOTS-418-A56)

<400> SEQUENCE: 1077

```
Thr Pro Phe Pro Gln Thr Ser Lys Lys Ile Gly Asp Asp Ala Thr Leu
1               5                   10                  15

Ser Cys Asn Arg Asn Asn Thr Asn Asp Tyr Val Val Met Ser Ala Trp
                20                  25                  30

Tyr Lys Glu Pro Asn Ser Ile Ile Leu Leu Ala Ala Lys Ser Asp Val
            35                  40                  45

Leu Tyr Phe Asp Asn Tyr Thr Lys Asp Lys Ile Ser Tyr Asp Ser Pro
    50                  55                  60

Tyr Asp Asp Leu Val Thr Thr Ile Thr Ile Lys Ser Leu Thr Ala Arg
65                  70                  75                  80

Asp Ala Gly Thr Tyr Val Cys Ala Phe Phe Met Thr Ser Pro Thr Asn
                85                  90                  95

Asp Thr Asp Lys Val Asp Tyr Glu Glu Tyr Ser Thr Glu Leu Ile Val
            100                 105                 110

Asn Thr Asp Ser Glu Ser Thr Ile Asp Ile Ile Leu Ser Gly Ser Thr
            115                 120                 125

His Ser Pro Glu Thr Ser Ser Glu Lys Pro Glu Asp Ile Asp Asn Phe
    130                 135                 140

Asn Cys Ser Ser Val Phe Glu Ile Ala Thr Pro Glu Pro Ile Thr Asp
145                 150                 155                 160

Asn Val Glu Asp His Thr Asp Thr Val Thr Tyr Thr Ser Asp Ser Ile
            165                 170                 175

Asn Thr Val Ser Ala Ser Ser Gly Glu Ser Thr Thr Asp Glu Thr Pro
            180                 185                 190

Glu Pro Ile Thr Asp Lys Glu Glu Asp His Thr Val Thr Asp Thr Val
            195                 200                 205

Ser Tyr Thr Thr Val Ser Thr Ser Ser Gly Ile Val Thr Thr Lys Ser
    210                 215                 220

Thr Thr Asp Asp Ala Tyr Asn Asp Asn Asp Thr Val Pro Ser Thr Thr
225                 230                 235                 240

Val Gly Ser Ser Thr Thr Ser Ile Ser Asn Tyr Lys Thr Lys Asp Phe
            245                 250                 255

Val Glu
```

<210> SEQ ID NO 1078
<211> LENGTH: 942
<212> TYPE: DNA
<213> ORGANISM: Artificial Sequence
<220> FEATURE:
<223> OTHER INFORMATION: nucleotide sequence of A56 protein
      (WOTS-418-A56)

<400> SEQUENCE: 1078

```
atgacacgat taccaatact tttgttacta atatcattag tatacgctac accttttcct        60
cagacatcta aaaaatagg tgatgatgca actctatcat gtaatcgaaa taatacaaat       120
gactacgttg ttatgagtgc ttggtataag gagcccaatt ccattattct tttagctgct       180
aaaagcgacg tcttgtattt tgataattat accaaggata aaatatctta cgactctcca       240
tacgatgatc tagttacaac tatcacaatt aaatcattga ctgctagaga tgccggtact       300
tatgtatgtg cattctttat gacatcaact acaaatgaca ctgataaagt agattatgaa       360
gaatactcca cagagttgat tgtaaataca gatagtgaat cgactataga cataatacta       420
tctggatcta cacattcacc ggaaactagt tctaagaaac ctgattatat agataattct       480
aattgctcgt cggtattcga aatcgcgact ccggaaccaa ttactgataa tgtagaagat       540
```

-continued

```
catacagaca ccgtcacata cactagtgat agcattaata cagtaagtgc atcatctgga    600
gaatccacaa cagacgagac tccggaacca attactgata aagaagatca tacagttaca    660
gacactgtct catacactac agtaagtaca tcatctggaa ttgtcactac taaatcaacc    720
accgatgatg cggatcttta tgatacgtac aatgataatg atacagtacc accaactact    780
gtaggcggta gtacaacctc tattagcaat tataaaacca aggactttgt agaaatattt    840
ggtattaccg cattaattat attgtcggcc gtggcaattt tctgtattac atattatata    900
tataataaac gttcacgtaa atacaaaaca gagaacaaag tc                       942
```

```
<210> SEQ ID NO 1079
<211> LENGTH: 314
<212> TYPE: PRT
<213> ORGANISM: Artificial Sequence
<220> FEATURE:
<223> OTHER INFORMATION: amino acid sequence of A56 protein
      (WOTS-418-A56)

<400> SEQUENCE: 1079

Met Thr Arg Leu Pro Ile Leu Leu Leu Ile Ser Leu Val Tyr Ala
1               5                   10                  15

Thr Pro Phe Pro Gln Thr Ser Lys Lys Ile Gly Asp Asp Ala Thr Leu
            20                  25                  30

Ser Cys Asn Arg Asn Asn Thr Asn Asp Tyr Val Val Met Ser Ala Trp
        35                  40                  45

Tyr Lys Glu Pro Asn Ser Ile Ile Leu Leu Ala Ala Lys Ser Asp Val
    50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Thr Thr Asn
            100                 105                 110

Asp Thr Asp Lys Val Asp Tyr Glu Glu Tyr Ser Thr Glu Leu Ile Val
        115                 120                 125

Asn Thr Asp Ser Glu Ser Thr Ile Asp Ile Ile Leu Ser Gly Ser Thr
    130                 135                 140

His Ser Pro Glu Thr Ser Ser Lys Lys Pro Asp Tyr Ile Asp Asn Ser
145                 150                 155                 160

Asn Cys Ser Ser Val Phe Glu Ile Ala Thr Pro Glu Pro Ile Thr Asp
                165                 170                 175

Asn Val Glu Asp His Thr Asp Thr Val Thr Tyr Thr Ser Asp Ser Ile
            180                 185                 190

Asn Thr Val Ser Ala Ser Ser Gly Glu Ser Thr Thr Asp Glu Thr Pro
        195                 200                 205

Glu Pro Ile Thr Asp Lys Glu Asp His Thr Val Thr Asp Thr Val Ser
    210                 215                 220

Tyr Thr Thr Val Ser Thr Ser Ser Gly Ile Val Thr Thr Lys Ser Thr
225                 230                 235                 240

Thr Asp Asp Ala Asp Leu Tyr Asp Thr Tyr Asn Asp Asn Asp Thr Val
                245                 250                 255

Pro Pro Thr Thr Val Gly Gly Ser Thr Thr Ser Ile Ser Asn Tyr Lys
            260                 265                 270

Thr Lys Asp Phe Val Glu Ile Phe Gly Ile Thr Ala Leu Ile Ile Leu
        275                 280                 285
```

```
Ser Ala Val Ala Ile Phe Cys Ile Thr Tyr Tyr Ile Tyr Asn Lys Arg
    290                 295                 300

Ser Arg Lys Tyr Lys Thr Glu Asn Lys Val
305                 310

<210> SEQ ID NO 1080
<211> LENGTH: 321
<212> TYPE: PRT
<213> ORGANISM: Artificial Sequence
<220> FEATURE:
<223> OTHER INFORMATION: amino acid sequence of A56 protein IHD-J UTTA
      (AB191189)
<220> FEATURE:
<221> NAME/KEY: VARIANT
<222> LOCATION: (316)..(316)
<223> OTHER INFORMATION: Xaa = any naturally occurring amino acid
      residue

<400> SEQUENCE: 1080

Met Thr Arg Leu Pro Ile Leu Leu Leu Ile Ser Leu Val Tyr Ala
1                 5                 10                 15

Thr Pro Phe Pro Gln Thr Ser Lys Lys Ile Gly Asp Asp Ala Thr Leu
                20                 25                 30

Ser Cys Asn Arg Asn Asn Thr Asn Asp Tyr Val Val Met Ser Ala Trp
            35                 40                 45

Tyr Lys Glu Pro Asn Ser Ile Ile Leu Leu Ala Ala Lys Ser Asp Val
        50                 55                 60

Leu Tyr Phe Asp Asn Tyr Thr Lys Asp Lys Ile Ser Tyr Asp Ser Pro
65                 70                 75                 80

Tyr Asp Asp Leu Val Thr Thr Ile Thr Ile Lys Ser Leu Thr Ala Arg
                85                 90                 95

Asp Ala Gly Thr Tyr Val Cys Ala Phe Phe Met Thr Ser Thr Thr Asn
            100                 105                 110

Asp Thr Asp Lys Val Asp Tyr Glu Glu Tyr Ser Thr Glu Leu Ile Val
        115                 120                 125

Asn Thr Asp Ser Glu Ser Thr Ile Asp Ile Ile Leu Ser Gly Ser Thr
    130                 135                 140

His Ser Pro Glu Thr Ser Ser Glu Lys Pro Glu Asp Ile Asp Asn Phe
145                 150                 155                 160

Asn Cys Ser Ser Val Phe Glu Ile Ala Thr Pro Glu Pro Ile Thr Asp
                165                 170                 175

Asn Val Glu Asp His Thr Asp Thr Val Thr Tyr Thr Ser Asp Ser Ile
            180                 185                 190

Asn Thr Val Ser Ala Ser Ser Gly Glu Ser Thr Thr Asp Glu Thr Pro
        195                 200                 205

Glu Pro Ile Thr Asp Lys Glu Glu Asp His Thr Val Thr Asp Thr Val
    210                 215                 220

Ser Tyr Thr Thr Val Ser Thr Ser Ser Gly Ile Val Thr Thr Lys Ser
225                 230                 235                 240

Thr Thr Asp Asp Ala Asp Leu Tyr Asp Thr Tyr Asn Asp Asn Asp Thr
                245                 250                 255

Val Pro Pro Thr Thr Val Gly Gly Ser Thr Thr Ser Ile Ser Asn Tyr
            260                 265                 270

Lys Thr Lys Asp Phe Val Glu Ile Phe Gly Ile Thr Ala Leu Ile Ile
        275                 280                 285

Leu Ser Ala Val Ala Ile Phe Cys Ile Thr Tyr Tyr Ile Tyr Asn Lys
    290                 295                 300
```

```
Arg Ser Arg Lys Tyr Lys Thr Glu Asn Lys Val Xaa Ile Phe Asp Leu
305             310             315             320

His

<210> SEQ ID NO 1081
<211> LENGTH: 315
<212> TYPE: PRT
<213> ORGANISM: Artificial Sequence
<220> FEATURE:
<223> OTHER INFORMATION: amino acid sequence of A56 protein Dryvax DPP20
      UTTA (JN654985)
<220> FEATURE:
<221> NAME/KEY: VARIANT
<222> LOCATION: (310)..(310)
<223> OTHER INFORMATION: Xaa = any naturally occurring amino acid
      residue

<400> SEQUENCE: 1081

Met Thr Arg Leu Pro Ile Leu Leu Leu Leu Ile Ser Leu Val Tyr Ala
1               5               10              15

Thr Pro Phe Pro Gln Thr Ser Lys Lys Ile Gly Asp Asp Ala Thr Leu
            20              25              30

Ser Cys Asn Arg Asn Asn Thr Asn Asp Tyr Val Val Met Ser Ala Trp
        35              40              45

Tyr Lys Glu Pro Asn Ser Ile Ile Leu Leu Ala Ala Lys Ser Asp Val
    50              55              60

Leu Tyr Phe Asp Asn Tyr Thr Lys Asp Lys Ile Ser Tyr Asp Ser Pro
65              70              75              80

Tyr Asp Asp Leu Val Thr Thr Ile Thr Ile Lys Ser Leu Thr Ala Arg
            85              90              95

Asp Ala Gly Thr Tyr Val Cys Ala Phe Phe Met Thr Ser Pro Thr Asn
            100             105             110

Asp Thr Asp Lys Val Asp Tyr Glu Glu Tyr Ser Thr Glu Leu Ile Val
        115             120             125

Asn Thr Asp Ser Glu Ser Thr Ile Asp Ile Ile Leu Ser Gly Ser Thr
    130             135             140

His Ser Pro Glu Thr Ser Ser Glu Lys Pro Glu Asp Ile Asp Asn Phe
145             150             155             160

Asn Cys Ser Ser Val Phe Glu Ile Ala Thr Pro Glu Pro Ile Thr Asp
            165             170             175

Asn Val Glu Asp His Thr Asp Thr Val Thr Tyr Thr Ser Asp Ser Ile
            180             185             190

Asn Thr Val Ser Ala Ser Ser Gly Glu Ser Thr Thr Asp Glu Thr Pro
        195             200             205

Glu Pro Ile Thr Asp Lys Glu Asp His Thr Val Thr Asp Thr Val Ser
    210             215             220

Tyr Thr Thr Val Ser Thr Ser Ser Gly Ile Val Thr Thr Lys Ser Thr
225             230             235             240

Thr Asp Asp Thr Tyr Asn Asp Asn Asp Thr Val Pro Ser Thr Thr Val
            245             250             255

Gly Ser Ser Thr Thr Ser Ile Ser Asn Tyr Lys Thr Lys Asp Phe Val
        260             265             270

Glu Ile Phe Gly Ile Thr Ala Leu Ile Ile Leu Ser Ala Val Ala Ile
    275             280             285

Phe Cys Ile Thr Tyr Tyr Ile Cys Asn Lys Arg Ser Arg Lys Tyr Lys
    290             295             300
```

```
Thr Glu Asn Lys Val Xaa Ile Phe Asp Leu His
305                 310                 315

<210> SEQ ID NO 1082
<211> LENGTH: 314
<212> TYPE: PRT
<213> ORGANISM: Artificial Sequence
<220> FEATURE:
<223> OTHER INFORMATION: amino acid sequence of A56 protein WR UTTA
      (NC_006998)

<400> SEQUENCE: 1082

Met Thr Arg Leu Pro Ile Leu Leu Leu Leu Ile Ser Leu Val Tyr Ala
1               5                   10                  15

Thr Pro Phe Pro Gln Thr Ser Lys Lys Ile Gly Asp Asp Ala Thr Leu
            20                  25                  30

Ser Cys Asn Arg Asn Asn Thr Asn Asp Tyr Val Val Met Ser Ala Trp
        35                  40                  45

Tyr Lys Glu Pro Asn Ser Ile Ile Leu Leu Ala Ala Lys Ser Asp Val
    50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Thr Thr Asn
            100                 105                 110

Asp Thr Asp Lys Val Asp Tyr Glu Glu Tyr Ser Thr Glu Leu Ile Val
            115                 120                 125

Asn Thr Asp Ser Glu Ser Thr Ile Asp Ile Ile Leu Ser Gly Ser Thr
    130                 135                 140

His Ser Pro Glu Thr Ser Ser Lys Lys Pro Asp Tyr Ile Asp Asn Ser
145                 150                 155                 160

Asn Cys Ser Ser Val Phe Glu Ile Ala Thr Pro Glu Pro Ile Thr Asp
            165                 170                 175

Asn Val Glu Asp His Thr Asp Thr Val Thr Tyr Thr Ser Asp Ser Ile
            180                 185                 190

Asn Thr Val Ser Ala Ser Ser Gly Glu Ser Thr Thr Asp Glu Thr Pro
    195                 200                 205

Glu Pro Ile Thr Asp Lys Glu Asp His Thr Val Thr Asp Thr Val Ser
    210                 215                 220

Tyr Thr Thr Val Ser Thr Ser Ser Gly Ile Val Thr Thr Lys Ser Thr
225                 230                 235                 240

Thr Asp Asp Ala Asp Leu Tyr Asp Thr Tyr Asn Asp Asn Asp Thr Val
            245                 250                 255

Pro Pro Thr Thr Val Gly Gly Ser Thr Thr Ser Ile Ser Asn Tyr Lys
            260                 265                 270

Thr Lys Asp Phe Val Glu Ile Phe Gly Ile Thr Ala Leu Ile Ile Leu
            275                 280                 285

Ser Ala Val Ala Ile Phe Cys Ile Thr Tyr Tyr Ile Tyr Asn Lys Arg
    290                 295                 300

Ser Arg Lys Tyr Lys Thr Glu Asn Lys Val
305                 310

<210> SEQ ID NO 1083
<211> LENGTH: 314
<212> TYPE: PRT
<213> ORGANISM: Artificial Sequence
```

-continued

```
<220> FEATURE:
<223> OTHER INFORMATION: amino acid sequence of A56 protein WR UTTA
      (NC_006998)

<400> SEQUENCE: 1083

Met Thr Arg Leu Pro Ile Leu Leu Leu Leu Ile Ser Leu Val Tyr Ala
1               5                   10                  15

Thr Pro Phe Pro Gln Thr Ser Lys Lys Ile Gly Asp Asp Ala Thr Leu
                20                  25                  30

Ser Cys Asn Arg Asn Asn Thr Asn Asp Tyr Val Val Met Ser Ala Trp
          35                  40                  45

Tyr Lys Glu Pro Asn Ser Ile Ile Leu Leu Ala Ala Lys Ser Asp Val
      50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
                85                  90                  95

Asp Ala Gly Thr Tyr Val Cys Ala Phe Phe Met Thr Ser Thr Thr Asn
              100                 105                 110

Asp Thr Asp Lys Val Asp Tyr Glu Glu Tyr Ser Thr Glu Leu Ile Val
          115                 120                 125

Asn Thr Asp Ser Glu Ser Thr Ile Asp Ile Ile Leu Ser Gly Ser Thr
      130                 135                 140

His Ser Pro Glu Thr Ser Ser Lys Lys Pro Asp Tyr Ile Asp Asn Ser
145                 150                 155                 160

Asn Cys Ser Ser Val Phe Glu Ile Ala Thr Pro Glu Pro Ile Thr Asp
              165                 170                 175

Asn Val Glu Asp His Thr Asp Thr Val Thr Tyr Thr Ser Asp Ser Ile
          180                 185                 190

Asn Thr Val Ser Ala Ser Ser Gly Glu Ser Thr Thr Asp Glu Thr Pro
      195                 200                 205

Glu Pro Ile Thr Asp Lys Glu Asp His Thr Val Thr Asp Thr Val Ser
      210                 215                 220

Tyr Thr Thr Val Ser Thr Ser Ser Gly Ile Val Thr Thr Lys Ser Thr
225                 230                 235                 240

Thr Asp Asp Ala Asp Leu Tyr Asp Thr Tyr Asn Asp Asn Asp Thr Val
              245                 250                 255

Pro Pro Thr Thr Val Gly Gly Ser Thr Thr Ser Ile Ser Asn Tyr Lys
              260                 265                 270

Thr Lys Asp Phe Val Glu Ile Phe Gly Ile Thr Ala Leu Ile Ile Leu
          275                 280                 285

Ser Ala Val Ala Ile Phe Cys Ile Thr Tyr Tyr Ile Tyr Asn Lys Arg
      290                 295                 300

Ser Arg Lys Tyr Lys Thr Glu Asn Lys Val
305                 310
```